US011446370B2

(12) United States Patent
Geurtsen et al.

(10) Patent No.: US 11,446,370 B2
(45) Date of Patent: Sep. 20, 2022

(54) **BIOCONJUGATES OF *E. COLI* O-ANTIGEN POLYSACCHARIDES, METHODS OF PRODUCTION THEREOF, AND METHODS OF USE THEREOF**

(71) Applicants: Janssen Pharmaceuticals, Inc., Titusville, NJ (US); GlaxoSmithKline Biologicals S.A., Rixensart (BE)

(72) Inventors: Jeroen Geurtsen, Vleuten (NL); Jan Theunis Poolman, Haarlem (NL); Kellen Cristhina Fae, Oegstgeest (NL); Pieter Jan Burghout, Pijnacker (NL); Eveline Marleen Weerdenburg, Uithoorn (NL); Patricia Ibarra Yon, Solothurn (CH); Darren Robert Abbanat, Cornwal, NY (US); Stefan Jochen Kemmler, Zurich (CH); Michael Thomas Kowarik, Zurich (CH); Manuela Mally, Watt (CH); Veronica Gambillara Fonck, Meilen (CH); Martin Edward Braun, Cham (CH); Maria Paula Carranza Sandmeier, Rudolfstetten (CH)

(73) Assignees: Janssen Pharmaceuticals, Inc., Titusville, NJ (US); GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 16/822,340

(22) Filed: Mar. 18, 2020

(65) Prior Publication Data

US 2020/0316184 A1    Oct. 8, 2020

Related U.S. Application Data

(60) Provisional application No. 62/819,746, filed on Mar. 18, 2019.

(51) Int. Cl.
| | | |
|---|---|---|
| *A61K 39/108* | (2006.01) | |
| *A61P 37/04* | (2006.01) | |
| *A61P 31/04* | (2006.01) | |
| *C07K 14/21* | (2006.01) | |
| *C07K 19/00* | (2006.01) | |
| *C12N 9/10* | (2006.01) | |
| *A61K 39/00* | (2006.01) | |

(52) U.S. Cl.
CPC .......... *A61K 39/0258* (2013.01); *A61P 31/04* (2018.01); *A61P 37/04* (2018.01); *C07K 14/21* (2013.01); *C07K 19/00* (2013.01); *C12N 9/1051* (2013.01); *C12Y 204/01* (2013.01); *A61K 2039/575* (2013.01); *A61K 2039/6037* (2013.01)

(58) Field of Classification Search
None
See application file for complete search history.

(56) References Cited

U.S. PATENT DOCUMENTS

| | | |
|---|---|---|
| 3,700,612 A | 10/1972 | Fath |
| 5,057,540 A | 10/1991 | Kensil |
| 5,370,872 A | 12/1994 | Cryz |
| 9,700,612 B2 | 7/2017 | Kowarik |
| 10,150,952 B2 | 12/2018 | Haas |
| 10,159,751 B2 | 12/2018 | Labovitiadi |
| 10,441,647 B2 | 10/2019 | Kowarik et al. |
| 10,525,145 B2 | 1/2020 | Labovitiadi et al. |
| 10,577,592 B2 | 3/2020 | Haas |
| 10,583,185 B2 | 3/2020 | Poolman et al. |
| 10,844,098 B2 | 11/2020 | Wu et al. |
| 10,940,192 B2 | 3/2021 | Kowarik et al. |
| 11,015,177 B2 | 5/2021 | Haas |
| 11,033,633 B2 | 6/2021 | Labovitiadi et al. |
| 2014/0038296 A1 | 2/2014 | Bernhard |
| 2015/0056224 A1 | 2/2015 | Dubensky, Jr. et al. |
| 2015/0238588 A1 | 8/2015 | Kowarik |
| 2018/0002679 A1 | 1/2018 | Haas |
| 2019/0078064 A1 | 3/2019 | Haas |
| 2020/0181586 A1 | 6/2020 | Haas |
| 2020/0316184 A1 | 10/2020 | Geurtsen |
| 2020/0353073 A1 | 11/2020 | Geurtsen et al. |

(Continued)

FOREIGN PATENT DOCUMENTS

| | | |
|---|---|---|
| CN | 101983070 | 3/2011 |
| GB | 2220211 | 1/1990 |

(Continued)

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Van Den Dobbelsteen et al.,"Immunogenicity and safety of tetravalent *Escherichia coli* O-antigen bioconjugate vaccine in animal models," Vaccine, vol. 34, No. 35, pp. 4152-4160 (2016).
Cryz Jr. et al., "Synthesis and Characterization of *Escherichia coli* O18 O-Polysaccharide Conjugate Vaccines," Infection and Immunity, vol. 58, No. 2, pp. 373-377 (1990).

(Continued)

*Primary Examiner* — Brian Gangle
(74) *Attorney, Agent, or Firm* — Ice Miller LLP

(57) ABSTRACT

A bioconjugate of an *E. coli* glucosylated O4 antigen polysaccharide covalently linked to a carrier protein and compositions thereof are provided. Also provided are recombinant host cells for producing the bioconjugate, and methods of producing the bioconjugate using the recombinant host cells. The recombinant host cells contain a nucleic acid encoding a glucosyl transferase capable of modifying the *E. coli* O4 antigen with glucose branching to produce the glucosylated O4 antigen polysaccharide. Bioconjugates of an *E. coli* glucosylated O4 antigen polysaccharide described herein can be used alone or in combination with one or more additional *E. coli* O-antigen polysaccharides to induce antibodies against an *E. coli* glucosylated antigen, and to vaccinate a subject against extra-intestinal pathogenic *E. coli* (ExPEC).

42 Claims, 12 Drawing Sheets

Specification includes a Sequence Listing.

(56) References Cited

U.S. PATENT DOCUMENTS

| | | |
|---|---|---|
| 2021/0004617 A1 | 1/2021 | Gouraud et al. |
| 2021/0154286 A1 | 5/2021 | Kowarik et al. |
| 2022/0088165 A1 | 3/2022 | Poolman et al. |

FOREIGN PATENT DOCUMENTS

| | | |
|---|---|---|
| GB | 2220211 A | 1/1990 |
| JP | 2011514155 | 5/2011 |
| JP | 2017507178 | 3/2017 |
| WO | 2003074687 A1 | 9/2003 |
| WO | 2006119987 A2 | 11/2006 |
| WO | 2007109812 A2 | 9/2007 |
| WO | 2007109813 A1 | 9/2007 |
| WO | 2009089396 A2 | 7/2009 |
| WO | 2009104074 A2 | 8/2009 |
| WO | 2011062615 | 5/2011 |
| WO | 2012078482 A1 | 6/2012 |
| WO | 2013034664 A1 | 3/2013 |
| WO | 2014037585 A1 | 3/2014 |
| WO | 2014057109 A1 | 4/2014 |
| WO | 2014102265 A1 | 7/2014 |
| WO | 2014111516 A1 | 7/2014 |
| WO | 2015052344 | 4/2015 |
| WO | 2015/082571 | 6/2015 |
| WO | 2015/124769 | 8/2015 |
| WO | 2015117711 A1 | 8/2015 |
| WO | 2015124769 A1 | 8/2015 |
| WO | 2015/158403 | 10/2015 |
| WO | 2016/082597 | 6/2016 |
| WO | 2016107818 A1 | 7/2016 |
| WO | 2016107819 A1 | 7/2016 |
| WO | 2017035181 A1 | 3/2017 |
| WO | 2017/067964 | 4/2017 |
| WO | 2017/216286 | 12/2017 |
| WO | 2018/077853 | 5/2018 |
| WO | 2018077853 A1 | 5/2018 |
| WO | 2019016187 A1 | 1/2019 |

OTHER PUBLICATIONS

Ihssen et al., "Production of glycoprotein vaccines in *Escherichia coli*," Microbial Cell Factories, vol. 9, No. 61, pp. 1-13 (2010).
Poolman et al., "Extraintestinal Pathogenic *Escherichia coli*, a Common Human Pathogen: Challenges for Vaccine Development and Progress in the Field," Journal of Infectious Diseases, vol. 213, pp. 6-13 (2016).
Jiang et al., "Tungsten-Induced Protein Aggregation: Solution Behavior," Wiley InterScience, vol. 98, No. 12, pp. 4695-4710 (2009).
Seidl et al., "Tungsten-Induced Denaturation and Aggregation of Epoetin Alfa During Primary Packaging as a Cause of Immunogenicity," Pharm. Res., vol. 29, pp. 1454-1467 (2012).
"Typhoid Vi Polysaccharide Vaccine Typhim VI," Sanofi Pasteur Inc., vol. 3., pp. 1-26 (Mar. 2014).
Stenutz R et al, "The structures of *Escherichia coli* O-polysaccharide antigens.", FEMS Microbiol Rev. May 2006;30(3):382-403.
V. Szijarto et al, "Diagnostic Potential of Monoclonal Antibodies Specific to the Unique O-Antigen of Multidrug-Resistant Epidemic *Escherichia coli* Clone ST131-O25b:H4", Clinical and Vaccine Immunology, (Apr. 30, 2014), vol. 21, No. 7, doi:10.1128/CVI. 00685-13, ISSN 1556-6811, pp. 930-939, XP055179667.
Rogers B.A. et al., "*Escherichia coli* O25b-ST131: a pandemic, multiresistant, community-associated strain", Journal of Antimicrobial Chemotherapy, 2011, vol. 66, No. 1, pp. 1-14.
Pitout et al., "Extraintestinal Pathogenic *Escherichia coli*: An Update on Antimicrobial Resistance, Laboratory Diagnosis and Treatment," Expert Rev. Anti. Infect. Then, vol. 10, No. 10, pp. 1165-1176 (2012).
Mario F Feldman et al, "Engineering N-linked protein glycosylation with diverse O antigen lipopolysaccharide structures in *Escherichia coli*", Proceedings of the National Academy of Sciences, vol. 102, No. 8, pp. 3016-3021, (Feb. 9, 2005).
Fratamico et al., "*Escherichia coli* serogroup O2 and O28ac O-antigen gene cluster sequences and detection of pathogenic *Escherichia coil* O2 and O28ac by PCR," Canadian Journal of Microbiology, vol. 56, No. 4, pp. 308-316 (2010).
Jann et al., "Structural Comparison of the O6 Specific Polysaccharides From *Escherichia coli* O6:K2:H1, *Escherichia coli* O6:K13:H1, and *Escherichia coli* O6:K54:H10," Carbohydrate Research, vol. 263, No. 2, pp. 217-225 (1994).
Jansson et al., "Structural studies of the *Escherichia coli* O-antigen 6," Carbohydrate Research, vol. 131, No. 2, pp. 277-283 (1984).
Wacker et al., "N-linked glycosylation in Campylobacter jejuni and its functional transfer into *Escherichia coli*," Science, vol. 298, No. 5599, pp. 1790-1793 (2002).
Debroy et al., "Detection of O antigens in *Escherichia coli*," Animal Health Research Reviews, vol. 12, No. 2, pp. 169-185 (2011).
Datsenko et al., "One-step inactivation of chromosomal genes in *Escherichia coli* K-12 using PCR products," PNAS, vol. 97, No. 12, pp. 6640-6645 (2000).
Blanco et al., "Virulence factors and 0 groups of *Escherichia coli* isolates from patients with acute pyelonephritis, cystitis and asymptomatic bacteriuria," Eur. J. Epidemiol., vol. 12, No. 2, pp. 191-198 (1996).
Molina-Lopez et al., "Drug resistance, serotypes, and phylogenetic groups among uropathogenic *Escherichia coli* including O25-ST131 in Mexico City," J Infect Dev Ctries, vol. 5, No. 12, pp. 840-849 (2011).
Terai et al., "*Escherichia coli* Virulence Factors and Serotypes in Acute Bacterial Prostatitis," Int. Journal of Urology, vol. 4, No. 3, pp. 289-294 (1997).
Kenne et al., "Structural studies of the *Escherichia coli* O-antigen 25," Carbohydrate Research, vol. 122, No. 2, pp. 249-256 (1983).
Fundin et al., "NMR analysis of the O-antigen polysaccharide from *Escherichia coli* strain F171," Magnetic Resonance in Chemistry, vol. 41, No. 3, pp. 202-205 (2003).
Johnson et al., "*Escherichia coli* sequence type ST131 as an emerging fluoroquinolone-resistant uropathogen among renal transplant recipients," Antimicrob Agents Chemother. vol. 54, No. 1, pp. 546-550 (2010).
Banerjee et al., "A new clone sweeps clean: the enigmatic emergence of *Escherichia coli* sequence type 131," Antimicrob Agents Chemother. vol. 58, No. 9, pp. 4997-5004 (2014).
Lukac et al., "Toxoid of Pseudomonas aeruginosa exotoxin A generated by deletion of an active-site residue," Infect Immun, vol. 56, No. 12, pp. 3095-3098 (1988).
Szijarto et al. "The rapidly emerging ESBL-producing *Escherichia coil* O25-ST131 clone carries LPS core synthesis genes of the K-12 type," FEMS Microbiol. Lett., vol. 332, pp. 131-136 (2012).
Clermont et al.,"The CTX-M-15-producing *Escherichia coli* diffusing clone belongs to a highly virulent B2 phylogenetic subgroup," J. Antimicrob. Chemother., vol. 61, No. 5, pp. 1024-1028 (2008).
Blanco et al.,"Molecular epidemiology of *Escherichia coli* producing extended-spectrum {beta}-lactamases in Lugo (Spain): dissemination of clone O25b:H4-ST131 producing CTX-M-15," J. Antimicrob. Chemother., vol. 63, pp. 1135-1141 (2009).
Phan et al., "The serum resistome of a globally disseminated multidrug resistant uropathogenic *Escherichia coil* clone," PLOS Genetics, vol. 9, No. 10, pp. 1-18 (2013).
Stevenson et al., "Structure of the O antigen of *Escherichia coli* K-12 and the sequence of its rfb gene cluster," J. Bacteriol., vol. 176, No. 13, pp. 4144-4156 (1994).
Amor et al., "Distribution of core oligosaccharide types in lipopolysaccharides from *Escherichia coli*," Infect. Immun., vol. 68, No. 3, pp. 1116-1124 (2000).
Jansson et al., "Structural studies of the O-specific side-chains of the *Escherichia coli* O2 lipopolysaccharide," Carbohydrate Res., vol. 161, pp. 273-279 (1987).
A. Cross et al, "Safety And Immunogenicity Of A Polyvalent *Escherichia coli* Vaccine In Human Volunteers", Journal of Infectious Diseases. JID, Chicago, IL., (Oct. 1, 1994), vol. 170, No. 4, doi:10.1093/infdis/170.4.834, ISSN 0022-1899, pp. 834-840, XP055311603.
Cryz S J et al, "Synthesis and characterization of a polyvalent *Escherichia coli* O-polysaccharide-toxin A conjugate vaccine", Vac-

(56) References Cited

OTHER PUBLICATIONS cine, Elsevier Ltd, GB, (Jan. 1, 1995), vol. 13, No. 5, doi:10.1016/0264-410X(94)00009-C, ISSN 0264-410X, pp. 449-453, XP004057719.
Int'l Search Report and Written Opinion dated Jun. 15, 2015 in Int'l Application No. PCT/EP2015/053739, 10 pages.
Int'l Search Report and Written Opinion dated Oct. 27, 2016 in Int'l Application No. PCT/US2016/048278, 16 pages.
Jadhav et al., "Virulence characteristics and genetic affinities of multiple drug resistant uropathogenic *Escherichia coli* from a Semi Urban Locality in India," PLOS One, vol. 6, No. 3, (2011), 7 pages.
Mora et al, "Emergence of clonal groups O1:HNM-D-ST59, O15:H1-D-ST393, O20:H34/HNM-D-ST354, O25b:H4-B2-ST131 and ONT:H21,42-B1-ST101 among CTX-M-14-producing *Escherichia coli* clinical isolates in Galicia, northwest Spain," International J. of Antimicrob. Agents, vol. 37, No. 1, pp. 16-21 (2011).
Clermont et al., "Rapid Detection of the O25b-ST131 clone of *Escherichia coil* encompassing the CTX-M-15-producing strains," Journal of Antimicrobial Chemotherapy, vol. 64, No. 2, pp. 274-277 (2009).
Glover et al., "Chemoenzymatic synthesis of Glycopeptides with PglB, a bacterial oligosaccharyl transferase from Campylobacter jejuni," Chemistry and Biology, Current Biology, vol. 12, No. 12, pp. 1311-1316 (2005).
Laurentin et al., "A Microtiter Modification of the anthrone-sulfuric acid colorimetric assay for glucose-based carbohydrates", Analytical Biochemistry, 315, pp. 143-145, 2003.
Russo et al., "A killed, genetically engineered derivative of a wild-type extraintestinal pathogenic *E coli* strain is a vaccine candidate", Elsevier, Vaccine 25, pp. 3859-3870, 2007.
Russo et al., "Medical and Exonomic impact of extraintestinal infections due to *Escherichia coli*: focus on an Increasingly important endemic problem", Elsevier, Microbes and Infection 5, pp. 449-456, 2003.
Kohler et al., "What defines extraintestinal pathogenic *Escherichia coli*", Elsevier, International journal of Medical Microbiology 301, pp. 642-647, 2011.
Ho et al., Preclinical Laboratory Evaluation of a Bivalent *Staphylococcus aureus* Saccharide-Exotoxin A Protein Conjugate Vaccine, Human vaccines, 2:3, pp. 89-98, May/Jun. 2006.
Lipsitch, "Bacterial vaccines and Serotype Replacement: Lessons from Haemophilus Influenzae and Prospects for *Streptococcus pneumoniae*", Emerging Infectious Diseases, vol. 5, No. 3, May/Jun. 1999, 10 pages.
Schito et al., "The ARESC study: an international survey on the antimicrobial resistance of pathogens involved in uncomplicated urinary tract infections", Elsevier, International Journal of Antimicrobial Agents 34, pp. 407-413, 2009.
Foxman, "Epidemiology of Urinary Tract Infections: Incidence, morbidity, and Economic Costs", The American Journal of Medicine, vol. 113(1A), 5S-13S, Jul. 2002.
Johnson et al., Extraintestinal Pathogenic *Escherichi coli*: "The other bad *E coli*", J Lab Clin Med., 139(3), pp. 155-162, 2002.
Kim et al., "Efficiency of a pneumococcal Opsonophagocytic Killing Assay Improved by Multiplexing and by Colloring Colonies", Clinical and Dianostic laboratory Immunology, pp. 616-621, Jul. 2003.
Int'l Search Report and Written Opinion dated Jul. 20, 2017 in Int'l Application No. PCT/US2016/048278, 9 pages.
Int'l Preminary Report on Patentability dated Feb. 14, 2019 in Int'l Application No. PCT/EP2017/077123, 16 pages.
Written Opinion dated Dec. 21, 2018 in Int'l Application No. PCT/EP2017/077123, 8 pages.
Written Opinion of the International Preliminary Examining Authority dated Sep. 11, 2018 in PCT/EP2017/077123, 8 pages.
Written opinion of the Int'l Searching Authority dated Jan. 24, 2018 in Int'l Application No. PCT/EP2017/077123, 6 pages.
Int'l Search Report dated Jan. 24, 2018 in Int'l Application No. PCT/EP2017/077123, 6 pages.
Stoute et al., "A Preliminary Evaluation of a Recombinant Circumsporozoite Protein Vaccine Against Plasmodium Falciparum Malaria," New England Journal of Medicine, vol. 336, pp. 86-91 (1997).
Extended Search Report dated Apr. 12, 2017 in EP Application No. 16195256.9, 8 pages.
Frenck, et al., "Safety and Immunogenicity of a vaccine for extra-intestinal pathogenic *Escherichia coli* (ESTELLA): a phase 2 randomised controlled trial," Lancet Infect. Dis. vol. 1, No. 6, pp. 631-640 (2019).
International Search Report and Written Opinion for App. No. PCT/US2020/023415, dated Jun. 12, 2020, 21 pages.
Abbanat et al., "Development and Qualification of an Opsonophagocytic Killing Assay To Assess Immunogenicity of a Bioconjugated *Escherichia coli* Vaccine," Clin Vaccine Immunol 24:e00123-17. https://doi.org/10.1128/CVI.00123-17. 2017.
DebRoy et al., "Comparison of O-Antigen Gene Clusters of All O-Serogroups of *Escherichia coli* and Proposal for Adopting a New Nomenclature for O-Typing," PLoS ONE 11(1): e0147434. doi:10.1371/journal.pone.0147434, 2016.
DebRoy et al., "Correction: Comparison of O-Antigen Gene Clusters of All O-Serogroups of Escherichia coli and Proposal for Adopting a New Nomenclature for O-Typing," PLoS ONE 11(4): e0154551. doi:10.1371/journal.pone.0154551, 2016.
Feldman et al., "Engineering N-linked protein glycosylation with diverse O antigen lipopolysaccharide structures in *Escherichia coli*," PNAS, 102(8):3016-3021, 2005.
Frenck et al., "Long-term Immunogenicity and Safety of ExPEC4V Vaccine Against Extraintestinal Pathogenic *Escherichia coli* Disease in Healthy Participants," Abstract 5587, ASM Microbe, 2018.
Hayashi et al., "Highly accurate genome sequences of *Escherichia coli* K-12 strains MG1655 and W3110," Molecular Systems Biology Feb. 21, 2006; doi:10.1038/msb4100049.
Ho et al., "Preclinical Laboratory Evaluation of a Bivalent Staphylococcus aureus Saccharide-Exotoxin A Protein Conjugate Vaccine," Human Vaccines 2:3, 89-98, May/Jun. 2006.
Huttner et al., "Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial," 2017, Lancet Infect Dis, http://dx.doi.org/10.1016/S1473-3099(17)30108-1.
Iguchi et al., "A complete view of the genetic diversity of the *Escherichia coli* O-antigen biosynthesis gene cluster," DNA Research, 2015, 22(1), 101-107.
Ireton et al., "Adjuvants containing natural and synthetic Toll-like receptor 4 ligands," 2013, Expert Rev Vaccines 12 793-807.
Jann et al., "Structural comparison of the O4-specific polysaccharides from *E. coli* O4:K6 and *E. coli* O4:K52," Carbohydrate Research, 248:241-250,1993.
Jansson et al., "Structural Studies of the O-Antigen Polysaccharide of *Escherichia coli* O4," Carbohydrate Research, 134:283-291, 1984.
Pawlowski et al., "Preparation of pneumococcal capsular polysaccharide-protein conjugate vaccines utilizing new fragmentation and conjugation technologies," Vaccine 18 (2000) 1873-1885.
Poolman et al., "The history of pneumococcal conjugate vaccine development: dose selection," Expert Rev. Vaccines 12(12), 1379-1394(2013).
Reed et al., "Key roles of adjuvants in modern vaccines," Nature Medicine, 19(12):1597-1608,2013.
Robbins et al., "Synthesis, characterization, and immunogenicity in mice of Shigella sonnei O-specific oligosaccharide-core-protein conjugates," PNAS, 106(19):7974-7978, 2009.
Wacker et al., "Substrate specificity of bacterial oligosaccharyltransferase suggests a common transfer mechanism for the bacterial and eukaryotic systems," PNAS, 103(18):7088-7093, 2006.
Zhu et al., "QS-21: A Potent Vaccine Adjuvant," Nat Prod Chem Res, 3(4):1000e1 13, 2016.
Saade et al., "Characertization of *Escherichia coli* isolates potentially covered by ExPEC4V and ExPEC10V, that were collected from post-transrectal ultrasound-guided prostate needle biopsy," Vaccine, vol. 38, No. 33, 2020, pp. 5100-5104.

(56) References Cited

OTHER PUBLICATIONS

Int'l Search Report and Written Opinion dated Jun. 6, 2020 in Int'l Application No. PCT/US2020/023404, 11 pages.

\* cited by examiner

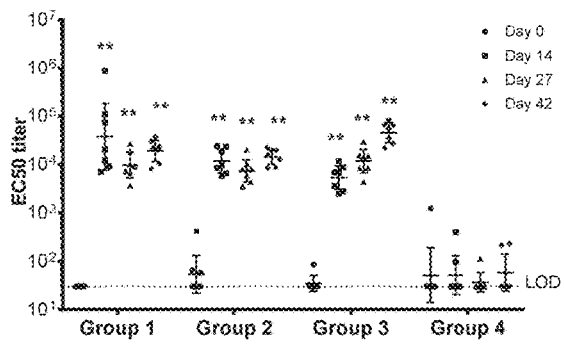
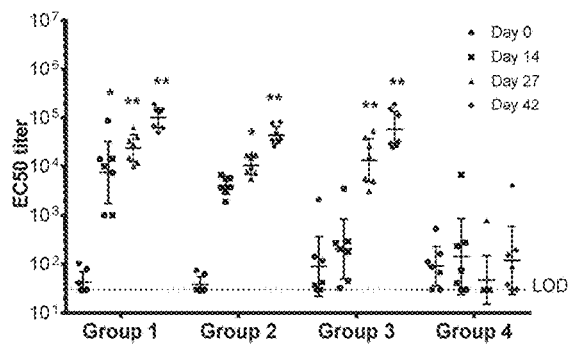
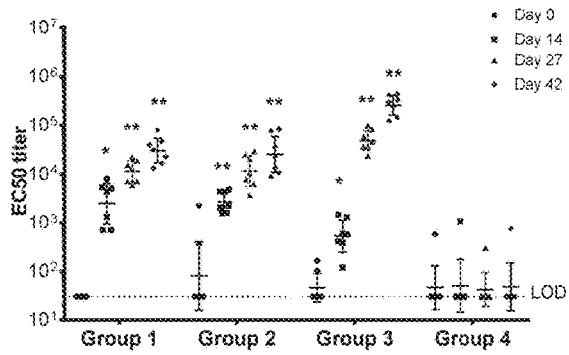
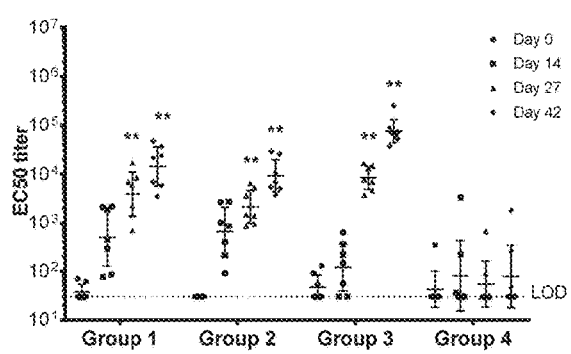
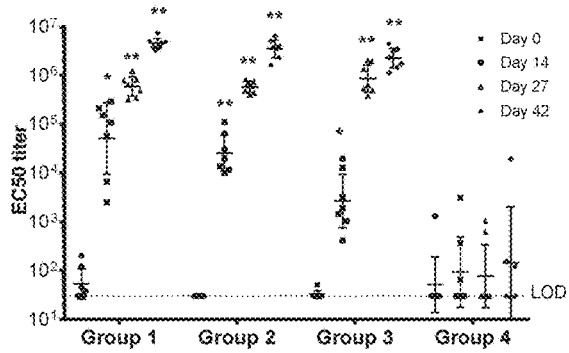
Fig. 8 - continued

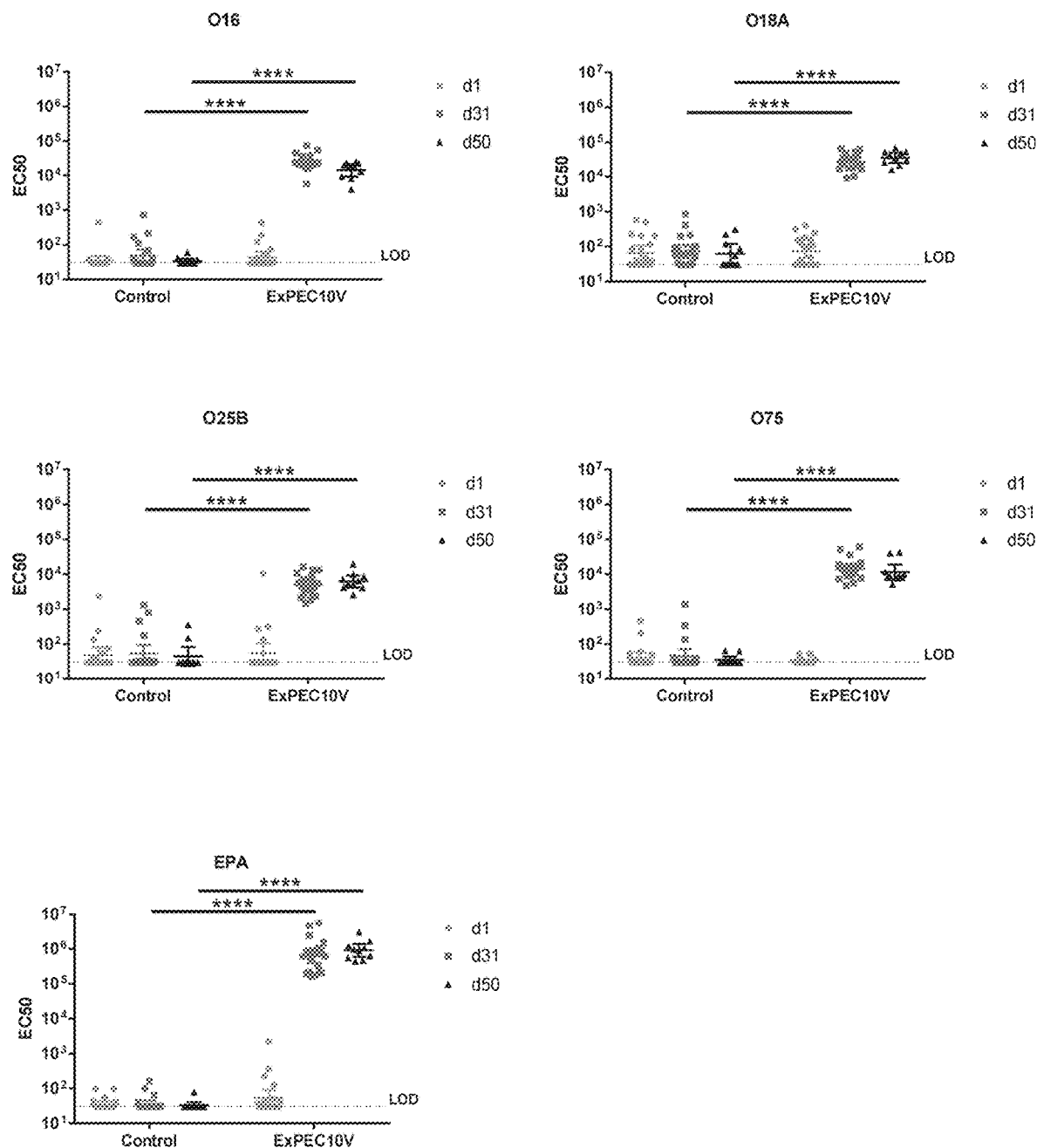
Fig. 9 - continued

BIOCONJUGATES OF E. COLI O-ANTIGEN POLYSACCHARIDES, METHODS OF PRODUCTION THEREOF, AND METHODS OF USE THEREOF

CROSS REFERENCE TO RELATED APPLICATION

This application claims priority to U.S. Provisional Application No. 62/819,746 filed on Mar. 18, 2019, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "004852_11654_Sequence-Listing", creation date of Mar. 18, 2020, and having a size of 199 KB. The sequence listing submitted via EFS-Web is part of the specification and is herein incorporated by reference in its entirety.

BACKGROUND OF THE INVENTION

Extraintestinal pathogenic *Escherichia coli* (ExPEC) strains are normally harmless inhabitants of the human gastrointestinal tract, alongside commensal *E. coli* strains. ExPEC isolates cannot readily be distinguished from commensal isolates by serotype, although many clonal lineages are dominated by ExPEC, as defined by O-antigen, capsule and flagellar antigen serotypes (abbreviated as O:K:H, for example O25:K1:H4). In contrast to commensal *E. coli*, ExPEC strains express a broad array of virulence factors enabling them to colonize the gastrointestinal tract, as well as to cause a wide range of extraintestinal infections, which are associated with a significant healthcare cost burden due to hospitalization and death. Neonates, the elderly, and immunocompromised patients are particularly susceptible to ExPEC infection, including invasive ExPEC disease (IED).

ExPEC strains are the most common cause of urinary tract infections (UTI) and important contributors to surgical site infections and neonatal meningitis. The strains are also associated with abdominal and pelvic infections and nosocomial pneumonia, and are occasionally involved in other extraintestinal infections, such as osteomyelitis, cellulitis, and wound infections. All these primary sites of infection can result in ExPEC bacteremia. ExPEC is the most common cause of community-onset bacteremia and a major causative pathogen in nosocomial bacteremia and is found in about 17% to 37% of clinically significant blood isolates. Patients with an ExPEC-positive blood culture typically suffer sepsis syndrome, severe sepsis, or septic shock. Increasing resistance of ExPEC against first-line antibiotics including the cephalosporins, fluoroquinolones, and trimethoprim/sulfamethoxazole has been observed. The emergence and rapid global dissemination of ExPEC sequence type 131 (ST131) is considered a main driver of increased drug resistance, including multi-drug resistance. This clone is found in 12.5% to 30% of all ExPEC clinical isolates, exhibits mostly serotype O25b:H4, and shows high levels of resistance to fluoroquinolones, which is often accompanied by trimethoprim/sulfamethoxazole resistance and extended-spectrum beta-lactamases conferring resistance to cephalosporins.

The O-antigen comprises the immunodominant component of the cell wall lipopolysaccharide (LPS) in Gram-negative bacteria, including *E. coli*. There are currently >180 serologically unique *E. coli* O-antigens identified, with the vast majority of ExPEC isolates classified within less than 20 O-antigen serotypes. Full-length *E. coli* O-antigens are typically comprised of about 10 to 25 repeating sugar units attached to the highly conserved LPS core structure, with each component synthesized separately by enzymes encoded predominantly in the rfb and rfa gene clusters, respectively. Following polymerization of the O-antigen, the O-antigen polysaccharide backbone may be modified, typically through the addition of acetyl or glucose residues. These modifications effectively increase serotype diversity by creating antigenically distinct serotypes that share a common polysaccharide backbone, but differ in side branches. Genes encoding O-antigen modifying enzymes typically reside outside of the rfb cluster on the chromosome, and in some cases, these genes are found within lysogenic bacteriophages.

ExPEC isolates belonging to the O4 serogroup have been commonly identified in contemporary surveillance studies of U.S. and EU blood isolates. The structure of the O4 polysaccharide was determined as →2) α-L-Rha (1→6) α-D-Glc (1→3) α-L-FucNAc (1→3) β-D-GlcNAc (1→ from an *E. coli* O4:K52 strain (Jann et al., *Carbohydr. Res.* (1993) v. 248, pp. 241-250). A distinct form of the O4 polysaccharide structure was determined for O4:K3, O4:K6 and O4:K12 strains, in which the structure above was modified by the addition of an α-D-Glc (1→3) linked to the rhamnose residue of the polysaccharide (Jann et al., 1993, supra), this form of the polysaccharide referred to herein below as 'glucosylated O4'. The enzymes responsible for the O-antigen modification within *E. coli* O4 strains were not identified.

Efforts toward the development of a vaccine to prevent ExPEC infections have focused on O-antigen polysaccharide conjugates. A 12-valent O-antigen conjugate vaccine was synthesized through extraction and purification of O-antigen polysaccharide and chemical conjugation to detoxified *Pseudomonas aeruginosa* exotoxin A and tested for safety and immunogenicity in a Phase 1 clinical study (Cross et al., *J. Infect. Dis.* (1994) v. 170, pp. 834-40). This candidate vaccine was never licensed for clinical use. A bioconjugation system in *E. coli* has been developed recently, in which the polysaccharide antigen and the carrier protein are both synthesized in vivo and subsequently conjugated in vivo through the activities of the oligosaccharyl transferase PglB, a *Campylobacter jejuni* enzyme, expressed in *E. coli* (Wacker et al., *Proc. Nat. Acad. Sci.* (2006) v. 103, pp. 7088-93). This N-linked protein glycosylation system is capable of the transfer of diverse polysaccharides to a carrier protein, allowing for straightforward methods to purify the conjugate.

Bioconjugation has been used successfully to produce conjugate polysaccharide for an *E. coli* four-valent O-antigen candidate vaccine (Poolman and Wacker, *J. Infect. Dis.* (2016) v. 213(1), pp. 6-13). However, the development of a successful ExPEC vaccine requires coverage of predominant serotypes, and the presence of further O-antigen modifications in subsets of ExPEC isolates presents a further challenge in covering isolates displaying unmodified and modified LPS.

BRIEF SUMMARY OF THE INVENTION

In view of increasing antibiotic resistance among ExPEC isolates and the presence of further O-antigen modifications among predominant O-serotypes, there is a need for improved prophylactic and therapeutic treatments for these infections. The invention satisfies this need by defining the genetic composition of contemporary clinical isolates, including identifying the genes encoding O-antigen modifying enzymes, thus allowing for the engineering of recombinant host cells capable of synthesizing bioconjugates of the O-antigens including bioconjugates comprising selected O-antigen modifications.

In one aspect, provided herein is a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+) as shown in Table 1, wherein n is an integer of 1 to 100, preferably 1 to 50, e.g. 3 to 50, e.g. 5 to 40, e.g. 7 to 25, e.g. 10 to 20.

In a particular embodiment, the *E. coli* glucosylated O4 antigen polysaccharide is covalently linked to an Asn residue in a glycosylation site comprising a glycosylation consensus sequence having SEQ ID NO: 1, preferably having SEQ ID NO: 2, in the carrier protein.

In some embodiments, the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In a particular embodiment, the carrier protein is a detoxified exotoxin A of *Pseudomonas aeruginosa* (EPA). In such embodiments, the EPA preferably comprises 1 to 20, preferably 1 to 10, preferably 2 to 4, glycosylation consensus sequences having SEQ ID NO: 1, the consensus sequences preferably having SEQ ID NO: 2.

In a particular embodiment, the carrier protein comprises four glycosylation consensus sequences (EPA-4). In a preferred embodiment, the carrier protein comprises SEQ ID NO: 3.

In another aspect, provided herein is a composition or immunogenic composition comprising a bioconjugate of an *E. coli* glucosylated O4 antigen polysaccharide covalently linked to a carrier protein as described herein.

In some embodiments, a composition or immunogenic composition comprises at least one additional antigen polysaccharide covalently linked to a carrier protein.

In some embodiments, a composition or immunogenic composition comprises at least one additional antigen polysaccharide covalently linked to a carrier protein, wherein the at least one additional antigen polysaccharide is selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide. In specific embodiments, the *E. coli* O1A antigen polysaccharide comprises the structure of Formula (O1A) as shown in Table 1, wherein n is an integer of 1 to 100, preferably 3 to 50, for example 5 to 40, e.g. 7 to 25, e.g. 10 to 20. In specific embodiments, the *E. coli* O2 antigen polysaccharide comprises the structure of Formula (O2) as shown in Table 1, wherein n is an integer of 1 to 100, preferably 3 to 50, for example 5 to 40, e.g. 7 to 25, e.g. 10 to 20. In specific embodiments, the *E. coli* O6A antigen polysaccharide comprises the structure of Formula (O6A) as shown in Table 1, wherein n is an integer of 1 to 100, preferably 3 to 50, for example 5 to 40, e.g. 7 to 25, e.g. 10 to 20. In specific embodiments, the *E. coli* O8 antigen polysaccharide comprises the structure of Formula (O8) as shown in Table 1, wherein n is an integer of 1 to 100, preferably 3 to 50, for example 5 to 40, e.g. 7 to 25, e.g. 10 to 20. In specific embodiments, the *E. coli* O15 antigen polysaccharide comprises the structure of Formula (O15) as shown in Table 1, wherein n is an integer of 1 to 100, preferably 3 to 50, for example 5 to 40, e.g. 7 to 25, e.g. 10 to 20. In specific embodiments, the *E. coli* O16 antigen polysaccharide comprises the structure of Formula (O16) as shown in Table 1, wherein n is an integer of 1 to 100, preferably 3 to 50, for example 5 to 40, e.g. 7 to 25, e.g. 10 to 20. In specific embodiments, the *E. coli* O18A antigen polysaccharide comprises the structure of Formula (O18A) as shown in Table 1, wherein n is an integer of 1 to 100, preferably 3 to 50, for example 5 to 40, e.g. 7 to 25, e.g. 10 to 20. In specific embodiments, the *E. coli* O25B antigen polysaccharide comprises the structure of Formula (O25B) as shown in Table 1, wherein n is an integer of 1 to 100, preferably 3 to 50, for example 5 to 40, e.g. 7 to 25, e.g. 10 to 20. In specific embodiments, the *E. coli* O75 antigen polysaccharide comprises the structure of Formula (O75) as shown in Table 1, wherein n is an integer of 1 to 100, preferably 3 to 50, for example 5 to 40, e.g. 7 to 25, e.g. 10 to 20.

In certain embodiments, each of the additional *E. coli* O1A, O2, O6A, O8, O15, O16, O18A, O25B, and/or O75 antigen polysaccharides is covalently bound to an Asn reside in a glycosylation site comprising a glycosylation consensus sequence having SEQ ID NO: 1, preferably having SEQ ID NO: 2, in each of the carrier protein. In particular embodiments, each of the carrier protein is a detoxified exotoxin A of *Pseudomonas aeruginosa* (EPA). Preferably, each EPA comprises 1-10, preferably 2-4, preferably 4 glycosylation sites each comprising a glycosylation consensus sequence having SEQ ID NO: 2. In particular embodiments, each EPA comprises SEQ ID NO: 3.

In particular embodiments, the composition or immunogenic composition comprises at least the *E. coli* O1A, O2, glucosylated O4, O6A and O25B antigen polysaccharides each covalently linked to a carrier protein. In particular embodiments, the composition or immunogenic composition comprises at least the *E. coli* O1A, O2, glucosylated O4, O6A, O8, O15, O16, O25B, and O75 antigen polysaccharides each covalently linked to a carrier protein. In particular embodiments, the composition or immunogenic composition comprises at least the *E. coli* O1A, O2, glucosylated O4, O6A, O8, O15, O16, O18A, O25B, and O75 antigen polysaccharides each covalently linked to a carrier protein.

In a particular aspect, provided is a composition or immunogenic composition that comprises:

a bioconjugate of an *E. coli* glucosylated O4 antigen polysaccharide covalently linked to a detoxified Exotoxin A of *P. aeruginosa* (EPA-4) carrier protein comprising SEQ ID NO: 3, wherein the *E. coli* glucosylated O4 antigen polysaccharide comprises the structure of Formula (O4-Glc+);

(ii) a bioconjugate of an *E. coli* O1A antigen polysaccharide covalently linked to an EPA-4 carrier protein, wherein the *E. coli* O1A antigen polysaccharide comprises the structure of Formula (O1A);

(iii) a bioconjugate of an *E. coli* O2 antigen polysaccharide covalently linked to an EPA-4 carrier protein, wherein the *E. coli* O2 antigen polysaccharide comprises the structure of Formula (O2);

(iv) a bioconjugate of an *E. coli* O6A antigen polysaccharide covalently linked to an EPA-4 carrier protein, wherein the *E. coli* O6A antigen polysaccharide comprises the structure of Formula (O6A);

(v) a bioconjugate of an *E. coli* O8 antigen polysaccharide covalently linked to an EPA-4 carrier protein, wherein the *E. coli* O8 antigen polysaccharide comprises the structure of Formula (O8);

(vi) a bioconjugate of an *E. coli* O15 antigen polysaccharide covalently linked to an EPA-4 carrier protein, wherein the *E. coli* O15 antigen polysaccharide comprises the structure of Formula (O15);

(vii) a bioconjugate of an *E. coli* O16 antigen polysaccharide covalently linked to an EPA-4 carrier protein, wherein the *E. coli* O16 antigen polysaccharide comprises the structure of Formula (O16);

(viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* O75 antigen polysaccharide covalently linked to an EPA-4 carrier protein, wherein the *E. coli* O75 antigen polysaccharide comprises the structure of Formula (O75), wherein the structure of each of Formulas (O4-Glc+), (O1A), (O2), (O6A), (O8), (O15), (O16), (O18A), (O25B), and (O75) is shown in Table 1, and each n is independently an integer of 1 to 100, preferably 1 to 50, e.g. 3 to 50, e.g. 5 to 40, e.g. 7 to 25, e.g. 10 to 20.

In certain embodiments, such composition or immunogenic composition further comprises:

(x) a bioconjugate of an *E. coli* O18A antigen polysaccharide covalently linked to an EPA-4 carrier protein, wherein the *E. coli* O18A antigen polysaccharide comprises the structure of Formula (O18A), wherein the structure of Formula (O18A) is shown in Table 1, and n in this structure is an integer of 1 to 100, preferably 1 to 50, e.g. 3 to 50, e.g. 5 to 40, e.g. 7 to 25, e.g. 10 to 20.

In certain embodiments, a bioconjugate of an *E. coli* O25B antigen polysaccharide is present in a composition described herein is at a concentration that is about 1.5-6 times, e.g. about 2 to 4 times, higher than a concentration of any other bioconjugate in the composition.

In certain embodiments, a composition described herein comprises bioconjugates of *E. coli* O1A, O2, glucosylated O4, O6A, O8, O15, O16, O25B, and O75 antigen polysaccharides, wherein the bioconjugates of O1A:O2:glucosylated O4:O6A:O8:O15:O16:O25B:O75 are present in a ratio by weight of polysaccharide of 1:1:1:1:1:1:1:2:1, or 2:1:1:2:1:1:1:4:1.

In certain embodiments, a composition described herein comprises bioconjugates of *E. coli* O1A, O2, glucosylated O4, O6A, O8, O15, O16, O18A, O25B, and O75 antigen polysaccharides, wherein the bioconjugates of O1A:O2: glucosylated O4:O6A:O8:O15:O16:O18A:O25B:O75 are present in a ratio by weight of polysaccharide of 1:1:1:1:1: 1:1:1:2:1, or 2:1:1:2:1:1:1:1:4:1.

In certain embodiments, a concentration of a bioconjugate of an *E. coli* O25B antigen polysaccharide in a composition described herein is 2 to 50 μg/mL, preferably 8 to 40 μg/mL, e.g. 16-32 μg/mL.

In another aspect, provided herein is a method of inducing antibodies against an *E. coli* glucosylated O4 antigen in a subject, comprising administering to the subject a bioconjugate of an *E. coli* glucosylated O4 antigen as described herein, or a composition or immunogenic composition as described herein.

In a particular embodiment, the antibodies have opsonophagocytic activity.

In another aspect, provided herein is a method of vaccinating a subject against extra-intestinal pathogenic *E. coli* (ExPEC), comprising administering to the subject a bioconjugate of an *E. coli* glucosylated O4 antigen polysaccharide as described herein, or a composition or immunogenic composition as described herein. In certain aspects, provided herein is a bioconjugate of an *E. coli* glucosylated O4 antigen polysaccharide as described herein, or a composition or immunogenic composition as described herein, for use in inducing antibodies against an *E. coli* glucosylated O4 antigen. In certain aspects, provided herein is a bioconjugate of an *E. coli* glucosylated O4 antigen polysaccharide as described herein, or a composition or immunogenic composition as described herein, for use in vaccination against extra-intestinal pathogenic *E. coli* (ExPEC). In certain aspects, provided herein is the use of a bioconjugate of an *E. coli* glucosylated O4 antigen polysaccharide as described herein, or a composition or immunogenic composition as described herein, for the manufacture of a medicament for inducing antibodies against an *E. coli* glucosylated O4 antigen in a subject. In certain aspects, provided herein is the use of a bioconjugate of an *E. coli* glucosylated O4 antigen polysaccharide as described herein, or a composition or immunogenic composition as described herein, for the manufacture of a medicament for vaccinating a subject against extra-intestinal pathogenic *E. coli* (ExPEC).

In another aspect, provided herein is a recombinant host cell for producing a bioconjugate of an *E. coli* glucosylated O4 antigen polysaccharide covalently linked to a carrier protein, wherein the glucosylated O4 antigen polysaccharide comprises the structure of Formula (O4-Glc+) as shown in Table 1, wherein n is integer of 1 to 100, preferably 1 to 50, e.g. 3 to 50, e.g. 5 to 40, e.g. 7 to 25, e.g. 10 to 20, the host cell comprising:
(i) a nucleotide sequence of an rfb gene cluster for the *E. coli* O4 antigen polysaccharide;
(ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide;
(iii) nucleotide sequences encoding a translocase and a glycosyltransferase having at least 80% sequence identity to SEQ ID NOs: 7 and 8 respectively, wherein the translocase is capable of translocating bactoprenol-linked glucose and the glycosyltransferase is capable of glucosylating bactoprenol;
(iv) a nucleotide sequence encoding the carrier protein; and
(iv) a nucleotide sequence encoding an oligosaccharyl transferase capable of covalently linking the *E. coli* glucosylated O4 antigen polysaccharide to the carrier protein to produce the bioconjugate.

In a particular embodiment, a recombinant host cell comprises a nucleotide sequence encoding a glucosyl transferase that is capable of modifying the *E. coli* O4 antigen polysaccharide to produce the *E. coli* glucosylated O4 antigen polysaccharide and having an amino acid sequence that has at least 90%, preferably at least 95%, preferably at least 98% sequence identity to SEQ ID NO: 4. In certain embodiments, the glucosyl transferase comprises SEQ ID NO: 4.

In certain embodiments, the recombinant host cell comprises a nucleotide sequence encoding a translocase that is capable of translocating bactoprenol-linked glucose and having at least 90%, preferably at least 95%, preferably at least 98% sequence identity to SEQ ID NO: 7. In certain embodiments, the translocase comprises SEQ ID NO: 7.

In certain embodiments, the recombinant host cell comprises a nucleotide sequence encoding a glycosyltransferase that is capable of glucosylating bactoprenol and having at least 90%, preferably at least 95%, preferably at least 98% sequence identity to SEQ ID NO: 8. In certain embodiments, the glycosyltransferase comprises SEQ ID NO: 8. In certain embodiments, the recombinant host cell comprises a nucleotide sequence that encodes an oligosaccharyl transferase comprising the amino acid sequence of SEQ ID NO: 6. In preferred embodiments, the oligosaccharyl transferase comprises the amino acid sequence of SEQ ID NO: 6 having mutation N311V, more preferably SEQ ID NO: 6 having both mutations Y77H and N311V.

In certain embodiments, the recombinant host cell comprises a nucleotide sequence encoding a carrier protein comprising at least one glycosylation site comprising a glycosylation consensus sequence having SEQ ID NO: 1, preferably having SEQ ID NO: 2.

In certain embodiments, the rfb gene cluster for the E. coli O4 antigen polysaccharide comprises a sequence that encodes the enzymes that create the E. coli O4 antigen polysaccharide (Formula (O4-Glc−) in Table 1) and is at least 80%, e.g. at least 90%, e.g. at least 95%, e.g. at least 98% identical to SEQ ID NO: 9. In certain embodiments the rfb gene cluster comprises SEQ ID NO: 9.

In certain embodiments, the recombinant host cell comprises a nucleotide sequence encoding a carrier protein, wherein the carrier protein is selected from the group consisting of detoxified Exotoxin A of P. aeruginosa (EPA), E. coli flagellin (FliC), CRM197, maltose binding protein (MBP), Diphtheria toxoid, Tetanus toxoid, detoxified hemolysin A of S. aureus, clumping factor A, clumping factor B, E. coli heat labile enterotoxin, detoxified variants of E. coli heat labile enterotoxin, Cholera toxin B subunit (CTB), cholera toxin, detoxified variants of cholera toxin, E. coli Sat protein, the passenger domain of E. coli Sat protein, Streptococcus pneumoniae Pneumolysin, Keyhole limpet hemocyanin (KLH), P. aeruginosa PcrV, outer membrane protein of Neisseria meningitidis (OMPC), and protein D from non-typeable Haemophilus influenzae.

In a particular embodiment, a recombinant host cell encodes a detoxified exotoxin A of Pseudomonas aeruginosa (EPA) carrier protein, preferably EPA comprising 1-10, preferably 2-4, preferably 4 glycosylation sites each comprising a glycosylation consensus sequence having SEQ ID NO: 2. In a preferred embodiment, EPA comprises the amino acid sequence of SEQ ID NO: 3.

Preferably, a recombinant host cell is E. coli, e.g. an E. coli K-12 strain, such as strain W3110.

In another aspect, provided is a method of producing a bioconjugate of an E. coli glucosylated O4 antigen polysaccharide covalently linked to a carrier protein, wherein the E. coli glucosylated O4 antigen polysaccharide comprises the structure of Formula (O4-Glc+) as shown in Table 1, wherein n is an integer of 1 to 100, preferably 1 to 50, e.g. 3 to 50, e.g. 5 to 40, e.g. 7 to 25, e.g. 10 to 20, the method comprising culturing the recombinant host cell of the invention under conditions for production of the bioconjugate. In some embodiments, the method further comprises isolating the bioconjugate from the recombinant host cell.

In another aspect, provided is a bioconjugate produced by a method as described herein. In another aspect, provided is a composition comprising a bioconjugate produced by a method as described herein.

In another aspect, provided is a method for making a recombinant host cell for producing a bioconjugate of an E. coli glucosylated O4 antigen polysaccharide covalently linked to a carrier protein, wherein the glucosylated O4 antigen polysaccharide comprises the structure of Formula (O4-Glc+) as shown in Table 1, wherein n is an integer of 1 to 100, preferably 1 to 50, e.g. 3 to 50, e.g. 5 to 40, e.g. 7 to 25, e.g. 10 to 20, the method comprising introducing one or more recombinant nucleic acid molecules into a cell to produce the recombinant host cell, wherein the recombinant host cell comprises:

(i) a nucleotide sequence of an rfb gene cluster for the E. coli O4 antigen polysaccharide;

(ii) a nucleotide sequence encoding a glucosyl transferase having at least 80% sequence identity to SEQ ID NO: 4, wherein the glucosyl transferase is capable of modifying the E. coli O4 antigen polysaccharide to produce the E. coli glucosylated O4 antigen polysaccharide;

(iii) nucleotide sequences encoding a translocase and a glycosyltransferase having at least 80% sequence identity to SEQ ID NOs: 7 and 8 respectively, wherein the translocase is capable of translocating bactoprenol-linked glucose and the glycosyltransferase is capable of glucosylating bactoprenol;

(iv) a nucleotide sequence encoding the carrier protein; and (v) a nucleotide sequence encoding an oligosaccharyl transferase capable of covalently linking the E. coli glucosylated O4 antigen polysaccharide to the carrier protein to produce the bioconjugate.

In a particular embodiment thereof, the glucosyl transferase that is capable of modifying the E. coli O4 antigen polysaccharide to produce the E. coli glucosylated O4 antigen polysaccharide has an amino acid sequence that has at least 90%, preferably at least 95%, preferably at least 98% sequence identity to SEQ ID NO: 4. In certain embodiments, the glucosyl transferase comprises SEQ ID NO: 4.

In certain embodiments, the oligosaccharyl transferase comprises the amino acid sequence of SEQ ID NO: 6, preferably of SEQ ID NO: 6 comprising the amino acid mutation N311V. In certain embodiments, the oligosaccharyl transferase comprises SEQ ID NO: 6 having the amino acid mutations Y77H and N311V.

In certain embodiments, the rfb gene cluster for the E. coli O4 antigen polysaccharide comprises a sequence that encodes the enzymes that create the E. coli O4 antigen polysaccharide (Formula (O4-Glc−) in Table 1) and is at least 80%, e.g. at least 90%, e.g. at least 95%, e.g. at least 98% identical to SEQ ID NO: 9. In certain embodiments the rfb gene cluster comprises SEQ ID NO: 9.

In certain embodiments, the translocase is capable of translocating bactoprenol-linked glucose and has at least 90%, preferably at least 95%, preferably at least 98% sequence identity to SEQ ID NO: 7. In certain embodiments, the translocase comprises SEQ ID NO: 7.

In certain embodiments, the glycosyltransferase is capable of glucosylating bactoprenol and has at least 90%, preferably at least 95%, preferably at least 98% sequence identity to SEQ ID NO: 8. In certain embodiments, the glycosyltransferase comprises SEQ ID NO: 8.

In certain embodiments, the carrier protein comprises at least one glycosylation site comprising a glycosylation consensus sequence having SEQ ID NO: 1, preferably having SEQ ID NO: 2. In certain embodiments, the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In a particular embodiment, the carrier protein is a detoxified exotoxin A of *Pseudomonas aeruginosa* (EPA), preferably wherein the EPA comprises 1-10, preferably 2-4, preferably 4, glycosylation sites each comprising a glycosylation consensus sequence having SEQ ID NO: 2. In particular embodiments, the carrier protein is EPA with four glycosylation consensus sequences (EPA-4), preferably wherein the carrier protein comprises SEQ ID NO: 3.

In some embodiments, the recombinant host cell is an *E. coli* cell, e.g. from an *E. coli* K12 strain, such as from a W3110 strain.

In another aspect, provided is a method of preparing a bioconjugate of an $O_x$ antigen polysaccharide covalently linked to a carrier protein, the method comprising:
(i) providing a recombinant host cell comprising:
  a. a nucleotide sequence of an rfb gene cluster for the $O_x$-antigen polysaccharide;
  b. a nucleotide sequence encoding the carrier protein comprising at least one glycosylation site comprising a glycosylation consensus sequence having SEQ ID NO: 1, preferably having SEQ ID NO: 2; and
  c. a nucleotide sequence encoding an oligosaccharyl transferase $PglB_y$; and
(ii) culturing the recombinant host cell under conditions for production of the bioconjugate,
wherein:
when the $O_x$-antigen is O1A antigen polysaccharide, the $PglB_y$ comprises the amino acid mutations of N311V, K482R, D483H, and A669V;
when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a GtrS having at least 80% identity to SEQ ID NO: 4, and nucleotide sequences encoding a GtrA and a GtrB having at least 80% sequence identity to SEQ ID NOs: 7 and 8 respectively;
when the $O_x$-antigen is O6A antigen polysaccharide, the $PglB_y$ comprises the amino acid mutations of N311V, K482R, D483H, and A669V;
when the $O_x$-antigen is O8 antigen polysaccharide, the $PglB_y$ comprises no amino acid mutations at positions 77, 80, 287, 289, 311, 482, 483 and 669;
when the $O_x$-antigen is O15 antigen polysaccharide, the $PglB_y$ comprises the amino acid mutation of N311V, K482R, D483H, and A669V;
when the $O_x$-antigen is O16 antigen polysaccharide, the $PglB_y$ comprises the amino acid mutations of Y77H, S80R, Q287P, K289R, and N311V;
when the $O_x$-antigen is O18A antigen polysaccharide, the $PglB_y$ comprises no amino acid mutations at positions 77, 80, 287, 289, 311, 482, 483 and 669; and
when the $O_x$-antigen is O75 antigen polysaccharide, the $PglB_y$ comprises the amino acid mutation of N311V,
wherein in each case the amino acid mutations are relative to the wild-type $PglB_y$ having the amino acid sequence of SEQ ID NO: 6.

In certain embodiments, the carrier protein is detoxified exotoxin A of *Pseudomonas aeruginosa* (EPA). Preferably, the EPA carrier protein comprises 1-10, preferably 2-4, preferably 4, glycosylation sites each comprising a glycosylation consensus sequences having SEQ ID NO: 2. In a particular embodiment, the EPA carrier protein comprises SEQ ID NO: 3.

In another aspect, provided is a bioconjugate produced by a method of preparing a bioconjugate of an $O_x$ antigen polysaccharide covalently linked to a carrier protein as described herein. In another aspect, provided is a composition comprising such a bioconjugate. In such embodiments, a composition comprises at least 2, preferably at least 3, more preferably at least 5, still more preferably at least 7 of such bioconjugates.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

In the drawings:

FIG. 4A shows serum antibody levels measured by ELISA at day 0, 14 and 42 post-immunization; individual titers (log 10 EC50 titer) and GMT±95% CI are shown; the grey dotted line indicates the threshold above which the dilution curves of the samples have a 4PL fitting; FIG. 4B shows the results of the opsonophagocytic (OPK) assay to determine the functionality of the antibodies in serum samples obtained at day 42 post-immunization with glucosylated O4 (O4-Glc+)-EPA bioconjugate (4.0 µg); Wilcoxon rank sum test and Bonferroni correction; *P≤0.05, ***P≤0.0001;

FIG. 10 shows the overall study design for a phase 1/2a clinical trial with ExPEC10V vaccine in humans.

DETAILED DESCRIPTION OF THE INVENTION

Figure 1:
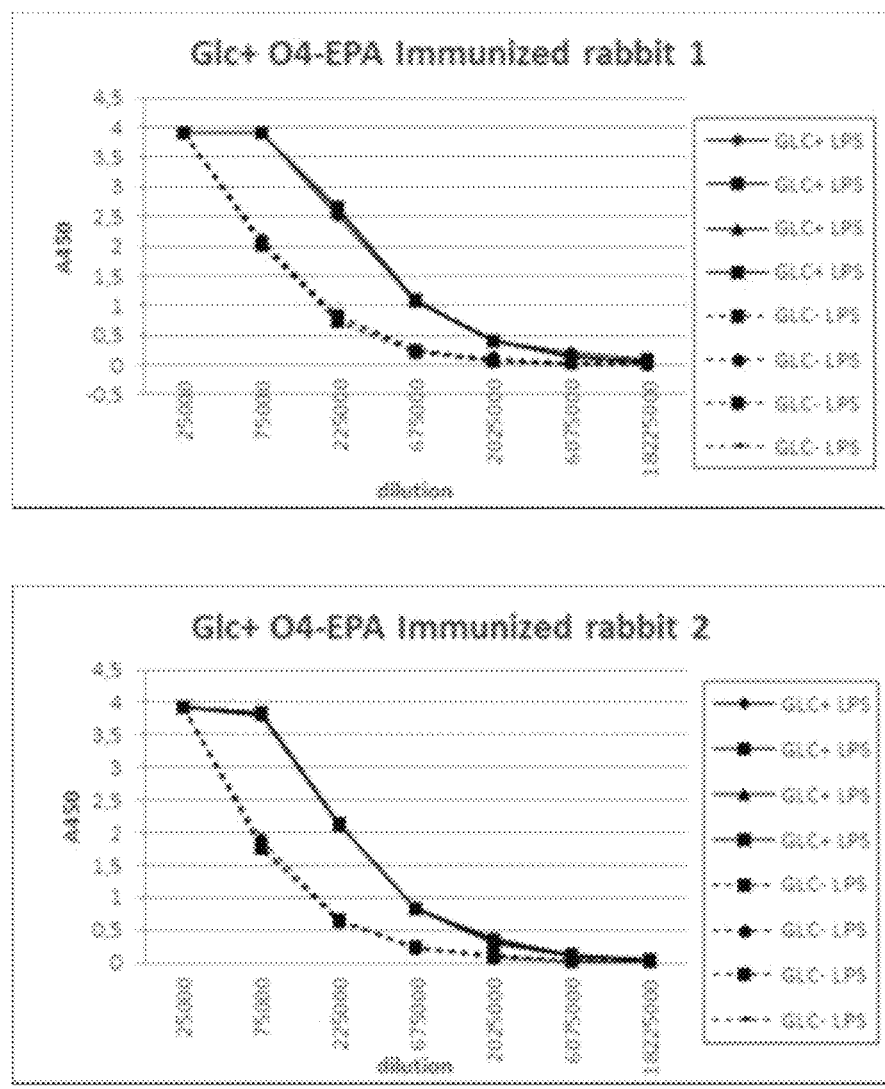
FIG. 1 shows ELISA IgG titers against unmodified (GLC−) or glucose-modified (GLC+) O4 LPS in sera from two rabbits immunized with Glc-modified O4 polysaccharide bioconjugate as described in Example 4; ELISA titers were determined in quadruplicate.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series.

Those skilled in the art will recognize or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The identification of an O-antigen structural modification, namely glucose branching, within the *E. coli* O4 serotype (Jann et al., 1993) presents a challenge to the discovery and development of a glycoconjugate vaccine targeting bacterial isolates within this serotype. The proportion of clinical contemporary O4 isolates expressing the unmodified (not having a glucose side-branch) and modified (having a glucose side-branch) forms of the O4 O-antigen is unknown. Obtaining information on this characteristic is critical for selecting the relevant antigenic structure. In addition, the extent to which vaccine induced antibodies elicited to one form of the O4 polysaccharide will cross-react with the other form has not been determined. Purification of O-antigen free from lipid A and subsequent chemical conjugation to a carrier protein is a lengthy and laborious process. Additionally, the purification, lipid A detoxification and chemical conjugation processes can result in loss of epitopes, antigen heterogeneity and reduced immunogenicity of the conjugated polysaccharide. Synthesis of glycoconjugates by bioconjugation can overcome these limitations of classical purification and chemical conjugation, but the in vivo synthesis of glucose-branched O4 O-antigen requires the activity of a polysaccharide branching enzyme, which lies outside of the rfb gene cluster. To date, the O-antigen modifying enzyme responsible for glucose-branching in O4 *E. coli* strains has not been identified. Cloning the O4 rfb gene cluster into the bioconjugation *E. coli* strain expressing PglB will not be sufficient to synthesize the glucose-branched O4 glycoconjugate, but rather would only produce non-glucose-branched O4 bioconjugates (the structure of the glycan thereof is shown in Formula (O4) in Table 1). As used herein, the terms "glucosylated O4", "glucose-branched O4", "O4 Glc+" and "Glc+O4" O-antigen refer to O4 O-antigen with a glucose side-branch, and the structure thereof is shown in formula (O4-Glc+) in Table 1.

Disclosed herein is the gene encoding the O-antigen modifying enzyme responsible for glucose branching of the *E. coli* O4 antigen polysaccharide. Also disclosed herein are host cells, e.g., recombinantly engineered host cells comprising nucleic acid encoding enzymes capable of producing bioconjugates comprising the glucosylated O4 antigen polysaccharide covalently bound to a carrier protein in vivo. Such host cells can be used to generate bioconjugates comprising the glucosylated O4 antigen linked to a carrier protein, which can be used in, e.g., the formulation of therapeutic and/or prophylactic compositions (e.g., vaccines). Further provided herein are compositions comprising bioconjugates of the glucosylated O4 antigen polysaccharide, alone or in combination with other *E. coli* antigens (e.g., O1, O2, O6, O8, O15, O16, O18, O25, and/or O75 antigen polysaccharides and subserotypes thereof). The compositions can be used in prophylactic and/or therapeutic methods, e.g., vaccination of hosts against infection with *E. coli*, and are useful in the generation of antibodies, which can be used, e.g., in therapeutic methods such as for immunization of subjects.

As used here, the terms "O-antigen," "O-antigen polysaccharide," "O-antigen saccharide," and "OPS" refer to the O-antigen of Gram-negative bacteria. Typically, an O-antigen is a polymer of immunogenic repeating polysaccharide units. In a particular embodiment, the terms "O-antigen," "O-antigen polysaccharide," and "OPS" refer to the O-antigen of *Escherichia coli*. Different serotypes of *E. coli* express different O-antigens. In *E. coli*, the gene products involved in O-antigen biogenesis are encoded by the rfb gene cluster.

As used herein, "rfb cluster" and "rfb gene cluster" refer to a gene cluster that encodes enzymatic machinery capable of synthesizing an O-antigen backbone structure. The term rfb cluster can apply to any O-antigen biosynthetic cluster, and preferably refers to a gene cluster from the genus *Escherichia*, particularly *E. coli*.

As used herein, the term "O1A" refers to the O1A antigen of *E. coli* (a subserotype of *E. coli* serotype O1). The term "O2" refers to the O2 antigen of *E. coli* (*E. coli* serotype O2). The term "O6A" refers to the O6A antigen of *E. coli* (a subserotype of *E. coli* serotype O6). The term "O8" refers to the O8 antigen of *E. coli* (*E. coli* serotype O8). The term "O15" refers to the O15 antigen of *E. coli* (*E. coli* serotype O15). The term "O16" refers to the O16 antigen of *E. coli* (*E. coli* serotype O16). The term "O18A" refers to the O18A antigen of *E. coli* (a subserotype of *E. coli* serotype O18). The term "O25B" refers to the O25B antigen from *E. coli* (a subserotype of *E. coli* serotype O25). The term "O75" refers to the O75 antigen of *E. coli* (*E. coli* serotype O75).

The structures of *E. coli* O-antigen polysaccharides referred to throughout this application are shown below in Table 1. A single repeating unit for each *E. coli* O-antigen polysaccharide is shown.

TABLE 1

Structures of *E. coli* O-antigen Polysaccharides

| *E. coli* O-antigen Polysaccharide | Structure of Repeating Unit[1] |
|---|---|
| Non-glucosylated O4 antigen polysaccharide (O4-Glc−) | [→2)-α-L-Rhap-(1→6)-α-D-Glcp-(1→3)-α-L-FucpNAc-(1→3)-β-D-GlcpNAc-(1→]$_n$ |
| Glucosylated O4 antigen polysaccharide (O4-Glc+) | α-D-Glcp<br>1<br>↓<br>3<br>[→2)-α-L-Rhap-(1→6)-α-D-Glcp-(1→3)-α-L-FucpNAc-(1→3)-β-D-GlcpNAc-(1→]$_n$ |
| O1A antigen polysaccharide (O1A) | [→3)-α-L-Rhap-(1→3)-α-L-Rhap-(1→3)-β-L-Rhap-(1→4)-β-D-GlcpNAc-(1→]$_n$<br>2<br>↑<br>1<br>β-D-ManpNAc |
| O2 antigen polysaccharide (O2) | [→3)-α-L-Rhap-(1→2)-α-L-Rhap-(1→3)-β-L-Rhap-(1→4)-β-D-GlcpNAc-(1→]$_n$<br>2<br>↑<br>1<br>α-D-Fucp3NAc |
| O6A antigen polysaccharide (O6) | [→4)-α-D-GalpNAc-(1→3)-β-D-Manp-(1→4)-β-D-Manp-(1→3)-α-D-GlcpNAc-(1→]$_n$<br>2<br>↑<br>1<br>β-D-Glcp |

TABLE 1-continued

Structures of *E. coli* O-antigen Polysaccharides

| *E. coli* O-antigen Polysaccharide | Structure of Repeating Unit[1] |
|---|---|
| O8 antigen polysaccharide (O8) | α-D-Manp3Me-(1→[3)-β-D-Manp-(1→2)-α-D-Manp-(1→2)-α-D-Manp-(1→]$_n$ |
| O15 antigen polysaccharide (O15) | [→2)-β-D-Galp-(1→3)-α-L-FucpNAc-(1→3)-β-D-GlcpNAc-(1→]$_n$ |
| O16 antigen polysaccharide (O16) | [→2)-β-D-Galf-(1→6)-α-D-Glcp-(1→3)-α-L-Rhap-(1→3)-α-D-GlcpNAc-(1→]$_n$<br>　　　　　　　　　　　　　　　2<br>　　　　　　　　　　　　　　　↑<br>　　　　　　　　　　　　　　　Ac |
| O18A antigen polysaccharide (O18A) | [→2)-α-L-Rhap-(1→6)-α-D-Glcp-(1→4)-α-D-Galp-(1→3)-α-D-GlcpNAc-(1→]$_n$<br>　　　　　　　　　　　　　　　　　　　　3<br>　　　　　　　　　　　　　　　　　　　　↑<br>　　　　　　　　　　　　　　　　　　　　1<br>　　　　　　　　　　　　　　　　　　β-D-GlcpNAc |
| O25B antigen polysaccharide (O25B) | β-D-Glcp<br>　1<br>　↓<br>　6<br>[→4)-α-D-Glcp-(1→3)-α-L-Rhap-(1→3)-β-D-GlcpNAc-(1→]$_n$<br>　　3　　　　　　　　2<br>　　↑　　　　　　　　↑<br>　　1　　　　　　　　Ac<br>α-L-Rhap |
| O75 antigen polysaccharide (O75) | β-D-Manp<br>　1<br>　↓<br>　4<br>[→3)-α-D-Galp-(1→4)-α-L-Rhap-(1→3)-β-D-GlcpNAc-(1→]$_n$ |

[1] Each n is independently an integer of 1 to 100, such as 1-50, 1-40, 1-30, 1-20, and 1-10, 3-50, 3-40, e.g. at least 5, such as 5-40, e.g. 7-30, e.g. 7 to 25, e.g. 10 to 20, but in some instances can be 1-2.

All monosaccharides described herein have their common meaning known in the art. Monosaccharides can have the D or L configuration. If D or L is not specified, the sugar is understood to have the D configuration. Monosaccharides are typically referred to by abbreviations commonly known and used in the art. For example, Glc refers to glucose; D-Glc refers to D-glucose; and L-Glc refers to L-glucose. Other common abbreviations for monosaccharides include: Rha, rhamnose; GlcNAc, N-acetylglucosamine; GalNAc, N-acetylgalactosamine; Fuc, fucose; Man, mannose; Man3Me, 3-O-methyl-mannose; Gal, galactose; FucNAc, N-acetylfucosamine; and Rib, ribose. The suffix "f" refers to furanose and the suffix "p" refers to pyranose.

The terms "RU," "repeat unit," and "repeating unit" as used with respect to an O-antigen refer to the biological repeat unit (BRU) of an O-antigen as it is synthesized in vivo by cellular machinery (e.g., glycosyltransferases). The number of RUs of an O-antigen may vary per serotype, and in embodiments of the invention typically varies from about 1-100 RUs, preferably about 1 to 50 RUs, such as 1-50 RUs, 1-40 RUs, 1-30 RUs, 1-20 RUs, and 1-10 RUs, and more preferably at least 3 RUs, at least 4 RUs, at least 5 RUs, such as 3-50 RUs, preferably 5-40 RUs, e.g. 7-25 RUs, e.g. 10-20 RUs. However, in some instances, the number of RUs of an O-antigen can be 1-2. The structure of each O-antigen that is specifically described herein is shown containing one RU with the variable "n" designating the number of RUs. In each O-antigen polysaccharide in a bioconjugate of the invention, n is independently an integer of 1-100, such as 1-50, 1-40, 1-30, 1-20, 1-10, preferably at least 3, more preferably at least 5, such as 3-50, preferably 5-40 (e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40), but in some instances can be 1-2. In some embodiments n is indepently an integer of about 7-25, e.g. about 10-20. The values may vary between individual O-antigen polysaccharides in a composition, and are provided here as average values, i.e. if a bioconjugate is described herein as having an n that is independently an integer of 5-40, the composition contains a majority of O-antigen polysaccharides with 5-40 repeat units, but may also contain some O-antigen polysaccharides that have less than 5 repeat units or more than 40 repeat units.

The term "glycoconjugate" refers to a sugar or saccharide antigen (e.g., oligo- and polysaccharide)-protein conjugate linked to another chemical species, including but not limited to proteins, peptides, lipids, etc. Glycoconjugates can be prepared chemically, e.g., by chemical (synthetic) linkage of the protein and sugar or saccharide antigen. The term glycoconjugate also includes bioconjugates.

The term "bioconjugate" refers to a conjugate between a protein (e.g., a carrier protein) and a sugar or saccharide antigen (e.g., oligo- and polysaccharide) prepared in a host cell background, preferably a bacterial host cell, e.g. an *E. coli* host cell, wherein host cell machinery links the antigen to the protein (e.g., N-links). Preferably, the term "bioconjugate" refers to a conjugate between a protein (e.g., carrier protein) and an O-antigen, preferably an *E. coli* O-antigen (e.g., O1A, O2, glucosylated O4, O6A, O8, O15, O16, O18A, O25B, O75, etc.) prepared in a host cell background, wherein host cell machinery links the antigen to the protein (e.g., N-links). Because bioconjugates are prepared in host cells by host cell machinery, the antigen and protein are covalently linked via a glycosidic linkage or bond in a bioconjugate. Bioconjugates can be prepared in recombinant host cells engineered to express the cellular machinery needed to synthesize the O-antigen and/or link the O-antigen to the target protein. Bioconjugates, as described herein, have advantageous properties over chemically prepared glycoconjugates where the glycans are purified from bacterial cell walls and subsequently chemically coupled to a carrier protein, e.g., bioconjugates require fewer chemicals in manufacture and are more consistent in terms of the final product generated, and contain less or no free (i.e. unbound to carrier protein) glycan. Thus, in typical embodiments, bioconjugates are preferred over chemically produced glycoconjugates.

The term "about," when used in conjunction with a number, refers to any number within ±1, ±5 or ±10% of the referenced number.

The term "percent (%) sequence identity" or "% identity" describes the number of matches ("hits") of identical amino acids of two or more aligned amino acid sequences as compared to the number of amino acid residues making up the overall length of the amino acid sequences. In other terms, using an alignment, for two or more sequences the percentage of amino acid residues that are the same (e.g. 90%, 95%, 97% or 98% identity) may be determined, when the sequences are compared and aligned for maximum correspondence as measured using a sequence comparison algorithm as known in the art, or when manually aligned and visually inspected. The sequences which are compared to determine sequence identity may thus differ by substitution(s), addition(s) or deletion(s) of amino acids. Suitable programs for aligning protein sequences are known to the skilled person. The percentage sequence identity of protein sequences can, for example, be determined with programs such as CLUSTALW, Clustal Omega, FASTA or BLAST, e.g using the NCBI BLAST algorithm (Altschul S F, et al (1997), Nucleic Acids Res. 25:3389-3402).

For example, for amino acid sequences, sequence identity and/or similarity can be determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J. Mol. Biol. 48:443, the search for similarity method of Pearson and Lipman, 1988, Proc. Nat. Acad. Sci. U.S.A. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al, 1984, Nucl. Acid Res. 12:387-395, preferably using the default settings, or by inspection. In certain embodiments, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

Another example of a useful algorithm is the BLAST algorithm, described in: Altschul et al, 1990, J. Mol. Biol. 215:403-410; Altschul et al, 1997, Nucleic Acids Res. 25:3389-3402; and Karin et al, 1993, Proc. Natl. Acad. Sci. U.S.A. 90:5873-5787. A particularly useful BLAST program is the WU-BLAST-2 program which was obtained from Altschul et al, 1996, Methods in Enzymology 266:460-480. WU-BLAST-2 uses several search parameters, most of which are set to the default values.

An additional useful algorithm is gapped BLAST as reported by Altschul et al, 1993, Nucl. Acids Res. 25:3389-3402.

The term "Invasive Extraintestinal pathogenic *Escherichia coli* (ExPEC) disease (IED)" is defined herein as an acute illness consistent with systemic bacterial infection, which is microbiologically confirmed either by the isolation and identification of *E. coli* from blood or other normally sterile body sites, or by the isolation and identification of *E. coli* from urine in a patient with presence of signs and symptoms of invasive disease (systemic inflammatory response syndrome (SIRS), sepsis or septic shock) and no other identifiable source of infection.

Bioconiugates of *E. coli* Glucosylated O4 Antigen Polysaccharides

In one aspect, provided herein is a bioconjugate of an *E. coli* glucosylated O4 antigen polysaccharide covalently linked to a carrier protein. As used herein, the term "O4" refers to the O4 antigen from *E. coli* (*E. coli* serotype O4). O-antigen structural modification is known to exist within the *E. coli* O4 serotype. In particular, some O4 serotypes express a modified O-antigen having a branched glucose unit. As used herein, "glucosylated O4 antigen," "glucosylated O4 antigen polysaccharide, "O4-Glc+ antigen polysaccharide," and "O4-Glc+ antigen" refer to an O4 antigen (e.g., *E. coli* O4 antigen) having a glucose branch, in which D-glucose is linked to L-rhamnose in the repeating unit L-Rha→D-Glc→L-FucNAc→D-GlcNAc. In a particular embodiment, an *E. coli* glucosylated O4 antigen polysaccharide comprises the structure of formula (O4-Glc+), as shown in Table 1, wherein n is an integer of 1 to 100. In preferred embodiments, n is an integer of 3 to 50, e.g. 5 to 40, e.g. 7 to 25, e.g. 10 to 20.

*E. coli* O4 strains, independent of glucose branching status, carry a substantially identical rfb gene cluster encoding the genes responsible for production of the O4 antigen polysaccharide. However, in vivo synthesis of the modified O4 antigen having glucose branching requires the activity of a polysaccharide branching enzyme, which lies outside of the rfb gene cluster. To the best of the knowledge of the inventors, the identity of the polysaccharide branching enzyme responsible for glucose modification of the O4 antigen has remained unknown to date. Here, the inventors discovered the sequence of the polysaccharide branching enzyme responsible for glucose modification of the O4 antigen. Identification of this enzyme enables production of bioconjugates of the modified O4 antigen polysaccharide having glucose branching. The glucose modified form of the O4 antigen polysaccharide is present in predominant serotypes and can thus be used to provide an improved immune response, e.g for prophylactic or therapeutic use.

In particular, provided herein is the sequence of a gtrS gene encoding a glucosyltransferase enzyme specific for *E. coli* serotype O4 that glucosylates the O4 antigen. In general, the gtrA, gtrB, and gtrS genes encodes the enzymes responsible for O-antigen glucosylation. While the gtrA and gtrB genes in different serotypes are highly homologous and interchangeable, the gtrS gene encodes a serotype specific O-antigen glucosyl transferase. The gtrS gene of *E. coli* serotype O4 encodes the GtrS enzyme that modifies the O4 antigen by introducing glucose branching. Characterization of contemporary clinical *E. coli* isolates of the O4 serotype revealed the presence of gtrS in 78% of tested isolates, indicating that *E. coli* O4 antigen polysaccharide modified with the addition of a glucose residue is predominant in current infecting isolates.

In one embodiment, provided herein is a nucleic acid of a gtrS gene from *E. coli* serotype O4 encoding a GtrS glucosyltransferase comprising the amino acid sequence of SEQ ID NO: 4. In another embodiment, a gtrS nucleic acid encodes a GtrS protein from *E. coli* serotype O4 that is about 80%, 85%, 90%, 95%, 96%, 97%, 98%, 99%, or 100% identical to the amino acid sequence of SEQ ID NO: 4, preferably 98%, 99%, or 100% identical to the amino acid sequence of SEQ ID NO: 4. A GtrS protein that is at least 80% identical to the amino acid sequence of SEQ ID NO: 4 is capable of specifically glucosylating the *E. coli* O4 antigen polysaccharide to obtain a glucosylated O4 antigen having the structure of Formula (O4-Glc+) as shown in Table 1. One of ordinary skill in the art will be able to make mutated forms of the GtrS protein of SEQ ID NO: 4 having at least 80% sequence identity to SEQ ID NO: 4, and test such sequences for glucosylation activity of the *E. coli* O4 antigen in view of the present disclosure. Recombinant host cells comprising nucleic acid sequence encoding the glucosyl transferase gtrS gene of *E. coli* serotype O4, and use of the recombinant host cells in production of the glucose modified O4 antigen polysaccharides and bioconjugates thereof are described in greater detail below.

Sequences for gtrA and gtrB encoded proteins, which function as bactoprenol-linked glucose translocase (GtrA, flips the bactoprenol-linked glucose over the inner membrane to the periplasm) and bactoprenol glucosyl transferase (GtrB, links glucose to bactoprenol), respectively, may comprise amino acid sequences that are at least about 80% identical to SEQ ID NOs: 7 and 8, respectively. In certain embodiments, nucleic acid sequences encoding GtrA and GtrB proteins that are at least about 80%, 85%, 90%, 95%, 96%, 97%, 98%, 99%, or 100% identical to SEQ ID NOs: 7 and 8, respectively, and having bactoprenol-linked glucose translocase and bactoprenol glucosyl transferase activity, respectively, are also present in the host cells of the invention, that further comprise an O4-specific rib locus, the O4-specific GtrS encoding sequence described above, an oligosaccharyl transferase as described herein, and a sequence encoding a carrier protein having one or more glycosylation consensus sequences as described herein, to produce bioconjugates of *E. coli* glucosylated O4 serotype (comprising glycan structure of Formula (O4-Glc+) in Table 1).

Bioconjugates of an *E. coli* glucosylated O4 antigen polysaccharide provided herein are covalently linked to a carrier protein, preferably by a glycosidic linkage. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Bioconjugation with various different carrier proteins containing the required consensus glycosylation sequence has been described, showing that a wide range of proteins can be glycosylated using this technology (see, e.g. WO 06/119987, WO 2015/124769, WO 2015/158403, WO 2015/82571, WO 2017/216286, and WO 2017/67964, together showing a wide variety of carrier proteins that were successfully used in bioconjugation).

In certain embodiments a carrier protein is modified, e.g., modified in such a way that the protein is less toxic and/or more susceptible to glycosylation. In a specific embodiment, the carrier proteins used herein are modified such that the number of glycosylation sites in the carrier proteins is maximized in a manner that allows for lower concentrations of the protein to be administered, e.g., in an immunogenic composition, particularly in its bioconjugate form.

Thus, in certain embodiments, the carrier proteins described herein are modified to include 1, 2, 3, 4, 5, 6, 7, 8, 9, 10 or more glycosylation sites than would normally be associated with the carrier protein (e.g., relative to the number of glycosylation sites associated with the carrier protein in its native/natural, i.e., "wild-type" state). Introduction of glycosylation sites into a carrier protein can be accomplished by insertion of a glycosylation consensus sequence anywhere in the primary structure of the protein by, e.g., adding new amino acids to the primary structure of the protein such that a glycosylation site is added in full or in part, or by mutating existing amino acids in the protein in order to generate a glycosylation site. One of ordinary skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In some embodiments, a glycosylation consensus sequence can be extended by addition of lysine residues for more efficient glycosylation.

Exemplary examples of glycosylation consensus sequences that can be inserted into or generated in a carrier protein include Asn-X-Ser(Thr), wherein X can be any amino acid except Pro (SEQ ID NO: 1); and Asp(Glu)-X-Asn-Z-Ser(Thr), wherein X and Z are independently selected from any amino acid except Pro (SEQ ID NO: 2).

In some embodiments, the *E. coli* glucosylated O4 antigen polysaccharide is covalently linked to an asparagine (Asn) residue in the carrier protein (e.g., N-linked), wherein the Asn residue is present in a glycosylation site comprising a glycosylation consensus sequence having SEQ ID NO: 1, more preferably having SEQ ID NO: 2. Typically, a carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequences having the amino acid sequence of SEQ ID NO: 1, and more preferably the amino acid sequence of SEQ ID NO: 2.

In particular embodiments, a carrier protein is a detoxified Exotoxin A of *P. aeruginosa*. For EPA, various detoxified protein variants have been described in literature and could be used as carrier proteins. For example, detoxification can be achieved by mutating and deleting the catalytically essential residues L552V and ΔE553 according to Lukac et al., 1988, *Infect Immun,* 56: 3095-3098, and Ho et al., 2006, *Hum Vaccin,* 2:89-98. As used herein, "EPA" refers to a detoxified Exotoxin A of *P. aeruginosa*. In those embodiments, wherein the carrier protein is EPA, an *E. coli* glucosylated O4 antigen polysaccharide can be covalently linked to an Asn residue in a glycosylation site comprising a glycosylation consensus sequence having SEQ ID NO: 1, and preferably covalently linked to an Asn residue in a glycosylation site comprising a glycosylation consensus sequence having SEQ ID NO: 2. Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably the amino acid sequence of SEQ ID NO: 2.

In some embodiments, the EPA carrier protein comprises four glycosylation sites each comprising a glycosylation consensus sequence, for instance a glycosylation site comprising a glycosylation consensus sequence having SEQ ID NO: 2. As used herein, "EPA-4 carrier protein" and "EPA-4" refer to a detoxified Exotoxin A of *P. aeruginosa* carrier protein comprising four glycosylation sites each comprising a glycosylation consensus sequences having SEQ ID NO: 2. An exemplary preferred example of an EPA-4 carrier protein is EPA carrier protein comprising the amino acid sequence of SEQ ID NO: 3.

Compositions

In another aspect, provided herein is a composition comprising a bioconjugate of an *E. coli* glucosylated O4 antigen polysaccharide covalently linked to a carrier protein. The compositions provided herein can include any bioconjugate of an *E. coli* glucosylated O4 antigen polysaccharide covalently linked to a carrier protein (e.g., EPA) described herein.

In some embodiments, a composition is an immunogenic composition. As used herein, an "immunogenic composition" refers to a composition that can elicit an immune response in a host or subject to whom the composition is administered. Immunogenic compositions can further comprise a pharmaceutically acceptable carrier. In some embodiments, a composition is a pharmaceutical composition further comprising a pharmaceutically acceptable carrier. As used herein, a "pharmaceutically acceptable carrier" refers to a diluent, adjuvant, excipient or vehicle with which a composition is administered, and that is non-toxic and should not interfere with the efficacy of the active ingredient. For example, saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable pharmaceutically acceptable carriers are described in "Remington's Pharmaceutical Sciences" by E. W. Martin.

In one embodiment, a composition of the invention comprises the bioconjugates of the invention in a Tris-buffered saline (TBS) pH 7.4 (e.g. containing Tris, NaCl and KCl, e.g. at 25 mM, 137 mM and 2.7 mM, respectively). In other embodiments, the compositions of the invention comprise bioconjugates of the invention in about 10 mM $KH_2PO_4$/$Na_2HPO_4$ buffer at pH of about 7.0, about 5% (w/v) sorbitol, about 10 mM methionine, and about 0.02% (w/v) polysorbate 80. In other embodiments, the compositions of the invention comprise bioconjugates of the invention in about 10 mM $KH_2PO_4$/$Na_2HPO_4$ buffer at pH of about 7.0, about 8% (w/v) sucrose, about 1 mM EDTA, and about 0.02% (w/v) polysorbate 80 (see e.g. WO 2018/077853 for suitable buffers for bioconjugates of *E. coli* O-antigens covalently bound to EPA carrier protein).

In some embodiments, the compositions described herein are monovalent formulations, and contain one *E. coli* O-antigen polysaccharide, e.g., in isolated form or as part of a glycoconjugate or bioconjugate, such as the *E. coli* glucosylated O4 antigen polysaccharide. Also provided herein are compositions (e.g., pharmaceutical and/or immunogenic compositions) that are multivalent compositions, e.g., bivalent, trivalent, tetravalent, etc. compositions. For example, a multivalent composition comprises more than one antigen, such as an *E. coli* O-antigen, glycoconjugate, or bioconjugate thereof. In particular embodiments, multivalent compositions provided herein comprise a bioconjugate of an *E. coli* glucosylated O4 antigen polysaccharide, and at least one additional antigen.

In one embodiment, a composition (e.g., pharmaceutical and/or immunogenic composition) is a monovalent composition comprising a bioconjugate of an *E. coli* glucosylated O4 antigen polysaccharide covalently linked to a carrier protein as described herein.

In another embodiment, a composition (e.g., pharmaceutical and/or immunogenic composition) is a multivalent composition comprising an *E. coli* glucosylated O4 antigen polysaccharide covalently linked to a carrier protein as described herein, and at least one additional antigen.

In some embodiments, the additional antigen is antigen saccharide or polysaccharide, more preferably an *E. coli* O-antigen polysaccharide, such as *E. coli* O-antigens of one or more of the O1, O2, O6, O8, O15, O16, O18, O25, and O75 serotypes and subserotypes thereof. In some embodiments, each of the additional *E. coli* O-antigen polysaccharides is a glycoconjugate, meaning that the *E. coli* O-antigen polysaccharide is covalently linked to another chemical species, e.g., protein, peptide, lipid, etc., most preferably a carrier protein, such as by chemical or enzymatic methods. In preferred embodiments, each of the additional *E. coli* O-antigen polysaccharides is a bioconjugate in which the O-antigen polysaccharide is covalently linked to, e.g. a carrier protein, via a glycosidic bond enzymatically by host cell machinery. Compositions provided herein in certain embodiments can comprise 1-20 additional glycoconjugates, more preferably bioconjugates of *E. coli* O-antigen polysaccharides, such as 1, 2, 3, 4, 5, 6, 7, 8, 9, 10, 11, 12, 13, 14, 15, 16, 17, 18, 19 or 20 additional glycoconjugates or preferably bioconjugates of *E. coli* O-antigen polysaccharides. Other antigens can be included in the compositions provided herein, such as peptide, protein, or lipid antigens, etc.

In some embodiments, a composition (e.g., pharmaceutical and/or immunogenic composition) comprises a bioconjugate of an *E. coli* glucosylated O4 antigen polysaccharide, and at least one additional antigen polysaccharide selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide. Preferably, each of the additional O-antigen polysaccharides is covalently linked to a carrier protein, and is more preferably a bioconjugate.

In one embodiment, an O1A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O1A antigen polysaccharide comprises the structure of formula (O1A) as shown in Table 1, wherein n is an integer of 1-100, preferably 3-50, e.g. 5-40, e.g. 7 to 25, e.g. 10 to 20. Preferably, the O1A antigen polysaccharide is part of a bioconjugate and is covalently linked to a carrier protein, e.g., EPA.

In one embodiment, an O2 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O2 antigen polysaccharide comprises the structure of formula (O2) as shown in Table 1, wherein n is an integer of 1-100, preferably 3-50, e.g. 5-40, e.g. 7 to 25, e.g. 10 to 20. Preferably, the O2 antigen polysaccharide is part of a bioconjugate and is covalently linked to a carrier protein, e.g., EPA.

In one embodiment, an O6A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O6A antigen polysaccharide comprises the structure of formula (O6A) as shown in Table 1, wherein n is an integer of 1-100, preferably 3-50, e.g. 5-40, e.g. 7 to 25, e.g. 10 to 20. Preferably, the O6A antigen polysaccharide is part of a bioconjugate and is covalently linked to a carrier protein, e.g., EPA.

In one embodiment, an O8 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O8 antigen polysaccharide comprises the structure of formula (O8) as shown in Table 1, wherein n is an integer of 1-100, preferably 3-50, e.g. 5-40, e.g. 7 to 25, e.g. 10 to 20. Preferably, the O8 antigen polysaccharide is part of a bioconjugate and is covalently linked to a carrier protein, e.g., EPA.

In one embodiment, an O15 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O15 antigen polysaccharide comprises the structure of formula (O15) as shown in Table 1, wherein n is an integer of 1-100, preferably 3-50, e.g. 5-40, e.g. 7 to 25, e.g. 10 to 20. Preferably, the O15 antigen polysaccharide is part of a bioconjugate and is covalently linked to a carrier protein, e.g., EPA.

In one embodiment, an O16 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O16 antigen polysaccharide comprises the structure of formula (O16) as shown in Table 1, wherein n is an integer of 1-100, preferably 3-50, e.g. 5-40, e.g. 7 to 25, e.g. 10 to 20. Preferably, the O16 antigen polysaccharide is part of a bioconjugate and is covalently linked to a carrier protein, e.g., EPA.

In one embodiment, an O18A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O18A antigen polysaccharide comprises the structure of formula (O18A) as shown in Table 1, wherein n is an integer of 1-100, preferably 3-50, e.g. 5-40, e.g. 7 to 25, e.g. 10 to 20. Preferably, the O18A antigen polysaccharide is part of a bioconjugate and is covalently linked to a carrier protein, e.g., EPA.

In one embodiment, an O25B antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O25B antigen polysaccharide comprises the structure of formula (O25B) as shown in Table 1, wherein n is an integer of 1-100, preferably 3-50, e.g. 5-40, e.g. 7 to 25, e.g. 10 to 20. Preferably, the O25B antigen polysaccharide is part of a bioconjugate and is covalently linked to a carrier protein, e.g., EPA.

In one embodiment, an O75 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O75 antigen polysaccharide comprises the structure of formula (O75) as shown in Table 1, wherein n is an integer of 1-100, preferably 3-50, e.g. 5-40, e.g. 7 to 25, e.g. 10 to 20. Preferably, the O75 antigen polysaccharide is part of a bioconjugate and is covalently linked to a carrier protein, e.g., EPA.

In another embodiment, a composition (e.g., a pharmaceutical and/or immunogenic composition) comprises at least the *E. coli* O1A, O2, glucosylated O4, O6A and O25B antigen polysaccharides, preferably bioconjugates of the O1A, O2, glucosylated O4, O6A and O25B antigen polysaccharides covalently linked to a carrier protein, e.g., EPA (i.e., a pentavalent composition).

In a preferred embodiment, a composition (e.g., a pharmaceutical and/or immunogenic composition) comprises at least the *E. coli* O1A, O2, glucosylated O4, O6A, O8, O15, O16, O25B and O75 antigen polysaccharides, preferably bioconjugates of the O1A, O2, glucosylated O4, O6A, O8, O15, O16, O25B and O75 antigen polysaccharides covalently linked to a carrier protein, e.g., EPA (i.e., a 9-valent composition).

In another preferred embodiment, a composition (e.g., a pharmaceutical and/or immunogenic composition) comprises at least the *E. coli* O1A, O2, glucosylated O4, O6A, O8, O15, O16, O18A, O25B and O75 antigen polysaccharides, preferably bioconjugates of the O1A, O2, glucosylated O4, O6A, O8, O15, O16, O18A, O25B and O75 antigen polysaccharides covalently linked to a carrier protein, e.g., EPA (i.e., a 10-valent composition).

Also contemplated herein are compositions which optionally further comprise additional O-antigens (e.g., in isolated form, or as part of a glycoconjugate or bioconjugate) from other *E. coli* serotypes.

In some embodiments, each of the additional *E. coli* O1A, O2, O6A, O8, O15, O16, O18A, O25B, and/or O75 antigen polysaccharides is covalently linked to a carrier protein. The O-antigen polysaccharide can be linked to a carrier protein by chemical or other synthetic methods, or the O-antigen polysaccharide can be part of a bioconjugate, and is preferably part of a bioconjugate. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Preferably, the carrier protein is EPA.

In some embodiments, each of the additional *E. coli* O1A, O2, O6A, O8, O15, O16, O18A, O25B, and/or O75 antigen polysaccharides, particularly when part of a bioconjugate, is covalently linked to an asparagine (Asn) residue in the carrier protein, wherein the Asn residue is present in a glycosylation site comprising a glycosylation consensus sequence Asn-X-Ser(Thr), wherein X can be any amino acid except Pro (SEQ ID NO: 1), preferably wherein the Asn residue is present in a glycosylation site comprising a glycosylation consensus sequence Asp(Glu)-X-Asn-Z-Ser (Thr), wherein X and Z are independently selected from any amino acid except Pro (SEQ ID NO: 2). The carrier protein can comprise 1-10 glycosylation sites, preferably 2 to 4 glycosylation sites, most preferably 4 glycosylation sites, each comprising a glycosylation consensus sequence. In a particular embodiment, the carrier protein is EPA-4 carrier protein, for instance EPA-4 carrier protein comprising the amino acid sequence of SEQ ID NO: 3.

In a particular embodiment, provided herein is a composition (e.g., pharmaceutical and/or immunogenic composition) comprising: (i) a bioconjugate of an *E. coli* glucosylated O4 antigen polysaccharide covalently linked to a detoxified Exotoxin A of *P. aeruginosa* carrier protein comprising SEQ ID NO: 3 (EPA-4 carrier protein), wherein the *E. coli* glucosylated O4 antigen polysaccharide comprises the structure of Formula (O4-Glc+); (ii) a bioconjugate of an *E. coli* O1A antigen polysaccharide covalently linked to an EPA-4 carrier protein, wherein the *E. coli* O1A antigen polysaccharide comprises the structure of Formula (O1A); (iii) a bioconjugate of an *E. coli* O2 antigen polysaccharide covalently linked to an EPA-4 carrier protein, wherein the *E. coli* O2 antigen polysaccharide comprises the structure of Formula (O2); (iv) a bioconjugate of an *E. coli* O6A antigen polysaccharide covalently linked to an EPA-4 carrier protein, wherein the *E. coli* O6A antigen polysaccharide comprises the structure of Formula (O6A); (v) a bioconjugate of an *E. coli* O8 antigen polysaccharide covalently linked to an EPA-4 carrier protein, wherein the *E. coli* O8 antigen polysaccharide comprises the structure of Formula (O8); (vi) a bioconjugate of an *E. coli* O15 antigen polysaccharide covalently linked to an EPA-4 carrier protein, wherein the *E. coli* O15 antigen polysaccharide comprises the structure of Formula (O15); (vii) a bioconjugate of an *E. coli* O16 antigen polysaccharide covalently linked to an EPA-4 carrier protein, wherein the *E. coli* O16 antigen polysaccharide comprises the structure of Formula (O16); (viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* O75 antigen polysaccharide covalently linked to an EPA-4 carrier protein, wherein the *E. coli* O75 antigen polysaccharide comprises the structure of Formula (O75), wherein each of the Formulas is provided in Table 1, and for each of the Formulas independently n is an integer of 1 to 100, e.g. 1 to 50, preferably 3 to 50, e.g. 5 to 40.

In a particular embodiment, said composition (e.g. pharmaceutical and/or immunogenic composition) further comprises: (x) a bioconjugate of an *E. coli* O18A antigen polysaccharide covalently linked to an EPA-4 carrier protein, wherein the *E. coli* O18A antigen polysaccharide comprises the structure of Formula (O18A) as shown in Table 1, wherein n for this structure is an integer of 1 to 100, e.g. 1 to 50, preferably 3 to 50, e.g. 5 to 40.

In some embodiments, a composition provided herein comprises a bioconjugate of an *E. coli* glucosylated O4 antigen polysaccharide, and at least a bioconjugate of an *E. coli* O25B antigen polysaccharide, wherein the bioconjugate of the *E. coli* O25B antigen polysaccharide is present in the composition at a concentration that is about 1.5 to 6 times, e.g. about 2 to 4 times higher, such as 1.5, 2, 3, 4, 5 or 6 times higher than the concentration of any of the other bioconjugates present in the composition.

In particular embodiments, a composition comprises bioconjugates of *E. coli* O1A, O2, glucosylated O4, O6A, O8, O15, O16, O25B, and O75 antigen polysaccharides, wherein the bioconjugates of O1A:O2:glucosylated O4:O6A:O8: O15:O16:O25B:O75 are present in a ratio (by weight of O-antigen polysaccharide) of 1:1:1:1:1:1:1:2:1, or 2:1:1:2: 1:1:1:4:1.

In particular embodiments, a composition comprises bioconjugates of *E. coli* O1A, O2, glucosylated O4, O6A, O8, O15, O16, O18A, O25B, and O75 antigen polysaccharides, wherein the bioconjugates of O1A:O2:glucosylated O4:O6A:O8:O15:O16:O18A:O25B:O75 are present in a ratio (by weight of O-antigen polysaccharide) of 1:1:1:1:1: 1:1:1:2:1, or 2:1:1:2:1:1:1:1:4:1.

In some embodiments, a composition provided herein comprises a bioconjugate of an *E. coli* glucosylated O4 antigen polysaccharide, and at least a bioconjugate of an *E. coli* O25B antigen polysaccharide, wherein the bioconjugate of the *E. coli* O25B antigen polysaccharide is present in the composition at a concentration of 2 to 50 µg/mL, preferably 8 to 40 µg/mL, more preferably 16-32 µg/mL, such as 16, 18, 20, 22, 24, 26, 28, 30, or 32 µg/mL. In such embodiments, the concentration of the bioconjugate of the *E. coli* O25B antigen polysaccharide is preferably about 1.5 to 6 times, e.g., about 2 to 4 times higher, such as 1.5, 2, 3, 4, 5, or 6 times higher than the concentration of any of the other bioconjugates present in the composition.

In certain embodiments, the compositions described herein (e.g., pharmaceutical and/or immunogenic compositions) comprise, or are administered in combination with, an adjuvant. The adjuvant for administration in combination with a composition described herein may be administered before (e.g. within 72 hours, 48 hours, 24 hours, 12 hours, 6 hours, 2 hours, 1 hour, 10 minutes), concomitantly with, or after (e.g. within 72 hours, 48 hours, 24 hours, 12 hours, 6 hours, 2 hours, 1 hour, 10 minutes) administration of said composition. As used herein, the term "adjuvant" refers to a compound that when administered in conjunction with or as part of a composition described herein augments, enhances and/or boosts the immune response to an *E. coli* O-antigen polysaccharide in a bioconjugate, but when the adjuvant compound is administered alone does not generate an immune response to the *E. coli* O-antigen polysaccharide in the bioconjugate. In some embodiments, the adjuvant enhances an immune response to an *E. coli* O-antigen polysaccharide in a bioconjugate thereof and does not produce an allergy or other adverse reaction. Adjuvants can enhance an immune response by several mechanisms including, e.g., lymphocyte recruitment, stimulation of B and/or T cells, and stimulation of macrophages.

Examples of suitable adjuvants include, but are not limited to, aluminum salts (alum) (such as aluminum hydroxide, aluminum phosphate, aluminum sulfate and aluminum oxide, including nanoparticles comprising alum or nano-alum formulations), calcium phosphate, monophosphoryl lipid A (MPL) or 3-de-O-acylated monophosphoryl lipid A (3D-MPL) (see e.g., United Kingdom Patent GB2220211, EP0971739, EP1194166, U.S. Pat. No. 6,491,919), AS01, AS02, AS03 and AS04 (all GlaxoSmithKline; see e.g. EP1126876, U.S. Pat. No. 7,357,936 for AS04, EP0671948, EP0761231, U.S. Pat. No. 5,750,110 for AS02), MF59 (Novartis), imidazopyridine compounds (see WO2007/ 109812), imidazoquinoxaline compounds (see WO2007/

109813), delta-inulin, STING-activating synthetic cyclic-dinucleotides (e.g. US20150056224), combinations of lecithin and carbomer homopolymers (e.g. U.S. Pat. No. 6,676,958), and saponins, such as QuilA and QS21 (see e.g. Zhu D and W Tuo, 2016, Nat Prod Chem Res 3: e113 (doi:10.4172/2329-6836.1000e113), Matrix M, Iscoms, Iscomatrix, etc, optionally in combination with QS7 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Further examples of adjuvants are liposomes containing immune stimulants such as MPL and QS21 such as in AS01E and AS01B (e.g. US 2011/0206758). Other examples of adjuvants are CpG (Bioworld Today, Nov. 15, 1998) and imidazoquinolines (such as imiquimod and R848). See, e.g., Reed G, et al., 2013, *Nature Med*, 19: 1597-1608. In certain embodiments, the adjuvant contains a toll-like receptor 4 (TLR4) agonist. TLR4 agonists are well known in the art, see e.g. Ireton G C and S G Reed, 2013, Expert Rev Vaccines 12: 793-807. In certain embodiments, the adjuvant comprises a TLR4 agonist comprising lipid A, or an analog or derivative thereof, such as MPL, 3D-MPL, RC529 (e.g. EP1385541), PET-lipid A, GLA (glycopyranosyl lipid adjuvant, a synthetic disaccharide glycolipid; e.g. US20100310602, U.S. Pat. No. 8,722,064), SLA (e.g. Carter D et al, 2016, Clin Transl Immunology 5: e108 (doi: 10.1038/cti.2016.63), which describes a structure-function approach to optimize TLR4 ligands for human vaccines), PHAD (phosphorylated hexaacyl disaccharide), 3D-PHAD (the structure of which is the same as that of GLA), 3D-(6-acyl)-PHAD (3D(6A)-PHAD) (PHAD, 3D-PHAD, and 3D(6A)PHAD are synthetic lipid A variants, see e.g. avantilipids.com/divisions/adjuvants, which also provide structures of these molecules), E6020 (CAS Number 287180-63-6), ONO4007, OM-174, and the like.

In certain embodiments, the compositions described herein do not comprise, and are not administered in combination with, an adjuvant.

In certain embodiments, the compositions described herein are formulated to be suitable for the intended route of administration to a subject. For example, the compositions (e.g., pharmaceutical and/or immunogenic) described herein can be formulated for subcutaneous, parenteral, oral, sublingual, buccal, intradermal, transdermal, colorectal, intraperitoneal, rectal administration, intravenous, intranasal, intratracheal, intramuscular, topical, transdermal, or intradermal administration. In a specific embodiment, a composition provided herein (e.g., pharmaceutical and/or immunogenic) is formulated for intramuscular injection.

Methods of Use

Bioconjugates and compositions provided herein can be used to induce antibodies against an *E. coli* glucosylated O4 antigen in a subject, and to vaccinate a subject against *E. coli*, in particular extra-intestinal pathogenic *E. coli* (ExPEC). As used herein, "subject" means any animal, preferably a mammal, to whom will be or has been administered a bioconjugate or composition provided herein. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc. In certain embodiments, a subject is a human.

A human subject may be of any age. In certain embodiments, a subject is a human of about two months to about 18 years old, e.g. of 1 year to 18 years old. In certain embodiments, a subject is a human of at least 18 years old. In certain embodiments, a subject is a human of 15 to 50 years old, e.g. 18 to 45 years old, e.g. 20 to 40 years old. In certain embodiments, a subject is a human male. In certain embodiments, a subject is a human female. In certain embodiments, a subject is immunocompromised. In certain embodiments, a subject is a human of at least 50 years, at least 55 years, at least 60 years, at least 65 years old. In certain embodiments, a subject is a human that is not older than 100 years, not older than 95 years, not older than 90 years, not older than 85 years, not older than 80 years, or not older than 75 years. In certain embodiments, a subject is a human of at least 60 years old, and not older than 85 years old. In certain embodiments, a subject is a human in stable health. In certain embodiments, a subject is a human adult of at least 60 and not more than 85 years old in stable health. In certain embodiments, a subject is a human that has a history of a urinary tract infection (UTI, i.e. a bacterial infection in the urethra, bladder, ureters, and/or kidneys), i.e. having had at least one UTI episode in his or her life. In certain embodiments, a subject is a human that has a history of UTI in the past twenty, fifteen, twelve, ten, nine, eight, seven, six, five, four, three, two or one years. In certain embodiments, a subject is a human that has a history of UTI in the past two years. In certain embodiments, a subject is a human subject that has a history of recurrent UTI, i.e. having had at least two UTIs in six months or at least three UTIs in one year. In certain embodiments, a subject is a human subject that has a history of recurrent UTI in the past two years. In certain embodiments, a subject is a human of 60 years or older in stable health. In certain embodiments, a subject is a human of 60 years or older that has a history of UTI in the past two years. In certain embodiments, a subject is a human of at least 60 years and less than 75 years old that has a history of UTI in the past two years. In certain embodiments, a subject is a human subject of 75 years or older that has a history of UTI in the past two years. In certain embodiments, a subject is a patient scheduled for undergoing elective urogenital and/or abdominal procedures or surgeries, e.g. transrectal ultrasound-guided prostate needle biopsy (TRUS-PNB).

In one aspect, provided herein is a method of inducing antibodies against an *E. coli* glucosylated O4 antigen in a subject, comprising administering to the subject any of the bioconjugates of an *E. coli* glucosylated O4 antigen covalently linked to a carrier protein described herein, or a composition comprising a bioconjugate of an *E. coli* glucosylated O4 antigen covalently linked to a protein, alone or further in combination with other *E. coli* O-antigen polysaccharides or glycoconjugates or bioconjugates thereof.

In certain embodiments, the antibodies induced, elicited or identified against an *E. coli* glucosylated O4 antigen have opsonophagocytic activity. In particular embodiments, the antibodies induced, elicited or identified are cross-reactive antibodies capable of mediating opsonophagocytic killing of both *E. coli* glucosylated and non-glucosylated O4 strains.

In certain embodiments, the antibodies induced, elicited or identified against an *E. coli* glucosylated O4 antigen specifically recognize unmodified and glucose modified O4 antigen polysaccharide. In certain embodiments, the antibodies induced, elicited or identified against an *E. coli* glucosylated O4 antigen specifically recognize *E. coli* of the O4 serotype. In certain embodiments, the antibodies induced by a bioconjugate of an *E. coli* glucosylated O4 antigen bind preferentially to glucosylated O4 antigen as compared to non-glucosylated O4 antigen.

Antibodies induced by the bioconjugates and compositions described herein can include immunoglobulin molecules and immunologically active portions of immunoglobulin molecules, i.e., molecules that contain an antigen binding site that specifically binds to an *E. coli* O-antigen polysaccharide, e.g., glucosylated O4 antigen polysaccharide.

Antibodies induced, elicited or identified using the bioconjugates or compositions provided herein can be used to monitor the efficacy of a therapy and/or disease progression. Any immunoassay system known in the art can be used for this purpose including, but not limited to, competitive and noncompetitive assay systems using techniques such as radioimmunoassays, ELISA (enzyme linked immunosorbent assays), electrochemiluminescence (ECL)-based immunoassays, "sandwich" immunoassays, precipitin reactions, gel diffusion precipitin reactions, immunodiffusion assays, immunoradiometric assays, fluorescent immunoassays, protein A immunoassays and immunoelectrophoresis assays. Several of these assays, e.g. ECL-based immunoassays, can be done in multiplex format, and typically multiplex assay formats are preferred.

Antibodies induced, elicited or identified using a bioconjugate of an *E. coli* glucosylated O4 antigen polysaccharide can be used to detect *E. coli* O4 strains, particularly glucosylated O4 strains, for example, from a plurality of *E. coli* strains and/or to diagnose an infection by an *E. coli* O4 or glucosylated O4 strain.

In another aspect, provided herein is a method of vaccinating a subject against *E. coli* (e.g. extra-intestinal pathogenic *E. coli*, ExPEC), comprising administering to the subject any of the bioconjugates of an *E. coli* glucosylated O4 antigen covalently linked to a carrier protein described herein, or a composition comprising a bioconjugate of an *E. coli* glucosylated O4 antigen covalent linked to a carrier protein, alone or further in combination with other *E. coli* O-antigens or glycoconjugates or bioconjugates thereof. One skilled in the art will understand that the subject will be vaccinated against *E. coli* strains whose O antigens or glycoconjugates or bioconjugates thereof are present in the composition administered. For example, administration of a composition comprising O1A, O2, glucosylated O4, O6A, and O25B antigen polysaccharides can be used to a vaccinate a subject against *E. coli* serotypes O1A, O2, O4, O6A, and O25B.

In certain embodiments, vaccination is for preventing an invasive ExPEC disease (IED), e.g., urosepsis, bacteremia, sepsis, etc. In certain embodiments, vaccination is to prevent or reduce the occurrence or severity of urinary tract infections. In certain embodiments, an IED can be hospital-acquired, e.g. in patients undergoing urogenital and/or abdominal procedures or surgeries. In certain embodiments, an IED can be healthcare-associated, e.g. in patients receiving health care for another condition, for instance via central lines, catheters, etc, e.g. in a hospital, ambulatory surgical center, end-stage renal disease facility, long-term care facility, etc. In certain embodiments, the IED can be community-acquired, e.g. in a patient that was not recently exposed to healthcare risks.

In another aspect, provided herein is a method of inducing an immune response against *E. coli* (e.g., ExPEC) in a subject, comprising administering to the subject any of the bioconjugates of an *E. coli* glucosylated O4 antigen covalently linked to a carrier protein described herein, or a composition comprising a bioconjugate of an *E. coli* glucosylated O4 antigen covalently linked to a carrier protein, alone or further in combination with other *E. coli* O-antigens or glycoconjugates or bioconjugates thereof. In one embodiment, the subject has an *E. coli* (e.g., ExPEC) infection at the time of administration. In a preferred embodiment, the subject does not have an *E. coli* (e.g., ExPEC) infection at the time of administration.

In certain embodiments, the compositions and bioconjugates described herein can be administered to a subject to induce an immune response that includes the production of antibodies, preferably antibodies having opsonophagocytic activity. Such antibodies can be isolated using techniques known to one of skill in the art (e.g., immunoaffinity chromatography, centrifugation, precipitation, etc.).

The ability of the bioconjugates and compositions described herein to generate an immune response in a subject can be assessed using any approach known to those of skill in the art or described herein. In some embodiments, the ability of a bioconjugate to generate an immune response in a subject can be assessed by immunizing a subject (e.g., a mouse, rat, rabbit, or monkey) or set of subjects with a bioconjugate described herein and immunizing an additional subject (e.g., a mouse, rat, rabbit, or monkey) or set of subjects with a control (PBS). The subjects or set of subjects can subsequently be challenged with ExPEC and the ability of the ExPEC to cause disease (e.g., UTI, bacteremia, or other disease) in the subjects or set of subjects can be determined. Those skilled in the art will recognize that if the subject or set of subjects immunized with the control suffer(s) from disease subsequent to challenge with the ExPEC but the subject or set of subjects immunized with a bioconjugate(s) or composition thereof described herein suffer less from or do not suffer from disease, then the bioconjugate is able to generate an immune response in a subject. The ability of a bioconjugate(s) or composition thereof described herein to induce antiserum that cross-reacts with an O antigen from ExPEC can be tested by, e.g., an immunoassay, such as an ELISA (see e.g., Van den Dobbelsteen et al, 2016, Vaccine 34: 4152-4160), or an ECL-based immunoassay.

For example, the ability of the bioconjugates described herein to generate an immune response in a subject can be assessed using a serum bactericidal assay (SBA) or opsonophagocytic killing assay (OPK assay, or OPKA), which represents an established and accepted method that has been used to obtain approval of glycoconjugate-based vaccines. Such assays are well-known in the art and, briefly, comprise the steps of generating and isolating antibodies against a target of interest (e.g., an O antigen polysaccharide, e.g., *E. coli* glucosylated O4 antigen polysaccharide) by administering to a subject (e.g., a mouse, rat, rabbit, or monkey) a compound that elicits such antibodies. Subsequently, the bactericidal capacity of the antibodies can be assessed by, e.g., culturing the bacteria in question (e.g., *E. coli* of the relevant serotype) in the presence of the antibodies and complement and—depending on the assay—neutrophilic cells and assaying the ability of the antibodies to mediate killing and/or neutralization of the bacteria, e.g., using standard microbiological approaches. For an example of OPK assay for *E. coli* bioconjugate vaccines, see e.g. Abbanat et al, 2017, Clin. Vaccine Immunol. 24: e00123-17. An OPK assay can be performed in monoplex or multiplex format, of which multiplex format (e.g. testing multiple serotypes at the same time) is typically preferred. A multiplex OPK assay is sometimes referred to herein as "MOPA".

In some embodiments, the methods described herein comprise administering an effective amount of bioconjugates of an *E. coli* glucosylated O4 antigen covalently linked to a carrier protein described herein, or a composition comprising a bioconjugate of an *E. coli* glucosylated O4 antigen covalently linked to a carrier protein, alone or further in combination with other *E. coli* O-antigens or glycoconjugates or bioconjugates thereof. In one embodiment, an "effective amount" is an amount that vaccinates a subject against *E. coli* (e.g., ExPEC). In another embodiment, an "effective amount" is an amount that induces an immune response against *E. coli* (e.g., ExPEC) in a subject, such as an immune response including the production of antibodies, preferably antibodies having opsonophagocytic activity.

In particular embodiments, wherein a composition provided herein comprises a bioconjugate of an *E. coli* glucosylated O4 antigen polysaccharide and at least a bioconjugate of an *E. coli* O25B antigen polysaccharide, an effective amount of the *E. coli* O25B antigen polysaccharide is about 1.5 to 6 times, e.g. about 2 to 4 times higher, such as 1.5, 2, 3, 4, 5 or 6 times higher than the concentration of any of the other bioconjugates present in the composition. In such embodiments, an effective amount of the *E. coli* O25B antigen polysaccharide is for instance about 5 to 18 µg per administration, such as 5, 6, 7, 8, 9, 10, 11, 12, 13, 14, 15, 16, 17, 18 µg per administration.

In certain embodiments, a bioconjugate or composition according to the invention is administered to a subject once. In certain embodiments, a bioconjugate or composition according to the invention is administered to a subject more than once, e.g. in a prime-boost regimen. In certain embodiments, the time between two administrations is at least two weeks, at least one month, at least two months, at least three months, at least six months, at least one year, at least two years, at least five years, at least ten years, or at least fifteen years. In humans, a desired immune response can typically be generated by a single administration of a bioconjugate or composition according to the invention. In certain embodiments, a repeat administration after for instance ten years is provided.

Host Cells

Provided herein are host cells, e.g., prokaryotic host cells, capable of producing *E. coli* O antigens and bioconjugates comprising such *E. coli* O antigens. The host cells provided herein preferably are modified to comprise (e.g., through genetic engineering) one or more of the nucleic acids encoding host cell machinery (e.g., glycosyltransferases) used to produce *E. coli* O-antigen polysaccharides and/or bioconjugates thereof.

Any host cells known to those of skill in the art can be used to produce the *E. coli* 0 antigen polysaccharides described herein (e.g., *E. coli* glucosylated O4 antigen polysaccharide) and bioconjugates comprising the *E. coli* O antigen polysaccharides described herein (e.g., a bioconjugate of *E. coli* glucosylated O4 antigen polysaccharide) including archaea, prokaryotic host cells, and eukaryotic host cells. In a preferred embodiment, a host cell is a prokaryotic host cell. Exemplary prokaryotic host cells for use in production of the *E. coli* O antigen polysaccharides described herein and bioconjugates comprising the *E. coli* O antigen polysaccharides described herein include, but are not limited to, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species.

In a specific embodiment, the host cell used to produce the *E. coli* O antigen polysaccharides described herein and bioconjugates comprising the *E. coli* O antigen polysaccharides described herein is a prokaryotic host cell, and is preferably *E. coli*.

In certain embodiments, the host cells used to produce the *E. coli* O antigen polysaccharides and bioconjugates described herein are engineered to comprise heterologous nucleic acids, e.g., heterologous nucleic acids comprising rfb gene clusters of a desired O antigen serotype, heterologous nucleic acids that encode one or more carrier proteins and/or glycosyltransferases. In a specific embodiment, heterologous rfb genes, and/or heterologous nucleic acids that encode proteins involved in glycosylation pathways (e.g., prokaryotic and/or eukaryotic glycosylation pathways) can be introduced into the host cells described herein. Such nucleic acids can encode proteins including, but not limited to, oligosaccharyl transferases and/or glycosyltransferases.

Sequences of various genes and gene clusters encoding glycosyltransferases useful in making recombinant host cells that can, e.g., be used to prepare *E. coli* O antigen polysaccharides and bioconjugates thereof are described herein. Those skilled in the art will appreciate that due to the degeneracy of the genetic code, a protein having a specific amino acid sequence can be encoded by multiple different nucleic acids. Thus, those skilled in the art will understand that a nucleic acid provided herein can be altered in such a way that its sequence differs from a sequence provided herein, without affecting the amino acid sequence of the protein encoded by the nucleic acid.

Provided herein are host cells (e.g., recombinant host cells) for producing a bioconjugate of an *E. coli* glucosylated O4 antigen polysaccharide, O1A antigen polysaccharide, O2 antigen polysaccharide, O6A antigen polysaccharide, O8 antigen polysaccharide, 015 antigen polysaccharide, O16 antigen polysaccharide, O18A antigen polysaccharide, O25B antigen polysaccharide, or O75 antigen polysaccharide. The host cells provided herein comprise nucleic acids encoding enzymes (e.g., glycosyltransferases) capable of producing the *E. coli* O antigen polysaccharide. The host cells provided herein can naturally express nucleic acids capable of producing an O antigen of interest, or the host cells can be made to express such nucleic acids. In certain embodiments the nucleic acids are heterologous to the host cells and introduced into the host cells using genetic approaches known in the art. For example, the nucleic acids can be introduced into the host cell by genetic manipulation (e.g., the gene cluster is expressed on a plasmid or plasmids or integrated into the host cell genome (see, e.g., International Patent Application Publications WO 2014/037585, WO 2014/057109, WO 2015/052344).

In one embodiment, provided herein is a host cell (e.g., recombinant host cell) capable of producing a bioconjugate of an *E. coli* glucosylated O4 antigen polysaccharide covalently linked to a carrier protein. Such a host cell comprises, preferably by engineering a precursor cell, a nucleic acid sequence encoding a gtrS gene, which, to the best of the knowledge of the inventors, was identified herein for the first time as encoding a polysaccharide branching enzyme capable of transferring glucose to the *E. coli* O4 antigen (i.e., a glucosyltransferase specific to the *E. coli* O4 antigen polysaccharide), and particularly to L-Rha via an α-1,3-glycosidic linkage. An example of an amino acid sequence of such branching enzyme is provided in SEQ ID NO: 4. Other examples comprise amino acid sequences that are at least 80% identical thereto. Exemplary examples of nucleic acid sequence encoding gtrS genes specific to the *E. coli* O4 antigen polysaccharide include, but are not limited to, SEQ ID NO: 5, or degenerate nucleic acid sequences thereto that encode SEQ ID NO: 4, or nucleic acid sequences that encode functional O4-specific GtrS enzymes that have at least 80% identity to SEQ ID NO: 4.

In a specific embodiment, a host cell (e.g., recombinant host cell) capable of producing a bioconjugate of an *E. coli* glucosylated O4 antigen polysaccharide covalently linked to a carrier protein, comprises a nucleotide sequence encoding a glucosyl transferase having at least 80% sequence identity to SEQ ID NO: 4, such as about 80%, 85%, 90%, 91%, 92%, 93%, 94%, 95%, 95%, 97%, 98%, 99%, or 100% sequence identity to SEQ ID NO: 4. In view of the redundancy in the genetic code, one of ordinary skill in the art can make variants of nucleic encoding the amino acid sequences of glucosyl transferases, e.g., using codon optimized sequences, if desired.

In certain embodiments, a host cell (e.g., recombinant host cell) capable of producing a bioconjugate of an *E. coli* glucosylated O4 antigen polysaccharide covalently linked to a carrier protein, comprising a nucleotide sequence encoding a glucosyl transferase (GtrS) having at least 80% sequence identity to SEQ ID NO: 4, further comprises a nucleotide sequence encoding a bactoprenol-linked glucose translocase (GtrA) having at least 80% sequence identity to SEQ ID NO: 7, and a nucleotide sequence encoding a bactoprenol glucosyl transferase (GtrB) having at least 80% sequence identity to SEQ ID NO: 8. In certain embodiments, said nucleic acid sequences encode GtrA and GtrB proteins that are at least about 80%, 85%, 90%, 95%, 96%, 97%, 98%, 99%, or 100% identical to SEQ ID NOs: 7 and 8, respectively, and have bactoprenol-linked glucose translocase (SEQ ID NO: 7) and bactoprenol glucosyl transferase (SEQ ID NO: 8) activity, respectively. In view of the redundancy in the genetic code, one of ordinary skill in the art can make variants of nucleic encoding the amino acid sequences of bactoprenol-linked glucose translocases and of bactoprenol glucosyl transferases, e.g., using codon optimized sequences, if desired.

A host cell (e.g., recombinant host cell) capable of producing a bioconjugate of an *E. coli* glucosylated O4 antigen polysaccharide covalently linked to a carrier protein provided herein further comprises a nucleotide sequence of an rfb gene cluster for the *E. coli* O4 antigen polysaccharide. An example of an rfb gene cluster useful for production of the *E. coli* O4 antigen polysaccharide is provided herein as SEQ ID NO: 9. Another example can be found in GenBank, locus AY568960. Degenerate nucleic acid sequences encoding the same enzymes as encoded by this sequence, or sequences that encode enzymes that are at least 80% identical, preferably at least 85%, 90%, 91%, 92%, 93%, 94%, 95%, 96%, 97%, 98%, 99% identical, can also be used.

In a specific embodiment, provided herein is a host cell (e.g., a recombinant host cell, preferably a recombinant prokaryotic host cell, preferably a recombinant *E. coli* host cell) that produces glucosylated O4 antigen polysaccharide, wherein the host cell comprises gtrS, an rfb gene cluster for the *E. coli* O4 antigen polysaccharide, and nucleic acid encoding a carrier protein. Such host cells can be engineered using recombinant approaches to comprise one or more plasmids comprising the gtrS gene, the rfb gene cluster, and/or nucleic acid encoding a carrier protein, or to comprise some or all of the relevant genes such as gtrS, the rfb cluster and/or the nucleic acid encoding the carrier protein integrated into the host cell genome. In certain embodiments, the genes or gene clusters have been integrated into the genome of the host cell using homologous recombination. An advantage of integration of genes into the genome of the host cell is stability in the absence of antibiotic selection.

In another specific embodiment, provided herein is a host cell (e.g., a recombinant host cell, preferably a recombinant prokaryotic host cell) that produces glucosylated O4 antigen polysaccharide, wherein the host cell comprises GtrS (glucosyltransferase), as well as the enzymes encoded by the O4 rfb cluster. In certain embodiments, some or all of the aforementioned enzymes are heterologous to the host cell.

In other specific embodiments, provided herein is a host cell (e.g. a recombinant host cell, preferably a recombinant prokaryotic host cell) that produces *E. coli* glucosylated O4 antigen polysaccharide, preferably a bioconjugate of *E. coli* glucosylated O4 antigen polysaccharide, wherein the host cell further comprises a nucleotide sequence encoding an oligosaccharyl transferase and/or a nucleotide sequence encoding a carrier protein. In one specific embodiment, the oligosaccharyl transferase is heterologous to the host cell. In another specific embodiment, the carrier protein is heterologous to the host cell. Preferably, the host cell comprises a heterologous nucleotide sequence encoding a glucosyl transferase having at least 80% sequence identity to SEQ ID NO: 4. In preferred embodiments, the rfb genes of the O4 cluster are heterologous to the host cell. Preferably the sequence encoding the enzyme that is capable of introducing the branched glucose side chain to the O4 antigen, i.e. the gtrS gene (encoding a glucosyl transferase having at least 80% sequence identity to SEQ ID NO:4) is heterologous to the host cell. A nucleic acid is heterologous to the host cell if the same sequence is not naturally present in said host cell. Heterologous nucleic acid can for instance be introduced in a parent cell by genetic engineering, e.g by transformation (e.g. chemical transformation or electroporation) and/or recombination. In certain embodiments, heterologous nucleic acid such as a desired rfb locus, gtrS coding sequence, carrier protein encoding sequence, and/or glycosyltransferase encoding sequence are integrated into the genome of the host cell, preferably a bacterial host cell, preferably an *E. coli* host cell. In preferred embodiments, the endogenous rfb locus and if applicable gtrS coding sequence have been inactivated, preferably deleted from the genome of the recombinant host cell as compared to a predecessor thereof, and preferably these are replaced by the desired heterologous rfb locus, and if applicable desired gtrS coding sequence, respectively. In certain embodiments the host cell is a K-12 of *E. coli* (as a non-limiting example, *E. coli* strain W3110 is a K-12 strain), or a B strain of *E. coli* (as a non-limiting example, *E. coli* strain BL21 is a B strain), or any other well-defined strain of *E. coli*, e.g. laboratory strains or production strains, in contrast to primary wild-type isolates. In preferred embodiments, the host cell is derived from *E. coli* that does not express O4 antigen or glucosylated O4 antigen, by introduction into such *E. coli* of the O4 rfb locus and the gtrS gene encoding a glucosyl transferase having at least 80% sequence identity to SEQ ID NO:4. Advantages of using well-characterized strains, such as *E. coli* K-12 or *E. coli* B, as precursors for host cells is the possibility to use a similar production process for different O-antigen bioconjugates, since the characteristics of the production strain are well-defined. Even though bioconjugates of different O-antigens will behave differently and expression processes can be optimized per production strain, at least the basic process for production of O-antigen bioconjugates will be more predictable using such well-defined precursor strains than when unknown strains such as wild-type isolates are used as precursors for production of host strains. This way, experience with production of earlier described E. coli O-antigen bioconjugates such as O1A, O2, O6A and O25B bioconjugates as described in for instance WO 2015/124769 and WO 2017/035181 can be used as basis to design production of other E. coli O-antigen bioconjugates. Unlike gtrS, the gtrA and gtrB genes are not serotype-specific, and in certain embodiments these are homologous to the host cell (e.g. E. coli K12 strain W3110 includes gtrA and gtrB genes that are capable of functioning together with the O4-serotype specific recombinantly introduced gtrS gene encoding a glucosyl transferase of SEQ ID NO: 4 or a glucosyl transferase that is at least 80% identical thereto, replacing the endogenous gtrS gene). In other embodiments, one or both of gtrA and gtrB genes (encoding GtrA and GtrB proteins that are at least about 80% identical to SEQ ID NOs: 7 and 8, respectively, and having bactoprenol-linked glucose translocase and bactoprenol glucosyl transferase activity respectively, are also recombinantly introduced in the host cell, for instance in case the host cell does not have endogenous gtrA and/or gtrB genes.

Also provided herein are host cells (e.g., recombinant host cells) capable of producing a bioconjugate of an E. coli O1A, O2, O6A, O8, O15, O16, O18A, O25B, or O75 antigen polysaccharide covalently linked to a carrier protein. Such host cells (e.g., recombinant host cells) comprise nucleotide sequence of an rfb gene cluster specific to the O-antigen polysaccharide. The rfb gene clusters can be isolated from wild-type E. coli strains, and combined with nucleic acids encoding an oligosaccharyl transferase (e.g., PglB) and carrier protein (e.g., EPA) within one host cell to obtain a recombinant host cell that produces the E. coli O-antigen of interest or bioconjugate thereof. For example, such host cells can be engineered using recombinant approaches to comprise one or more plasmids comprising the rfb gene cluster, oligosaccharyl transferase (e.g., PglB) and carrier protein (e.g., EPA) using bioconjugation technology such as that described in WO 2014/037585, WO 2009/104074, and WO 2009/089396. Preferably the host cells comprise the rfb gene clusters integrated into their genome. The nucleic acids encoding oligosaccharyl transferase, carrier protein, and where applicable gtrS gene, are in certain embodiments also integrated into the genome of the host cell. Heterologous or homologous gtrA and gtrB genes are in certain embodiments also integrated into the genome of the host cell.

Preparation of bioconjugates for O1A, O2, O6A and O25B antigens has been described in detail in WO 2015/124769 and WO 2017/035181. Exemplary gene clusters for each E. coli O antigen (rfb loci) have been described in Iguchi A, et al, DNA Research, 2014, 1-7 (doi: 10.1093/dnares/dsu043), and in DebRoy C, et al, PLoS One. 2016, 11(1):e0147434 (doi: 10.1371/journal.pone.0147434; correction in: Plos One. 2016, 11(4):e0154551, doi: 10.1371/journal.pone.0154551). Nucleic acid sequences for the rfb clusters and amino acid sequences for proteins encoded therein can also be found in public databases, such as GenBank. Exemplary sequences for rfb clusters that can be used in production strains for bioconjugates with polysaccharide antigens of the serotypes disclosed herein, are also provided in SEQ ID NOs: 9 and 11-19. Thus, for each of the desired bioconjugates mentioned above, the respective rfb cluster can be introduced into a host cell, to obtain host cells with the specific rfb cluster for the desired O-antigen, as well as containing nucleic acid encoding oligosaccharyltransferase and carrier protein. For reasons indicated above, preferably the host cells are recombinant host cells, and preferably are derived from strains with relatively well-known characteristics, such as E. coli laboratory or production strains, e.g. E. coli K12 or E. coli BL21, etc. Preferably, the rfb clusters are heterologous to the host cell, e.g. introduced into a precursor cell of the host cell, and preferably integrated into the genome thereof. Preferably an original rfb gene cluster, if such was present in a precursor cell, has been replaced by the rfb gene cluster for the O-antigen of interest in the host cell, to enable production of bioconjugate of the O-antigen of interest. Preferably the oligosaccharyltransferase is heterologous to the host cell, and in certain embodiments nucleic acid encoding such oligosaccharyltransferase is integrated into the genome of the host cell.

Any of the host cells provided herein (e.g., recombinant host cells, preferably recombinant prokaryotic host cells) comprise nucleic acids encoding additional enzymes active in the N-glycosylation of proteins, e.g., the host cell provided herein can further comprise a nucleic acid encoding an oligosaccharyl transferase or nucleic acids encoding other glycosyltransferases.

The host cells provided herein comprise a nucleic acid that encodes an oligosaccharyl transferase. Oligosaccharyl transferases transfer lipid-linked oligosaccharides to asparagine residues of nascent polypeptide chains that comprise an N-glycosylation consensus motif. The nucleic acid that encodes an oligosaccharyl transferase can be native to the host cell, or can be introduced into the host cell using genetic approaches. In preferred embodiments, the oligosaccharyl transferase is heterologous to the host cell. E. coli does not naturally comprise an oligosaccharyl transferase, and hence if E. coli is used as a host cell for production of bioconjugates, a heterologous oligosaccharyl transferase is comprised in such host cell, e.g. upon introduction by genetic engineering. The oligosaccharyl transferase can be from any source known in the art in view of the present disclosure.

In certain embodiments, an alternative to an oligosaccharyl transferase with N-glycosyltransferase activity, such as an O-glycosyltransferase, e.g. as a non-limiting example PglL, can be used, in conjunction with its own, different, glycosylation consensus sequence in the carrier protein, as for instance described in WO 2016/82597. Other glycosyltransferases, such as O-glycosyltransferases, can thus also be used as an oligosaccharyltransferase according to the invention.

In certain preferred embodiments, the oligosaccharyl transferase is an oligosaccharyl transferase from Campylobacter. For example, in one embodiment, the oligosaccharyl transferase is an oligosaccharyl transferase from Campylobacter jejuni (i.e., pglB; see, e.g., Wacker et al., 2002, Science 298:1790-1793; see also, e.g., NCBI Gene ID: 3231775, UniProt Accession No. O86154). In another embodiment, the oligosaccharyl transferase is an oligosaccharyl transferase from Campylobacter lari (see, e.g., NCBI Gene ID: 7410986).

In specific embodiments, the oligosaccharyl transferase is PglB oligosaccharyl transferase from Campylobacter jejuni, including the natural (wild-type) protein or any variant thereof, such as those described in International Patent Application Publications WO 2016/107818 and WO 2016/107819. PglB can transfer lipid-linked oligosaccharides to asparagine residues in the consensus sequences SEQ ID NO: 1 and SEQ ID NO: 2. In particular embodiments, the PglB oligosaccharyl transferase comprises SEQ ID NO: 6, or a variant thereof. In certain embodiments one or more endogenous glycosylation consensus sequences in a wild-type PglB have been mutated to avoid PglB autoglycosylation, e.g. SEQ ID NO: 6 comprising the mutation N534Q. Examples of variant PglB oligosaccharyl transferases suitable for use in the recombinant host cells provided herein include the PglB oligosaccharyl transferase of SEQ ID NO: 6 comprising at least one mutation selected from the group consisting of N311V, K482R, D483H, A669V, Y77H, S80R, Q287P, and K289R. In one particular embodiment, a variant PglB oligosaccharyl transferase has SEQ ID NO: 6 comprising the mutation N311V. In another particular embodiment, a variant PglB oligosaccharyl transferase has SEQ ID NO: 6 comprising the mutations Y77H and N311V. In another particular embodiment, a variant PglB oligosaccharyl transferase has SEQ ID NO: 6 comprising the mutations N311V, K482R, D483H, and A669V. In another particular embodiment, a variant PglB oligosaccharyl transferase has SEQ ID NO: 6 comprising the mutations Y77H, S80R, Q287P, K289R, and N311V. It was found and described herein that certain PglB oligosaccharyl transferase variants give surprisingly improved yields in production of *E. coli* O-antigen bioconjugates of specific serotypes. The improved or optimal PglB variant for a given *E. coli* O-antigen was not predictable. The invention in certain aspects therefore also provides methods for producing bioconjugates of specific *E. coli* O-antigens, using specific PglB variants as the oligosaccharyl transferase. Further variants of PglB that are at least 80%, 85%, 90%, 91%, 92%, 93%, 94%, 95%, 96%, 97%, 98%, 99% identical to SEQ ID NO: 6 and still have oligosaccharyl transferase activity, preferably having one or more of the specific amino acids on the indicated positions disclosed in combination herein (e.g. 77Y, 80S, 287Q, 289K, 311N, 482K, 483D, 669A; or 311V; or 311V, 482R, 483H, 669V; or 77H, 80R, 287P, 289R, 311V; or 77H, 311V; etc) can also be used for production of bioconjugates.

In a specific embodiment, a host cell (e.g., recombinant host cell) capable of producing a bioconjugate of an *E. coli* glucosylated O4 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V, or more preferably SEQ ID NO: 6 comprising the mutations Y77H and N311V.

In other specific embodiments, a host cell (e.g., recombinant host cell) capable of producing a bioconjugate of an *E. coli* O1A, O6A, or O15 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations N311V, K482R, D483H, and A669V.

In a specific embodiment, a host cell (e.g., recombinant host cell) capable of producing a bioconjugate of an *E. coli* O16 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations Y77H, S80R, Q287P, K289R, and N311V.

In a specific embodiment, a host cell (e.g., recombinant host cell) capable of producing a bioconjugate of an *E. coli* O75 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V.

In a specific embodiment, a host cell (e.g., recombinant host cell) capable of producing a bioconjugate of an *E. coli* O8, O18A, O25B, or O2 antigen polysaccharide covalently linked to a carrier protein further comprises a nucleotide sequence encoding PglB oligosaccharyl transferase from *Campylobacter jejuni* having the amino acid sequence of SEQ ID NO: 6, preferably wherein SEQ ID NO: 6 comprises no amino acid mutations at positions 77, 80, 287, 289, 311, 482, 483, and 669.

In some embodiments, any of the host cells provided herein comprise a nucleic acid encoding a carrier protein, e.g., a protein to which the O-antigen polysaccharide(s) produced by the host cell glycosylation machinery can be attached to form a bioconjugate. The host cell can comprise a nucleic acid encoding any carrier protein known to those skilled in the art in view of the present disclosure including, but not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In preferred embodiments, a host cell further comprises a nucleic acid encoding detoxified Exotoxin A of *P. aeruginosa* (EPA). Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably having the amino acid sequence of SEQ ID NO: 2. In a specific embodiment, a host cell further comprises a nucleic acid encoding EPA-4 carrier protein comprising SEQ ID NO: 3.

In certain embodiments, the carrier proteins used in the generation of the bioconjugates by the host cells described herein comprise a "tag," i.e., a sequence of amino acids that allows for the isolation and/or identification of the carrier protein. For example, adding a tag to a carrier protein can be useful in the purification of that protein and, hence, the purification of conjugate vaccines comprising the tagged carrier protein. Exemplary tags that can be used herein include, without limitation, histidine (HIS) tags (e.g., hexahistidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified. In other embodiments, the carrier protein does not comprise a tag.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia carotovorans* pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI). In one embodiment, the signal sequence comprises SEQ ID NO: 10. A signal sequence may be cleaved off after translocation of the protein to the periplasm and may thus no longer be present in the final carrier protein of a bioconjugate.

In certain embodiments, additional modifications can be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein). In certain embodiments, when nucleic acids are deleted from the genome of the host cells provided herein, they are replaced by a desirable sequence, e.g., a sequence that is useful for production of an O antigen polysaccharide or bioconjugate thereof.

Exemplary genes or gene clusters that can be deleted in host cells (and, in some cases, replaced with other desired nucleic acid sequences) include genes or gene clusters of host cells involved in glycolipid biosynthesis, such as waaL (see, e.g., Feldman et al., 2005, *PNAS USA* 102:3016-3021), the lipid A core biosynthesis cluster (waa), galactose cluster (gal), arabinose cluster (ara), colonic acid cluster (wc), capsular polysaccharide cluster, undecaprenol-p biosynthesis genes (e.g. uppS, uppP), und-P recycling genes, metabolic enzymes involved in nucleotide activated sugar biosynthesis, enterobacterial common antigen cluster (eca), and prophage O antigen modification clusters like the gtrABS cluster or regions thereof. In a specific embodiment, the host cells described herein are modified such that they do not produce any O antigen polysaccharide other than a desired O antigen polysaccharide, e.g., glucosylated O4 antigen polysaccharide.

In a specific embodiment, the waaL gene is deleted or functionally inactivated from the genome of a host cell (e.g., recombinant host cell) provided herein. The terms "waaL" and "waaL gene" refer to the O-antigen ligase gene encoding a membrane bound enzyme with an active site located in the periplasm. The encoded enzyme transfers undecaprenylphosphate (UPP)-bound O antigen to the lipid A core, forming lipopolysaccharide. Deletion or disruption of the endogenous waaL gene (e.g., ΔwaaL strains) disrupts transfer of the O-antigen to lipid A, and can instead enhance transfer of the O-antigen to another biomolecule, such as a carrier protein.

In another specific embodiment, one or more of the waaL gene, gtrA gene, gtrB gene, gtrS gene, and the rfb gene cluster is deleted or functionally inactivated from the original genome of a prokaryotic host cell provided herein.

In one embodiment, a host cell used herein is *E. coli* that produces a bioconjugate of glucosylated O4 antigen polysaccharide, wherein the waaL gene is deleted or functionally inactivated from the genome of the host cell, and a gtrS gene specific to *E. coli* O4 antigen polysaccharide is inserted. In certain embodiments for production strains for bioconjugates of the glucosylated O4 O-antigen, a gtrS gene encoding a glucosyl transferase having at least 80% sequence identity to SEQ ID NO:4 is inserted in the place of a gtrS gene of the parent strain, so as to replace the gtrS gene in that parent strain with the one that is responsible for glucosylation of the O4 antigen. An example of such a parent strain is *E. coli* K-12 strain W3110. The gtrA and gtrB genes can be homologous to the parent strain, or alternatively one or both of these genes can be heterologous to the parent strain. Typically, and unlike the gtrS gene, these gtrA and gtrB genes are not specific for the O-antigen structure.

Also provided herein are methods of making recombinant host cells. Recombinant host cells produced by the methods described herein can be used to produce bioconjugates of *E. coli* O antigens. The methods comprise introducing one or more recombinant nucleic acid molecules into a cell to produce the recombinant host cell. Typically, the recombinant nucleic acid molecules are heterologous. Any method known in the art in view of the present disclosure can be used to introduce recombinant nucleic acid molecules into a host cell. Recombinant nucleic acids can be introduced into the host cells described herein using any methods known to those of ordinary skill in the art, e.g., electroporation, chemical transformation, by heat shock, natural transformation, phage transduction, and conjugation. In specific embodiments, recombinant nucleic acids are introduced into the host cells described herein using a plasmid. For example, the heterologous nucleic acids can be expressed in the host cells by a plasmid (e.g., an expression vector). In another specific embodiment, heterologous nucleic acids are introduced into the host cells described herein using the method of insertion into the genome as for instance described in International Patent Application Publication WO 2014/037585, WO 2014/057109, or WO 2015/052344.

In one embodiment, a method of making a recombinant host cell for producing a bioconjugate of an *E. coli* glucosylated O4 antigen polysaccharide covalently linked to a carrier protein comprises introducing one or more recombinant nucleic acid molecules into a cell, preferably an *E. coli* cell, to produce the recombinant host cell. In such embodiments, the recombinant nucleic acid molecules introduced into the cell include (i) a nucleotide sequence of an rfb gene cluster for the *E. coli* O4 antigen polysaccharide; (ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide; (iii) a nucleotide sequence encoding a carrier protein; and (iv) a nucleotide sequence encoding an oligosaccharyl transferase capable of covalently linking the *E. coli* glucosylated O4 antigen polysaccharide to the carrier protein to produce the bioconjugate. In preferred embodiments, the nucleotide sequence encoding a glucosyl transferase having at least 80% sequence identity to SEQ ID NO: 4 replaces the endogenous gtrS gene. Deleting the endogenous gtrS has the advantage that it will not interfere with generation of the glucosylated O4 antigen polysaccharide structure. In certain embodiments, the nucleotide sequence of the rfb gene cluster for the *E. coli* O4 antigen polysaccharide replaces the endogenous rfb gene cluster of the parent strain that is used to make the recombinant host cell. If the cell does not yet encode gtrA and/or gtrB genes, nucleotide sequences encoding a translocase (gtrA) and a glycosyltransferase (gtrB), having at least 80% identity to SEQ ID NOs: 7 and 8, respectively, can be introduced into the cell. If the cell already encodes gtrA and gtrB genes (such as for instance the case in *E. coli* K-12 strain W3110), there is no need to introduce or change these genes.

In a specific embodiment, the glucosyl transferase (gtrS specific for adding glucose branch to O4 antigen) has SEQ ID NO: 4.

In a specific embodiment, the oligosaccharyl transferase is PglB from *C. jejuni*. In one such embodiment, the oligosaccharyl transferase comprises the amino acid sequence of SEQ ID NO: 6. In another such embodiment, the oligosaccharyl transferase comprises the amino acid sequence of SEQ ID NO: 6 comprising the mutation N311V. In another such embodiment, the oligosaccharyl transferase comprises the amino acid sequence of SEQ ID NO: 6 comprising the mutations Y77H and N311V.

In another specific embodiment, the carrier protein comprises at least one glycosylation site comprising a glycosylation consensus sequence having SEQ ID NO: 1, preferably SEQ ID NO: 2. In another specific embodiment, the carrier protein is EPA, preferably EPA-4, such as EPA-4 comprising SEQ ID NO: 3.

E. coli strains that are used routinely in molecular biology as both a tool and a model organism can for instance be used as parents for host cells in certain embodiments according to the invention. Non-limiting examples include E. coli K12 strains (for example, such as W1485, W2637, W3110, MG1655, DH1, DH5a, DH10, etc.), B strains (e.g. BL-21, REL606, etc.), C strains, or W strains. In one particular embodiment, the host strain is derived from parent strain W3110. This strain can for instance be obtained from the E. coli Genetic Stock Center at Yale. For more information on E. coli, see e.g. Ecoliwiki.net.

Methods of Producing Conjugates and Bioconjugates

Also provided are methods of producing glycoconjugates of the E. coli O antigen polysaccharides described herein. Glycoconjugates, including bioconjugates, can be prepared in vitro or in vivo, e.g., using the recombinant host cells described herein for production.

In some embodiments, glycoconjugates can be prepared by chemical synthesis, i.e., prepared outside of host cells (in vitro). For example, an E. coli O antigen polysaccharide can be conjugated to carrier proteins using methods known to those of ordinary skill in the art, including by means of using activation reactive groups in the polysaccharide/oligosaccharide as well as the carrier protein. See, e.g., Pawlowski et al., 2000, Vaccine 18:1873-1885; and Robbins, et al., 2009, *Proc Natl Acad Sci USA* 106:7974-7978), the disclosures of which are herein incorporated by reference. Such approaches comprise extraction of antigenic polysaccharides/oligosaccharides from host cells, purifying the polysaccharides/oligosaccharides, chemically activating the polysaccharides/oligosaccharides, and conjugating the polysaccharides/oligosaccharides to a carrier protein.

In some embodiments, the host cells described herein can be used to produce bioconjugates comprising an E. coli O antigen polysaccharide covalently linked to a carrier protein. Methods of producing such bioconjugates using host cells are known in the art. See, e.g., WO 2003/074687 and WO 2006/119987. Such methods comprise culturing any of the recombinant host cells described herein under conditions for production of the bioconjugate. Bioconjugates can be isolated, separated, and/or purified from recombinant host cells using any method known in the art in view of the present disclosure. For example, bioconjugates can be purified by any method known in the art for purification of a protein, for instance, by chromatography (e.g., ion exchange, anionic exchange, affinity, and sizing column chromatography), centrifugation, differential solubility, or by any other standard technique for the purification of proteins. See, e.g., methods described in WO 2009/104074. Further, the bioconjugates can be fused to heterologous polypeptide sequences to facilitate purification. The actual conditions used to purify a particular bioconjugate will depend, in part, on factors such as net charge, hydrophobicity, and/or hydrophilicity of the bioconjugate, and will be apparent to those skilled in the art. Preparation of bioconjugates for O1A, O2, O6A, and O25B, as well as vaccine compositions comprising these, have for instance been described in WO 2015/124769 and in WO 2017/035181.

Also provided are bioconjugates produced by the methods described herein, i.e., using the recombinant host cells described herein.

In some embodiments, a method of preparing a bioconjugate of an E. coli O-antigen polysaccharide covalently linked to a carrier protein comprises: (i) providing a recombinant host cell comprising (a) nucleotide sequence of an rfb gene cluster for the O-antigen polysaccharide; (b) a nucleotide sequence encoding a carrier protein, preferably EPA, comprising at least one glycosylation site comprising a glycosylation consensus sequence having SEQ ID NO: 1, preferably SEQ ID NO: 2, and more preferably comprising four glycosylation sites each comprising a glycosylation consensus sequence having SEQ ID NO: 2; and (c) nucleotide sequence encoding an oligosaccharyl transferase, for instance PglB oligosaccharyl transferase or variant thereof.

In certain embodiments, E. coli O-antigen polysaccharides produced using the recombinant host cells described herein are covalently bound to the carrier protein at a particular polysaccharide to protein ratio by weight (w/w). This ratio of amount of O-antigen polysaccharide by weight covalently bound to the carrier protein by weight is referred to as the "glycan/protein ratio" or "polysaccharide/protein ratio" or "PS/protein ratio". In some embodiments, the O-antigen polysaccharide is covalently bound to the carrier protein at a polysaccharide to protein (w/w) ratio of about 1:20 to 20:1, preferably 1:10 to 10:1, more preferably 1:3 to 3:1. In certain non-limiting embodiments for bioconjugates described herein, glycan/protein ratio is about 0.1 to 0.5, such as 0.1, 0.15, 0.2, 0.25, 0.3, 0.35, 0.4, 0.45, or 0.5. In such embodiments, the weight ratio of the O-antigen polysaccharide: protein is about 1:10 to 1:2, such as 1:10:1:9:1:8, 1:7, 1:6, 1:5, 1:4, 1:3, or 1:2, depending on the particular O-antigen serotype. In certain embodiments the glycan/protein ratio is from about 0.15 to about 0.45. In general, a higher glycan/protein ratio of O-antigen polysaccharide to carrier protein is preferred, because a high amount of carrier protein can lead to immunological interference in some instances. Also, a higher glycan/protein ratio would help getting sufficient O-antigen polysaccharide dosed in the form of bioconjugate, while keeping the amount of carrier protein relatively low, which is especially beneficial for multivalent compositions where multiple serotypes are to be covered by the composition, e.g. compositions comprising bioconjugates from at least 4 different O-antigens, at least 5 different O-antigens, at least 6 different O-antigens, at least 7 different O-antigens, at least 8 different O-antigens, at least 9 different O-antigens, at least 10 different O-antigens, etc.

A glycan/protein ratio of a conjugate according to the invention can be determined by determining the protein amount and the glycan amount. Protein amount can be determined by measurement of UV absorbance at 280 nm (A280). Glycan amount can be determined based on ion chromatography with pulsed amperometric detection (IC-PAD) of a sugar in the repeat unit (e.g. of Man for 08 in Table 1, and of GlcNAc for the other glycans in Table 1), after which the structural information of the repeat unit can be used to calculate the total glycan amount (e.g. the repeat unit of O1A has a molar mass of 845 Da and one mole of such a repeat unit contains one mole of GlcNAc, enabling calculation of the total glycan amount when the amount of GlcNAc has been determined by IC-PAD).

In some embodiments, a bioconjugate of an E. coli O25B antigen polysaccharide covalently linked to a carrier protein produced using a recombinant host cell according to the cells and methods described herein has a certain degree of acetylation at position 2 of the L-Rh sugar. The degree of O-acetylation of O25B antigen polysaccharide in a bioconjugate is preferably at least 30%, preferably at least 50%, such as at least 50%, 55%, 60%, 65%, 70%, 75%, 80%, 85%, 90%, 95%, or 100%.

Similarly, the degree of O-acetylation of an *E. coli* O16 antigen polysaccharide in a bioconjugate is preferably at least 30%, preferably at least 50%, such as at least 50%, 55%, 60%, 65%, 70%, 75%, 80%, 85%, 90%, 95%, or 100%.

In specific embodiments, a method of preparing a bioconjugate of an O-antigen polysaccharide comprises providing a recombinant host cell comprising nucleic acid sequence encoding a particular oligosaccharyl transferase enzyme, particularly a PglB oligosaccharyl transferase or variant thereof, depending on the O-antigen polysaccharide bioconjugate to be produced. The particular oligosaccharyl transferase enzyme variant may impact the yield of bioconjugate produced by the host cell. Typically, a higher yield is preferred, since the yield will impact the costs for producing a specific bioconjugate, which is especially important for multivalent compositions comprising several different bioconjugates.

In one particular embodiment, when the O-antigen is O1A, O6A, or O15 antigen polysaccharide, the PglB oligosaccharyl transferase comprises the amino acid mutations of N311V, K482R, D483H, and A669V, wherein the amino acid mutations are relative to the wild-type PglB having the amino acid sequence of SEQ ID NO: 6.

In another particular embodiment, when the O-antigen is glucosylated O4 antigen polysaccharide, the PglB oligosaccharyl transferase comprises the amino acid mutation N311V, or the amino acid mutations of Y77H and N311V, wherein the amino acid mutations are relative to the wild-type PglB having the amino acid sequence of SEQ ID NO: 6.

In another particular, embodiment, when the O-antigen is O16 antigen polysaccharide, the PglB oligosaccharyl transferase comprises the amino acid mutations of Y77H, S80R, Q287P, K289R, and N311V, wherein the amino acid mutations are relative to the wild-type PglB having the amino acid sequence of SEQ ID NO: 6.

In another particular embodiment, when the O-antigen is O75 antigen polysaccharide, the PglB oligosaccharyl transferase comprises the amino acid mutation of N311V, wherein the amino acid mutations are relative to the wild-type PglB having the amino acid sequence of SEQ ID NO: 6.

In another particular embodiment, when the O-antigen is O8, O18A, O25B, or O2 antigen polysaccharide, the PglB oligosaccharyl transferase comprises the amino acid sequence of SEQ ID NO: 6, wherein SEQ ID NO: 6 comprises no amino acid mutations at positions 77, 80, 287, 289, 311, 482, 483, and 669. In certain embodiments thereof, the PglB oligosaccharyl transferase comprises the amino acid sequence of SEQ ID NO: 6.

In some embodiments, bioconjugates of O-antigen polysaccharides produced by recombinant host cells encoding the oligosaccharyl transferase enzymes per the O-antigen/PglB oligosaccharyl transferase pairings indicated above preferably have one or more of the preferred attributes described herein, e.g., glycan/protein ratio and/or percent of multi-glycosylated carrier protein.

EMBODIMENTS

Embodiment 1 is a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+):

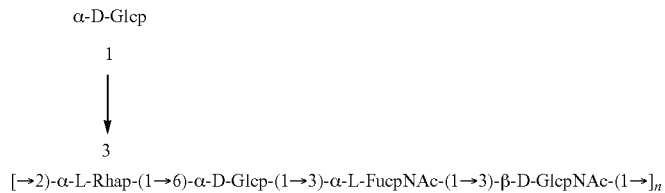

wherein n is an integer of 1 to 100, preferably 3 to 50, for example 5 to 40, for example 7 to 25, for example 10 to 20.

Embodiment 2 is the bioconjugate of embodiment 1, wherein the *E. coli* glucosylated O4 antigen polysaccharide is covalently linked to an Asn residue in a glycosylation site comprising a glycosylation consensus sequence having SEQ ID NO: 1, preferably having SEQ ID NO: 2, in the carrier protein.

Embodiment 3 is the bioconjugate of embodiment 1 or embodiment 2, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

Embodiment 4 is the bioconjugate of embodiment 3, wherein the carrier protein is detoxified exotoxin A of *Pseudomonas aeruginosa* (EPA), preferably comprising 1 to 20, preferably 1 to 10, preferably 2 to 4, glycosylation consensus sequences having SEQ ID NO: 1, the consensus sequences preferably having SEQ ID NO: 2.

Embodiment 5 is the bioconjugate of embodiment 4, wherein the carrier protein comprises four glycosylation consensus sequences (EPA-4), preferably wherein the carrier protein comprises SEQ ID NO: 3.

Embodiment 6 is a composition comprising the bioconjugate of any one of embodiments 1-5.

Embodiment 7 is an immunogenic composition comprising the bioconjugate of any one of embodiments 1-5.

Embodiment 8 is the composition of embodiment 6 or immunogenic composition of embodiment 7, comprising at least one additional antigen polysaccharide covalently linked to a carrier protein.

Embodiment 9 is the composition or immunogenic composition of embodiment 8, wherein the at least one additional antigen polysaccharide is selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide.

Embodiment 10 is the composition or immunogenic composition of embodiment 9, wherein (i) the *E. coli* O1A antigen polysaccharide comprises the structure of Formula (O1A):

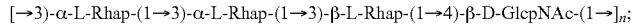
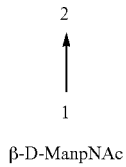

(ii) the *E. coli* O2 antigen polysaccharide comprises the structure of Formula (O2):

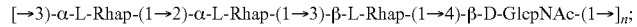
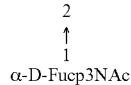

(iii) the *E. coli* O6A antigen polysaccharide comprises the structure of Formula (O6A):

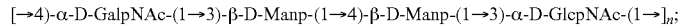

(iv) the *E. coli* O8 antigen polysaccharide comprises the structure of Formula (O8):

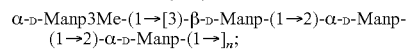

(v) the *E. coli* O15 antigen polysaccharide comprises the structure of Formula (O15):

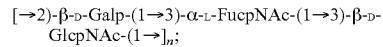

(vi) the *E. coli* O16 antigen polysaccharide comprises the structure of Formula (O16):

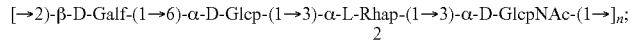

(vii) the *E. coli* O18A antigen polysaccharide comprises the structure of Formula (O18A):

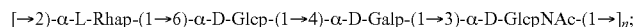
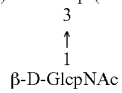

(viii) the *E. coli* O25B antigen polysaccharide comprises the structure of Formula (O25B):

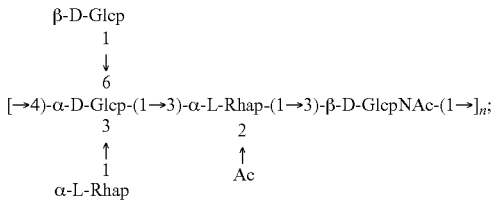

and
(ix) the *E. coli* O75 antigen polysaccharide comprises the structure of Formula (O75):

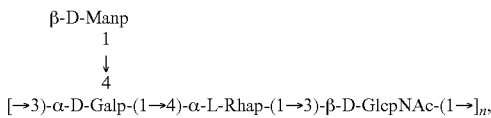

wherein each n is independently an integer of 1 to 100, preferably of 3 to 50, e.g. 5 to 40, e.g. 7 to 25, e.g. 10 to 20.

Embodiment 11 is the composition or immunogenic composition of embodiment 10, wherein each of the additional *E. coli* O1A, O2, O6A, O8, O15, O16, O18A, O25B, and/or O75 antigen polysaccharides is covalently bound to an Asn residue in a glycosylation site comprising a glycosylation consensus sequence having SEQ ID NO: 1, preferably having SEQ ID NO: 2, in each of the carrier protein.

Embodiment 12 is the composition or immunogenic composition of embodiment 11, wherein each of the carrier protein is a detoxified exotoxin A of *Pseudomonas aeruginosa* (EPA).

Embodiment 13 is the composition or immunogenic composition of embodiment 12, wherein each EPA comprises 1-10, preferably 2-4, glycosylation sites each comprising a glycosylation consensus sequence having SEQ ID NO: 2.

Embodiment 14 is the composition or immunogenic composition of embodiment 12, wherein each EPA comprises four glycosylation sites each comprising a glycosylation consensus sequence having SEQ ID NO: 2.

Embodiment 15 is the composition or immunogenic composition of embodiment 12, wherein each EPA comprises SEQ ID NO: 3.

Embodiment 16 is the composition or immunogenic composition of any one of embodiments 9-15, comprising at least the *E. coli* O1A, O2, glucosylated O4, O6A, and O25B antigen polysaccharides each covalently linked to a carrier protein.

Embodiment 17 is the composition or immunogenic composition of any one of embodiments 9-15, comprising at least the *E. coli* O1A, O2, glucosylated O4, O6A, O8, O15, O16, O25B and O75 antigen polysaccharides each covalently linked to a carrier protein.

Embodiment 18 is the composition or immunogenic composition of any one of embodiments 9-15, comprising at least the *E. coli* O1A, O2, glucosylated O4, O6A, O8, O15, O16, O18A, O25B, and O75 antigen polysaccharides each covalently linked to a carrier protein.

Embodiment 19 is a composition comprising:
(i) a bioconjugate of an *E. coli* glucosylated O4 antigen polysaccharide covalently linked to a detoxified Exotoxin A of *P. aeruginosa* (EPA-4 carrier protein) comprising SEQ ID NO: 3, wherein the *E. coli* glucosylated O4 antigen polysaccharide comprises the structure of Formula (O4-Glc+);
(ii) a bioconjugate of an *E. coli* O1A antigen polysaccharide covalently linked to an EPA-4 carrier protein, wherein the *E. coli* O1A antigen polysaccharide comprises the structure of Formula (O1A);
(iii) a bioconjugate of an *E. coli* O2 antigen polysaccharide covalently linked to an EPA-4 carrier protein, wherein the *E. coli* O2 antigen polysaccharide comprises the structure of Formula (O2);
(iv) a bioconjugate of an *E. coli* O6A antigen polysaccharide covalently linked to an EPA-4 carrier protein, wherein the *E. coli* O6A antigen polysaccharide comprises the structure of Formula (O6A);
(v) a bioconjugate of an *E. coli* O8 antigen polysaccharide covalently linked to an EPA-4 carrier protein, wherein the *E. coli* O8 antigen polysaccharide comprises the structure of Formula (O8);
(vi) a bioconjugate of an *E. coli* O15 antigen polysaccharide covalently linked to an EPA-4 carrier protein, wherein the *E. coli* O15 antigen polysaccharide comprises the structure of Formula (O15);
(vii) a bioconjugate of an *E. coli* O16 antigen polysaccharide covalently linked to an EPA-4 carrier protein, wherein the *E. coli* O16 antigen polysaccharide comprises the structure of Formula (O16);
(viii) a bioconjugate of an *E. coli* O25B antigen polysaccharide covalently linked to an EPA-4 carrier protein, wherein the *E. coli* O25B antigen polysaccharide comprises the structure of Formula (O25B); and
(ix) a bioconjugate of an *E. coli* O75 antigen polysaccharide covalently linked to an EPA-4 carrier protein, wherein the *E. coli* O75 antigen polysaccharide comprises the structure of Formula (O75),
wherein each of the structures of Formulas (O4-Glc+), (O1A), (O2), (O6A), (O8), (O15), (O16), (O25B), and (O75) is shown in Table 1, and each n is independently an integer of 1 to 100, preferably 3 to 50, e.g. 5 to 40, e.g. 7 to 25, e.g. 10 to 20.

Embodiment 20 is the composition of embodiment 19, further comprising:
(x) a bioconjugate of an *E. coli* O18A antigen polysaccharide covalently linked to an EPA-4 carrier protein, wherein the *E. coli* O18A antigen polysaccharide comprises the structure of Formula (O18A) shown in Table 1, and n is an integer of 1 to 100, preferably 3 to 50, e.g. 5 to 40, e.g. 7 to 25, e.g. 10 to 20.

Embodiment 21 is a method of inducing antibodies against an *E. coli* glucosylated O4 antigen in a subject, comprising administering to the subject the bioconjugate of any one of embodiments 1-5, or the composition or immunogenic composition of any one of embodiments 6-20.

Embodiment 22 is the method of embodiment 21, wherein the antibodies have opsonophagocytic activity.

Embodiment 23 is a method of vaccinating a subject against *E. coli*, in particular extra-intestinal pathogenic *E. coli* (ExPEC), comprising administering to the subject the bioconjugate of any one of embodiments 1-5, or the composition or immunogenic composition of any one of embodiments 6-20.

Embodiment 24 is the bioconjugate of any one of embodiments 1-5, or the composition or immunogenic composition of any one of embodiments 6-20 for use in inducing antibodies against an *E. coli* glucosylated O4 antigen.

Embodiment 25 is the bioconjugate of any one of embodiments 1-5, or the composition or immunogenic composition of any one of embodiments 6-20 for use in vaccination against extra-intestinal pathogenic E. coli (ExPEC).

Embodiment 26 is a recombinant host cell for producing a bioconjugate of an E. coli glucosylated O4 antigen polysaccharide covalently linked to a carrier protein, wherein the glucosylated O4 antigen polysaccharide comprises the structure of Formula (O4-Glc+) as shown in Table 1, wherein n is an integer of 1 to 100, preferably of 3 to 50, e.g. of 5 to 40, the host cell comprising:
(i) a nucleotide sequence of an rfb gene cluster for the E. coli O4 antigen polysaccharide;
(ii) a nucleotide sequence encoding a glucosyl transferase having at least 80% sequence identity to SEQ ID NO: 4, wherein the glucosyl transferase is capable of modifying the E. coli O4 antigen polysaccharide to produce the E. coli glucosylated O4 antigen polysaccharide;
(iii) nucleotide sequences encoding a translocase and a glycosyltransferase having at least 80% sequence identity to SEQ ID NOs: 7 and 8 respectively, wherein the translocase is capable of translocating bactoprenol-linked glucose and the glycosyltransferase is capable of glucosylating bactoprenol;
(iv) a nucleotide sequence encoding the carrier protein; and
(v) a nucleotide sequence encoding an oligosaccharyl transferase capable of covalently linking the E. coli glucosylated O4 antigen polysaccharide to the carrier protein to produce the bioconjugate.

Embodiment 27 is the recombinant host cell of embodiment 26, wherein:
the glucosyl transferase has the amino acid sequence of SEQ ID NO: 4;
the oligosaccharyl transferase comprises the amino acid sequence of SEQ ID NO: 6, preferably SEQ ID NO: 6 comprising the amino acid mutation N311V, more preferably SEQ ID NO:6 comprising the amino acid mutations Y77H and N311V; and
the carrier protein comprises at least one glycosylation site comprising a glycosylation consensus sequence having SEQ ID NO: 1, preferably having SEQ ID NO: 2.

Embodiment 28 is the recombinant host cell of embodiment 26 or embodiment 27, wherein the carrier protein is selected from the group consisting of detoxified Exotoxin A of P. aeruginosa (EPA), E. coli flagellin (FliC), CRM197, maltose binding protein (MBP), Diphtheria toxoid, Tetanus toxoid, detoxified hemolysin A of S. aureus, clumping factor A, clumping factor B, E. coli heat labile enterotoxin, detoxified variants of E. coli heat labile enterotoxin, Cholera toxin B subunit (CTB), cholera toxin, detoxified variants of cholera toxin, E. coli Sat protein, the passenger domain of E. coli Sat protein, Streptococcus pneumoniae Pneumolysin, Keyhole limpet hemocyanin (KLH), P. aeruginosa PcrV, outer membrane protein of Neisseria meningitidis (OMPC), and protein D from non-typeable Haemophilus influenzae.

Embodiment 29 is the recombinant host cell of any one of embodiments 26-28, wherein the carrier protein is a detoxified exotoxin A of Pseudomonas aeruginosa (EPA).

Embodiment 30 is the recombinant host cell of embodiment 29, wherein the EPA comprises 1-10, preferably 2-4, glycosylation sites each comprising a glycosylation consensus sequence having SEQ ID NO: 2.

Embodiment 31 is the recombinant host cell of embodiment 30, wherein the carrier protein is EPA with four glycosylation consensus sequences (EPA-4), preferably wherein the carrier protein comprises SEQ ID NO: 3.

Embodiment 32 is the recombinant host cell of any one of embodiments 26-31, which is an E. coli cell, e.g. an E. coli K-12 strain, such as strain W3110.

Embodiment 33 is a method of producing a bioconjugate of an E. coli glucosylated O4 antigen polysaccharide covalently linked to a carrier protein, wherein the E. coli glucosylated O4 antigen polysaccharide comprises the structure of Formula (O4-Glc+) as shown in Table 1, wherein n is an integer of 1 to 100, preferably of 3 to 50, e.g. of 5 to 40, the method comprising culturing the recombinant host cell of any one of embodiments 26-32 under conditions for production of the bioconjugate.

Embodiment 34 is the method of embodiment 33, further comprising isolating the bioconjugate from the recombinant host cell.

Embodiment 35 is a bioconjugate produced by the method of embodiment 33 or 34.

Embodiment 36 is a composition comprising the bioconjugate of embodiment 35.

Embodiment 37 is a method for making a recombinant host cell for producing a bioconjugate of an E. coli glucosylated O4 antigen polysaccharide covalently linked to a carrier protein, wherein the glucosylated O4 antigen polysaccharide comprises the structure of Formula (O4-Glc+) as shown in Table 1, wherein n is an integer of 1 to 100, preferably of 3 to 50, e.g. of 5 to 40, the method comprising introducing one or more recombinant nucleic acid molecules into a cell to produce the recombinant host cell, wherein the recombinant host cell comprises:
(i) a nucleotide sequence of an rfb gene cluster for the E. coli O4 antigen polysaccharide;
(ii) a nucleotide sequence encoding a glucosyl transferase having at least 80% sequence identity to SEQ ID NO: 4, wherein the glucosyl transferase is capable of modifying the E. coli O4 antigen polysaccharide to produce the E. coli glucosylated O4 antigen polysaccharide;
(iii) nucleotide sequences encoding a translocase and a glycosyltransferase having at least 80% sequence identity to SEQ ID NOs: 7 and 8 respectively, wherein the translocase is capable of translocating bactoprenol-linked glucose and the glycosyltransferase is capable of glucosylating bactoprenol;
(iv) a nucleotide sequence encoding the carrier protein; and
(v) a nucleotide sequence encoding an oligosaccharyl transferase capable of covalently linking the E. coli glucosylated O4 antigen polysaccharide to the carrier protein to produce the bioconjugate.

Embodiment 38 is the method of embodiment 37, wherein:
the glucosyl transferase has SEQ ID NO: 4;
the oligosaccharyl transferase comprises the amino acid sequence of SEQ ID NO: 6, preferably SEQ ID NO: 6 comprising the amino acid mutation N311V; and
the carrier protein comprises at least one glycosylation site comprising a glycosylation consensus sequence having SEQ ID NO: 1, preferably having SEQ ID NO: 2.

Embodiment 39 is the method of embodiment 37 or embodiment 38, wherein the carrier protein is selected from the group consisting of detoxified Exotoxin A of P. aeruginosa (EPA), E. coli flagellin (FliC), CRM197, maltose binding protein (MBP), Diphtheria toxoid, Tetanus toxoid, detoxified hemolysin A of S. aureus, clumping factor A, clumping factor B, E. coli heat labile enterotoxin, detoxified variants of E. coli heat labile enterotoxin, Cholera toxin B subunit (CTB), cholera toxin, detoxified variants of cholera toxin, E. coli Sat protein, the passenger domain of E. coli Sat protein, Streptococcus pneumoniae Pneumolysin, Keyhole limpet hemocyanin (KLH), P. aeruginosa PcrV, outer membrane protein of Neisseria meningitidis (OMPC), and protein D from non-typeable Haemophilus influenzae.

Embodiment 40 is the method of any one of embodiments 37-39, wherein the carrier protein is a detoxified exotoxin A of *Pseudomonas aeruginosa* (EPA).

Embodiment 41 is the method of embodiment 40, wherein the EPA comprises 1-10, preferably 2-4, glycosylation sites each comprising a glycosylation consensus sequence having SEQ ID NO: 2.

Embodiment 42 is the method of embodiment 41, wherein the carrier protein is EPA with four glycosylation consensus sequences (EPA-4), preferably wherein the carrier protein comprises SEQ ID NO: 3.

Embodiment 43 is the method of any one of embodiments 37-42, wherein the cell is an *E. coli* cell, e.g. from an *E. coli* K12 strain, such as from a W3110 strain.

Embodiment 44 is a composition according to embodiment 19 or embodiment 20, wherein the bioconjugate of the O25B antigen polysaccharide is present in the composition at a concentration that is about 1.5-6 times, e.g. about 2 to 4 times, higher than the concentration of any of the other bioconjugates.

Embodiment 45 is a composition according to embodiment 44, wherein the bioconjugates of O1A:O2:glucosylated O4:O6A:O8:O15:O16:O25B:O75 are present in a ratio by weight of polysaccharide of 1:1:1:1:1:1:1:2:1, or 2:1:1:2:1:1:1:4:1.

Embodiment 46 is a composition according to embodiment 44, wherein the bioconjugates of O1A:O2:glucosylated O4:O6A:O8:O15:O16:O18A:O25B:O75 are present in a ratio by weight of polysaccharide of 1:1:1:1:1:1:1:1:2:1, or 2:1:1:2:1:1:1:1:4:1.

Embodiment 47 is a composition according to any one of embodiments 44 to 46, wherein a concentration of the bioconjugate of the O25B antigen polysaccharide is 2 to 50 μg/mL, preferably 8 to 40 μg/mL, e.g. 16-32 μg/mL.

EXAMPLES

The following examples of the invention are to further illustrate the nature of the invention. It should be understood that the following examples do not limit the invention and the scope of the invention is to be determined by the appended claims.

Example 1: Epidemiological Data of *E. coli* Infections

To determine the O-serotype distribution of bacteremia-causing *E. coli*, global surveillance studies were performed. Between 2011 and 2017, more than 3200 *E. coli* bloodstream isolates were collected from patients≥60 years of age hospitalized in countries within North America, Europe, the Asia-Pacific region, and South America. Each strain was analyzed for O antigen serotype using classical agglutination techniques and sequence-based O-genotyping. See Table 2.

Isolated human blood samples were analyzed to determine the identity of pathogens therein and their antibiotic resistance patterns. *E. coli* isolates were obtained from the samples following the analysis. *E. coli* identity was verified by MALDI-TOF MS. Further analysis on the *E. coli* isolates was performed using an antisera-based agglutination assay to determine their O-antigen serotype (DebRoy et al. (2011) Animal health research reviews/Conference of Research Workers in Animal Diseases 12, 169-185). Isolates un-typeable by the agglutination method, were further analyzed by whole-genome sequencing followed by O-genotyping based on O-serotype specific wzy and wzx gene sequences.

TABLE 2 distribution of the most common bacteremia-associated *E. coli* O-serotypes from a collection of 3217 blood isolates collected globally between 2011 and 2017, based on O-serotyping by agglutination plus O-genotyping of isolates un-typeable by agglutination. Subjects were hospitalized in the following countries: USA, Canada, Argentina, Brazil, UK, Germany, Spain, Italy, The Netherlands, France, Japan, Thailand, South Korea and Australia.

| O-serotype | Prevalence n (%) |
| --- | --- |
| O25 | 737 (22.9%) |
| O2 | 268 (8.3%) |
| O6 | 261 (8.1%) |
| O1 | 255 (7.9%) |
| O75 | 145 (4.5%) |
| O15 | 110 (3.4%) |
| O8 | 104 (3.2%) |
| O16 | 103 (3.2%) |
| O4 | 96 (3.0%) |
| O18 | 91 (2.8%) |

Stratification of on geographical location in the global set of bacteremia-associated *E. coli* showed a prevalence of the top 10 O-serotypes independent of location, suggesting these to be the predominant O-serotypes globally associated with bacteremia-causing *E. coli*.

In the global set of bacteremia-associated multi-drug resistant *E. coli* isolates (n=345), i.e. those strains that are resistant to at least three classes of clinically relevant antimicrobial drugs, the prevalence of the top 10 O-serotypes is 75.4%.

All information from epidemiology analysis taken together, the 10 predominant O-serotypes could cover an estimated 60-80% of *E. coli*-associated bacteremia infections, assuming coverage of subportions of the un-typeable strains.

A multivalent vaccine covering a significant proportion of bacteremia-causing *E. coli* serotypes would be very useful. The O-serotypes of Table 2 would thus be good candidates for an O-antigen based multivalent vaccine. Such a vaccine could beneficially be prepared using bioconjugation technology.

One of the serotypes in the top-10 (Table 2) is O4. It would thus be beneficial to prepare a bioconjugate vaccine that includes O-antigen polysaccharide of *E. coli* serotype O4 coupled to a carrier protein.

Example 2: Characterization of Contemporary O4 Clinical Isolates for Genes Encoding O-Antigen Modifying Enzymes Two variants of *E. coli* O4 antigen polysaccharide have been described (see, e.g. Jann B, et al., 1993, Carbohydr. Res. 248: 241-250), one having an unbranched structure (structure shown as (O4-Glc−) in Table 1) and another variant substituted with an additional glucose side-branch (structure shown as (O4-Glc+) in Table 1). The proportion in which these two variants are found in contemporary clinical isolates was not known. Although both variants react with O4 antisera, it was also not known whether immunological differences between these variants exist. Moreover, an enzyme responsible for attaching the glucose side-branch to generate the (O4-Glc+) antigen polysaccharide was hitherto not identified, and a putative coding sequence thereof is likely residing outside the O4 rfb gene cluster.

A set of 32 agglutination-confirmed *E. coli* O4 clinical isolates originally isolated during the period of 2011-2012 from subjects in the United States and the European Union were subjected to whole genome sequence analysis. Extracted rfb gene cluster sequences from the 32 sequenced O4 isolates were aligned with those of the reference strain and compared at the nucleotide level. Except for some naturally occurring single nucleotide polymorphisms, the characterized isolates all displayed an rfb cluster that was identical to the O4 reference strain, indicating that *E. coli* O4 strains, independent of their Glc-branching status, carry an identical rfb gene cluster. Thus, to generate the *E. coli* O4-Glc+ antigen polysaccharide, a gene with unknown sequence that encodes an *E. coli* O4-specific branching enzyme and that must reside somewhere outside of the *E. coli* O4 rfb gene cluster is likely needed. The sequence of this unknown gene needs to be identified and employed if one wants to produce bioconjugates with the *E. coli* O4-Glc+ antigen polysaccharides in a strain that would otherwise only produce bioconjugates with *E. coli* O4-Glc- antigen polysaccharides.

The whole-genome sequence data were then analyzed for the presence of genes outside of the rfb gene cluster that may encode O-antigen modifying enzymes. Homologs of gtrAB in *Shigella flexneri* were first identified in *E. coli* O4. An open reading frame downstream of gtrAB in *E. coli* was then putatively identified as the *E. coli* O4-specific gene gtrS, that could encode the putative *E. coli* O4 specific branching enzyme GtrS responsible for adding a glucose branch to the *E. coli* O4 antigen.

The amino acid sequence of the *E. coli* O4 specific GtrS enzyme is provided as SEQ ID NO: 4. An exemplary nucleic acid sequence encoding this protein is provided as SEQ ID NO: 5.

Of the characterized *E. coli* O4 isolates, approximately 80% were found to carry the here identified gtrS gene (26 out of 32). Prevalence of the *E. coli* O4-specific gtrS sequence was also determined by PCR using sequence specific primers in an independent set of 20 agglutination-confirmed *E. coli* O4 clinical isolates isolated during the period of 2014-2016 from subjects in the United States and the European Union. This analysis demonstrated that 17 out of 20 isolates carried the O4 gtrS sequence, which corresponds to a prevalence of 85%.

Example 3: Cloning of O4 gtrS into *E. coli* W3110, Production and Structural Confirmation of Glc-Modified O4 Bioconjugates To test whether bioconjugates comprising O4-antigen polysaccharide modified with a branching glucose could be prepared, *E. coli* O4-antigen EPA bioconjugate production strains with the putative branching enzyme were constructed. For this, the endogenous O16-gtrS gene was substituted by the putative O4-gtrS gene (SEQ ID NO: 5, see Example 2) and the O16 rfb cluster was replaced with the O4 rfb cluster in *E. coli* strain W3110 ΔwzzE-wecG ΔwaaL ΔwbbI-J-K by homologous recombination. Alternatively, in some strains, the O4 rfb cluster was encoded on a plasmid.

Subsequently, plasmids encoding a detoxified exotoxin A of *Pseudomonas aeruginosa* (EPA) carrier protein (a variant either having 2 or 4 consensus glycosylation sites, referred to as 'EPA-2' and 'EPA-4', respectively), and oligosaccharyl transferase PglB were introduced into the strains. O4-EPA bioconjugates modified with Glc were produced by growing the *E. coli* production strains in bioreactor cultures, and induction of PglB and EPA expression by IPTG and arabinose, respectively. The O4-EPA bioconjugates were extracted from the biomass periplasmic extract.

To confirm the detailed polysaccharide composition and linkage of the O4-EPA bioconjugates, multiple NMR experiments were performed on the bioconjugates having EPA-4 carrier protein (data not shown). The assignments obtained agreed with literature published (Jansson, P. E., et al., 1984, Carbohydr. Res. 134(2): 283-291; Jann B, et al., 1993, Carbohydr. Res. 248: 241-250). The 1D spectrum recorded at 313K showed a large HOD signal and small sharp signals from the O4 pentasaccharide RU with five anomeric, two NAc and two H6 signals (Rha and FucNAc).

The 1D proton assignments were confirmed by use of 2D proton-proton and proton-carbon correlation NMR experiments. First, 2D TOCSY (120 ms) experiments demonstrated the expected cross peaks from H1 and H6 (for Rha and FucNAc) for the O4 pentasaccharide RU and small peaks from the terminal RU and EPA. In the methyl region, TOCSY showed cross peaks from H6 to H1 for α-Rha and H6 to H5 for α-FucNAc for the O4 RU. Other peaks observed were from EPA amino acids and terminal Rha (tRha). Second, a carbon NMR spectrum contained well-dispersed and diagnostic single peaks for the O4 RU. The carbons were profiled indirectly through the attached protons by use of the HSQC experiment. The HSQC-DEPT experiment gave inverted peaks for $CH_2$ groups. The HSQC gave cross peaks for the O4 pentasaccharide RU [5 anomeric, ring, two N-acetyl and two methyl (Rha & FucNAc)] groups as well as EPA amino acids in characteristic regions. Each of the proton/carbon pairs for the O4 could be assigned based on the proton assignments and literature.

The structural characterization experiments thus confirmed that Glc-branched O4 bioconjugates (comprising polysaccharide antigen structures as indicated by Formula (O4-Glc+) in Table 1) could be produced, using the putative *E. coli* O4-gtrS gene identified in Example 2.

Example 4: Immunogenicity of a Glc-Branched O4 Bioconjugate in Rabbits

Glc-modified O4 bioconjugates (i.e. having glycans with the structure of Formula (O4-Glc+) as shown in Table 1) were used for rabbit immunization by applying a speedy-rabbit protocol (Eurogentec). Sera from immunized rabbits were analyzed by ELISA for anti-O4 IgG titers against purified O4 lipopolysaccharide (LPS) with (Glc+; i.e. containing glucosylated O4 polysaccharide) or without Glc-branching (Glc−; i.e. containing non-glucosylated O4 polysaccharide). Immunization with the bioconjugate resulted in high IgG titers in both rabbits (FIG. 1). In both cases, antibody titers induced by the O4 bioconjugate were higher against Glc+ LPS as compared to Glc− LPS.

Figure 2:
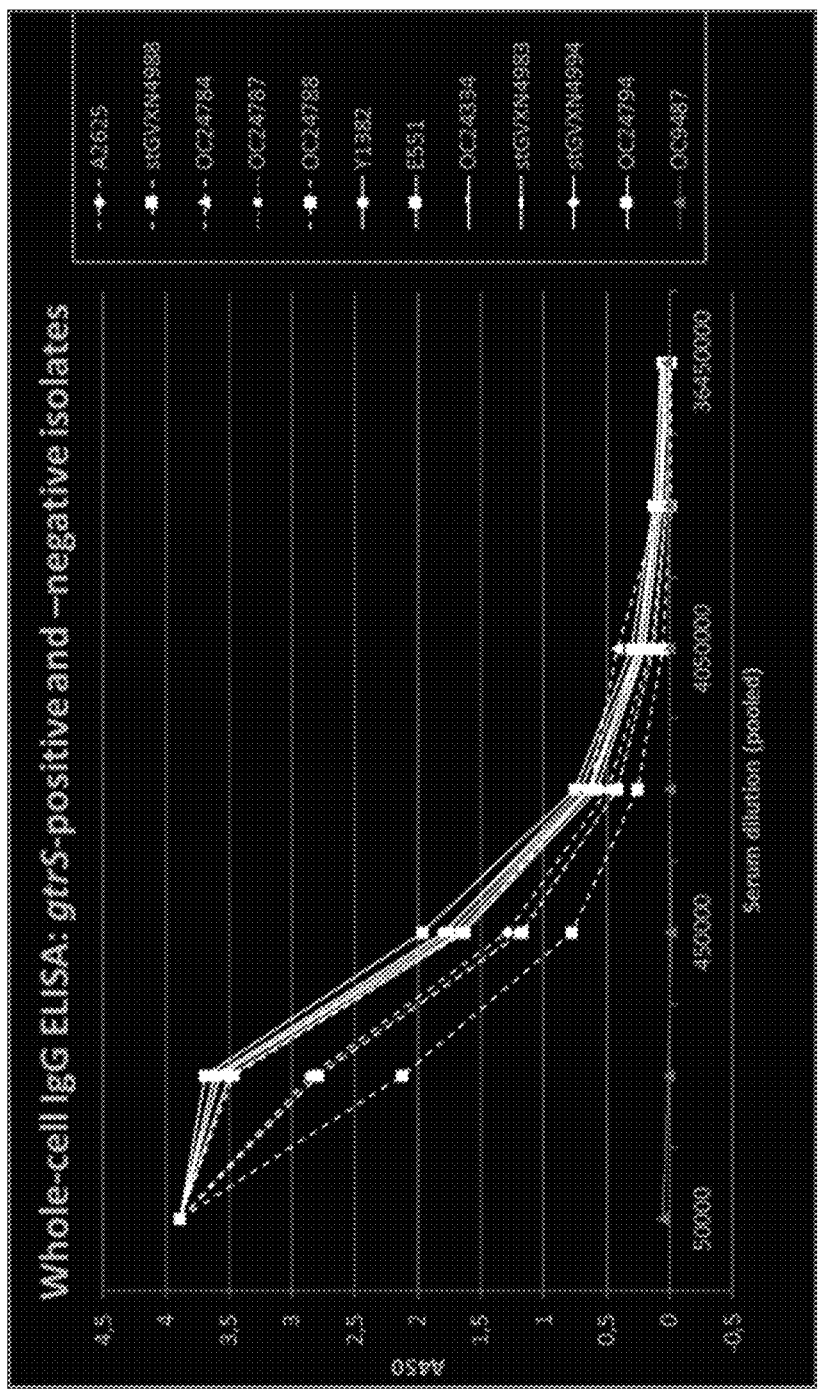
FIG. 2 shows IgG titers in whole cell ELISAs with pooled sera from rabbits immunized with a Glc-modified O4 bioconjugate against *E. coli* O4 isolates with characterized gtrS status as described in Example 4; the following isolates were gtrS-negative: A2625, stGVXN4988, OC24784, OC24787 and OC24788; the following isolates were gtrS-positive: Y1382, E551, OC24334, stGVXN4983, stGVXN4994 and OC24794; the negative control strain OC9487 (ATCC 35383; serotype O75) was also included.

Sera were also pooled and used in whole cell ELISA studies with test sets of *E. coli* O4 isolates with characterized gtrS status. Five gtrS-negative (no Glc-branching) and six gtrS-positive (Glc-branching) *E. coli* O4 isolates and a negative control strain were tested. Pooled sera from rabbits immunized with a Glc-modified O4 bioconjugate contained high titers of IgG specifically recognizing the tested O4 isolates (FIG. 2). In concordance with the LPS ELISA, all tested O4 isolates were recognized by the immune sera. The gtrS-positive isolates displayed an overall higher binding than the gtrS-negative isolates (FIG. 2). In particular, the following isolates were gtrS-positive: Y1382, E551, OC24334, stGVXN4983, stGVXN4994 and OC24794, and the following isolates were gtrS-negative: A2625, stGVXN4988, OC24784, OC24787, and OC24788. Immune sera did not bind the negative control strain of a non-related O-serotype, *E. coli* OC9487 (ATCC 35383).

The profiles of LPS extracted from the test set of gtrS-positive and -negative isolates in silver-stained polyacrylamide gels did not reveal marked differences between isolates expressing unmodified and modified forms of the O4 antigen confirming that the observed differences are not explained by quantitative differences in LPS expression levels (data not shown).

Figure 3:
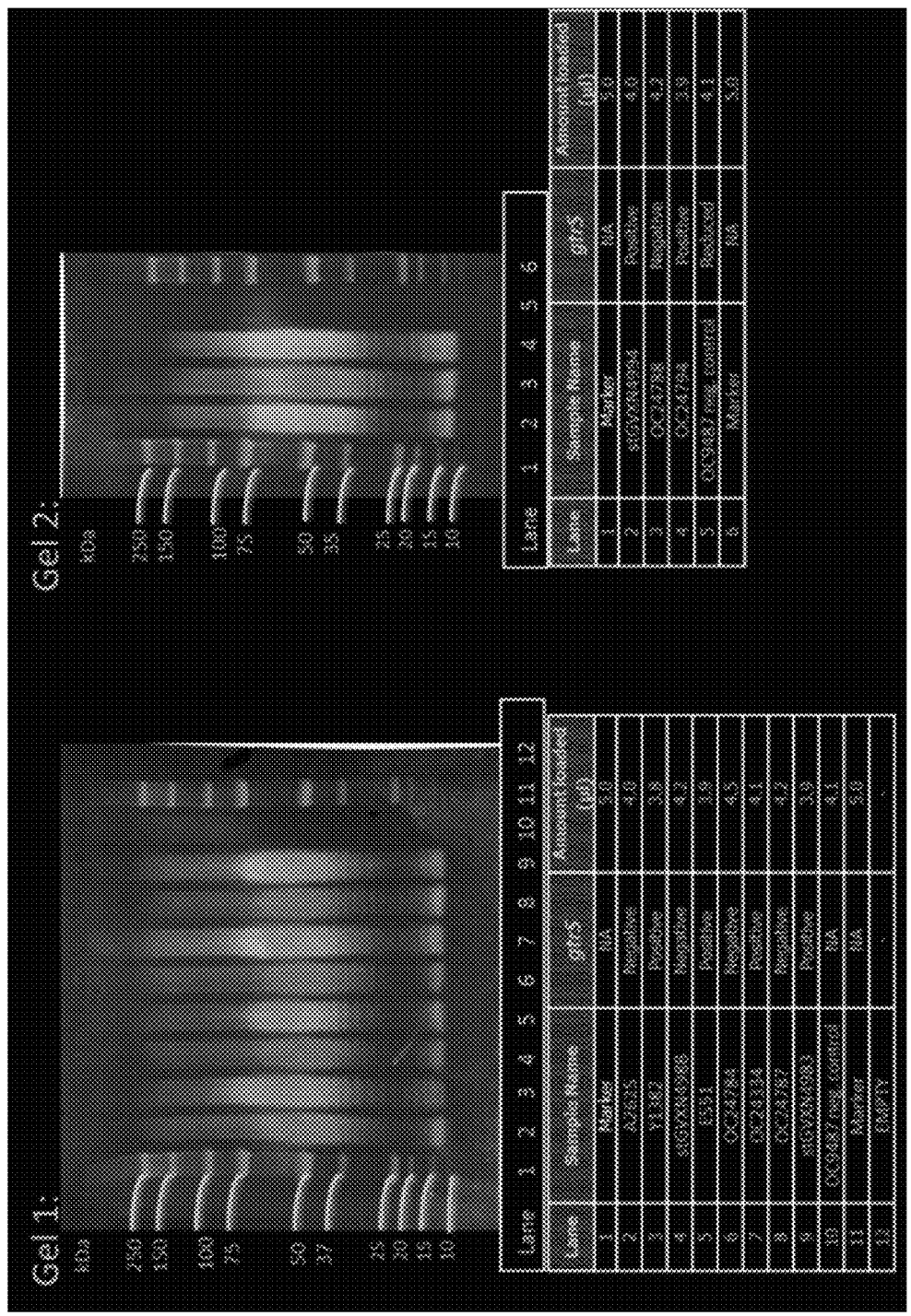
FIG. 3 shows Western blots of LPS extracted from gtrS-positive and -negative O4 isolates probed with pooled sera from rabbits immunized with modified O4 polysaccharide.

Western blots of extracted LPS using pooled immune sera were performed to assess recognition of O4 O-antigen by IgGs elicited in response to immunization with a Glc-modified O4 bioconjugate. Binding of both modified and unmodified O4 LPS by IgGs from modified O4 immunized rabbits was observed and included specific recognition of LPS bands spanning a wide range of sizes, including high molecular weight LPS bands (FIG. 3).

In the further experiments below, when reference is made to 'O4' bioconjugate or production strains or 'EcoO4', the bioconjugate or production strain of Glc-branched O4 (having glycan structure (O4-Glc+) in Table 1) is meant, unless specifically indicated otherwise (the terms 'O4' and 'O4-Glc+' are thus used interchangeably for bioconjugates or production strains in those experiments).

Example 5: Immunogenicity of a Glc-Branched O4 Bioconjugate in Rats

Sprague Dawley rats were immunized intramuscularly 3 times with formulation buffer or (O4-Glc+)-EPA bioconjugate (i.e. bioconjugate of glucosylated O4 antigen polysaccharide covalently coupled to EPA carrier protein; carrier protein was EPA-2 as described in Example 3 above) at 3 different doses (0.04 µg, 0.40 µg or 4.0 µg). Serum antibody levels were measured by ELISA at day 0, 14 and 42 post-immunization.

Figure 4A:
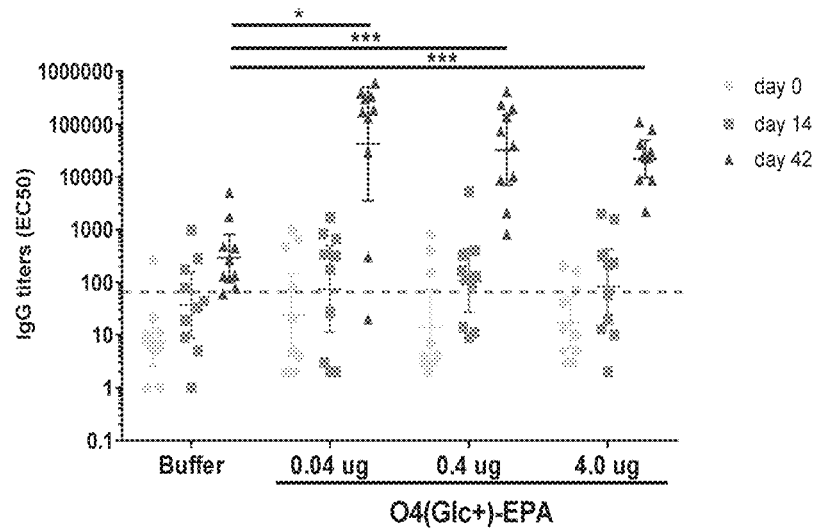
FIGS. 4A and 4B show antibody responses induced by glucosylated O4 (O4-Glc+)-EPA bioconjugates.
Figure 4B:
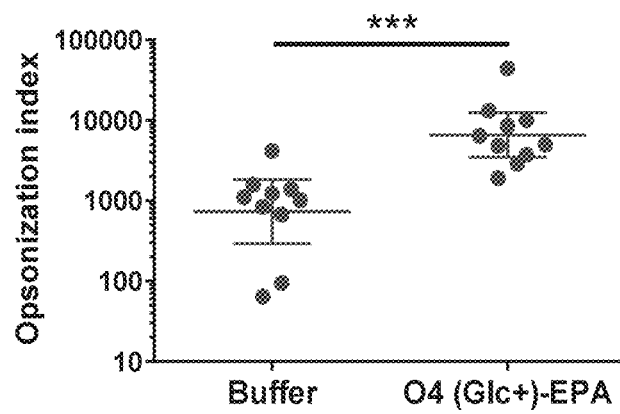

Immunization with 0.04 µg, 0.40 µg and 4.00 µg of (O4-Glc+)-EPA bioconjugate induced significant increase in the levels of IgG antibodies at day 42 post-immunization when compared to formulation buffer (FIG. 4A). The antibodies induced by (O4-Glc+)-conjugate were functional, i.e., capable of mediating killing of (O4-Glc+) E. coli strain (FIG. 4B).

Figure 5:
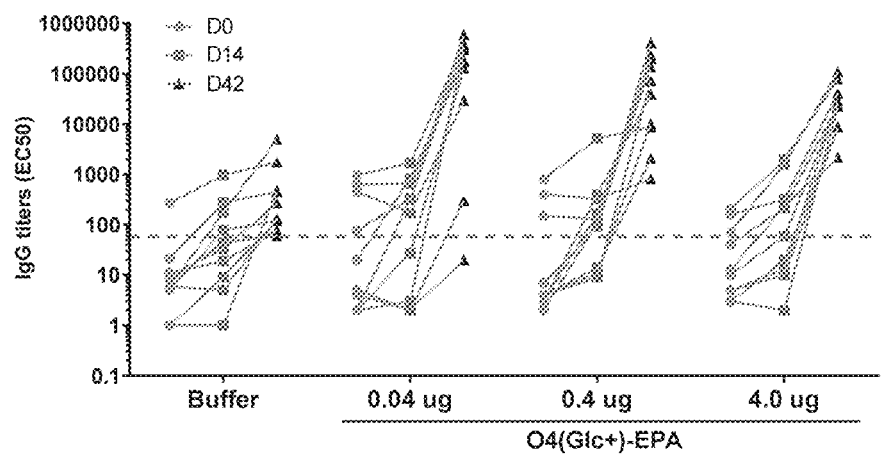
FIG. 5 shows the boost effect of glucosylated O4 (O4 Glc+)-EPA bioconjugate in Sprague Dawley rats immunized at 3 different doses as described in Example 4; serum antibody levels were measured by ELISA at day 0, 14 and 42 post-immunization; individual titers (log 10 EC50 titer) are shown for each animal; the lines between the data points connect IgG titers for each animal in time; the grey dotted line indicates the threshold above which the dilution curves of the samples have a 4PL fitting; statistical analysis was performed with Wilcoxon signed-rank test and Bonferroni correction for multiple comparisons (day 14 vs day 0, P=0.012 for 4.0 µg/dose; day 42 vs day 0, P=0.006 for all doses; day 42 vs day 14, P=0.006 for all doses)

Antibody levels induced by 0.04 µg, 0.40 µg and 4.0 µg of (O4-Glc+)-EPA bioconjugate were significantly increased at day 42 as compared to those detected at baseline (day 42 vs day 0, P=0.006 for all doses) and at day 14 post-immunization (day 42 vs day 14, P=0.006 for all doses) (FIG. 5). In the group that received 4.0 µg of bioconjugate, titers were also significantly increased at day 14 compared to day 0, indicating that a single dose of 4.0 µg of (O4-Glc+)-EPA bioconjugate induces significant increase in IgG titers (day 14 vs day 0, P=0.012). The significant increase in IgG titers observed between day 14 and 42, for all three concentrations of bioconjugate tested showed that a third dose of (O4-Glc+)-EPA bioconjugate is able to boost antibody responses (FIG. 5).

Figure 6:
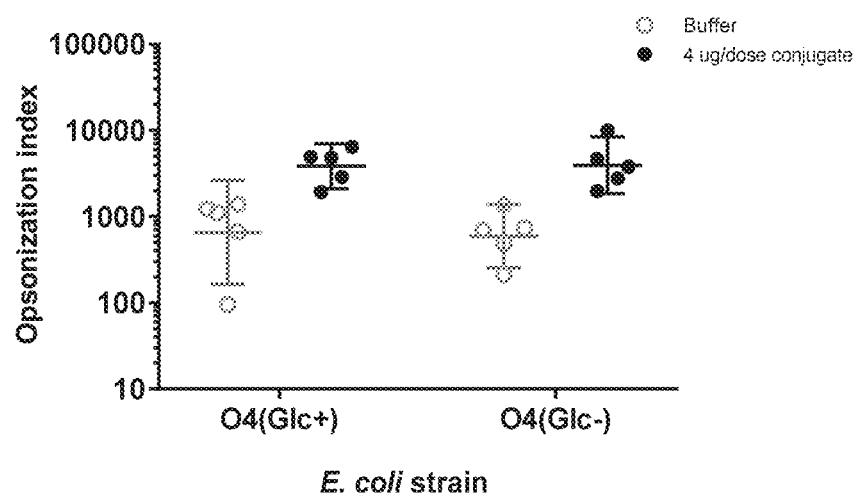
FIG. 6 shows the functionality of antibodies induced by O4-Glc+-EPA bioconjugate; Sprague Dawley rats were immunized intramuscularly 3 times with formulation buffer or O4(Glc+)-EPA bioconjugate at 4.00 µg/dose; functionality of the antibodies was determined by opsonophagocytic killing assay (OPKA) using O4(Glc+) and O4(Glc−) *E. coli* strains; individual opsonic titers (O1) and GMT±95% CI are shown.

Functionality of antibodies induced by O4-Glc+-EPA conjugate in the rats immunized intramuscularly 3 times with formulation buffer or the bioconjugate at 4.00 µg/dose was determined by opsonophagocytic killing assay (OPKA) using O4(Glu+) and O4(Glu−) E. coli strains. The antibodies induced by (O4-Glc+)-EPA bioconjugate were functional, i.e., capable of mediating killing of an (O4-Glc+) E. coli strain (FIG. 4B, FIG. 6). Notably, antibodies induced by (O4-Glc+)-EPA bioconjugate were capable of mediating killing of both (O4-Glc+) and (O4-Glc−, i.e. having glycans with structure of Formula (O4-Glc−) in Table 1, i.e. O4 polysaccharide without Glc-branching) E. coli strains (FIG. 6).

In conclusion, antibodies induced by O4-Glc+-EPA bioconjugate are cross-reactive and capable of mediating killing of E. coli O4 strains with and without glucose branching.

Example 6: Production Strains for E. coli O-Antigen Bioconjugates and Resulting Bioconjugate Products In addition to (O4-Glc+)-EPA bioconjugates prepared as described above, nine (9) other bioconjugates were produced. In particular, the additionally produced bioconjugates included E. coli O1A-EPA bioconjugate, O2-EPA bioconjugate, O6A-EPA bioconjugate, O8-EPA bioconjugate, O15-EPA bioconjugate, O16-EPA bioconjugate, O18A-EPA bioconjugate, O25B-EPA bioconjugate, and O75-EPA bioconjugate. The chemical structures of the glycans of these conjugates can be seen in the respective Formulas in Table 1. A composition comprising the 10 bioconjugates is referred to herein as 'ExPEC10V'. A composition comprising the O1A-EPA, O2-EPA, O6A-EPA and O25B-EPA bioconjugates is referred to as 'ExPEC4V' (and was previously described in for instance WO 2015/124769 and WO 2017/035181).

*Escherichia coli* W3110 Parental Strain

The non-pathogenic E. coli K12 strain W3110 was used as the parental strain for the construction of all ten production strains. The E. coli K12 strain W3110 was obtained from the Coli Genetic Stock Center (Yale University, New Haven (Conn.), USA, product number CGSC #4474). Its relevant genotype was previously described (E. coli W3110, F-, lambda-, IN(rrnD-rrnE)1, rph-1) and its genomic sequence was previously published (Hayashi K, et al., 2006, Mol. Syst. Biol. 2006.0007 (doi:10.1038/msb4100049). The E. coli W3110 strain was genetically modified to enable production of each of the E. coli O-antigen bioconjugates (Table 3).

Bioconjugate Production Strains

The "ExPEC4V" and "ExPEC10V" compositions both comprise the O2-EPA and O25B-EPA bioconjugates from the same production strains. The "ExPEC4V" composition comprises the O1A-EPA bioconjugate from the stGVXN4411 or stLMTB10217 production strains, while the "ExPEC10V" composition comprises the O1A-EPA bioconjugate from the stLMTB10217 production strain. The "ExPEC4V" composition comprises the O6A-EPA bioconjugate from the stGVXN4112 production strain, while the "ExPEC10V" composition comprises the O6A-EPA bioconjugate from the stLMTB10923 production strain. Furthermore, the "ExPEC10V" composition comprises the O4-EPA (i.e. (O4-Glc+)-EPA), O8-EPA, O15-EPA, O16-EPA, O18A-EPA, and O75-EPA bioconjugates from production strains that are not used for "ExPEC4V". Different production strains could vary in the plasmids for expression of the EPA carrier protein and/or the oligosaccharyl transferase PglB, as indicated below. An overview of several production strains is given in Table 3 below.

TABLE 3

Overview of genetic engineering of E. coli production strains for
O-antigen bioconjugates for ExPEC4V and ExPEC10V vaccine compositions

| | | Genomic mutations | | | Plasmids | |
| --- | --- | --- | --- | --- | --- | --- |
| Serotype | Strain name | rfb gene cluster | waaL | gtrABS | pglB | epa |
| O1A (ExPEC4V) | stGVXN4411 | Δrfb::O1A rfb upecGVXN_032 | ΔwaaL | — | pGVXN970 | pGVXN1076 |
| O1A (ExPEC4V; ExPEC10V) | stLMTB10217 | Δrfb::O1A rfb upecGVXN_032 | ΔwaaL | — | pGVXN1221 | pGVXN1076 |
| O2 | stGVXN4906 | Δrfb::O2 rfb upecGVXN_116 | ΔwaaL | — | pGVXN971 | pGVXN1076 |
| O4 | BVEC-L-00684 | Δrfb::O4 rfb CCUG11450 | ΔwaaL | ΔgtrS::gtrS O4 | pGVXN1217 | pGVXN1076 |
| O6A (ExPEC4V) | stGVXN4112 | Δrfb::O6A rfb CCUG11309 | ΔwaaL | — | pGVXN114 | pGVXN659 |
| O6A (ExPEC10V) | stLMTB10923 | Δrfb::O6A rfb CCUG11309 | ΔwaaL | — | pGVXN1221 | pGVXN1076 |
| O8 | stLMTB11734 | Δrfb::O8 rfb E2420 | ΔwaaL | ΔgtrABS | pGVXN970 | pGVXN1076 |
| O15 | stLMTB11738 | Δrfb::O15 rfb OC24891 | ΔwaaL | ΔgtrABS | pGVXN1221 | pGVXN1076 |
| O16 | stLMTB11739 | Δrfb::O16 rfb OC24208 | ΔwaaL | ΔgtrABS | pGVXN2381 | pGVXN1076 |
| O18A | BVEC-L-00559 | Δrfb::O18A rfb OC24255 | ΔwaaL | ΔgtrABS | pGVXN970 | pGVXN1076 |
| O25B | stGVXN4459 | Δrfb::O25B rfb upecGVXN_138 | ΔwaaL | ΔgtrABS | pGVXN970 | pGVXN1076 |
| O75 | stLMTB11737 | Δrfb::O75 rfb CCUG31 | ΔwaaL | ΔgtrABS | pGVXN1217 | pGVXN1076 |

O-Antigen Biosynthesis (rfb) Gene Cluster

In all E. coli O-antigen production strains, the naturally occurring E. coli W3110 genomic O16::IS5-antigen biosynthesis (rfb) gene cluster was replaced by the selected O-antigen-specific biosynthesis clusters from E. coli strains of the selected serotype, encoding for the serotype-specific O-antigen structures (see Table 1 for these O-antigen structures). The ten donor rib clusters were selected or confirmed after whole-genome analysis of E. coli blood isolates. Replacement of the W3110 O16::IS5 rib gene cluster, which is defective in O-antigen biosynthesis, has been achieved in a single homologous recombination event. In case of the O16 and O18A rib gene clusters, the donor DNA recombined via the flanking gnd and rmlCA genes, while the rib gene cluster for the other strains recombined via the flanking gnd and galF genes. Sequences of the rib clusters in the production strains are provided in SEQ ID NOs: 9 and 11-19.

O-Antigen Ligase (waaL) Gene

All E. coli O-antigen production strains carry an artificially introduced deletion of the E. coli W3110 genomic O-antigen ligase encoded by the waaL gene. In the ΔwaaL strains the transfer of the O-antigen to lipid A is disrupted, which instead directs transfer of the O-antigen to the carrier protein to increase product yield.

O-Antigen Glucosylation (gtrABS) Genes

In the E. coli O8, O15, O16, O18A, O25B, and O75 production strains the E. coli W3110 genomic gtrABS genes, which are responsible for O16 O-antigen glucosylation, have been deleted. While the gtrA and gtrB genes in different serotypes are highly homologous and interchangeable, the gtrS gene encodes a serotype-specific O-antigen glycosyl transferase. In E. coli W3110 GtrS can transfer a glucose (Glc) residue to the GlcNAc sugar in the α-L-Rha-(1→3)-D-GlcNAc motif of the E. coli O16 O-antigen. In the E. coli O1A, O2 and O6A production strains no deletion or replacement of the gtrABS gene has occurred. These O-antigens miss the α-L-Rha-(1→3)-D-GlcNAc motif that is the natural substrate for E. coli O16 gtrS. In the E. coli O4 production strain, the W3110 gtrS gene has been replaced with the E. coli O4 gtrS gene to accommodate proper glucosylation of the E. coli O4 O-antigen.

Oligosaccharyl Transferase PglB

All E. coli O-antigen production strains expressed a variant of the C. jejuni glycosyl transferase PglB, which can transfer the O-antigen onto an amino acid consensus sequence on a carrier protein by N-glycosylation. PglB has broad substrate recognition, but due to low product yields several production strains were prepared expressing a PglB variant having modified substrate specificities, which resulted in improved product yield (see e.g. WO 2016/107818, WO 2016/107819). The pglB gene was placed behind an Isopropyl β-D-1-thiogalactopyranoside (IPTG) inducible promoter on a plasmid. Table 4 below lists the PglB variants encoded by the plasmids used for production of the E. coli O-antigen production strains for the bioconjugates for the ExPEC4V and ExPEC10V compositions described above. Further plasmids with variation in vector backbone, antibiotic resistance marker, and/or alternative PglB variants have also been tested successfully for bioconjugate production.

TABLE 4

PglB and EPA plasmids used in E. coli O-antigen Production Strains

| Plasmid name | Gene | Description[1] |
| --- | --- | --- |
| pGVXN114 | PglB | C. jejuni codon usage; SpR |
| pGVXN970 | pglB | E. coli codon usage optimized; SpR |
| pGVXN971 | pglB$^{N534Q}$ | E. coli codon usage optimized; The natural glycosylation site of PglB was inactivated; SpR |

TABLE 4-continued

PglB and EPA plasmids used in E. coli O-antigen Production Strains

| Plasmid name | Gene | Description[1] |
|---|---|---|
| pGVXN1217 | pglB$^{N311V}$ | E. coli codon usage optimized; Substrate optimized PglB; SpR |
| pGVXN1221 | pglB$^{N311V, K482R, D483H, A669V}$ | E. coli codon usage optimized; Substrate optimized PglB; SpR |
| pGVXN2381 | pglB$^{Y77H, S80R, Q287P, K289R, N311V}$ | E. coli codon usage optimized; Substrate optimized PglB; SpR |
| pGVXN659 | EPA-4 | EPA with four bioconjugation sites; AmpR |
| pGVXN1076 | EPA-4 | EPA with four bioconjugation sites; KanR |

[1]SpR, spectinomycin resistant;
AmpR, ampicillin resistant;
KanR, kanamycin resistant Carrier Protein (EPA)

All E. coli O-antigen production strains expressed a genetically detoxified P. aeruginosa ADP-ribosyltransferase toxoid (EPA) as a carrier protein for the O-antigen. The EPA toxoid differs from wild-type EPA toxin in two residues: Leu552 was changed to Val and Glu553 (in the catalytic domain) was deleted. Glu553 deletions were reported to significantly reduce toxicity. In addition to the detoxification mutation, four (EPA-4) consensus N-glycosylation site motifs were introduced. The epa gene was placed behind a L-Arabinose (Ara) inducible promoter on a plasmid (Table 4). Table 4 is limited to the plasmids used in production strains for bioconjugates used in the "ExPEC4V" and "ExPEC10V" compositions described above. Plasmids with variation in vector backbone, antibiotic resistance marker, and/or EPA variants, e.g. varying in the number of consensus N-glycosylation site motifs (e.g. having two such motifs, EPA-2), have also been tested successfully for bioconjugate production.

Example 7: Optimizing the Oligosaccharyltransferase for Generation of Bioconjugates with Glucosylated O4 (O4-Glc+) Antigen Yield optimization for bioconjugate production can be achieved by modification of the C. jejuni oligosaccharyl transferase PglB, which can lead to a more efficient or higher degree of N-glycosylation of the O-antigen of interest to the EPA carrier protein. In an E. coli strain for production of bioconjugate with glucosylated O4 (O4-Glc+) O-antigen polysaccharide, such optimization strategy was applied and resulted in an (O4-Glc+)-specific optimized PglB variant improving bioconjugate product yield.

In this approach, an O4-Glc+O-antigen polysaccharide producing strain containing an EPA-expression plasmid was transformed with a variety of different PglB expression plasmids, each of which contained different amino acid substitutions in the PglB protein, altering substrate specificity. Bioconjugate production level and profile of each strain was assessed at shake-flask level in osmotic shock experiments, and readout was performed by capillary electrophoresis immunoassays on the periplasmic extract using O4-Glc+-specific monoclonal antibodies.

Figure 7:
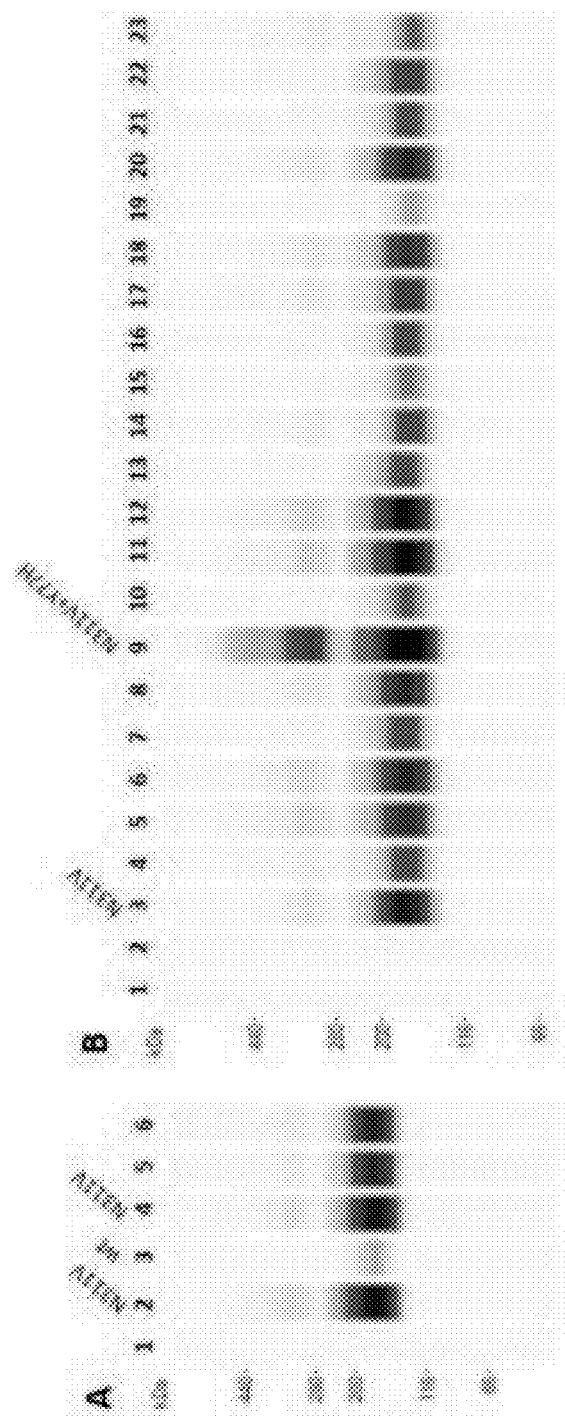
FIG. 7 shows capillary electrophoresis readout of PglB screen visualizing O4-Glc+ bioconjugate production for each tested strain in a blot-like image, using monoclonal antibodies to detect O4-Glc+ bioconjugate in the periplasmic fraction. Mono-glycosylated product approximately 180 kDa, di-glycosylated product approximately 320 kDa and tri-glycosylated product approximately 450 kDa. A) First screening round. Wt PglB in lane 3, N311V-PglB in lanes 2 and 4, empty control strain in lane 1 and other PglB variants in lanes 5 and 6. B) Second screening round. N311V PglB in lane 3, N311V+Y77H PglB in lane 9, empty control strain in lanes 1 and 2, other PglB variants in remaining lanes.

One of the tested PglB variants containing an N311V amino acid substitution was found to improve product yield of glucosylated O4 bioconjugates significantly (FIG. 7A).

In a further improvement where the N311V PglB-variant was further modified, an Y77H amino acid substitution further enhanced O4-Glc+-specific product yield and showed an increased degree of di- and tri-glycosylated product compared to the N311V PglB-variant, where other modifications were found to be neutral or had a negative effect on product yield (FIG. 7B). Plasmid pLMTB4008 (SpR) encodes E. coli codon usage optimized, (O4-Glc+)-substrate optimized, PglB variant with mutations Y77H and N311V.

The PglB variant with optimized substrate specificity for O4-Glc+O-antigen polysaccharide, containing N311V and Y77H amino acid substitutions relative to wild-type (wt) C. jejuni glycosyl transferase PglB, was found to double bioconjugate yield compared to the first round optimized PglB-N311V variant.

Similarly using screens, the most optimal yielding PglB variants were also determined for E. coli O-antigen bioconjugate production of the of the other nine serotypes in the ExPEC10V composition.

For bioconjugates having the O1A, O6A, or O15 antigen polysaccharide, PglB with amino acid mutations N311V, K482R, D483H, and A669V was found to give the highest yields.

For bioconjugates having the O2, O8, O18A, or O25B antigen polysaccharide, wild-type PglB (i.e. not having amino acid mutations at positions 77, 80, 287, 289, 311, 482, 483 and 669) was found to give the highest yields.

For bioconjugates having the O16 antigen polysaccharide, PglB with amino acid mutations Y77H, S80R, Q287P, K289R, and N311V was found to give the highest yields.

For bioconjugates having the O75 antigen polysaccharide, PglB with amino acid mutation N311V was found to give the highest yields.

It can be seen from these results that the optimal PglB variant is different for different O-antigens, and that the optimal PglB variant for producing a bioconjugate with a given O-antigen polysaccharide is unpredictable.

Example 8: Bioconjugates of O-Antigens from 10 E. coli Serotypes and their Quality Attributes O-glycan residues of the target O-antigens are structurally diverse and have variable repeating units. The specificity and affinity of the glycosyl transferase PglB is linked to the glycan structure. Thus, making a bioconjugate that has the desired quality attributes, e.g., purity, glycan/protein ratio, etc., is a challenging, non-straightforward, task. The right combination of PglB and EPA carrier protein determines the yield and may influence glycosylation efficiency. By optimizing the PglB and carrier proteins, bioconjugates having the desired quality attributes were produced. It may be also important to maintain a lower threshold value of total carrier protein, particularly when one or more O-antigen bioconjugates are combined together and administered in a single composition or vaccine, because very high amounts of carrier protein may lead to immunological interference. In order to avoid such a phenomenon, conjugates having a higher glycan/protein ratio are preferred. Hence, for ExPEC10V vaccine, bioconjugates with at least comparable (to the previously described ExPEC4V vaccine that has been subject to clinical trials) glycosylation ratio were developed.

The bioconjugates were each produced by culturing the respective host cells (Example 6, Table 3) in bioreactors (10 L and/or 200 L volumes) and expression of the bioconjugates, following methods previously described. Each drug substance was manufactured batch-wise by bacterial fed-batch fermentation to generate biomass containing the expressed bioconjugates of the corresponding polysaccharide serotype. Cells were cultured and induced with IPTG and arabinose. The bioconjugates were isolated from the periplasm of the cells in the bioreactor cultures by osmotic shock followed by chromatographic purification. This process was performed for each of the 10 bioconjugates.

The E. coli O-antigen bioconjugates thus prepared that are drug substances (DSs) for ExPEC10V and ExPEC4V showed comparable critical quality attributes: (1) process-related purity (measured by RP-HPLC) was higher than 95%, (2) polysaccharide/protein ratio ranged between about 0.1-0.5, mostly between 0.15 and 0.45, (3) bacterial endotoxin (Ph. Eur. 2.2.3) was less than 0.5 EU/µg polysaccharide. The average length of the individual polysaccharide chains was typically between about 10-20 repeating units (measured using high resolution SDS-PAGE).

The structures of the polysaccharide repeat units were confirmed (by NMR and MS/MS of the conjugates, intact or trypsin-digested) to be the ones shown in the Formulas for the corresponding serotypes in Table 1, for all ten bioconjugates that are DSs for the ExPEC10V composition described above.

The O18 serotype had the lowest yields of bioconjugate production amongst the ten serotypes of which bioconjugates were made for the ExPEC10V composition.

ExPEC10V drug product (DP) comprises a mixture of the ten monovalent DSs described above.

Example 9: Toxicology of ExPEC10V Vaccine

A single-dose pilot toxicity and local tolerance study (non-GLP) with ExPEC10V was conducted in female NZW rabbits. One group (n=2) received an intramuscular (IM) injection (on Day 0) of the control (saline), and a second group (n=4) received an IM injection of ExPEC10V at 105.6 µg total polysaccharide (PS)/dose (9.6:9.6:9.6:9.6:9.6:9.6: 9.6:9.6:19.2:9.6 µg PS per dose, for respectively O-serotypes O1A, O2, O4, O6A, O8, O15, O16, O18A, O25B and O75) using a dosing volume of 0.6 mL (176 µg PS/mL). Necropsy was performed on Day 2.

There were no mortalities observed. In addition, there were no vaccine-related effects noted for clinical observations (including injection site effects using Draize scoring), body weight, food consumption, and body temperature. Histopathologically, there were no vaccine-related changes observed at the administration site or draining (iliac) lymph node. A minimal increase in germinal center formation in the spleen was observed in one out of four treated animals (Day 2), and was considered a normal, immunological response to the injected vaccine. Overall, the administration of a single IM dose of ExPEC10V to female rabbits was well-tolerated.

Example 10: Immunogenicity of ExPEC10V Blended Formulation in Rabbits

An ExPEC4V vaccine (comprising bioconjugates of E. coli O1A, O2, O6A, and O25B serotypes) has previously been shown to be immunogenic for these four serotypes in rats, rabbits, and humans (see e.g. WO 2015/124769; WO 2017/035181; Huttner et al, 2017, Lancet Infect Dis, http://dx.doi.org/10.1016/S1473-3099(17)30108-1; R W Frenck Jr, et al, abstract 5587, ASM Microbe 2018). The novel bioconjugates of the invention having the E. coli glucosylated O4 serotype were shown to be immunogenic in Examples 4 and 5 above. Immunogenicity of the bioconjugates of E. coli serotypes O8, O15, O16, O18A, and O75 (all having EPA-2 as carrier protein in this experiment) when separately administered (monovalent) to rats confirmed that also each of these bioconjugates was immunogenic, since ELISA data indicated that each of these bioconjugates could elicit high levels of E. coli O-antigen specific antibodies (not shown).

Immunogenicity of the 10-valent vaccine that contained a mixture of the 10 bioconjugates as described above was also tested. New Zealand White (NZW) rabbits (female, 12-16 weeks old) received 3 intramuscular immunizations with ExPEC10V or saline administered 2 weeks apart (Table 5; administration at days 0, 14, and 27). The 10 polysaccharides that are part of the ExPEC10V vaccine used in these experiments were conjugated to the carrier protein EPA containing 4 sites of glycosylation (EPA-4). The vaccine was formulated in 3 different doses: Group 1 ('high dose'): 8 ug/dose of O1A, O2, O6A, O4, O8, O15, O16, O18 and O75 and 16 ug/dose of O25B; Group 2 ('medium dose'): 4 ug/dose of O2, O4, O8, O15, O16, O18 and O75, 8 ug/dose of O1A and O6A and 16 ug/dose of O25B; Group 3 ('low dose'): 0.4 ug/dose of O2, O4, O8, O15, O16, O18 and O75, 0.8 ug/dose of O1A and O6A and 1.6 ug/dose of O25B. Animals from the control group (Group 4) received only saline (0.9% (w/v) sodium chloride solution) (Table 5).

Antibody responses were evaluated at day 0 (pre-immunization) and days 14, 27 and 42 post-immunization. Serum antibody levels induced by each of the bioconjugates included in the vaccine and the carrier protein EPA were measured by ELISA (total IgG), using type-specific LPS as coating material. The antibody titers were reported as EC50 values that correspond to the half maximal effective concentration based on duplicates of 12-step titration curves plotted in a 4-parameter logistic nonlinear regression model. Functional activity was determined by OPK.

TABLE 5

Description of experimental groups.

| Experimental groups | Dosing (µg/PS) O1A:O2:O6A:O25B:O4:O8:O15:O16:O18A:O75 | Sample size |
|---|---|---|
| Group 1 (high dose) | 8:8:8:16:8:8:8:8:8:8 | 7 |
| Group 2 (medium dose) | 8:4:8:16:4:4:4:4:4:4 | 7 |
| Group 3 (low dose) | 0.8:0.4:0.8:1.6:0.4:0.4:0.4:0.4:0.4:0.4 | 7 |
| Group 4 (control) | 0.9% (w/v) sodium chloride solution | 7 |

Figure 8:
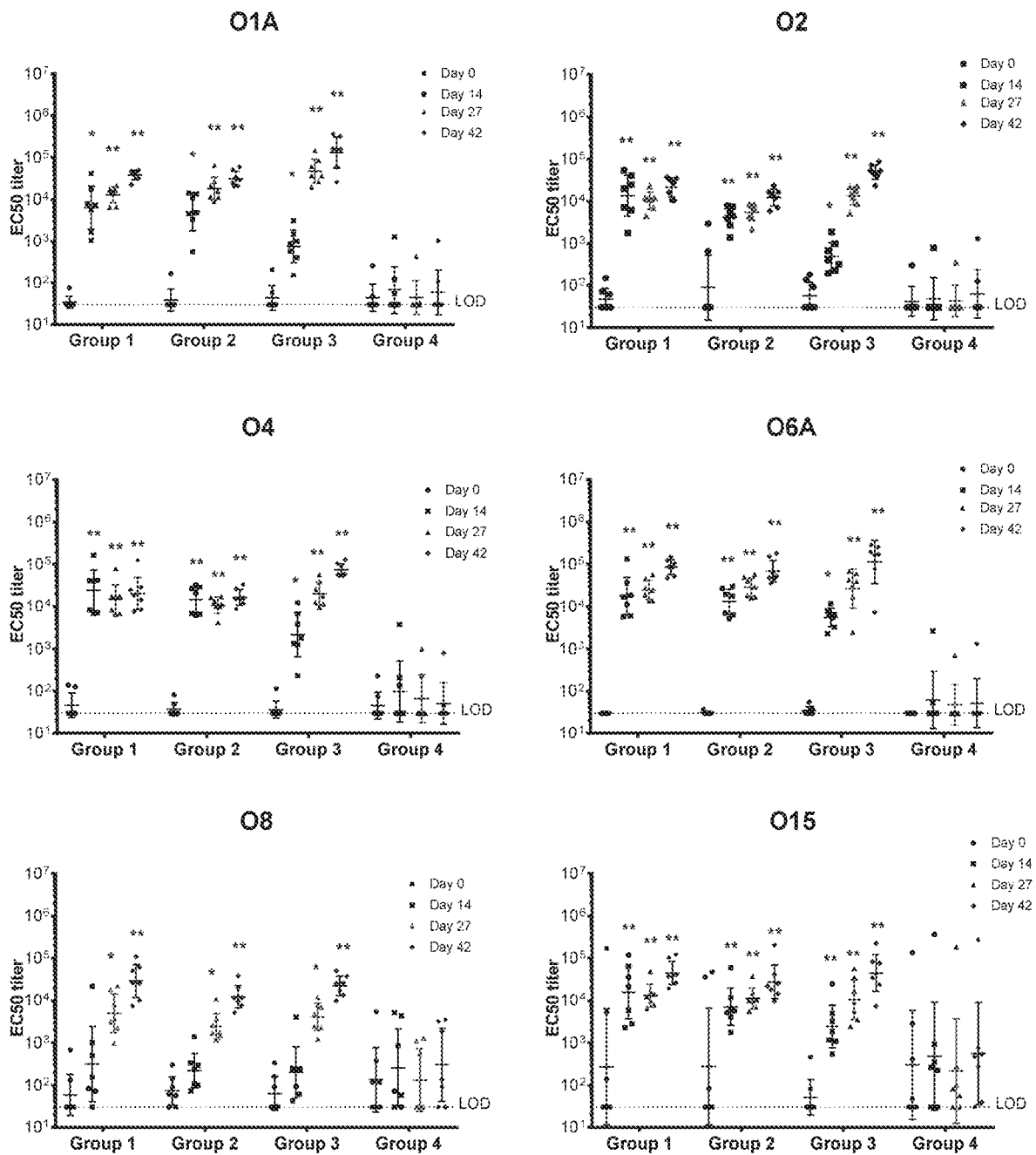
FIG. 8 shows antibody responses induced by ExPEC10V vaccine in New Zealand White rabbits. Animals received 3 intramuscular immunizations with ExPEC10V or saline administered 2 weeks apart. ExPEC10V vaccine was administered at 3 different concentrations (group 1: high dose, group 2: medium dose and group 3: low dose, Table 11) and a control group received only saline (group 4, 0.9% (w/v) sodium chloride solution). Antibody levels were measured by ELISA at day 0 (pre-vaccination) and days 14, 27 and 42 (post-vaccination). Individual titers (EC50 titer) and geometric mean titers (GMT)±95% CI are shown. Wilcoxon Rank Sum test with Bonferroni correction for multiple comparisons. Comparisons ExPEC10V vaccinated animals (group 1, 2 and 3) versus saline control (group 4). *p≤0.05, p≤0.01; *p≤0.001; ****p≤0.0001. LOD: limit of detection.

Results are shown in FIG. 8 and summarized in Table 6.

TABLE 6

Summary of *E. coli* O-antigen specific antibody responses induced by ExPEC10V in NZW rabbits.

| ExPEC10V dose | O1A | O2 | O6A | O25B | O4 | O8 | O15# | O16 | O18A | O75 |
|---|---|---|---|---|---|---|---|---|---|---|
| Antibody responses day 14 post-vaccination | | | | | | | | | | |
| High | * | ** | ** | * | ** | ns | ** | ** | * | ns |
| Mid | * | ** | ** | ** | ** | ns | ** | ** | ns | ns |
| Low | * | * | * | * | * | ns | ** | ** | ns | ns |
| Antibody responses day 27 post-vaccination | | | | | | | | | | |
| High | ** | ** | ** | ** | ** | * | ** | ** | ** | ** |
| Mid | ** | ** | ** | ** | ** | * | ** | ** | * | ** |
| Low | ** | ** | ** | ** | ** | * | ** | ** | ** | ** |
| Antibody responses day 14 post-vaccination | | | | | | | | | | |
| High | ** | ** | ** | ** | ** | ** | ** | ** | ** | ** |
| Mid | ** | ** | ** | ** | ** | ** | ** | ** | ** | ** |
| Low | ** | ** | ** | ** | ** | ** | ** | ** | ** | ** |

Serotype-specific antibody responses in which p values were statistically significant are shown by asterisks.
Serotype-specific antibody responses in which p values were not statistically significant are designated as ns.
Wilcoxon Rank Sum test with Bonferroni correction for multiple comparisons. Comparisons ExPEC10V vaccinated animals (Group 1, 2 and 3) versus saline control (Group 4).
* $p \leq 0.05$,
** $p \leq 0.01$.
P values were statistically significant after excluding an outlier animal from the control group (sensitivity analysis).

The high dose of ExPEC10V (Group 1) induced significantly higher IgG antibody levels at all time-points investigated (Days 14, 27 and 42 post-immunization) when compared to saline control for O1A, O2, O4, O6A, O16, O18A and O25B (FIG. 8, Table 6). Significantly higher antibody titers induced by O8 and O75 conjugates when compared to saline control were observed at Days 27 and 42 post-immunization (FIG. 8, Table 6).

The medium dose of ExPEC10V (Group 2) and the low dose (Group 3) induced significantly higher antibody levels at all time-points investigated (Days 14, 27 and 42 post-immunization) when compared to saline control for O1A, O2, O4, O6A, O16 and O25B (FIG. 8, Table 6). Significantly higher antibody titers induced by O8, O18A and O75 conjugates when compared to saline control were observed at Days 27 and 42 post-immunization suggesting that the boost dose in rabbits increases the response to these O-serotypes (FIG. 8, Table 6).

For O15 conjugates, sensitivity analysis omitting an outlier animal from the control group showed that all three doses of ExPEC10V vaccine induced a significant increase in antibody responses when compared to saline control at Days 14, 27 and 42 post-immunization (FIG. 8, Table 6).

Antibodies induced by the carrier protein EPA were significantly higher than EPA antibody titers in the saline-treated (control) group for the three doses of ExPEC10V tested (high, medium and low) at all time points investigated (Days 14, 27 and 42) (FIG. 8).

Between dose comparisons (not shown) showed that at Day 14 post-vaccination, the high dose of ExPEC10V induced significantly higher antibody responses when compared to the low dose for most of the conjugates tested (O1A, O2, O4, O6A, O15, O16, O18A and O25B). The medium dose of ExPEC10V also induced significantly higher antibody responses compared to the low dose for O1A, O2, O4, O18A, O25B and O75. For O8 conjugate, all three formulations of ExPEC10V induced similar levels of antibodies at Day 14 post-vaccination.

The low dose of ExPEC10V induced a significant increase in antibody responses at Day 42 post vaccination (after a prime and two boost doses) when compared to the high and medium doses of ExPEC10V for O1A, O2, O4, O16, O25B and O75 conjugates. These findings are in line with other experiences with conjugate vaccines, where for instance no clear relationship between dose and the magnitude of the antibody response to primary vaccination was observed in infants vaccinated with pneumococcal conjugate vaccine (Poolman J T, et al. Expert Rev Vaccines. 2013, 12(12):1379-94).

There were no significant differences between the three doses of ExPEC10V tested at Day 42 post-vaccination for O6A, O8 and O15 conjugates. For the O18A conjugate, the high dose of ExPEC10V induced a significantly higher antibody response when compared to the medium dose at Day 42 post-vaccination.

For the carrier protein (EPA), the high and medium dose of ExPEC10V induced significantly higher antibody responses when compared to the low dose at day 14 post-vaccination. The high dose of the vaccine also induced significantly higher antibody responses when compared to the low dose at day 42 post-vaccination.

In conclusion, the three formulations of ExPEC10V (high, medium and low), administered via intramuscular injection on Days 0, 14, 27 are immunogenic in rabbits.

So far, functional antibodies capable of killing *E. coli* strains induced by this vaccine in rabbits were shown for serotypes O1A, O2, O4, O6A, O15, O16 and O25B.

In a further experiment, a GMP batch of the ExPEC10V vaccine (see Example 8 above for production) was prepared and injected into NZW rabbits as part of a toxicology study (Table 7). In this study, NZW rabbits (males and females) received 3 intramuscular injections (0.6 mL) of the ExPEC10V vaccine (day 1, 15 and 29) and a control group received 0.9% (w/v) sodium chloride solution (saline). Each dose of the vaccine contained 9.6 μg polysaccharide (PS) for serotypes O1A, O2, O4, O6A, O8, O15, O16, O18A and O75 and 19.2 μg PS for serotypes O25B, corresponding to 105.6 μg total PS (176 μg total PS/mL) and 382.8 μg of total EPA (638 μg EPA/mL). IgG titers against O-antigens and carrier protein (EPA) were determined from samples collected during the pre-treatment period (day 1) and days 31 and 50 post-immunization.

Figure 9:
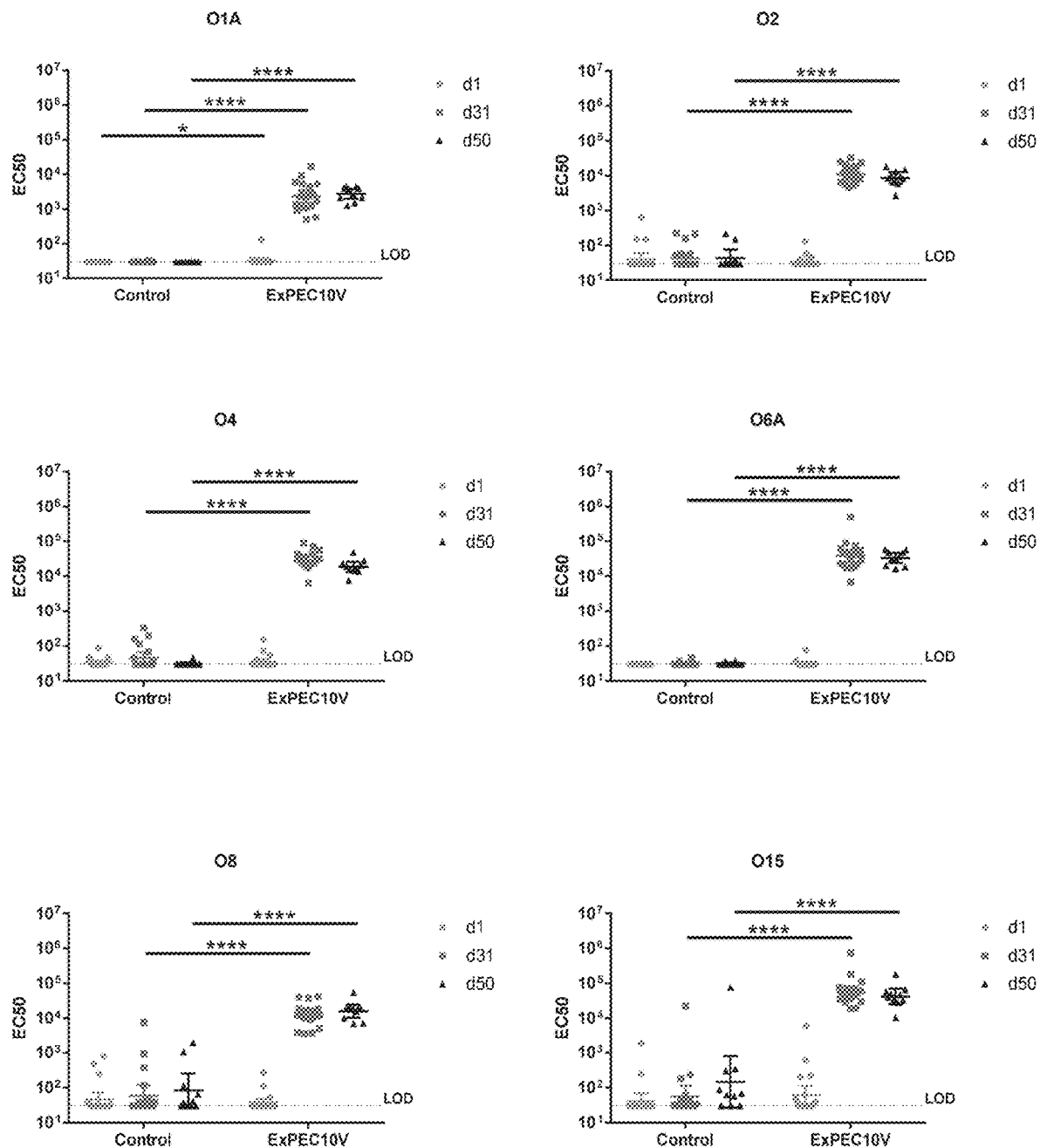
FIG. 9 shows antibody responses induced by ExPEC10V. New Zealand White rabbits received 3 intramuscular immunizations with ExPEC10V (105.6 µg total polysaccharide) or 0.9% w/v sodium chloride solution (control). IgG titers were determined by ELISA at day 1 (pre-immunization, n=20/group), day 31 (post-immunization, n=20/group) and day 50 (post-immunization, n=10/group). Plots show individual titers and geometric mean±95% confidence interval for each group. Differences in IgG titers between the ExPEC10V and control group were analyzed using a Tobit model with a likelihood ratio test. P-values≤0.05 were considered significant. *P≤0.05, ****P≤0.0001.

A significant increase in antibody responses against all O-antigens and the carrier protein EPA were observed at day 31 and 50 post-vaccination in the group that received ExPEC10V when compared to the control group that received only saline (FIG. 9, Table 8). For O1A serotype, a significantly higher antibody response was also observed at day 1 (baseline) when vaccinated animals were compared with the controls. These results suggest that some animals were pre-exposed to E. coli or have antibodies that cross-react with O1A-LPS.

TABLE 7

Experimental groups and ExPEC10V dose used in NZW rabbits.

| Groups | Treatment | Dose | Dosing days | Main (day 31) (males/females) | Recovery (day 50) (males/females) |
|---|---|---|---|---|---|
| 1 | control | 0 | 1, 15, 29 | 10 | 10 |
| 2 | ExPEC10V | 105.6 μg PS* | 1, 15, 29 | 10 | 10 |

*Each dose (0.6 mL dosing volume) contains 9.6:9.6:9.6:9.6:9.6:9.6:9.6:9.6:19.2:9.6 μg polysaccharide (PS) for serotypes O1A, O2, O4, O6A, O8, O15, O16, O18A, O25B, O75, respectively (176 μg total PS/mL). Each dose contains 382.8 μg EPA protein (638 μg EPA/mL).

TABLE 8

Immunogencity of ExPEC10V in NZW rabbits as part to a toxicology study.

| Treatment | Antibody responses day 14 post-vaccination | | | | | | | | | |
|---|---|---|---|---|---|---|---|---|---|---|
| ExPEC10V | O1A | O2 | O6A | O25B | O4 | O8 | O15 | O16 | O18A | O75 |
| Day 31 | **** | **** | **** | **** | **** | **** | **** | **** | **** | **** |
| Day 50 | **** | **** | **** | **** | **** | **** | **** | **** | **** | **** |

Antibody responses induced by ExPEC10V. Serotypes in which a significant increase in antibody responses was observed in the vaccine group compared to control are shown by asterisks. Tobit model with a likelihood ratio test.
**** P ≤ 0.0001.

Example 11: Phase 1/2a Trial with the ExPEC10V Vaccine in Humans

At present, there is no vaccine available to prevent IED. The serotypes comprising the ExPEC10V vaccine (O1A, O2, O4, O6A, O8, O15, O16, O18A, O25B and O75) were selected to address invasive disease caused by the majority of clinically relevant ExPEC strains that also represent the majority of ExPEC isolates causing antimicrobial resistant IED, including ST131. The selected serotypes are representative for the ten prevalent ExPEC O-serotypes causing bloodstream infections in the older population and responsible for approximately 70% of bloodstream infections caused by ExPEC.

Since the mechanism of action of conjugate vaccines in the prevention of invasive disease is not expected to be affected by antibiotic resistance mechanisms, it is believed that ExPEC10V vaccine provides protection against IED caused by drug-resistant- and drug-susceptible O1A, O2, O4, O6A, O8, O15, O16, O18A, O25B and O75 serotypes.

There is preceding clinical experience with ExPEC4V, an earlier vaccine candidate which comprised a subset of four of the E. coli O-antigen conjugates (O1A, O2, O6A and O25B) also found in ExPEC10V. Based on the results from four clinical studies (two completed phase 1 studies, one completed phase 2 study and an ongoing phase 2 study), ExPEC4V was well-tolerated by the study participants and no vaccine-related safety signals were observed at doses up to 16 μg polysaccharide (PS) per serotype (O1A, O2, O6A and O25B). Most adverse events (AEs) were Grade 1 and 2, very few Grade 3 AEs were reported. Late-onset solicited local AEs (AEs which start after Day 5 post-vaccination) were observed mainly with the higher doses of ExPEC4V. In each study, the ExPEC4V vaccine was shown to be immunogenic, demonstrating a dose-dependent vaccine immune response, and O-antigen specific Immunoglobulin G (IgG) titer increases, as measured by enzyme-linked immunosorbent assay (ELISA). Functional activity of the antibodies was demonstrated with an ExPEC4V-optimized opsonophagocytic killing assay (OPKA). Co-analysis of ELISA and OPKA test results showed correlation between the assay responses (Pearson correlation coefficients≥0.61 and ≥0.48 for Day 30 and Day 360, respectively in a Phase 2 clinical trial [study 4V-BAC2001]), substantiating the use of ELISA as a primary measure of ExPEC4V antibody titers and to predict functional antibody activity. Analysis of the immunogenicity data has demonstrated the durability of the immune response through three years after vaccination with ExPEC4V. It has now also been observed that sera from humans vaccinated with ExPEC4V and that had high titers of serotype-specific opsonophagocytic antibodies, when passively transferred into mice that were subsequently intraperitoneally challenged with E. coli strains of O25B or O2 serotype, were able to mediate protection in vivo (not shown). Hence, ExPEC4V-specific opsonophagocytic human antibodies mediate bacterial killing in vivo, which is in line with other conjugate vaccines in which the proposed mechanism of protection is by induction of opsonophagocytic antibodies that mediate bacterial killing.

ExPEC10V includes a total of ten serotypes and increases coverage from about 50% (ExPEC4V) to approximately 70% of bloodstream infections caused by ExPEC in adults aged 60 years and older. Based on the clinical experience with ExPEC4V, and on the pre-clinical data for ExPEC10V as discussed in the examples above, it is expected that administration of ExPEC10V will induce immune responses to E. coli serotypes O1A, O2, O4, O6A, O8, O15, O16, O18A, O25B and O75 also in humans.

A randomized, observer-blind, first-in-human phase 1/2a study to evaluate the safety, reactogenicity, and immunogenicity of three different doses of the ExPEC10V vaccine is conducted in humans aged 60 to 85 years in stable health (study 10V-BAC1001). The study design includes 2 cohorts: A total of 1,004 participants are enrolled in the study with 404 participants (100 participants/ExPEC10V dose) aged ≥60 to ≤85 years in stable health in Cohort 1 and an additional of 600 participants aged ≥60 years in stable health with a history of UTI in the past 5 years in Cohort 2.

ExPEC10V is a 10-valent vaccine candidate in development for the prevention of invasive extraintestinal pathogenic *Escherichia coli* (ExPEC) disease (IED) in adults 60 years of age and older. ExPEC10V consists of the O-antigen polysaccharides (PSs) of the ExPEC serotypes O1A, O2, O4, O6A, O8, O15, O16, O18A, O25B and O75 separately bioconjugated to the carrier protein, a genetically detoxified form of exotoxin A (EPA) derived from *Pseudomonas aeruginosa*, and its production has been described above. The O4 PS is the glucosylated form, having the structure of Formula (O4-Glc+) in Table 1.

Objectives and Endpoints

COHORT 1—Phase 1/2a observer-blind period with open-label long-term follow-up period (N=404):

| Objectives | Endpoints |
| --- | --- |
| Primary | |
| To evaluate the safety and reactogenicity of different doses of ExPEC10V in participants ≥60 to ≤85 years of age | Solicited local and systemic adverse events (AEs) collected for 14 days post-vaccination (from Day 1 to Day 15) Unsolicited AEs collected from the administration of the study vaccine until 29 days post-vaccination (from Day 1 to Day 30) Serious adverse events (SAEs) collected from the administration of the study vaccine until Day 181 |
| To evaluate the dose-dependent immunogenicity of ExPEC10V on Day 15 in participants ≥60 to ≤85 years of age | Antibody titers for ExPEC10V, as determined by multiplex electrochemiluminescent (ECL)-based immunoassay and multiplex opsonophagocytic assay (MOPA) on Day 15 |
| Secondary | |
| To evaluate the correlation between multiplex ECL-based immunoassay (total antibody) and MOPA (functional antibody) serum titers on Day 15 | Antibody titers for ExPEC10V, as determined by multiplex ECL-based immunoassay and MOPA on Day 15 |
| To evaluate the dose-dependent immunogenicity of ExPEC10V on Days 30 and 181 in participants ≥60 to ≤85 years of age | Antibody titers for ExPEC10V, as determined by multiplex ECL-based immunoassay and MOPA on Days 30 and 181 |
| To evaluate, in the long-term follow-up (LTFU) period, the safety of the ExPEC10V dose selected for further clinical development based on the Day 30 primary analysis in participants ≥60 to ≤85 years of age | SAEs related to the study vaccine or study procedures collected from Day 182 until the end of the study |
| To evaluate, in the LTFU period, the immunogenicity of the ExPEC10V dose selected for further clinical development based on the Day 30 primary analysis | Antibody titers for ExPEC10V, as determined by multiplex ECL-based immunoassay and MOPA at Year 1 (Day 366), Year 2 (Day 731) and Year 3 (Day 1096) |

COHORT 2—Double-blind period with double-blind long-term follow-up period (N=600):

| Objectives | Endpoints |
| --- | --- |
| Primary | |
| To evaluate the safety and reactogenicity of the selected dose of ExPEC10V in participants ≥60 years of age with a history of UTI in the past 5 years | Solicited local and systemic AEs collected for 14 days post-vaccination (from Day 1 to Day 15) Unsolicited AEs collected from the administration of the study vaccine until 29 days post-vaccination (from Day 1 to Day 30) SAEs collected from the administration of the study vaccine until Day 181 |

| Objectives | Endpoints |
| --- | --- |
| To evaluate the immunogenicity of the selected dose of ExPEC10V on Day 30 in participants ≥60 years of age with a history of UTI in the past 5 years | Antibody titers for ExPEC10V, as determined by multiplex ECL-based immunoassay and MOPA on Day 30 |
| Secondary | |
| To evaluate the correlation between multiplex ECL-based immunoassay (total antibody) and MOPA (functional antibody) serum titers on Day 30 in participants ≥60 years of age with a history of UTI in the past 5 years | Antibody titers for ExPEC10V, as determined by multiplex ECL-based immunoassay and MOPA on Day 30 |
| To evaluate the immunogenicity of the selected dose of ExPEC10V on Days 15 and 181 in participants ≥60 years of age with a history of UTI in the past 5 years | Antibody titers for ExPEC10V, as determined by multiplex ECL-based immunoassay and MOPA on Days 15 and 181 |

| Objectives | Endpoints |
| --- | --- |
| To evaluate, in the LTFU period, the safety of the selected dose of ExPEC10V in participants ≥60 years of age with a history of UTI in the past 5 years | SAEs related to the study vaccine or study procedures collected from Day 182 until the end of the study |
| To evaluate, in the LTFU period, the immunogenicity of the selected dose of ExPEC10V in participants ≥60 years of age with a history of UTI in the past 5 years | Antibody titers for ExPEC10V, as determined by multiplex ECL-based immunoassay and MOPA at Year 1 (Day 366), Year 2 (Day 731), and Year 3 (Day 1096) |
| Exploratory | |
| To evaluate the effect of ExPEC10V on the intestinal (stool) microbiome by metagenomic analyses | Metagenomics of stool samples from a selected subset of participants to evaluate the effect of ExPEC10V on: Prevalence of pathogens (eg, *Clostridium difficile*) in the intestinal flora Prevalence of ExPEC10V serotypes in the intestinal flora |

Overall Design

This is a randomized, multicenter, interventional study including two cohorts.

Figure 10A:
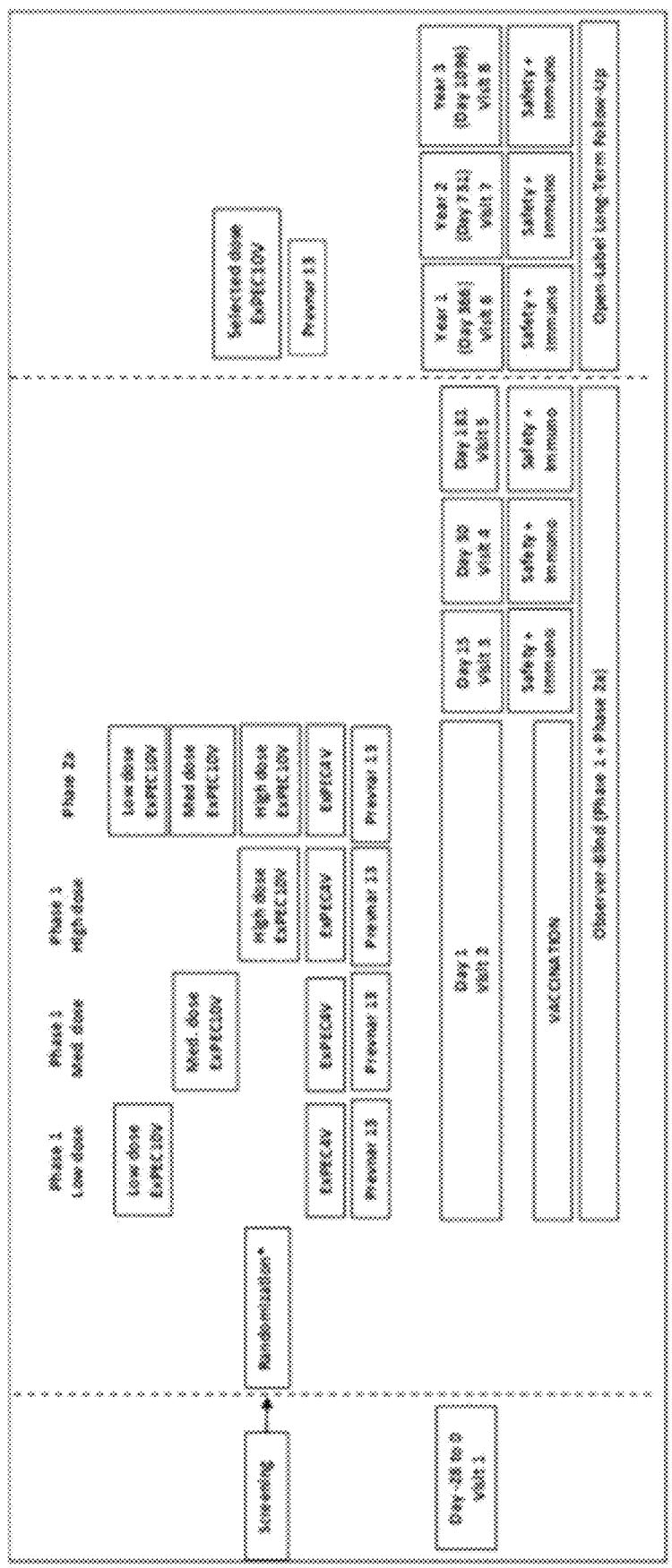
FIG. 10A shows the overall study design for Cohort 1.

For Cohort 1, the study has an observer-blind, active-controlled design, and a total of 404 adult participants aged ≥60 to ≤85 years in stable health with or without a history of UTI are included. The study design for Cohort 1 is comprised of three periods: a maximum of 28-day screening period, an observer-blinded 181-day follow-up period with vaccination on Day 1 and an open-label LTFU period which lasts from Day 182 until 3 years (Day 1096) post-vaccination (FIG. 10A). Only participants from the ExPEC10V selected dose group (approximately 100 participants) and participants from the Prevnar 13 group progress to the LTFU period. The end of Cohort 1 is the last participant's Year 3 visit (Day 1096).

Figure 10B:
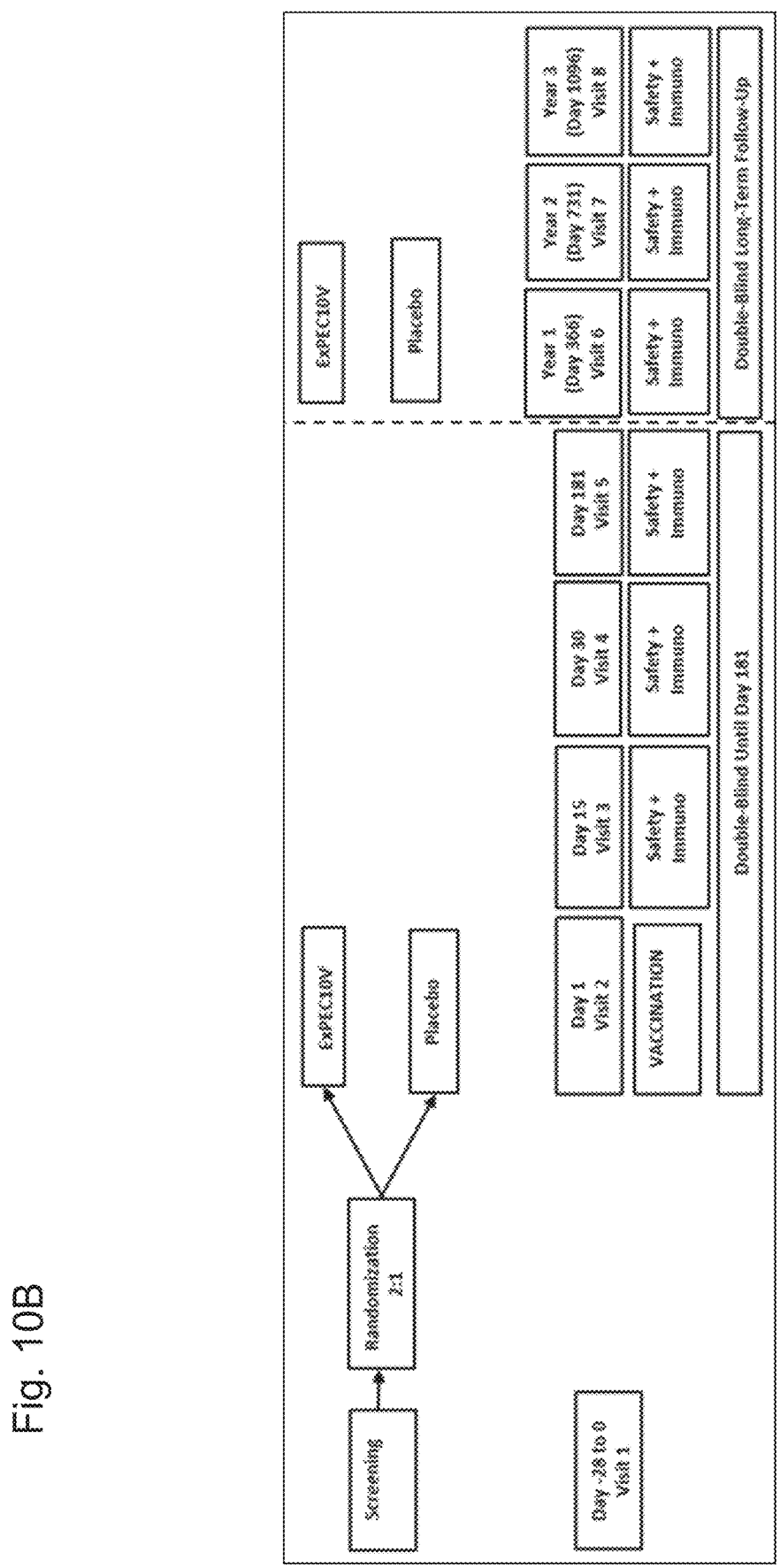
FIG. 10B shows the overall study design for Cohort 2. See Example 11 for details.

For Cohort 2, the study has a double-blind, placebo-controlled design, and a total of 600 adult participants aged ≥60 years in stable health with a history of UTI in the past 5 years is included. Enrollment commences after completion of the Phase 1/2a primary analysis and ExPEC10V dose selection from Cohort 1. The study design for Cohort 2 is comprised of three periods: a maximum 28-day screening period, a double-blind 181-day follow-up period with vaccination on Day 1, and a double-blind LTFU period which lasts from Day 182 until 3 years (Day 1096) post-vaccination (FIG. 10B). All participants in Cohort 2 progress to the LTFU period. The end of study is the last participant's Year 3 visit (Day 1096) in Cohort 2.

Cohort 1: Phase 1

In Phase 1 of Cohort 1, a total of 84 participants are enrolled in a staggered approach following stepwise dose-escalating procedures with safety evaluations in place before progressing from one step to the next. An internal Data Review Committee (DRC) is commissioned for this study to review the physical examination data (baseline as well as targeted), baseline demographic data and the 14-day post-vaccination safety data (including solicited local and systemic AEs, unsolicited AEs, SAES, clinical laboratory data and vital signs) of these 84 Phase 1 participants. In this phase of the study, participants were enrolled and randomized in six steps:

Step 1: Four sentinel participants were enrolled and randomized; two participants in the ExPEC10V low dose group (Table 11), and one participant each in the ExPEC4V and Prevnar 13 groups.

Step 2: Twenty-four participants were enrolled and randomized; 18 participants in the ExPEC10V low dose group (Table 11), and three participants each in the ExPEC4V and Prevnar 13 groups.

Step 3: Four sentinel participants were enrolled and randomized; two participants in the ExPEC10V medium dose group (Table 11), and one participant each in the ExPEC4V and Prevnar 13 groups.

Step 4: Twenty-four participants were enrolled and randomized; 18 participants in the ExPEC10V medium dose group (Table 11), and three participants each in the ExPEC4V and Prevnar 13 groups.

Step 5: Four sentinel participants were enrolled and randomized; two participants in the ExPEC10V high dose group (Table 11), and one participant each in the ExPEC4V and Prevnar 13 groups.

Step 6: Twenty-four participants were enrolled and randomized; 18 participants in the ExPEC10V high dose group (Table 11), and three participants each in the ExPEC4V and Prevnar 13 groups.

All participants received a single intramuscular (IM) injection of either ExPEC10V (1 of 3 doses), ExPEC4V or Prevnar 13 on Day 1 per the assigned study vaccination groups. The four sentinel participants at each of Steps 1, 3 and 5 were contacted by telephone 24 hours post-vaccination to collect safety information. The blinded 24-hour post-vaccination safety data in each group of four sentinel participants were reviewed by the principal investigator (PI), study responsible physician (SRP) and sponsor medical lead (SML). Randomization of additional participants for the next step was halted until this Day 2 sentinel safety evaluation was completed.

In the absence of any clinically significant findings, an additional 24 participants (for Steps 2, 4, and 6) were enrolled and randomized to one of three study vaccination groups (Table 11) to receive a single IM injection of either ExPEC10V (1 of 3 doses), ExPEC4V or Prevnar 13 on Day 1.

After vaccination of an additional 24 participants at each dose level (low dose in Step 2, medium dose in Step 4, and high dose in Step 6), 14-day post-vaccination safety data of all 28 (4+24) participants at each dose level was reviewed by the DRC before progressing to the next dose level or Phase 2a.

Cohort 1: Phase 2a

Based on acceptable safety and reactogenicity (in the absence of any safety concerns or any events meeting a specific study pausing rule) as determined by DRC after the review of 14-day post-vaccination safety data for the initial 84 participants, the remaining 320 participants from Cohort 1 were randomized and dosed in Phase 2a of the study. These additional 320 participants were enrolled and randomized in parallel in a ratio of 2:2:2:1:1 to one of the five study vaccination groups to receive a single IM injection of either ExPEC10V (1 of 3 doses), ExPEC4V or Prevnar 13 on Day 1 (Table 11).

In addition to performing the 14-day safety review for the initial 84 participants, the DRC also evaluates safety data of Cohort 1 over the course of the study and review any events that meet a specific study vaccination pausing rule or any other safety issue that may arise.

For Cohort 1, the primary analysis occurs when all participants have completed the Day 30 visit (Visit 4) or have discontinued earlier. The final analysis occurs when all participants have completed the Day 181 visit or have discontinued earlier. For participants progressing to the open-label long-term follow-up (LTFU) period (ExPEC10V selected dose group and Prevnar 13 group), yearly follow-up analyses include safety and immunogenicity data (multiplex ECL-based immunoassay and MOPA) collected up to the time of the visit at Year 1 (Day 366), Year 2 (Day 731) and Year 3 (Day 1096) after vaccination.

Cohort 2

In Cohort 2, the safety, reactogenicity, and immunogenicity of the selected dose of ExPEC10V (based on the primary analysis results of Cohort 1) is evaluated in participants aged ≥60 years in stable health with a history of UTI in the past 5 years. For Cohort 2, the study has a double-blind, placebo-controlled design, and a total of 600 participants are enrolled and randomized in parallel in a 2:1 ratio (400 participants in the ExPEC10V group and 200 in the placebo group).

All participants receive a single IM injection of either the selected dose of ExPEC10V or placebo on Day 1 per the assigned study vaccination groups (Table 12).

For Cohort 2, the primary analysis includes safety and immunogenicity data and occurs when all participants have completed the Day 30 visit (Visit 4) or have discontinued earlier. The final analysis occurs when all participants have completed the Day 181 visit or have discontinued earlier. For all participants, yearly follow-up analyses include safety and immunogenicity data (multiplex ECL-based immunoassay and MOPA) collected up to the time of the visit at Year 1 (Day 366), Year 2 (Day 731), and Year 3 (Day 1096) after vaccination.

A stool sample analysis is performed in a selected subset of participants to evaluate the effect of ExPEC10V on the prevalence of pathogens (eg, *Clostridium difficile*) and ExPEC10V serotypes in the intestinal flora using metagenomics.

Number of Participants

A total of 1004 participants is enrolled in the study; 404 participants in Cohort 1 and 600 participants in Cohort 2.

Intervention Groups

Description of Interventions

ExPEC10V: *E. coli* bioconjugate vaccine in phosphate buffered solution containing O-antigen PS of ExPEC serotypes O1A, O2, O4, O6A, O8, O15, O16, O18A, O25B and O75 separately bioconjugated to the EPA carrier protein. Single 0.5 mL IM (deltoid) injection of one of the three doses of ExPEC10V on Day 1.

ExPEC4V: *E. coli* bioconjugate vaccine in saline buffer solution containing O-antigen PS of ExPEC serotypes O1A, O2, O6A, O25B (4:4:4:8 µg PS/ExPEC serotypes) separately bioconjugated to the EPA carrier protein. Single 0.5 mL IM (deltoid) injection of ExPEC4V on Day 1.

Prevnar 13: Sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein. Single 0.5 mL IM (deltoid) injection on Day 1, supplied in a single-dose prefilled syringe.

Placebo: normal saline. Single 0.5 mL IM (deltoid) injection of placebo on Day 1.

The ExPEC study intervention materials are described in Table 9.

TABLE 9

| | | | | | | | | | | | | |
|---|---|---|---|---|---|---|---|---|---|---|---|---|
| BAC1001MV ExPEC Study Vaccines. | | | | | | | | | | | | |
| Study Arm | O1A (µg) | O2 (µg) | O4 (µg) | O6A (µg) | O8 (µg) | O15 (µg) | O16 (µg) | O18A (µg) | O25B (µg) | O75 (µg) | EPA (µg) | PS (Total) (µg) |
| Low dose ExPEC10V | 4 | 4 | 4 | 4 | 4 | 4 | 4 | 4 | 8 | 4 | 160 | 44 |
| Medium dose ExPEC10V | 8 | 4 | 4 | 8 | 4 | 4 | 4 | 4 | 16 | 4 | 221 | 60 |

TABLE 9-continued

BAC1001MV ExPEC Study Vaccines.

| Study Arm | O1A (μg) | O2 (μg) | O4 (μg) | O6A (μg) | O8 (μg) | O15 (μg) | O16 (μg) | O18A (μg) | O25B (μg) | O75 (μg) | EPA (μg) | PS (Total) (μg) |
|---|---|---|---|---|---|---|---|---|---|---|---|---|
| High dose ExPEC10V | 8 | 8 | 8 | 8 | 8 | 8 | 8 | 8 | 16 | 8 | 320 | 88 |
| ExPEC4V | 4 | 4 | — | 4 | — | — | — | — | 8 | — | 72 | 20 |

EPA = a genetically detoxified form of exotoxin A derived from *Pseudomonas aeruginosa*;
PS = polysaccharide
ExPEC4V consists of the O-antigen polysaccharides (PSs) of the ExPEC serotypes O1A, O2, O6A, and O25B separately bioconjugated to the EPA carrier protein.
ExPEC10V consists of the O-antigen polysaccharides (PSs) of the ExPEC serotypes O1A, O2, O4, O6A, O8, O15 O16, O18A, O25B and O75 separately bioconjugated to the EPA carrier protein.
Dose is based on PS only.
The EPA (μg) are measured values.

ExPEC10V is composed of 10 monovalent drug substances (DSs). For this clinical study, 2 different concentrations (medium and high) of drug product (DP) are produced (Table 10). A third (low) concentration is obtained in the clinic by diluting the high concentration 1:1 with dilution buffer, which is the same as the formulation buffer. Each DP is formulated in Sodium/Potassium phosphate buffer at pH 7.0 (0.02% [w/w] Polysorbate 80, 5% [w/w] sorbitol, 10 mM methionine).

TABLE 10

Composition of ExPEC10V vaccine for phase ½a clinical study

| Ingredient Active[a] | Amount (μg/mL)[a] | | |
|---|---|---|---|
| | Low Concentration[b] | Medium Concentration | High Concentration |
| O-antigen polysaccharide | | | |
| EcoO1A | 8 | 16 | 16 |
| EcoO2 | 8 | 8 | 16 |
| EcoO4 | 8 | 8 | 16 |
| EcoO6A | 8 | 16 | 16 |
| EcoO8 | 8 | 8 | 16 |
| EcoO15 | 8 | 8 | 16 |
| EcoO16 | 8 | 8 | 16 |
| EcoO18A | 8 | 8 | 16 |
| EcoO25B | 16 | 32 | 32 |
| EcoO75 | 8 | 8 | 16 |
| Carrier protein | | | |
| EPA | 320 | 441 | 640 |
| Excipients | | | |
| $KH_2PO_4$ | | 6.19 mM | |
| $Na_2HPO_4$ | | 3.81 mM | |
| Sorbitol | | 5% (w/w) | |
| Methionine | | 10 mM | |
| Polysorbate 80 | | 0.02% (w/w) | |

EPA = genetically detoxified *P. aeruginosa* exotoxin A used as carrier protein
[a] The active ingredient is a biologically synthesized conjugate composed of the PS antigen and a carrier protein (EPA); the dose is calculated on the PS moiety only.
[b] The "low concentration" is obtained in the clinic by diluting the "high concentration" 1:1 with dilution buffer Safety Evaluations Key safety assessments include solicited local and systemic AEs, unsolicited AEs, SAEs, physical examinations, vital sign measurements, and clinical laboratory tests.

Immunogenicity Evaluations

Key immunogenicity assessments of collected sera include the assessment of ExPEC10V and ExPEC4V serotype-specific total IgG antibody levels elicited by the vaccine as measured by a multiplex ECL-based immunoassay, and ExPEC10V and ExPEC4V serotype-specific functional antibodies as measured by an opsonophagocytic killing assay (OPKA) in multiplex format (MOPA). Immunogenicity assessments of pneumococcal antibody titers elicited by Prevnar 13 are not performed.

The levels of serum antibodies induced by ExPEC10V are measured by a multiplex electrochemiluminescent (ECL)-based immunoassay. This assay combines high binding carbon electrodes in a multi-spot 96-well format microplate that is coated with different *E. coli* O-LPS antigens or the carrier protein EPA. The levels of antigen-specific antibodies present in serum samples are detected using a secondary antibody (anti-human IgG) labeled with SULFO-TAG. The SULFO-TAG emits light in the presence of electrical stimulation at an intensity that increases proportionally to the amount of bound IgG antibodies. This assay was qualified according to International Conference on Harmonisation (ICH) recommendations.

The levels of functional antibodies induced by ExPEC10V are measured by a multiplex opsonophagocytic assay (MOPA). Briefly, heat-inactivated serum samples are serially diluted and incubated with different *E. coli* strains that are specifically resistant to different types of antibiotics. After that, human complement and phagocytic cells (HL60) are added to the reaction and, after a second incubation period, an aliquot of the reaction mix is transferred to different PVDF hydrophilic membrane filter plates containing media supplemented with specific antibiotic that selectively allow growth of a strain that is resistant to that particular antibiotic. After overnight grown, the colony forming units (CFUs) are counted to determine the number of surviving bacteria. This assay was qualified according to ICH recommendations.

For ExPEC10V serotype antibodies as measured by multiplex ECL-based immunoassay and MOPA, and EPA as measured by multiplex ECL-based immunoassay only, the following measures of immunogenicity are evaluated and tabulated by the study vaccination groups, for all immunogenicity time points:

proportion of participants with a ≥2-fold and ≥4-fold increase in serum antibody titers from Day 1 (pre-vaccination)

geometric mean titer (GMT)

GMR: fold change from baseline, calculated from the post-baseline/baseline value.

For the LTFU period, descriptive summaries of immunogenicity are provided for each serotype.

Dose selection for later phases considers the totality of the evidence available at the time of the primary analysis of Cohort 1 (Day 30 results).

TABLE 11

Cohort 1: Vaccination Schedule

| Study Vaccination Group | Vaccination on Day 1 | Phase 1 Step 1 Sentinel participants (Low dose) | Step 2 Additional participants (Low dose) | Step 3 Sentinel participants (Medium dose) | Step 4 Additional participants (Medium dose) | Step 5 Sentinel participants (High dose) | Step 6 Additional participants (High dose) | Phase 2a Step 7 Additional Phase 2a Participants | Total |
|---|---|---|---|---|---|---|---|---|---|
| G1 | Low dose ExPEC10V* | 2 | 18 | | | | | 80 | 100 |
| G2 | Medium dose ExPEC10V* | | | 2 | 18 | | | 80 | 100 |
| G3 | High dose ExPEC10V* | | | | | 2 | 18 | 80 | 100 |
| G4 | ExPEC4V** | 1 | 3 | 1 | 3 | 1 | 3 | 40 | 52 |
| G5 | Prevnar 13*** | 1 | 3 | 1 | 3 | 1 | 3 | 40 | 52 |
| Total | | 4 | 24 | 4 | 24 | 4 | 24 | 320 | 404 |

*ExPEC10V consists of the O-antigen polysaccharides (PSs) of the ExPEC serotypes O1A, O2, O4, O6A, O8, O15, O16, O18A, O25B and O75 separately bioconjugated to the carrier protein, a genetically detoxified form of exotoxin A (EPA) derived from *Pseudomonas aeruginosa*.
**ExPEC4V consists of the O-antigen polysaccharides (PSs) of the ExPEC serotypes O1A, O2, O6A, and O25B separately bioconjugated to the carrier protein, a genetically detoxified form of exotoxin A (EPA) derived from *Pseudomonas aeruginosa*.
*** Prevnar 13, Pneumococcal 13-valent conjugate vaccine (Diphtheria CRM197 protein) is a sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein.

TABLE 12

Cohort 2: Vaccination Schedule

| Study Vaccination Group | Vaccination on Day 1 | Total |
|---|---|---|
| G6 | ExPEC10V$^a$ | 400 |
| G7 | Placebo | 200 |
| Total | | 600 |

$^a$ExPEC10V consists of the O-antigen polysaccharides (PSs) of the ExPEC serotypes O1A, O2, O4, O6A, O8, O15, O16, O18A, O25B, and O75 separately bioconjugated to the carrier protein, a genetically detoxified form of exotoxin A (EPA) derived from *Pseudomonas aeruginosa*.

The randomization ratio for the participants enrolled in Cohort 2 of the study is 2:1 (ExPEC10V:Placebo). The ExPEC10V dose used in Cohort 2 is based on the primary analysis (Day 30) results of Cohort 1.

Status

Enrollment and vaccination of Cohort 1 of the study described above was completed. The study is ongoing in a blinded manner. Based on ongoing review of the safety data, no major safety issues were identified, and the ExPEC10V vaccine has an acceptable safety profile.

The analysis of the immunogenicity of the Cohort 1 clinical samples is ongoing in a blinded fashion. The ECL data were 100% Acceptance Quality Limits (AQL) checked and uploaded for data management. Analysis of the MOPA samples is ongoing. Data unblinding and statistical analysis is performed by using a clinical research organization (CRO).

The Cohort 2 vaccinations are started once the ExPEC10V dose for that Cohort has been identified based on the finalized primary analysis of the Day 30 results from Cohort 1.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

SEQUENCES

```
SEQ ID NO: 1 (Glycosylation consensus sequence)
Asn-X-Ser(Thr), wherein X can be any amino acid except Pro SEQ ID NO: 2 (Optimized glycosylation consensus sequence)
Asp(Glu)-X-Asn-Z-Ser(Thr), wherein X and Z are independently selected from any
amino acid except Pro SEQ ID NO: 3 (EPA carrier protein comprising 4 glycosylation consensus
sequences (EPA-4))
G SGGGDQNATG SGGGKLAEEA FDLWNECAKA CVLDLKDGVR SSRMSVDPAI ADTNGQGVLH YSMVLEGGND
ALKLAIDNAL SITSDGLTIR LEGGVEPNKP VRYSYTRQAR GSWSLNWLVP IGHEKPSNIK VFIHELNAGN
QLSHMSPIYT IEMGDELLAK LARDATFFVR AHESNEMQPT LAISHAGVSV VMAQAQPRRE KRWSEWASGK
VLCLLDPLDG VYNYLAQQRC NLDDTWEGKI YRVLAGNPAK HDLDIKDNNN STPTVISHRL HFPEGGSLAA
LTAHQACHLP LEAFTRHRQP RGWEQLEQCG YPVQRLVALY LAARLSWNQV DQVIRNALAS PGSGGDLGEA
IREQPEQARL ALTLAAAESE RFVRQGTGND EAGAASADVV SLTCPVAKDQ NRTKGECAGP ADSGDALLER
NYPTGAEFLG DGGDVSFSTR GTQNWTVERL LQAHRQLEER GYVFVGYHGT FLEAAQSIVF GGVRARSQDL
DAIWRGFYIA GDPALAYGYA QDQEPDARGR IRNGALLRVY VPRWSLPGFY RTGLTLAAPE AAGEVERLIG
HPLPLRLDAI TGPEEEGGRV TILGWPLAER TVVIPSAIPT DPRNVGGDLD PSSIPDKEQA ISALPDYASQ
PGKPPREDLK LGSGGGDQNA T SEQ ID NO: 4 (O4 GtrS amino acid sequence)
MNNLIMNNWCKLSIFIIAFILLWLRRPDILTNAQFWAEDSVFWYKDAYENGFLSSLTTPRNGYFQTVSTFIVGLTALL
NPDYAPFVSNFFGIMIRSVIIWFLFTERFNFLTLTTRIFLSIYFLCMPGLDEVHANITNAHWYLSLYVSMILIARNPS
SKSWRFHDIFFILLSGLSGPFIIFILAASCFKFINNCKDHISVRSFINFYLRQPYALMIVCALIQGTSIILTFNGTRS
SAPLGFSFDVISSIISSNIFLFTFVPWDIAKAGWDNLLLSYFLSVSILSCAAFVFVKGTWRMKVFATLPLLIIIFSMA
```

| SEQUENCES |
| --- |
| KPQLTDSAPQLPTLINGQGSRYFVNIHIAIFSLLCVYLLECVRGKVATLFSKIYLTILLFVMGCLNFVITPLPNMNWR
EGATLINNAKTGDVISIQVLPPGLTLELRKK

SEQ ID NO: 5 (Example O4 gtrS nucleic acid sequence)
ATGAATAATTTAATTATGAATAACTGGTGTAAATTATCTATATTTATTATTGCATTTATTTTGCTATGGCTTAGAAGG
CCGGATATACTCACAAACGCACAATTTTGGGCAGAAGATTCCGTTTTCTGGTATAAGGACGCCTATGAGAACGGATTC
TTAAGTTCACTAACAACGCCTAGGAATGGGTATTTCCAGACTGTTTCTACATTTATAGTTGGTCTGACTGCTTTATTA
AATCCAGATTATGCACCTTTTGTTTCTAATTTTTTTGGCATAATGATTCGCTCAGTAATTATATGGTTTTTATTTACA
GAAAGATTCAACTTCCTCACATTGACTACTAGGATTTTCTTATCTATTTATTTTCTATGCATGCCTGGATTGGATGAA
GTTCATGCAAATATAACAAATGCACATTGGTATTTGTCATTATATGTATCAATGATCCTGATAGCTCGCAATCCAAGT
TCAAAATCATGGAGGTTTCATGATATATTCTTTATCTTGCTATCCGGGCTCAGTGGCCCATTTATAATTTTCATTTTA
GCAGCTTCATGCTTTAAATTTATAAATAATTGTAAAGATCATATTAGTGTAAGATCTTTCATAAATTTCTACTTGCGT
CAGCCATACGCATTAATGATTGTTTGCGCTTTAATTCAAGGAACTTCTATAATTCTAACTTTCAATGGCACACGTTCC
TCAGCACCGCTAGGATTCAGTTTTGATGTGATTTCGTCTATTATATCATCGAATATTTTTTATTTACATTTGTCCCA
TGGGATATTGCAAAGGCTGGGTGGGATAATTTACTGTTATCTTATTTTTTGTCTGTTTCGATTTTGTCGTGTGCGGCC
TTTGTTTTTGTTAAAGGTACGTGGCGAATGAAAGTATTTGCAACTTTACCATTGCTAATTATAATATTTTCAATGGCA
AAACCACAATTGACAGACTCGGCACCTCAATTGCCAACACTTATTAATGGGCAAGGTTCAAGATACTTCGTAAATATA
CATATTGCGATATTCTCTTTGCTATGTGTTTACTTACTTGAGTGCGTCAGGGGGAAAGTGGCAACTTTATTTTCCAAA
ATATACTTAACAATTTTGCTATTCGTGATGGGATGTTTGAATTTTGTTATCACCCCACTCCCAAACATGAACTGGAGG
GAAGGTGCTACTTTGATTAATAATGCAAAAACTGGTGATGTCATTTCGATTCAAGTGCTACCACCTGGCCTAACACTT
GAACTAAGGAAAAATAA SEQ ID NO: 6 (Example PglB sequence ('wild-type'))
MLKKEYLKNPYLVLFAMIILAYVFSVFCRFYWVWWASEFNEYFFNNQLMIISNDGYAFAEGARDMIAGFHQPNDLSYY
GSSLSALTYWLYKITPFSFESIILYMSTFLSSLVVIPTILLANEYKRPLMGFVAALLASIANSYYNRTMSGYYDTDML
VIVLPMFILFFMVRMILKKDFFSLIALPLFIGIYLWWYPSSYTLNVALIGLFLIYTLIFHRKEKIFYIAVILSSLTLS
NIAWFYQSAIIVILFALFALEQKRLNFMIIGILGSATLIFLILSGGVDPILYQLKFYIFRSDESANLTQGFMYFNVNQ
TIQEVENVDLSEFMRRISGSEIVFLFSLFGFVWLLRKHKSMIMALPILVLGFLALKGGLRFTIYSVPVMALGFGFLLS
EFKAIMVKKYSQLTSNVCIVFATILTLAPVFIHIYNYKAPTVFSQNEASLLNQLKNIANREDYVVTWWDYGYPVRYYS
DVKTLVDGGKHLGKDNFFPSFALSKDEQAAANMARLSVEYTEKSFYAPQNDILKTDILQAMMKDYNQSNVDLFLASLS
KPDFKIDTPKTRDIYLYMPARMSLIFSTVASFSFINLDTGVLDKPFTFSTAYPLDVKNGEIYLSNGVVLSDDFRSFKI
GDNVVSVNSIVEINSIKQGEYKITPIDDKAQFYIFYLKDSAIPYAQFILMDKTMFNSAYVQMFFLGNYDKNLFDLVIN
SRDAKVFKLKI SEQ ID NO: 7 (example gtrA amino acid sequence; E. coli W3110 yfdG, GenBank:
BAA16209.1)
MLKLFAKYTSIGVLNTLIHWVVFGVCIYVAHTNQALANFAGFVVAVSFSFFANAKFTFKASTTTMRYMLYVGFMGTLS
ATVGWAADRCALPPMITLVTFSAISLVCGFVYSKFIVFRDAK SEQ ID NO: 8 (example gtrB amino acid sequence-E. coli W3110 yfdH, GenBank:
BAA16210.1)
MKISLVVPVFNEEEAIPIFYKTVREFEELKSYEVEIVFINDGSKDATESIINALAVSDPLVVPLSFTRNFGKEPALFA
GLDHATGDAIIPIDVDLQDPIEVIPHLIEKWQAGADMVLAKRSDRSTDGRLKRKTAEWFYKLHNKISNPKIEENVGDF
RLMSRDVVENIKLMPERNLFMKGILSWVGGKTDIVEYVRAERIAGDTKFNGWKLWNLALEGITSFSTFPLRIWTYIGL
VVASVAFIYGAWMILDTIIFGNAVRGYPSLLVSILFLGGIQMIGIGVLGEYIGRTYIETKKRPKYIIKRVKK SEQ ID NO: 9 (example O4 rfb locus nucleotide sequence-O4-EPA production
strain BVEC-L-00684f)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCGGGCGTGACCATTATGAACGTGCGTCAG
GGCGAACCTTTAGGTTTAGGCCGCTCACTCCATTTTGTGTGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGGA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGAGCTGGACTCAGAC
ATCATGGCCTAGGTCGCTATGTGCTTTCTGCCGATATTTGGCCGGACTGGAACGTACTCAGCCTGGTGCATGGGA
CGTATTCAGCTGACTGATGCTATTGCCGAGCTGGCGAAAAAACAATCCGTTGATGCAATGCTGATGACCGGCGACAGT
TACGACTGCGGCAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGTGAAAATACTTGTTACTGGTGGCGCAGGATTTATTGGTTCAGCTGTAGTTCGTCACATT
ATAAATAATACGCAGGATAGTGTTGTTAATGTCATAAATTAACGCGGAAACCGGGAATCACTTGCTGATGTT
TCTGATTCTGAACGCTATGTTTTTGAACATGCGGATATTTGCGATGCACCTGCAATGGCACGGATTTTTGCTCAGCAT
CAGCCGGATGCAGTGATGCACCTGGCTGCTGAAAGCCATGTTGACCGTTCAATTACAGGCCCTGCGGCATTTATTGAA
ACCAATATTGTTGGTACTTATGTCCTTTTGGAAGCCGCTCGCAATTACTGGTCTGCTCTTGATAGCGACAAGAAAAT
AGCTTCCGTTTTCATCATATTTCTACTGACGAAGTATATGGTGATTTGCCTCATCCTGACGAGGTAAATAATACGAAA
GAATTACCCTTATTTACTGAGACAACAGCTTACGCGCCAAGCAGCCCTTATTCCGCATCCAAAGCATCCAGCGATCAT
TTAGTCCGCGCGTGGAAACGTACCTATGGTTTACCGACCATTGTGACTAATTGCTCTAACAATTATGGTCCTTATCAT
TTCCCCGGAAAAATTGATTCCATTGGTATTCTCAATGCTCTGGAAGGTAAAGCATTACCTATTTATGGTAAAGGGGAT
CAAATTCGCGACTGGCTGTATGTTGAAGATCATGCGCGTGCGTTATATACCGTCGTAACCGAAGGTAAAGCGGGTGAA
ACTTATAACATTGGTGGGCACAACGAAAGAAAAACATAGATGTAGTGCTCACTATTTGTGATTTGCTGGATGAGATT
GTACCGAAAGAGAAATCTTATCGTGAGCAAATCACTTATGTTGCCGATCGTCCGGGACACGATCGCCGTTATGCGATT
GATGCTGAGAATATTGGTCGCGAATTGGGATGGAAACCACAGGAAACGTTTGAGAGCGGGATTCGGAAGACAGTGGAA |

| SEQUENCES |
|---|
| TGGTATCTGTCCAATACAAAATGGGTTGATAATGTGAAAAGTGGTGCCTATCAATCGTGGATTGAAGAGAACTATGAG |
| GGCCGCCAGTAATGAATATCCTCCTTTTTGGCAAAACAGGGCAGGTAGGTTGGGAACTACAGCGTGCTCTGGCACCTC |
| TGGGTAACTTGATTGCTCTTGATGTTCATTCCACTGATTATTGTGGCGATTTCAGTAACCCCGAAGGTGTGGCTGAAA |
| CCGTCAAAAAAATTCGCCCAGATGTTATTGTTAATGCTGCTGCTCATACCGCGGTAGATAAGGCTGAGTCAGAACCAG |
| AATTTGCACAATTACTCAATGCGACCAGCGTTGAAGCAATTGCAAAAGCGGCTAATGAAGTTGGGGCTTGGGTAATTC |
| ATTACTCAACTGACTACGTCTTCCCTGGAAATGGCGACATGCCATGGCTCGAGACTGATGTAACCGCTCCGCTCAATG |
| TTTATGGCAAAACCAAATTGGCTGGAGAAAGAGCATTACAAGAACATTGCGCAAAGCATCTTTATTTTCCGTACCAGCT |
| GGGTATATGCAGGTAAAGGAAATAACTTTGCCAAAACAATGTTACGTCTGGCAAAAGAGCGCGAAGAACTGGCTGTGA |
| TAAACGATCAGTTTGGCGCACCAACAGGTGCTGAATTGCTGGCTGATTGCACCGCTCATGCCATTCGCGTGGCATTAA |
| AAAAACCAGAAGTTGCTGGCTTGTACCATCGGTAGCAAATGGCACAACAACCTGGCACGATTACGCCGCGCTAGTAT |
| TCGAAGAAGCCCGTAAAGCAGGGATTGACCTTGCACTTAACAAACTCAACGCCGTACCAACAACGGCTTATCCTACTC |
| CAGCCCGCCGTCCTCATAATTCTCGCCTCAATACCGAAAAGTTTCAGCAGAACTTTGCGCTTGTCTTGCCTGACTGGC |
| AGGTGGGCGTGAAACGTATGCTCAACGAATTATTTACGACTACGGCAATTTAACAAATTTTTGCATCTCGCTCATGAT |
| GCCAGAGCGGGATGAATTAAAAGGAATGGTGAAATGAAAACGCGTAAAGGTATTATTCTGGCTGGTGGTTCCGGCACT |
| CGTCTTTATCCTGTGACGATGGCAGTGAGTAAACAACTGCTGCCGATTTATGATAAGCCGATGATTTATTATCCGCTT |
| TCAACGCTTATGTTAGCGGGTATTCGCGATATTCTTATTATCAGTACGCCACAGGATACACCGCGTTTCCAACAATTG |
| TTGGGGGACGGGAGTCAGTGGGGCTTAATCTACAGTATAAAGTACAACCGAGTCCGGATGGCCTGGCGCAAGCGTTT |
| ATTATTGGTGAAGACTTTATTGGTGGTGATGATTGTGCACTCGTACTTGGCGATAATATCTTCTATGGACACGACTTG |
| CCGAAATTAATGGAAGCTGCTGTTAACAAAGAAATCGGTGCAACGGTATTTGCTTATCACGTCAATGATCCTGAACGT |
| TATGGTGTCGTGGAGTTTGATAATAACGGTACTGCAATTAGCCTGGAAGAAAAACCGCTGGAACCAAAAAGTAACTAT |
| GCGGTTACTGGGCTTTATTTCTATGACAATGATGTTGTAGAAATGGCGAAAAACCTTAAGCCTTCTGCCCGTGGCGAA |
| CTGGAAATTACCGTATATTAACCGTATTTATATGGAGCAGGGACGTTTGTCTGTCGCTATGATGGGCGTGGTTATGCC |
| TGGTTGGATACTGGTACACATCAAAGTCTTATTGAAGCAAGTAACTTCATTGCCACCATTGAAGAGCGTCAGGGATTA |
| AAGGTATCTTGCCCGGAAGAGATTGCTTACCGTAAAGGGTTTATTGATGCTGAGCAGGTGAAAGTATTAGCCGAACCG |
| CTGAAGAAAAATGATTATGGTCAGTATCTGCTAAAAATGATTAAAGGTTATTAATAAAATGAACGTAATTAAAACTGA |
| AATTCCTGATGTGCTGATTTTTGAACCAAAAGTTTTTGGTGATGAACGTGGCTTCTTTTTTGAGAGTTTTAACCAGAA |
| AGTATTTGAAGAAGCTGTAGGACGGAAGGTTGAATTTGTTCAGGATAACCATTCTAAGTCTAAAATAAATGTATTGCG |
| TGGGATGCATTATCAAACACAAAATACTCAAGGAAAACTGGTTCGGGTAATTTCTGGTTCAGTATATGATGTTGCCGT |
| AGATTTAAGAGAAAAATCAAAGACATTTGGCAAATGGGTGGGTGTAGAATTATCTGGGAATAATAAAAGACAATTGTG |
| GATCCCCGAAGGTTTTGCCCATGGTTTTTATGTGTTGGAGGAGAATACCGAATTTGTTTATAAATGTACCGATACTTA |
| TAACCCTGCTCATGAACACACATTGCTATGGAATGATCCAACTATCAATATAAGTTGGCCAATCATACAAAACTGCAA |
| GCCAATTATTTCTGAAAAAGATGCTAATGGACATCTTTTTTCACATAAAACCTATTTCTGAAATGCAATATTATGAGT |
| TTAATTAGAAACAGTTTCTATAATATTGCTGGTTTTGCTGTGCCGACATTAGTTGCAGTCCCTGCTTTGGGGATTCTT |
| GCCAGGCTGCTTGGACCGGAGAATTTTGGACTTTTCACACTAGCATTCGCTTTGATAGGATATGCAAGTATTTTCGAC |
| GCCGGGATTAGTCGAGCTGTAATCAGAGAAATCGCTCTTTATCGAGAAAGTGAAAAAGAGCAAATACAAATTATTTCG |
| ACAGCAAGTGTAATCGTACTATTCTTAGGGGTGGTTGCAGCTTTGTTACTTTATTTTAGTAGTAATAAAGTTGTTGAG |
| TTATTGAATGTTAGTTCCGTTTATATTGAAACAGCAGTGCGTGCATTCTCTGTTATTTCATTTATAATACCGTGTAT |
| CTGATTAACCAGATTTGGCTTGGTTATCTGGAAGGGCTAGAAAAATTTGCAAATATAAATGTTCAGAGAATGATTTCT |
| AGCACAAGCTTGGCTATATTACCAGTGATATTTTGTTATTACAATCCCTCGTTGCTTTATGCTATGTATGGGTTGGTG |
| GTTGGGCGTGTGATTTCATTTTTGATTAGCGCAATAATTTGTCGAGATATTATTCTTAAAAGTAAACTTTACTTTAAT |
| GTGGCAACTTGCAATCGTCTTATCTCTTTTGGTGGATGGATAACAGTTAGTAATATCATAAGCCCAATCATGGCATAT |
| TTCGACCGCTTTATCATCTCTCATATTATGGGGGCTTCGAGAATTGCATTTTATACAGCGCCCTCAGAGGGTGTATCA |
| AGGTTAATTAATATCCCATATGCTTTGGCAAGAGCTCTATTTCCTAAATTGGCATATAGCAATAATGATGATGAACGA |
| AAAAAATTACAACTACAGAGCTACGCAATTATAAGCATTGTATGTCTACCCATAGTTGTTATTGGTGTCATTTTTGCC |
| TCATTCATAATGACAACATGGATGGGACCTGATTATGCCTTAGAAGCAGCAACTATCATCAGAAACAAACTTATTGCTGGT |
| TTTTTCTTTAACTCTTTAGCGCAAATACCTTATGCATACTTGCAATCTATCGGAAAGTCAAAAATTACCGCATTTGTG |
| CATCTCATAGAACTTGCGCCATACTTATTATTATTGTATTACTTCACAATGCATTTCGGCATAATTGGCACGGCAATC |
| GCTTGGTCACTTAGAACATTTTGTGATTTTGTTATACTACTTTCGATATCGAGAAGAAAATGATTGCGGTTGATATTG |
| CGCTTGCAACCTACAATGGTGCTAATTTTATTCGGCAACAGATTGCTATCCAGAAACAAACTTATAGAAATTGGC |
| GTCTTATAATAAGTGATGATAACTCGAGTGATGATACTGTTGATATTATTAAGGATATGATGTCTAACGACAGTCGTA |
| TCTATTTGGTAGGAAATAAAAGACAAGGAGGGGTTATTCAGAACTTTAATTATGCTCTTTCACAAACTACATCTGAAA |
| TTGTGTTACTATGTGACCAGGATGACATTTGGCCGGAGGAGCGTCTGGAAATTCTTATAGATAAATTTAAGGCCTTGC |
| AGCGTAATGATTTTGTTCCGGCAATGATGTTTACTGATTTGAAATTAGTAGACGAAAATAATTGTTTGATTGCAGAAA |
| GTTTTTATCGAACGAATAATATTAATCCACAAGATAATCTGAAAAATAATAATCTTCTGGCGTTCAACGGTATATG |
| GCTGTACTTGCATCATGAATAAGAAACTTGTTGATATTGCATTGCCTATACCTACATATGCACATATGCATGATCAAT |
| GGTTGGCATTATTAGCGAAGCAATATGGTAACATTTTTATTTCGACTATGCGTCTGTTCGTTATAGGCAACATTCTA |
| CAAATGTTGTTGGTGGTAGAAATAAAACGCCATTTCAAAAATTTAATTCCATACAAAAAACCTAAAAAGGATTAATT |
| TGCTAGTGGATAGAACTGTTGCTTTAATTAAATCAAATAACGATTTCTATCCAGGGAATAAAATGGAAAATAAAATTG |
| ATTACTTAAAATTTGGAGTGAATGAAGTATTACCTTATCTTTTAAAGGAAACAAGAAAGTTTTTTCACTTTGTGTAT |
| TAATTAGTTTGGCATTACAAAAATGATATATTTATTATTTTTTTGCACTGTTTATGATCTGTACGTTTTTAACACA |
| CAGGCGACAGGCATTATATGTTGTATCTGCGTTAGTATTTCTTTTTTGGCTTTAACCTATCCATCAGGAGGGACTG |
| GATAGGTTATTTTCTCCATTATGACTGCATGGTTAATGAGCAGTGTAATAATGGTTTTATAATGTTTGAACCTGGATA |
| TGAATTAATTGTTTCCTTATTGGATATTTGGGATTTCAGACAATTATTATTTTATAGCCGCTGTAAATGTAATTCT |
| AATATTAAATTTTGCAAAGCATTTTGAAAACGGAAGTTTTGTTATTGTTGCGATAATGTGCATGTTCCTTTGGAGTGT |
| TTATGTTGAGGCGATTAGACAGGCTCTGGCCTTATCTATAGTTATATTTGGGATTCATTCTCTTTTTTGGGTAGAAA |
| AAGGAAATTTATAACATTAGTATTATTTGCGTCAACTTTCCATATAACTGCTTTGATTTGTTTTCTTCTAATGACTCC |
| TCTATTTTCAAAGAAATTAAGCAAGATAATAAGTTATAGCCTATTAATTTTCAGTAGCTTCTTTTTCGCTTTTTCTGA |
| AACCATATTAAGTGCACTCCTTGCAATTTTGCCAGAAGGATCCATTGCCAGTGAAAAATTAAGTTTTTACTTAGCAAC |
| CGAGCAATACAGGCCACAGTTATCTATTGGGAGTGGCACTATTCTTGACATTATACTTATTTTTCTGATATGTGTAAG |
| TTTTAAACGAATAAAGAAATATATGCTCGCTAATTATAATGCTGCAAATGAGATATTGCTTATTGGTTGCTGTCTTTA |
| TATTTCTTTCGGTATTTTTATCGGGAAAATGATGCCAGTTATGCTCGCTGGTTGGTATTGGTTTTCCATTTGTTAT |
| AGTACTTCTTTATATTAACTTGGGTTATTCAGAATATTTAAGAGGTATATAAATAAAAGAGGGTGTGGGTATAGCAA |
| ATTATTAATTGCTTTTTATTTTTTGCTACAAATTTTGCGACCATTAACATATGATTATAGCTATTATAATATAATGCA |
| CCAGGATACTTTGCTGAATAGGTTTGATGCATTAGATGATGCATCATTAAGACAATCAGCGAAGAGAAATGTTTCGA |
| TTTGGGAAAGATAGGATATGGTTTCTTATGTAGTATATAAATATCCTGCATTCATTCGGATAATTTCCTATGGAAGTGT |
| CCTTTGCTCTGTCTGTCCTCATTTGTTGAAATTTTATGTTAATAAGAAGCTTTAGATAACCACTTAGGAACTGTATGT |
| TTGATCTGTCCAAAAATTATATTATTGTAAGTGCGACGGCGCTGGCTTCCGGAGGTGCATTAACTATATTAAAGCAAT |

| SEQUENCES |
|---|
| TTATAAAACATGCATCACAAAATTCAAATGACTATATTATGTTTGTATCTGCGGGATTGGAGTTGCCGGTCTGTGATA |
| ACATCATTTACATAGAAAACACACCAAAAGGATGGTTGAAAAGAATATATTGGGATTGGTTCGGTTGTCGGAAGTTTA |
| TCTCGGAACATAAGATTAACGTTAAGAAAGTAATTTCTCTACAAAATTCCAGTTTGAATGTTCCTTACGAACAGATTA |
| TTTACTTGCACCAGCCAATTCCTTTTAGTAAAGTTGATTCTTTTTTAAAAAATATCACATCCGATAACGTAAAGCTTT |
| TTTTATATAAAAAGTTTTATTCCTATTTTATATTTAAATATGTGAATGCCAATACAACCATCGTAGTGCAAACGAATT |
| GGATGAAAAAAGGAGTGCTGGAGCAATGTGATAAAATTAGTACCGAAAGGGTCCTTGTTATAAAACCTGATATCAAAG |
| CATTTAATAATACTAATTTTGATGTAGATATGGATGTATCTGCAAAAACACTCTTATATCCAGCGACACCACTTACCT |
| ATAAAAATCATTTGGTCATTCTGAAGGCGTTGGTTATTTTAAAGAAAAAGTATTTTATAGATGATCTGAAATTCCAAG |
| TGACTTTTGAAAAGAATAGGTACAAAAATTTTGATAAGTTTGTGCAATTAAATAACTTAAGCAAAAACGTTGATTATC |
| TCGGCGTTCTTTCATACTCGAACTTGCAAAAAAAATATATGGCGGCATCTTTAATCGTTTTTCCTAGCTATATCGAAT |
| CATATGGGTTACCACTCATCGAAGCTGCTAGTTTAGGAAAAAAAATCATTAGTAGTGATCTTCCTTATGCCCGGGATG |
| TTTTAAAGGATTATAGCGGCGTAGATTTTGTAATTTACAATAATGAAGATGGCTGGGCTAAGGCGTTGTTTAATGTTT |
| TAAATGGCAATTCGAAGCTCAATTTTAGGCCTTATGAAAAGATAGTCGTTCATCTTGGCCACAGTTCTTCTCTATTT |
| TGAAATAAGGTGTATTATGTTTAATGGTAAAATATTGTTAATTACTGGTGGTACGGGGTCTTTCGGTAATGCTGTTCT |
| AAGACGTTTTCTTGACACTGATATCAAAGAAATACGTATTTTTTCCCGGGATGAAAAAAAACAAGATGACATGAGGAA |
| AAAATATAATAATCCGAAACTTAAGTTCTATATAGGTGATGTTCGCGACTATTCGAGTATCCTCAATGCTTCTCGAGG |
| TGTTGATTTTATTTATCATGCTGCAGCTCTGAAGCAAGTACCTTCCTGCGAATTCCACCCAATGGAAGCTGTAAAAAC |
| GAATGTTTTAGGTACGGAAAACGTACTGGAAGCGGCAATAGCTAATGGAGTTAGGCGAATTGTATGTTTGAGTACAGA |
| TAAAGCTGTATATCCTATCAATGCAATGGGTATTTCCAAAGCGATGATGGAAAAAGTAATGGTAGCAAAATCGCGCAA |
| TGTTGACTGCTCTAAAACGGTTATTTGCGGTACACGTTATGGCAATGTAATGGCATCTCGTGGTTCAGTTATCCCATT |
| ATTTGTCGATCTGATTAAATCAGGTAGACCAATGACGATAACAGACCCTAATATGACTCGTTTCATGATGACTCTCGA |
| AGACGCTGTTGATTTGGTTCTTTACGCATTTGAACATGGCAATAATGGTGATATTTTTGTCCAAAAGGCACCTGCGGC |
| TACCATCGAAACGTTGGCTATTGCACTCAAAGAATTACTTAATGTAAACCAACACCCTGTAAATATAATCGGCACCCG |
| ACACGGGAAAAACTGTACGAAGCGTTATTGAGCCGAGAGGAAATGATTGCAGCGGAGGATATGGGTGATTATTATCG |
| TGTTCCACCAGATCTCCGCGATTTGAACTATGGAAAATATGTGGAACATGGTGACCGTCGTATCTCGGAAGTGGAAGA |
| TTATAACTCTCATAATACTGATAGGTTAGATGTTGAGGGAATGAAAAAATTACTGCTAAAACTTCCTTTTATCCGGGC |
| ACTTCGGTCTGGTGAAGATTATGAGTTGGATTCATAATATGAAAATTTTAGTTACTGGCGCTGCAGGGTTTATCGGTC |
| GAAATTTGGTATTCCGGCTTAAGGAAGCTGGATATAACGAACTCATTACGATAGATCGTAACTCTTCTTTGGCGGATT |
| TAGAGCAGGGACTTAAGCAGGCAGATTTTATTTTTCACCTTGCTGGGGTAAATCGTCCCGTGAAGGAGTGTGAATTTG |
| AAGAGGGAAATAGTAATCTAACTCAACAGATTGTTGATATCCTGAAAAAAACAATAAAAATACTCCTATCATGCTGA |
| GTTCTTCCATCCAGGCTGAATGTGATAACGCTTATGGAAAGAGTAAAGCAGCTGCGGAAAAAATCATTCAGCAGTATG |
| GGGAAACGACAAACGCTAAATATTATATTTATCGCTTGCCGAATGTATTCGGTAAGTGGTGTCGACCAAATTATAACT |
| CCTTTATAGCAACTTTCTGCCATCGCATTGCAAATGATGAAGCTATTACAATTAATGATCCTTCAGCAGTTGTAAATC |
| TGGTGTATATAGATGACTTTTGTTCTGACATATTAAAGCTATTAGAAGGAGCGAACGAAACTGGTTACAGGACATTTG |
| GTCCAATTTATTCTGTTACTGTTGGTGAAGTGGCACAATTAATTTACCGGTTTAAAGAAAGTCGCCAAACATTAATCA |
| CCGAAGATGTAGGTAATGGATTTACACGTGCATTGTACTCAACATGGTTAGTTACCTGTCTCCTGAACAGTTTGCGT |
| ATACGGTTCCTTCTTATAGTGATGACAGAGGGGTATTCTGTGAAGTATTGAAAACGAAAAACGCGGGCCAGTTTTCGT |
| TCTTTACTGCGCATCCAGGAATTACTCGGGGTGGTCATTATCATCATTCCAAAAATGAGAAATTTATTGTCATCCGAG |
| GAAGTGCTTGTTTCAAATTTGAAAATATTGTCACGAGTGAACGATATGAACTTAATGTTTCCTCTGATGATTTTAAAA |
| TTGTTGAAACAGTTCCGGGATGGACGCATAACATTACTAATAATGGCTCGGATGAGCTAGTTGTTATGCTTTGGGCAA |
| ATGAAATATTTAATCGTTCTGAACCAGATACTATAGCGAGAGTTTTATCGTGAAAAAATTGAAAGTCATGTCGGTTGT |
| TGGGACTCGTCCAGAAATTATTCGACTCTCGCGTGTCCTTGCAAAATTAGATGAATATTGTGACCACCTTATTGTTCA |
| TACCGGGCAAAACTACGATTATGAACTGAATGAAGTTTTTTTCAAAGATTTGGGTGTTCGCAAACCTGATTATTTTCT |
| TAATGCCGCAGGTAAAAATGCAGCAGAGACTATTGGACAAGTTATCATTAAAGTTGATGAGGTCCTTGAACAGGAAAA |
| ACCAGAAGCCATGTTAGTACTTGGCGATACTAACTCCTGTATTTCAGCAATACCAGCAAAGCGTCGAAGAATTCCGAT |
| CTTCCATATGGAGGCTGGGAATCGTTGTTTTGACCAACGCGTACCGGAAGAAACTAACAGAAAAATAGTTGATCATAC |
| CGCTGATATCAATATGACATATAGTGATATCGCGCGTGAATATCTTCTGGCTGAAGGTGTACCAGCCGATAGAATTAT |
| TAAAACCGGTAGCCCAATGTTTGAAGTACTCACTCATTATATGCCGCAGATTGATGGTTCCGATGTACTTTCTCGCCT |
| GAATTTAACACCTGGGAATTTCTTTGTGGTAAGTGCCCACAGAGAAGAAAATGTTGATACCCCTAAACAACTTGTGAA |
| ACTGGCGAATATACTTAATACCGTGGCTGAAAAATATGATGTCCCGGTAGTTGTTTCTACTCATCCTCGCACTCGTAA |
| CCGCATCAACGAAACGGTATTCAATTCCATAAAAATATCTTGCTTCTTAAGCCATTAGGATTTCACGATTACAACCA |
| TCTGCAAAAAATGCACGTGCTGTTTTATCGGATAGTGGGACTATTACAGAAGAGTCCTCCATTATGAACTTCCCTGC |
| ACTCAATATACGAGAAGCGCACGAACGCCCGGAAGGCTTCGAAGAAGGGGCAGTAATGATGGTCGGTCTTGAATCTGA |
| TCGCGTTTTACAGGCATTAGAAATTATTGCAACACAGCCTCGTGGAGAAGTACGCTTACTTCGTCAGGTTAGTGACTA |
| TAGCATGCCAAATGTTTCAGATAAAGTTCTGCGTATTATCCATTCATATACTGACTACGTTAAACGGGTTGTCTGGAA |
| GCAATACTAATGAAACTTGCATTAATCATTGATGATTATTTGCCCCATAGCACACGCGTTGGGGCTAAAATGTTTCAT |
| GAGTTAGGCCTTGAATTACTGAGCAGAGGCCATGATGTAACTGTAATTACGCCTGACATCTCATTACAAGCAATTTAT |
| TCTATTAGTATGATTGATGGTATAAAGGTTTGGCGTTTCAAAAGTGGACCTTTAAAGGATGTAGGTAAGGCTAAACGT |
| GCCATAAATGAAACTCTTTTATCTTTTCGCGCATGGCGCGCATTTAAGCACCTCATTCAACATGATACATTTGATGGT |
| ATCGTTTATTATTCCCCCTCTATTTTTGGGGCGACTTGGTTAAAAAAATAAAACAACGATGCCAGTGCCCAAGCTAT |
| CTGATCCTAAGGGATATGTTTCCACAGTGGGTCATTGATGCAGGTATTGTTGAAAGCCGGTTTTGAAAGCTGAAAAATAT |
| TTTAGGTATTTTGAAAAAAAGTCATATCAGCAGGCTGGCCGGATAGGGGTAATGTCTGATAAGAATCTTGAGATATTT |
| CGCCAGACCAATAAAGGTTATCCGTGTGAAGTTTTACGTAATTGGGCCTCAATGACTCCTGTGTCTGCCAGCGATGAT |
| TATCATTCACTTCGTCAAAAATACGATCTAAAAGATAAAGTCATTTTTTTCTATGGCGGTAATATTGGGCATGCTCAG |
| GATATGGCAAACTTAATGCGCCTTGCGCGTAATATGATGCGTTATCATGATGCTCATTTCCTGTTTATAGGGCAGGGT |
| GATGAAGTTGAGCTGATAAAATCTCTTGCTGCAGAATGGAATTTAACTAATTTCACCATCTACCTTCAGTGAACCAG |
| GAAGAGTTTAAATTAATTTTTATCTGAAGTTGATGTCGGCCTGTTCTCCCTTTCATCTCGCCATTCTTCACATAATTTC |
| CCCGGAAAATTACTAGGGTATATGGTTCAATCAATCCCGATCCTTGGGAGTGTGAATGGCGGCAATGATTAATGGAT |
| GTAATTAATAAGCACAGAGCCGGTTTCATTCATGTTAATGGTGAAGATGATAAACTGTTTGAATCTGCACAATTGCTT |
| CTTAGTGATTCAGTTTTAAGAAAACAGCTAGGTCAGAACGCTAATGTGTTGTTAAAGTCTCAATTTTCGGTTGAATCG |
| GCGGCACATACTATCGAAGTCCGACTGGAGGCTGGAGAATGCGTTTAGTTGATGACAATATTCTGGATGAACTTTTTC |
| GCACTGCAGCAAATTCTGAACGTTTGCGCGCTCATTATTTATTGCACGCATCTCATCAGGAGAAGGGTTCAACGTTTAC |
| TTATTGCATTTGTACGCGACAGCTATGTTGAACCCCATTGGCATGAGTTACCGCATCAGTGGGAAATGTTTGTCGTCA |
| TGCAAGGGCAATTAGAAGTTTGTTTGTATGAGCAAAATGGTGAGATCAAAAACAGTTTGTTGTTGGAGACGGTACGG |
| GAATAAGCGTCGTGAATTTTCCCCAGGAGATATACATAGTGTCAAATGCCTGTCACCAAAAGCCCTTATGTTGGAGA |
| TAAAGGAGGGGCCATTTGACCCACTCAAAGCTAAGGCTTTTTCTAAGTGGTTATAGGGCGATACACCACCGTTTATTC |
| TTCTATCTTATTCTATACATGCTGGGTTACCATCTTAGCTTCTTCAAGCCGCGCAACCCCGCGGTGACCACCCCTGAC |

| SEQUENCES |
|---|
| AGGAGTAGCTAGCATTTGACCACCCCTGACAGGATTAGCTAGCATATGAGCTCGAGGATATCTACTGTGGGTACCCGG<br>GATCCGTGTAGGCTGGAGCTGCTTCGAAGTTCCTATACTTTCTAGAGAATAGGAACTTCGGAATAGGAACTAAGGAGG<br>ATATTCATAT |

SEQ ID NO: 10 (example signal sequence for EPA carrier protein)
MKKIWLALAG LVLAFSASA SEQ ID NO: 11 (example O1A rfb locus nucleotide sequence-O1A-EPA
production strain stGVXN4411 and stLMTB10217)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCGTGAAGATACTTGTTACTAGGGGCGCAGGATTTATTGGTTCTGCTGTAGTTCGT
CACATTATAAATAATACGCAGGATAGTGTTGTTAATGTCGATAAATTAACGTACGCCGGAAACCTGGAATCACTTGCT
GATGTTTCTGACTCTGAACGCTATGTTTTTGAACATGCGGATATTTGCGATGCTGCTGCAATGGCGCGGATTTTTGCT
CAGCATCAGCCGGATGCAGTGATGCACCTGGCTGCTGAAAGCCATGTGGATCGTTCAATTACAGGCCCTGCGGCATTT
ATTGAAACCAATATTGTTGGTACTTATGTCCTTTTGGAAGCGGCTCGCAATTACTGGTCTGCTCTTGATGGCGACAAG
AAAAATAGCTTCCGTTTTCATCATATTTCTACTGACGAAGTCTATGGTGATTTGCCTCATCCTGACGAAGTAAATAAT
AAAGAACAATTACCCCTCTTTACTGAGACGACAGCTTACGCGCCTAGTAGTCCTTATTCCGCATCAAAAGCATCCAGC
GATCATTTAGTCCGCGCGTGGAAACGTACCTATGGTTTACCGACTATTGTGACTAACTGTTCGAATAACTACGGTCCT
TATCACTTTCCGGAAAAATTGATTCCACTAGTAATTCTTAATGCTCTGGAAGGTAAGGCATTACCTATTTATGGCAAA
GGGGATCAAATTCGTGACTGGCTGTATGTTGAAGATCATGCGCGTGCGTTATATACCGTAGTTACTGAAGGTCAAGCG
GGTGAAACCTATAACATTGGCGGACACAACGAAAAGAAAAACATCGATGTTGTGCTGACTATTTGTGATTTGTTGGAC
GAGATAGTCCCGAAAGAGAAATCTTATCGTGAGCAAATTACTTATGTTGCTGATCGCCCAGGGCATGATCGCCGTTAT
GCGATTGATGCTGAGAAGATTGGTCGCGAATTGGGATGGAAACCACAGGAAACGTTTGAGAGTGGGATTCGTAAAACG
GTGGAATGGTATTTGGCTAATGCAAAATGGGTTGATAATGTGAAAAGTGGTGCCTATCAATCGTGGATTGAACAGAAC
TATGAGGGCCGCCAGTAATGAATATCCTCCTTTTTGGCAAAACAGGGCAGGTAGGTTGGGAACTACAGCGTGCTCTGG
CACCTCTGGGTAATTTGATTGCTCTTGATGTTCACTCCACTGATTACTGTGGTGATTTTAGTAACCCTGAAGGTGTGG
CTGAAACAGTCAAAAGAATTCGACCTGATGTTATTGTTAATGCTGCGGCTCACACCGCAGTAGATAAGGCTGAGTCAG
AACCCGAATTTGCACAATTACTCAATGCGACTAGCGTTGAATCAATTGCAAAAGCGGCAAATGAAGTTGGGGCTTGGG
TAATTCATTACTCAACTGACTACGTATTCCCTGGAAATGGCGACACGCCATGGCTGGAGATGGATGCAACCGCACCGC
TAAATGTTTACGGTGAAACCAAGTTAGCTGGAGAAAAAGCATTACAAGAGCATTGTGCGAAGCACCTAATTTTCCGTA
CCAGCTGGGTCTATGCAGGTAAAGGAAATAATTTCGCCAAAACGATGTTGCGTCTGGCAAAAGAGCGTGAAGAACTAG
CCGTTATTAATGATCAGTTTGGTGCGCCAACAGGTGCTGAACTGCTGGCTGATTGTACGGCACATGCCATTCGTGTCG
CACTGAATAAACCGGATGTCGCAGGCTTGTACCATTTGGTAGCCAGTGGTACCACAACCTGGTACGATTATGCTGCGC
TGGTTTTTGAAGAGGCGCGCAATGCAGGCATTCCTCTTGCACTCAACAAGCTCAACGCAGTACCAACAACTGCCTATC
CTACACCAGCTCGTCGTCCACATAACTCTCGCCTTAATACAGAAAAATTTCAGCAGAATTTTGCGCTTGTATTGCCTG
ACTGGCAGGTTGGTGTGAAACGCATGCTCAACGAATTATTTACGACTACAGCAATTTAATAGTTTTTGCATCTTGTTC
GTGATGGTGGAGCAAGATGAATTAAAAGGAATGATGAAATGAAAACGCGTAAAGGTATTATTTTAGCGGGTGGTTCTG
GTACTCGTCTTTATCCTGTGACTATGGTCGTCAGTAAACAGCTATTACCTATATATGATAAACCGATGATCTATTATC
CGCTTTCTACACTGATGTTAGCGGGTATTCGCGATATTCTGATTATTAGTACGCCACAGGATACTCCTCGTTTTCAAC
AACTGCTGGGTGACGGTAGCCAGTGGGGCCTGAATCTTCAGTACAAAGTGCAACCGAGTCCGGATGGTCTTGCGCAGG
CATTTATTATCGGTGAAGAGTTTATTGGTGGTGATGATTGTGCTTTGGTACTTGGTGATAATATCTTCTACGGTCACG
ACCTGCCTAAGTTAATGGATGCCGCTGTTAACAAAGAAAGTGGTGCAACGGTATTTGCCTATCACGTTAATGATCCTG
AACGCTATGGTGTCGTTGAGTTTGATAAAAACGGTACGGCGATCAGCCTGGAAGAAAAACCGCTACAACCAAAAAGTA
ATTATGCGGTAACCGGGCTTTATTTTTATGATAACGACGTTGTCGAAATGGCGAAAAATCTTAAGCCTTCTGCCCGCG
GTGAACTGGAAATTACCGATATTAACCGTATCTATATGGAACAAGGGCGTTTATCTGTTGCCATGATGGGGCGTGGTT
ATGCGTGGTTAGACACGGGGACACATCAGAGCCTGATTGAGGCAAGCAACTTTATTGCAACAATTGAAGAGCGTCAGG
GGCTGAAAGTTTCCTGCCCGGAAGAAATTGCTTACCGTAAAGGGTTTGTTGATGCTGAGCAGGTGAAAGTATTAGCTG
AACCTCTGAAAAAAAATGCTTATGGTCAGTATCTGCTGAAAATGATTAAAGGTTATTAATAAAATGAACGTAATTAAA
ACAGAAATTCCTGATGTACTGATTTTTGAACCGAAAGTTTTTGGTGATGAGCGTGGTTTCTTTTTTGAGAGCTTTAAC
CAGAAGGTTTTTGAGGAAGCTGTAGGCCGCAAAGTTGAATTTGTTCAGGATAACCATTCGAAGTCTAGTAAAGGTGTT
TTACGCGGGCTGCATTATCAGTTGGAACCTTATGCACAAGGAAAATTGGTGCGTTGCGTTGTCGGTGAAGTTTTTGAC
GTAGCTGTTGATATTCGTAAATCGTCATCGACTTTTGGCAAATGGGTTGGGGTGAATTTATCTGCTGAGAATAAGCGG
CAATTGTGGATTCCTGAGGGATTTGCACATGGTTTTTTAGTGCTGAGTGAGACGGCGGAGTTTTTGTATAAGACGACA
AATTATTATCATCCTCAGAGTGATAGAGGAATAAAATGGGATGATCCAAGCATCAATATTTCATGGCCAGTCGATTCA
CAAGTGCTGCTATCAGCTAAAGATAATAAGCATCCTCCATTAACAAAGATTGAAATGTATAGTTAAGATCACGATAAA
TCTTGGAAGGGTTGCAAAATTGAATAAAATAGTGAGCAAAAGTGAAATAAGGAACGTAATCCACAATGCTGGCTATAT
GATGATTACTCAGATAGCTTTATATGTTGCACCATTATTTATACTGAGTTATCTGTTAAAAACACTGGGGGTTGCACA
GTTTGGTAATTATGCCTTAATACTATCAATCGTTGCATATTTACAGATTATAACGGATTATGGTTTTTCTTTTAGTGC
AAGTCGTGCGATCTCACAGAATAGAGAGGACAAAGAATATATATCAAAAATTTATCTGTCAACTATGACTATCAAGTT
GGCGATATGCGCTTTCTTATTCTTATTGCTCATGCTATTTTTAAATCTTTTGCCTGTGCAAGCTGAATTAAAACAAGG
AATATTATATGGATATCTTCTTGTAATAGGAAATACTTTCCAACCACAATGGTTTTTCCAAGGTATCGAAAAATTAAA
AATCATAGCCCTTTCTAATGTTATATCAAGATGCGCCGCGTGTTTACTTGTATTTATCTATGTGAGGAATAGCGAGGA

| SEQUENCES |
|---|
| TTTACAAAAAGCACTTTTAGTACAGTCACTTCCATTAGTAATTTCTGCGATTGGATTAAATATATTTATATTGAAATA |
| TATCAATATTATTTTTCCGGAAAAAAAATTATTTAAGGTAATTTTAAAAGAAGGTAAGGATTTTTTCTTGCATCACT |
| TTATTCTGTTATTCTCAATAATAGTGGCATTTTTCTATTAGGGATTTTTACTAATCCTGTTATTGTTGGTGTATATGC |
| CGCCGCTGAAAAGATAGTCAAGGCCGTATTGTCGCTATTTACACCACTGACGCAAGCTATATATCCTTATAATTGTCG |
| TAAGTTTTCACTATCCGTATTTGACGGCATTGAGGCAGCAAAAAAAACTGGTATACCAATTATAATTTTAGCATTTAT |
| AGCTGCTGTTATCGTTGCAATTACCTTACCTGTTGCAATCGACTATCTTAATTTTCCAAAAGAAACAATTTTTGTAGG |
| TCAAATATTAAGTGCATGGATCTTTTTTGGTGTTCTTAATAATGTATTCGGCATTCAGATATTGAGTGCATCAGGAAG |
| AAGTAAAATATATAGTAGGATGGTATTCGTATCAGCGCTTATAACATTACTTTTGATTACTCTATTATTGCAGTTTTG |
| TAACGCCACTGGAGTGGCATGTGCAATATTATTGGGTGAAATGTTCTTATCAATATTGTTACTTAAGCGATATAAAAA |
| AATAATTTAAGGAATAGTTATGAAGAAGTTATTATTAGTGTTCGGTACTAGGCCTGAAGCAATAAAGATGGCCTCTAT |
| CATTGAATTATTAAAAAAAGATTGTAGATTCGAATATAAAATATGTGTGACAGGCCAACATAAAGAGATGCTTGATCA |
| AGTTATGCAAGTATTTGATGTTAAACCTGATTATAATTTACGGATTATGCAGCCTGGGCAAACATTAGTATCTATAGC |
| AACAAATATACTCTCACGGTTAAGTGAAGTTTTAATTATAGAAAAGCCAGATATTATACTTGTGCATGGGGATACAAC |
| GACTACCCTTGCTGCTACTTTAGCTGGGTATTACCACCAAATAAAAGTTTGTCATGTGGAAGCAGGATTAAGAACAGG |
| GGATATTTACTCTCCTTGGCCTGAAGAGGGCAATCGTAAAGTTACAGGGGCATTAGCATGTATTCATTTCGCCCCAAC |
| AGAGAGATCAAAAGATAATCTCCTGAGGGAGGGGGTCAAAGTAAATAATATATTTGTAACGGGTAATACCGTCATCGA |
| CTCTTTATTTATTGCAAAAGATATCATAGATAATGACCCTAATATAAAGAACGCTTTACATAATAAATTTAATTTTCT |
| TGATAAAAGCCGACGAGTAGTACTTATAACAGGTCATCGAAGAGAAAATTTCGGGAAAGGTTTTGAAGATATATGCTT |
| TGCAATAAAGGAATTAGCTTTCATTTATCCTAATGTAGATTTTATTTATCCGGTGCATCTTAATCCCAATGTAATGGA |
| ACCAGTACATCGTATATTAGATAATATATGTAATATTTACCTTATTGAGCCCTTGGATTATTTTGCCTTTTGTTTATTT |
| AATGAATGAGTCATATTTAATATTGACTGATTCAGGGGGGATACAAGAAGAAGCGCCTTCGTTAGGTAAACCGGTTTT |
| GGTTATGCGTGATACTACTGAACGCCCTGAGGCGGTTGAGGCTGGTACTGTTGTATTAGTGGGGACTTCTAAGATAAA |
| AATAGTAAATAAAGTAACGGAGCTATTAAACAATGCTGATATCTACAATGCTATGTCTCTGTTACATAATCCATATGG |
| CGATGGAACAGCTGCTCAAAAAATTCTTAATGTGCTCGCCCAAGAGCTAATTTAATTTAAGCTAAAAATATGTTATTA |
| ATTATTGCTGATTATCCAAACGAAATGAATATGCGCGAGGGAGCTATGCAACGAATAGATGCGATAGACTCTCTCATT |
| CGAGATCGCAAGCGAGTGTATTTGAATATTTCATTCAAAAAGCATCTAGTTCGCTCAAATAGTTCCTTTAATAATGTT |
| ATAGTTGAAAATCTAAATGCAATTATTCACAGAAACATCATAAAACAGTACATGCAAAAATCAACAACTATATATGTT |
| CATTCTGTTTATAATTTATTAAAGGTTATAACGCTCATTGATCTAAAAAAAACAATTCTTGATATACATGGTGTTGTA |
| CCGGAAGAACTTTTGGCAGATAATAAAAAATTACTTAGTAAAGTATATAACATGGTGGAAAAAAAAGGTGTCCTTGGA |
| TGCAAAAAATTAATACACGTCAGTACAGAAATGCAAAAACACTATGAAGCAAAATATGGAGTAAACTTGGCTGAAAGG |
| TCAATAGTGCTCCCGATTTTTGAATATAAAAATATAACCCAATCGCAAAACAAATGGACAGAAAATAAAATACGAAGT |
| ATCTATCTTGGAGGATTACAAACATGGCAAAATATTGATAAAATGATTCAAGTTTGTGATGACACAGTGATAAACAAT |
| GAAGCAGGTAAGTATGAATTCAACTTTTTCATCCCAGAGTAACTTGGAAGGGTTTATAGATAAATATTCGTTAAAA |
| TTACATAATATCAATGCTAATGCATCTACGCTATCACGTGATGAAGTAATTCCCTTTCTAAAAGAATGTCATATTGGT |
| TTTGTATTGCGCGATGATATAATAGTAAACAGAGTTGCGTGCCCTACAAAATTGGTTGAATATTTAGAGTGTGGTGTC |
| GTTCCAGTTGTGCTCTCCCCACTTATAGGTGATTTTTATTCGAGGGATATCAATACATTACTACAGAGGAAATGGCT |
| AACAGAAGTATAAGTTTGTTGGATCTTGAAAAAATGGCTGCACATAATTTACAAATTTTGACTTCTTATCAGAAGAGA |
| ACCTACAAGGCACAGAAAGAACTTATTGCTCAACTGTGCTGAATTTTTTACATATATAAAATTATGTAAGCATATCGC |
| GGGTCAGGTAATTGTATGCGTATCAAATATAAAGATAACGGTTATATATTATGTTTTCTATTATGTTTCATTTTGAGC |
| TACTTAGTTTTACTCAAATCTGACTACTTTCCTGCTGATTTTCTGCCATATACAGAAATATACGATGGGACATACGGA |
| GAAATCAATAATATTGAGCCTGCCTTTTTATATTTAACACGGTTGTTTCATTATTTAAATTTCCCCTATATATTTTT |
| GCAATGTTAGTTTGTGCCTTATGTTTAAGTTGGAAAATAAAATATGCAAGAAAATAATTAAAGATAGTTATATATAT |
| TTGTTCTTGTATGTATATGTATCATTTTATGTGTTTTTGCATGAAATGACTCAATTGCGCATAGCAATTGCAGTCACT |
| ATGTGCTATGTGTCGGTTTATTATTACTTTTATAAAAATTGTATTAAACATGCACTGCCATGGATGGTGTTGGCTATT |
| TTGTTTCATTACAGCGCCTTGCTTTTATTTATGTCATTATTTATACAGTTATAGGAGGTTATTAATAGTAATTATA |
| GGGTTTGTAATATGTATGAGCTTTTTAAACGTGTATGCAGATACAATTGCACTATATTTGCCAAATGAAAAAATAGTA |
| AATTATTTATATAGTATTTCATCATCATTAGACAATAGAAATGATTTGGCAATATTCAACCTGAATAATATAATATTT |
| TTATCAATATTTATTTTGATCTTTTATCTTAGCCGATATATAAAATTAAATGATAATGAGGCGAAGTTTATTAAGTAT |
| GTGCAATGTTCAGGAATATTAGCCTTTTGTATTTTCTTTCTGGCTAGTGGAGGTCCCGGTCATTGCTTTATCGAACTGCA |
| GAGTTGCTGCGAATATTTTATCCGATGGCTTTAGTATTAATCCTTTCGCATATAAAAAATAATAATATGCGTTATTTT |
| ATTGCAGTCATTATAGTTATCCTTTCAGGCTTAATGTTGTTTATAACACTAAGGGCTGTATCAATAGTTGGTCAAGGA |
| TTTATAAAATGAATGTTGCTATTTTGTTGTCTACGTATAATGGCGAAAAATATTTAGAGGAACAACTGGATTCATTGCT |
| GCTTCAAAGTTATCAGGATTTTGTAGTGTATATCCGTGATGACGGATCATCTGATAGAACTGTAAATATAATAAACCA |
| ATACGTAATGAAAGATAACAGATTTATTAACGTGGGTAATTCAGAAAATCTTGGTTGTGCTGCTTCGTTTATTAATTT |
| ATTAAGAAATGCTTCAGCCCGATATTTATATGTTTTGTGACCAAGATGATTATTGGCTTCCGAATAAATTACAGCGTGC |
| TGTGGATTATTTTTCGGCTATTGATCCTTTACAACCTACCTTGTATCATTGCGATCTAAGCGTTGTTGATGAAAAACT |
| TAATATTATACAAATTCATTTTTGCAGCATCAGAAAATGTCAGCGTATGATTCAATGAGAAAAAATAATCTTTTCAT |
| ACAAATTTTGTTGTTGGTTGTTCATGTGCTGTTAATGCTTCACTTGCGGAATTTGTTCTTTCGCGAATTGGAGAGCA |
| GCATGTAAAAATGATAGCTATGCATGACTGGTGGTTAGCCGTGACTGCAAAACTTTTTGGTCGAATCCATTTTGATAA |
| TACTCAAACGATTCTTTATCGACAACATCAGGGCAATGTATTAGGTGCAAAATCATCAGGTATGATGCGTTTTATTCG |
| ATTAGGATTAAATGGGCAAGGGATTTCGCGAGTAGTATCTTTTAGAAAAAAGTTTGTGCGCAAAATAAGCTTCTTTT |
| AGATGTCTATGATAAAGATTTAAATCTTGAGCAAAAAAAATCTATCAGGCTTGTAATTGAGGGCCTTAAAGAGAACTC |
| TTCAATTGCTGACCTTTTAAAATGTTTCTATCATGGTAGCTATATGCAAGGTTTTAAACGTAATCTTGCCTTAATATA |
| TTCAGTTCTTTACACAAAAAAAAGAAGATAGTGTATCCTTATGAAAAAAATTGCTATTATCGGTACTGTTGGCATACC |
| AGCATCATATGCGGATTTGAAACATTAGTTGAAAATTTAACAAGATACAATTCCTCGGGAGTTGAATATAATGTTTT |
| TTGTTCATCGTTTCACTACAAATCCCACCAAAAAAACATATGGGGCCCGTTTAATTTATATTCCGCTAAAGCCAA |
| TGGATGGCAGAGCATTGCGTATGACATAATTTCGTTAGCATATTCTATTTTTTTGAAGCCTGATGTGATTCTGATTTT |
| AGGGGTTTCTGGTTGTTCATTTTTGCCTTTCTTCAAACTCTTAACACGCGCTAAGTTTATTACTAATATTGATGGCCT |
| GGAATGGCGAAGAGATAAATGGAATTCAAAAGTGAAACGTTTCTTAAAATTTTCAGAAAAAATCGCAGTTCAATATTC |
| GGATGTCGTTATTACGGATAATGAGGCAATTTCTGAGTACGTTTTTAACGAGTATAATAAAGATAGCCGAGTTATTGC |
| CTATGGAGGGGATCATGCATGGTTAAATACTGAGGATGTATTTACAACAAGAAATTATAAAAGCGATTACTACCTTTC |
| TGTATGTCGTATCGAACCCGAAAACAATGTAGAATTAATTTTAAAAACATTTTCAAAGCTAAAATATAAAATAAAATT |
| TATTGGAAATTGGAATGGCAGCGAGTTTGGAAAGAAACTTAGGCTGCATTATTCTAACTATCCAAATATTGAAATGAT |
| TGATCCGATTTATGATCTTCAACAATTATTTCACTTACGAAATAATTGCATAGGATATATACATGGTCATTCGGCTGG |
| AGGAACAAACCCTTCTTTAGTCGAGGCAATGCATTTTAGTAAACCTATATTTGCATATGATTGTAAGTTTAATAGGTA |
| CACTACTGAAAATGAAGCATGTTATTTTTCTAATGAATCTGACCTCGCAGAGAAAATCATAATGCATTGTGAGCTATC |
| ATTAGGTGTCTCTGGCACGAAAATGAAAGAAATTGCTAACCAGAAATACACTTGGAGACGAATAGCAGAAATGTATGA |

| SEQUENCES |
|---|
| GGATTGCTATTAACTCTGTTAAACTTCAAATCTTTTACAATATATGGCATGACTATAAGCGCATTAATTGTTTTTCAA
GCCGCTCTCGCGGTGACCACCCCCTGACAGGGGATCCGTGTAGGCTGGAGCTGCTTCGAAGTTCCTATACTTTCTAGA
GAATAGGAACTTCGGAATAGGAACTAAGGAGGATATTCATATGGATAAAGCCGTAAGCATATAAGCATGGATAAGCTA
TTTATACTTTAATAAGTACTTTGTATACTTATTTGCGAACATTCCAGGCCGCGAGCATTCAGCGCGGTGATCACACCT
GACAGGAGTATGTAATGTCCAAGCAACAGATCGGCGTAGTCGGTATGGCAGTGATGGGACGCAACCTTGCGCTCAACA
TCGAAAGCCGTGGTTATACCGTCTCTATTTTCAACCGTTCCCGTGAGAAGACGGAAGAAGTGATTGCCGAAAATCCAG
GCAAGAAACTGGTTCCTTACTATACGGTGAAAGAGTTTGTCGAATCTCTGGAAACGCCTCGTCGCATCCTGTTAATGG
TGAAAGCAGGTGCAGGCACGGATGCTGCTATTGATTCCCTCAAACCATATCTCGATAAAGGAGACATCATCATTGATG
GTGGTAACACCTTCTTCCAGGACACTATTCGTCGTAATCGTGAGCTTTCAGCAGAGGGCTTTAACTTCATCGGTACCG
GTGTTTCTGGCGGTGAAGAGGGGGCGCTGAAAGGTCCTTCTATTATGCCTGGTGGCCAGAAAGAAGCCTATGAATTGG
TAGCACCGATCCTGACCAAAATCGCCGCCGTAGCTGAAGACGGTGAACCATGCGTTACCTATATTGGTGCCGATGGCG
CAGGTCACTATGTGAAGATGGTTCACAACGGTATTGAATACGGCGATATGCAGCTGATTGCTGAAGCCTATTCTCTGC
TTAAAGGTGGCCTGAACCTCACCAACGAAGAACTGGCGCAGACCTTTACCGAGTGGAATAACGGTGAACTGAGCAGTT
ACCTGATCGACATCACCAAAGATATCTTCACCAAAAAAGATGAAGACGGTAACTACCTGGTTGATGTGATCCTGGATG
AAGCGGCTAACAAAGGTACCGGTAAATGGACCAGCCAGACGCGCTGGATCTCGGCGAACGCTGTCGCTGATTACCG
AGTCTGTGTTTGCACGTTATATCTCTTCTCGAAAGATCAGCGTGTTGCCGCATCTAAAGTTCTCTCTGGTCCGCAAG
CACAGCCAGCAGGCGACAAGGCTGAGTTCATCGAAAAAGTTCGTCGTGCGCTGTATCTGGGCAAAATCGTTTCTTACG
CCCAGGGCTTCTCTCAGCTGCGTGCTGCGCTCTGAAGAGTACAACTGGGATCTGAACTACGGCGAAATCGCGAAGATTT
TCCGTGCTGGCTGCATCATCCGTGCGCAGTTCCTGCAGAAAATCACCGATGCTTATGCCGAAAATCCACAGATCGCTA
ACCTGTTGCTGGCTCCGTACTTCAAGCAAATTGCCGATGACTACCAGCAGGCTGCGTGATGTCGTTGCTTATGCAG
TACAGAACGGTATTCCGGTTCCGACCTTCTCCGCAGCGGTTGCCTATTACGACAGCTACCGTGCTGCTGTTCTGCCTG
CGAACCTGATCCAGGCACAGCGTGACTATTTTGGTGCGCATACTTATAAGCGTATCGATAAAGAAGGTGTGTTCCATA
CCGAATGGCTGGATTAA

SEQ ID NO: 12 (example O2 rfb locus nucleotide sequence-O2-EPA
production strain stGVXN4906)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGATCAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTATTCAAAGTTTTCCAGGATTTTCCTTGTTTCCAGACGGATTGGTAAGACAATTAGC
GTTTGAATTTTTCGGGTTTAGCGCGAGTGGGTAACGCTCGTCATCATAGGCATGCATGCAGTGCTTCTGGTAGCTGT
AAAGCCAGGGGCGGTAGCGTGCATTAATACCTCTATTAATCAAACTGAGAGCCGCTTATTTCACGCATGCTCTGAAG
TAATATGGAATAAATTAAGTGAAAATACTTGTTACTGGTGGCGCAGGATTTATTGGTTCAGCTGTAGTTCGTCACATT
ATAAATAATACGCAGGATAGTGTTGTTAATGTCGATAAATTAACGTACGCCGGAAACCGGGAATCACTTGCTGATGTT
TCTGATTCTGAACGCTATGTTTTTGAACATGCGGATATTTGCGATGACGCTGCACCTGACGGATTTTTGCTCAACGAA
CAGCCGGATGCAGTGATGCACCTGGCTGCTGAAAGCCATGTTGACCGTTCAATTACAGGCCCTGCGGCATTTATTGAA
ACCAATATTGTTGGTACTTATGTCCTTTTGGAAGCCGCTCGCAATTACTGGTCTGCTCTTGATAGCGACAAGAAAAT
AGCTTCCGTTTTCATCATATTTCTACTGACGAAGTCTATGGTGATTTGCCTCATCCAGATGAAGTAAATAATACAGAA
GAATTACCCTTATTTACTGAGACGACAGCTTACGCGCCAAGCAGCCCTTATTCCGCATCCAAAGCATCCAGCGATCAT
TTAGTCCGCGCATGGAAACGTACGTATGGTTTACCGACCATTGTGACTAATTGCTGAACAACTATGGTCCGTATCAC
TTCCCGGAAAAGCTTATTCCATTGGTTATTCTTAATGCACTGGAAGGTAAGGCATTACCTATTTATGGCAAAGGGGAT
CAAATTCGCGACTGGTTGTATGTAGAGGATCATGCTCGTGCGTTATATACCGTCGTAACCGAAGGTAAAGCGGGTGAA
ACTTATAACATTGGCGGACACAACGAAAAGAAAAACATCGATGTTGTCTGACTATTTGTGATTTGTTGATGAGAGATT
GTACCGAAAGAGAAATCTTATCGTGAGCAAATTACTTATGTTGCTGATCGCCCAGGGCATGATCGCCGTTATGCAATT
GATGCCGATAAAATTAGCCGCGAATTGGGCTGGAAACCACAGGGAAACGTTTGAGAGCGGGATTCGCAAACGGTGGAA
TGGTATCTGGCTAATACAAATTGGGTTGAGAATGTGAAAAGCGGTGCTTATCAGTCATGGATCGAACAAAACTATGAG
GGCCGTCAGTAATGAATATCCTGCTTTTCGGCAAAACAGGGCAGGTGGGTTTGGGAACTGCAGCGTGCTCTGGCGCCGC
TGGGTAATCTGATCGCTCTTGATGTTCACTCCACTAATTATTGTGGAGATTTCAGCAACCCCGAAGGTGTGGCAGAAA
CCGTCAAAAAAATTCGTCCTGACGTTATTGTTAATGCTGCTGCTCACACTGCAGTAGATAAAGCAGAATCAGAACCGG
ATTTCGCACAATTACTTAACGCGACAAGCGTCGAAGCGATTGCAAAAGCTGCTAATGAAGTCGGGGCCTGGGTTATAC
ACTACTCTACTGATTATGTTTTCCCAGGCAGTGGTGACCGGCGCATGGCTGGAAACGGATGCAACAGCACCGCTAAATG
TTTACGGTGAAACAAAATTAGCTGGGGAAAAGGCATTACAAGAACATTGCGCAAAGCATCTTATTTTCCGTACCAGCT
GGGTATACGCTGGTAAAGGAAATAACTTTGCTAAAACGATGTTGCGTTTGGCAAAAGAACGCGAAGAACTGGCTGTGA
TAAACGATCAGTTTGGCGCACCAACAGGTGCTGAATTGCTGGCTGATTGCACCGCTCATGCCATTCGCGTGGCATTAA
AAAAACCAGAAGTCGCTGGCTTGTACCATCTGGTAGCAAGTGGCACAACAACCTGGCACGATTATGCTGCGCTGGTTT
TTGAAGAGGCGCGCAAAGCAGGGATTAATCTTGCACTTAACAAACTTAACGCCGTGCCAACAACGCCGTTTCCACAC
CAGCCCGTCGACCCCATAACTCTCGCCTCAATACAGAAAAGTTTCAGCAGAATTTGCGCTTGTCTTGCCTGACTGGC
AGGTGGGCGTGAAACGTATGCTCAACGAATTATTTACGACTACGGCAATTTAACAAATTTTTGCATCTCGCTCATGAT
GCCAGAGCGGGATGAATTAAAAGGAATGGTGAAATGAAAACGCGTAAAGGTATTATTCTGGCTGGTGGTTCCGGCACT
CGTCTTTATCCTGTGACGATGGCAGTGAGTAAACAATTGCTGCCGATTTATGATAAGCCGATGATTTATTATCCGCTT
TCAACGCTTATGTTAGCGGGTATTCGCGATATTCTTATTATTAGTACGCCACAGGATACACCGCGTTTCCAACAATTA
TTGGGGACGGGAGCCAGTGGGTCTTAATCTACAGTATAAAGTACAACCGAGTCCGGATGGCCTGGCGCAAGCGTTT
ATTATTGGCGAAGACTTTATTGGTGGTGATGATATTGTGCACTCGTACTTGGCGATAATATCTTCTATGGACACGACTTG
CCGAAATTGATGGAAGCTGCTGTTAACAAAGAAAGCGGTGCAACGGTATTGCTTATCACGTTAATGATCCTGAACGC
TATGGTGTCGTGGAGTTTGATAATAACGGTACGGCAATTAGCCTGGAAGAAAAACCGCTGGAGCCAAAAAGCAACTAT
GCGGTTACTGGGCTTTATTTCTATGACAATGACGTTGTGGAAATGGCTAAAAACCTTAAGCCTTCTGCCCGTGGCGAA
CTGGAAATTACCGATATTAACCGTATTTATATGGAACAAGGACGTTTGTCTGTAGCCATGATGGGCGTGGCTATGCA |

SEQUENCES

```
TGGTTGGATACAGGGACGCATCAAAGCCTTATTGAAGCAAGTAACTTCATTGCAACAATTGAAGAGCGTCAGGGATTA
AAGGTATCTTGCCCGGAAGAGATTGCTTACCGTAAAGGGTTTATTGATGCCGAGCAGGTGAAAGTATTAGCCGAACCG
CTTATCAAGAATCAATATGGTCAATATTTGCTGAAAATGATCAGCGAATAGTATATGGGAACTCAATGATGGATATTA
AATTAATCTCTTTGCAAAAACATGGGGATGAGCGCGGTGCATTAATTGCTCTTGAAGAGCAACGAAATATACCTTTCG
AAGTCAAAAGAATATATTACATACTTGAGACTCTTAATGGAGTAAGACGCGGATTTCATGCGCACAAGGTTACTCGTC
AGTTAGCTATTGTAGTCAAGGGAGCTTGTAAATTTCATCTGGATAATGGTAAAGAAACAAAGCAGGTGGAACTTAATG
ATCCAACAATTGCGTTGCTGATAGAACCCTATATATGGCATGAAATGTATGATTTTAGTGATGATTGTGTGCTGCTTG
TAATTGCGGATGATTTCTATAAAGAGTCTGATTATATCCGCAATTATGATGATTTTATTAGAAGAGTAAATTCAATTG
AGAATTCATAAGCTAAGTGACGTCCAGACAACATCAATTGGTGATGGAACAACTATCTGGCAGTTTGTTGTGATACTA
AAAGGTGCTGTAATTGGTAATAATTGCAACATCTGTGCAAATACCTTAATTGAAAATAACGTTGTAATTGGTAACAAT
GTCACAGTCAAAAGCGGTGTGTATATTTGGGATGGCGTTAAAATAGAGGATAATGTTTTTATTGGTCCTTGTGTAGCA
TTTACAAATGATAAGTATCCTCGCTCTAAAGTCTATCCTGATGAATTTTTGCAAACAATAATACGCAAAGGAGCATCA
ATAGGTGCTAACGCAACCATCCTGCCAGGAATTGAAATTGGTGAAAAAGCAATCGTTGGTGCGGGGAGTGTTGTAACC
AAAAATGTACCGCCATGCGCAATAGTAGTAGGTAATCCAGCTCGATTTATTAAATGGGTAGAGGATAATGAATAAAAT
TGATTTTTTAGATCTTTTTGCAATTAACCAGCGACAGCACAAAGAATTAGTCTCTGCGTTTAGTAGGGTGCTAGATTC
TGGTTGGTATATCATGGGCGAAGAACTTGAGCAGTTCGAGAAAGAGTTCGCAGAATACTGTGGAGTTAAGTATTGCAT
TGGTGTAGCAAATGGCCTTGATGCGTTGATACTAGTATTGAGGGCATGGAAAGAACTTGGCTATCTTGAAGACGGTGA
CGAGGTATTAGTACCGGCAAATACATATATTGCTTCTATTCTTGCTATAACAGAGAACAAACTTGTTCCTGTTCTTGT
TGAACCAGATATAGAAACTTATAATATTAATCCTGCTTTAATTGAAAATTACATTACGGAAAAAACTAAAGCAATATT
ACCGGTTCACTTATATGGTCTATTGTGCAATATGCCAGAAATTAGTGCAATCGCCAGAAAATATAATCTGTTGATTCT
TGAAGATTGTGCACAAGCACATGGTGCAATACGTGATGGTCGCAAAGCTGGAGCTTGGGGGGATGCTGCAGGATTTAG
TTTTTATCCAGGAAAAAACCTTGGAGCTTTGGGGGATGCGGGAGCTGTTACTACAAATAATGCAGAATTATCCTCAAC
TATAAAAGCTTTGCGAAATTATGGGTCACATAAGAAATATGAAAATATTTATCAGGGATTGAATAGTCGATTGGATGA
ACTGCAAGCAGCCTTATTGCGTGTAAAAATCCATACATTACCGGAAGATACTGCGATTCGGCAAAGGATTGCTGAAAA
ATATATTCGTGAAATAAAAAACCCTGCGATTACGTTACCAGTGTACGAAGGCCAAGGTGCGCATGTTTGGCATTTATT
TGTAGTAAGAATCGCTAATCGTGAAAATTCCAGTCATACTTATTAGAGAAGGGTATCAAAACCTTAATTCACTATCC
ATTACCACCCCATAAGCAGCAAGCATATCAAAATATGTCTAGCCTTAGCCTTCCAATTACTGAGCAAATTCATGATGA
AGTCATTTCTTTACCTATAAGTCCGGTAATGAGTGAAGATGATGTCAATTATGTAATCAAAATGGTCAATGATTACAA
GTAATGAAAAAATTTCTTCAGGTAACTATATTATCCGCTATCTATACATTCATTAAAATGATTGCGGGTTTTATCATC
GGTAAGGTAGTAGCAATTTATACAGGGCCATCAGGGGTAGCAATGCTTGGCCAAGTGCAAAGTTTAATCACAATAGTT
GCAGGTACTACCTCTGCACCTGTAAGCACAGGCCTTGTTCGATATACTGCGGAAAATTGGCAAGAAGGACAAGAAGCA
TGCGCGCCATGGTGGCGCGCATGCTTAAGGGTTACTCTGTTTTTATTCTTGCTTATTATTCCCGTTGTTATTATATTG
TCGAAAAATATTAGTGAGTTACTTTTTAGCGATGGACAATACACATGGTTAATCATTTTCGCATGTTGTATATTGCCA
TTCTCCATTATAAATACATTGATCGCTTCAGTTTTAAATGGTCAACAATTTTATAAGCAATATATATTGGTTGGGATG
TTTTCTGTATTCATTTCTACTATGTTTATGATTTTGTTGATTGTAGCTTATAATCTTAAAGGTGCATTGATTGCCACA
GCTATAAATAGTGCTATTGCTGGTCTTGTATTGGTTTTATTTTGTCTCAATAAATCTTGGTTTAGATTTAAATATTGG
TGGGGTAAAACGGATAAAGACAAAATTATAAAAATTATTCATTATACTCTGATGGCTCTGGTTTCTGTTATCTCCATG
CCTACAGCATTGATGTGTATTAGAAAAATATTGATTGCTAAAACTGGTTGGGAGGATGCAGGGCAATGGCAGGCCGTA
TGGAAGATATCTGAGGTTTATCTTGGTGTTGTGACAATTGCTTTGTCAACATATTTCTTACCAAGATTGACAATTATA
AAAACAAGTTTCCTTATAAAAAAAGAAGTAAATAGTACTATATTATACATAATATCTATTACTTCATTCATGGCGTTG
AGTATCTATTTATTCCGCGATTTGGTAATAACAGTTTTATTTACTGAACAGTTTCGCTCAGCTCGTGAATTATTTTTA
TTACAACTTATAGGGGATGTAATAAAAATTGCTGGGGTTTCTTTATGCATACCCTCTTCAAAGTCAGGGGCATACTAAA
CTATTCATCAGTTCAGAAGTGATTTTTTCTATGCTCTTTATCATTACCACCTATATTTTGTTGTAAATTATGGAGTA
CATGGTGCTAACATAAGTTATGTCATTACATATAGTTTATATTTTGTGTTTGCATTTGTGTTTACTAATTTTATTAAT
GTTAGAAGAAATAATTAAAAACAGAGGTTGAATTTTGAAAATAATTATACCTGTCTTAGGATTTGGCAGGGCTGGTGG
TGAAAGAGTTCTTTCTAAGCTGGCAACTGAATTGATGAATTATGGACATGATGTAAGTTTTGTTGTTCCAGATAATAG
AACTAATCCATATTATGCTACCACAGCAAAATTGTCACGAGTGAAATCTAGTCAAAACCGTGTAAAAATATTGAGAAT
CATTAAAAATTACTATAATCTGTGGCGTAAATGCATAGAGTTAAATCCTGATGCTGTAGTTGCTAGTTTTCATTTGAC
TGCCTATCTTGTCGCATTATTACCAATCACCCGTCGTAAGAAATATATTATTATTCAGGCGTATGAAGTTAATTTTTT
TGATAATATAATATGGAAATTAATAGCGGGTTTAACATATTATTTACCGCTTAAAAAAATACTAAATAGTCCTAATTT
GCTTCCTCATAAACATGATGATTTTATAGGAGTAGTTCCTGCAGGAGTAGATTTAAACGTTTTCTATCCGAAACCATC
AAATAGGTTATTAAATGGTCACACATCAATAGGGATTATTGGTAGAAAAGAGAAGCACAAAGGAACTAGCGAAATTAT
TTCAGTATTGTGTTCACTGGAAAATAAAGCTGGAATTATAATCAATATTGCGATCTATCTTGAAGAAGTTGATAAGCA
GCGTTTAATCGCTGCCGGGTTTCAGGTTAATTTTTTTCCGATTACTTCTGATTTAGAATTGGCATCCTTTTATCGAAG
CAATGACATCATGATTGCTGTTGGGTTAATTGAAGATGGCGCTTTCCATTATCCTTGTGCTGAATCAATGGCTTGTGG
TTGTCTTGTTATTTCAAATTATGCGCCACTTACTGAAACTAACAGTGTACTTAAATTAGTCAAGTTTGATGCTTGCAA
ACTTGGTGAAGCAATTAATCTTTGTCTCAATCTTGACCTAGAAGAAAAAAGCAAGAAAATCCAATCTAATATTTCTGT
GTTGAATAAATATGACTGGAAAATTGTTGGTGAAACTTTCAATAGTTTATTGTTAGATGCAAATAAATAGTATACGTT
GATGGGGAAAATATGAATATTGTTAAAACTGATATTCCAGATCTGATCGTTCTTGAACCAAAAGTGTTTAGTGATGAA
CGCGGCTTTTTTATGGAGAGTTATAATCAGATTGAATTTGAGAAGGCAATAGGAAGGCACGTAAATTTTGTTCAGGAT
AATCATTCAAAATCTAGTAAAGGCGTACTACGTGGGTTGCATTATCAATTAGCACCGTATGCACAGGCTAAATTAGTT
CGATGTGTTGTAGGTCAGGTATTTGATGTTGCTGTTGATCTTAGAAAAAATTCACCAACGTTCAAAAAATGGTTTGGA
ATAACCCTTTCCGCAGAAAATAAACGACAATTATGGATACCCGAAGGATTTGCTCATGGTTTCTTGGTGACCAGTGAT
GAAGCTGAGTTCATTTATAAGACAACTAACTACTATGCTCCTGGTCATCAGCAAGCAATTATTTACAATGATCCTATT
TTAAACATCGATTGGCCTTTCTGCAGTAGTGCTCTGTCATTATCACAAAAAGATCAAGAAGCAAAATTATTTTCAGAA
TTATTGGACAGTGAACTGTTCTAATAAAGTGTGCCACCTTATCGTCTGAAAGGATAGGTGGTTGCTTATATTTTTTG
AGTATGTTTGTATAATGACAGAAAATAGTCCGAAATATAAACACGATAAAAGCTTAATAAGTTTTATCTACTTATTTT
TTATATTTACACTTATTGTAGGCTTTATTATCGCAAATACCCAGTTTTTGGGGCGAAGTAGAGACTATGATAATTATA
TACAGATCTTTTCTGGTAAAGAAGGGGAGGGGGTTCTTGAATTATTTTATCGCGGATTGATGTTAATAACGACCAGCT
ATGAAACTATCATTTTTATAATTTTAACATGTTCTTTTTTTATAAAGGCAAGGTTTCTCGCTAACTATTCGCGTAATT
TTTCAGGCTTGACCTTATTCTTTATTTATTATGCAAGCGTTGCACTTTGGGTTTTAGATTATACTCAATTCAGAAATG
GTCTATGTATTTCCATTTTAATGTTTTCCGTATACTATTTATTTATAAATAAACCGACTTATTTTTATTTCTCGGTAT
TATGTGCAATTGCAACTCATTGGTCTGCTTTGCCTTTTTTGCTTTTATATCCTTTTGTCTATTCAACAAAAATAAGAC
GCCTTGGTTATTTTTGTTTCAGTATTCTTGTTTTGATTGCGATCTCAGGAGAAGGAAAAGAGATCATATCTTTTATAA
GAAATTTTGGAGTGGGACAAAAATAGGAAATGAAGCTGGTGTAAATTTAATAAATTCATTATCCCTTACCGCTATTT
CCTGGTTTATTATTAGTTACATATCAAGCATTGGAAATGAAAGGAGAAATTTAAGGCTTTTCTTTTGTTATGGTGTCA
TGCAATACGTGACTTTTAGCCTTTTCTCTCTACCTGTTATGGCTTTCCGTATTTTGGAAATGTATTTTTTCCTTATGC
```

| SEQUENCES |
|---|
| TAACCATTGGGGTGTTTATTAAGCAAAAAAGAATTATTATTTTATTTTTTGCAAAGTGTTAATTTTATTGTATCTAA |
| CATACTATTATCATATGGTCTTTGGAGTGATTAATGTGTAAGGCTAAGGTGTTGGCTATAATTGTTACTTACAACCCG |
| GAAATTATTCGATTGACGGAATGTATTAACTCTTTAGCCCCACAAGTTGAGAGAATAATTCTTGTAGATAATGGCTCA |
| AATAATAGTGATTTGATAAAAAATATCAGTATTAATAACCTTGAAATTATTTTACTTTCGGAAAACAAAGGCATTGCA |
| TTTGCTCAGAACCATGGTGTTAAGAAGGGCCTGGAAGCAAAAGAGTTTGACTATTTATTTTTCTCAGATCAGGATACT |
| TGCTTTCCTAGCGATGTTATTGAAAAACTTAAGAGTACATTTACGAAAAATAATAAAAAAGGTAAAAATGTTGCTTGT |
| GCTTCTCCTTTTTTTAAAGACCATCGTTCAAATTATATGCATCCGTCAGTCAGCCTAAATATTTTTACGAGTACAAAA |
| GTTATATGTAGTGAAGTAGACGATGATCTTTATCCCTCGCATGTTATTGCTTCTGGGATGTTAATGTCTCGTGAAGCA |
| TGGCGCGTCGTCGGACCATTTTGTGAAAAACTCTTTATAGACTGGGTTGATACAGAATGGTGTTGGCGTGCATTAGCT |
| AATAATATGATTATTGTTCAGACACCATCAGTCATCATTTCTCATGAACTTGGGTATGGGCAGAAAATTTTGCTGGT |
| CGATCTGTTACAATACATAATTCTTTCAGAAATTTTTATAAAATACGCAATGCAATATACTTAATGCTGCATTCAAAT |
| TATAGCTTCAAGTATCGTTATCATGCTTTTTTTCATGCGACAAAGAATGTTGTATTTGAAATTTATATTCGAAAGAA |
| AAATTAAATTCACTGAAGGTTTGTTTTAAAGCTGTACGTGATGGTATGTTCAATAATTTTTAATACGAAAATAGTTAG |
| GCTCAAGGTGTTTAAATGGAAGAAAATAATATGAAGACGGTCGCTGTAGTTGGCACAGTGGGTGTTCCTGCTTGTTAT |
| GGTGGGTTCGAATCACTTGTTCAGAATCTAATTGATTATCAATCTGATGGTATACAATATCAGATATTTTGCTCTTCA |
| AAAAAATATGATAAAAAATTTAAAAATTATAAAAATGCAGAATTAATCTATTTGCCGATAAATGCCAATGGCGTCTCT |
| AGCATAATTTATGATATTATGTGTTTAATTATTTGTTTATTCAAAAGGCCAGATGTTGTTTTAATATTGGGGGTGTCT |
| GGTTGTTTATTTCTACCAATTTATAAACTATTTTCAAAATCAAAGATTATTGTCAATATTGATGGGCTTGAATGGCGT |
| AGAAATAAATGGGGAACGTTTGCTAAGAAATTTCTTAAAATATCTGAGGCGATATCTATTAGAATAGCTGATATTATC |
| ATTTCAGATAATCAAGCAATAGCTGATTATGTGGAAAATAAGTACAAGAAAAAAGTGTAGTTATAGCTTATGGCGGA |
| GATCATGCCACTAATCTTAGTACACCGATAGACAATGATCAAAAAAAGAAGGTTATTATTTGGGGCTTTGTAGGATA |
| GAGCCTGAGAATAATATAGAAATGATTCTGAATGCCTTCATTAATACAGATAAAAAATTAAATTTATGGGTAATTGG |
| GATAACAGCGAGTATGGACGCCAGCTAAAAAAATATTATTCAAACTATCCAAATATCACCCTACTAGAACCTAACTAT |
| AATATTGAAGAGCTTTATAAACTAAGAAAAAATTGTCTTGCATACATTCATGGACATCCGGCTGGTGGAACAACCCT |
| TCTTTAGTTGAAGCGATGCATTTTAATATTCCTATTTTTGCTTTCGATTGTGACTTTAATCGTTACACAACTAACAAT |
| TTAGCTCATTACTTTAATGATTCTGAACAACTTAGCTTATTAGCAGAAAGTTTGTCTTTTGGAAATCTTAAATGTCGA |
| GTATTAGATTTAAAAAATTATGCTGAAGATATGTATAACTGGAGGCATATAGCTGCTATGTATGAATCTATTTATTAA |
| ACGCATTAACAATAATATAATTGACCTTATATAGCAGGGAAAGATCACGTAACGATGCGGCGCGATCCCCATATG |
| AATATCCTCCTTAGTTCCTATTCCGAAGTTCCTATTCTTTCTAGAGAATAGGAACTTCGGAATAGGAACTAAGGAGGA |
| TATTCATATGGATAAAGCCGTAAGCATATAAGCATGGATAAGCTATTTATACTTTAATAAGTACTTTGTATACTTATT |
| TGCGAACATTCCAGGCCGCGAGCATTCAGCGCGGTGATCACACCTGACAGGAGTATGTAATGTCCAAGCAACAGATCG |
| GCGTAGTCGGTATGGCAGTGATGGGACGCAACCTTGCGCTCAACATCGAAAAGCCGTGGTTATACCGTCTCTATTTCA |
| ACCGTTCCCGTGAGAAGACGGAAGAAGTGATTGCCGAAAATCCAGGCAAGAAACTGGTTCCTTACTATACGGTGAAAG |
| AGTTTGTCGAATCTCTGGAAACGCCTCGTCGCATCCTGTTAATGGTGAAAGCAGGTGCAGGCACGGATGCTGCTATTG |
| ATTCCCTCAAACCATATCTCGATAAAGGAGACATCATCATTGATGGTGGTAACACCTTCTTCCAGGACACTATTCGTC |
| GTAATCGTGAGCTTTCAGCAGAGGGCTTTAACTTCATCGGTACCGGTGTTTCTGGCGGTGAAGAGGGGGCGCTGAAAG |
| GTCCTTCTATTATGCCTGGTGGCCAGAAAGAAGCCTATGAATTGGTAGCACCGATCCTGACCAAATCGCCGCCGTAG |
| CTGAAGACGGTGAACCATGCGTTACCTATATTGGTGCCGATGGCGCAGGTCACTATGTGAAGATGGTTCACAACGGTA |
| TTGAATACGGCGATATGCAGCTGATTGCTGAAGCCTATTCTCTGCTTAAAGGTGGCCTGAACCTCACCAACGAAGAAC |
| TGGCGCAGACCTTTACCGAGTGGAATAACGGTGAACTGAGCAGTTACCTGATCGACATCACCAAAGATATCTTCACCA |
| AAAAAGATGAAGACGGTAACTACCTGGTTGATGTGATCCTGGATGAAGCGGCTAACAAAGGTACCGGTAAATGGACCA |
| GCCAGAGCGCGCTGGATCTCGGCGAACCGCTGTCGCTGATTACCGAGTCTGTGTTTGCACGTTATATCTCTTCTCTGA |
| AAGATCAGCGTGTTGCCGCATCTAAAGTTCTCTCTGGTCCGCAAGCACAGCCAGCAGGCGACAAGGCTGAGTTCATCG |
| AAAAAGTTCGTCGTGCGCTGTATCTGGGCAAAATCGTTTCTTACGCCCAGGGCTTCTCTCAGCTGCGTGCTGCGTCTG |
| AAGAGTACAACTGGGATCTGAACTACGGCGAAATCGCGAAGATTTTCCGTGCTGGCTGCATCATCCGTGCGCAGTTCC |
| TGCAGAAAATCACCGATGCTTATGCCGAAAATCCACAGATCGCTAACCTGTTGCTGGCTCCGTACTTCAAGCAAATTG |
| CCGATGACTACCAGCAGGCGCTGCGTGATGTCGTTGCTTATGCAGTACAGAACGGTATTCCGGTTCCGACCTTCTCCG |
| CAGCGGTTGCCTATTACGACAGCTACCGTGCTGCTGTTCTGCCTGCGAACCTGATCCAGGCACAGCGTGACTATTTTG |
| GTGCGCATACTTATAAGCGTATCGATAAAGAAGGTGTGTTCCATACCGAATGGCTGGATTAA |

SEQ ID NO: 13 (example O6A rfb locus nucleotide sequence-O6A-EPA
production strain stGVXN4112 and stLMTB10923)
ATGACGAATTTAAAAGCAGTTATTCCTGTAGCGGGTCTCGGAACTGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATTTGCCCGCCGGGCGTGACAATTATGAACGTGCGTCAG
GGCGAACCTTTAGGTTTGGGCCACTCCATTTTATGTGCACGACCTGCATCATTGGTGACAATCCATTTGTCGTGGTGCTG
CCAGACGTTGTGATCGACGACGCCAGCGCCGACCCGCTGCGCTACAACCTTGCTGCCATGATTGCGCGCTTCAACGA
ACGGGCCGCAGCCAGGTGCTGGCAAAACGTATGCCGGGTGACCTCTCTGAATACTCTGTCATCCAGACCAAAGAGCCG
CTGGACCGCGAAGGTAAAGTCAGCCGCATTGTTGAATTCATCGAAAAACCGGATCAGCCGCAGAGCTGGACTCAGAC
ATCATGGCCGTTGGTCGCTATGTGCTTTCTGCCGATATTTGGCCGGAACTTGAACGCACTCAGCCTGGTGCATGGGGG
CGTATTCAGCTGACTGATGCCATTGCCGAACTGGCGAAAAACAGTCCGTTGATGCCATGCTGATGACCGGCGACAGC
TACGACTGCGGTAAAAAATGGGTTATATGCAAGCGTTCGTGAAGTATGGACTACGCAACCTCAAAGAAGGGCGAAG
TTCCGTAAAGGGATTGAGAAGCTGTTAAGCGAATAATGAAAATCTGACCGGATGTAACGGTTGATAAGAAAATTATAA
CGGCAGTGAAGATTAGCGGCGAAAGTAATTTGTTGCGAATTTTCCTGCCGTTGTTTATATAAACAATCAGAATAACA
ACGACTTAGCAATAGGATTTTCGTCAAAGTTTTCCAGGATTTTCCTTGTTTCCAGAGCGGATTGGTAAGACAATTAGC
ATTTGAATTTTACGGGTTTAGCGCGAGTGGGTAACGCTCGTCACATCGTAGACATGCATGCAGTGCTCTGGTAGCTGT
AAAGCCAGGGGCGGTAGCGTGCTGAAATTATAAAGTCATTCTTATAGAACATCGCATTTCAATAATATAATTACACCT
AAATGAATAGGATACAACGTGTGCACAATTATTTAAGGCTTAAAGATAAAATAAAAAACGTATTTTAGGGTTGTATA
TATTGCAGTTATTTAATTATATCGCGCCATTGGTAATTATCCCTATCCTGATAAAATATATTGGGTTGGGGGAATATG
GGGAATTGGTCTATATTACATCTATTTATTCAAATAGTGGCTTTGATTATTGATTTTGACTGCTTTACTTACACAGGACCTG
TGGTTGCTGCGAGACATAGATGTGAGACCCAAAATTTACAGCGCTATTACTCAATAGTTGTTCTTTTAAAATCATTGC
TTTTTATAATTGCATTAACATGTGTATTTTTATTGTGCAGATTAAATATAGTCCACTTGTCATTTTTTGGGTTTTTGT
CAATTTTTCTATGCACTATTGGTAATATATTATCGCCCAATTGGTTTTTGCAGGGGATTGGTGATTTTAAAAAACTTT
CATACTCACAAGTAATAGTGAGAATAACATTGTTTATCATACTTCTTGTTTATGTCTGTAGTGGCGGAGATAATGTTT
TTATCCTAAGTTTTTTGCAAAATGCAACATTACTCATATGCTGTATATACTTATGGCCAAATATTCATATTAGCCATG
TTGTTCATCTTAAACCTAATGAATGCATTGTGGAATTTAAGAAGGCAGGAAATGTTTTTATTGGCGTAATAGGTACGA

| SEQUENCES |
|---|
| TTGGTTACAATGGTCTAATTCCTGTGTTAATTGGAAACCTTTGCGGTAATACGAGTCTTGGTGTTTTTTCAATCGTTC |
| AAAAAATGACAACAGCATGTCAAAGTCTAATTAATCCAATATCACAGTATATGTTATCTCAAGTTTCAGAAATTAAAC |
| CTCAAGATAAACTGTTTTATTATAGAATTAAAAAAAGTTTTTTTGTGCATTTAACAATTAGCATAATTGCATGTTTAT |
| GTTATATGGGGTTAGGGCAATATGTGGCGACTTTTATAGGTAAAGTTGACGTTTCATTTGTTATTATTTTATTTGCGT |
| CAATAATTACCATTTTTTCATCTTTAAATAATGTCCTTGGTATACAGTTTCTTATACCGACAGATAATGTAAAAATAC |
| TACGAAGTATAAATGTTATGGCGGGAATTATTGTTGTTAGTTTGTCCTGGCTGTTAATATCACGCTTTGACATTCTGG |
| GGGGGGTTTTATTAAACCTAATTGGTGAGTTTCTTGTATTCAGTATGCTAGCTTTTATTGCCCATCGAAAGTGGGGAG |
| CGAGAGTATAATGAAAGTGAAGGCGGTTCCTGCTATTACATTCTATTTAAGTTTAATGCTGACAATTTTAGTGTTACT |
| GTTTGGTAATGAACCAAATAAATCACAATATATCCTTGTTATAGCAACGATAACAGTTTTTTATATCGCATATATCAC |
| TAATAAAATAACTTCTCCGGCCAGCCTTCTCGTTATATCATCTTTTGTGTTTTTAGGTTGTCGCCCTTTATTATCTTT |
| GTTTGCAAACTATGATTATAGGATTGCCGATTGGTTTATTGAAGGATATATGGATGACGATGTGATTTTGGCTAACTA |
| TGCTATAACACTAATGTATTATGGTTATACATTGGGACTAATTCTATGCAAAAATACTGAAAAATTTTATCCGCATGG |
| TCCTTATCCTGAAAAACAATTGCTAAAAATAAAGTTTCTTTTGACTTTATTTTTTCTGGGTTCGATAGGTATGGTTGT |
| AAAAGGGATATTCTTTTTTAACTTTATAGAATCTAATAGTTATGTTGATATTTATCAATCAAATATAACAACGCCAAT |
| AGGTTATGATTTTCTATCTTATTTATTTTATTGTTCTTTTTCCTTATATGTGCGTTTCATATACAGTTCAGAACAAA |
| TAAAAAATTTCTTTTTATTGCGATATGCATTGCTGCATTTAGCACCTTGAAGGGTAGTCGTAGTGAAGCTATAACGTT |
| TCTTTTAACGGTTACATGTATATATTTTAATGAAGTAAAGACAAGAAACTTACGTCTGCTGATTACAATGATTTTTGT |
| TTTTAGCGTCATTTTTGTGATTAGTGAATTTATCTCAATGTGGCGCACTGGAGGGAGTTTTTTTCAATTAATGCAGGG |
| TAATAATCCTGTTATAAACTTTGTATACGGCATGGGAGTATCATATCTTTCCATTTATCAATCAGTAAAACTACAACT |
| ATTGTCAGGGGGATATAATGTTACCTATCTATTCAGCCAGTTAATAATAACTTGCTCGTCAATATTTAATGTCAAATT |
| GAGCTTGCCGGAAATAAGCTATAGCCATTTGGCCTCATACACAGCAAACCCAGAACTATATAATCTTGGGTTCGGACT |
| TGGGGGGAGTTATTTAGCAGAATCGTTTTTAGCATTTGGTCTGATTGGATGTTTCATTATACCCTTTTTACTTTTACT |
| TAATTTAAATGTATTGGAAAAATATACAAAAAACAAACCAATTATATATTTTGTTTATTATAGTGTGTTGCCACCTAT |
| ATTATTCACACCAAGAGAGACTTTGTTCTATTTCTTCCCCTATCTTGTCAAAAGTATATTTGTTGCTTTTTTAGTTAC |
| ATTATACATCCAGTATAAAAAGGATTGACCAAAATGTCAGAAAAAAATGTCAGCATAATAATCCCAAGTTATAACAGG |
| GCTCATATTCTTAAGGAGGTCATACCAAGTTATTTTCAGGATGAGACTTTAGAGGTTATAGTTATCAATGATGGATCA |
| ACAGATAATACAAATAGTGTATTAGCTGAACTGAAGGAAAAATATTCTCAGTTAGTTATTTTAGAAAATGAAACGAAT |
| AAAAAACAGATGTATTCTAAAAACCGAGGGATTGAAATAGCCAAAGGGAAATATATTTTTTTTGGTGATGATGACTCT |
| TACCTCTTACCCGGTGTTATATCTCGGTTATTGGCTACAAAATATGAGACAGGCGCTGATGTAATCGGCGCAAGATA |
| CTTTATATGAATAATAACGAGAAACAATTGAAGATTGCATAAATCGACATAAAAAGAGGGCGTTTTGTTAGTGAT |
| CTAAATAGATTGGATTTTAGTTATACATGTGATTTGGACCATCCGATTGAATGTTTTTATGCACAGCCTTTTGTTCTA |
| GCTGAAAGGGAACTAATATCGAAATATCGATTTGATATATCTTATACGGGAAACTGCTATCGTGAGGAAACTGATTTC |
| ATGCTATCTCTATTTATTAAAAATAAAAAATTTATATATGATTCAAAGGCTTTGTTAATAAATTTACCTCCAAGAAAA |
| GCGACGGGAGGGGCAAGAACAGCTAATCGATTAAAATATCATTACGAAAGTTGCATAAATAATTATAGATTTTTAAAA |
| AAATATAATGATAATTTGAATCTTCTTTCAGGACAAAAGCATGCTATATTTTACCGACAGTGTCAATTCGTTCTGCTA |
| AAAATGAAGTCGTTTATCGGGAAGTTTTTAAAATGATTATATATATCGCCGCGTATAATGGTTCAGGAGGGCAAGGTG |
| GGGTGGAAAGGGTTGTTGCCCAACAATGTAACATTCTTAAAAATTTGGGGGTTAAAGTCATTATACTTGATAAAACAT |
| ACTTCAAATTTCTAACAAAATTCGTAACAAAAAAATACAAGTAGCACTTTATCCAATATTAGTTTCTCTTTATTTAA |
| CCTTACAAAAATTACGTGGCGTGACGTTTAAAGTTATTGCACATGGCTATTGTTCTCCTTTTTATAGGAATGACATCT |
| TAATAGCTCATGGCAATATGAAATGTTATTTTCAAACAGTCATGAATAAAAAACCTAATCGGTTGCTCTGGCAGTGGTC |
| TTTTATCTTTCTATGAGCGTTGGGCTGGAGCATTTTCAAAAAATATCTGGGCTGTTTCAAATAAGGTTAAAAGTGAAT |
| GGAATGAGCTTTACAATATTAATTCACATAAAATCAAAGTTGTTCGAAATTTATAAATCTTGCACAATTTGATTACA |
| CTGATGTTAATGAAGCAGAATATGTGACATTTGTCGGGCGATTGAAAAAGGAAAAGGAATAGATGATCTGTATTACA |
| TATGTAAAAATCTGCCAGATACTTCCTTCCATTTAGTTTCAAGTATTCCCGCCCCACAAAATTTTGCTTCGCTAAATA |
| ATGTTCTGACCAGCATTGCTGTCCCCTATGCGAAAATGCCAGAAATATTTAAGAAATCCAGAGTACTTATTTTACCGT |
| CCTATTATGAAGGATATGAGCTGGTTACTATTGAAGCGCTATGCTGTGGTTGCCCTGTGATAGGCTATAATGTTGGTG |
| CAATTAGAGAGTTGTATGCAGAAAGTTTTCCTGGCGTATTTATTGCCAATAATAAAGAAGATTTAGCACAAGTAGCCT |
| ACAAATTAATTAGTCTTGATAATGAAAAATATTATCATTTGAGACAAACTATTTATAGCAAGCGTGAGCTTTTTTCTG |
| AAGAGAGATATGCGGAAATTTTAACGGCGGCATTTAATGAAAAAAAATAAGAAACTCTGTCTCATTTCAATTAACTCA |
| TATAATGAACTTACCGGAGGAGGAGTATATTTACGTACGCTTGTTAGTTTTCTACAAAAACAGAATGTTAATTTAACA |
| CTTATTGATAAAAAATCCTCAGGTAAACTATTCGAAGACAATACTTTTCAACATATATCATTTATTAAAGGTAAACGT |
| CAGGATATAATATCCAGGCTTTTTTTTATACCATCATTTTATGTCCCTTATATTTTCTCAATAATTAAAATTTTACGG |
| AAGCAAGATATTCTTGCTTTTCACAACTCTCGGCTTGGATTGTTATGTCTGCTTTTTAGAATACTCATGCCCCACAAA |
| AAGATCATATTGTTTACGGATAACTTCGAATATGACTTAATAAGACAAAAAGATAAAAACATAACTACTTTTATTGAA |
| AAATTAATTGTTTATCTCAATGAATTTATCGGGCTTAAGAATTCAGATTTAGTTAGCTATATTACCCGGCAAGATAAA |
| AATGCAATGGATAAATTTTATGGGATTAAAAAAAGCAGAAATTTAATTCTCCCTGTGATATTTAGTAGAGAAAAACCA |
| ACTGATGTATTGTCAGCTCACTTTATTAATGAGTATAATCGATTGAATAATGATAATAGGAAAAAAGTAGTATTTACT |
| GCATCTTTTGATTTTTTTCCAAATATAGATGCTGCCAACTATGTTTAAATGCAGCAAAGTCTAATAATGATTATTGC |
| TATATTTTGGCAGGTAGGAAAAGTACTACTTTGAATCTTCCTGATTTGGATAATTTATTTTTTTCGATAATCTATCT |
| AATAGTGAAATGTCATATTTATTATCTGCTTGTGATGTTTTTATTCTCCTATAGTTTTAGGAAGTGGAATGAAAACA |
| AAAATTGCAGAAGCACTATCATATGGATTATATATTTATGCGACAGAGCATTCCTTAATCGGCTATGATGAAATTATA |
| CACAATAAGGAGTGTGTTAAAAAAATCTCACATTTGGATGAGGAATTTCCTAAAGATTTCAAGATGAAAAGTATCAAT |
| AAACAGCTAATAATGTCTTATCAGCAAAAATATTATTCACATTATCGGTTTAATGGCCATGAACTTGATATAATAAAT |
| TTTGACGATTAGTTAGTGGAGATATAATATGAACATATTAGTAACTGGTGGTGCTGGATATATCGGATCTCATACGGC |
| TATTGAATTACTGAATGCAGGTCATGAGTTATCGTTCTGGACAATTTCAGTAATGCTTCATACAAGTGTATCGAAAA |
| AATAAAAGAAATTACTCGACGTGATTTTATAACAATTACTGAAGATGTCGGGTGTAGGAAGACACTCTCCGCTATTTT |
| CGAGAAACACGCCATAGATATAGTTATTCATTTTGCTGGCTTTAAATCTGTTTCAGAGTCTAAAAGTGAACCCTTAAA |
| GTATTACCAGAATAATGTTGGAGTGACCATTACTTTATTACAGGTAATGGAAGAGTACAGAATTAAAAAATTTATCTT |
| TAGTTCATCTGCGACAGTCTATGGTGAACCAGAGATAATTCCAATTCCAGAAACAGCTAAAATTGGAGGAACTACGAA |
| TCCATATGGCACATCGAAGTATTTTGTTGAAAAAATTCTAGAGGATGTTAGTTCCACGGGAAAACTGGATATAATTTG |
| CTTGAGATATTTTAATCCTGTCGGTGCTCATTCTAGTGGTAAAATAGGTGAGGCTCCATCTGGTATCCCTAATAATCT |
| TGTTCCTTATTTATTGGATGTTGCGAGTGGTAAACGTGATAAATTATTTATTATGGCAATGATTACCCTACTAATGA |
| TGGAACAGGTGTAAGGGATTTTATTCATGTTGTTGACTTAGCGAAAGGTCATTTGGCTGCAATGAATTATTTAAGTAT |
| CAATTCGGGATATAATATCTTTAATCTTGGTACAGGAAAGGTTATTCGGTACTTGAATTAATCACTACATTTGAAAA |
| ATTAACAAACATTAAGGTCAATAAATCTTTTATAGAGAGAAGGGCAGGGGATGTTGCGTCTTGTTGGGCTGATGCAGA |
| TAAAGCTAATTCTTTATTGGACTGGCAAGCCGAACAAACTCTAGAACAGATGTTATTGGACTCGTGGCGTTGGAAAAA |
| AAATTATCCAGACGGATTCTGAATATAAAAGGTTTCAGTTTTATGAATCAATCAGAGCAGAGAAAAAAAATACTGGTT |

SEQUENCES

```
CTTACACCTCGCTTTCCCTACCCTGTCATTGGAGGGGATAGATTAAGAGTCTATATGTTATGTAAAGAACTTTCCAAA
AAATATGATCTTATTCTTCTGAGCTTATGTGATCAACCACTAGAACTTGAAATAAATATAAATGACTCGGTCTTCAAA
GAAATTCATCGTGTCTATCTACCAAAATATAAATCATATTATAATGTATTAAAAGCTTTGGTTACGCAAAAACCGTTG
CAAATTGCTTATTATCAATCGGACACATTTAAGAATAAATACAATAAATTAATTAAACAATGCGATGCAGTATTTTGT
CATCTGATAAGAGTTGCTGATTATGTTAAGGATACAGACAAGTTCAAAATTCTTGATATGACAGATGCAATATCTTTG
AATTACAGTCGCGTTAAAAAATTAGCAAGTAAAAAAAGTTTGCGTGCAATTATTTATTCTCTGGAACAAAAAAGATTA
GAATCATATGAACGTTCTGTGGCGAATCTTTTTGATTTGACCACTTTTATTTCATCCGTAGACCGTGACTATCTCTAC
CCTAATCTGGGCAGTAATATCCATATAGTCAATAATGGGGTTGATACATCAGCCTTGAGATATATAAAAAGAGAAATA
AAAATCGATAAGCCTGTGGAACTTATATTTATCGGAAATATGTATTCTTTACAAAATATGGATGCTGCAAAACATTTT
GCTAAGAATATTTTACCTTGCTTGTATGATGAGTTTAATATTATTTTTAAAGTGATTGGTAAGATCTCAGAAACTAAT
AAAAATATATTAAATTCATTTAAAAATACAATTGCTTTAGGTACTGTTGATGATATCAATTCTTCCGCTTCTACAGGG
CATATAGGTATATGTCCTGTTCGTCTTGGAGCAGGCGTACAAAATAAAATTCTTGAATACATGGCTTTAGGTTTACCA
TGTATTACATCTAGCATTGGTTATGAAGGTATTAATGCAAATCAGGTAGCGAAATTTTTGTTGCAGATACAGTAGAG
CAATATAAAAACGTACTAAGAGAAATAATTTACGATTATAATCGTTATACTGAAGTGGCTGAAAATGCCCGTAGTTTT
GTAGAAAATAATTTTCTTGGGAATCAAAAGTTGCCAATTTAATGAATACATTAGATGAGAAATTATATGAACAATAA
TAAAATTATTACACCTATCATTATGGCTGGTGGTTCAGGCAGTCGGTTGTGGCCACTATCAAGAATTCTCTATCCGAA
ACAATTTCTTAGCCTAATCGGTAGTCATACCATGCTTCAAACAACGGCTAATCGTCTGGATGGTTTGGATTGTACCAA
CCCTTATGTCATTTGTAATGAACAATACCGCTTTATAGTTGCTGAACAGCTTAGAAAAATCGATAGATTGACTTCAAA
GAATATCATCCTTGAGCCTGTTGGGCGTAACACTGCCCCTGCAATTGCATTAGCGGCGTTGCTGATGTCTAAGTCTGA
TAAAAGTGCAGATGATCTTATGCTCGTACTGGCTGCAGATCACGTTATACACGATGAAGAAAAATTTTGTAACGCTGT
TAGATCGGCAATTCCATACGCTGCTGATGGGAAATTGGTAACATTTGGTATAATTCCAGACAAAGCAGAAACTGGTTA
TGGTTATATACATCGAGGACAATATATTAATCAGGAAGATTCGGATGCATTTATAGTGTCATCATTTGTTGAAAAGCC
AAATCATGAGACAGCCACTAAATATCTTGCTTCCGGTGAGTATTATTGGAATAGCGGTATGTTTTTGTTTAGTGCAAA
TCGTTATATAGAGGAACTTAAACAATTTCGGCCTGATATTTTATCCGCTTGTGAAAAAGCAATTGCTTCAGCGAACTT
TGACCTTGATTTTGTGCGTTTAGATGAAAGTTCTTTCTCTAAGTGCCCTGAAGAATCAATTGATTACGCTGTAATGGA
AAAAACAAAAGACGCAATTGTTATTCCAATGGATGCTGGCTGGAGTGATGTCGGTTCATGGTCTTCTCTTTGGGAAAT
TAATGATAAAGACTCAGACGGCAACGTAATAGTTGGGGATATTTTCTCTCATGAAACAAAGAATTCTTTCATATATGC
CGAATCGGGAATTGTTGCTACAGTTGGAGTGGAAAATTTAGTTGTTGTCCAAACAAAGGATGCTGTTCTTGTCTCAGA
GAGAAATAAAGTTCAGGATGTAAAGAAAATAGTAGAACAAATTAAAAATTCAGGTCGTAGCGAGCATTATGTTCATCG
CGAAGTATATCGTCCTTGGGGTAAATATGATTCCATTGACACAGGGGAGCGTTATCAGGTCAAACGTATAACAGTAAA
TCCTGGTGAAGGACTTTCTTTACAAATGCACCATCATAGGGCAGAACATTGGATCATAGTTTCTGGAACTGCAAGGGT
GACTATAGGTTCTGAAACTAAGATTCTTAGCGAAAATGAATCTGTTTACATACCTCTTGGTGTAATACACTGCTTGGA
AAATCCAGGGAAATTCCTCTTGATTTAATTGAAGTTCGTTCTGGATCTTATTTAGAAGAAGACGATGTTATCCGTTT
TCAGGACCGATATGGTCGTAGCTAAATTTTGATAATGTAACGTTAGTAGAAGAGCGCTAATATTTTAGTTAATCTG
TAATAAGTATTATTTGTTTAAGGTATATCATGTCGAGTTTACCCTGCTTTAAAGCCTATGATATTCGCGGGAAATTAG
GCGAAGAACTGAATGAAGATATTGCCTGGCGCATTGGTCGCGCTTATGGCGAATTTCTCAAACCGAAAACCATTGTGT
TAGGCGGTGACGTCCGACTCACCAGCGAAACCTTAAAACTGGCGCTGGCGAAGGGGTTACAGGATGCGGGCGTCGATG
TGCTGGATATTGGCATGTCCGGCACCGAAGAGATCTATTTCGCCACGTTCCATCTCGGCGTGGATGGCGGCATCGAAG
TTACCGCCAGCCATAACCCGATGGATTACAACGGCATGAAACTGGTGCGCGAAGGGGCTCGCCCGATCAGCGGTGATA
CCGGACTGCGCGACATCCAGCGTCTGGCAGAAGCCAACGACTTTCCTCCCGTTGATGAAACCAAACGCGGTCGCTATC
AGCAAATCAATCTGCGTGACGCTTACGTTGATCACCTGTTCGGTTATATCAACGTCAAAAACCTCACGCCGCTCAAGC
TGGTGATTAACTCCGGGAACGGCGCGGCGGGTCCGGTGGTGGACGCCATTGAAGCCCGCTTTAAAGCCCTCGGCGCAC
CCGTGGAATTAATCAAAGTGCACAACACGCCGGACGGCAATTTCCCCAACGGTATTCCTAACCCGCTACTGCCGGAAT
GTCGCGACGACACCCGCAATGCGGTCATCAAACACGGCGCGGATATGGGCATTGCCTTTGATGGCGATTTTGACCGCT
GTTTCCTGTTTGACGAAAAAGGGCAGTTTATTGAGGGCTACTACATTTGTCGGCCTGCGGCAGAAGCGTTCCTCGAAA
AAAATCCCGGCGCGAAGATCATCCACGATCCACGTCTCTCCTGGAACACCGTTGATGTGGTGACTGCCGCAGGCGGCA
CCCCGGTAATGTCGAAAACCGGACACGCCTTTATTAAAGAACGTATGCGCAAGGAAGACGCTATCTACGGTGGCGAAA
TGAGCGCCCACCATTACTTCCGTGATTTCGCTTACTGCGACAGCGGCATGATCCCGTGGCTGCTGGTCGCCGAACTGG
TGTGCCTGAAAGGAAAAACGCTGGGCGAACTGGTGCGCGACCGGATGGCAGCGTTTCCGGCAAGCGGTGAGATCAACA
GCAAACTGGCACACCCCGTTGAGGCGATTAACCGCGTGGAACAGCACTTTAGCCGCGAGGCGCTGGCGGTGGATCGCA
CCGATGGCATCAGCATGACCTTTGCCGACTGGCGCTTTAACCTGCGCTCCTCTAACACCGAACCGGTGGTGCGGTTGA
ATGTGGAATCGCGCGGCGATGTACCGCTGATGGAAGAAAAGACAAAACTTATCCTTGAGTTACTGAACAAGTAATTCA
GTAATTTCATATAAATGGGTTTTAAAAAACGGAAAAGATGAGATATCCGGTGTGGTATATCAAGGTAATGCTATTCA
GTATCTCTATGAGTGAGTTAACATCTATACCACATTTAAGCCGCACACTTCGGGATCCCCATATGAATATCCTCCTTA
GTTCCTATTCCGAAGTTCCTATTCTTCTAGAGAATAGGAACTTCGGAATAGGAACTAAGGAGGATATTCATATGGAT
AAAGCCGTAAGCATATAAGCATGGATAAGCTATTTATACTTTAATAAGTACTTTGTATACTTATTTGCGAACATTCCA
GGCCGCGAGCATTCAGCGCGGTGATCACACCTGACAGGAGTATGTAATGTCAAGCAACAGATCGGCGTAGTCGGTAT
GGCAGTGATGGGACGCAACCTTGCGCTCAACATCGAAAGCCGTGGTTATACCGTCTCTATTTTCAACCGTTCCCGTGA
GAAGACGGAAGAAGTGATTGCCGAAATCCAGGCAAGAAACTGGTTCCTTACTATACGGTGAAGAGTTTGTCGAATC
TCTGGAAACGCCTCGTCGCATCCTGTTTAATGGTGAAACAGGTGCAGGCACGGATGCTCCTATTGATTCCCTCAAACC
ATATCTCGATAAAGGAGACATCATCATTGATGGTGGTAACACCTTCTTCCAGGACACTATTCGTCGTAATCGTGAGCT
TTCAGCAGAGGGCTTTAACTTCATCGGTACCGGTGTTTCTGGCGGTGAAGAGGGGGCGCTGAAAGGTCCTTCTATTAT
GCCTGGTGGCCAGAAAGAAGCCTATGAATTGGTAGCACCGATCCTGACCAAAATCGCCGCCGTAGCTGAAGACGGTGA
ACCATGCGTTACCTATATTGGTGCCGATGGCGCAGGTCACTATGTGAAGATGGTTCACAACGGTATTGAATACGGCGA
TATGCAGCTGATTGCTGAAGCCTATTCTCTGCTAAAGGTGCCTGAACCTCACCAACGAAGAACTGGCGCAGACCTT
TACCGAGTGGAATAACGGTGAACTGAGCAGTTACCTGATCGACATCACCAAAGATATCTTCACCAAAAAAGATGAAGA
CGGTAACTACCTGGTTGATGTGATCCTGGATGAAGCGGCTAACAAAGGTACCGGTAAATGGACCAGCCAGAGCGCGCT
GGATCTCGGCGAACCGCTGTCGCTGATTACCGAGTCTGTGTTTGCACGTTATATCTCTTCTCTGAAAGATCAGCGTGT
TGCCGCATCTAAAGTTCTCTCTGGTCCGCAAGCACAGCCAGCAGGCGACAAGGCTGAGTTCATCGAAAAAGTTCGTCG
TGCGCTGTATCTGGGCAAAATCGTTTCTTACGCCCAGGGCTTCTCTCAGCTGCGTGCTGCTCGAGAGTACAACTG
GGATCTGAACTACGGCGAAATCGCGAAGATTTTCCGTGCTGGCTGCATCATCGTGCGCAGTTCCTGCAGAAAATCAC
CGATGCTTATGCCGAAAATCCACAGATCGCTAACCTGTTGCTGGCTCCGTACTTCAAGCAAATTGCCGATGACTACCA
GCAGGCGCTGCGTGATGTCGTTGCTTATGCAGTACAGAACGGTATTCCGGTTCCGACCTTCTCCGCAGCGGTTGCCTA
TTACGACAGCTACCGTGCTGCTGTTCTGCCTGCGAACCTGATCCAGGCACAGCGTGACTATTTTGGTGCGCATACTTA
TAAGCGTATCGATAAGAAGGTGTGTTCCATACCGAATGGCTGGATTAA
```

SEQ ID NO: 14 (example O8 rfb locus nucleotide sequence-O8-EPA production strain stLMTB11734)

ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCGATCGCTTAAGATCTAGGATTTCATTATGTTACTTCCTGTAATTATGGCTGGTG
GTACCGGCAGTCGTCTCTGGCCGATGTCACGCGAGCTTTATCCGAAACAGTTCCTCCGCCTGTTCGGGCAGAACTCCA
TGCTGCAGGAAACCATCACCCGACTCTCGGGCCTTGAAATCCATGAACCGATGGTCATCTGTAACGAAGAGCACCGCT
TCCTGGTGGCTGAACAGCTACGCCAGCTCAATAAGCTGTCGAATAATATTATTCTTGAGCCGGTCGGGCGCAACACCG
CCCCGGCCATCGCCCTGGCAGCCCTTCAGGCCACCCGCGACGGCGACGACCCGCTGATGCTGGTTCTCGCCGCTGACC
ATATCATCAATAACCAGTCGGCCTTCCACGACGCCATCCGGGTCGCCGAGCAGTATGCTGATGAAGGTCATCTGGTCA
CCTTCGGTATCGTGCCGAATGCCCCGGAAACTGGCTACGGTTACATTCAGCGCGGCGTGGCGCTCACCGATAGTGCCC
ATTCCGCGTACCAGGTGGCCCGCTTTGTGGAGAAGCCGGATCGCGAGCGCGCCGAGGCTTACCTCGCCTCCGGGGAGT
ACTACTGGAACAGCGGCATGTTTATGTTCCGCGCCAAGAAATACCTCATCGAGCTGGCCAAATACCGTCGGATATCC
TGGAAGCCTGCCAGGCTGCGGTGAATGCCCGCCGATAATGCAGCGATTTCATCAATATCCCGCATGATATTTTCTGCG
AGTGCCCGGATGAGTCCGTGGACTATGCCGTTATGGAGAAAACCGCCGATGCGGTGGTGGTCGGTCTCGATGCTGACT
GGAGCGACGTCGGCTCCTGGTCCGCACTATGGGAGGTCAGCCCGAAAGACGAGCAGGGCAATGTCCTCAGCGGTGACG
CGTGGGTACACAACAGCGAAAACTGCTACATCAACAGCGACGAGAAGCTAGTGGCGGCCATTGGCGTAGAGAATCTGG
TGATTGTCAGCACTAAGGACGCCGTGCTGGTGATGAATCGCGAGCGTTCCCAGGACGTGAAGAAGGCGGTCGAGTTCC
TCAAGCAGAACCAGCGCAGCGAGTACAAGCGCCACCGTGAGATTTACCGCCCCTGGGGCCGTTGCGACGTAGTGGTCC
AGACCCCGCGCTTCAACGTCAACCGCATCACGGTGAAACCAGGCGGTGCCTTCTCGATGCAGATGCACCACCATCGCG
CCGAGCATTGGGTTATTCTCGCCGGCACCGGTCAGGTGACTGTCAACGGTAAGCAGTTCCTGTTGTCCGAGAACCAGT
CCACCTTTATTCCGATTGGCGCCGAGCACTGCCTGGAAAACCCTGGCTGTATTCCGCTGGAAGTGCTGGAGATCCAGT
CGGGGGCGTACCTTGGCGAGGACGACATTATTCGTATTAAAGACCAGTATGGTCGTTGCTCAATTATTTTCGGGACAAG
ACGCAGAATGACACAGTTAACTTGTTTTAAAGCTTATGACATCCGTGGTGAACTGGGTGAGGAACTGAACGAGGACAT
CGCCTACCGTATCGGTCGCGCCTACGGCGAATTTCTGAAACCCGGGAAGATAGTGGTGGGGGGCGATGTGCGCCTCAC
AAGCGAGTCGCTGAAGCTGGCGCTGGCCCGCGGGTTAATGGACGCCGGTACCGACGTGCTGGACATCGGCCTGAGCGG
TACCGAAGAGATTTACTTTGCCACCTTCCACCTTGGGGTAGATGGTGGCATCGAGGTGACCGCGAGCCACAATCCTAT
GAACTACAACGGCATGAAGCTGGTGCGCGAGAATGCGAAGCCCATCAGCGGCGACACCGGCCTGCGGGATATCCAGCG
CCTGGCGGAGGAAAACCAGTTCCCGCCAGTGGACCCGGCGCGTCGCGGGACCCTGAGCAAGATATCGGTACTGAAGGA
GTATGTTGACCATCTGATGAGCTACGTGGACTTCTCGAACTTCACCCGTCCACTGAAGTTGGTGGTGAACTCCGGAAA
CGGGGCTGCGGGGCACGTGATTGATGAGGTGGAGAAACGCTTCGCGGCGGCTGGGGTGCCGGTAACCTTTATCAAGGT
GCATCACCAGCCGGATGGCCATTTCCCTAACGGTATCCCGAATCCGCTGCTGCCGGAGTGCCGCCAGGATACCGCCGA
CGCGGTGCGCGAGCATCAGGCCGACATGGGGATTGCCTTTGACGGCGACTTGATCGCTGCTTCCTGTTCGATGACGA
AGCTTCGTTTATCGAGGGGTATTACATTGTCGGCCTGCTGGCTGAGGCGTTCCTGCAGAAGCAGCCGGGAGCGAAAAT
CATTCACGACCCGCGCTTGACGTGGAACACGGTAGACATCGTGACCCGCAACGGCGGCCAGCCGGTGATGTCGAAGAC
GGGGCATGCGTTCATCAAGGAGCGGATGCGTCAGGAAGACGCTATCTACGGCGGGAGATGAGTGCGCACCATTACTT
CCGCGATTTCGCCTACTGCGATAGCGGGATGATCCCGTGGCTGCTGGTGGCGGAGCTGCTGTGTCTGAAGAACAGCTC
GCTGAAATCGCTGGTGGCGGACCGCCAGAAGGCGTTCCCTGCGTCGGGAGAGATCAACCGCAAGCTAAGTAATGCTGC
TGAGGCGATCGCCCGACATCCGGGCGCAGTATGAGCCGGCGGCTGCACATCGACACACAACGGACGGGATCAGTATTGA
ATACCCTGAATGGCGCTTTAACCTGCGCACGTCTAACACCGAGCCGGTGGTGCGTCGAACGTTGAGTCCAGAGCTGA
TGTGGCGCTTATGAATGAAAAACGACCGAGCTGTTACACCTGTTAAGCGGGGAATAAGGTGAGAGATTTACTAACGA
CGATTTATCGTTATCGGGGATTTATCTGGAGCAGTGTTAAACGTGATTTTCAGGCACGCTATCAAACTAGTATGCTGG
GCGCACTATGGCTCGTTTTTACAACCGCTCTCTATGATTCTGGTCTATACCCTGGTTTTTCCGAGGTGATGAAGGCAA
GAATGCCCGATAATACCGGGTCGTTTGCCTATAGTATTTATCTCTGTTCCGGGGTACTGACCTGGGGATTATTTACTG
AGATGCTGGATAAAGGTCAGAGCGTATTTATTAACAATGCTAATCTGATCAAGAAACTCAGTTTTCCGAAAATCTGTC
TGCCGATCATCGTGACGTTATCGGCGGTGCTAAATTTCGCGATTATTTTCAGTCGTTTCTAATTTTTATCATTGTCA
CCGGTAACTTCCCCGGCTGGCTCTTTCTCGGTGATACCGGTCCTGCTTTTGCAGATCCTGTTTGCCGGTGGGCTGG
GGATAATCCTTGGTGTCATGAACGTCTTTTTCAGGGATGTGGGGCAACTGGTTGGCGTTGCGCTGCAATTCTGGTTTT
GGTTCACACCCATTGTTTATGTACTGAATTCATTACCTGCATGGGCAAAAATCTGATGATGTATAACCCGATGACTC
GGATCATGCAATCTTATCAGTCCATCTTCGCCTATCATCTGGCCCCCAACTGGTATTCGCTATGGCCAGTATTGGCTC
TCGCCATTATTTTCTGCGTCATCGGTTTCAGGATGTTCCGCAAGCATGCGGCGGATATGGTGGATGAATTATAATGAG
TTATATCAGAGTAAATAATGTCGGTAAGGCGTATCGCCAGTATCACTCAAAGACCGGGAGACTGATCGAATGGTTATC
CCCTCTGAATACCAAACGCCATAATTTGAAATGGATCCTCCGCGATATTAATTTCGAAGTCGCTCCGGGCGAGGCTGT
CGGTATTATCGGTATCAACGGTGCAGGCAAGAGTACCCTGCTTAAACTCATAACCGGGACGTCCAGGCCGACGACTGG
AGAAATTGAAATCTCCGGACGTGTCGCTGCATTACTCGAATTGGGGATGGGGTTTCATTCTGATTTCACTGGTCGGCA
GAATGTTTATATGTCTGGGCAACTGTTGGGGTTATCGTCAGAGAAATAACTGAACTGATGCCGCAAATTGAAGAGTT
TGCTGAGATTGGGGACTATATCGATCAACCTGTGCGCTCTACTCCAGTGGGATGCAAGTTCGATTAGCTTTTAGTGT
AGCGACGGCTATCCGTCCTGATGTGCTAATTATCGATGAGGCATTATCGTTGGGGATGCATATTTCCAGCATAAAAG
CTTTGAGCGTATTCGAAAATTTCGTCAGGAAGGGACCACGCTGTTGCTGGTATCCCATGATAAACAAGCGATCCAAAG
CATTTGCGACCGGGCCATTTTATTGAATAAAGGCCAAATTGAAATGGAAGGTGAACCTGAAGCAGTGATGGATTATTA
CAATGCTCTTCTGGCCGATAAACAAAATCAGTCCATTAAACAAGTTGAGCATAATGGTAAAACGCAAACTGTTTCAGG
CACTGGTGAGGTGACTATCTCTGAGGTTCATCTTCTCGATGAACAGGGCAATGTGACTGAATTTGTTTCGGTAGGGCA
TCGTGTCAGCTTGCAGGTCAACGTTGAGGTCAAGGACGATATTCCTGAGCTTGTTGTCGGATATATGATTAAGGATCG

| SEQUENCES |
|---|
| ACTTGGGCAGCCGATTTTCGGGACCAATACGTACCATCTCAATCAGACACTCACCTCCCTGAAAAAAGGAGAAAAGCG |
| TTCGTTCTTATTTTCTTTCGATGCGAGATTGGGGGTTGGCTCCTATTCTGTCGCTGTCGCGTTGCATACTTCCAGTAC |
| GCACCTCGGCAAAAACTATGAATGGCGCGATCTGGCCGTGGTATTCAACGTCGTTAACACGGAACAACAAGAGTTTGT |
| CGGCGTGTCCTGGTTGCCGCCTGAACTGGAGATTTCTTAATGGGTTCGTCGTTTTATCGTTCATTTGAAGAACGACAC |
| AGAGGTTCGGTTGAAGAAATCAAGCGCCGCTTGAGTTTTTATTTACCTTTTCTTGCAGGTCTGAAGGACATTTATCCT |
| GATGGCGTGATTGCGGATATTGGTTGCGGACGTGGCGAATGGTTGGAGATCCTGACTGAAAATGGCATTGCGAACATC |
| GGCGTCGATCTCGATGATGGCATGCTGGCGCGCGCCAGGGAGGCCGGACTGAATGTGCAGAAAATGGATTGTCTGCAG |
| TTTTTGCAAAGTCAGGCGGATCAGAGCCTGATAGCGTTGACCGGTTTTCATATTGCTGAGCATTTGCCGTTTGAGGTC |
| CTGCAGCAACTCGCCATGCATACCCTACGGGTGCTGAAACCAGGTGGTTTGCTGATCCTCGAAACGCCGAACCCGGAG |
| AATGTAAGCGTCGGCACCTGTTCATTTTATATGGATCCAACGCATAATCATCCTCTGCCACCGCCACTGCTTGAGTTT |
| TTACCTATTCATTATGGTTTTACCCGAGCAATTACCGTTCGTCTGCAGGAAAAAGAGGTTCTTCAATCTCCGGATGCA |
| GCCGTTAATTTGGTCGATGTACTCAAAGGGGTGAGCCCCGACTACAGCATCATTGCTCAGAAAGCAGCGCCAACAGAT |
| ATTCTTGAACGCTTTGACACCCTGTTTACCCAGCAGTACGGTCTGACGCTGGATGCTCTGAGCAACCGTTACGATGCG |
| ATTTTGCGCCAACAGTTTTCGTCCGTTGTCTCACGGCTGGAGACGTTGAACCAAACCTATATGCAACAGATAAGCCAA |
| ATGTCAGAGACTATTCAGACGTTGCAAGGTGAGGTTGACGATCTGAGTCATGTCATCGATCAGAACCATCAGCTTCAT |
| CAGCAAATGGCGGATTTACATAACAGTCGTTCATGGCGTATTACTCAACCACTACGCTGGTTGTCTTTGCAACGTCAA |
| TTATTACGTCAGGAAGGGGCTAAAGTGCGAGCCCGTAGGGCTGGGAAAAAAATATTGCGCAAAGGGATGGCGCTCTCG |
| CTGGTCTTTTTCCATCGTTACCCTAAGTCTAAGGTTTATCTGTTTAAGGTTCTGAGAAAAACTGGCTGCTATACATTG |
| CTACAACGTTTGTTCCAACGCGTAATGCTGGTGCAATCTGACACGATGATGATGCAGTCCAGAAGATATGATGTGGGT |
| ACTGAAGAAATGACAAGTCGCGCGATGAGTATTTATAACGAATTAAAAAATAAAAATACGGAGAAATAACGATGCGTA |
| TTGTCATAGATTTACAAGGCGCACAGACGGAAAGCCGCTTTCGTGGCATCGGTCGTTATAGTATCGCAATCGCCAGAG |
| GCATAATCAGAAATAACAGCCGGCATGAGATTTTCATCGCGCTATCCGCCATGCTGGATGAGTCGATTGCAAATATTA |
| AGGCGCAATTTGCCGATCTCCTGCCGGCAGAAAATATAGTCGTATGGCATGCCGTAGGCCCTGTTCGTGCGATGGACC |
| AAGGTAATGAATGGCGTCGGGAGAGCGCAGAATGATTCGGGAAGCGTTTCTTGAATCATTGTGTCCAGATGTCGTTT |
| TCATTACGAGTTTGTTTGAAGGTCATGTCGACGATGCGGCTACATCGGTACACAAATTTAGTCGTCAGTATAAAGTAG |
| CCGTACTGCACCACGATCTTATCCCCTCGTGCAGGCGGAAACCTATCTGCAGGACGATGTATACAAACCCTACTATT |
| TACAGAAAGTTGAGTGGTTAAAAAACGCTGACCTTTTGTTGACTAACTCTGCTTATACCGCACAGGAAGCGATCGAGC |
| ATCTGCATTTACAGGGCGATCATGTGCAGAATATTGCAGCCGCAGTCGATTCTCAGTTTTGTATGGCGGAGGTGGCAG |
| CGAGCGAAAAAGAGACCGTCCTTGGCCATTACGGTATTCAGCGCGAGTTCATGTTGTATGCGCCCGGAGGATTTGACT |
| CAAGGAAAAACTTTAAACGGTTGATTGAGGCCTATGCCGGGCTCAGTGATGCCTTACGTCGCAGTCATCAACTGGTCA |
| TCGTCAGTAAGCTTTCCATCGGTGATCGTCAGTATCTGGAATCCCTTGCGTCAGGTAATGGTTTACAGCAGGGCGAAC |
| TGGTACTCACTGGTTATGTGCCGGAAGATGAGCTGATCCAGCTCTATCGCCTATGTAAGCTGTTCATCTTTGCTTCAC |
| TACATGAAGGTTTTGGGTTGCCGGTTCTGGAAGCAATGTCGTGCGGTGCGCCGGTGATTGGCTCAAATGTCACCAGTA |
| TTCCTGAAGTCATCGGTAATCCTGAGGCATTATTCGACCCGTATTCTGTCTCTTCCATGAGGGATAAGATCGCGCAAT |
| GTTTGACTGATGATACCTTCCTCGCGCGTCTGAAAGAAATGGCGCAGCAGCAAGCGCGTAATTTCTCTTGGGATAAAG |
| CTGCGGTGACTGCTCTGGAAGCTTTCGAAAAGATCGCGGTAGAAGACACCGGTACTGCGCAGGTTTTGCCTGAAGCTT |
| TGATTCAGAAGATCCTTGCTATCTCACAAGGGCAGCCAGATGACCGGCATCTGCGCTTGTGCGCAACGGCCATTGATT |
| ACAATCTGAAAACGGCAGAACTTTATCAAATCGACGATAAATCGCTGAACTGGCGTGTGGAAGGCCCATTCGATAGCT |
| CATATAGTCTGGCGTTGGTCAACCGCGAATTTGCCCGGGCACTCTCAGCCGATGGTGTAGAGGTTTTATTGCATTCCA |
| CTGAAGGACCAGGTGATTTTGCCCCAGATGCCTCGTTTATGGCACAGTCGGAAAATAGTGATCTTCTGGCATTTTATA |
| ATCAATGTCAGACCCGCAAGAGTAACGAAAAGATAGATATTATTAGCAGAAATATCTATCCACCGCGGGTTACCAAAA |
| TGGATGCCAAAGTAAAATTCCTTCATTGTTATGCTTGGGAAGAAACGGGCTTTCCGCAACCGTGGATCAATGAATTTA |
| ATCGGGAACTTGACGGAGTGCTGTGTACTTCGGAACATGTTCGTAAAATACTGATTGATAACGGACTGAATGTGCCCG |
| CATTTGTTGTTGGCAATGGCTGTGACCATTGGCTCAATATCCCAGCCGAGACGACAAAAGATGTGGATCACGGAACAT |
| TCCGTTTCCTGCACGTCTCTTCTTGTTTCCCACGCAAAGGGATACAGGCAATGCTTCAGGCTTTGGGGGAAGGCGTTCA |
| CTCGTCGTGACAATGTTATCTTAATCATTAAGACTTTTAACAATCCGCACAATGAATTGACGCATGGCTGGCTCAGG |
| CCCAGGCTCAATTCATAGACTATCCCAAAGTTGAAGTGATCAAAGAGGATATGTCAGCCACCGAGCTTAAAGGGCTTT |
| ATGAAAGCTGTGATGTTTTGGTTGCTCCAGGTTGCGCTGAAGGCTTTGGTTTACCTATTGCTGAAGCAATGCTGAGTG |
| GGCTACCGGCTATCGTCACCAATTGGAGCGGGCAACTTGATTTTGTTAATTCACAAAATTCATGGCTGGTTGACTATC |
| AGTTCACTCGGGTAAAAACGCACTTTGGTCTGTTTTCCTCAGCCTGGGCCAGTGTGGATATTGACAACTTAACAGATG |
| CATTAAAAGCGGCAGCCTCAACCGATAAATCAGTGCTGCGTGACATGGCCAATGCTGGTCGCGAGCTTCTTCTGCAGC |
| AGTTTACCTGGAAAGCGGTGGCTGATCGTTCTTGCCAGGCGGTCAAGACTCTGCGTGCGCATATTGATATTGCACAGC |
| ATCGGGCGCGCATTGGCTGGGTGACGACCTGGAACAGAAATGTGGGATCGCAACCTATTCCCAGCATCTGGTGGAAA |
| GCGCACCTCATGGCGCGGATGTTGTTTTGCTCCCCAGGTCAGCGCTGGCGATCTTGTGTGCAGACGAAGAGTTTG |
| TACTTCGCAACTGGATTGTAGGTAAAGAGAGCAACTATCTGGAAAACCTCCAGCCACACACATTGATGCTCTGAGACTCG |
| ATGTCATTGTGATCCAATTCAACTATGGATTCTTTAATCATCGAGAACTGTCGGCGTTTATTCGTCGCCAGCATGACG |
| CCGGTCGTTCAGTTGTTATGACGATGCATCAACTGTGGATCCGCTGGAAAAAGAGCCGAGCTGGAATTTCCGTCTTG |
| CTGAAATGAAAGAGGCGCTGGCACTTTGCGACCGGTTGTTGGTGCATTCGATTGCCGATATGAACGCCTTAAAGATT |
| TAGGCTTAACTGCGAATGTTGCTTTATTCCCGCACGGTGTTATCAACTACTCCGCAGCGAGCGTCACACGTCAACAGC |
| AGTCTTTACCGCTAATTGCGAGCTATGGCTTCTGCTTACCGCATAAGGGCCTGATGGAACTAGTAGAATCCGTCCATA |
| GACTCAAGCAAGCCGGTAAACCGGTTCGTTTACGACTGGTGAACGCAGAGTATCCTGTTGGGGAGTCACGCGATCTGG |
| TGGCAGAGCTTAAAGCTGCTGCTCAGCAGTTAGGTGTTACCGATCTGATTGAGATGCATAATGATTTCCTACCTGATG |
| CGGAGAGTCTGCGGTTGCTTTCAGAAGCCGATCTTCTGATTTTTGCTTATCAGAATACTGGGGAGTCTGCTAGCGGGG |
| CGGTACGTTATGGTATGGCGACTCAAAAACCTGTTGCGGTAACGCCCCTGGCGATATTTGATGATTTGGACGATGCCG |
| TCTTTAAATTTGATGGATGCAGCGTCGATGATATCAGTCAGGGGATTGACCGGATCCTGAATTCCATCCGTGAACAGA |
| ACTCTTGGGCAACCAGGACTCAACAACGTGCCGATGCATGGCGGGAACAACATGATTATCAAGCTGTTTCACGCCGTC |
| TGGTTAATATGTGTCAAGGCTTAGCTAAAGCTAAATATTTTAAATAAAAAATATCTCTTGTATTTTTGCCTTTGAA |
| TACAAGAGGGGTTAGATAATGTGTCATTTATTATGAAAATTATTTTTGCTACTGAGCCAATTAAATACCCATTAACGG |
| GCATCGGTCGGTATTCCCTGGAGCTGGTTAAGCGGCTGGCGGTCGCCCGCGAAATTGAAGAATTAAAGCTATTTCACG |
| GTGCGTCGTTTATAGAACAGATCCCTTTGGTGGAGAATAAAAGCGATACCAAAGCCAGCAATCATGGTCGTCTGTCGG |
| CGTTTCTACGCCGACAGACGCTGTTGATTGAGGCTTATCGCTTGCAGCGGATCCAGCGGTGGGCATTGCGCG |
| ACTATAAGGATTATATCTACCATGGCCCCAATTTTTATCTGCCGCATAAACTGGAACGCGCCGTGACCACGTTTCATG |
| ACATATCCATTTTTACCTGCCCGGAATATCATCCAAAAGATCGGGTTCGCTATATGGAGAAGTCCCTGCATGAGAGTC |
| TGGATTCGGCAAAGCTGATCCTGACCGTTTCTGATTTCTCGCGCAGTGAAATTATCCGCTTGTTCAACTATCCGGCGG |
| AGCGGATCGTAACCACCAAGCTAGCCTGCAGCAGTGACTATATCCCACGCAGCCCGGCAGAGTGTCTGCCGGTACTGC |
| AGAAATATCAGCTGGCGTGGCAGGCCTACGCGCTATATATCGGCACTATGGAGCCACGTAAAAATATCCGAGGCCTGC |
| TGCATGCCTATCAGCTGCTACCGATGGAGATCCGCATGCGCTATCCGCTAATCCTTAGCGGCTATCGCGGCTGGGAAG |

| SEQUENCES |
|---|
| ACGATGTGCTGTGGCAGTTAGTCGAGCGCGGTACTCGGGAAGGCTGGATCCGTTACCTCGGATATGTTCCGGATGAAG<br>ACCTGCCGTATCTGTACGCAGCGGCCAGAGTCTTTGTTTATCCCTCCTTCTACGAGGGATTCGGTTTACCTATTCTTG<br>AAGCGATGTCTTGCGGTGTGCCGGTAGTATGCTCCAATGTCACCTCTTTGCCTGAGGTTGTTGGCGATGCCGGCCTCG<br>TTGCCGATCCTAATGATATAGACGCGATTAGCGCGCAAATTTTGCAGAGCCTGCAAGATGATAGCTGGCGGGAAATCC<br>CCACCGCGCGCGGTCTTGCTCAGGCGAAACAGTTTTCGTGGGAGAACTGTGCGACACAGACCATTAACGCCTATAAAT<br>TACTCTAAGGGTGTCAGTTGAGAGTTCTACACGTCTATAAGACTTACTATCCCGATACCTACGGCGGTATTGAGCAGG<br>TCATTTATCAGCTAAGTCAGGGCTGCGCCCGCCGGGGAATCGCAGCCGATGTTTTCACTTTTAGCCCGGACAAAGATA<br>CAGGTCCTGTCGCTTACGAAGATCATCGGGTCATTTATAATAAACAGCTTTTTGAAATTGCCTCCACGCCGTTTTCGC<br>TGAAAGCGTTAAAGCGTTTTAAGCTGATTAAAGATGACTACGATATCATCAACTACCATTTTCCGTTTCCCTTTATGG<br>ATATGCTGCATCTTTCGGCGCGGCCTGACGCCAGGACTGTGGTGACCTATCACTCTGATATAGTGAAACAAAAACGGT<br>TAATGAAGCTGTACCAGCCGCTGCAGGAGCGATTTCTCAGCGGCGTAGATTGCATCGTTGCCTCGTCGCCCAATTACG<br>TGGCTTCCAGCCAGACCCTGAAAAAATATCTGGATAAAACGGTGGTGATCCCGTTTGGTCTGGAGCAGCAGGACGTGC<br>AGCACGATCCGCAGAGGGTCGCGCACTGGCGGGAAACTGTCGGCGATAAGTTCTTTCTCTTCGTCGGCACTTTCCGCT<br>ACTACAAAGGGCTGCATATTCTGATGGATGCCGCTGAGCGTAGCCGACTGCCAGTGGTGGTTGTAGGGGGCGGGCCGC<br>TGGAATCGGAAGTGCGGCGTGAAGCGCAGCAGCGCGGGCTGAGCAATGTGATGTTTACCGGCATGCTCAACGACGAAG<br>ATAAGTGACATTCTCTTCCAGCTCTGCCGGGGCGTGGTATTCCCCTCGCATCTGCGCTCTGAGGCGTTTGGCATTACGT<br>TATTGGAAGGCGCACGCTTTGCAAGGCCGCTGATCTCTTGCGAGATCGGTACAGGTACCTCTTTCATTAACCAGGACA<br>AAGTGAGTGGTTGCGTGATTCCGCCGAATGATAGCCAGGCGCTGGTGGAGGCGATGAATGAGCTCTGGAATAACGAGG<br>AAACCTCCAACCGCTATGGCGAAAACTCGCGTCGTCGTTTTGAAGAGATGTTTACTGCCGACCATATGATTGACGCCT<br>ATGTCAATCTCTACACTACATTGCTGGAAAGCAAATCCTGAGCGGCCGCGAGCTCGTCGACTCGAGGATCCGTGTAGG<br>CTGGAGCTGCTTCGAAGTTCCTATACTTTCTAGAGAATAGGAACTTCGGAATAGGAACTAAGGAGGATATTCATATGG<br>ATAAAGCCGTAAGCATATAAGCATGGATAAGCTATTTATACTTTAATAAGTACTTTGTATACTTATTTGCGAACATTC<br>CAGGCCGCGAGCATTCAGCGCGGTGATCACACCTGACAGGAGTATGTAATGTCCAAGCAACAGATCGGCGTAGTCGGT<br>ATGGCAGTGATGGGACGCAACCTTGCGCTCAACATCGAAAGCCGTGGTTATACCGTCTCTATTTTCAACCGTTCCCGT<br>GAGAAGACGGAAGAAGTGATTGCCGAAAATCCAGGCAAGAAACTGGTTCCTTACTATACGGTGAAAGAGTTTGTCGAA<br>TCTCTGGAAACGCCTCGTCGCATCCTGTTAATGGTGAAAGCAGGTGCAGGCACGGATGCTGCTATTGATCCCTCAAA<br>CCATATCTCGATAAAGGAGACATCATCATTGATGGTGGTAACACCTTCTTCCAGGACACTATTCGTCGTAATCGTGAG<br>CTTTCAGCAGAGGGCTTTAACTTCATCGGTACCGGTGTTTCTGGCGGTGAAGAGGGGGCGCTGAAAGGTCCTTCTATT<br>ATGCCTGGTGGCCAGAAAGAAGCCTATGAATTGGTAGCACCGATCCTGACCAAAATCGCCGCGTAGCTGAAGACGGT<br>GAACCATGCGTTACCTATATTGGTGCCGATGGCCAGGTCACTATGTGAAGATGGTTCACAACGGTATTGAATACGGC<br>GATATGCAGCTGATTGCTGAAGCCTATTCTCTGCTTAAAGGTGGCCTGAACCTCACCAACGAAGAACTGGCGCAGACC<br>TTTACCGAGTGGAATAACGGTGAACTGAGCAGTTACCTGATCGACATCACCAAAGATATCTTCACCAAAAAAGATGAA<br>GACGGTAACTACCTGGTTGATGTGATCCTGGATGAAGCGGCTAACAAAGGTACCGGTAAATGGACCAGCCAGAGCGCG<br>CTGGATCTCGGCGAACCGCTGTCGCTGATTACCGAGTCTGTGTTTGCACGTTATATCTCTTCTCTGAAAGATCAGCGT<br>GTTGCCGCATCTAAAGTTCTCTCTGGTCCGCAAGCACAGCCAGCAGGCGACAAGGCTGAGTTCATCGAAAAAGTTCGT<br>CGTGCGCTGTATCTGGGCAAAATCGTTTCTTACGCCCAGGGCTTCTCTCAGCTGCGTGCTGCGTCTGAAGAGTACAAC<br>TGGGATCTGAACTACGGCGAAATCGCGAAGATTTTCCGTGCTGGCTGCATCATCCGTGCGCAGTTCCTGCAGAAAATC<br>ACCGATGCTTATGCCGAAAATCCACAGATCGCTAACCTGTTGCTGGCTCCGTACTTCAAGCAAATTGCCGATGACTAC<br>CAGCAGGCGCTGCGTGATGTCGTTGCTTATGCAGTACAGAACGGTATTCCGGTTCCGACCTTCTCCGCAGCGGTTGCC<br>TATTACGACAGCTACCGTGCTGCTGTTCTGCCTGCGAACCTGATCCAGGCACAGCGTGACTATTTTGGTGCGCATACT<br>TATAAGCGTATTGATAAAGAAGGTGTGTTCCATACCGAATGGCTGGATTAA |

SEQ ID NO: 15 (example O15 rfb locus nucleotide sequence-O15-EPA
production strain stLMTB11738)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCGGGCGTGACCATTATGAACGTGCGTCAG
GGCGAACCTTTAGGTTTAGGCCACTCCATTTTGTGTGCGCGAACCATTTGTGCTGACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCGGAACGTACTCAGCCTGGTCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCTGTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCATGAGCAAAACTAAACTAAATGTTCTTTACCTTGCAATAAGTCAGGGTGCCAAT
TACCTACTGCCATTATTAATTTTTCCTTATCTTGTTAGAGTCATTGGTGTATCGAATTTTGGTGATCTGAGTTTTTCA
TTGATAACTATACAAGTGTTGTTAATGGTTGTTGAATATGGTTTTGGATATAGTGGGACAAGAGAAATAGCACTAAAT
AACGATAAAAAATACCATTCTGAATTTTTTGCGGTGTGGTGCTTGCTCGTTTTATATTAATGCTAATTGCAGCTATA
ATACTCATAATACTCTGTTTTTTTTATGTTTTAACGACGTTAAGTCTTTGTTATGTGTTGGTTTTCTGTCCGTAATT
GCAGGTGTTTTCAATCCAAATTGGTTTTTGCAAGGTAAGGAAATGATGAGTGCGATGCCTGTGCTCACTATTTTCA
CGAGGCATAGCAGTCGTTGCAGTTTATCTAATTATAAAACCCGAACGCCGATGTACATCAGTGCCTTATTATTGAGC
ATGCCATATATTTTGTATTCATTCGTGGCGTTGCCTACTTACTTATTATCAAGGAGATTTTTTATGTAGGCCACCG
ATAAAGAAATTCAAGTAATTTTAAAAAATGGATTTCATTTTTTTGTTCAACACTTGCGACTAGTGCATACACAATG
TTGACCCCTCTTGTATTGGGTGGCGTATCTGGAAAGTTTGATGTAGGCATCTTTAACTCAGCTAACATGATCAAACAA
GGTTTGGCTGGACTTGCATCACCATTAGTCCAAGCTTTTTATCCAAGAATTAACATTTTGCAAAGAGAGAATCCATAT
ATTGCAAACTTAAAATCTAGAATGATTCTTAAATACTTGCTTGTTTTTTACATGGCTTTAGCAATACCATTTTTACTT
TTTGCCAACCAATTATCATTATTAATATTCGGCATGAAAGGTGAAGTAATTGCAGGTGCAATGCAATTAATGACATTG
CTTCCTATATTCATAGGTTTTAATACAGTTGTCGGGTTACTTGTATTAGTACCTAATGGGATGCAAAAACAGTATTTC
AAATCTATTTTCCTAGGAACTATTACTTGTTTAAGCATAGTTTATCCAGCATGTAAATATTATGGAGCAACGGGTGCG
ATTGTGAGTCTTATTGTAGCTGAAATTTTCGTTGGCATGGGAATGCTTAAACAATTCATTAAAGTAAATAAAACCGTA
TGTAGGCCTCATAAATTATGAATATCTCGGTAATAATATCTGTTTGGAAACGCCCAGTTCAATTAGAATTGATTCTCT

| SEQUENCES |
|---|
| CTGAGCTCGATTCTCAGGCTAAAGACAATAGTCTACACCTAGAAGTAATTGTTTCCGATAGTCATAGTGGTAAAGAAA |
| TTGATGATGTAGTTGCTGATAATATTCATAAAAAGAAAAATATTAATATTATCCATCAACATACTAAAAATATACTCT |
| CCGCTAAGCGCAATTTCGGAGCATCCCTAGCCCATGGGGATTATTTAATATTTCTTGATGATGATTGTATACCCGCAA |
| GTGGATATATATCATCGTTGCTGAACTATTTAAAAAAAATGAATAGTAAAAGCGTTTTATGTGGGGAAGTTAGATTCG |
| AAAATGAACTCATTGAGACCAGCAATTACTATCGCTACAGGAACTCTTTACACCCTAAGTTTAGTGATAGTCCTGATA |
| TCTCTATGAATGCCTGGACTTTTGTCGCAATGAATTGTGTTCTTGATAGAAAGGCATTTTCATCAGGTATAGTTTCAT |
| ATAATGAAAATTTTATTGGTTATGGTTGTGAAGATCATGAGTTTGGGTGGCAACTTGAAAAAAATGACTTCAAAATTA |
| TTTTTGCTGATTTTAAAATATTACATCACGAATACAGTGGCGATATAGAAGGATATACAAAAAAAATTCGTGCTACAG |
| CACGTGATGGTATGAATGTATTAAGCAAAGTAAGGCCTGAAATGTTTTCTACTAATAAAAATTATTCCTAGTTGAGA |
| AAATATTTAGTAAACACAAAACGTTTAGTAAAATATGCCAATCAATATTTTTCAATAAATTTATTTTTAAAAAAATAA |
| TACAATTTTTAAAAAAAACAGATGCAAATAAAAAACTCTATTTCCCAATTCTTTACAGATATGTGTTGATTTCGGCAT |
| ATATACATGGTATTGGAGAGCGTGGCACCTCAAAAACAGATGATTTGCTTAAGAACTGGTATATATAGATGATGCTAT |
| CTTCATTTATTAAGACATTTGTATGGAAGGTAAAAACAATGAAGTATAATGCATTGATGGCTTTTTTATTATTTTTT |
| GTTGTTTTTTTAGATTGTCGCTGATAATACCTTTCTTATATTTGGCATTTATTCCTGCATTTTTTGGTATTATGTAT |
| TTAGTGCGTAATTTTATGATTACTATGGGCAATGGATTGGTATCTATAGATCGTAAAAATTTGTTGCTGTTATCTATA |
| TTCATAATTATTTTTTATTTTGTTTGGTTTTCGATTTGTTTCAAAAAAGCCATTCTTTTCAAAGTTATTTTACCGTT |
| AGATTATTTATGTTGTTTTTATTTTCATTTGTTCCTGCGTATTATTTAGTAAATAGATTCATAAAGGGTGACTTGAAA |
| TTAATGGAGCGAATATTAGTGTATTCTCTGGGTTCAAATAGTTATTTTTTTGGTATGTATATAAGTCCAGAGTTA |
| AAAAGATTGTTATATACTTTCTTTGGTATGTCTGACTCTGTTAATCTTTGGGAACAAAATGCTAAAGTAAGAGGATTT |
| GGGTTGTCGGGTGAAATAAATTTCATGACACCATTTTTGATGATCTATATGTCATTTTTTATGATGAAAAGGCGTTAT |
| GCTTTAATTACTTTAATTTGTCTGACTCAAATCGTAAATTCTAACATGGCTGTGATTGCAGCCATTATTGGTATCGGT |
| TGCTCTAGACTTAATATTAATATAAAAATTGCAACAGTATTGATTTTGGGAGTTTTAGTTTATAGCTTAGGAGCGGTG |
| TTCTTTCCTCGATTTTATGATGAGTTCGTTTCTGGAGATGGCACAAGAACTCTGGATATCTTATTACAGCAACATGTG |
| TTTGTTGTAGGTAATTTAGATTTTTTTAATATTATATTTGGATTACAGCAAAACATATCTTCATCAATCCCCGATATT |
| AAACAAAGTTCGGATATGGGCTGGGTTATACTGTTTAATTACGGTGGGTTAACATTTATTACACTCTTTTTATTTTTA |
| ATCTTTACTATTTCTATTGCGACATTTGGAATGACATATCAAGCAATTATATGGATGTTAATTGGGATAATTTTCAAT |
| ACCAAAGGTTTAGTTTTAGGATCTAACGGCTATTTCTTTCTATCTTTTATATATATGTTTTTGAATAGAGTAACACTT |
| AGTGGACAGAGTTCAATTACTAATAAGTTAGGTCAAGTAAGTAAATAGCTTCCAGAGTATATTTGTCAATGATTTGAG |
| GTTCGGTTATTATGTTTTCATCTAAAACACTGTTAATTACTGGTGGTACTGGCTCTTTCGGGAATGCTGTATTAAATA |
| GATTTCTTGATACAGATATTGCAGAAATCCGTATATTTAGTCGTGATGAAAAAAAACAAGATGATATGCGGAAAAAT |
| ACAATAATCAAAAATTAAAGTTCTATATTGGTGATGTCAGAGATTACCGTAGTATTTTGAATGCGACTCGCGGTGTTG |
| ATTTTATATATCATCGCAGCGGCACTTAAGCAAGTTCCATCATGTGAATTTCATCCTATGGAAGCCGTTAAAACTAATA |
| TCCTTGGTACGGAAAATGTTCTTGAAGCAGCTATAGCGAATGAAGTGAAGAGGGTTGTATGCCTAAGTACTGATAAAG |
| CTGTATACCCGATTAACGCAATGGGTATTTCAAAAGCTATGATGGAAAAGGTCATGGTCGCGAAATCCCGTAATGTTG |
| ATCGCAATAAAACAGTAATATGTGGTACCCGTTATGGGAATGTTATGGCATCTCGCGGTTCAGTTATTCCATTATTTG |
| TTGATCTTATTAGAGCGGGCAAGCCACTCACAATAACTGATCCTAATATGACCCGCTTTATGATGACTCTTGAGGATG |
| CGGTAGATTTAGTTCTTTATGCGTTTGAACATGGTAATAATGGTGATATCTTTGTGCAAAAAGCACCTGCAGCAACTA |
| TTGACACATTAGCTATTGCTTTAAAGGAATTACTAAATGTTCCTGACCATCCGGTAAATGTCATTGGAACGCGTCATG |
| GCGAGAAATTATATGAAGCTCTACTTAGTCGTGAGGAAATGATCGCTGCTATAGATATGGGCGATTATTACCGTGTCC |
| CGCCAGATCTTCGTGACCTTAATTATGGCAAATATGTTGAGCAAGGTGATAGCCGAATATCTGAAATAGAAGATTATA |
| ACTCTCATAATACTCAACGGTTAGATGTTGAAGGCATGAAAGAGCTCTTGCTAAAATTAGCCTTTATTCGAGCAATTC |
| GTGCTGGTGAAAAATATAATCTGGATTCATGATATGAAAATATTAGTTACTGGTGCAAATGGTTTTATTGGTCGTAAT |
| TTATGTTTGAGGCTTGAGGAACTTGGTTATAAAGATCTTATTAGAATTGATCGAGAATCAACGAAGCAAGATCTTGAA |
| CAAGGCTTACAGGATGCCGATTTTATTTATCACTTAGCTGGTATCAATAGACCTAAGACTGATGATGAGTTTATTTCT |
| GGAAACAGTGATTTAACAAAGCATATAGTTGAGTATCTCCTTTCTATTGGTAAGAATACACCAATTATGCTAAGTTCT |
| TCGATACAAGCTGAACTTAATAATGCTTATGGGGTTAGCAAAGCTGTAGCTGAAAGCTATGTCGAAAAATATGCTGCT |
| GCTAGTGGTTCTTCGTATTATATTTTCAGATATCCAAACGTTTTTGGTAAATGGTGTAAGCCAAACTATAATTCTTTT |
| ATAGCAACTTTTTGCTACAATATTTCCAATGATATTGAGATTACTATCAATGATGCAGCAGCGCCAGTCAATCTGGTC |
| TATATTGATGATGTTTGTACTGATGCTATAGCTCTTCTCTCTGGGACGGTTGAAAGTGGATATAAAGTTGTTGCACCA |
| ATTTATTCAACAACAGTTGGTGAAGTTGCAGAATTAATTTATAGCTTCAAAAATAGCCGTTCCACCCTGATCACAGAG |
| GCTGTCGGGGCGGGATTTACCCGTGCATTGTATTCTACATGGCTGAGTTATTTACCAGCAGAGAAGTTTGCGTACAAG |
| GTACCTTTTTATGGGGATGCCCGCGGAGTCTTTTGTGAGATGTTGAAAACGCCTTCAGCGGGGCAGTTTTCATTTTTT |
| ACTGCTCACCCTGGTATTACGCGTGGCGGACATTACCATCACACAGTAAAAATGAGAAGTTTTTGGTCATTCGGAGTCAG |
| GCATGCTTTAAATTTGAACATGTGATTACCGGTGAGCGATATGAACTGAAAGTTTCATCGGGTGAGTTTAAGATTGTT |
| GAAACAGTTCCTGGTTGGACACATGACATTACAAATATTGGAACTGATGAATTAATAGTCATGCTCTGGGCAAATGAA |
| ATTTTCAACCGTGATGAGCCCGATACTATTGCGAGACCTCTATAATGAAAAATTAAAAGTTATGTCTGTTGTTGGAA |
| CCCGTCCTGAGATTATCCGTTTGTCGAGGGTTCTTGCTAAGTTTGATAAGTACTGCGAGCATATTATTGTCCATACTG |
| GTCAAAATTATGATTACGAATTAAATGAAGTGTTCTTCAATGACTTGGGTGTTCGAAAACCTGATTATTTTTTAAATG |
| CAGCGGGTAAAATGCGGCGGAAACCATTGGTCAGGTTATTATTAAGGTAGATGAAGTATTAGAAATCGAAAAACCTG |
| AAGCAATACTGGTATTGGGCGATACGAATTCATGTATTTCTGCCATTCCGGCCAAACGCCGTAAAGTGCCTATATTTC |
| ATATGGAAGCAGGTAACCGTTGTTTCGACATAACGCGTGCCTGAAGAAACCAACAGACGTATTGTTGACCATACGGCTG |
| ATATCAATATGACCTACAGTGATATTGCTCGTGAATATCTCTTGGCTGAAGGTATCCCAGCTGATCGGATCATAAAAA |
| CTGGTAGCCCTATGTTTGAGGTTCTTTCATATTATATGCCCCAAATTGATGGTTCAGATGTGCTATCGCGTTTGAATC |
| TACAGTCTGGTGAGTTTTTGTAGTAAGTGCGCATCGTGAAGAGAATGTTGATTCTCCAAAACAGCTCGTAAAGCTTG |
| CGAACATTCTAAATACTGTTGCTGAAAAATATAATCTTCCAGTTATTGTCTCCACACACCCAAGGACACGTAACCGAA |
| TCCGTGAGCAAGGAATTGAATTTCATTCAAATATAAATCTACTGAAAACCATTGGGTTTCCATGATTATAACCACTTGC |
| AGAAGAACTCACGAGCTGTGCTTTCAGATAGCGGTACTATCACTGAAGAGTCATCCATCATGAATTTCCCAGCGGTAA |
| ACATCCGGGAAGCGCATGAGCGTCCGGAAGGCTTTGAGGAAGCATCCGTCATGATGGTGGGGTTAGAGTGTGAACGCG |
| TATTACAAGCGCTGGATATTCTGGCAACACAACCGCGAGGTGAAGTCCGTCTTTTACGTCAGGTTAGTGATTACAGCA |
| TGCCAAATGTGTCGGATAAAGTTGTCAGAATTGTTCACTCTTACACAGATTATGTTAAGAGAGTCGTCTGGAAAGAAT |
| ATTGATGAAACTTGCTTTAATCATAGATGATTACCTGCCCAACAGTACTCGTGTTGGTGCAAAAATGTTTCATGAACT |
| TGCTCAAGAATTTATCCAGCGTGGGCACGATGTTACGGTAATTACTCCTGGTACGGGCATGCAAGAAGAGATTTCTTT |
| TGATACCTTTCAGGGGGTAAAAACATGGCGTTTTAAAAGCGGGCCGTCCAAGGATGTAAGTAAAATTCAGCGAGCGGT |
| CAATGAAACGCTTTTGTCCTATCGGGCGTGGAAAGCCATCAAAAAATGGGTAAAAAAGAGACCTTTGAGGGGGTGAT |
| TTATTATTCACCTTCCATATTCTGGGGGCCTTTAGTTAAAAAAATTAAAGCTCGTTGCCAATGTCCTGCTTATCTTAT |
| TTTAAGAGATATGTTTCCACAATGGGTAATTGATGCAGGAATGCTTAATGCTGGTTCCCCAATAGAACGCTACTTTCG |
| TCTTTTTGAAAAAATATCTTATCGTCAGGCAAATCGTATTGGACTTATGTCTGATAAGAATCTTGATGTTTTTCGGAA |

| SEQUENCES |
|---|
| AGATAATAAAGGCTATCCGTGCGAAGTTTTGCGTAATTGGGCATCCCTAACACCAACGATCATACCCAAGGATTATAT<br>ACCACTACGTAAGCGACTTGGCCTAGAGGATAAAACCATTTTCTTCTATGGTGGAAACATAGGTCATGCACAGGACAT<br>GACAAACTTGATGCGACTTGTGAGAAACATGGCAGCATATCCTCAAGCTCATTTCCTATTTATTGGCCAGGGGGATGA<br>AGTTGAATTAATTAATTCATTAGCATCTGAGTGGGCATTGACGAATTTCACCTATTTGCCCTCGGTTAACCAAGATGA<br>ATTTAAGTTCATTTTGTCGGAAATGGATATCGGCTTGTTTTCTCTTTCCGCTAGACACTCTTCCCATAATTTTCCTGG<br>TAAGTTATTAGGCTATATGGTTCAGTCGCTACCTATTTTAGGTAGCGTAAATGCCGGAAATGATTTGCTCGACATTGT<br>CAATCAAAATAATGCGGGATTAATCCATGTCAATGGTGAGGACGATAAATTATGTCAATCTGCGCTATTAATGTTGCA<br>TGATATTGATGTGCGCCGGCAACTTGGTTCGGGGGCGAATATATTGTTGAAAGAACAATTCTCCGTTGAGTCTGCGGC<br>ACAGACGATAGAAATGAGGTTGGAGGCATGCAATGCGATTAATTGATAATGACCAACTCGACGAATTATATGATCAAG<br>CCGGGCAATCGGAACGTTTACGTTCCCACCTTATGATGCACGGCTCGCATCAAGAAAAGGTACAGCGTTTACTTATTG<br>CATTAGTAAAGGGCAGCTATGTTGAACCGCATTATCACGAACTTCCTCATCAGTGGGAAATGTTCATTGTTATGGAGG<br>GGCAACTTCAGGTTTGTTTGTATGGTAGAAATGGTGAGGTTATAAAGCAATTTATAGCAGGAGATAATACTGGAATGA<br>GCATTGTGGAGTTTTCTCCGGGCGATATACACAGTGTCGAATGCCTATCTCCGCGTGCTCTTATGGTGGAAGTTAAGG<br>AGGGGCCATTTGACCCTTCTTTTGCAAAATCGTTCGTGTGAGCGGCCGCGAGCTCGTCGACTCGAGGATCCGTGTAGG<br>CTGGAGCTGCTTCGAAGTTCCTATACTTTCTAGAGAATAGGAACTTCGGAATAGGAACTAAGGAGGATATTCATATGG<br>ATAAAGCCGTAAGCATATAAGCATGGATAAGCTATTTATACTTTAATAAGTACTTTGTATACTTATTTGCGAACATTC<br>CAGGCCGCGAGCATTCAGCGCGGTGATCACACCTGACAGGAGTATGTAATGTCAAGCAACAGATCGGCGTAGTCGGT<br>ATGGCAGTGATGGGACGCAACCTTGCGCTCAACATCGAAAGCCGTGGTTATACCGTCTCTATTTTCAACCGTTCCCGT<br>GAGAAGACGGAAGAAGTGATTGCCGAAAATCCAGGCAAGAAACTGGTTCCTTACTATACGGTGAAAGAGTTTGTCGAA<br>TCTCTGGAAACGCCTCGTCGCATCCTGTTAATGGTGAAAGCAGGTGCAGGCACGGATGCTGCTATTGATTCCCTCAAA<br>CCATATCTCGATAAAGGAGACATCATCATTGATGGTGGTAACACCTTCTTCCAGGACACTATTCGTCGTAATCGTGAG<br>CTTTCAGCAGAGGGCTTTAACTTCATCGGTACCGGTGTTTCTGGCGGTGAAGAGGGGCGCTGAAAGGTCCTTCTATT<br>ATGCCTGGTGGCCAGAAAGAAGCCTATGAATTGGTAGCACCGATCCTGACCAAAATCGCCGCCGTAGCTGAAGACGGT<br>GAACCATGCGTTACCTATATTGGTGCCGATGGCGCAGGTCACTATGTGAAGATGGTTCACACAGGTATTGAATACGGC<br>GATATGCAGCTGATTGCTGAAGCCTATTCTCTGCTTAAAGGTGGCCTGAACCTCACCAACGAAGAACTGGCGCAGACC<br>TTTACCGAGTGGAATAACGGTGAACTGAGCAGTTACCTGATCGACATCACCAAAGATATCTTCACCAAAAAGATGAA<br>GACGGTAACTACCTGGTTGATGTGATCCTGGATGAAGCGGCTAACAAAGGTACCGGTAAATGGACCAGCCAGAGCGCG<br>CTGGATCTCGGCGAACCGCTGTCGCTGATTACCGAGTCTGTGTTTGCACGTTATATCTCTTCTCTGAAAGATCAGCGT<br>GTTGCCGCATCTAAAGTTCTCTCTGGTCCGCAAGCACAGCCAGCAGGCGACAAGGCTGAGTTCATCGAAAAAGTTCGT<br>CGTGCGCTGTATCTGGGCAAAATCGTTTCTTACGCCCAGGGCTTCTCTCAGCTGCGTGCTGCGTCTGAAGAGTACAAC<br>TGGGATCTGAACTACGGCGAAATCGCGAAGATTTTCCGTGCTGGCTGCATCATCCGTGCGCAGTTCCTGCAGAAAATC<br>ACCGATGCTTATGCCGAAAATCCACAGATCGCTAACCTGTTGCTGGCTCCGTACTTCAAGCAAATTGCCGATGACTAC<br>CAGCAGGCGCTGCGTGATGTCGTTGCTTATGCAGTACAGAACGGTATTCCGGTTCCGACCTTCTCCGCAGCGGTTGCC<br>TATTACGACAGCTACCGTGCTGCTGTTCTGCCTGCGAACCTGATCCAGGCACAGCGTGACTATTTTGGTGCGCATACT<br>TATAAGCGTATTGATAAAGAAGGTGTGTTCCATACCGAATGGCTGGATTAA |

SEQ ID NO: 16 (example 016 rfb locus nucleotide sequence-016-EPA
production strain stLMTB11739)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGACGCCAGGTGCTGGCAAAACGTATGCCGGGTGACCTCTCTGAATACTCCGTCATCCAGATAAAGAGCCG
CTGGACCGTGAGGGTAAAGTCAGCCGCATTGTTGAATTTATCGAAAAACCGGATCAGCCGCAGACGCTGGACTCAGCAG
ATCATGGCCGTAGGTCGCTATGTGCTTTCTGCCGATATTTGGCCGGAACTGGAACGTACTCAGCCTGGTGCATGGGA
CGTATTCAGCTGACTGATGCTATTGCCGAGCTGGCGAAAAAACAATCCGTTGATGCAATGCTGATGACCGGCGACAGT
TACGACTGCGGCAAAAAATGGGCTATATGCAGGCGTTTGTGAAGTATGCCTACGCAACCTGAAGAAGGGCGAAG
TTCCGTAAAGGTATTGAGAAGCTGTTAAGCGAATAATGAAAATCTGACCGGATGTAACGGTTGATAAGAAAATTATAA
CGGCAGTGAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCATCATAGGCATGCATGCAGTGCTTCGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGTGAAAATACTTGTTACTGGTGGCGCAGGATTATTGGTTCAGCTGTAGTTCGTCACATT
ATAAATAATACGCAGGATAGTGTTGTTAATGTCGATAAATTAACGTACGCCGGAAACCGGGAATCACTTGCTGATGTT
TCTGATTCTGAACGCTATGTTTTTGAACATGCGGATATTTGCGATGCACCTGCAATGCACGGATTTTTGCTCAGCAT
CAGCCGGATGCAGTGATGCACCTGGCTGCTGAAAGCCATGTTGACCGTTCAATTACAGGCCCTGCGGCATTTATTGAA
ACCAATATTGTTGGTACTTATGTCCTTTTGGAAGCCGCTCGCAATTACTGGTCTGCTCTTGATAGCGACAAGAAAAAT
AGCTTCCGTTTTCATCATATTTCTACTGACGAAGTCTATGGTGATTTGCCTCATCCAGATGAAGTAAATAATACAGAA
GAATTACCCTTATTTACTGAGACGACAGCTTACGCGCCAAGCAGCCCTTATCCGCATCCAAAGCATCCAGCGATCAT
TTAGTCCGCGCGTGGAAACGTACATATGGTTTACCGACAATTGTGACTAATTGCTCGAACAACTATGGTCCTTATCAT
TTCCCGGAAAAGCTTATTCCACTGGTTATTCTTAATGCACTGGAAGGTTAAGGCATTACCTATTTATGGCAAAGGAGAT
CAGATCCGCGACTGGTTGTATGTTGAAGATCATGCGCGTGCGTTATATACCGTCGTAACCGAAGGTAAAGCGGGTTGAA
ACTTATAACATTGGTGGGCACAACGAAAAGAAAAACATCGATGTAGTGCTCACTATTTGTGATTTGCTGGATGAGATT
GTACCGAAAGAAATCCTTATCGTGAGCAAATCACTTATGTCGTCATGCCAGCAGCCACGATCGCCGCTATGCTATT
GATGCTGAGAAGATTGGTCGCGCATTGGGATGGAAACCACAGGAAACGTTTGAGAGCGGGATTCGTAAAACGGTGGAA
TGGTACCTGTCCAATACAAAATGGGTTGATAATGTGAAAGTGGTGCCTATCAATCGTGGATTGAACAGAACTATGAG
GGCCGCCAGTAATGAATATCCTCCTTTTTGGCAAAACAGGGCAGGTAGGTTGGGAACTACAGCGTGCTCTGGCACCTT
TGGGTAATTTGATTGCTTTGATGTTCACTCTACTGATTATTGCGGTGATTTTAGTAATCCTGAAGGTGTAGCTGAAA
CCGTAAGAAGCATTCGGCCGGATATTATTGTCAATGCAGCCGCTCACCACGCAGTGACAAAGCAGATGAGACCGG
AGTTTGCACAATTAATTAACGCAACAAGTGTCGAAGCGATTGCGAAAGCAGCAAATGAAGTTGGAGCCTGGGTTATCC
ATTACTCGACTGATTACGTCTTCCCTGGAAATGGCGATATGCCATGGCTGGAGACGGATGCAACCGCACCACTAAATG
TTTACGGTGAAACCAAGTTAGCCGGAGAAAAAGCGTTACAGGAATATTGCGCGAAGCATCTTATTTTCCGGACCAGCT
GGGTCTATGCAGGAAAAGGAAATAACTTCGCCAAAACGATGTTACGTCTGGCAAAAGAGCGTGAAGAATTAGCGGTTA
TTAACGATCAGTTTGGTGCGCCAACAGGTGCTGAACTGCTGGCTGATTGTACAGCACATGCCATTCGTTGCGCACTGA
ATAAACCGGATGTCGCAGGCTTGTACCATTTGGTAGCCAGTGGTACCACAACCTGGTACGATTATGCTGCGCTGGTTT

| SEQUENCES |
|---|
| TTGAAGAGGCGCGCAAAGCAGGCATTCCCCTTGCACTCAACAAGCTCAACGCAGTACCAACAACAGCCTATCCTACAC |
| CAGCTCGTCGTCCACATAACTCTCGCCTTAATACAGAAAAATTTCAGCAGAACTTTGCGCTTGTCTTGCCTGACTGGC |
| AGGTTGGCGTGAAACGAATGCTCAATGAATTATTTACGACTACAGCAATTTAATAGTTTTTGCATCTTGTTCGTGATG |
| GTGGAGCAAGATGAATTAAAAGGAATGATGAAATGAAAATGCGTAAAGGTATTATTTTAGCGGGTGGTTCTGGTACAC |
| GTCTTTATCCTGTGACTATGGCTGTCAGTAAACAGCTATTACCTATTTATGATAAACCGATGATCTATTACCCGCTCT |
| CTACACTGATGTTGGCGGGTATTCGCGATATTTTGATTATCAGTACACCTCAGGATACTCCTCGTTTTCAACAATTGC |
| TGGGTGACGGTAGCCAGTGGGGCCTGAATCTTCAGTACAAAGTGCAACCTAGCCCAGTGGCCTCGCGCAGGCATTTA |
| TCATCGGTGAAGAGTTTATTGGTGGTGATGATTGTGCTTTGGTTCTTGGTGATAATATCTTTTACGGTCACGATCTGC |
| CGAAGCTAATGGAGGCCGCTGTTAACAAAGAAAGTGGTGCAACGGTATTTGCCTATCACGTTAATGATCCAGAACGCT |
| ATGGTGTCGTTGAGTTTGATAAAAACGGTACGGCAATCAGTCGGAAGAAAAACCGTTAGAACCAAAGAGTAATTACG |
| CCGTTACAGGTCTGTACTTTTATGATAACGACGTGGTTCAGATGGCGAAAAACTTGAAGCCGTCTGCACGTGGTGAGT |
| TAGAAATTACAGATATTAACCGTATTTATCTTGAGCAGGGACGTCTGTCTGTCGCGATGATGGGGCGTGGCTACGCGT |
| GGCTGGACACGGGGACTCATCAGAGTCTGATAGAAGCAAGTAATTTTATTGCGACAATTGAAGAGCGCAGGGATTGA |
| AGGTTTCCTGTCCTGAAGAGATTGCATTTCGTAAAGGTTTTATTGATGTTGAGCAAGTAAGAAAATTAGCTGTACCAC |
| TAATAAAGAATAATTATGGGCAGTATCTTTATAAAATGACGAAGGATTCAAATTAATGAATGTGATTAGAACTGAAAT |
| TGAAGATGTGCTAATTCTGGAGCCAAGAGTATTTGGTGATGATAGAGGTTTCTTTTATGAGAGCTTTAATCAATCAGC |
| ATTTGAACATATTCTAGGCTATCCGGTCAGCTTTGTTCAAGACAATCACTCACGTTCATCAAAAAATGTACTCAGAGG |
| CCTTCACTTTCAACGCGGCGAGTACGCACAAGATAAACTTGTACGCTGCACTCATGGAGCAGTTTTTGATGTTGCTGT |
| TGATATTCGACCCAATTCGGTATCCTTTGGTAAATGGGTTGGTGTTCTGCTTTCAGCTGATAATAAGCAGCAGTTGTG |
| GATACCAAAAGGGTTTGCTCATGGCTTTTTGGTTCTGTCTGATATCGCTGAATTTCAATATAAAACTACAAACTATTA |
| TCATCCTGAAAGCGATTGTGGAATATGTTGGAATGATGAACGCATTGCAATTGATTGGCCCCAAACATCAGGGTTAAT |
| CCTTTCGCCAAAAGATGAAAGGCTCTTTACGTTAGATGAGCTTATCAGATTAAAATTAATTGCATGAATACGAATAAA |
| TTATCTTTAAGAAGAAACGTTATATATCTGGCTGTCGTTCAAGGTAGCAATTATCTTTTACCATTGCTTACATTTCCA |
| TATCTTGTAAGACACTTGGTCCTGAAAATTTCGGTATATTCGGTTTTTGCCAAGCGACTATGCTATATATGATAATG |
| TTTGTTGAATATGGTTTCAATCTCACAGCAACTCAGAGTATTGCCAAAGCAGCAGATAGTAAAGATAAAGTAACGTCT |
| ATTTTTTGGGCGGTGATATTTTCAAAAATAGTTCTTATCGTCATTACATTGATTTTCTTAACGTCGATGACCTTGCTT |
| GTTCCTGAATATAACAAGCATGCCGTAATTATATGGTCGTTTGTTCCTGCATTAGTCGGGAATTTAATCTACCCTATC |
| TGGCTGTTTCAGGGAAAAGAAAAAATGAAATGGCTGACTTTAAGTAGTATTTTATCCCGCTTGGCTATTATCCCTCTA |
| ACATTTATTTTTGTGAACACAAAGTCAGATATAGCAATTGCCGGTTTATTCAGTCAAGTGCAAATCTGGTTGCTGGA |
| ATTATTGCACTAGCTATCGTTGTTCATGAAGGTTGGATTGGTAAAGTTACGCTATCATTACATAATGTGCGTCGATCT |
| TTAGCAGACGGTTTTCATGTTTTTATTTCCACATCTGCTATTAGTTTATATTCTACGGGAATAGTTATTATCCTGGGA |
| TTTATATCTGGACCAACGTCCGTAGGGAATTTTAATGCGGCCAATACTATAAGAAACGCGCTTCAAGGGCTATTAAAT |
| CCTATCACCCAAGCAATATACCCAAGAATATCAAGTACGCTTGTTCTTAATCGTGTGAAGGGTGTGATTTTAATTAAA |
| AAATCATTGACCTGCTTGAGTTTGATTGGTGGTGCTTTTTCATTAATTCTGCTCTTGGGTGCATCTATACTAGTAAAA |
| ATAAGTATAGGGCCGGGATATGATAATGCAGTGATTGTGCTAATGATTATATCGCCTCTGCCTTTTCTTATTTCATTA |
| AGTAATGTCTATGGCATTCAAGTTATGCTGACCCATAATTATAAGAAAGAATTCAGTAAGATTTTAATCGCTGCGGGT |
| TTGTTGAGTTTGTTGTTGATTTTTCCGCTAACAACTCTTTTTAAAGAGATTGGTGCAGCAATAACATTGCTTGCAACA |
| GAGTGCTTAGTTACGTCACTCATGCTGATGTTCGTAAGAAATAATAAATTACTGGTTTGCTGAGGATTTTATGTACGA |
| TTTATATCATTGTTGGTTCTGGTTTGTTTGGTGCCGTTTGTGCGAATGAGTTAAAAAAGCTAAACAAAAAAGTTTTAGT |
| GATTGAGAAAAGAAATCATATCGGTGGAAATGCGTACACAGAGGACTGTGAGGGTATCCAGATTCATAAATATGGTGC |
| ACATATTTTTCATACCAATGATAAATATATATGGGATTACGTTAATGATTTAGTAGAATTTAATCGTTTTACTAATTC |
| TCCACTGGCGATTTATAAAGACAAATTATTCAACCTTCCTTTTAATATGAATACTTTCCACCAAATGTGGGGAGTTAA |
| AGATCCTCAAGAAGCTCAAAATATCATTAATGCTCAGAAAAAAAAGTATGGTGACAAGGTACCTGAAAATTTGGAGGA |
| GCAGGCGATTTCATTAGTTGGGGAGGACTTATACCAAGCATTGATAAAGGGTTATACGGAGAAGCAGTGGGGAAGAAG |
| TGCAAAAGAATTGCCTGCATTTATTATTAAGCGAATCCCAGTGAGATTTACGTTTGATAACAATTATTTTTTCCGATCG |
| CTATCAAGGTATTCCGGTGGGAGGCTACACTAAGCTTATTGAAAAAATGCTTGAAGGTGTGGACGTAAAATTAGGCAT |
| TGATTTTTTGAAAGACAAAGATTCTCTAGCGAGTAAAGCCCATAGAATCATCTACACTGGACCCATTGATCAGTACTT |
| CGACTATAGGTTTGGAGCGTTAGAATATCGCTCTTTAAAATTTGAGACGGAACGCCATGAATTTCCAAACTTCCAAGG |
| GAATGCAGTAATAAATTCACTGATGCTAATGTACCATATACCGAAGATAATTGAGCATAAACATTTTGACTATGTTGA |
| GACAAAGCATACGGTTGTTACAAAAGAATATCCATTAGAGTGGAAAGTTGGCGACGAACCCTACTATCCAGTTAATGA |
| TAATAAAAACATGGAGCTTTTTAAGAAATATAGAGAGTTAGCTAGCAGAAGACAAGGTTATATTTGGCGGGCGTTT |
| GGCCGAGTATAAATATTATGATATGCATCAAGTGATATCTGCCGCTCTTTATCAAGTGAAAAATATAATGAGTACGGA |
| TTAATGATCTATCTTGTAATTAGTGTCTTTCTCATTACAGCTTGTCTGTTTATATCTTAAGAAGGATATATTTTAT |
| CCAGCCGTATGCGTTAATATCATCTTCGCACTGGTCTTATTGGGATATGAAATAACGTCAGATATATATGCTTTTCAG |
| TTAAATGACGCTACGTTGATTTTCTACTTTGCAATGTTTTGACATTTACCCTGTCATGTTTATTGACGGAAAGTGTA |
| TTAGATCTAAATATCAGAAAAGTCAATAATGCTATTTATAGCATACCATCGAAGAAAGTGCATAATGTAGGCTTGTTA |
| GTTATTTCTTTTTCGATGATATATATATGCATGAGGTTAAGTAACTACCAGTTCGGGACTAGCTTACTTAGCTATATG |
| AATTTGATAAGAGATGCTGATGTTGAAGACACATCAAGAAATTTCTCAGCATACATGCAGCCAATCATTCTAACTACT |
| TTTGCTTTATTTATTGGTCTAAAAAATTTACTAATACAAAGGTAAGTAAAACATTTACTTTACTTGTTTTATTGTA |
| TTCATCTTTGCAATTATACTGAATACTGGTAAGCAAATTGTCTTTATGGTTATCATCTCTTATGCATTCATCGTAGGT |
| GTTAATAGAGTAAAACATTATGTTTATCTTATTACAGCTGTAGGTGTTCTATTCTCCTTGTATATCGTCTTTTTACGT |
| GGACTGCCTGGGGGATGGCATATTATCTATCCATGTATTTGGTCAGCCCTATAATCGCGTTTCAGGAGTTTTATTTT |
| CAGCAAGTATCTAACTCTGCCAGTTCTCATGTCTTTTGGTTTTTTGAAAGGCTGATGGGCTATTAACAGGTGGAGTC |
| TCTATGTCGTTGCATAAAGAATTTGTGTGGGTGGGTTTGCCAACAAATGTTTATACTGCTTTTTCGGATTATGTTTAT |
| ATTTCCGCGGAGCTAAGCTATTTGATGATGGTTATTCATGGCTGTATTTCAGGTGTTTTATGGAGATTGTCTCGAAAT |
| TACATATCTGTGAAAATATTTATTCATATTTTATTATACCTTTCTTTCTTTTTATCATGAAAGCTTTCATGACT |
| AATATTAGCAGTTGGATACAAATAACTCTTTGTATCATAGTATTCTCTCAATTTCTTAAGGCCCAGAAAATAAAGTGA |
| AAATGTATTTTTGAATGATTTAAATTTCTCTAGACGCGATGCTGGATTTAAAGCAAGAAAAGATGCACTGGACATTG |
| CTTCAGATTATGAAAACATTTCTGTTGTTAACATTCCTCTATGGGGTGGAGTAGTCCAGAGAATTATTAGTTCTGTTA |
| AGCTTAGTACATTTCTCTGCGGTCTTGAAAATAAAGATGTTTAATTTTCAATTTCCCGATGGCCAAACCATTTGGC |
| ATATATTGTCATTCTTTCACCGCCTTCTAAAATTTAGAATAGTACCTCGATTGATATTGATTAAGAGGAG |
| GAGGGGTAGTGATTCTGTCGGCTTGCTACCTGTGATATGGTCATAAGTCACAATCCACAAATGACAAAGTACCTTA |
| GTAAATATATGTCTCAGGATAAAATCAAAGACATAAAAATATTTGATTACCTCGTCTCATCGATGTGGAGCATCGAG |
| ATGTTACGGATAAGCAACGAGGGGTCATATATGCTGGCAACCTTTCTAGGCATAAATGTCTTTCATATATACTGAAG |
| GATGCGATTTTACTCTCTTTGGTGTCAACTATGAAATAAAGATAATCCTAAATATCTTGGAAGTTTTGATGCTCAAT |
| CTCCGGAAAAGATTAACCTCCCAGGCATGCAATTTGGACTCATTTGGGATGGAGATTCTGTCGAAACCTGTAGTGGTG |
| CCTTTGGCGACTATTTAAAGTTTAATAACCCTCATAAGACATCTCTTTATCTTTCAATGGAACTTCCAGTATTTATAT |

| SEQUENCES |
|---|
| GGGATAAAGCCGCCCTTGCGGATTTCATTGTAGATAATAGAATAGGATATGCAGTGGGATCAATCAAAGAAATGCAAG
AGATTGTTGACTCCATGACAATAGAAACTTATAAGCAAATTAGTGAGAATACAAAAATTATTTCTCAGAAAATTCGAA
CAGGAAGTTACTTCAGGGATGTTCTTGAAGAGGTGATCGATGATCTTAAAACTCGCTAAACGATATGGTCTCTGTGGT
TTTATTCGGCTTGTTAGAGATGTCTTATTGACTCGTGTATTTTACCGGAACTGTAGAATTATTCGATTTCCCTGCTAT
ATTCGCAATGATGGTAGCATTAATTTTGGTGAAAATTTCACAAGTGGAGTCGGTCTCAGGCTGGATGCATTTGGACGT
GGCGTGATTTTTTTTCCGATAATGTGCAAGTTAACGACTATGTTCATATCGCCTCAATTGAGAGCGTTACGATAGGT
CGGGATACGCTTATTGCAAGTAAAGTATTTATTACCGATCATAATCACGGTTCCTTTAAGCACTCTGATCCAATGAGT
TCGCCAAATATACCTCCAGACATGCGCACGTTGGAATCTTCAGCTGTTGTAATTGGCCAGAGGGTTTGGTTGGGTGAG
AATGTGACGGTTTTGCCTGGAACAATTATTGGTAATGGAGTCGTAGTCGGCGCCAATTCTGTTGTTAGAGGTTCTATT
CCCGAAAATACTGTCATTGCGGGAGTACCAGCAAAAATCATAAAGAAATACAATCATGAGACCAAATTATGGGAAAAA
GCATAGTCGTTGTTTCTGCGGTCAATTTTACCACTGGCGGTCCATTTACCATTTTGAAAAAATTTTTGGCAGCAACTA
ATAATAAAGAAAATGTCAGTTTTATCGCATTAGTCCATTCTGCTAAAGAGTTAAAAGAAAGTTATCCATGGGTTAAAT
TCATTGAGTTTCCTGAGGTTAAAGGGTCGTGGCTAAAACGTTTGCACTTTGAATATGTAGTTTGTAAAAAACTTTCAA
AAGAGCTGAATGCTACGCATTGGATTTGTCTGCATGATATTACGGCCAATGTCGTCACTAAAAAAAGATATGTGTATT
GTCATAACCCTGCCCCTTTTATAAAGGAATTTTATTCCGTGAAATTCTTATGGAGCCTAGCTTTTTCTTATTTAAAA
TGCTATACGGGCTGATATATAAAATAAACATTAAAAAAATACTGCAGTGTTTGTTCAACAATTCTGAGTGAAAGAAA
AATTTATCAAGAAATATTCTATAAATAACATCATTGTCAGTCGGCCAGAAATTAAATTATCTGATAAAAGCCAACTTA
CTGATGATGATTCTCAATTTAAGAATAACCCTTCTGAGTTGACAATATTTTACCCTGCTGTTCCACGAGTATTTAAAA
ATTACGAGCTTATTATTAGTGCAGCAAGGAAATTGAAAGAACAATCCAATATTAAATTTCTGCTTACTATCAGTGGTA
CAGAAAATGCGTATGCAAAATATATTATCAGTCTTGCAGAAGGACTGGATAATGTTCATTTCCTCGGGTACTTGGATA
AAGAAAAAATCGATCATTGTTATAATATTTCAGATATAGTTTGTTTTCCCTCTAGGTTAGAAACATGGGGATTGCCGT
TGTCTGAGGCTAAAGAGCGAGGTAAGTGGGTATTAGCATCAGATTTCCCATTTACTAGAGAAACTCTTGGTAGTTATG
AAAAGAAAGCTTTTTTTGATTCTAATAACGATGACATGTTAGTTAAACTTATTATTGACTTCAAAAAAGGTAACCTCA
AAAAAGATATCTCTGATGCAAATTTCATTTATCGTAATGAAAATGTATTAGTTGGGTTTGATGAACTAGTTAATTTTA
TTACTGAAGAACATTGAAATGGTATATATAATAATCGTTTCCCACGGACATGAAGACTACATCAAAAAATTACTCGAA
AATCTTAATGCTGACGATGAGCACTACAAGATTATCGTACGCGACAACAAAGACTCTCTATTATTGAAACAAATATGC
CAGCATTATGCAGGCCTGGACTATATTAGTGGAGGTGTATACGGCTTTGGTCATAATAATAATATTGCGGTGGCGTAT
GTAAAGGAAAAATATAGACCCGCAGATGATGATTACATTTTGTTTTTGAATCCCGATATCATCATGAAGCATGATGAT
TTGCTGACATATATTAAATATGTCGAAAGTAAGCGTTATGCTTTTAGTACATTATGCCTGTTCCAGATGAAGCGAAA
TCTTTACATGATTATTCCGTAAGAAAATTTCCTGTGCTTTCTGATTTTATTGTGTCATTTATGTTAGGGATTAATAAA
ACAAAAATTCCTAAAGAAAGTATCTATTCTGATACGGTTGTTGATTGGTGCGCAGGATCATTTATGCTGGTACGTTTT
TCAGATTTTGTGCGTGTAAATGGCTTCGATCAAGGTTACTTTATGTACTGTGAAGATATTGACCTGTGCTTGAGGCTT
AGCCTGGCTGGTGTCAGACTTCATTATGTTCCCGCTTTTCATGCGATACATTATGCTCATCATGACAATCGAAGTTTT
TTTTCAAAAGCCTTCAGATGGCACTTAAAAAGTACTTTTAGATATTTAGCCAGAAAACGTATTTTATCAAATCGCAAC
TTTGATCGAATTTCATCAGTTTTTCACCCGTAAGAGCTCGGTACCCGGGCCTAGGGTGTAGGCTGGAGCTGCTTCGAA
GTTCCTATACTTTCTAGAGAATAGGAACTTCGGAATAGGAACTAAGGAGGATATTCATATCCGTCGACGGCGGCCGC
CTGCAGGCATGCAAGCTTGATCCATATGGATCGCTAGCTTAATTAAAATAAAGCCGTAAGCATATAAGCATGGATAAGC
TATTTATACTTTAATAAGTACTTTGTATACTTATTTGCGAACATTCCAGGCCGCGAGCATTCAGCGCGGTGATCACAC
CTGACAGGAGTATGTAATGTCCAAGCAACAGATCGGCGTAGTCGGTATGGCAGTGATGGGACGCAACCTTGCGCTCAA
CATCGAAAGCCGTGGTTATACCGTCTCTATTTTCAACCGTTCCCGTGAGAAGACGGAAGAAGTGATTGCCGAAAATCC
AGGCAAGAAACTGGTTCCTTACTATACGGTGAAAGAGTTTGTCGAATCTCTGGAAACGCCTCGTCGCCATCCTGTTAAT
GGTGAAAGCAGGTGCAGGCACGGATGCTGCTATTGATTCCCTCAAACCATATCTCGATAAAGGAGACATCATCATTGA
TGGTGGTAACACCTTCTTCCAGGACACTATTCGTCGTAATCGTGAGCTTTCAGCAGGGGCTTTAACTTCATCGGTAC
GGGTGTTTCTGGCGGTGAAGAGGGGCGCTGAAAGGTCCTTCTATTATGCCTGGTGGCCAGAAAGAAGCCTATGAATT
GGTAGCACCGATCCTGACCAAAATCGCCGCCGTAGCTGAAGACGGCGAACATGCGTTACCTATATTGGTGCCGATGG
CGCAGGTCACTATGTGAAGATGGTTCACAACGGTATTGAATACGGCGATATGCAGCTGATTGCTGAAGCCTATTCTCT
GCTTAAAGGTGGCCTGAACCTCACCAACGAAGAACTGGCGCAGACCTTTACCGAGTGGAATAACGGTGAACTGAGCAG
TTACCTGATCGACATCACCAAAGATATCTTCACCAAAAAAGATGAAGACGGTAACTACCTGGTTGATGTGATCCTGGA
TGAAGCGGCTAACAAAGGTACGGGTAAATGGACCAGCCAGAGCGCGCTGGATCTCGGCGAACCGCTGTCGCTGATTAC
CGAGTCTGTGTTTGCACGTTATATCTCTTCTCTGAAAGATCAGCGTGTTGCCGCATCTAAAGTTCTCTCTGGTCCGCA
AGCACAGCCAGCAGGCGACAAGGCTGAGTTCATCGAAAAGTTCGTCGTGCGCTGTATCTGGGCAAATCGTTTCTTA
CGCCCAGGGCTTCTCTCAGCTGCGTGCTGCGTCTGAAGAGTACAACTGGGATCTGAACTACGGCGAAATCGCGAAGAT
TTTCCGTGCTGGCTGCATCATCCGTGCGCAGTTCCTGCAAAAAATCACCGATGCTTATGCCGAAAATCCACAGATCGC
TAACCTGTTGCTGGCTCCGTACTTCAAGCAAATTGCCGATGACTACCAGCAGGCGCTGCGTGATGTCGTTGCTTATGC
AGTACAGAACGGTATTCCGGTTCCGACCTTCTCCGCAGCGGTTGCCTATTACGACAGCTACCGTGCTGCTGTTCTGCC
TGCGAACCTGATCCAGGCACAGCGTGACTATTTTGGTGCGCATACTTATAAGCGTATTGATAAAGAAGGTGTGTTCCA
TACCGAATGGCTGGATTAA |

SEQ ID NO: 17 (example O18A rfb locus nucleotide sequence-O18A-EPA
production strain BVEC-L-00559)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCAGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGCCGTAGGTCGCTATGTGCTTTCTGCCGATATTGGCCGGAACTGGAACGTACTCAGCCTGGTGCATGGGGA
CGTATTCAGCTGACTGATGCTATTGCCGAGCTGGCGAAAAACAATCCGTTGATGCAATGCTGATGACCGGCGACAGT
TACGACTGCGGCAAAAAAATGGGCTATATGCAGGCGTTTGTGAAGTATGGCCTACGCAACTCGAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGTGAAAATACTTGTTACTGGTGGCGCAGGATTATTGGTTCAGCTGTAGTTCGTCACATT

| SEQUENCES |
|---|
| ATAAATAATACGCAGGATAGTGTTGTTAATGTCGATAAATTAACGTACGCCGGAAACCGGGAATCACTTGCTGATGTT |
| TCTGATTCTGAACGCTATGTTTTTGAACATGCGGATATTTGCGATGCACCTGCAATGGCACGGATTTTTGCTCAGCAT |
| CAGCCGGATGCAGTGATGCACCTGGCTGCTGAAAGCCATGTTGACCGTTCAATCACAGGCCCTGCGGCATTTATTGAA |
| ACCAATATTGTTGGTACTTATGTCCTTTTGGAAGCCGCTCGCAATTACTGGTCTGCTCTTGATAGCGACAAGAAAAT |
| AGCTTCCGTTTTCATCATATTTCTACTGACGAAGTCTATGGTGATTTGCCTCATCCAGATGAAGTAAATAATACAGAA |
| GAATTACCCTTATTTACTGAGACGACAGCTTACGCGCCAAGCAGCCCTTATTCCGCATCCAAAGCATCCAGCGATCAT |
| TTAGTCCGCGCGTGGAAACGTACATATGGTTTACCGACAATTGTGACTAATTGCTCGAACAACTATGGTCCTTATCAT |
| TTCCCGGAAAAGCTTATTCCACTGGTTATTCTTAATGCACTGGAAGGTAAGGCATTACCTATTTATGGCAAAGGAGAT |
| CAGATCCGCGACTGGTTGTATGTTGAAGATCATGCGCGTGCGTTATATACCGTCGTAACCGAAGGTAAAGCGGGTGAA |
| ACTTATAACATTGGTGGGCACAACGAAAAGAAAAACATCGATGTAGTGCTCACTATTTGTGATTTGCTGGATGAGATT |
| GTACCGAAAGAGAAATCTTATCGTGAGCAAATCACTTATGTTGCTGATCGTCCGGGACACGATCGCCGCTATGCTATT |
| GATGCTGAGAAGATTGGTCGCGCATTGGGATGGAAACCACAGGAAACGTTTGAGAGCGGGATTCGTAAAACGGTGGAA |
| TGGTACCTGTCCAATACAAAATGGGTTGATAATGTGAAAGTGGTGCCTATCAATCGTGGATTGAACAGAACTATGAG |
| GGCCGCCAGTAATGAATATCCTCCTTTTTGGCAAAACAGGGCAGGTAGGTTGGGAACTACAGCGTGCTCTGGCACCTT |
| TGGGTAATTTGATTGCTTTTGATGTTCACTCTACTGATTATTGCGGTGATTTTAGTAATCCTGAAGGTGTAGCTGAAA |
| CCGTAAGAAGCATTCGGCCGGATATTATTGTCAATGCAGCCGCTCACACCGCAGTAGACAAAGCAGAATCAGAACCGG |
| AGTTTGCACAATTAATTAACGCAACAAGTGTCGAAGCGATTGCGAAAGCAGCAAATGAAGTTGGAGCCTGGGTTATCC |
| ATTACTCGACTGATTACGTCTTCCCTGGAAATGGCGATATGCCATGGCTGGAGACGGATGCAACCGCACCACTAAATG |
| TTTACGGTGAAACCAAGTTAGCCGGAGAAAAAGCGTTACAGGAATATTGCGCGAAGCATCTTATTTTCCGGACCAGCT |
| GGGTCTATGCAGGAAAAGGAAATAACTTCGCCAAAACGATGTTACGTCTGGAAGAAAAGCGTGAAGAATTAGCGGTTA |
| TTAACGATCAGTTTGGTGCGCCAACAGGTGCTGAACTGCTGGCTGATTGTACAGCACATGCCATTCGTGTCGCACTGA |
| ATAAACCGGATGTCGCAGGCTTGTACCATTTGGTAGCCAGTGGTACCACAACCTGGTACGATTATGCTGCGCTGGTTT |
| TTGAAGAGGCGCGCAAAGCAGGCATTCCCCTTGCACTCAACAAGCTCAACGCAGTACCAACAACAGCCTATCCTACAC |
| CAGCTCGTCGTCCACATAACTCTCGCCTTAATACAGAAAAATTTCAGCAGAACTTTGCGCTTGTCTTGCCTGACTGGC |
| AGGTTGGCGTGAAACGAATGCTCAATGAATTATTTACGACTACAGCAATTTAATAGTTTTGCATCTTGTTCGTGATG |
| GTGGAGCAAGATGAATTAAAAGGAATGATGAAATGAAAATGCGTAAAGGTATTATTTTAGCGGGTGGTTCTGGTACAC |
| GTCTTTATCCTGTGACTATGGCTGTCAGTAAACAGCTATTACCTATTTATGATAAACCGATGATCTATTACCCGCTCT |
| CTACACTGATGTTGGCGGGTATTCGCGATATTTTGATTATCAGTACACCTCAGGATACTCCTCGTTTTCAACAATTGC |
| TGGGTGACGGTAGCCAGTGGGGCCTGAATCTTCAGTACAAAGTGCAACCTAGCCCAGATGGCCTCGCGCAGGCATTTA |
| TCATCGGTGAAGAGTTTATTGGTGGTGATGATTGTGCTTTGGTTCTTGGTGATAATATCTTTTACGGTCACGATCTGC |
| CGAAGCTAATGGAGGCCGCTGTTAACAAAGAAAGTGGTGCAACGGTATTTGCCTATCACGTTAATGATCCAGAACGCT |
| ATGGTGTCGTTGAGTTTGATAAAAACGGTACGGCAATCAGTCTGGAAGAAAAACCGTTAGAACCAAAGAGTAATTACG |
| CCGTTACAGGTCTGTACTTTTATGATAACGACGTGGTTCAGATGGCGAAAAACTTGAAGCCGTCTGCACGTGGTGAGT |
| TAGAAATTACAGATATTAACCGTATTTATCTTGAGCAGGGACGTCGTCGTCGCGATGATGGGCGTGGCTACGCGT |
| GGCTGGACACGGGGACTCATCAGAGTCTGATAGAAGCAAGTAATTTTATTGCGACAATTGAAGAGCGCCAGGGATTGA |
| AGGTTTCCTGTCCTGAAGAGATTGCATTTCGTAAAGGTTTTATTGATGTTGAGCATTTTTTCATAATGTAAGTGCTACCAC |
| TAATAAAGAATAATTATGGGCAGTATCTTTATAAAATGACGAAGGATTCAAATTAATGAATGTGATTAGAACTGAAAT |
| TGAAGATGTGCTAATTCTGGAGCCAAGAGTATTTGGTGATGATAGAGGTTTCTTTTATGAGAGCTTTAATCAATCAGC |
| ATTTGAACATATTCTAGGCTATCCGGTCAGCTTTGTTCAAGACAATCACTCACGTTCATCAAAAAATGTACTCAGAGG |
| CCTTCACTTTCAACGCGGCGAGTACGCACAAGATAAACTTGTACGCTGCACTCATCGAGCAGTTTTTGATGTTGCTGT |
| TGATATTCGACCCAATTCGGTATCCTTTGGTAAATGGGTTGGTGTTCTGCTTTCAGCTGATAATAAGCAGCAGTTGTG |
| GATACCAAAAGGGTTTGCTCATGGCTTTTTGGTTCTGTCTGATATCGCTGAATTTCAATATAAAACTACAAACTATTA |
| TCATCCTGAAAGCGATTGTGGAATATGTTGGAATGATGAACGCATTGCAATTGATTGGCCCCAAACATCAGGGTTAAT |
| CCTTTCGCCAAAAGATGAAAGGCTCTTTACGTTAGATGAGCTTATCAGATTAAAATTAATTGCATGAGGCCGGCCTTA |
| AGGAGGACTAGTCCCGGCGCGCCATGAGTTTAATCAAAAACAGTTTTTGGACCTTTGCGGGTATGTACTTCCAGCTA |
| TTGTGACACTACCAGCTTTGGGTATTATGGGGCGAAAATTAGGCCCCAGAATTATTTGTGTATTCACTTTGGCATTAG |
| CTGTTGTGGGTTATGCAAGCATTTTTGATGCAGGCCTTACTCGCGCAGTGATACGAGAAGTCGCAATTGAAAAAGATA |
| ATGAAGAAATAAGTTGAAAATTATTTCTTCAGCGACAGTTGTAATTATTTATTTGAGTTTGGCCGCCTCACTCTTAT |
| TATTTTTTTTAGTGGTCATATCGCATTGCTACTGAACATTAGTGAGACTTTTTTCATAATGTAAGTGCTCGTCTTA |
| AAATTCTCGCAGCATCCATACCATTATTTTTGATTACTCAAATATGGTTGTCAATTTTAGAAGGTGAAGAAAGATTTG |
| GTTTACTTAATATCTACAAATCAATTACGGGAGTGATATTAGCAATCTCACCGGCATTATTTATACTTATTAAACCCT |
| CTTTGATGTATGCGATAATAGGCTTAGTTCTAGCAAGGTTTTTATGTTTATTTTGGCTTTTATAATTTGTCACGATA |
| AAGTGCTTAAAGCTAAACTAACAATCGATATATCAACAATTAAAAGATTGTTTATGTTCGGTGGTTTGGATTACAGTAA |
| GTAATATCATCAGCCCTGTGCTATCATATTTGATAGGTTTATTGTTTCAAATCAACTTGGGGCTGCTAATGTTGCTT |
| TTTATACTGCACCATCAGAAATTATTTCTCGGCTTAGTATAATTCCAGGTCGTTTTCAAGAGCCTTATTTCCAAGAT |
| TAGCTAATGCAAATAATTCCGCTGAAAGATATAAAACGAAAAGATTAATTACAATTTCACTTTTAATAATCATCACCC |
| CTATTTTTTTGTATTGGCGTGTTATTTTCAGAGAAGATAATGTTTTATGGATAGTGGGGGCATCATTTTTTGGTGAGCCTG |
| GTTTGGTATTATCAATATTACTGATTGGCTTTATTTTAATGGATTGGCACAAGTACCATTTGCCAGTATTCAATCCC |
| GAGGTCATGCTAAGATAACTGCATTTGTTCATCTCTTAGAGTTGTTTCCTTATTTATTACTTTTATTTTACCTCATAA |
| AAGCACATGGGGTTGTTGGCGCGGGTATTGCGTGGGTCAGTGAGGATGATAGTAGATTATATAGCATTAAGTCTTTTGG |
| ACGGTAGTATATTAATAAATAAAATTCAAAATGCAAGTTAATAACTCAAGTTAATGATTCGGTGGTAGGCAATTTAT |
| AATGATATATATATTAACTTTAACTCTTCTTCTAGTTATAGCCATAATGTTTTCTCTTCTCGGCACAAAAAGTAGGAT |
| CACATCTCCATTACCTTTGCATTTTTTACCATGGTTACTAACTTTAATTGTCGGGATAAGTAATTACGATCAATTTTA |
| CGAGTTTAATGAAAGAAGCTTTTACTCTTTGTTGATTTGGTTTACAGTTATTTTTATATTTTATTTCATAGGGGAACT |
| GGTTAATTATAAACGTGAAAATATAAATGTTTATTATGGTCTTTCACATATTAAAATGAATGTAAAAATATTGGAT |
| CATTGTCATCCCAATTTCATTATATACCATTTTCGAAATATATATGGTGGATAAGGGGGAGCAGATGGATTCTTTCT |
| CAATTTACGTCTTGCAAATACATTGGAGGGCTATACGGGTAAAAATTTATCTTAATGCCTGCTGTATATCCTCTAAT |
| GATGGCTATGTTCGCAATTGTTTGTCTAACAAAAACTTCCAAATTAAATAAATACTCCATTTATTCTGGATGTTTTT |
| GTATTGTATTGGCACAATGGGAAAATTTTCAATATTAACGCCAATATTGACATATTTAATTATTTATGACTTCAAACA |
| TAGATTAAAAGTAAAAAAAACAATAAAGTTTACATTGTTGATAATTATATTAGCTTTAACTTTGCATTTTACACGTAT |
| GGCTGAGAATGACCACTCAACATTTTTATCTATTTTAGGGCTCTATATTTATTCACCAATAATTGCTTTAGGCCAGTT |
| GAATGAAGTAAAAATAGTAGTCATTTTGGTGAGTATACGTTTAGATTCATATATGCATAAATAATAAAATTGGCCTTAT |
| TAAAGAATTGCCAGTAAATACTATTCTTGACTATTCATACGTTCCTGTACCAACAAATGTATATACTGCACTTCAACC |
| ATTTTACCAGGATTTTGGTTATACTGGCATCATATTTGGAGCAGTATTATACGGACTAATATATGTGAGTTTATACAC |
| GGCCGGTGTTCGTGAAATAATACACCAGGCATTACTGATTTACGCATTGTTTTCAGTTAGCAGTGCAACGGCTTTCTT |
| CGCTGAAACGCTAGTAACGAATTTAGCTGGAAATGTGATGTTAGTATTATGTACCATCTTACTATGGCGATTTACAGT |
| AATATGCAAACCAGTACAGTAACCATTCTAATGGCCACCTACAATGGCGAGGCCTTCATCAAAAATCAGATTTTGTCA |

| SEQUENCES |
|---|
| CTACAACAACAAACATTTTCTAACTGGCGGTTATTTATTCAGGATGATGGGTCTACAGACAATACTATATCTATAATA
AAAAACTTCCAAAAATCTGACTCCAGAATTCGGCTAGTTGATGATAATTTGAAAGGTCAAGGTGCAGGAAAAAATTTT
TTATCGCTGATAAAGTACAGCGAGACAGATTATACAATTTATTGTGACCAAGATGATATTTGGTTAGAAAACAAAATA
TTTGAATTAGTAAAGTATGCAAATGAAATTAAATTGAATGTATCAGATGCGCCTTCGCTAGTTTATGCTGATGGCTAT
GCTTATATGGATGGTGAGGGTACAATCGATTTTTCTGGGATATCTAACAATCATGCTGATCAATTAAAGGATTTTCTT
TTTTTTAATGGTGGATACCAAGGATGTTCTATTATGTTCAATCGTGCAATGACCAAATTTCTTCTGAATTATCGAGGA
TTTGTATATCTACATGACGATATCACAACATTAGCTGCATACGCTCTTGGTAAAGTTTATTTTCTCCCGAAATACCTT
ATGTTATATAGACAGCACACGAATGCGGTAACTGGTATCAAAACATTCCGCAATGGATTGACTTCTAAATTTAAATCA
CCAGTAAACTATCTTTTATCACGAAAACATTATCAGGTAAAAAAATCTTTTTTTGAATGTAACAGCTCTATCTTATCA
GAGACGAATAAAAAAGTTTTTTTGGATTTTATTTCATTTGTGAATCAAATAATAAATTTACAGATTTTTTTAAGTTA
TGGCGAGGTGGGTTTAGATTAAATAACAGTAGAACTAAATTATTATTAAAATTCTTAATACGGAGAAAATTTAGCGAA
TGATTTCAATACTTACACCTACTTTTAATCGGCAACATACTTTATCAAGGCTATTCAATTCTCTTATATTACAAACTG
ATAAAGATTTTGAGTGGATAATAATTGATGATGGTAGTATAGATGCAACAGCGGTACTTGTAGAAGATTTTAGAAAAA
AATGTGATTTTGACTTGATTTATTGCTATCAGGAAAATAATGGTAAGCCCATGGCTTTAAACGCTGGTGTTAAAGCTT
GTAGAGGCGATTATATCTTTATTGTTGACAGTGATGATGCACTAACTCCCGATGCCATAAAATTAATTAAAGAATCAA
TACATGATTGCTTATCTGAGAAGGAAAGTTTCAGCGGAGTCGGTTTTAGAAAAGCATATATAAAAGGGGGATTATTG
GTAATGATTTAAATAATTCTTCAGAACATATATACTATTTAAATGCGACTGAGATTAGCAATTTAATAAATGGTGATG
TTGCATATTGTTTAAAAAAGAAAGTTTGGTAAAAAATCCATTCCCCGTATAGAAGATGAAAAATTTGTTCCAGAAT
TATATATTTGGAATAAAATAACTGACAAGGCGAAGATTCGATTTAACATAAGCAAAGTTATATATCTTTGTGAGTATC
TTGATGATGGTCTTTCTAAAAATTTCCATAACCAGCTTAAAAAATACCCAAAGGGGTTTAAGATTTATTACAAAGATC
AAAGAAAACGAGAGAAAACTTATATAAAAAAAACAAAGATGCTAATTAGATATTTGCAATGTTGTTATTATGAGAAAA
TAAAATGAAAATACTATTTGTCATTACAGGTTTAGGCCTTGGAGGTGCTGAGAAGCAGGTTTGTCTTTTAGCTGATAA
ATTAAGTTTAAGCGGGCACCATGTAAAGATTATTTCACTTGGACATATGTCTAATAATAAAGTCTTTCCTAGCGAAAA
TAATGTTAATGTCATTAATGTAAATATGTCAAAAAACATTTCTGGAGTTATAAAAGGTTGTGTCAGAATTAGAGATGT
TATAGCTAATTTCAAACCAGACATTGTACACAGTCATATGTTTCATGCAAACATTATCACTAGATTGTCTGTAATTGG
AATCAAAACAGACCTGGTATTATATCAACTGCACATAATAAAAATGAAGGTGGGTATTTCAGAATGCTCACATATAG
AATAACCGATTGTTTAAGTGATTGTTGTACAAATGTTAGCAAAGAAGCAGTGGATGAGTTTTTACGGATAAAAGCCTT
TAATCCCGCTAAAGCAATTACTATGTATAATGGGATAGATACCAATAAAATTTAAATTTGATTTATTGGCAAGGAGGGA
AATTCGAGACGGTATTAATATAAAAAATGATGATATATTATTACTTGCTGCAGGTCGTTTAACGTTAGCTAAAGATTA
TCCTAATTTATTGAATGCAATGACTCTGCTTCCTGAACACTTTAAACTTATTATTATTGGTGATGGTGAATTGCGTGA
CGAAATTAATATGCTTATAAAAAAATTGCAATTATCTAATAGGGTGTCCTTGTTGGGAGTTAAAAAAAATATTGCTCC
CTATTTTTCTGCATGTGATATTTTTGTTCTCTCTTCTCGTTGGGAAGGATTTGGATTAGTCGTGGCAGAAGCTATGTC
ATGTGAGCGAATTGTTGTTGGCACGGATTCAGGGGGAGTAAGAGAAGTTATTGGTGACGATGATTTTCTTGTACCCAT
ATCTGATTCAACACAACTTGCAAGCAAATTGAAAAATTGTCTTTGAGCCAGATACGTGATCACATTGGTTTTCGGAA
TCGTGAGCGTATTTAAAAAATTTCTCAATAGATACTATTATTATGCAGTGGCAAGAACTCTATGGAACTATAATTTG
CTCAAAACATGAAAGGTAGATTTATATTTGGAACGTGTCTTTTGTTTGAATTTAATTCAATCTCAATTGAGATTTTTG
TATTTCAAAAATACCATCATAGCTAACGATGATTGGTATTTATTTTAAGATGCTTTCTATAAATATATTGACGTTTTT
AATGCGCCGAAACGATTGGGCTGGGAACAGAGAAGTAAAACTGTTTTGAGAATGAAGAGTTTTTGAGATGTTTATGGA
TATTAAAAATTGATCCAGTGAATTAATTATTTATAATAAATCAAGATTTAATGTTAATAAATGATAATCTTTTCTGAC
ACTCATATTATTATGAGTGGTACGTTTGGTAAACGGTAAACTATTATATGACAGCTAGAACAACTAAAGTTTTGCAC
TTACAATTACTCCCACTCTTAAGTGGCGTTCAAAGGGTAACATTAAACGAAATTAGTGCGTTATATACTGATTATGAT
TATACACTAGTTTGCTCAAAAAAAGGTCCACTAACAAAAGCATTGCTGGAATATGATGTCGATTGTCATTGTATCCCC
GAACTTACGAGAGAAATTACCGTAAAGAATGATTTTAAAGCATTGTTCAAGCTTTATAAGTTCATAAAAAAAAGAAAAA
TTTGACATTGTGCATACACATTCTTCAAAAACAGGTATTTTGGGGCGAGTTGCTGCCAAATTAGCACGTGTTGGAAAG
GTGATCCACACTGTACATGGTTTTTCTTTTCCAGCCGCATCTAGTAAAAAAAGTTATTACCTTTATTTTTTCATGGAA
TGGATAGCAAAGTTCTTTACGGATAAGTTAATCGTCTTGAATGTAGATGATGAATATATAGCAATAAACAAATTAAAA
TTCAAGCGGGATAAAGTTTTTTTAATTCCTAATGGAGTAGACACTGATAAGTTTTCTCCTTTAGAAAATAAAATTTAT
AGTAGCACCTTGAATCTAGTAATGGTTGGTAGATTATCCAAGCAAAAAGATCCTGAGACATTATTGCTTGCTGTTGAA
AAACTGCTGAATGAAATGTTAATGTTAAGCTGACACTTGTAGGAGATGGTGAACTAAAAGAACAGTTAGAAAGCAGG
TTCAAACGGCAAGATGGACGTATAATTTTTCATGGATGGTCAGATAACATTGTTAATATTTTAAAAGTTAATGATCTT
TTTATATTACCTTCTCTTTGGGAGGGTATGCCATTAGCAATTTTAGAAGCATTGAGCTGTGGACTTCCATGTATAGTC
ACTAATATTCCAGGTAATAATAGCTTAATAGAAGATGGCTATAATGGTTGTTTGTTTGAAATTAGAGATTGTCAGTTA
TTATCTCAAAAAATCATGTCATATGTTGGTAAGCCAGAACTGATTGCACAGCAATCTACCAATGCACGATCATTTATT
CTGAAAAATTATGGATTAGTTAAAAGAAATAATAAGGTCAGACAGCTATATGATAATTAAGAGCTCGGTACCCGGGCC
TAGGGTGTAGGCTGGAGCTGCTTCGAAGTTCCTATACTTTCTAGAGAATAGGAACTTCGGAATAGGAACTAAGGAGGA
TATTCATATCCGTCGACGGCGGCCGCCCTGCAGGCATGCAAGCTTGATCCATATGGATCGCTAGCTTAATTAAATAAA
GCCGTAAGCATATAAGCATGGATAAGCTATTTATACTTTAATAAGTACTTTGTATACTTTTATTTGCGAACATTCCAGGC
CGCGAGCATTCAGCGCGGTGATCACACCTGACAGGAGTATGTAATGTCCAAGCAACAGATCGGCGTAGTCGGTATGGC
AGTGATGGGACGCAACCTTGCGCTCAACATCGAAAGCCGTGGTTATACCGTCTCTATTTTCAACCGTTCCCGTGAGAA
GACGGAAGAAGTGATTGCCGAAAATCCAGGCAAGAAACTGGTTCCTTACTATACGGTGAAAGAGTTTGTCGAATCTCT
GGAAACGCCTCGTCGCATCCTGTTAATGGTGAAAGCAGGTGCAGGCACGGATCGTGCTGCTATTGATTCCCTCAAACCATA
TCTCGATAAAGGAGACATCATCATTGATGGTGGTAACACCTTCTTCCAGGACACTATTCGTCGTAATCGTGAGCTTTC
AGCAGAGGGCTTTAACTTCATCGGTACCGGTGTTTCTGGCGGTGAAGAGGGGGCGCTGAAAGGTCCTTCTATTATGCC
TGGTGGCCAGAAAGAAGCCTATGAATTGGTAGCACCGATCCTGACCAAAATCGCCGCCGTAGCTGAAGACGGTGAACC
ATGCGTTACCTATATTGGTGCCGATGGCGCAGGTCACTATGTGAAGATGGTTCACAACGGTATTGAATACGGCGATAT
GCAGCTGATTGCTGAAGCCTATTCTCTGCTTAAAGGTGGCCTGAACCTCACCAACGAAGAACTGGCGCAGACCTTTAC
CGAGTGGAATAACGGTGAACTGAGCAGTTACCTGATCGACATCACCAAAGATATCTTCACCAAAAAGATGAAGACGG
TAACTACCTGGTTGATGTGATCCTGGATGAAGCGGCTAACAAAGGTACGGGTAAATGGACCAGCCAGAGCGCGCTGGA
TCTCGGCGAACCGCTGTCGCTGATTACCGAGTCTGTGTTTGCACGTTATATCTCTTCTCTGAAAGATCAGCGTGTTGC
CGCATCTAAAGTTCTCTCTGGTCCGCAAGCACAGCCAGCAGGCGACAAGGCTGAGTTCATCGAAAAAGTTCGTCGTGC
GCTGTATCTGGGCAAATCGTTTCTTACGCCCAGGGCTTCTCTCAGCTGCTGCGTCTGAAGAGTACAACTGGGA
TCTGAACTACGGCGAAATCGCGAAGATTTTCCGTGCTGGCTGCATCATCCGTGCTGCTTCCTGCAAAAAATCACCGA
TGCTTATGCCGAAAATCCACAGATCGCTAACCTGTTGCTGGCTCCGTACTTCAAGCAAATTGCCGATGACTACCAGCA
GGCGCTGCGTGATGTCGTTGCTTATGCAGTACAGAACGGTATTCCGGTTCCGACCTTCTCCGCAGCGGTTGCCTATTA
CGACAGCTACCGTGCTGCTGTTCTGCCTGCGAACCTGATCCAGGCACAGCGTGACTATTTTGGTGCGCATACTTATAA
GCGTATTGATAAAGAAGGTGTGTTCCATACCGAATGGCTGGATTAA |

SEQ ID NO: 18 (example O25B rfb locus nucleotide sequence-O25B-EPA production strain stGVXN4459)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCAGTGAAGATACTTGTTACTGGTGGCGCAGGATTTATTGGTTCTGCTGTTGTTCG
TCACATAATAAATAACGCAAGATAGTGTTGTTAATGTCGATAAATTAACATGCCGGAAACCTGGAATCACTTGC
AGATGTTTCTGATTCTGAACGCTATTTCTTTGAACATGCGGATATTTGTGATGCAGCTGCAATGGCACGGATTTTTGC
TCAGCATCAGCCGGATGCAGTGATGCACCTGGCAGCTGAAAGCCATGTTGACCGTTCAATTACAGGCCCTGCGGCATT
TATTGAAACCAATATTGTGGGTACTTATGTCCTTTTAGAAGCGGCTCGGAATTATTGGTCTGGTCTGGATGATGAAAA
GAAAAAAAACTTCCGTTTTCATCATATTTCTACTGATGAGGTGTATGGTGACTTACCCCATCCGGATGAAGTAAATAG
CAATGAAACGTTGCCGCTATTTACGGAAACGACAGCATACGCGCAAGTAGTCCATATTCTGCTTCTAAAGCTTCCAG
CGATCATTTGGTTCGCGCATGGAAACGTACTTATGGTTTACCGACCATTGTGACTAATTGCTCGAACAACTATGGTCC
TTATCATTTCCCGGAAAAGCTTATTCCACTGGTTATTCTTAATTCACTGGAAGGTAAGGCATTACCTATTTATGGCAA
AGGAGATCAGATCCGCGACTGGTTGTATGTAGAGGATCATGCTCGAGCGTTATATACCGTCGTAACCGAAGGTAAAGC
GGGCGAAACTTATAACATTGGTGGACACAACGAAAAGAAAAACATCGACGTAGTGTTCACTATTTGTGATTGTTGGA
TGAGATAGTCCCGAAAGAGAAATCTTACCGCGAGCAAATTACTTATGTTACCGATCGTCCGGGACACGATCGCCGTTA
TGCGATTGATGCTGAGAAGATTGGTCGCGAATTGGGATGGAAACCACAGGAAACGTTTGAGAGTGGGATTCGTAAAAC
GGTGGAATGGTACCTGTCCAATACAAAATGGGTTGATAATGTGAAAAGTGGTGCCTATCAATCGTGGATTGAACAGAA
CTATGAGGGCCGCCAGTAATGAATATCCTCCTTTTTGGCAAAACAGGGCAGGTAGGTTGGGAACTACAGCGTGCTCTG
GCACCTCTGGGTAATTTGATTGCTCTTGATGTTCACTCCACTGATTACTGTGGTGATTTTAGTAATCCTGAAGGTGTA
GCTGAAACCGTAAGAAGCATTCGGCCTGATATTATTGTCAACGCAGCCGCTCACACCGCAGTAGACAAAGCAGAATCA
GAACCGAAGTTTGCACAATTACTGAACGCGACGAGTGTCGAAGCGATCGCGAAAGCAGCCAATGAAGTCGGCGCCTGG
GTTATTCACTACTCTACTGACTACGTATTTCCGGGGACCGGTGAAATACCATGGCAGGAGGAGGATGCAACCGCACCG
CTAAATGTTTACGGTGAAACCAAGTTAGCGGGAGAAAAAGCATTACAAGAGCATTGTGCGAAGCACCTTATTTTCCGG
ACCAGCTGGGTCTATGCAGGTAAAGGAAATAACTTCGCCAAAACAATGTTGCGTCTGGCAAAAGAGCGTGAAGAATTA
GCCGTTATTAATGATCAGTTTGGTGCGCCAACTGGCGCAGAGTTACTGGCTGATTGTACGGCACATGCTATTCGTGTG
GCACTGAATAAACCGGAAGTCGCAGGCTTGTACCATCTGGTAGCTAGTGGTACCACACGTGGCACGATTATGCTGCG
CTGGTTTTTGAAGAGGCGCGCAAAGCAGGCATTCCCCTTGCACTCAACAAGCTCAACGCAGTACCAACAACAGCCTAT
CCTACACCAGCTCGTCGTCCACATAACTCTCGCCTTAATACAGAAAATTTCAGCAGAACTTTGCGCTTGTCTTGCCT
GACTGGCAGGTTGGCGTGAAACGAATGCTTAACGAATTATTTACGACTACAGCAATTTAATAGTTTTTGCATCTTGTT
CGTAATGGTGGAGCAAGATGTATTAAAAGGAGTATTGAAATGAAAACGTTGTCTCGCTATGATGGGGCGTGGC
TATGCATGGCTGGATACAGGGACGCATCAAAGTCTTATTGAAGCAAGCAACTTCATTGCCACCATTGAAGAGCGCCAG
GGACTAAAGGTTTCCTGTCCGGAAGAAATTGCTTATCGTAAAGGGTTTATTGATGCTGAGCAGGTAAAGTATTAGCC
GAACCGTTGAAGAAAATGCTTATGGTCAGTATCTGCTCAAAATGATTAAAGGTTATTAATAAGATGAACGTAATTAA
AACTGAAATTCCTGATGTGCTGATTTTTGAACCAAAAGTTTTTGGGATTGAACGTGGCTTCTTTTTGAGAGTTTTAA
TCAGAGGATTTTTGAAGAAGCAGTAGGTCGTAAGGTTGAGTTTGTTCAGGATAACCATTCTAAGTCCAGTAAAGGTGT
TTTACGTGGTCTTCATTATCAGTTAGAACCTTATGCTCAAGGAAAACTGGTGCGCTGTGTTGTTGGCGAGGTTTTTGA
TGTTGCGGTTGATATTCGTAAATCGTCACCTACATTTGGGAAATGGGTTGGGGGTGAATTTGTCTGCTGAGAATAAGCG
TCAGTTGTGGATTCCTGAGGGATTTGCACATGGTTTTTTGGTGCTGAGTGATTTAGCAGAAGTTTTATATAAAACGAA
TCAATATTATGCTCCATCACATGAAAAAAATATTATATGGAATGACCTCTTGCTTAATATTTAAATGGCCGAGCACAGC
ACTGATCACTCTGTCTGATAAGGATGCAAATGGGGAAAGATTTGAACTAAGTGAGTTTTGAAATGTCTCTCTTAAAAC
ATAGTATATGGAATGTTGCGGGCTACTTTATACCAACATTAATTGCAATTCCCGCCTTTGGATTAATTGCGAGGAAAA
TTGGTGTAGAACTATTTGGTTTGTATACGTTAGCAATGATTTTTATAGGGTATGCAAGTATATTTGATGCTGGGTTAA
CAAGAGCTGTTGTGCGTGAAATAGCATTACTAAAAAACAGAGTGGACGATTGTAATACGATAATAGTAACTTCTATTA
TCGCTGTGATATTTTAGGGTTTATCGGAGGCGGGGAGTGTTTCTGCTTAAAGGCGATATTATTGAACTGTTAAATA
TCTCACCAATATATTACGCCGATTCGATAAAGTCTCTAGTATTATTATCATCTCTGATACCTGTATTCTTAGTCACGC
AAATACTATTAGCAGAGCTTGAGGGTCGGGAATATTTTGGGATTCTAAATATACAAAAAAGTGTAGGGAATTCTTTAA
TTGCAGGGTTACCTGCATTATTTGTTTTAATTAATCAAACGCTTTTTTCTGCAATTATTGGTGTAGCGATTGCAAGAG
TTATATGCTTGTGGTTAAGCTACATTATGAGCAGGGAAAGAATAACTATCGATATCTCATTTTTTCAATAACTGTTT
TAAAGCGGTTATTTAGATATGGCGGGTGGGTAACTATAAGTAACATAATATCTCCTATATTAGCGAGTATGGATAGAT
TTATTCTATCCCATATCCAGGGAGCATCAAAAATATCATTCTATACAGTCCCTAATGAGCTGGTAACTAGGCTTGGAA
TAGTTCCAGGCTCTCTTGGGAAAGCTGTTTTTCCAAAATTAAGTCATGCAAGGAATTTTACAGCGTCATATGCAGAGC
AAAAAAAAGCTTATATATTAATGACTGTCATTGTAATGCCTTTGGTTTTATTTGTATATTATTACGCAAAGTTTATTT
TAACATTGTGGATGGGGGCTGAGTATGCAGGGATTTCGGTCGAAATATTACGGATTATGCTTATAGGGTATATTTTA
ACTGTTATTCACAAATCTCTTTTGCCAACATACAGGCCTTTGGAAAAGCAAAATACACTGCATACATCCATATGATGG -continued

| SEQUENCES |
|---|
| AATTTATTCCTTATTTGATAATGTTATATATAATTTCAAAGGAATATGGGGTTATTGGTGTTGCGTGGTTATGGACAA |
| TTCGAGTAATAATTGATTTTTTGATGCTTTTATATATGAGTTATCGTTGTAATAATCTTATGAAAAAAGGGTAGCCTG |
| ATGATATATATTGTGGTATTAAATTGGAATGGGGCTATAGATACCATTAATTGTGTTAAAAGTTTAATGGATTTAAAT |
| GTTAGCGATTATAAAATTATCATTGTTGATAACTGTTCTATGGATAACTCATATGATACTATAAAAGAAAATCTTAAT |
| TCATTATATATTGCTGATAAAAGTATCATTGAGGTGAAGTATGAGGATAGAAATAAATATAAAACCTTAGAAAACGAT |
| AAAATCATATTAATACAATCTCCGCAAAATAATGGGTACGCAAGTGGTAATAATATTGGCATAGAGTTCGCTCTTAAT |
| CAGGAGAATATGAAATACGTCTGGGTTCTGAATAATGATACTGAAGTGGATAAAGAGGCTTTAACTCATTTAATTAGT |
| AAATGTGATTCAGATAAAAGTATAGGGATTTGCGGTTCTCGTTTAGTCTATTTTGCCGACAGAGAGATGCAGCAAGGA |
| CTAGGTGGGGTGCATAACAAATGGTTATGCACTACAAAAAATTATGAAATGGGAAGATTAGTTTCCAAAAAATATGAT |
| GATGAAGTCATTAGTAATGATATAGATTATATAATTGGCGCATCGATGTTTTCTCTAGAGAATGTTTGGAAACAGTT |
| GGATTGATGAATGAAGAATATTTTTTATACTATGAAGAGTTAGATATTTGCCTCAGAGCAAAAGCAAAGAACTTTAAA |
| TTAGGTATTTGCTCAGAAAGTTTGGTTTATCATAAAATAGGTGCAAGTACTGATGGGGGAAAGAGCATGATGGCTGAT |
| CTTTGCTCAATAAAAAATAGGCTGGTCATTACAGAAAGGTTTTATCCCCAATATTATTGGACGGTATGGTTGTCACTT |
| TTTGTTGTAGCATTTAACCGTGCTAGAAGAGGTGAGTTTAATAAGATGAAAAGATGTTTGAATGTTATGTTTAACTTC |
| AAACGAAACAAAGGTAGCAAATGCCATTAGAATATGCACTTAATCATGGTGTTAATAAATCTATAGTTTGATATGTTA |
| TTAAAGGGTATTTAATGAAAGTGGCTTTTTTATCTGCTTATGATCCACTATCTACATCCAGTTGGTCTGGCACACCTT |
| ATTATATGCTAAAGGCATTATCGAAGAGAAATATTTCCATTGAAATATTAGGACCGGTCAAATAGCTATATGATATACA |
| TGTTAAAAGTATATAAATTAATATTAAGGTGTTTCGGAAAAGAATATGATTATAGTCATTCGAAGTTGCTTTCCAGGT |
| ATTACGGTAGAATATTCGGTAGGAAATTAAAAAAAATTGATGGTTTGGATTTTATTATCGCACCTGCAGGTTCCTCAC |
| AAATTGCTTTTTTAAAAACAACCATACCAATAATATATCTATCGGATACAACATATGATCAATTAAAAAGCTATTATC |
| CGAATTTAAATAAAAAAACAATTATAAATGATGAGGATGCAAGTTTAATCGAACGCAAGGCTATTGAAAAAGCAACAG |
| TAGTATCTTTCCCATCTAAATGGGCAATGGATTTTTGCAGGAATTATTACAGATTAGATTTTGATAAATTAGTTGAAA |
| TACCATGGGGGCTAATTTATTTGATGATATTCACTTTGCTAATAAAAATATAATTCAAAAGAATAGTTATACTTGTC |
| TTTTCTTGGGAGTTGATTGGGAAAGAAAAGGTGGGAAAACAGCCTTGAAAGCAATTGAATATGTAAGGCAGTTATATG |
| GGATCGATGTTAGACTAAAAATTTGTGGATGTACTCCGAATCAAAAGATTTTACCTACTTGGGTTGAATTAATTGATA |
| AAGTAGATAAAAATAACGTTGACGAATATCAGAAATTCATCGATGTGTTATCTAACGCTGATATACTTCTTTTACCAA |
| CCATTGCTGAATGTTATGGAATGGTATTTTGTGAAGCTGCTGCTTTTGGATTGCCTGTTGTCGCTACAGATACAGGTG |
| GAGTCAGTTCTATAGTTATCAACGAAAGGACGGGGATATTATTAAGACCCGTTAGACTATAAGCACTTTGGAAATG |
| CAATTCATAAAATAATTAGTTCCGTAGAGACTTATCAAAACTACTCCCAAAACGCAAGAATTAGATATAATAATATAT |
| TGCATTGGGACAATGGGCTAAAAAGATAATTGAGATTATGTATGAGCATAAGAATAGAAGAATCAAATAGCACAAAA |
| AGAATTATATGTTTATTTATACTTTTTCTTGTTTCCCTGATTTTTTGTTTTATACATTAGGGGTTGATAATTTTAGC |
| ATTTCAACGATAATCTCAATTACATTGCTTTTTGTTTTTTTAAGAGCTAAAAATATTTGCAAAGATAATTTTCTAATA |
| ATAGTAGCGTTATTCATATTGTTGTGTTTTAACTGTTTGTTAAGTATGCTATTTAATATTGAACAGGCTTTAACATTT |
| AAAGTTGTACTTTCAATATATAGCATCTTAATAATGGCATACGTCTCCTCTTGTTATGCACAGACGTTGTGGTTATGT |
| TCTGAAGAAATACTTAAGAGATCCGTCTTTTATTTGTTCGCATTTCTTTGCCTTATTGGCATTATAAGTATTCTTTTA |
| CAGAAGACTGAGATTATACATGATAAAAGTATGATTCTTTTTCCTGAACCATCAGCATTTGCATTGGTTTTTATACCT |
| ATCTTTTCATTTTGTTTATACTATACAAGAGGGGGGGGCTACTATTGCTCTATATATTATCTTTGGGTATTGCGTTA |
| GGTATCCAGAATTTAACAATGTTGGTAGGCATTGTGATTAGTGTTTTTGTGATGAAAAAAATAACTATAAGGCAAACT |
| ATTGTTATACTTTTGGGGGCATGGATTTTTTCCATGATATTAAGTGATTTAGACATTTCTTACTATACATCGCGGCTT |
| GATTTTAAAAATACTACGAACCTATCAGTGCTTGTATATCTTTCAGGAATTGAAAGAGCTTTCTTGAATTTTATTACA |
| AGTTATGGTCTTGGTATTGGTTTTCAACAAATGGGAGTGAATGGGGAGATAGGAATATATCAACAATTTTAGCTGAA |
| CTTGATGCCCCTATGTTAAATATATACGATGGCTCATTTATTTCTTCTAAGTTAATATCTGAGTTTGGGGTTATTGGT |
| GCATTAATGTGTATTTTCTATTTTTTTATTTTTCCCGATTTTATCTGCGTTTCAAAAAAAGTAAGAGATATTCACCG |
| CAGTATATTTTAGCATATAGCTTCTACATGTGTTTCTTCATCCCTCTTTTTATACGTGGTGCTGGTTATATAAACCCC |
| TATGTGTTTATGTTATTTTCATCAATATTTTTGTGCAAATATCACGCTAAAATCTTTGATGAAATCTAATGTCCAG |
| ATAGCTATATAATAGTAGATTATATTATCATTATCACGTAAATTACATATTAATAGCATATATGATAACTAGGACATA |
| AATAATGTGCATTAAAAAAAAACTTAAGTTAATTAAACGATATGGCCTTTATGGTGGTCTTAGGCTTCTTAAAGATAT |
| ATTCTTAACAAAATTTTTATTTTGTTCAAATGTTAGGATTATTAGATTTCCATGTTATATTAGAAAAGATGGAAGTGT |
| TAGTTTTGGAAAAGGTTTTACATCAGGTGTAGGATTACGAGTTGATGCCGTAGTTTCCATTGGAGA |
| AAATGTTCAAATTAATGACTATGTTCACATCGCGGCTATTAATAATGTCATTATTGGTAGAGATACATTAATAGCAAG |
| TAAAGTATTTATTAGTGATCATAATCATGGTATTTTTCTAAATCCGATATCCATAGTTCACCAACTATTATTCCTTC |
| GTCTAGGCCCCTTGAATCTGCACCTGTGTATATTGGAGAGCGTGTGTGGATTGCGAAAATGTGACAATATTACCAGG |
| TGCGTGTATAGGTAATGGTGTAGTTATTGGCGCAAACAGTGTTGTTGTGGTGAGATTCCTAATAATGTGATCATTGC |
| TGGTGTTCCAGCTAAAATTGTTAAAAAATATAACTATGAGCGTATGCAATGGGAAAGAATATAGTTGTAATATCGGCT |
| GTTAATTTTACAACCGGAGGCCCCTTTACCGTACTAAAAAATGTGCTTACAGCAACTAAAGATAGAGCCGAATGTAAA |
| TTTATTGCACTGGTTCATAGCTCTGCTGAACTAATGGAATTATTTCCGTGGGTTGAATTTATAGAGTATCCAGAAGTC |
| AAGTCTTCGTGGGTTAAAAGATTATATTTCGAATATATAACTTGCAATAGATTATCTAAGGTGATTAAGGCAACTCAT |
| TGGGTATGCTTACATGATATTACAGCAAATGTTAGTGTACCCTATAGATTTGTTATTGCCACAATCCTGCACCGTTC |
| TATAAATATTTAAGCTATCGAGATATTATAGGAGAACCTAAATTTATCTTTTTTATCTTTTTTATGGGCTTTTATAC |
| AATATCAATATAAAAAGAACACAGCAGTTTTTGTTCAGCAGCAGTGGCTAAAAAAGAATTCGAAAAAAAATATAAG |
| TTAAAGAATGTTGTTGGTTAGTCGCCCTGAAGATATTTGCCCTTTTGAAAGTGATTGGTTTGGTAAGAAATAATAATAAA |
| AAGGATGTGAGGATATTTTACCCAGCAGTGCCCCGTATATTTAAAAACTTTGAAGTTATCATACGTGCTGCACAAATA |
| TTACAAGATAAAAATATTCATTTTTATCTTACTTTTGATGGTACTGAAAATAAGTATGCAAAAAGAATATATAAATTA |
| GCTTCCGAACTGAAAAATGTACATTTCCTCGGTTACCTTAATGCAACCGAGATGGTTAACTTTTATCAAGATTCAGAT |
| ATTATTTGTTTCCCATCGAAACTAGAAACGTGGGGATTACCATTATCAGAAGCTAAAACATACAAAAATGGATATTT |
| GCGGCAGACTTACCTTATGCTCATGAAGTTTTATATAACTATTCAAATAGATATTTTCCATTTGACGATGAGAAA |
| ATACTTGTTCGCTACATATTAGAGTACACAAGTAAAAATATGCATGAAGATATAAAAAATAGTAGGGTGAATTTTAAT |
| AATGATGCATTGACTGGTTTTGAACAGTTTATTGAATATATCCTCAAGGGGAACTGACGTGGTTTATATTATAATCGT |
| TTCACATGGCCATGATGACTATATAGAAATCTTTTATTAAATTTAAAGTTGCCCTCTGGAAGATTTAAAATAATAGT |
| TCGTGATAACAAAGTTCAATGGTTTTAAAAAAAACATGCGAAAAAATTGCGTAACCTATTTGCATGGAGGGCAATA |
| TGGATTTGGACATAATAATAACATAGCAGTGTCATATATAATTAATAACTTCATGATTATGAATATGATTATTTTCT |
| CTTTCTTAACCCCGATGTATTCATAACCAGTGAAAGTTTGATTAATTATGTTGATTATATAATTAGTAATGATTATAA |
| GTTTAGCACATTATGTCTTTATCGAGATTTTACTAAAAGCAAACATGATTATTCAATACGGAGTTTTCCAACTTTATA |
| TGATTTTCTTGTTCTTTTTATTGGGGGTGAATAAAAGTAAAATTAAGAAGGAAAATATACTTTCTGATACTGTAGT |
| TGATTGGTGTGCTGGCTCATTTATGCTTATTCATGCTTTAAGTTTCTTAAATGTGAATGGTTTTGATCAAAAATATTT |
| TATGTATTGTGAAGATATTGACCTTTGTATGCGTTTAAAATTAAGTGGAGTAGATCTTTACTATACTCCCCATTTTGA |
| TGCTATTCATTATGCGCAGCATGAAAATAGAAGAATATTTACTAAAGCATTTCGATGGCATATAAGGAGTATTACGCG |

-continued

| SEQUENCES |
|---|
| CTACATATTACGGAAACCAATTCTTTCTTATAAAAACTATAGAAAAATTACATCCGAACTGGTAAAGTGATTAAGGAT
CCGTGTAGGCTGGAGCTGCTTCGAAGTTCCTATACTTTCTAGAGAATAGGAACTTCGGAATAGGAACTAAGGAGGATA
TTCATATGGATAAAGCCGTAAGCATATAAGCATGGATAAGCTATTTATACTTTAATAAGTACTTTGTATACTTATTTG
CGAACATTCCAGGCCGCGAGCATTCAGCGCGGTGATCACACCTGACAGGAGTATGTAATGTCCAAGCAACAGATCGGC
GTAGTCGGTATGGCAGTGATGGGACGCAACCTTGCGCTCAACATCGAAAGCCGTGGTTATACCGTCTCTATTTTCAAC
CGTTCCCGTGAGAAGACGGAAGAAGTGATTGCCGAAAATCCAGGCAAGAAACTGGTTCCTTACTATACGGTGAAAGAG
TTTGTCGAATCTCTGGAAACGCCTCGTCGCATCCTGTTAATGGTGAAAGCAGGTGCAGGCACGGATGCTGCTATTGAT
TCCCTCAAACCATATCTCGATAAAGGAGACATCATCATTGATGGTGGTAACACCTTCTTCCAGGACACTATTCGTCGT
AATCGTGAGCTTTCAGCAGAGGGCTTTAACTTCATCGGTACCGGTGTTTCTGGCGGTGAAGAGGGGGCGCTGAAAGGT
CCTTCTATTATGCCTGGTGGCCAGAAAGAAGCCTATGAATTGGTAGCACCGATCCTGACCAAAATCGCCGCCGTAGCT
GAAGACGGTGAACCATGCGTTACCTATATTGGTGCCGATGGCGCAGGTCACTATGTGAAGATGGTTCACAACGGTATT
GAATACGGCGATATGCAGCTGATTGCTGAAGCCTATTCTCTGCTTAAAGGTGGCCTGAACCTCACCAACGAAGAACTG
GCGCAGACCTTTACCGAGTGGAATAACGGTGAACTGAGCAGTTACCTGATCGACATCACCAAAGATATCTTCACCAAA
AAAGATGAAGACGGTAACTACCTGGTTGATGTGATCCTGGATGAAGCGGCTAACAAAGGTACCGGTAAATGGACCAGC
CAGAGCGCGCTGGATCTCGGCGAACCGCTGTCGCTGATTACCGAGTCTGTGTTTGCACGTTATATCTCTTCTCTGAAA
GATCAGCGTGTTGCCGGCATCTAAAGTTCTCTCTGGTCCGCAAGCACAGCCAGCAGGCGACAAGGCTGAGTTCATCGAA
AAAGTTCGTCGTCGCTGTATCTGGGCAAAATCGTTTCTTACGCCCAGGGCTTCTCTCAGCTGCGTGCTGCGTCTGAA
GAGTACAACTGGGATCTGAACTACGGCGAAATCGCGAAGATTTTCCGTGCTGGCTGCATCATCCGTGCGCAGTTCCTG
CAGAAAATCACCGATGCTTATGCCGAAAATCCACAGATCGCTAACCTGTTGCTGGCTCCGTACTTCAAGCAAATTGCC
GATGACTACCAGCAGGCGCTGCGTGATGTCGTTGCTTATGCAGTACAGAACGGTATTCCGGTTCCGACCTTCTCCGCA
GCGGTTGCCTATTACGACAGCTACCGTGCTGCTGTTCTGCCTGCGAACCTGATCCAGGCACAGCGTGACTATTTTGGT
GCGCATACTTATAAGCGTATTGATAAAGAAGGTGTGTTCCATACCGAATGGCTGGATTAA |

SEQ ID NO: 19 (example 075 rfb locus nucleotide sequence-075-EPA
production strain stLMTB11737)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCATCTTCACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCACCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTTCTGGTAGCTGT
AAAGCCAGGGGCGGTAGCGTGCATTAATACCTCTATTAATCAAACTGAGAGCGCCGCTTATTTCACAGCATGCTCTGAAG
TAATATGGAATAAATTAAGCTAGCAGTGAAGATACTTGTTACTGGTGGCGCAGGATTTATTGGTTCTGCTGTTGTTCG
TCACATAATAAATAATACGCAAGATAGTGTTGTTAATGTCGATAAATTAACATACGCCGGAAACCTGGAATGCTCGC
TGAAATTTCTGATTCTGAACGTTATTCATTTGAGCATGCAGATATCTGCGATGCCGAAGCGATGGCTCGTATTTTCGC
ACAGCACCAGCCAGACGCGGTGATGCACCTGGCAGCAGAGAGCCACGTTGACCGCTCAATAACTGGCCCTGCGGCATT
TATTGAAACCAATATTGTGGGTACTTATGTTCTTTTAGAAGCGGCGCAATTATTGGTCTGGTCTGGATGATGAAAA
GAAAAAAAACTTCCGCTTTCATCATATTTCTACTGATGAGGTGTATGGTGACTTACCCCATCCGGATGAAGTAAATAG
CAATGAAACGTTGCCGCTATTTACGGAAATGACAGCATACGCGCCAAGTAGTCCATATTCTGCTTCTAAAGCTTCCAG
CGATCATTTGGTTCGCGCATGGAAACGTATTATGGTTTACCGACCATTGCTGCTAATTGCTCGAACAACTATGCTCC
TTATCATTTCCCGGAAAAGCTTATTCCACTGGTTATTCTTAATGCACTGGAAGGTAAGGCATTACCTATTTATGGCAA
AGGAGATCAGATCCGCGACTGGTTGTATGTAGAGGATCATGCTGAGCGTTATATACCGTCGTAACCGAAGGTAAAGC
GGGCGAAACTTATAACATTGGTGGACACAACGAAAAGAAAAACATCGACGTAGTGTTCACTATTGTGATTTGTTGGA
TGAGATAGTCCCGAAAGAGAAATCTTATCGTGAGCAAATTACCTATTGTGCTGCCCCAGGGCATGATGCCGGTTA
TGCAATTGATGCCGATAAAATTAGCCGCGAATTGGGCTGGAAACCACAGGAAACGTTTGAGAGCGGGATTCGTAAAAC
TGTGGAATGGTATCTGTCCAATACAAAATGGGTTGATAATGTGAAAGTGGTGCCTATCAATCGTGGATTGAACAGAA
CTATGGGGGCCGCCACTAATGAATATCCTCCTTTTTGGCAAAACAGGGCAGGTTGGTTGGGAACTACAGCGTGCTCTG
GCACCTCTGGGTAATTTGATTGCTCTTGATGTTCACTCCACTGATTACTGTGGTGATTTTTAGTAACCCTGAAGGTGTG
GCTGAAACCGTTAGAAGCATTCGGCCTGATATTATTGTCAACGCAGCCGCTCACACCGCAGTAGACAAAGCAGAATCA
GAACCGGAGTTTGCACAATTACTGAACGCGACGAGTGTCGAAGCGATCGCGAAAGCAGCCAATGAAGTCGGCGCTTGG
GTTATTCACTACTCTACTGACTACGTATTTCCGGGGACCGGTGAAATACCATGGCAGGAGGAGGATGCAACCGCACCG
CTAAATGTTTACGGTGAAACCAAGTTAGCAGGAGAAAAAGCATTACAAGAGCATTGTGGCGAAGCACCTTATTTCCGG
ACCAGCTGGGTCTATCAGGTAAAGGAAATAACTTCGCCAAAACGATGTTGCGTCTGGCAAAGAGCGTGAAGAATTA
GCCGTTATTAATGATCAGTTTGGTGCGCCAACTGGCGCAGAGTTGCTGGCTGATTGTACGGCACATGCCATTCGTGTG
GCACTGAATAAACCGGAAGTCGCAGGTTTGTACCATCTGGTAGCCAGTGGTACCACAACCTGGCACGATTATGCTGCG
CTGGTTTTTGAAGAGGCGCGCAAAGCAGGCATTCCCCTTGCACTCAACAAGCTCAACGCAGTACCAACAACAGTCTAT
CCTACACCAGCTCGTCGTCCACATAACTCTCGCCTTAATACAGAAAAAATTTCAGCAGACTTTGCGCTTGTCTTGCCT
GACTGGCAGGTTGGTGTGAAACGCATGCTCAACGAATTATTTACGACTACAGCAATTTAATAGTTTTTGCATCTTGTT
CGTGATGGTGGAACAAGATGAATTAAAAGGAATGATGGAATGAATACGCGTAAAGGTATTATTTTAGCGGGTGGTTCT
GGTACACGTCTTTATCCTGTGACTATGGCTGTCAGTAAACAGCTGTTACCGATTTATGATAAACCGATGATCTATTAC
CCGCTCTCTACACTGATGTTGGCGGGTATTCGCGATATTTTGATTATCAGCACGCCACAGGATACTCCTCGTTTTCAA
CAACTGCTGGGTGATGGGAGCCAGTGGGGGCTAAATCTTCACTACAAAGTGCCGGATGGTCTTGCGCAG
GCATTTATCATCGGTGAAGAGTTTATCGGTGGTGATGATTGTGCTTTGGTACTTGGTGATAATATCTTCTACGGTCAC
GACCTGCCTAAGTTAATGGATGCCGCTGTTAACAAAGAAGTGGTGCAACGGTATTGCCTATCACGTTAATGATCCT
GAACGCTATGGTGTCGTTGAGTTTGATAAAAACGGTACTGCAATCAGCCTGGAAGAAAAACCGTTACAACCAAAAGT
AATTATGCGGTAACCGGGCTTTATTTCTATGATAACTACGTTGTGGAAATGGCGAAAAATCTTAAGCCTTCTGCCCGC
GGTGAACTGGAAATTACCGATATTAACCGTATCTATATGGAACAGGGGCATTTATCTGTTGCCATGATGGGACGTGGA
TATGCCTGGCTGGACACGGGGACACATCAAAGTCTTATTGAAGCAAGCAACTTCATTGCCACCATTGAAGAGCGCCAG -continued

| SEQUENCES |
|---|
| GGCTTGAAAGTTTCCTGCCCGGAAGAAATTGCTTACCGTAAAGGGTTTATTGATGCTGAGCAGGTGAAAGTATTAGCT |
| AAACCGCTGAAAAAAATGCTTATGGTCAGTATCTGCTAAAAATGATTAAAGGTTATTAATAAAATGAATGTTATTAA |
| AACAGAAATTCCAGATGTACTGATTTTTGAACCGAAAGTTTTTGGTGATGAGCGTGGTTTCTTTATGGAAAGCTTTAA |
| TCAGAAAGTTTTCGAAGAGGCTGTAGGGCGGAAGGTTGAATTTGTTCAGGATAATCATTCTAAATCGTGTAAAGGTGT |
| ACTTAGAGGGTTTACACTTTCAGCTTCCTCCCCTTTGAGCAGGCAAAATTAGTAAGGTGTATAGTTGGCGAGGTATTTGA |
| TGTTGCAGTAGACATTAGACCTAATTCTGAAACATTTGGTTCATGGGTTGGAGTAACTCTTTCGTCAGAAAATAAAAG |
| GCAGCTATGGATTCCAGAAGGATTCGCCCATGGTTTTTTAACTTTAAGTGATATTGCAGAGTTTGTTTATAAAACTAA |
| CAACTATTATTCTTTAAATCATGAAAGGGGAGTCATTTGGAACGATGAGGAAATTAACATTGCCTGGCCCTCTCAATC |
| AGAGAAGATTCTGTCACAGAAAGATATTAATTTACCATCATTTAGATTTGTTCAAATGTTTAGCAAGTAGTGTTATCT |
| TTACACTGCACATAGTCATCATTTTTTATGCTTTAAGTAAATTATATTGCACATCTATAACACAAAGCGCAATAATAT |
| TTCGACCTGATGAAGGTTTGTGGTTATTTATCTTTCTAGGCGTTTTTTATGACTAAAATAGTTGTGGTTTCTACAGCT |
| CCAATATTCCCGACAAATAATGGGTACAAAAGTTCTGTATTAGGAAGAATTGATGAGTTATTAAATGAGGATAATGAG |
| GTCGTTTTGATTGAAATAAACCTTGAAATGTTACGGAAAAGAAAGATGAATTAATACCAACAAGATTTAATAATATT |
| CAAAGATATGAAGTAAAAAAAATATCTAGATCATTTATTGCCGAGTTACAAATATTATTTGATATCAGAACTCGGTAT |
| GAACAATTATTTTCTTCTGCTGACATTAGAGATAACATAAAAAAGATAATTGATTTAGAAAAACCTTCTATTATTATT |
| GCTGAGTCTATATGGGCGTTGCAAGCATTGCCTATTGAAATTAGTGCGAGAATACACTGTGTTATTCATGATGTGGCA |
| ACTGATTTCTTTAAAGAAATGTTTGTATCTCATAATGAGGTTGTACGAAAAATTTTGTTTTTTAATGATTACCTAAAG |
| TTGAAAATTACTGAAGAAAATATTATCAAACGTTTGAGAGTTGAGCAATTTATCTTTCTGACAGAAGAAGATAAATGT |
| TGGTATAAAACAAGATACAATATTGATGAGGGTTGTTGTTCCTTAGCGAGCAATCATCTTTATGTAGAAAAGATTAAG |
| AGAACTATCAATTTCCAAACCCCTTTCCTGCTTATTCCCGGTAGCATTGAATTTTCACAAAATTTTTACGGCTTAAAT |
| TGGTTTATAAAAAATATATATCCTGGATTAAATAGGAAAATAAGAATAGTTGTAACAGGAAAGGCATCAGATAAAAAA |
| ATAAAGATGTTAAACTGTGGAGAGGAAATTACCTTTACGGGAGAGCTTGACTTTTCCACATATAATAAACTTAGCTCA |
| ACATGCTTGTGTGTTATTGCACCGATTACAACGGGCACTGGAATTAAAATAAAAATATTAGAAGCTGTACAAAAAGGT |
| ATTCCTGTACTTACAACAAAATTTGCTTCAAAAGGAATATGTTCCAATTTATGTTTTTATTGCGAGGAGGATACTGAC |
| ACAAACTTTGTCAATTTAATTAACAGTTTTCTTGAAACGACATTAAGAGTCCAAGAATGAATTTATTGCTTTTTTCAG |
| TCCTTGCGTTTGGTTTAATATTGGCTTTGGCCCATAATAATAAAGTGGAGATATTAACGCATACTTAATGTTTTTTC |
| TCGTGGTCCTAATGGTATTAATATCAGGGCTGCGTATGAATGATAGTGATTATATCGAATACAGGAAAATGTATAATG |
| AAGTGCCTATTTTATGTGACTTTAGTCTCGCATCTATAAGAGATATACATGGGGAGGTAGGCTATCTATTCTTATCAT |
| CAATCTTTAAAACTTTATGCTTGCCATTTCAATTATTTCTTTTTTTTATTGCTTTTTTATCACTCCTGCTTACATATT |
| TTTCATTCAGAAAAATAAGTTTAATACCGATACTATCGTTAGTTTTTATTTAAGCCATGCTTTTATAGTTAGAGATT |
| TGATTCAAATTAGGGCAGGATTAGCTGTTAGCATATCATTATATTCAATAATTAAATTTAAAGGAAATAAAAGTATAA |
| TTACAGGAGTTTTATTTGCTTCTTTGATTCATTCTGGGGCGCTTATTATTGCTCTTTGTTATCCCTTTTTTCAAAAAAA |
| AATACATAACATTAAAAATGATGTTGTTTTTATTTTTAGTGTCAATTATTTTTTCTTATTTGAATGGGCTTAATTTAT |
| CGATACAACTCTTATCTCAATATAGTTTGCTTCCAACTGCAATTTCGAATTATGTTGGTGGGAAGAATATGATTATC |
| GGGTGAGTATATTTACTAATCCGGTTTTTATTAAAGGTGTTTTTTAATTGTCTTAATGCACAAATATGTACTTTCAG |
| ATATTAAAAATGAGAAAATTATAGTGCTTTATAACTTATATGTTTTAGGTGTATTAGCTATGGTTGCATTGAGTGGGA |
| TGGCTATTCTTTCAGGCCGTCTTTCATCCTTTCTGACACTAGGTGAAAGCATTTTAATTGTATATGCTCTGTTCTACA |
| AAAGAAATACACCTCTGGCGTTTCTAATTTTTTCTTTTTTAACAATTGTGCAATTAGGATATGATCTATTTATTTCTA |
| ATGTGCATCCTGAGCTTACTCTGATTATATTTGGGTGAATCTAAGTGAAAAATAATAAAATAGGCATACTTATCTCTA |
| AAATACAAAATCTTGGACCTGTGAATGTAGTACGAGGATTGATAAAAGAAAATAAAAAAATATGCTTTTACTGTTTTT |
| GTTTAACAAATAGCGTAGATAAAAAATATATATGATGAGTTATGCTGTTTAGGAGCCAAGGTTATATTAATACCAGATG |
| GTACTTGGTTCAGCAAAATTTTATTTGTGAGAAGTTTTTTAAAGGAACATCCACATAATATCTTACATTCACATGGGA |
| TCACGGCCGATATGTTTTCTTACTTTCTGAATGGCGTGAAAATATCTACTATTCACAATAGACTAGATGAGGATTATA |
| TCCCATTATTTGGCGCGGTTAAAGGGAATGCTATATATTATCTTCATCGTTTTATATTACGAAGATTTAATCATATCG |
| TTGCTTGCTCAGCAGCGGTCCAATCAAAACTGAAACAATCGAAAGTAAAAACTAAAATAACCACCATCCAGAATGGGA |
| TTGATATAACTAGGTTTAAGCACACTTGAGTCTGATAAAAAAAAATTATTGAGGGAAAAACACGGATTTGATAGTGAAA |
| AAAGAATATTTATATATTGTGGCTCGTTATCATTAAGGAAAAATATTGCTTACCTCTTGGAACACTTAGCCATCGAAG |
| AAAATGATATATTTTAATTCTAGGTGATGGTGAACTTTTTAGATATTGTAAGGATAAATATTCTAAAGATTTACGGT |
| ATATATTTATGGGAAGATTGAATGCCCTCTTGAATATTATCAAGATATTTTTGTTTCCGCTTCTTTATCGG |
| AAGGGCTCCCCTTGGCACTATTAGAAGCTGCCTCTACTGGGTGCTATTTATATGTTAGCGATATAGAGCCCCATAGAG |
| AAATTGCATCTCTATTAGGAGAGGAAAATATTTCTATGTTTAAAATTAAGGATGGATCATATAATTATTTGCAACCTA |
| AAATAAAAAAGCTGACTATAACGCTCTTTCTGACGATAAACTTTACAATATATCCGATAAAAAATGTCAAATCTTT |
| ATGACAAACTTTTTGTTTCTTTATTAGAGCAGAGGCACTAATATAATGATTTTATGTTTCGGTAATTTCTCATGGTCAT |
| TTCAAAACTCTTAAGGAATTAGGAGCAGTATCAAAATTAAATAATCACAGCAGAATTAAAGTTATCATCAAAGATAAT |
| TTAGGAGAGAGCGAGCTTTTGGATTTTTGTCAGGAAAACAAAATAACTTATTTAAGGTCTAAAGAGAAAAAAGGATTT |
| GGAGAGAATAATAATGAAGTTTTTTCCTCTATATCCTCCTTAATTACTAAGGAAGATTTTTTGTGGTTATGAATCCT |
| GATATATATATTGAGTGCTCTGATCTATTAGATAGTCGTAGATGAGTGTGGTTCAGCGAATGTTAATCTAGCAACGATA |
| AATTTATACAGGGATTTTGATAAAAAAACATATGATAACTCAGTAAGGAAATTTCCCTCGGCAATTGATTTTTTATG |
| TCATTTTTATTTAAGAAAAATGACTGTGTAGTAAATAAGAACAAAATAACGAAACCAACATATGTTGATTGGGCTGCA |
| GGTTCTTTTCTAATATTTAATGCCTTCTTTTATTCAAAACTCAACGGATTCAACGAAAAGTATTTTATGTATTGCGAA |
| GATATTGATATATGTTGGCGAGCTAAAAAACACTTCAATACTTCAGTTTTATACTATCCATGCTATGCAGCAATTCAT |
| TTGGCACAATTTAACAATCGTAGGATTTTTAGTAGACATTTCATTTGGCATATAAAAAGTATTATCCTTTTTTTATTA |
| TATAAAAATGGTATGCTGCGTTCTAGTAAGTTGCTTAATGCTAATATTCTTTAAGAGGTGAGAATGATACCTGTTA |
| TTTTGGCTGGTGGTTCGGGAAGTCGCTTGTGGCCACTTTCACGAGAAAGTTCCCCAAGCAGTTTTTAAAGTTGACTG |
| GCAGTTTGACAATGTTGCAGTCAACATTGTCACGTCTTAATAATTTAAATGCTGATGATTCAATAGTTATATGCAACG |
| AAGAGCATAGATTTATTGTTGCAGAACAATTAAGAGAGTTAGGCAACTTTCTCGTTCCTGTTAATAACATTATTCTTGAACCCAAAG |
| GTCGTAATACAGCCCCTGCTATAACACTCGCAGCATTAGCAGCAAAAAGAAAATTCGCTGATGAAGATCCATTGATTC |
| TTATTTTAGCTGCAGATCACAACATCAAGACGAACATGTTTTCTGTGAGGCAATTAATAAGGCGTCATCTTTAGCTA |
| GTTATGGAAAACTAGTGACTTTTGGTATCGTTCCATTCAAACCTGAAACTGGGTATGGCTATATTCGTCGCGGTGATG |
| AAGTGCCTGTAGATGAGCAGCATGCGGTGGCCTTTGAAGTGGCGCAGTTTGTCGAAAAACCGAATCTGGAAACCGCGC |
| AGGCCTATGTGGCAAGCGGCGAATATTACTGGAACAGCGGTATGTTCCTGTTCCGTGCCGGACGCTATCTCGAAGAAC |
| TGAAAAAGTATCGTCCGGATATTCTCGATGCCTGTGAAAAAGCGATGAGCGCCGTCGATCCGGATCTCGATTTTATTC |
| GTGTGGATGAAGAGGCGTTTCTCGCTTGTCCGGAAGAGTCGGTGGATTACGCGGTCATGGAATGCACGGCAGATGCCG |
| TTGTGGTGCCGATGGATGCGGGCTGGAGCGATGTCGGTTCCTGGTCTTCATTATGGGAGATCAGCGCCCACACCGCCG |
| AGGGCAACGTTTGCCACGGCGATGTGATTAATCACAAAACTGAAAACAGCTATGTGTACGCCGAATCGGCCTGGTCA |
| CCACCGTCGGGGTGAAAGATTTGGTGGTAGTGCAGACCAAAGATGCAGTGCTGATTGCCGACCGTAATGCGGTGCAGG |
| ATGTGAAGAAAGTGGTCGAGCAGATCAAAGCTGATGGTCGCCATGAGCATCGGGTGCATCGCGAAGTGTATCGTCCGT |

SEQUENCES

```
GGGGCAAATATGACTCTATCGACGCGGGCGACCGCTACCAGGTGAAACGCATCACCGTGAAACCGGGCGAAGGTTTGT
CGGTACAGATGCATTATCATCGCGCGGAACACTGGGTGGTTGTCGCGGGAACGGCAAAAGTCACTATCAACGGTGATA
TCAAACTGCTTGGTGAAAACGAGTCCATTTATATTCCGCTGGGGGCGATGCACTGCCTGGAAAACCCGGGGAAAATAG
ATTTAGAATTAATTGAAGTTCGCTCTGGTGCATATCTTGAAGAAGATGATGTTATTAGATGTTATGATCGCTATGGAC
GAAAGTAATATATAATAATTATTTCAGAATTAGAAATGATAATTATAAGTTTTCGTCTGGATAAACAATAGATAGTAT
GGGTTGGAAAATATGAGTTCTTTAACTTGTTTTAAAGCTTACGACATTCGCGGGAAATTAGGTGAAGAACTGAATGAA
GATATCGCCTGGCGCATTGGTCGCGCCTATGGCGAATTTCTCAAACCGAAAACCATTGTGTTAGGCGGTGATGTCCGT
CTCACCAGCGAAACCTTAAAACTGGCGCTGGCAAAAGGTTTACAGGATGCGGGCGTCGATGTGCTGGATATTGGCATG
TCCGGCACCGAAGAGATTTATTTCGCCACGTTCCATCTCGGCGTGGATGGCGGCATTGAAGTTACCGCCAGCCATAAT
CCGATGGATTACAACGGCATGAAGCTGGTGCGCGAAGGGCTCGCCCGATCAGCGGTGATACCGGACTGCGCGACGTC
CAGCGTCTGGCAGAAGCTAACGACTTTCCTCCCGTCGATGAAACCAAACGCGGTCGCTATCAGCAAATCAATCTGCGT
GACGCTTACGTTGATCACCTGTTCGGTTATATCAATGTCAAAAACCTTACGCCGCTCAAGCTGGTGATCAACTCCGGG
AATGGCGCAGCGGGTCCGGTGGTGGACGCTATCGAAGCCCGCTTTAAAGCCCTCGGCGCACCGGTGGAGTTAATCAAA
GTGCATAACACGCCGGACGGCAATTTCCCCAACGGTATTCCTAACCCGTTGCTGCCGGAATGTCGCGACGACACCCGC
AATGCGGTCATCAAACACGGCGCGGATATGGGCATTGCCTTTGATGGCGATTTTGACCGCTGTTTCCTGTTTGACGAA
AAAGGGCAGTTTATTGAGGGCTACTACATTGTCGGCCTGCTGGCAGAAGCGTTCCTCGAAAAAAATCCCGGCGCGAAG
ATCATCCACGATCCACGTCTCTCCTGGAACACCATTGATGTGGTGACGGCCGCGGGCGGCACGCCGGTGATGTCGAAA
ACAGGACACGCCTTATTAAAGAACGTATGCGCAAGGAAGACGCCATCTACGGTGGCGAAATGAGCGCTCACCATTAC
TTCCGCGATTTCGCTTACTGTGACAGCGGCATGATCCCCGTGGCTGCTGGTCGCCGAACTGGTGTGCCTGAAAGGAAAA
ACGCTGGGCGAACTGGTGCGCGACCGGATGGCGGCGTTTCCGGCAAGCGGTGAGATCAACAGAAAACTGGCGCACCCT
GTTGAGGCGATTAACCGCGTGGAACAGCATTTTAGCCGTGAGGTGCTGGCGGTGGATCGCACCGATGGCATCAGCATG
ACCTTTGCCGACTGGCGCTTTAACCTGCGCTCTTCCAACACCGAACCGGTGGTGCGCCTGAATGTGGAATCTCGCGGT
GATGTTCAGGTTATGGTAATCCATACTCAAGAAATATTATCAATTTTGACGTCATAAAGAATAAGCCCTGACAAGTTA
GGGCTTAATTAATATATATTTTTTTGAATTGGGGATTTGTGGTAAGATTTTTAATATGTTTATTTAATGTGGTTGAAT
TAATGTTGACTGGAAAATAATAATGAGAACGAAAAAAGCATTACACAACTTTAAAGTTGATTTATTAATTACTTTTTT
ATTGGTTTTGCTAGGGTTTTATATTCGAACTGTTTTTGTTTCAAAAATGGGAAGTGATATTACTGGAGTGATGTTACT
ATTCACACAGTTGACAGCATATCTCAATTTGGCAGAATTAGGTATTGGAATTGCAGCTGCCAGCGTATTATATAAACC
GCTCAGCGAGAATGAATACAATAAAATAACTTACATAATATCTTTGCTCTCAGTCATATACAAATATATATTTGTGTT
TGTTTTGATTCTTGGCGTTGTTATAGGTATCTGTATTTATTACTTTATTGATTCTGTAAAGGTTGTAAATGGCGTTTT
TTTATATTGGGCTTTGTTCGTTTTTAATACATCGTTGACATATAGTTATGCTAAATACTCCACATTATTAACTGCTAA
TCAGCGGTACTCAGCAGTAAGAAAAATTCAAGGTGGCGGAAAAGTTATAATAATTGTATTTCAGATATTAATTTTGTG
CTTTACGCAAAGTTTCATACTTTATTTGTTAGTTGAGACTTTAGGTATTTTTTCTAAGATTTTGATTTTTAAAAAAAT
AATTGGGAACGGAAATCAATATCTCAGTAATGAGGTTTTACTTATTGAAAGCGATAAACTTTTGATAAAAAAAGAATT
AAAAATAAGAATAAAAAAATATGTTCTTCCATAAAATAGGTGCTGTGCTTGTCCTTAATACAGACTACCTGCTTGTATC
AAAGTTTCTGACATTAAGTTATGTGACAATTTTTGGCAGCTATATGATGGTATTTCAGATAGTAACTGTTTTGATGTC
AAGTTTTGTTAATGCTATTACTGCAGGAATGGGTAATTACTTAATTAATAAAGATAATGTGATCTTTTAGAAATTAAGGAAATTAC
ACGTCAATTTTATGTGATATTTATCGCCTTTGCAACATTCATATCACTAAATATGTTTTTTCTTGTTAATGATTTTAT
CGCAAAATGGATAGGTGTTAATTATACATTAAGTAACACCCTAGTTGCATTAATGATTGTTAACGTATTCATTAGTGT
TGTCAGGGTACCTTCTGATATATTAAAAAACGCAAGTGGACATTTTGGTGATATTTATTATCCATTATTAGAAGGTGT
GCTGAATATTACGATATCCATCATTTTGGCTATCATTATTGGATTACCTGGCATTATTATAGGGACAATAGTATCTAA
CTTAATAGTAATAATGCTTGCGAAACCATTATATCTTTACTCTAAGTTATTTAATCTTAGAAATCCGACGAGGGTTTA
TTTTGAATTTATTTCTCGGCCTATGTTATATTCATTATGTGTGATTGGGGTGAGCTATTTATTGCGCGATGAAATATA
TTCATTTAAAGTAAGTACATGGTTGGATTTTATTAACAAGCTACTCTTAGTCTCTACTCCTAGCATATTGGTAATATG
TGCTATTTTCTCTACGGATAGTGACTTTAGATTATTTTTTCAGAAAAATTATATATGTGATTATGAAGAAATAAAAATT
TCGAAAATGTATTAATCGAAATTATGCAACGAGCTTTATTTTGCAACATGATATGTGACTCTTTTCGCGAATAGGAGTA
AGGATCCGTGTAGGCTGGAGCTGCTTCGAAGTTCCTATACTTTCTAGAGAATAGGAACTTCGGAATAGGAACTAAGGA
GGATATTCATATGGATAAAGCCGTAAGCATATAAGCATGGATAAGCTATTTATACTTTAATAAGTACTTTGTATACTT
ATTTGCGAACATTCCAGGCCGCGAGCATTCAGCGCGGTGATCACACCTGACAGGAGTATGTAATGTCCAAGCAACAGA
TCGGCGTAGTCGGTATGGCAGTGATGGGACGCAACCTTGCGCTCAACATCGAAGCCGTGGTTATACCGTCTCTATTT
TCAACCGTTCCCGTGAGAAGACGGAAGAAGTGATTGCCGAAAATCCAGGCAAGAAACTGGTTCCTTACTATACGGTGA
AAGAGTTTGTCGAATCTCTGGAAACGCCTCGTCGCATCCTGTTAATGGTGAAAGCAGGTGCAGGCACGGATGCTGCTA
TTGATTCCCTCAAACCATATCTCGATAAAGGAGACATCATCATTGATGGTGGTAACACCTTCTTCCAGGACACTATTC
GTCGTAATCGTGAGCTTTCAGCAGAGGGCTTTAACTTCATCGGTACCGGTGTTTCTGGCGGTGAAGAGGGGGCGCTGA
AAGGTCCTTCTATTATGCCTGGTGGCCAGAAAGAAGCCTATGAATTGGTAGCACCCGATCCTGACCAAAATCGCCGCCG
TAGCTGAAGACGGTGAACCATGCGTTACCTATATTGGTGCCGATGGCGCAGGTCACTATGTGAAGATGGTTCACAACG
GTATTGAATACGGCGATATGCAGCTGATTGCTGAAGCCTATTCTCTGCTTAAAGGTGGCCTGAACCTCACCAACGAAG
AACTGGCGCAGACCTTTACCGAGTGGAATAACGGTGAACTGAGCAGTTACCTGATCGACATCACCAAAGATATCTTCA
CCAAAAAGATGAAGACGGTAACTACCTGGTTGATGTGATCCTGGATGAAGCGGCTAACAAAGGTACCGGTAAATGGA
CCAGCCAGAGCGCGCTGGATCTCGGCGAACCGCTGTCGCTGATTACCGAGTCTGTGTTTGCACGTTATATCTCTTCTC
TGAAAGATCAGCGTGTTGCCGCATCTAAAGTTCTCTGGTCCGCAAGCACAGCCAGCAGGCGACAAGGCTGAGTTCA
TCGAAAAAGTTCGTCGTGCGCTGTATCTGGGCAAAATCGTTTCTTACGCCCAGGGCTTCTCTCAGCTGCGTGCTGCGT
CTGAAGAGTACAACTGGGATCTGAACTACGGCGAAATCGCGAAGATTTTCCGTGCTGGCTGCATCATCCGTGCGCAGT
TCCTGCAGAAAATCACCGATGCTTATGCCGAAAATCACAGATCGCTAACCTGTTGCTGGCTCCGTACTTCAAGCAAA
TTGCCGATGACTACCAGCAGGCGCTGCGTGATGTCGTTGCTTATGCAGTACAGAACGGTATTCCGGTTCCGACCTTCT
CCGCAGCGGTTGCCTATTACGACAGCTACCGTGCTGCTGTTCTGCCTGCAACCTGATCCAGGCACAGCGTGACTATT
TTGGTGCGCATACTTATAAGCGTATTGATAAAGAAGGTGTGTTCCATACCGAATGGCTGGATTAA
```

The invention claimed is:

1. A bioconjugate of an *E. coli* glucosylated O4 antigen polysaccharide covalently linked to a carrier protein, wherein the *E. coli* glucosylated O4 antigen polysaccharide comprises the structure of Formula (O4-Glc+):

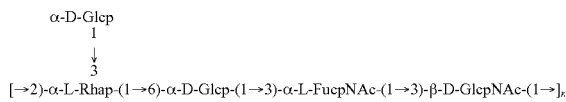

wherein n is an integer of 1 to 100.

2. The bioconjugate of claim 1, wherein the *E. coli* glucosylated O4 antigen polysaccharide is covalently linked to an Asn residue in a glycosylation site comprising a glycosylation consensus sequence having SEQ ID NO: 1 in the carrier protein.

3. The bioconjugate of claim 1, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

4. A composition comprising the bioconjugate of claim 1 and a pharmaceutically acceptable carrier.

5. The composition of claim 4, comprising at least one additional antigen polysaccharide covalently linked to a carrier protein.

6. The composition of claim 5, wherein the at least one additional antigen polysaccharide is selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide.

7. The composition of claim 6, wherein each carrier protein is EPA comprising SEQ ID NO: 3.

8. The composition of claim 6, comprising at least the *E. coli* O1A, O2, glucosylated O4, O6A, O8, O15, O16, O18A, O25B, and O75 antigen polysaccharides each covalently linked to a carrier protein, wherein (i) the *E. coli* O1A antigen polysaccharide comprises the structure of Formula (O1A):

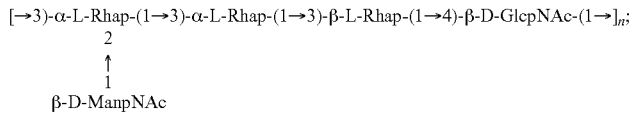

(ii) the *E. coli* O2 antigen polysaccharide comprises the structure of Formula (O2):

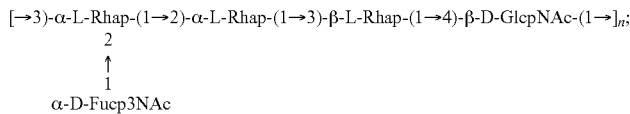

(iii) the *E. coli* O6A antigen polysaccharide comprises the structure of Formula (O6A):

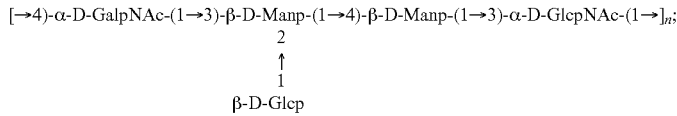

(iv) the *E. coli* O8 antigen polysaccharide comprises the structure of Formula (O8):

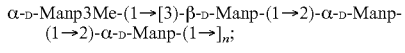

(v) the *E. coli* O15 antigen polysaccharide comprises the structure of Formula (O15):

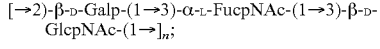

(vi) the *E. coli* O16 antigen polysaccharide comprises the structure of Formula (O16):

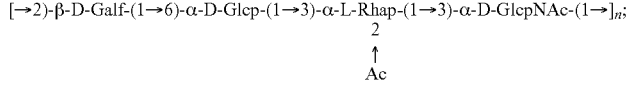

(vii) the *E. coli* O18A antigen polysaccharide comprises the structure of Formula (O18A):

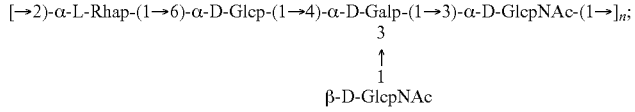

(viii) the *E. coli* O25B antigen polysaccharide comprises the structure of Formula (O25B):

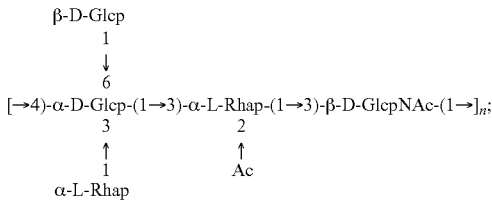

and (ix) the *E. coli* O75 antigen polysaccharide comprises the structure of Formula (O75):

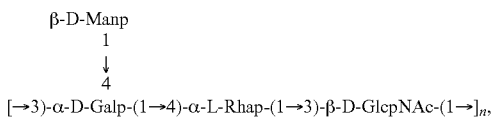

wherein each n is independently an integer of 1 to 100.

9. The composition of claim 8, wherein each n is an integer of 5 to 40.

10. The composition of claim 9, wherein each n is independently an integer of 10 to 20.

11. The bioconjugate of claim 1, wherein n is an integer of 5 to 40.

12. The bioconjugate of claim 11, wherein n is an integer of 10 to 20.

13. The bioconjugate of claim 12, wherein the carrier protein comprises SEQ ID NO: 3.

14. The bioconjugate of claim 11, wherein the carrier protein comprises SEQ ID NO: 3.

15. The bioconjugate of claim 1, wherein the carrier protein comprises SEQ ID NO: 3.

16. A composition comprising:

(i) a bioconjugate of an *E. coli* glucosylated O4 antigen polysaccharide covalently linked to a detoxified Exotoxin A of *P. aeruginosa* (EPA carrier protein) comprising SEQ ID NO: 3, wherein the *E. coli* glucosylated O4 antigen polysaccharide comprises the structure of Formula (O4-Glc+);

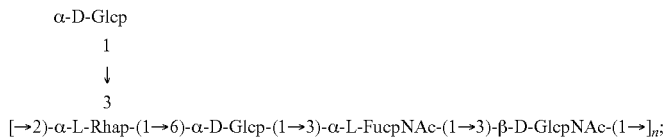

(ii) a bioconjugate of an *E. coli* O1A antigen polysaccharide covalently linked to an EPA carrier protein comprising SEQ ID NO: 3, wherein the *E. coli* O1A antigen polysaccharide comprises the structure of Formula (O1A);

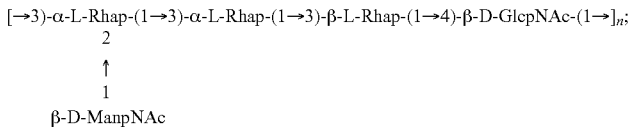

(iii) a bioconjugate of an *E. coli* O2 antigen polysaccharide covalently linked to an EPA carrier protein comprising SEQ ID NO: 3, wherein the *E. coli* O2 antigen polysaccharide comprises the structure of Formula (O2);

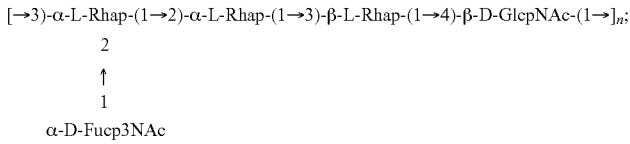

(iv) a bioconjugate of an *E. coli* O6A antigen polysaccharide covalently linked to an EPA carrier protein comprising SEQ ID NO: 3, wherein the *E. coli* O6A antigen polysaccharide comprises the structure of Formula (O6A);

[→4)-α-D-GalpNAc-(1→3)-β-D-Manp-(1→4)-β-D-Manp-(1→3)-α-D-GlcpNAc-(1→]ₙ;
2
↑
1
β-D-Glcp (v) a bioconjugate of an *E. coli* O8 antigen polysaccharide covalently linked to an EPA carrier protein comprising SEQ ID NO: 3, wherein the *E. coli* O8 antigen polysaccharide comprises the structure of Formula (O8);

α-D-Manp3Me-(1→[3)-β-D-Manp-(1→2)-α-D-Manp-(1→2)-α-D-Manp-(1→]ₙ;

(vi) a bioconjugate of an *E. coli* O15 antigen polysaccharide covalently linked to an EPA carrier protein comprising SEQ ID NO: 3, wherein the *E. coli* O15 antigen polysaccharide comprises the structure of Formula (O15);

[→2)-β-D-Galp-(1→3)-α-L-FucpNAc-(1→3)-β-D-GlcpNAc-(1→]ₙ;

(vii) a bioconjugate of an *E. coli* O16 antigen polysaccharide covalently linked to an EPA carrier protein comprising SEQ ID NO: 3, wherein the *E. coli* O16 antigen polysaccharide comprises the structure of Formula (O16);

[→2)-β-D-Galf-(1→6)-α-D-Glcp-(1→3)-α-L-Rhap-(1→3)-α-D-GlcpNAc-(1→]ₙ;
2
↑
Ac (viii) a bioconjugate of an *E. coli* O25B antigen polysaccharide covalently linked to an EPA carrier protein comprising SEQ ID NO: 3, wherein the *E. coli* O25B antigen polysaccharide comprises the structure of Formula (O25B);

β-D-Glcp
1
↓
6
[→4)-α-D-Glcp-(1→3)-α-L-Rhap-(1→3)-β-D-GlcpNAc-(1→]ₙ;
3    2
↑    ↑
1    Ac
α-L-Rhap (ix) a bioconjugate of an *E. coli* O75 antigen polysaccharide covalently linked to an EPA carrier protein comprising SEQ ID NO: 3, wherein the *E. coli* O75 antigen polysaccharide comprises the structure of Formula (O75);

β-D-Manp
1
↓
4
[→3)-α-D-Galp-(1→4)-α-L-Rhap-(1→3)-β-D-GlcpNAc-(1→]ₙ;

and (x) a bioconjugate of an *E. coli* O18A antigen polysaccharide covalently linked to an EPA carrier protein comprising SEQ ID NO: 3, wherein the *E. coli* O18A antigen polysaccharide comprises the structure of Formula (O18A);

[→2-α-L-Rhap-(1→6)-α-D-Glcp-(1→4)-α-D-Galp-(1→3)-α-D-GlcpNAc-(1→]ₙ;
3
↑
1
β-D-GlcpNAc wherein each n is independently an integer of 1 to 100.

17. A composition according to claim 16, wherein the bioconjugate of the O25B antigen polysaccharide is present in the composition at a concentration that is about 1.5-6 times-higher than the concentration of any of the other bioconjugates.

18. A composition according to claim 17, wherein the bioconjugates of O1A:O2:glucosylated O4:O6A:O8:O15:O16:O18A:O25B:O75 are present in a ratio by weight of polysaccharide of 1:1:1:1:1:1:1:1:2:1, or 2:1:1:2:1:1:1:1:4:1.

19. A composition according to claim 17, wherein the concentration of the bioconjugate of the O25B antigen polysaccharide is 2 to 50 µg/mL.

20. The composition of claim 16, wherein each n is independently an integer of 5 to 40.

21. The composition of claim 20, wherein each n is independently an integer of 10 to 20.

22. A method of inducing antibodies against an *E. coli* glucosylated O4 antigen in a subject, comprising administering to the subject the bioconjugate of claim 1.

23. The method of claim 22, wherein the subject is a human.

24. A method of vaccinating a subject against *E. coli*, comprising administering to the subject the bioconjugate of claim 1.

25. The method of claim 24, wherein the *E. coli* is an extra-intestinal pathogenic *E. coli* (ExPEC).

26. The method of claim 25, wherein the subject is a human.

27. The method of claim 24, wherein the subject is a human.

28. A method of inducing antibodies against *E. coli* in a subject, comprising administering to the subject the composition of claim 4.

29. The method of claim 28, wherein the subject is a human.

30. A method of vaccinating a subject against *E. coli*, comprising administering to the subject the composition of claim 4.

31. The method of claim 30, wherein the *E. coli* is an extra-intestinal pathogenic *E. coli* (ExPEC).

32. The method of claim 30, wherein the subject is a human.

33. A method of inducing antibodies against *E. coli* in a subject, comprising administering to the subject the composition of claim 6.

34. The method of claim 33, wherein the subject is a human.

35. A method of vaccinating a subject against *E. coli*, comprising administering to the subject the composition of claim 6.

36. The method of claim 35, wherein the *E. coli* is an extra-intestinal pathogenic *E. coli* (ExPEC).

37. The method of claim 35, wherein the subject is a human.

38. A method of inducing antibodies against *E. coli* in a subject, comprising administering to the subject the composition of claim 8.

39. The method of claim 38, wherein the subject is a human.

40. A method of vaccinating a subject against *E. coli*, comprising administering to the subject the composition of claim 8.

41. The method of claim 40, wherein the *E. coli* is an extra-intestinal pathogenic *E. coli* (ExPEC).

42. The method of claim 40, wherein the subject is a human.

* * * * *

SEQUENCE LISTING

<160> NUMBER OF SEQ ID NOS: 19

<210> SEQ ID NO 1
<211> LENGTH: 3

```
<212> TYPE: PRT
<213> ORGANISM: Artificial Sequence
<220> FEATURE:
<223> OTHER INFORMATION: glycosylation consensus sequence
<220> FEATURE:
<221> NAME/KEY: VARIANT
<222> LOCATION: (2)..(2)
<223> OTHER INFORMATION: any amino acid residue except Pro
<220> FEATURE:
<221> NAME/KEY: VARIANT
<222> LOCATION: (3)..(3)
<223> OTHER INFORMATION: Ser orThr

<400> SEQUENCE: 1

Asn Xaa Xaa
1

<210> SEQ ID NO 2
<211> LENGTH: 5
<212> TYPE: PRT
<213> ORGANISM: Artificial Sequence
<220> FEATURE:
<223> OTHER INFORMATION: optimized glycosylation consensus sequence
<220> FEATURE:
<221> NAME/KEY: VARIANT
<222> LOCATION: (1)..(1)
<223> OTHER INFORMATION: Asp or Glu
<220> FEATURE:
<221> NAME/KEY: VARIANT
<222> LOCATION: (2)..(2)
<223> OTHER INFORMATION: any amino acid residue except Pro
<220> FEATURE:
<221> NAME/KEY: VARIANT
<222> LOCATION: (4)..(4)
<223> OTHER INFORMATION: any amino acid residue except Pro
<220> FEATURE:
<221> NAME/KEY: VARIANT
<222> LOCATION: (5)..(5)
<223> OTHER INFORMATION: Ser or Thr

<400> SEQUENCE: 2

Xaa Xaa Asn Xaa Xaa
1               5

<210> SEQ ID NO 3
<211> LENGTH: 652
<212> TYPE: PRT
<213> ORGANISM: Artificial Sequence
<220> FEATURE:
<223> OTHER INFORMATION: EPA carrier protein comprising 4 glycosylation
      consensus sequences (EPA-4)

<400> SEQUENCE: 3

Gly Ser Gly Gly Gly Asp Gln Asn Ala Thr Gly Ser Gly Gly Gly Lys
1               5                   10                  15

Leu Ala Glu Glu Ala Phe Asp Leu Trp Asn Glu Cys Ala Lys Ala Cys
            20                  25                  30

Val Leu Asp Leu Lys Asp Gly Val Arg Ser Ser Arg Met Ser Val Asp
        35                  40                  45

Pro Ala Ile Ala Asp Thr Asn Gly Gln Gly Val Leu His Tyr Ser Met
    50                  55                  60

Val Leu Glu Gly Gly Asn Asp Ala Leu Lys Leu Ala Ile Asp Asn Ala
65                  70                  75                  80

Leu Ser Ile Thr Ser Asp Gly Leu Thr Ile Arg Leu Glu Gly Gly Val
                85                  90                  95

Glu Pro Asn Lys Pro Val Arg Tyr Ser Tyr Thr Arg Gln Ala Arg Gly
            100                 105                 110
```

```
Ser Trp Ser Leu Asn Trp Leu Val Pro Ile Gly His Glu Lys Pro Ser
            115                 120                 125
Asn Ile Lys Val Phe Ile His Glu Leu Asn Ala Gly Asn Gln Leu Ser
130                 135                 140
His Met Ser Pro Ile Tyr Thr Ile Glu Met Gly Asp Glu Leu Leu Ala
145                 150                 155                 160
Lys Leu Ala Arg Asp Ala Thr Phe Phe Val Arg Ala His Glu Ser Asn
                165                 170                 175
Glu Met Gln Pro Thr Leu Ala Ile Ser His Ala Gly Val Ser Val Val
            180                 185                 190
Met Ala Gln Ala Gln Pro Arg Arg Glu Lys Arg Trp Ser Glu Trp Ala
        195                 200                 205
Ser Gly Lys Val Leu Cys Leu Leu Asp Pro Leu Asp Gly Val Tyr Asn
    210                 215                 220
Tyr Leu Ala Gln Gln Arg Cys Asn Leu Asp Asp Thr Trp Glu Gly Lys
225                 230                 235                 240
Ile Tyr Arg Val Leu Ala Gly Asn Pro Ala Lys His Asp Leu Asp Ile
                245                 250                 255
Lys Asp Asn Asn Asn Ser Thr Pro Thr Val Ile Ser His Arg Leu His
            260                 265                 270
Phe Pro Glu Gly Gly Ser Leu Ala Ala Leu Thr Ala His Gln Ala Cys
        275                 280                 285
His Leu Pro Leu Glu Ala Phe Thr Arg His Arg Gln Pro Arg Gly Trp
    290                 295                 300
Glu Gln Leu Glu Gln Cys Gly Tyr Pro Val Gln Arg Leu Val Ala Leu
305                 310                 315                 320
Tyr Leu Ala Ala Arg Leu Ser Trp Asn Gln Val Asp Gln Val Ile Arg
                325                 330                 335
Asn Ala Leu Ala Ser Pro Gly Ser Gly Asp Leu Gly Glu Ala Ile
            340                 345                 350
Arg Glu Gln Pro Glu Gln Ala Arg Leu Ala Leu Thr Leu Ala Ala Ala
        355                 360                 365
Glu Ser Glu Arg Phe Val Arg Gln Gly Thr Gly Asn Asp Glu Ala Gly
    370                 375                 380
Ala Ala Ser Ala Asp Val Val Ser Leu Thr Cys Pro Val Ala Lys Asp
385                 390                 395                 400
Gln Asn Arg Thr Lys Gly Glu Cys Ala Gly Pro Ala Asp Ser Gly Asp
                405                 410                 415
Ala Leu Leu Glu Arg Asn Tyr Pro Thr Gly Ala Glu Phe Leu Gly Asp
            420                 425                 430
Gly Gly Asp Val Ser Phe Ser Thr Arg Gly Thr Gln Asn Trp Thr Val
        435                 440                 445
Glu Arg Leu Leu Gln Ala His Arg Gln Leu Glu Glu Arg Gly Tyr Val
    450                 455                 460
Phe Val Gly Tyr His Gly Thr Phe Leu Glu Ala Ala Gln Ser Ile Val
465                 470                 475                 480
Phe Gly Gly Val Arg Ala Arg Ser Gln Asp Leu Asp Ala Ile Trp Arg
                485                 490                 495
Gly Phe Tyr Ile Ala Gly Asp Pro Ala Leu Ala Tyr Gly Tyr Ala Gln
            500                 505                 510
Asp Gln Glu Pro Asp Ala Arg Gly Arg Ile Arg Asn Gly Ala Leu Leu
        515                 520                 525
Arg Val Tyr Val Pro Arg Trp Ser Leu Pro Gly Phe Tyr Arg Thr Gly
```

```
                        530                 535                 540
Leu Thr Leu Ala Ala Pro Glu Ala Gly Glu Val Glu Arg Leu Ile
545                 550                 555                 560

Gly His Pro Leu Pro Leu Arg Leu Asp Ala Ile Thr Gly Pro Glu Glu
                565                 570                 575

Glu Gly Gly Arg Val Thr Ile Leu Gly Trp Pro Leu Ala Glu Arg Thr
                580                 585                 590

Val Val Ile Pro Ser Ala Ile Pro Thr Asp Pro Arg Asn Val Gly Gly
                595                 600                 605

Asp Leu Asp Pro Ser Ser Ile Pro Asp Lys Glu Gln Ala Ile Ser Ala
                610                 615                 620

Leu Pro Asp Tyr Ala Ser Gln Pro Gly Lys Pro Arg Glu Asp Leu
625                 630                 635                 640

Lys Leu Gly Ser Gly Gly Gly Asp Gln Asn Ala Thr
                645                 650

<210> SEQ ID NO 4
<211> LENGTH: 421
<212> TYPE: PRT
<213> ORGANISM: Artificial Sequence
<220> FEATURE:
<223> OTHER INFORMATION: O4 GtrS amino acid sequence

<400> SEQUENCE: 4

Met Asn Asn Leu Ile Met Asn Asn Trp Cys Lys Leu Ser Ile Phe Ile
1               5                   10                  15

Ile Ala Phe Ile Leu Leu Trp Leu Arg Arg Pro Asp Ile Leu Thr Asn
                20                  25                  30

Ala Gln Phe Trp Ala Glu Asp Ser Val Phe Trp Tyr Lys Asp Ala Tyr
            35                  40                  45

Glu Asn Gly Phe Leu Ser Ser Leu Thr Thr Pro Arg Asn Gly Tyr Phe
        50                  55                  60

Gln Thr Val Ser Thr Phe Ile Val Gly Leu Thr Ala Leu Leu Asn Pro
65                  70                  75                  80

Asp Tyr Ala Pro Phe Val Ser Asn Phe Phe Gly Ile Met Ile Arg Ser
                85                  90                  95

Val Ile Ile Trp Phe Leu Phe Thr Glu Arg Phe Asn Phe Leu Thr Leu
                100                 105                 110

Thr Thr Arg Ile Phe Leu Ser Ile Tyr Phe Leu Cys Met Pro Gly Leu
                115                 120                 125

Asp Glu Val His Ala Asn Ile Thr Asn Ala His Trp Tyr Leu Ser Leu
130                 135                 140

Tyr Val Ser Met Ile Leu Ile Ala Arg Asn Pro Ser Ser Lys Ser Trp
145                 150                 155                 160

Arg Phe His Asp Ile Phe Ile Leu Leu Ser Gly Leu Ser Gly Pro
                165                 170                 175

Phe Ile Ile Phe Ile Leu Ala Ala Ser Cys Phe Lys Phe Ile Asn Asn
                180                 185                 190

Cys Lys Asp His Ile Ser Val Arg Ser Phe Ile Asn Phe Tyr Leu Arg
                195                 200                 205

Gln Pro Tyr Ala Leu Met Ile Val Cys Ala Leu Ile Gln Gly Thr Ser
                210                 215                 220

Ile Ile Leu Thr Phe Asn Gly Thr Arg Ser Ser Ala Pro Leu Gly Phe
225                 230                 235                 240

Ser Phe Asp Val Ile Ser Ser Ile Ile Ser Ser Asn Ile Phe Leu Phe
```

```
                   245                 250                 255
Thr Phe Val Pro Trp Asp Ile Ala Lys Ala Gly Trp Asp Asn Leu Leu
            260                 265                 270
Leu Ser Tyr Phe Leu Ser Val Ser Ile Leu Ser Cys Ala Ala Phe Val
            275                 280                 285
Phe Val Lys Gly Thr Trp Arg Met Lys Val Phe Ala Thr Leu Pro Leu
            290                 295                 300
Leu Ile Ile Ile Phe Ser Met Ala Lys Pro Gln Leu Thr Asp Ser Ala
305                 310                 315                 320
Pro Gln Leu Pro Thr Leu Ile Asn Gly Gln Gly Ser Arg Tyr Phe Val
            325                 330                 335
Asn Ile His Ile Ala Ile Phe Ser Leu Leu Cys Val Tyr Leu Leu Glu
            340                 345                 350
Cys Val Arg Gly Lys Val Ala Thr Leu Phe Ser Lys Ile Tyr Leu Thr
            355                 360                 365
Ile Leu Leu Phe Val Met Gly Cys Leu Asn Phe Val Ile Thr Pro Leu
            370                 375                 380
Pro Asn Met Asn Trp Arg Glu Gly Ala Thr Leu Ile Asn Asn Ala Lys
385                 390                 395                 400
Thr Gly Asp Val Ile Ser Ile Gln Val Leu Pro Pro Gly Leu Thr Leu
                        405                 410                 415
Glu Leu Arg Lys Lys
            420

<210> SEQ ID NO 5
<211> LENGTH: 1266
<212> TYPE: DNA
<213> ORGANISM: Artificial Sequence
<220> FEATURE:
<223> OTHER INFORMATION: Example 04 gtrS nucleic acid sequence

<400> SEQUENCE: 5
atgaataatt taattatgaa taactggtgt aaattatcta tatttattat tgcatttatt      60
ttgctatggc ttagaaggcc ggatatactc acaaacgcac aatttgtggc agaagattcc     120
gttttctggt ataaggacgc ctatgagaac ggattcttaa gttcactaac aacgcctagg     180
aatgggtatt tccagactgt ttctacattt atagttggtc tgactgcttt attaaatcca     240
gattatgcac cttttgtttc taattttttt ggcataatga ttcgctcagt aatttatatgg     300 tttttattta cagaaagatt caacttcctc acattgacta ctaggatttt cttatctatt     360 tatttttctat gcatgcctgg attggatgaa gttcatgcaa atataacaaa tgcacattgg     420
tatttgtcat tatatgtatc aatgatcctg atagctcgca atccaagttc aaaatcatgg     480
aggtttcatg atatattctt tatcttgcta tccgggctca gtggcccatt tataattttc     540
attttagcag cttcatgctt taaatttata aataattgta aagatcatat tagtgtaaga     600
tctttcataa atttctactt gcgtcagcca tacgcattaa tgattgtttg cgctttaatt     660
caaggaactt ctataattct aactttcaat ggcacacgtt cctcagcacc gctaggattc     720
agttttgatg tgatttcgtc tattatatca tcgaatattt ttttatttac atttgtccca     780
tgggatattg caaaggctgg gtgggataat ttactgttat cttatttttt gtctgtttcg     840
attttgtcgt gtgcggcctt tgtttttgtt aaaggtacgt ggcgaatgaa agtatttgca     900 acttaccat tgctaattat aatatttcca atggcaaaac cacaattgac agactcggca     960
cctcaattgc caacacttat taatgggcaa ggttcaagat acttcgtaaa atacacatat    1020
```

-continued

```
gcgatattct ctttgctatg tgtttactta cttgagtgcg tcaggggaa agtggcaact    1080 ttatttcca aaatatactt aacaattttg ctattcgtga tgggatgttt gaattttgtt    1140
atcaccccac tcccaaacat gaactggagg gaaggtgcta ctttgattaa taatgcaaaa    1200
actggtgatg tcatttcgat tcaagtgcta ccacctggcc taacacttga actaaggaaa    1260
aaataa                                                               1266
```

<210> SEQ ID NO 6
<211> LENGTH: 713
<212> TYPE: PRT
<213> ORGANISM: Artificial Sequence
<220> FEATURE:
<223> OTHER INFORMATION: Example PglB sequence ('wild-type')

<400> SEQUENCE: 6

```
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320
```

-continued

Asp Leu Ser Glu Phe Met Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
        355                 360                 365

Gly Gly Leu Arg Phe Thr Ile Tyr Ser Val Pro Val Met Ala Leu Gly
    370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
    450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710

<210> SEQ ID NO 7
<211> LENGTH: 120

```
<212> TYPE: PRT
<213> ORGANISM: Escherichia coli

<400> SEQUENCE: 7

Met Leu Lys Leu Phe Ala Lys Tyr Thr Ser Ile Gly Val Leu Asn Thr
1               5                   10                  15

Leu Ile His Trp Val Val Phe Gly Val Cys Ile Tyr Val Ala His Thr
            20                  25                  30

Asn Gln Ala Leu Ala Asn Phe Ala Gly Phe Val Val Ala Val Ser Phe
        35                  40                  45

Ser Phe Phe Ala Asn Ala Lys Phe Thr Phe Lys Ala Ser Thr Thr Thr
50                  55                  60

Met Arg Tyr Met Leu Tyr Val Gly Phe Met Gly Thr Leu Ser Ala Thr
65                  70                  75                  80

Val Gly Trp Ala Ala Asp Arg Cys Ala Leu Pro Pro Met Ile Thr Leu
                85                  90                  95

Val Thr Phe Ser Ala Ile Ser Leu Val Cys Gly Phe Val Tyr Ser Lys
            100                 105                 110

Phe Ile Val Phe Arg Asp Ala Lys
            115                 120

<210> SEQ ID NO 8
<211> LENGTH: 306
<212> TYPE: PRT
<213> ORGANISM: Escherichia coli

<400> SEQUENCE: 8

Met Lys Ile Ser Leu Val Val Pro Val Phe Asn Glu Glu Glu Ala Ile
1               5                   10                  15

Pro Ile Phe Tyr Lys Thr Val Arg Glu Phe Glu Glu Leu Lys Ser Tyr
            20                  25                  30

Glu Val Glu Ile Val Phe Ile Asn Asp Gly Ser Lys Asp Ala Thr Glu
        35                  40                  45

Ser Ile Ile Asn Ala Leu Ala Val Ser Asp Pro Leu Val Val Pro Leu
50                  55                  60

Ser Phe Thr Arg Asn Phe Gly Lys Glu Pro Ala Leu Phe Ala Gly Leu
65                  70                  75                  80

Asp His Ala Thr Gly Asp Ala Ile Ile Pro Ile Asp Val Asp Leu Gln
                85                  90                  95

Asp Pro Ile Glu Val Ile Pro His Leu Ile Glu Lys Trp Gln Ala Gly
            100                 105                 110

Ala Asp Met Val Leu Ala Lys Arg Ser Asp Arg Ser Thr Asp Gly Arg
        115                 120                 125

Leu Lys Arg Lys Thr Ala Glu Trp Phe Tyr Lys Leu His Asn Lys Ile
130                 135                 140

Ser Asn Pro Lys Ile Glu Glu Asn Val Gly Asp Phe Arg Leu Met Ser
145                 150                 155                 160

Arg Asp Val Val Glu Asn Ile Lys Leu Met Pro Glu Arg Asn Leu Phe
                165                 170                 175

Met Lys Gly Ile Leu Ser Trp Val Gly Gly Lys Thr Asp Ile Val Glu
            180                 185                 190

Tyr Val Arg Ala Glu Arg Ile Ala Gly Asp Thr Lys Phe Asn Gly Trp
        195                 200                 205

Lys Leu Trp Asn Leu Ala Leu Glu Gly Ile Thr Ser Phe Ser Thr Phe
210                 215                 220
```

```
Pro Leu Arg Ile Trp Thr Tyr Ile Gly Leu Val Ala Ser Val Ala
225                 230                 235                 240

Phe Ile Tyr Gly Ala Trp Met Ile Leu Asp Thr Ile Ile Phe Gly Asn
            245                 250                 255

Ala Val Arg Gly Tyr Pro Ser Leu Leu Val Ser Ile Leu Phe Leu Gly
            260                 265                 270

Gly Ile Gln Met Ile Gly Ile Gly Val Leu Gly Glu Tyr Ile Gly Arg
        275                 280                 285

Thr Tyr Ile Glu Thr Lys Lys Arg Pro Lys Tyr Ile Ile Lys Arg Val
        290                 295                 300

Lys Lys
305

<210> SEQ ID NO 9
<211> LENGTH: 14440
<212> TYPE: DNA
<213> ORGANISM: Artificial Sequence
<220> FEATURE:
<223> OTHER INFORMATION: example O4 rfb locus nucleotide sequence -
      O4-EPA production strain BVEC-L-00684f

<400> SEQUENCE: 9
atgacgaatt taaaagcagt tattcctgta gcgggtctcg ggatgcatat gttgcctgcc      60
actaaggcga tacccaaaga gatgctacca atcgtcgaca agccaatgat tcagtacatt     120
gttgacgaga ttgtggctgc agggatcaaa gaaatcctcc tggtaactca cgcgtccaag     180
aacgcggtcg aaaaccactt cgacacctct tatgagttag aatcactcct tgagcagcgc     240
gtgaagcgtc aactgctggc ggaagtacag tccatctgtc cgccgggcgt gaccattatg     300
aacgtgcgtc agggcgaacc tttaggttta ggccactcca tttttgtgtgc gcgacctgcc   360 attggtgaca acccatttgt cgtggtactg ccagacgttg tgatcgacga tgccagcgcc     420
gacccgctac gttacaacct tgctgccatg attgcacgtt tcaacgaaac gggccgcagc     480
caggtgctgg caaaacgtat gccgggtgac ctctctgaat actccgtcat ccagactaaa     540
gagccgctgg accgtgaggg taaagtcagc cgcattgttg aatttatcga aaaaccggat     600
cagccgcaga cgctggactc agacatcatg gccgtaggtc gctatgtgct ttctgccgat     660
atttggccgg aactgaacg tactcagcct ggtgcatggg gacgtattca gctgactgat     720
gctattgccg agctggcgaa aaaacaatcc gttgatgcaa tgctgatgac cggcgacagt     780
tacgactgcg gcaaaaaaat gggctatatg caggcgtttg tgaagtatgg cctacgcaac     840
ctgaaagaag gggcgaagtt ccgtaaaggt attgagaagc tgttaagcga ataatgaaaa     900
tctgaccgga tgtaacggtt gataagaaaa ttataacggc agtgaaaatt cgcagcaaaa     960
gtaatttgtt gcgaatcttc ctgccgttgt tttatataaa ccatcagaat aacaacgagt    1020
tagcagtagg gttttattca aagttttcca ggattttcct tgtttccaga gcggattggt    1080
aagacaatta gcgtttgaat ttttcgggtt tagcgcgagt gggtaacgct cgtcacatca    1140
taggcatgca tgcagtgctc tggtagctgt aaagccaggg gcggtagcgt gcattaatac    1200
ctctattaat caaactgaga gccgcttatt tcacagcatg ctctgaagta atatggaata    1260
aattaagtga aatacttgt tactggtggc gcaggattta ttggttcagc tgtagttcgt     1320
cacattataa ataatacgca ggatagtgtt gttaatgtcg ataaattaac gtacgccgga    1380
aaccgggaat cacttgctga tgtttctgat tctgaacgct atgttttga acatgcggat    1440 atttgcgatg cacctgcaat ggcacggatt tttgctcagc atcagccgga tgcagtgatg    1500
```

-continued

```
cacctggctg ctgaaagcca tgttgaccgt tcaattacag gccctgcggc atttattgaa    1560
accaatattg ttggtactta tgtccttttg gaagccgctc gcaattactg gtctgctctt    1620
gatagcgaca agaaaaatag cttccgtttt catcatattt ctactgacga agtatatggt    1680
gatttgcctc atcctgacga ggtaaataat acagaagaat tacccttatt tactgagaca    1740
acagcttacg cgccaagcag cccttattcc gcatccaaag catccagcga tcatttagtc    1800
cgcgcgtgga aacgtaccta tggtttaccg accattgtga ctaattgctc taacaattat    1860
ggtccttatc atttcccgga aaaattgatt ccattggtta ttctcaatgc tctggaaggt    1920
aaagcattac ctatttatgg taaagggggat caaattcgcg actggctgta tgttgaagat    1980
catgcgcgtg cgttatatac cgtcgtaacc gaaggtaaag cgggtgaaac ttataacatt    2040
ggtgggcaca acgaaaagaa aaacatagat gtagtgctca ctatttgtga tttgctggat    2100
gagattgtac cgaaagagaa atcttatcgt gagcaaatca cttatgttgc cgatcgtccg    2160
ggacacgatc gccgttatgc gattgatgct gagaatattg gtcgcgaatt gggatggaaa    2220
ccacaggaaa cgtttgagag cgggattcgg aagacagtgg aatggtatct gtccaataca    2280 aaatggggttg ataatgtgaa aagtggtgcc tatcaatcgt ggattgaaga gaactatgag    2340
ggccgccagt aatgaatatc ctcctttttg gcaaaacagg gcaggtaggt tgggaactac    2400
agcgtgctct ggcacctctg gtaacttga ttgctcttga tgttcattcc actgattatt    2460
gtggcgattt cagtaacccc gaaggtgtgg ctgaaaccgt caaaaaaatt cgcccagatg    2520
ttattgttaa tgctgctgct cataccgcgg tagataaggc tgagtcagaa ccagaatttg    2580
cacaattact caatgcgacc agcgttgaag caattgcaaa agcggctaat gaagttgggg    2640
cttgggtaat tcattactca actgactacg tcttccctgg aaatggcgac atgccatggc    2700
tcgagactga tgtaaccgct ccgctcaatg tttatggcaa aaccaaattg gctggagaaa    2760
gagcattaca agaacattgc gcaaagcatc ttatttccg taccagctgg gtatatgcag    2820
gtaaaggaaa taactttgcc aaaacaatgt tacgtctggc aaaagagcgc gaagaactgg    2880
ctgtgataaa cgatcagttt ggcgcaccaa caggtgctga attgctggct gattgcaccg    2940
ctcatgccat tcgcgtggca ttaaaaaaac cagaagttgc tggcttgtac catctggtag    3000
caaatggcac aacaacctgg cacgattacg ccgcgctagt attcgaagaa gcccgtaaag    3060
cagggattga ccttgcactt aacaaactca acgccgtacc aacaacggct tatcctactc    3120
cagcccgccg tcctcataat tctcgcctca ataccgaaaa gtttcagcag aactttgcgc    3180
ttgtcttgcc tgactggcag gtgggcgtga acgtatgct caacgaatta tttacgacta    3240
cggcaattta acaaattttt gcatctcgct catgatgcca gagcgggatg aattaaaagg    3300
aatggtgaaa tgaaaacgcg taaaggtatt attctggctg gtggttccgg cactcgtctt    3360
tatcctgtga cgatggcagt gagtaaacaa ctgctgccga tttatgataa gccgatgatt    3420
tattatccgc tttcaacgct tatgttagcg ggtattcgcg atattcttat tatcagtacg    3480
ccacaggata caccgcgttt ccaacaattg ttggggacg ggagtcagtg ggggcttaat    3540
ctacagtata agtacaacc gagtccggat ggcctggcgc aagcgtttat tattggtgaa    3600
gactttattg gtggtgatga ttgtgcactc gtacttggcg ataatatctt ctatggacac    3660
gacttgccga aattaatgga agctgctgtt aacaaagaaa tcggtgcaac ggtatttgct    3720
tatcacgtca atgatcctga acgttatggt gtcgtggagt ttgataataa cggtactgca    3780
attagcctgg aagaaaaacc gctggaacca aaaagtaact atgcggttac tgggctttat    3840
ttctatgaca atgatgttgt agaaatggcg aaaaaccttta agccttctgc ccgtggcgaa    3900
```

```
ctggaaatta ccgatattaa ccgtatttat atggagcagg gacgtttgtc tgtcgctatg   3960
atggggcgtg gttatgcctg gttggatact ggtacacatc aaagtcttat tgaagcaagt   4020
aacttcattg ccaccattga agagcgtcag ggattaaagg tatcttgccc ggaagagatt   4080
gcttaccgta aagggtttat tgatgctgag caggtgaaag tattagccga accgctgaag   4140
aaaaatgatt atggtcagta tctgctaaaa atgattaaag gttattaata aaatgaacgt   4200
aattaaaact gaaattcctg atgtgctgat ttttgaacca aaagtttttg gtgatgaacg   4260
tggcttcttt tttgagagtt ttaaccagaa agtatttgaa gaagctgtag gacggaaggt   4320
tgaatttgtt caggataacc attctaagtc taaaataaat gtattgcgtg ggatgcatta   4380
tcaaacacaa aatactcaag gaaaactggt tcgggtaatt tctggttcag tatatgatgt   4440
tgccgtagat ttaagagaaa atcaaagac atttggcaaa tgggtgggtg tagaattatc   4500
tgggaataat aaaagacaat tgtggatccc cgaaggtttt gcccatggtt tttatgtgtt   4560
ggaggagaat accgaatttg tttataaatg taccgatact tataaccctg ctcatgaaca   4620
cacattgcta tggaatgatc caactatcaa tataagttgg ccaatcatac aaaactgcaa   4680
gccaattatt tctgaaaaag atgctaatgg acatcttttt tcacataaaa cctatttctg   4740
aaatgcaata ttatgagttt aattagaaac agtttctata atattgctgg ttttgctgtg   4800
ccgacattag ttgcagtccc tgctttgggg attcttgcca ggctgcttgg accggagaat   4860
tttggacttt tcacactagc attcgctttg ataggatatg caagtatttt cgacgccggg   4920
attagtcgag ctgtaatcag agaaatcgct ctttatcgag aaagtgaaaa agagcaaata   4980
caaattattt cgacagcaag tgtaatcgta ctattcttag gggtggttgc agctttgtta   5040 ctttattta gtagtaataa agttgttgag ttattgaatg ttagttccgt ttatattgaa   5100
acagcagtgc gtgcattctc tgttatttca tttataatac ctgtgtatct gattaaccag   5160
atttggcttg gttatctgga agggctagaa aaatttgcaa atataaatgt tcagagaatg   5220
atttctagca caagcttggc tatattacca gtgatatttt gttattacaa tccctcgttg   5280
ctttatgcta tgtatgggtt ggtggttggg cgtgtgattt catttttgat tagcgcaata   5340
atttgtcgag atattattct taaaagtaaa ctttacttta atgtggcaac ttgcaatcgt   5400
cttatctctt ttggtggatg gataacagtt agtaatatca taagcccaat catggcatat   5460
ttcgaccgct ttatcatctc tcatattatg ggggcttcga gaattgcatt ttatacagcg   5520
ccctcagagg gtgtatcaag gttaattaat atcccatatg ctttggcaag agctctattt   5580
cctaaattgg catatagcaa taatgatgat gaacgaaaaa aattacaact acagagctac   5640
gcaattataa gcattgtatg tctacccata gttgttattg gtgtcatttt tgcctcattc   5700
ataatgacaa catggatggg acctgattat gccttagaag cagcaactat catgaaaata   5760
cttcttgctg gttttttctt taactcttta gcgcaaatac cttatgcata cttgcaatct   5820
atcggaaagt caaaaattac cgcatttgtg catctccatag aacttgcgcc atacttatta   5880
ttattgtatt acttcacaat gcatttcggc ataattggca cggcaatcgc ttggtcactt   5940
agaacatttt gtgattttgt tatactactt tcgatatcga gaagaaaatg attgcggttg   6000
atattgcgct tgcaacctac aatggtgcta atttttattcg gcaacagatt gaatctatcc   6060
agaaacaaac ttatagaaat tggcgtctta taataagtga tgataactcg agtgatgata   6120
ctgttgatat tattaaggat atgatgtcta acgacagtcg tatctatttg gtaggaaata   6180
aaagacaagg aggggttatt cagaacttta attatgctct ttcacaaact acatctgaaa   6240
```

-continued

```
ttgtgttact atgtgaccag gatgacattt ggccggagga gcgtctggaa attcttatag    6300
ataaatttaa ggccttgcag cgtaatgatt ttgttccggc aatgatgttt actgatttga    6360
aattagtaga cgaaaataat tgtttgattg cagaaagttt ttatcgaacg aataatatta    6420
atccacaaga taatctgaaa aataataatc ttctctggcg ttcaacggta tatggctgta    6480
cttgcatcat gaataagaaa cttgttgata ttgcattgcc tatacctaca tatgcacata    6540
tgcatgatca atggttggca ttattagcga agcaatatgg taacattttt tatttcgact    6600
atgcgtctgt tcgttatagg caacattcta caaatgttgt tggtggtaga aataaaacgc    6660
catttcaaaa atttaattcc atacaaaaaa acctaaaaag gattaatttg ctagtggata    6720
gaactgttgc tttaattaaa tcaaataacg atttctatcc agggaataaa atggaaaata    6780
aaattgatta cttaaaattt ggagtgaatg aagtattacc ttatcttttt aaaggaaaca    6840
agaaagtttt ttcactttgt gtattaatta gtttggcatt acaaaaatga tatatttatt    6900
attttttttt gcactgttta tgatctgtac gtttttaaca cacaggcgac aggcattata    6960
tgttgtatct gcgttagtat ttcttttttt ggctttaacc tatccatcag gaggggactg    7020
gataggttat tttctccatt atgactgcat ggttaatgag cagtgtaata atggtttat     7080 aatgtttgaa cctggatatg aattaattgt ttccttattt ggatatttgg gatttcagac    7140
aattattatt tttatagccg ctgtaaatgt aattctaata ttaaattttg caaagcattt    7200
tgaaaacgga agttttgtta ttgttgcgat aatgtgcatg ttcctttgga gtgtttatgt    7260
tgaggcgatt agacaggctc tggccttatc tatagttata tttgggattc attctctttt    7320
tttgggtaga aaaaggaaat ttataacatt agtattattt gcgtcaactt tccatataac    7380
tgctttgatt tgttttcttc taatgactcc tctatttttca aagaaattaa gcaagataat    7440
aagttatagc ctattaattt tcagtagctt cttttttcgct ttttctgaaa ccatattaag    7500
tgcactcctt gcaattttgc cagaaggatc cattgccagt gaaaaattaa gttttttactt   7560 agcaaccgag caatacaggc cacagttatc tattgggagt ggcactattc ttgacattat    7620
acttattttt ctgatatgtg taagttttaa acgaataaag aaatatatgc tcgctaatta    7680
taatgctgca aatgagatat tgcttattgg ttgctgtctt tatatttctt tcggtatttt    7740
tatcgggaaa atgatgccag ttatgactcg cattggttgg tatggttttc catttgttat    7800
agtacttctt tatattaact tgggttattc agaatatttt aagaggtata taaataaaag    7860
agggtgtggg tatagcaaat tattaattgc ttttttatttt ttgctacaaa ttttgcgacc    7920
attaacatat gattatagct attataatat aatgcaccag gatactttgc tgaataggtt    7980
tgatgcatta gatgatgcat cattaagaca atcagcgaag agaaaatgtt tcgatttggg    8040
aaagatagga tatggtttct tatgtagtat ataatatcct gcattcattc ggataatttc    8100
ctatggaagt gtccttttgct ctgtctgtcc tcatttgttg aaattttatg ttaataagaa    8160
gctttagata accacttagg aactgtatgt ttgatctgtc caaaaattat attattgtaa    8220
gtgcgacggc gctggcttcc ggaggtgcat taactatatt aaagcaattt ataaaacatg    8280
catcacaaaa ttcaaatgac tatattatgt ttgtatctgc gggattggag ttgccggtct    8340
gtgataacat catttacata gaaaacacac caaaaggatg gttgaaaaga atatattggg    8400
attggttcgg ttgtcggaag tttatctcgg aacataagat taacgttaag aaagtaattt    8460
ctctacaaaa ttccagtttg aatgttcctt acgaacagat tatttacttg caccagccaa    8520 ttcctttttag taaagttgat tctttttttaa aaatatcac atccgataac gtaaagcttt    8580
ttttatataa aaagttttat tcctattttta tatttaaata tgtgaatgcc aatacaacca    8640
```

```
tcgtagtgca aacgaattgg atgaaaaaag gagtgctgga gcaatgtgat aaaattagta    8700
ccgaaagggt ccttgttata aaacctgata tcaaagcatt taataatact aattttgatg    8760
tagatatgga tgtatctgca aaaacactct tatatccagc gacaccactt acctataaaa    8820
atcatttggt cattctgaag gcgttggtta ttttaaagaa aaagtatttt atagatgatc    8880
tgaaattcca agtgactttt gaaaagaata ggtacaaaaa ttttgataag tttgtgcaat    8940
taaataactt aagcaaaaac gttgattatc tcggcgttct ttcatactcg aacttgcaaa    9000
aaaaatatat ggcggcatct ttaatcgttt ttcctagcta tatcgaatca tatgggttac    9060
cactcatcga agctgctagt ttaggaaaaa aaatcattag tagtgatctt ccttatgccc    9120
gggatgtttt aaaggattat agcggcgtag attttgtaat ttacaataat gaagatggct    9180
gggctaaggc gttgtttaat gttttaaatg gcaattcgaa gctcaatttt aggccttatg    9240
aaaaagatag tcgttcatct tggccacagt tcttctctat tttgaaataa ggtgtattat    9300
gtttaatggt aaaatattgt taattactgg tggtacgggg tctttcggta atgctgttct    9360
aagacgtttt cttgacactg atatcaaaga aatacgtatt ttttcccggg atgaaaaaaa    9420
acaagatgac atgaggaaaa aatataataa tccgaaactt aagttctata taggtgatgt    9480
tcgcgactat tcgagtatcc tcaatgcttc tcgaggtgtt gattttattt atcatgctgc    9540
agctctgaag caagtacctt cctgcgaatt ccacccaatg gaagctgtaa aaacgaatgt    9600
tttaggtacg gaaaacgtac tggaagcggc aatagctaat ggagttaggc gaattgtatg    9660
tttgagtaca gataaagctg tatatcctat caatgcaatg ggtatttcca agcgatgat    9720
ggaaaaagta atggtagcaa atcgcgcaa tgttgactgc tctaaaacgg ttatttgcgg    9780
tacacgttat ggcaatgtaa tggcatctcg tggttcagtt atcccattat ttgtcgatct    9840
gattaaatca ggtagaccaa tgacgataac agaccctaat atgactcgtt tcatgatgac    9900
tctcgaagac gctgttgatt tggttcttta cgcatttgaa catggcaata atggtgatat    9960
ttttgtccaa aaggcacctg cggctaccat cgaaacgttg gctattgcac tcaaagaatt   10020
acttaatgta aaccaacacc ctgtaaatat aatcggcacc cgacacgggg aaaaactgta   10080
cgaagcgtta ttgagccgag aggaaatgat tgcagcggag gatatgggtg attattatcg   10140
tgttccacca gatctccgcg atttgaacta tggaaaatat gtggaacatg gtgaccgtcg   10200
tatctcggaa gtggaagatt ataactctca taatactgat aggttagatg ttgagggaat   10260
gaaaaaatta ctgctaaaac ttcctttat ccgggcactt cggtctggtg aagattatga   10320
gttggattca taatatgaaa attttagtta ctggcgctgc agggtttatc ggtcgaaatt   10380
tggtattccg gcttaaggaa gctggatata acgaactcat tacgatagat cgtaactctt   10440
ctttggcgga tttagagcag ggacttaagc aggcagattt tattttttcac cttgctgggg   10500
taaatcgtcc cgtgaaggag tgtgaatttg aagagggaaa tagtaatcta actcaacaga   10560
ttgttgatat cctgaaaaaa aacaataaaa atactcctat catgctgagt tcttccatcc   10620
aggctgaatg tgataacgct tatggaaaga gtaaagcagc tgcggaaaaa atcattcagc   10680
agtatgggga aacgacaaac gctaaatatt atatttatcg cttgccgaat gtattcggta   10740
agtggtgtcg accaaattat aactccttta tagcaacttt ctgccatcgc attgcaaatg   10800
atgaagctat tacaattaat gatccttcag cagttgtaaa tctggtgtat atagatgact   10860
tttgttctga catattaaag ctattagaag gagcgaacga aactggttac aggacatttg   10920
gtccaatttta ttctgttact gttggtgaag tggcacaatt aatttaccgg tttaaagaaa   10980
```

```
gtcgccaaac attaatcacc gaagatgtag gtaatggatt tacacgtgca ttgtactcaa    11040
catggttaag ttacctgtct cctgaacagt ttgcgtatac ggttccttct tatagtgatg    11100 acagagggt attctgtgaa gtattgaaaa cgaaaaacgc gggccagttt tcgttcttta    11160
ctgcgcatcc aggaattact cggggtggtc attatcatca ttccaaaaat gagaaattta    11220
ttgtcatccg aggaagtgct tgtttcaaat ttgaaaatat tgtcacgagt gaacgatatg    11280
aacttaatgt ttcctctgat gattttaaaa ttgttgaaac agttccggga tggacgcata    11340
acattactaa taatggctcg gatgagctag ttgttatgct ttgggcaaat gaaatattta    11400
atcgttctga accagatact atagcgagag ttttatcgtg aaaaaattga agtcatgtc    11460 ggttgttggg actcgtccag aaattattcg actctcgcgt gtccttgcaa aattagatga    11520
atattgtgac caccttattg ttcataccgg gcaaaactac gattatgaac tgaatgaagt    11580
ttttttcaaa gatttgggtg ttcgcaaacc tgattatttt cttaatgccg caggtaaaaa    11640
tgcagcagag actattggac aagttatcat taaagttgat gaggtccttg aacaggaaaa    11700
accagaagcc atgttagtac ttggcgatac taactcctgt atttcagcaa taccagcaaa    11760
gcgtcgaaga attccgatct tccatatgga ggctgggaat cgttgttttg accaacgcgt    11820 accgaagaa actaacagaa aaatagttga tcataccgct gatatcaata tgacatatag    11880
tgatatcgcg cgtgaatatc ttctggctga aggtgtacca gccgatagaa ttattaaaac    11940
cggtagccca atgtttgaag tactcactca ttatatgccg cagattgatg gttccgatgt    12000
actttctcgc ctgaatttaa cacctgggaa tttctttgtg gtaagtgccc acagagaaga    12060
aaatgttgat accccctaaac aacttgtgaa actggcgaat atactaata ccgtggctga    12120 aaaatatgat gtcccggtag ttgtttctac tcatcctcgc actcgtaacc gcatcaacga    12180
aaacggtatt caattccata aaaatatctt gcttcttaag ccattaggat ttcacgatta    12240
caaccatctg caaaaaatg cacgtgctgt tttatcggat agtgggacta ttacagaaga    12300
gtcctccatt atgaacttcc ctgcactcaa tatacgagaa gcgcacgaac gcccggaagg    12360
cttcgaagaa ggggcagtaa tgatggtcgg tcttgaatct gatcgcgttt tacaggcatt    12420
agaaattatt gcaacacagc ctcgtggaga agtacgctta cttcgtcagg ttagtgacta    12480
tagcatgcca aatgtttcag ataaagttct gcgtattatc cattcatata ctgactacgt    12540
taaacgggtt gtctggaagc aatactaatg aaacttgcat taatcattga tgattatttg    12600
ccccatagca cacgcgttgg ggctaaaatg tttcatgagt taggccttga attactgagc    12660
agaggccatg atgtaactgt aattacgcct gacatctcat tacaagcaat ttattctatt    12720
agtatgattg atggtataaa ggtttggcgt ttcaaaagtg gacctttaaa ggatgtaggt    12780
aaggctaaac gtgccataaa tgaaactctt ttatctttc gcgcatggcg cgcatttaag    12840
cacctcattc aacatgatac atttgatggt atcgtttatt attcccctc tattttttgg    12900 ggcgacttgg ttaaaaaaat aaaacaacga tgccagtgcc caagctatct gatcctaagg    12960
gatatgtttc cacagtgggt cattgatgca ggtatgttga agccggttc accaattgaa    13020 aaatatttta ggtattttga aaaaagtca tatcagcagg ctggccggat agggtaatg    13080 tctgataaga atcttgagat attttcgccag accaataaag gttatccgtg tgaagtttta    13140
cgtaattggg cctcaatgac tcctgtgtct gccagcgatg attatcattc acttcgtcaa    13200
aaatacgatc taaagataa agtcattttt ttctatggcg gtaatattgg gcatgctcag    13260
gatatggcaa acttaatgcg ccttgcgcgt aatatgatgc gttatcatga tgctcatttc    13320
ctgtttatag ggcagggtga tgaagttgag ctgataaaat ctcttgctgc agaatggaat    13380
```

-continued

```
ttaactaatt tcactcatct accttcagtg aaccaggaag agtttaaatt aattttatct    13440
gaagttgatg tcggcctgtt ctcccttca tctcgccatt cttcacataa tttccccgga    13500
aaattactag ggtatatggt tcaatcaatc ccgatccttg ggagtgtgaa tggcggcaat    13560
gatttaatgg atgtaattaa taagcacaga gccggtttca ttcatgttaa tggtgaagat    13620
gataaactgt ttgaatctgc acaattgctt cttagtgatt cagttttaag aaaacagcta    13680
ggtcagaacg ctaatgtgtt gttaaagtct caattttcgg ttgaatcggc ggcacatact    13740
atcgaagtcc gactggaggc tggagaatgc gtttagttga tgacaatatt ctggatgaac    13800 ttttttcgcac tgcagcaaat tctgaacgtt tgcgcgctca ttatttattg cacgcatctc    13860
atcaggagaa ggttcaacgt ttacttattg catttgtacg cgacagctat gttgaacccc    13920
attggcatga gttaccgcat cagtgggaaa tgtttgtcgt catgcaaggg caattagaag    13980
tttgtttgta tgagcaaaat ggtgagatcc aaaaacagtt tgttgttgga gacggtacgg    14040
gaataagcgt cgtggaattt tccccaggag atatacatag tgtcaaatgc ctgtcaccaa    14100
aagcccttat gttggagata aaggaggggc catttgaccc actcaaagct aaggcttttt    14160
ctaagtggtt atagggcgat acaccaccgt ttattcttct atcttattct atacatgctg    14220
ggttaccatc ttagcttctt caagccgcgc aaccccgcgg tgaccacccc tgacaggagt    14280
agctagcatt tgaccacccc tgacaggatt agctagcata tgagctcgag gatatctact    14340
gtgggtaccc gggatccgtg taggctggag ctgcttcgaa gttcctatac tttctagaga    14400
ataggaactt cggaatagga actaaggagg atattcatat                          14440
```

<210> SEQ ID NO 10
<211> LENGTH: 19
<212> TYPE: PRT
<213> ORGANISM: Artificial Sequence
<220> FEATURE:
<223> OTHER INFORMATION: example signal sequence for EPA carrier protein

<400> SEQUENCE: 10

Met Lys Lys Ile Trp Leu Ala Leu Ala Gly Leu Val Leu Ala Phe Ser
1               5                   10                  15

Ala Ser Ala

<210> SEQ ID NO 11
<211> LENGTH: 13043
<212> TYPE: DNA
<213> ORGANISM: Artificial Sequence
<220> FEATURE:
<223> OTHER INFORMATION: example O1A rfb locus nucleotide sequence -
      O1A-EPA production strain stGVXN4411 and stLMTB10217

<400> SEQUENCE: 11

```
atgacgaatt taaaagcagt tattcctgta gcgggtctcg ggatgcatat gttgcctgcc      60
actaaggcga tacccaaaga gatgctacca atcgtcgaca agccaatgat tcagtacatt     120
gttgacgaga ttgtggctgc agggatcaaa gaaatcctcc tggtaactca cgcgtccaag     180
aacgcggtcg aaaaccactt cgacacctct tatgagttag aatcactcct tgagcagcgc     240
gtgaagcgtc aactgctggc ggaagtacag tccatctgtc cgccgggcgt gaccattatg     300
aacgtgcgtc agggcgaacc tttaggttta ggccactcca ttttgtgtgc gcgacctgcc     360
attggtgaca acccatttgt cgtggtactg ccagacgttg tgatcgacga tgccagcgcc     420
gacccgctac gttacaacct tgctgccatg attgcacgtt tcaacgaaac gggccgcagc     480
```

```
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagcta gcgtgaagat acttgttact aggggcgcag gatttattgg ttctgctgta   1320
gttcgtcaca ttataaataa tacgcaggat agtgttgtta atgtcgataa attaacgtac   1380
gccggaaacc tggaatcact tgctgatgtt tctgactctg aacgctatgt ttttgaacat   1440
gcggatattt gcgatgctgc tgcaatggcg cggattttg ctcagcatca gccggatgca   1500
gtgatgcacc tggctgctga agccatgtg gatcgttcaa ttacaggccc tgcggcattt   1560
attgaaacca atattgttgg tacttatgtc cttttggaag cggctcgcaa ttactggtct   1620
gctcttgatg gcgacaagaa aaatagcttc cgttttcatc atatttctac tgacgaagtc   1680
tatggtgatt tgcctcatcc tgacgaagta aataataaag aacaattacc cctctttact   1740
gagacgacag cttacgcgcc tagtagtcct tattccgcat caaaagcatc cagcgatcat   1800
ttagtccgcg cgtggaaacg tacctatggt ttaccgacta ttgtgactaa ctgttcgaat   1860
aactacggtc cttatcactt tccggaaaaa ttgattccac tagtaattct taatgctctg   1920
gaaggtaagg cattacctat ttatggcaaa ggggatcaaa ttcgtgactg gctgtatgtt   1980
gaagatcatg cgcgtgcgtt atataccgta gttactgaag gtcaagcggg tgaaacctat   2040
aacattggcg gacacaacga aaagaaaaac atcgatgttg tgctgactat ttgtgatttg   2100
ttggacgaga tagtcccgaa agagaaatct tatcgtgagc aaattactta tgttgctgat   2160
cgcccagggc atgatcgccg ttatgcgatt gatgctgaga agattggtcg cgaattggga   2220
tggaaaccac aggaaacgtt tgagagtggg attcgtaaaa cggtggaatg gtatttggct   2280
aatgcaaaat gggttgataa tgtgaaaagt ggtgcctatc aatcgtggat tgaacagaac   2340
tatgagggcc gccagtaatg aatatcctcc tttttggcaa aacagggcag gtaggttggg   2400
aactacagcg tgctctggca cctctgggta atttgattgc tcttgatgtt cactccactg   2460
attactgtgg tgattttagt aaccctgaag gtgtggctga aacagtcaaa gaattcgac    2520 ctgatgttat tgttaatgct gcggctcaca ccgcagtaga taaggctgag tcagaacccg   2580
aatttgcaca attactcaat gcgactagcg ttgaatcaat tgcaaaagcg gcaaatgaag   2640
ttggggcttg ggtaattcat tactcaactg actacgtatt ccctggaaat ggcgacacgc   2700
catggctgga gatggatgca accgcaccgc taaatgttta cggtgaaacc aagttagctg   2760
gagaaaaagc attacaagag cattgtgcga agcacctaat tttccgtacc agctgggtct   2820
atgcaggtaa aggaaataat ttcgccaaaa cgatgttgcg tctggcaaaa gagcgtgaag   2880
```

```
aactagccgt tattaatgat cagtttggtg cgccaacagg tgctgaactg ctggctgatt    2940
gtacggcaca tgccattcgt gtcgcactga ataaaccgga tgtcgcaggc ttgtaccatt    3000
tggtagccag tggtaccaca acctggtacg attatgctgc gctggttttt gaagaggcgc    3060
gcaatgcagg cattcctctt gcactcaaca agctcaacgc agtaccaaca actgcctatc    3120
ctacaccagc tcgtcgtcca cataactctc gccttaatac agaaaaattt cagcagaatt    3180
ttgcgcttgt attgcctgac tggcaggttg gtgtgaaacg catgctcaac gaattattta    3240
cgactacagc aatttaatag tttttgcatc ttgttcgtga tggtggagca agatgaatta    3300
aaaggaatga tgaaatgaaa acgcgtaaag gtattatttt agcgggtggt tctggtactc    3360
gtctttatcc tgtgactatg gtcgtcagta acagctatt acctatatat gataaaccga    3420
tgatctatta tccgcttcct acactgatgt tagcgggtat tcgcgatatt ctgattatta    3480
gtacgccaca ggatactcct cgttttcaac aactgctggg tgacggtagc cagtggggcc    3540
tgaatcttca gtacaaagtg caaccgagtc cggatggtct tgcgcaggca tttattatcg    3600
gtgaagagtt tattggtggt gatgattgtg ctttggtact tggtgataat atcttctacg    3660
gtcacgacct gcctaagtta atggatgccg ctgttaacaa agaaagtggt gcaacggtat    3720
ttgcctatca cgttaatgat cctgaacgct atggtgtcgt tgagtttgat aaaaacggta    3780
cggcgatcag cctggaagaa aaaccgctac aaccaaaaag taattatgcg gtaaccgggc    3840
tttatttta tgataacgac gttgtcgaaa tggcgaaaaa tcttaagcct tctgcccgcg    3900
gtgaactgga aattaccgat attaaccgta tctatatgga acaagggcgt ttatctgttg    3960
ccatgatggg gcgtggttat gcgtggttag acacggggac acatcagagc ctgattgagg    4020
caagcaactt tattgcaaca attgaagagc gtcaggggct gaaagtttcc tgcccggaag    4080
aaattgctta ccgtaagggg tttgttgatg ctgagcaggt gaaagtatta gctgaacctc    4140
tgaaaaaaaa tgcttatggt cagtatctgc tgaaaatgat taaaggttat taataaaatg    4200
aacgtaatta aaacagaaat tcctgatgta ctgattttg aaccgaaagt ttttggtgat    4260
gagcgtggtt tcttttttga gagctttaac cagaaggttt ttgaggaagc tgtaggccgc    4320
aaagttgaat ttgttcagga taaccattcg aagtctagta aaggtgtttt acgcgggctg    4380
cattatcagt tggaacctta tgcacaagga aaattggtgc gttgcgttgt cggtgaagtt    4440
tttgacgtag ctgttgatat tcgtaaatcg tcatcgactt ttggcaaatg ggttggggtg    4500
aatttatctg ctgagaataa gcggcaattg tggattcctg agggatttgc acatggtttt    4560
ttagtgctga gtgagacggc ggagttttga taagacga caaattatta tcatcctcag    4620
agtgatagag gaataaaatg ggatgatcca agcatcaata tttcatggcc agtcgattca    4680
caagtgctgc tatcagctaa agataataag catcctccat taacaaagat tgaaatgtat    4740
agttaagatc acgataaatc ttggaagggt tgcaaaattg aataaaatag tgagcaaaag    4800
tgaaataagg aacgtaatcc acaatgctgg ctatatgatg attactcaga tagctttata    4860
tgttgcacca ttatttatac tgagttatct gttaaaaaca ctgggggttg cacagtttgg    4920
taattatgcc ttaatactat caatcgttgc atatttacag attataacgg attatggttt    4980
ttcttttagt gcaagtcgtg cgatctcaca gaatagagag gacaaagaat atatatcaaa    5040
aatttatctg tcaactatga ctatcaagtt ggcgatatgc gctttcttat tcttattgct    5100
catgctattt ttaaatcttt tgcctgtgca agctgaatta aaacaaggaa tattatatgg    5160
atatcttctt gtaataggaa atactttcca accacaatgg ttttccaag gtatcgaaaa    5220
```

```
attaaaaatc atagcccttt ctaatgttat atcaagatgc gccgcgtgtt tacttgtatt    5280
tatctatgtg aggaatagcg aggatttaca aaaagcactt ttagtacagt cacttccatt    5340
agtaatttct gcgattggat taaatatatt tatattgaaa tatatcaata ttattttcc    5400
ggaaaaaaaa ttatttaagg taattttaaa agaaggtaag gattttttc ttgcatcact    5460
ttattctgtt attctcaata atagtggcat ttttctatta gggattttta ctaatcctgt    5520
tattgttggt gtatatgccg ccgctgaaaa gatagtcaag gccgtattgt cgctatttac    5580
accactgacg caagctatat atccttataa ttgtcgtaag ttttcactat ccgtatttga    5640
cggcattgag gcagcaaaaa aaactggtat accaattata attttagcat ttatagctgc    5700
tgttatcgtt gcaattaccct tacctgttgc aatcgactat cttaattttc aaaagaaac    5760
aattttgta ggtcaaatat taagtgcatg gatctttttt ggtgttctta ataatgtatt    5820
cggcattcag atattgagtg catcaggaag aagtaaaata tatagtagga tggtattcgt    5880
atcagcgctt ataacattac ttttgattac tctattattg cagttttgta acgccactgg    5940
agtggcatgt gcaatattat tgggtgaaat gttcttatca atattgttac ttaagcgata    6000
taaaaaaata atttaaggaa tagttatgaa gaagttatta ttagtgttcg gtactaggcc    6060
tgaagcaata aagatggcct ctatcattga attattaaaa aaagattgta gattcgaata    6120
taaaatatgt gtgacaggcc aacataaaga gatgcttgat caagttatgc aagtatttga    6180
tgttaaacct gattataatt tacgattat gcagcctggg caaacattag tatctatagc    6240
aacaaatata ctctcacggt taagtgaagt tttaattata gaaagccag atattatact    6300
tgtgcatggg gatacaacga ctacccttgc tgctacttta gctgggtatt accaccaaat    6360
aaaagtttgt catgtggaag caggattaag aacaggggat atttactctc cttggcctga    6420
agagggcaat cgtaaagtta caggggcatt agcatgtatt catttcgccc caacagagag    6480
atcaaaagat aatctcctga gggaggggt caaagtaaat aatatatttg taacgggtaa    6540
taccgtcatc gactctttat ttattgcaaa agatatcata gataatgacc ctaatataaa    6600
gaacgcttta cataataaat ttaatttct tgataaaagc cgacgagtag tacttataac    6660
aggtcatcga agagaaaatt tcgggaaagg ttttgaagat atatgctttg caataaagga    6720
attagctttc attatccta atgtagattt tatttatccg gtgcatctta atcccaatgt    6780
aatggaacca gtacatcgta tattagataa tatatgtaat atttacctta ttgagccctt    6840
ggattatttg cctttttgttt atttaatgaa tgagtcatat ttaatattga ctgattcagg    6900
ggggatacaa gaagaagcgc cttcgttagg taaaccggtt ttggttatgc gtgatactac    6960
tgaacgccct gaggcggttg aggctggtac tgttgtatta gtggggactt ctaagataaa    7020
aatagtaaat aaagtaacgg agctattaaa caatgctgat atctacaatg ctatgtctct    7080
gttacataat ccatatggcg atggaacagc tgctcaaaaa attcttaatg tgctcgccca    7140
agagctaatt taatttaagc taaaaatatg ttattaatta ttgctgatta tccaaacgaa    7200
atgaatatgc gcgagggagc tatgcaacga atagatgcga tagactctct cattcgagat    7260
cgcaagcgag tgtatttgaa tatttcattc aaaaagcatc tagttcgctc aaatagttcc    7320
tttaataatg ttatagttga aaatctaaat gcaattattc acagaaacat cataaaacag    7380
tacatgcaaa aatcaacaac tatatatgtt cattctgttt ataatttatt aaaggttata    7440
acgctcattg atctaaaaaa aacaattctt gatatacatg gtgttgtacc ggaagaactt    7500
ttggcagata ataaaaaatt acttagtaaa gtatataaca tggtgaaaaa aaaggtgtc    7560
cttggatgca aaaaattaat acacgtcagt acagaaatgc aaaaacacta tgaagcaaaa    7620
```

```
tatggagtaa acttggctga aaggtcaata gtgctcccga ttttgaata taaaaatata   7680
acccaatcgc aaacaaatg acagaaaat aaaatacgaa gtatctatct tggaggatta    7740
caaacatggc aaaatattga taaaatgatt caagtttgtg atgacacagt gataaacaat   7800
gaagcaggta agtatgaatt caacttttc atcccacaga gtaacttgga agggtttata   7860
gataaatatt cgttaaaatt acataatatc aatgctaatg catctacgct atcacgtgat   7920
gaagtaattc cctttctaaa agaatgtcat attggttttg tattgcgcga tgatataata   7980
gtaaacagag ttgcgtgccc tacaaaattg gttgaatatt tagagtgtgg tgtcgttcca   8040
gttgtgctct ccccacttat aggtgatttt tattcgatgg gatatcaata cattactaca   8100
gaggaaatgg ctaacagaag tataagtttg ttggatcttg aaaaaatggc tgcacataat   8160
ttacaaattt tgacttctta tcagaagaga acctacaagg cacagaaaga acttattgct   8220
caactgtgct gaatttttta catatataaa attatgtaag catatcgcgg gtcaggtaat   8280
tgtatgcgta tcaaatataa agataacggt tatatattat gttttctatt atgtttcatt   8340
ttgagctact tagttttact caaatctgac tactttcctg ctgattttct gccatataca   8400
gaaatatacg atgggacata cggagaaatc aataatattg agcctgcctt tttatattta   8460
acacggttgt ttcattattt aaatttcccc tatatatttt ttgcaatgtt agtttgtgcc   8520
ttatgtttaa gttggaaaat aaaatatgca agaaaaataa ttaaagatag ttatatatat   8580
ttgttcttgt atgtatatgt atcatttat gtgtttttgc atgaaatgac tcaattgcgc    8640
atagcaattg cagtcactat gtgctatgtg tcggtttatt attactttta taaaaattgt   8700
attaaacatg cactgccatg gatggtgttg gctattttgt ttcattacag cgccttgctt   8760
ttatttatgt cattatttat atacagttat aggaggttat taatagtaat tatagggttt   8820
gtaatatgta tgagcttttt aaacgtgtat gcagatacaa ttgcactata tttgccaaat   8880
gaaaaaatag taaattattt atatagtatt tcatcatcat tagacaatag aaatgatttg   8940
gcaatattca acctgaataa tataatatt ttatcaatat ttatttgat cttttatctt     9000
agccgatata taaattaaa tgataatgag gcgaagttta ttaagtatgt gcaatgttca    9060
ggaatattag ccttttgtat tttctttctg gctagtggag tcccggtcat tgcttatcga   9120
actgcagagt tgctgcgaat attttatccg atggctttag tattaatcct ttcgcatata   9180
aaaaataata atatgcgtta ttttattgca gtcattatag ttatcctttc aggcttaatg   9240
ttgtttataa cactaagggc tgtatcaata gttggtcaag gattataaaa tgaatgttgc   9300
tattttgttg tctacgtata atggcgaaaa atatttagag gaacaactgg attcattgct   9360
gcttcaaagt tatcaggatt ttgtagtgta tatccgtgat gacggatcat ctgatagaac   9420
tgtaaatata ataaaccaat acgtaatgaa agataacaga tttattaacg tgggtaattc   9480
agaaaatctt ggttgtgctg cttcgtttat taatttatta agaaatgctt cagccgatat   9540
ttatatgttt tgtgaccaag atgattattg gcttccgaat aaattacagc gtgctgtgga   9600
ttatttttcg gctattgatc ctttacaacc taccttgtat cattgcgatc taagcgttgt   9660
tgatgaaaaa cttaatatta tacaaaattc attttttgcag catcagaaaa tgtcagcgta   9720
tgattcaatg agaaaaaata atcttttcat acaaaattt gttgttggtt gttcatgtgc    9780
tgttaatgct tcacttgcgg aatttgttct ttcgcgaatt ggagagcagc atgtaaaaat   9840
gatagctatg catgactggt ggttagccgt gactgcaaaa cttttggtc gaatccattt    9900
tgataatact caaacgattc tttatcgaca acatcagggc aatgtattag gtgcaaaatc   9960
```

```
atcaggtatg atgcgtttta ttcgattagg attaaatggg caagggattt cgcgagtagt   10020
atcttttaga aaaaaagttt gtgcgcaaaa taagcttctt ttagatgtct atgataaaga   10080
tttaaatctt gagcaaaaaa aatctatcag gcttgtaatt gagggcctta aagagaactc   10140
ttcaattgct gaccttttaa aatgtttcta tcatggtagc tatatgcaag gttttaaacg   10200
taatcttgcc ttaatatatt cagttcttta cacaaaaaaa agaagatagt gtatccttat   10260
gaaaaaaatt gctattatcg gtactgttgg cataccagca tcatatggcg gatttgaaac   10320
attagttgaa aatttaacaa gatacaattc ctcgggagtt gaatataatg tttttttgttc  10380 atcgtttcac tacaaatccc accaaaaaaa acataatggg gcccgtttaa tttatattcc   10440
gcttaaagcc aatggatggc agagcattgc gtatgacata atttcgttag catattctat   10500 tttttttgaag cctgatgtga ttctgatttt aggggtttct ggttgttcat ttttgccttt   10560
cttcaaactc ttaacacgcg ctaagtttat tactaatatt gatggcctgg aatggcgaag   10620
agataaatgg aattcaaaag tgaaacgttt cttaaaattt tcagaaaaaa tcgcagttca   10680
atattcggat gtcgttatta cggataatga ggcaatttct gagtacgttt ttaacgagta   10740
taataaagat agccgagtta ttgcctatgg aggggatcat gcatggttaa atactgagga   10800
tgtatttaca acaagaaatt ataaaagcga ttactacctt tctgtatgtc gtatcgaacc   10860
cgaaaacaat gtagaattaa ttttaaaaac attttcaaag ctaaaatata aaataaaatt   10920
tattggaaat tggaatggca gcgagtttgg aaagaaactt aggctgcatt attctaacta   10980
tccaaatatt gaaatgattg atccgattta tgatcttcaa caattatttc acttacgaaa   11040
taattgcata ggatatatac atggtcattc ggctggagga acaaaccctt ctttagtcga   11100
ggcaatgcat tttagtaaac ctatatttgc atatgattgt aagtttaata ggtacactac   11160
tgaaaatgaa gcatgttatt tttctaatga atctgacctc gcagagaaaa tcataatgca   11220
ttgtgagcta tcattaggtg tctctggcac gaaaatgaaa gaaattgcta accagaaata   11280
cacttggaga cgaatagcag aaatgtatga ggattgctat taactctgtt aaacttcaaa   11340
tcttttacaa tatatggcat gactataagc gcattaattg ttttttcaagc cgctctcgcg   11400 gtgaccaccc cctgacaggg gatccgtgta ggctggagct gcttcgaagt tcctatactt   11460
tctagagaat aggaacttcg gaataggaac taaggaggat attcatatgg ataaagccgt   11520
aagcatataa gcatggataa gctatttata ctttaataag tactttgtat acttatttgc   11580
gaacattcca ggccgcgagc attcagcgcg gtgatcacac ctgacaggag tatgtaatgt   11640
ccaagcaaca gatcggcgta gtcggtatgg cagtgatggg acgcaaccct gcgctcaaca   11700
tcgaaagccg tggttatacc gtctctattt tcaaccgttc ccgtgagaag acggaagaag   11760
tgattgccga aaatccaggc aagaaactgg ttccttacta tacggtgaaa gagtttgtcg   11820
aatctctgga aacgcctcgt cgcatcctgt taatggtgaa agcaggtgca ggcacggatg   11880
ctgctattga ttccctcaaa ccatatctcg ataaaggaga catcatcatt gatggtggta   11940
acaccttctt ccaggacact attcgtcgta atcgtgagct ttcagcagag ggctttaact   12000
tcatcggtac cggtgtttct ggcggtgaag agggggcgct gaaaggtcct tctattatgc   12060
ctggtggcca gaaagaagcc tatgaattgg tagcaccgat cctgaccaaa atcgccgccg   12120
tagctgaaga cggtgaacca tgcgttacct atattggtgc cgatggcgca ggtcactatg   12180
tgaagatggt tcacaacggt attgaatacg cgatatgca gctgattgct gaagcctatt   12240
ctctgcttaa aggtggcctg aacctcacca acgaagaact ggcgcagacc tttaccgagt   12300
ggaataacgg tgaactgagc agttacctga tcgacatcac caaagatatc ttcaccaaaa   12360
```

```
aagatgaaga cggtaactac ctggttgatg tgatcctgga tgaagcggct aacaaaggta    12420
ccggtaaatg gaccagccag agcgcgctgg atctcggcga accgctgtcg ctgattaccg    12480
agtctgtgtt tgcacgttat atctcttctc tgaaagatca gcgtgttgcc gcatctaaag    12540
ttctctctgg tccgcaagca cagccagcag gcgacaaggc tgagttcatc gaaaaagttc    12600
gtcgtgcgct gtatctgggc aaaatcgttt cttacgccca gggcttctct cagctgcgtg    12660
ctgcgtctga agagtacaac tgggatctga actacgcga aatcgcgaag attttccgtg    12720
ctggctgcat catccgtgcg cagttcctgc agaaaatcac cgatgcttat gccgaaaatc    12780
cacagatcgc taacctgttg ctggctccgt acttcaagca aattgccgat gactaccagc    12840
aggcgctgcg tgatgtcgtt gcttatgcag tacagaacgg tattccggtt ccgaccttct    12900
ccgcagcggt tgcctattac gacagctacc gtgctgctgt tctgcctgcg aacctgatcc    12960
aggcacagcg tgactatttt ggtgcgcata cttataagcg tatcgataaa gaaggtgtgt    13020
tccataccga atggctggat taa                                            13043
```

<210> SEQ ID NO 12
<211> LENGTH: 13790
<212> TYPE: DNA
<213> ORGANISM: Artificial Sequence
<220> FEATURE:
<223> OTHER INFORMATION: example O2 rfb locus nucleotide sequence -
      O2-EPA production strain stGVXN4906

<400> SEQUENCE: 12

```
atgacgaatt taaaagcagt tattcctgta gcgggtctcg ggatgcatat gttgcctgcc      60
actaaggcga tacccaaaga gatgctacca atcgtcgaca agccaatgat tcagtacatt     120
gttgacgaga ttgtggctgc agggatcaaa gaaatcctcc tggtaactca cgcgtccaag     180
aacgcggtcg aaaaccactt cgacacctct tatgagttag aatcactcct tgagcagcgc     240
gtgaagcgtc aactgctggc ggaagtacag tccatctgtc cgccgggcgt gaccattatg     300
aacgtgcgtc agggcgaacc tttaggttta ggccactcca ttttgtgtgc gcgacctgcc     360
attggtgaca acccatttgt cgtggtactg ccagacgttg tgatcgacga tgccagcgcc     420
gacccgctac gttacaacct tgctgccatg attgcacgtt tcaacgaaac gggccgcagc     480
caggtgctgg caaaacgtat gccgggtgac ctctctgaat actccgtcat ccagactaaa     540
gagccgctgg accgtgaggg taaagtcagc cgcattgttg aatttatcga aaaccggat     600
cagccgcaga cgctggactc agacatcatg gccgtaggtc gctatgtgct ttctgccgat     660
atttggccgg aactggaacg tactcagcct ggtgcatggg gacgtattca gctgactgat     720
gctattgccg agctggcgaa aaaacaatcc gttgatgcaa tgctgatgac cggcgacagt     780
tacgactgcg gcaaaaaaat gggctatatg caggcgtttg tgaagtatgg cctacgcaac     840
ctgaaagaag gggcgaagtt ccgtaaaggt attgagaagc tgttaagcga ataatgaaaa     900
tctgaccgga tgtaacggtt gataagaaaa ttataacggc agtgaaaatt cgcagcaaaa     960
gtaatttgtt gcgaatcttc ctgccgttgt tttatataaa ccatcagaat aacaacgagt    1020
tagcagtagg gttttattca agttttccag gatttttcct tgtttccaga gcggattggt    1080
aagacaatta gcgtttgaat ttttcgggtt tagcgcgagt gggtaacgct cgtcacatca    1140
taggcatgca tgcagtgctc tggtagctgt aaagccaggg gcggtagcgt gcattaatac    1200
ctctattaat caaactgaga gccgcttatt tcacagcatg ctctgaagta atatggaata    1260
aattaagtga aaatacttgt tactggtggc gcaggattta ttggttcagc tgtagttcgt    1320
```

```
cacattataa ataatacgca ggatagtgtt gttaatgtcg ataaattaac gtacgccgga   1380
aaccgggaat cacttgctga tgtttctgat tctgaacgct atgtttttga acatgcggat   1440
atttgcgatg cacctgcaat ggcacggatt tttgctcagc atcagccgga tgcagtgatg   1500
cacctggctg ctgaaagcca tgttgaccgt tcaattacag gccctgcggc atttattgaa   1560
accaatattg ttggtactta tgtccttttg gaagccgctc gcaattactg gtctgctctt   1620
gatagcgaca agaaaaatag cttccgtttt catcatattt ctactgacga agtctatggt   1680
gatttgcctc atccagatga agtaaataat acagaagaat tacccttatt tactgagacg   1740
acagcttacg cgccaagcag cccttattcc gcatccaaag catccagcga tcatttagtc   1800
cgcgcatgga aacgtacgta tggtttaccg accattgtga ctaattgctc gaacaactat   1860
ggtccgtatc acttcccgga aaagcttatt ccattggtta ttcttaatgc actgaaggt    1920 aaggcattac ctatttatgg caaaggggat caaattcgcg actggttgta tgtagaggat   1980
catgctcgtg cgttatatac cgtcgtaacc gaaggtaaag cgggtgaaac ttataacatt   2040
ggcggacaca acgaaaagaa aaacatcgat gttgtgctga ctatttgtga tttgttggat   2100
gagattgtac cgaaagagaa atcttatcgt gagcaaatta cttatgttgc tgatcgccca   2160
gggcatgatc gccgttatgc aattgatgcc gataaaatta gccgcgaatt gggctggaaa   2220
ccacaggaaa cgtttgagag cgggattcgc aaaacggtgg aatggtatct ggctaataca   2280
aattgggttg agaatgtgaa aagcggtgct tatcagtcat ggatcgaaca aaactatgag   2340
ggccgtcagt aatgaatatc ctgcttttcg gcaaaacagg gcaggtgggt tgggaactgc   2400
agcgtgctct ggcgccgctg gtaatctgat tcgctcttga tgttcactcc actaattatt   2460
gtggagattt cagcaacccc gaaggtgtgg cagaaaccgt caaaaaaatt cgtcctgacg   2520
ttattgttaa tgctgctgct cacactgcag tagataaagc agaatcagaa ccggatttcg   2580
cacaattact taacgcgaca agcgtcgaag cgattgcaaa agctgctaat gaagtcgggg   2640
cctgggttat acactactct actgattatg tttttcccagg cagtggtgac gcgccatggc   2700
tggaaacgga tgcaacagca ccgctaaatg tttacggtga aacaaaatta gctggggaaa   2760
aggcattaca agaacattgc gcaaagcatc ttattttccg taccagctgg gtatacgctg   2820
gtaaaggaaa taactttgct aaaacgatgt tgcgtttggc aaaagaacgc gaagaactgg   2880
ctgtgataaa cgatcagttt ggcgcaccaa caggtgctga attgctggct gattgcaccg   2940
ctcatgccat tcgcgtggca ttaaaaaaac cagaagtcgc tggcttgtac catctggtag   3000
caagtggcac aacaacctgg cacgattatg ctgcgctggt ttttgaagag cgcgcaaag   3060 cagggattaa tcttgcactt aacaaactta cgccgtgcc aacaacggcc tatcccacac   3120
cagcccgtcg accccataac tctcgcctca atacagaaaa gtttcagcag aactttgcgc   3180
ttgtcttgcc tgactggcag gtgggcgtga acgtatgct caacgaatta tttacgacta   3240
cggcaattta acaaattttt gcatctcgct catgatgcca gagcgggatg aattaaaagg   3300
aatggtgaaa tgaaaacgcg taaaggtatt attctggctg gtggttccgg cactcgtctt   3360
tatcctgtga cgatggcagt gagtaaacaa ttgctgccga tttatgataa gccgatgatt   3420
tattatccgc tttcaacgct tatgttagcg ggtattcgcg atattcttat tattagtacg   3480
ccacaggata caccgcgttt ccaacaatta ttggggacg ggagccagtg gggtcttaat   3540
ctacagtata aagtacaacc gagtccggat ggcctggcgc aagcgtttat tattggcgaa   3600
gactttattg gtggtgatga ttgtgcactc gtacttggcg ataatatctt ctatggacac   3660
```

```
gacttgccga aattgatgga agctgctgtt aacaaagaaa gcggtgcaac ggtatttgct    3720
tatcacgtta atgatcctga acgctatggt gtcgtggagt ttgataataa cggtacggca    3780
attagcctgg aagaaaaacc gctggagcca aaaagcaact atgcggttac tgggctttat    3840
ttctatgaca atgacgttgt ggaaatggct aaaaacctta agccttctgc ccgtggcgaa    3900
ctggaaatta ccgatattaa ccgtatttat atggaacaag gacgtttgtc tgtagccatg    3960
atggggcgtg gctatgcatg gttggataca gggacgcatc aaagcccttat tgaagcaagt    4020
aacttcattg caacaattga agagcgtcag ggattaaagg tatcttgccc ggaagagatt    4080
gcttaccgta aagggtttat tgatgccgag caggtgaaag tattagccga accgcttatc    4140
aagaatcaat atggtcaata tttgctgaaa atgatcagcg aatagtatat gggaactcaa    4200
tgatggatat taaattaatc tcttttgcaaa aacatgggga tgagcgcggt gcattaattg    4260
ctcttgaaga gcaacgaaat atacctttcg aagtcaaaag aatatattac atacttgaga    4320
ctcttaatgg agtaagacgc ggatttcatg cgcacaaggt tactcgtcag ttagctattg    4380
tagtcaaggg agcttgtaaa tttcatctgg ataatggtaa agaaacaaag caggtggaac    4440
ttaatgatcc aacaattgcg ttgctgatag aaccctatat atggcatgaa atgtatgatt    4500
ttagtgatga ttgtgtgctg cttgtaattg cggatgattt ctataaagag tctgattata    4560
tccgcaatta tgatgatttt attagaagag taaattcaat tgagaattca taagctaagt    4620
gacgtccaga caacatcaat tggtgatgga acaactatct ggcagtttgt tgtgatacta    4680
aaaggtgctg taattggtaa taattgcaac atctgtgcaa ataccttaat tgaaaataac    4740
gttgtaattg gtaacaatgt cacagtcaaa agcggtgtgt atatttggga tggcgttaaa    4800
atagaggata atgttttttat tggtccttgt gtagcattta caaatgataa gtatcctcgc    4860
tctaaagtct atcctgatga attttttgcaa acaataatac gcaaaggagc atcaataggt    4920
gctaacgcaa ccatcctgcc aggaattgaa attggtgaaa agcaatcgt tggtgcgggg    4980
agtgttgtaa ccaaaaatgt accgccatgc gcaatagtag taggtaatcc agctcgattt    5040
attaaatggg tagaggataa tgaataaaat tgattttta gatcttttg caattaacca    5100
gcgacagcac aaagaattag tctctgcgtt tagtagggtg ctagattctg ttggtatat    5160
catgggcgaa gaacttgagc agttcgagaa agagttcgca gaatactgtg gagttaagta    5220
ttgcattggt gtagcaaatg gccttgatgc gttgatacta gtattgaggg catgaaaga    5280
acttggctat cttgaagacg gtgacgaggt attagtaccg gcaaatacat atattgcttc    5340
tattcttgct ataacagaga acaaacttgt tcctgttctt gttgaaccag atatagaaac    5400
ttataatatt aatcctgctt taattgaaaa ttacattacg gaaaaaacta agcaatatt    5460
accggttcac ttatatggtc tattgtgcaa tatgccagaa attagtgcaa tcgccagaaa    5520
atataatctg ttgattcttg aagattgtgc acaagcacat ggtgcaatac gtgatggtcg    5580
caaagctgga gcttgggggg atgctgcagg atttagtttt tatccaggaa aaaaccttgg    5640
agctttgggg gatgcgggag ctgttactac aaataatgca gaattatcct caactataaa    5700
agctttgcga aattatgggt cacataagaa atatgaaaat atttatcagg gattgaatag    5760
tcgattggat gaactgcaag cagccttatt gcgtgtaaaa atccatacat taccggaaga    5820
tactgcgatt cggcaaagga ttgctgaaaa atatattcgt gaaataaaaa accctgcgat    5880
tacgttacca gtgtacgaag gccaaggtgc gcatgtttgg catttatttg tagtaagaat    5940
cgctaatcgt gaaaaattcc agtcatactt attagagaag ggtatcaaaa ccttaattca    6000
ctatccatta ccaccccata agcagcaagc atatcaaaat atgtctagcc ttagccttcc    6060
```

```
aattactgag caaattcatg atgaagtcat ttctttacct ataagtccgg taatgagtga    6120
agatgatgtc aattatgtaa tcaaaatggt caatgattac aagtaatgaa aaaatttctt    6180
caggtaacta tattatccgc tatctataca ttcattaaaa tgattgcggg ttttatcatc    6240
ggtaaggtag tagcaattta tacagggcca tcaggggtag caatgcttgg ccaagtgcaa    6300
agtttaatca caatagttgc aggtactacc tctgcacctg taagcacagg ccttgttcga    6360
tatactgcgg aaaattggca agaaggacaa gaagcatgcg cgccatggtg gcgcgcatgc    6420
ttaagggtta ctctgttttt attcttgctt attattcccg ttgttattat attgtcgaaa    6480
aatattagtg agttacttt tagcgatgga caatacacat ggttaatcat tttcgcatgt    6540
tgtatattgc cattctccat tataaataca ttgatcgctt cagttttaaa tggtcaacaa    6600
ttttataagc aatatatatt ggttgggatg ttttctgtat tcatttctac tatgtttatg    6660
attttgttga ttgtagctta taatcttaaa ggtgcattga ttgccacagc tataaatagt    6720
gctattgctg gtcttgtatt ggttttattt tgtctcaata atcttggtt tagatttaaa    6780 tattggtggg gtaaaacgga taaagacaaa attataaaaa ttattcatta tactctgatg    6840
gctctggttt ctgttatctc catgcctaca gcattgatgt gtattagaaa atattgatt    6900 gctaaaactg gttgggagga tgcagggcaa tggcaggccg tatggaagat atctgaggtt    6960
tatcttggtg ttgtgacaat tgctttgtca acatatttct taccaagatt gacaattata    7020 aaacaagtt tccttataaa aaagaagta atagtacta tattatacat aatatctatt    7080
acttcattca tggcgttgag tatctatttta ttccgcgatt tggtaataac agttttatt    7140 actgaacagt ttcgctcagc tcgtgaatta tttttattac aacttatagg ggatgtaata    7200
aaaattgctg gtttctttta tgcatacccct cttcaaagtc aggggcatac taaactattc    7260
atcagttcag aagtgattt ttctatgctc tttatcatta ccacctatat ttttgttgta    7320
aattatggag tacatggtgc taacataagt tatgtcatta catatagttt atattttgtg    7380 tttgcattg tgttactaa ttttattaat gttagaagaa ataattaaaa acagaggttg    7440
aattttgaaa ataattatac ctgtcttagg atttggcagg gctggtggtg aaagagttct    7500
ttctaagctg gcaactgaat tgatgaatta tggacatgat gtaagttttg ttgttccaga    7560
taatagaact aatccatatt atgctaccac agcaaaaatt gtcacgagta aatctagtca    7620
aaaccgtgta aaaatattga gaatcattaa aaattactat aatctgtggc gtaaatgcat    7680
agagttaaat cctgatgctg tagttgctag ttttcatttg actgcctatc ttgtcgcatt    7740
attaccaatc acccgtcgta agaaatatta ttatattcag gcgtatgaag ttaatttttt    7800
tgataatata atatggaaat taatagcggg tttaacatat tatttaccgc ttaaaaaaat    7860
actaaatagt cctaatttgc ttcctcataa acatgatgat tttataggag tagttcctgc    7920
aggagtagat ttaaacgttt tctatccgaa accatcaaat aggttattaa atggtcacac    7980
atcaataggg attattggta gaaaagagaa gcacaaagga actagcgaaa ttatttcagt    8040
attgtgttca ctggaaaata aagctggaat tataatcaat attgcgatct atcttgaaga    8100
agttgataag cagcgtttaa tcgctgccgg gtttcaggtt aattttttttc cgattacttc    8160 tgatttagaa ttggcatcct tttatcgaag caatgacatc atgattgctg ttgggttaat    8220
tgaagatggc gctttccatt atccttgtgc tgaatcaatg gcttgtggtt gtcttgttat    8280
ttcaaattat gcgccactta ctgaaactaa cagtgtactt aaattagtca agtttgatgc    8340
ttgcaaactt ggtgaagcaa ttaatctttg tctcaatctt gacctagaag aaaaaagcaa    8400
```

-continued

| | |
|---|---|
| agaaatccaa tctaatatttt ctgtgttgaa taaatatgac tggaaaattg ttggtgaaac | 8460 |
| tttcaatagt ttattgttag atgcaaataa atagtatacg ttgatgggga aaatatgaat | 8520 |
| attgttaaaa ctgatattcc agatctgatc gttcttgaac caaaagtgtt tagtgatgaa | 8580 |
| cgcggctttt ttatggagag ttataatcag attgaatttg agaaggcaat aggaaggcac | 8640 |
| gtaaattttg ttcaggataa tcattcaaaa tctagtaaag gcgtactacg tgggttgcat | 8700 |
| tatcaattag caccgtatgc acaggctaaa ttagttcgat gtgttgtagg tcaggtatttt | 8760 |
| gatgttgctg ttgatcttag aaaaaattca ccaacgttca aaaatggtt tggaataacc | 8820 |
| ctttccgcag aaaataaacg acaattatgg atacccgaag gatttgctca tggtttcttg | 8880 |
| gtgaccagtg atgaagctga gttcatttat aagcaacta actactatgc tcctggtcat | 8940 |
| cagcaagcaa ttatttacaa tgatcctatt ttaaacatcg attggccttt ctgcagtagt | 9000 |
| gctctgtcat tatcacaaaa agatcaagaa gcaaaattat tttcagaatt attggacagt | 9060 |
| gaactgttct aataaagtgt gccaccttat ccgtctgaag gataggtggt tgcttatatt | 9120 |
| tttttgagta tgtttgtata atgacagaaa atagtccgaa atataaacac gataaaagct | 9180 |
| taataagttt tatctactta tttttttatat ttacacttat tgtaggcttt attatcgcaa | 9240 |
| atacccagtt tttggggcga agtagagact atgataatta tatacagatc ttttctggta | 9300 |
| aagaaggggga gggggttctt gaattatttt atcgcggatt gatgttaata acgaccagct | 9360 |
| atgaaactat cattttttata attttaacat gttcttttttt tataaaggca aggtttctcg | 9420 |
| ctaactattc gcgtaatttt tcaggcttga ccttattctt tatttattat gcaagcgttg | 9480 |
| cactttgggt tttagattat actcaattca gaaatggtct atgtatttcc attttaatgt | 9540 |
| tttccgtata ctatttattt ataaataaac cgacttattt ttatttctcg gtattatgtg | 9600 |
| caattgcaac tcattggtct gctttgcctt ttttgctttt atatcctttt gtctattcaa | 9660 |
| caaaaataag acgccttggt tatttttgtt tcagtattct tgttttgatt gcgatctcag | 9720 |
| gagaaggaaa agagatcata tcttttataa gaaattttgg agtgggacaa aaaataggaa | 9780 |
| atgaagctgg tgtaaattta ataaattcat tatcccttac cgctatttcc tggtttatta | 9840 |
| ttagttacat atcaagcatt ggaaatgaaa ggagaaattt aaggcttttc ttttgttatg | 9900 |
| gtgtcatgca atacgtgact tttagccttt tctctctacc tgttatggct ttccgtatttt | 9960 |
| tggaaatgta ttttttcctt atgctaacca ttggggtgtt tattaagcaa aaaagaattt | 10020 |
| attattttat ttttttgcaaa gtgttaattt tattgtatct aacatactat tatcatatgg | 10080 |
| tctttggagt gattaatgtg taaggctaag gtgttggcta taattgttac ttacaacccg | 10140 |
| gaaattattc gattgacgga atgtattaac tctttagccc cacaagttga gagaataatt | 10200 |
| cttgtagata atggctcaaa taatagtgat ttgataaaaa atatcagtat taataacctt | 10260 |
| gaaattattt tactttcgga aaacaaaggc attgcatttg ctcagaacca tggtgttaag | 10320 |
| aagggcctgg aagcaaaaga gtttgactat ttattttttct cagatcagga tacttgctttt | 10380 |
| cctagcgatg ttattgaaaa acttaagagt acatttacga aaaataataa aaaaggtaaa | 10440 |
| aatgttgctt gtgcttctcc ttttttttaaa gaccatcgtt caaattatat gcatccgtca | 10500 |
| gtcagcctaa atatttttac gagtacaaaa gttatatgta gtgaagtaga cgatgatctt | 10560 |
| tatccctcgc atgttattgc ttctgggatg ttaatgtctc gtgaagcatg gcgcgtcgtc | 10620 |
| ggaccatttt gtgaaaaact ctttatagac tgggttgata cagaatggtg ttggcgtgca | 10680 |
| ttagctaata atatgattat tgttcagaca ccatcagtca tcatttctca tgaacttggg | 10740 |
| tatgggcaga aaattttttgc tggtcgatct gttacaatac ataattcttt cagaaatttt | 10800 |

```
tataaaatac gcaatgcaat atacttaatg ctgcattcaa attatagctt caagtatcgt   10860
tatcatgctt tttttcatgc gacaaagaat gttgtatttg aaattttata ttcgaaagaa   10920
aaattaaatt cactgaaggt ttgttttaaa gctgtacgtg atggtatgtt caataatttt   10980
taatacgaaa atagttaggc tcaaggtgtt taaatggaag aaaataatat gaagacggtc   11040
gctgtagttg gcacagtggg tgttcctgct tgttatggtg ggttcgaatc acttgttcag   11100
aatctaattg attatcaatc tgatggtata caatatcaga tattttgctc ttcaaaaaaa   11160
tatgataaaa aatttaaaaa ttataaaaat gcagaattaa tctatttgcc gataaatgcc   11220
aatggcgtct ctagcataat ttatgatatt atgtgtttaa ttatttgttt attcaaaagg   11280
ccagatgttg ttttaatatt gggggtgtct ggttgtttat ttctaccaat ttataaacta   11340
ttttcaaaat caaagattat tgtcaatatt gatgggcttg aatggcgtag aaataaatgg   11400
ggaacgtttg ctaagaaatt tcttaaaata tctgaggcga tatctattag aatagctgat   11460
attatcattt cagataatca agcaatagct gattatgtgg aaaataagta caagaaaaaa   11520
agtgtagtta tagcttatgg cggagatcat gccactaatc ttagtacacc gatagacaat   11580
gatcaaaaaa aagaaggtta ttatttgggg ctttgtagga tagagcctga gaataatata   11640
gaaatgattc tgaatgcctt cattaataca gataaaaaaa ttaaatttat gggtaattgg   11700
gataacagcg agtatggacg ccagctaaaa aaatattatt caaactatcc aaatatcacc   11760
ctactagaac ctaactataa tattgaagag ctttataaac taagaaaaaa ttgtcttgca   11820
tacattcatg gacactcggc tggtggaaca aaccccttctt tagttgaagc gatgcatttt   11880
aatattccta ttttttgcttt cgattgtgac tttaatcgtt acacaactaa caatttagct   11940
cattacttta atgattctga acaacttagc ttattagcag aaagtttgtc ttttggaaat   12000
cttaaatgtc gagtattaga tttaaaaaat tatgctgaag atatgtataa ctggaggcat   12060
atagctgcta tgtatgaatc tatttattaa acgcattaac aataaataaa ttgaccttat   12120
atagcaggga aagatcacgt aacgctgcgg cgcgccgatc cccatatgaa tatcctcctt   12180
agttcctatt ccgaagttcc tattctttct agagaatagg aacttcggaa taggaactaa   12240
ggaggatatt catatggata aagccgtaag catataagca tggataagct atttatactt   12300
taataagtac tttgtatact tatttgcgaa cattccaggc cgcgagcatt cagcgcggtg   12360
atcacacctg acaggagtat gtaatgtcca agcaacagat cggcgtagtc ggtatggcag   12420
tgatgggacg caaccttgcg ctcaacatcg aaagccgtgg ttataccgtc tctattttca   12480
accgttcccg tgagaagacg gaagaagtga ttgccgaaaa tccaggcaag aaactggttc   12540
cttactatac ggtgaaagag tttgtcgaat ctctggaaac gcctcgtcgc atcctgttaa   12600
tggtgaaagc aggtgcaggc acggatgctg ctattgattc cctcaaacca tatctcgata   12660
aaggagacat catcattgat ggtggtaaca ccttcttcca ggacactatt cgtcgtaatc   12720
gtgagctttc agcagagggc tttaacttca tcggtaccgg tgtttctggc ggtgaagagg   12780
gggcgctgaa aggtccttct attatgcctg gtggccagaa agaagcctat gaattggtag   12840
caccgatcct gaccaaaatc gccgccgtag ctgaagacgg tgaaccatgc gttacctata   12900
ttggtgccga tggcgcaggt cactatgtga agatggttca caacggtatt gaatacggcg   12960
atatgcagct gattgctgaa gccattctct gcttaaagg tggcctgaac ctcaccaacg   13020
aagaactggc gcagaccttt accgagtgga ataacggtga actgagcagt tacctgatcg   13080
acatcaccaa agatatcttc accaaaaaag atgaagacgg taactacctg gttgatgtga   13140
```

-continued

```
tcctggatga agcggctaac aaaggtaccg gtaaatggac cagccagagc gcgctggatc    13200
tcggcgaacc gctgtcgctg attaccgagt ctgtgtttgc acgttatatc tcttctctga    13260
aagatcagcg tgttgccgca tctaaagttc tctctggtcc gcaagcacag ccagcaggcg    13320
acaaggctga gttcatcgaa aaagttcgtc gtgcgctgta tctgggcaaa atcgtttctt    13380
acgcccaggg cttctctcag ctgcgtgctg cgtctgaaga gtacaactgg gatctgaact    13440
acggcgaaat cgcgaagatt ttccgtgctg gctgcatcat ccgtgcgcag ttcctgcaga    13500
aaatcaccga tgcttatgcc gaaaatccac agatcgctaa cctgttgctg gctccgtact    13560
tcaagcaaat tgccgatgac taccagcagg cgctgcgtga tgtcgttgct tatgcagtac    13620
agaacggtat tccggttccg accttctccg cagcggttgc ctattacgac agctaccgtg    13680
ctgctgttct gcctgcgaac ctgatccagg cacagcgtga ctattttggt gcgcatactt    13740
ataagcgtat cgataaagaa ggtgtgttcc ataccgaatg gctggattaa                13790
```

<210> SEQ ID NO 13
<211> LENGTH: 13777
<212> TYPE: DNA
<213> ORGANISM: Artificial Sequence
<220> FEATURE:
<223> OTHER INFORMATION: example O6A rfb locus nucleotide sequence -
    O6A-EPA production strain stGVXN4112 and stLMTB10923

<400> SEQUENCE: 13

```
atgacgaatt taaaagcagt tattcctgta gcgggtctcg ggatgcatat gttgcctgcc      60
actaaggcga tacccaaaga gatgctacca atcgtcgaca agccaatgat tcagtacatt     120
gttgacgaga ttgtggctgc agggatcaaa gaaatcctcc tggtaactca cgcgtccaag     180
aacgcggtcg aaaaccactt cgacacctct tatgagttag aatcactcct tgagcagcgc     240
gtgaagcgtc aactgctggc ggaagtacag tccatttgcc cgccgggcgt gacaattatg     300
aacgtgcgtc agggcgaacc tttaggtttg ggccactcca ttttatgtgc acgacctgcc     360
attggtgaca atccatttgt cgtggtgctg ccagacgttg tgatcgacga cgccagcgcc     420
gacccgctgc gctacaacct tgctgccatg attgcgcgct tcaacgaaac gggccgcagc     480
caggtgctgg caaaacgtat gccgggtgac ctctctgaat actctgtcat ccagaccaaa     540
gagccgctgg accgcgaagg taaagtcagc cgcattgttg aattcatcga aaaccggat      600
cagccgcaga cgctggactc agacatcatg gccgttggtc gctatgtgct ttctgccgat     660
atttggccgg aacttgaacg cactcagcct ggtgcatggg ggcgtattca gctgactgat     720
gccattgccg aactggcgaa aaaacagtcc gttgatgcca tgctgatgac cggcgacagc     780
tacgactgcg gtaaaaaaat gggttatatg caagcgttcg tgaagtatgg actacgcaac     840
ctcaaagaag gggcgaagtt ccgtaaaggg attgagaagc tgttaagcga ataatgaaaa     900
tctgaccgga tgtaacggtt gataagaaaa ttataacggc agtgaagatt agcggcgaaa     960
gtaatttgtt gcgaatttc ctgccgttgt tttatataaa caatcagaat aacaacgact    1020
tagcaatagg attttcgtca aagttttcca ggattttcct tgtttccaga gcggattggt    1080
aagacaatta gcatttgaat tttacgggtt tagcgcgagt gggtaacgct cgtcacatcg    1140
tagacatgca tgcagtgctc tggtagctgt aaagccaggg gcggtagcgt gctgaaatta    1200
taaagtcatt cttatagaac atcgcatttc aataatataa ttacacctaa atgaatagga    1260
tacaacgtgt gcacaattat ttaaggctta aagataaaat aaaaaacgta ttttaggggt    1320
tgtatatatt gcagttattt aattatatcg cgccattggt aattatccct atcctgataa    1380
```

```
aatatattgg gttgggggaa tatggggaat tggtctatat tacatctatt tatcaaatag    1440
tggctttgat tattgatttt ggctttactt acacaggacc tgtggttgct gcgagacata    1500
gatgtgagac ccaaaattta cagcgctatt actcaatagt tgttctttta aaatcattgc    1560
tttttataat tgcattaaca tgtgtatttt tattgtgcag attaaatata gtccacttgt    1620
cattttttgg gttttttgtca atttttctat gcactattgg taatatatta tcgcccaatt   1680 ggttttttgca ggggattggt gattttaaaa aactttcata ctcacaagta atagtgagaa   1740
taacattgtt tatcatactt cttgtttatg tctgtagtgg cggagataat gttttttatcc   1800 taagttttttt gcaaaatgca acattactca tatgctgtat atacttatgg ccaaatattc   1860
atattagcca tgttgttcat cttaaaccta atgaatgcat tgtggaattt aagaaggcag    1920
gaaatgtttt tattggcgta ataggtacga ttggttacaa tggtctaatt cctgtgttaa    1980
ttggaaacct ttgcggtaat acgagtcttg gtgttttttc aatcgttcaa aaaatgacaa    2040
cagcatgtca aagtctaatt aatccaatat cacagtatat gttatctcaa gtttcagaaa    2100
ttaaacctca agataaactg ttttattata gaattaaaaa aagttttttt gtgcatttaa    2160
caattagcat aattgcatgt ttatgttata tggggttagg gcaatatgtg gcgacttttta  2220 taggtaaagt tgacgtttca tttgttatta ttttatttgc gtcaataatt accatttttt    2280
catctttaaa taatgtcctt ggtatacagt ttcttatacc gacagataat gtaaaaatac    2340
tacgaagtat aaatgttatg gcgggaatta ttgttgttag tttgtcctgg ctgttaatat    2400
cacgctttga cattctgggg ggggttttat aaaacctaat tggtgagttt cttgtattca    2460
gtatgctagc ttttattgcc catcgaaagt ggggagcgag agtataatga aagtgaaggc    2520
ggttcctgct attacattct atttaagttt aatgctgaca atttttagtgt tactgtttgg    2580 taatgaacca aataaatcac aatatatcct tgttatagca acgataacag ttttttatat   2640
cgcatatatc actaataaaa taacttctcc ggccagcctt ctcgttatat catcttttgt    2700 gttttttaggt tgtcgcccctt tattatcttt gtttgcaaac tatgattata ggattgccga  2760
ttggtttatt gaaggatata tggatgacga tgtgattttg gctaactatg ctataacact   2820
aatgtattat ggttatacat tgggactaat tctatgcaaa aatactgaaa aatttttatcc  2880 gcatggtcct tatcctgaaa acaattgct aaaaataaag tttctttttga ctttattttt    2940 tctgggttcg ataggtatgg ttgtaaaagg gatattcttt tttaacttta tagaatctaa   3000
tagttatgtt gatatttatc aatcaaatat aacaacgcca ataggttatg attttctatc   3060
ttatttattt tattgttctt ttttccttat atgtgcgttt catatacagt tcagaacaaa    3120
taaaaaattt ctttttattg cgatatgcat tgctgcattt agcaccttga agggtagtcg   3180
tagtgaagct ataacgtttc ttttaacggt tacatgtata tattttaatg aagtaaagac    3240
aagaaactta cgtctgctga ttacaatgat ttttgttttt agcgtcattt ttgtgattag    3300
tgaatttatc tcaatgtggc gcactggagg gagtttttttt caattaatgc agggtaataa    3360
tcctgttata aactttgtat acggcatggg agtatcatat ctttccattt atcaatcagt    3420
aaaactacaa ctattgtcag ggggatataa tgttacctat ctattcagcc agttaataat    3480
aacttgctcg tcaatattta atgtcaaatt gagcttgccg gaaataagct atagccattt    3540
ggcctcatac acagcaaacc cagaactata taatcttggg ttcggacttg ggggagtta     3600 tttagcagaa tcgttttttag catttggtct gattggatgt ttcattatac ccttttttact  3660 tttacttaat ttaaatgtat tggaaaaata tacaaaaaac aaaccaatta tatattttgt    3720
ttattatagt gtgttgccac ctatattatt cacaccaaga gagactttgt tctatttctt    3780
```

```
cccctatctt gtcaaaagta tatttgttgc ttttttagtt acattataca tccagtataa    3840
aaaggattga ccaaaatgtc agaaaaaaat gtcagcataa aatcccaag ttataacagg     3900 gctcatattc ttaaggaggt cataccaagt tattttcagg atgagacttt agaggttata    3960
gttatcaatg atggatcaac agataataca aatagtgtat tagctgaact gaaggaaaaa    4020
tattctcagt tagttatttt agaaaatgaa acgaataaaa aacagatgta ttctaaaaac    4080
cgagggattg aaatagccaa agggaaatat atttttttg gtgatgatga ctcttacctc     4140
ttacccggtg ttatatctcg gttattggct acaaatatg agacaggcgc tgatgtaatc     4200
ggcgcaagaa tactttatat gaataataac gagaaaacaa ttgaagattg cataaatcga    4260
cataaaaaag aggggcgttt tgttagtgat ctaaatagat tggattttag ttatacatgt    4320
gatttggacc atccgattga atgttttat gcacagcctt ttgttctagc tgaaagggaa     4380
ctaatatcga aatatcgatt tgatatatct tatacgggaa actgctatcg tgaggaaact    4440
gatttcatgc tatctctatt tattaaaaat aaaaaattta tatgattc aaaggctttg      4500 ttaataaatt tacctccaag aaaagcgacg ggaggggcaa gaacagctaa tcgattaaaa    4560
tatcattacg aaagttgcat aaataattat agatttttaa aaaaatataa tgataatttg    4620
aatcttcttt caggacaaaa gcatgctata ttttaccgac agtgtcaatt cgttctgcta    4680
aaaatgaagt cgtttatcgg gaagttttta aaatgattat atatatcgcc gcgtataatg    4740
gttcaggagg gcaaggtggg gtggaaaggg ttgttgccca acaatgtaac attcttaaaa    4800
atttgggggt taaagtcatt atacttgata aaacatactt caaaatttct aacaaaattc    4860
gtaacaaaaa aatacaagta gcactttatc caatattagt ttctctttat ttaaccttac    4920
aaaaattacg tggcgtgacg tttaaagtta ttgcacatgg ctattgttct cctttttata    4980
ggaatgacat cttaatagct catggcaata tgaaatgtta ttttcaaaca gtcatgaata    5040
aaaaacctaa tcggttgtct ggcagtggtc tttatctttt ctatgagcgt tgggctggag    5100
cattttcaaa aaatatctgg gctgtttcaa ataaggttaa aagtgaatgg aatgagcttt    5160
acaatattaa ttcacataaa atcaaagttg ttcgaaattt tataaatctt gcacaatttg    5220
attacactga tgttaatgaa gcagaatatg tgacatttgt cgggcgattg gaaaaaggaa    5280
aaggaataga tgatctgtat tacatatgta aaaatctgcc agatacttcc ttccatttag    5340
tttcaagtat tcccgcccca caaaattttg cttcgctaaa taatgttctg accagcattg    5400
ctgtccccta tgcgaaaatg ccagaaatat ttaagaaatc cagagtactt attttaccgt    5460
cctattatga aggatatgag ctggttacta ttgaagcgct atgctgtggt tgccctgtga    5520
taggctataa tgttggtgca attagagagt tgtatgcaga agttttcct ggcgtattta     5580 ttgccaataa taaagaagat ttagcacaag tagcctacaa attaattagt cttgataatg    5640
aaaaatatta tcatttgaga caaactattt atagcaagcg tgagcttttt tctgaagaga    5700
gatatgcgga aattttaacg gcggcattta atgaaaaaaa ataagaaact ctgtctcatt    5760
tcaattaact catataatga acttaccgga ggaggagtat atttacgtac gcttgttagt    5820
tttctacaaa aacagaatgt taatttaaca cttattgata aaaaatcctc aggtaaacta    5880
ttcgaagaca atacttttca acatatatca tttattaaag gtaaacgtca ggatataata    5940
tccaggcttt tttttatacc atcatttat gtcccttata ttttctcaat aattaaaatt     6000
ttacggaagc aagatattct tgcttttcac aactctcggc ttggattgtt atgtctgctt    6060
tttagaatac tcatgcccca caaaaagatc atattgttta cggataactt cgaatatgac    6120
```

```
ttaataagac aaaaagataa aaacataact acttttattg aaaaattaat tgtttatctc   6180
aatgaattta tcgggcttaa gaattcagat ttagttagct atattacccg gcaagataaa   6240
aatgcaatgg ataaatttta tgggattaaa aaaagcagaa atttaattct ccctgtgata   6300
tttagtagag aaaaaccaac tgatgtattg tcagctcact ttattaatga gtataatcga   6360
ttgaataatg ataataggaa aaaagtagta tttactgcat cttttgattt ttttccaaat   6420
atagatgctg ccaactatgt tttaaatgca gcaaagtcta ataatgatta ttgctatatt   6480
ttggcaggta ggaaaagtac tactttgaat cttcctgatt tggataattt attttttttc   6540
gataatctat ctaatagtga aatgtcatat ttattatctg cttgtgatgt ttttttattct   6600
cctatagttt taggaagtgg aatgaaaaca aaaattgcag aagcactatc atatggatta   6660
tatatttatg cgacagagca ttccttaatc ggctatgatg aaattataca caataaggag   6720
tgtgttaaaa aaatctcaca tttggatgag gaatttccta aagatttcaa gatgaaaagt   6780
atcaataaac agctaataat gtcttatcag caaaaatatt attcacatta tcggtttaat   6840
ggccatgaac ttgatataat aaattttgac gattagttag tggagatata atatgaacat   6900
attagtaact ggtggtgctg gatatatcgg atctcatacg gctattgaat tactgaatgc   6960
aggtcatgag attatcgttc tggacaattt cagtaatgct tcatacaagt gtatcgaaaa   7020
aataaaagaa attactcgac gtgattttat aacaattact ggagatgctg ggtgtaggaa   7080
gacactctcc gctattttcg agaaacacgc catagatata gttattcatt ttgctggctt   7140
taaatctgtt tcagagtcta aaagtgaacc cttaaagtat taccagaata atgttggagt   7200
gaccattact ttattacagg taatggaaga gtacagaatt aaaaaattta tctttagttc   7260
atctgcgaca gtctatggtg aaccagagat aattccaatt ccagaaacag ctaaaattgg   7320
aggaactacg aatccatatg gcacatcgaa gtattttgtt gaaaaaattc tagaggatgt   7380
tagttccacg ggaaaactgg atataaattg cttgagatat tttaatcctg tcggtgctca   7440
ttctagtggt aaaataggtg aggctccatc tggtatccct aataatcttg ttccttattt   7500
attggatgtt gcgagtggta aacgtgataa attatttatt tatggcaatg attaccctac   7560
taatgatgga acaggtgtaa gggatttttat tcatgttgtt gacttagcga aaggtcattt   7620
ggctgcaatg aattatttaa gtatcaattc gggatataat atctttaatc ttggtacagg   7680
aaaaggttat tcggtacttg aattaatcac tacatttgaa aaattaacaa acattaaggt   7740
caataaatct tttatagaga gaagggcagg ggatgttgcg tcttgttggg ctgatgcaga   7800
taaagctaat tctttattgg actggcaagc cgaacaaact ctagaacaga tgttattgga   7860
ctcgtggcgt tggaaaaaaa attatccaga cggattctga atataaaagg tttcagtttt   7920
atgaatcaat cagagcagag aaaaaaaata ctggttctta cccctcgctt tccctaccct   7980
gtcattggag gggatagatt aagagtctat atgttatgta aagaactttc caaaaaatat   8040
gatcttattc ttctgagctt atgtgatcaa ccactagaac ttgaaataaa tataaatgac   8100
tcggtcttca aagaaattca tcgtgtctat ctaccaaaat ataaatcata ttataatgta   8160
ttaaaagctt tggttacgca aaaaccgttg caaattgctt attatcaatc ggacacattt   8220
aagaataaat acaataaatt aattaaacaa tgcgatgcag tattttgtca tctgataaga   8280
gttgctgatt atgttaagga tacagacaag ttcaaaattc ttgatatgac agatgcaata   8340
tcttttgaatt acagtcgcgt taaaaaatta gcaagtaaaa aaagtttgcg tgcaattatt   8400
tattctctgg aacaaaaaag attagaatca tatgaacgtt ctgtggcgaa tctttttgat   8460
ttgaccactt ttatttcatc cgtagaccgt gactatctct accctaatct gggcagtaat   8520
```

```
atccatatag tcaataatgg ggttgataca tcagccttga gatatataaa aagagaaata   8580
aaaatcgata agcctgtgga acttatattt atcggaaata tgtattcttt acaaaatatg   8640
gatgctgcaa aacattttgc taagaatatt ttaccttgct tgtatgatga gtttaatatt   8700
atttttaaag tgattggtaa gatctcagaa actaataaaa atatattaaa ttcatttaaa   8760
aatacaattg ctttaggtac tgttgatgat atcaattctt ccgcttctac agggcatata   8820
ggtatatgtc ctgttcgtct tggagcaggc gtacaaaata aaattcttga atacatggct   8880
ttaggtttac catgtattac atctagcatt ggttatgaag gtattaatgc aaaatcaggt   8940
agcgaaattt ttgttgcaga tacagtagag caatataaaa acgtactaag agaaataatt   9000
tacgattata atcgttatac tgaagtggct gaaaatgccc gtagttttgt agaaaataat   9060
ttttcttggg aatcaaaagt tgccaattta atgaatacat tagatgagaa attatatgaa   9120
caataataaa attattacac ctatcattat ggctggtggt tcaggcagtc ggttgtggcc   9180
actatcaaga attctctatc cgaaacaatt tcttagccta atcggtagtc ataccatgct   9240
tcaaacaacg gctaatcgtc tggatggttt ggattgtacc aacccttatg tcatttgtaa   9300
tgaacaatac cgctttatag ttgctgaaca gcttagaaaa atcgatagat tgacttcaaa   9360
gaatatcatc cttgagcctg ttgggcgtaa cactgcccct gcaattgcat tagcggcgtt   9420
gctgatgtct aagtctgata aaagtgcaga tgatcttatg ctcgtactgg ctgcagatca   9480
cgttatacac gatgaagaaa aattttgtaa cgctgttaga tcggcaattc catacgctgc   9540
tgatgggaaa ttggtaacat ttggtataat tccagacaaa gcagaaactg gttatggtta   9600
tatacatcga ggacaatata ttaatcagga agattcggat gcatttatag tgtcatcatt   9660
tgttgaaaag ccaaatcatg agacagccac taaatatctt gcttccggtg agtattattg   9720
gaatagcggt atgtttttgt ttagtgcaaa tcgttatata gaggaactta acaatttcg    9780 gcctgatatt ttatccgctt gtgaaaaagc aattgcttca gcgaactttg accttgattt   9840
tgtgcgttta gatgaaagtt cttttctctaa gtgccctgaa gaatcaattg attacgctgt   9900
aatgaaaaaa acaaaagacg caattgttat tccaatggat gctggctgga gtgatgtcgg   9960
ttcatggtct tctctctttgggg aaattaatga taaagactca gacggcaacg taatagttgg  10020
ggatattttc tctcatgaaa caaagaattc tttcatatat gccgaatcgg gaattgttgc   10080
tacagttgga gtgaaaatt tagttgttgt ccaaacaaag gatgctgttc ttgtctcaga    10140
gagaaataaa gttcaggatg taaagaaaat agtagaacaa attaaaaatt caggtcgtag   10200
cgagcattat gttcatcgcg aagtatatcg tccttggggt aaatatgatt ccattgacac   10260
aggggagcgt tatcaggtca aacgtataac agtaaatcct ggtgaaggac tttctttaca   10320
aatgcaccat cataggcag aacattggat catagtttct ggaactgcaa gggtgactat    10380
aggttctgaa actaagattc ttagcgaaaa tgaatctgtt tacataccctc ttggtgtaat  10440 acactgcttg gaaaatccag ggaaaattcc tctctgatta attgaagttc gttctggatc   10500
ttatttagaa gaagacgatg ttatccgttt tcaggaccga tatggtcgta gctaaatttt   10560
tgataatgta acgttagtag aagagcgcta atatttttag ttaatctgta ataagtatta   10620
tttgtttaag gtatatcatg tcgagtttac cctgctttaa agcctatgat attcgcggga   10680
aattaggcga agaactgaat gaagatattg cctggcgcat tggtcgcgct tatggcgaat   10740
ttctcaaacc gaaaaccatt gtgttaggcg gtgacgtccg actcaccagc gaaaccttaa   10800
aactggcgct ggcgaagggg ttacaggatg cgggcgtcga tgtgctggat attggcatgt   10860
```

```
ccggcaccga agagatctat ttcgccacgt tccatctcgg cgtggatggc ggcatcgaag   10920
ttaccgccag ccataacccg atggattaca acggcatgaa actggtgcgc gaagggctc    10980
gcccgatcag cggtgatacc ggactgcgcg acatccagcg tctggcagaa gccaacgact   11040
ttcctcccgt tgatgaaacc aaacgcggtc gctatcagca atcaatctg cgtgacgctt    11100
acgttgatca cctgttcggt tatatcaacg tcaaaaacct cacgccgctc aagctggtga   11160
ttaactccgg gaacggcgcg gcgggtccgg tggtggacgc cattgaagcc cgctttaaag   11220
ccctcggcgc acccgtggaa ttaatcaaag tgcacaacac gccggacggc aatttcccca   11280
acggtattcc taacccgcta ctgccggaat gtcgcgacga cacccgcaat gcggtcatca   11340
aacacggcgc ggatatgggc attgcctttg atggcgattt tgaccgctgt ttcctgtttg   11400
acgaaaaagg gcagtttatt gagggctact acattgtcgg cctgctggca gaagcgttcc   11460
tcgaaaaaaa tcccggcgcg aagatcatcc acgatccacg tctctcctgg aacaccgttg   11520
atgtggtgac tgccgcaggc ggcaccccgg taatgtcgaa aaccggacac gcctttatta   11580
aagaacgtat gcgcaaggaa gacgctatct acggtggcga aatgagcgcc caccattact   11640
tccgtgattt cgcttactgc gacagcggca tgatcccgtg gctgctggtc gccgaactgg   11700
tgtgcctgaa aggaaaaacg ctgggcgaac tggtgcgcga ccggatggca gcgtttccgg   11760
caagcggtga gatcaacagc aaactggcac accccgttga ggcgattaac cgcgtggaac   11820
agcactttag ccgcgaggcg ctggcggtgg atcgcaccga tggcatcagc atgacctttg   11880
ccgactggcg cttaacctg cgctcctcta acaccgaacc ggtggtgcgg ttgaatgtgg    11940
aatcgcgcgg cgatgtaccg ctgatggaag aaaagacaaa acttatcctt gagttactga   12000
acaagtaatt cagtaatttc atataaatgg gtttaaaaa acggaaaaga tgagatatcc    12060
ggtgtggtat atccaaggta atgctattca gtatctctat gagtgagtta acatctatac   12120
cacatttaag ccgcacactt cgggatcccc atatgaatat cctccttagt tcctattccg   12180
aagttcctat tctttctaga aataggaac ttcggaatag gaactaagga ggatattcat    12240
atggataaag ccgtaagcat ataagcatgg ataagctatt tatactttaa taagtacttt   12300
gtatacttat ttgcgaacat tccaggccgc gagcattcag cgcggtgatc acacctgaca   12360
ggagtatgta atgtccaagc aacagatcgg cgtagtcggt atggcagtga tgggacgcaa   12420
ccttgcgctc aacatcgaaa gccgtggtta taccgtctct attttcaacc gttcccgtga   12480
gaagacggaa gaagtgattg ccgaaaatcc aggcaagaaa ctggttcctt actatacggt   12540
gaaagagttt gtcgaatctc tggaaacgcc tcgtcgcatc ctgttaatgg tgaaagcagg   12600
tgcaggcacg gatgctgcta ttgattccct caaaccatat ctcgataaag gagacatcat   12660
cattgatggt ggtaacacct tcttccagga cactattcgt cgtaatcgtg agctttcagc   12720
agagggcttt aacttcatcg gtaccggtgt ttctggcggt gaagaggggg cgctgaaagg   12780
tccttctatt atgcctggtg gccagaaaga agcctatgaa ttggtagcac cgatcctgac   12840
caaaatcgcc gccgtagctg aagacggtga accatgcgtt acctatattg gtgccgatgg   12900
cgcaggtcac tatgtgaaga tggttcacaa cggtattgaa tacggcgata tgcagctgat   12960
tgctgaagcc tattctctgc ttaaaggtgg cctgaacctc accaacgaag aactggcgca   13020
gaccttacc gagtggaata cggtgaact gagcagttac ctgatcgaca tcaccaaaga    13080
tatcttcacc aaaaaagatg aagacggtaa ctacctggtt gatgtgatcc tggatgaagc   13140
ggctaacaaa ggtaccggta atggaccag ccagagcgcg ctggatctcg cgaaccgct    13200
gtcgctgatt accgagtctg tgtttgcacg ttatatctct tctctgaaag atcagcgtgt   13260
```

```
tgccgcatct aaagttctct ctggtccgca agcacagcca gcaggcgaca aggctgagtt    13320
catcgaaaaa gttcgtcgtg cgctgtatct gggcaaaatc gtttcttacg cccagggctt    13380
ctctcagctg cgtgctgcgt ctgaagagta caactgggat ctgaactacg gcgaaatcgc    13440
gaagattttc cgtgctggct gcatcatccg tgcgcagttc ctgcagaaaa tcaccgatgc    13500
ttatgccgaa aatccacaga tcgctaacct gttgctggct ccgtacttca gcaaattgc     13560 cgatgactac cagcaggcgc tgcgtgatgt cgttgcttat gcagtacaga acggtattcc    13620
ggttccgacc ttctccgcag cggttgccta ttacgacagc taccgtgctg ctgttctgcc    13680
tgcgaacctg atccaggcac agcgtgacta ttttggtgcg catacttata agcgtatcga    13740
taaagaaggt gtgttccata ccgaatggct ggattaa                             13777
```

<210> SEQ ID NO 14
<211> LENGTH: 15027
<212> TYPE: DNA
<213> ORGANISM: Artificial Sequence
<220> FEATURE:
<223> OTHER INFORMATION: example O8 rfb locus nucleotide sequence - O8-EPA production strain stLMTB11734

<400> SEQUENCE: 14

```
atgacgaatt taaaagcagt tattcctgta gcgggtctcg ggatgcatat gttgcctgcc      60
actaaggcga tacccaaaga gatgctacca atcgtcgaca agccaatgat tcagtacatt     120
gttgacgaga ttgtggctgc agggatcaaa gaaatcctcc tggtaactca cgcgtccaag     180
aacgcggtcg aaaaccactt cgacacctct tatgagttag aatcactcct tgagcagcgc     240
gtgaagcgtc aactgctggc ggaagtacag tccatctgtc cgccgggcgt gaccattatg     300
aacgtgcgtc agggcgaacc tttaggttta ggccactcca ttttgtgtgc gcgacctgcc     360
attggtgaca acccatttgt cgtggtactg ccagacgttg tgatcgacga tgccagcgcc     420
gacccgctac gttacaacct tgctgccatg attgcacgtt tcaacgaaac gggccgcagc     480
caggtgctgg caaaacgtat gccgggtgac ctctctgaat actccgtcat ccagactaaa     540
gagccgctga ccgtgagggt aaagtcagc cgcattgttg aatttatcga aaaaccggat      600
cagccgcaga cgctggactc agacatcatg gccgtaggtc gctatgtgct ttctgccgat     660
atttggccgg aactgaacg tactcagcct ggtgcatggg gacgtattca gctgactgat      720
gctattgccg agctggcgaa aaaacaatcc gttgatgcaa tgctgatgac cggcgacagt     780
tacgactgcg gcaaaaaaat gggctatatg caggcgtttg tgaagtatgg cctacgcaac     840
ctgaaagaag gggcgaagtt ccgtaaaggt attgagaagc tgttaagcga ataatgaaaa     900
tctgaccgga tgtaacggtt gataagaaaa ttataacggc agtgaaaatt cgcagcaaaa     960
gtaatttgtt gcgaatcttc ctgccgttgt tttatataaa ccatcagaat aacaacgagt    1020
tagcagtagg gttttattca aagttttcca ggattttcct tgtttccaga gcggattggt    1080
aagacaatta gcgtttgaat ttttcgggtt tagcgcgagt gggtaacgct cgtcacatca    1140
taggcatgca tgcagtgctc tggtagctgt aaagccaggg gcggtagcgt gcattaatac    1200
ctctattaat caaactgaga gccgcttatt tcacagcatg ctctgaagta atatggaata    1260
aattaagcta gcgatcgctt aagatctagg atttcattat gttacttcct gtaattatgg    1320
ctggtggtac cggcagtcgt ctctggccga tgtcacgcga gctttatccg aaacagttcc    1380
tccgcctgtt cgggcagaac tccatgctgc aggaaaccat cacccgactc tcgggccttg    1440
aaatccatga accgatggtc atctgtaacg aagagcaccg cttcctggtg gctgaacagc    1500
```

-continued

```
tacgccagct caataagctg tcgaataata ttattcttga gccggtcggg cgcaacaccg    1560
ccccggccat cgccctggca gcccttcagg ccacccgcga cggcgacgac ccgctgatgc    1620
tggttctcgc cgctgaccat atcatcaata accagtcggc cttccacgac gccatccggg    1680
tcgccgagca gtatgctgat gaaggtcatc tggtcacctt cggtatcgtg ccgaatgccc    1740
cggaaactgg ctacggttac attcagcgcg gcgtggcgct caccgatagt gcccattccg    1800
cgtaccaggt ggcccgcttt gtggagaagc cggatcgcga gcgcgccgag gcttacctcg    1860
cctccgggga gtactactgg aacagcggca tgtttatgtt ccgcgccaag aaatacctca    1920
tcgagctggc caaataccgt ccggatatcc tggaagcctg ccaggctgcg gtgaatgccg    1980
ccgataatgg cagcgatttc atcaatatcc cgcatgatat tttctgcgag tgcccggatg    2040
agtccgtgga ctatgccgtt atggagaaaa ccgccgatgc ggtggtggtc ggtctcgatg    2100
ctgactggag cgacgtcggc tcctggtccg cactatggga ggtcagcccg aaagacgagc    2160
agggcaatgt cctcagcggt gacgcgtggg tacacaacag cgaaaactgc tacatcaaca    2220
gcgacgagaa gctagtggcg gccattggcg tagagaatct ggtgattgtc agcactaagg    2280
acgccgtgct ggtgatgaat cgcgagcgtt cccaggacgt gaagaaggcg gtcgagttcc    2340
tcaagcagaa ccagcgcagc gagtacaagc gccaccgtga gatttaccgc ccctggggcc    2400
gttgcgacgt agtggtccag accccgcgct caacgtcaa ccgcatcacg gtgaaaccag    2460
gcggtgcctt ctcgatgcag atgcaccacc atcgcgccga gcattgggtt attctcgccg    2520
gcaccggtca ggtgactgtc aacggtaagc agttcctgtt gtccgagaac cagtccacct    2580
ttattccgat tggcgccgag cactgcctgg aaaaccctgg ctgtattccg ctggaagtgc    2640
tggagatcca gtcgggggcg taccttggcg aggacgacat tattcgtatt aaagaccagt    2700
atggtcgttg ctaattattt tcgggacaag acgcagaatg acacagttaa cttgttttaa    2760
agcttatgac atccgtggtg aactgggtga ggaactgaac gaggacatcg cctaccgtat    2820
cggtcgcgcc tacggcgaat ttctgaaacc cgggaagata gtggtggggg cgatgtgcg    2880 cctcacaagc gagtcgctga agctggcgct ggcccgcggg ttaatggacg ccggtaccga    2940
cgtgctggac atcggcctga gcggtaccga agagatttac tttgccacct ccaccttgg    3000 ggtagatggt ggcatcgagg tgaccgcgag ccacaatcct atgaactaca acggcatgaa    3060
gctggtcgcg gagaatgcga agcccatcag cggcgacacc ggcctgcggg atatccagcg    3120
cctggcggag gaaaaccagt tcccgccagt ggacccggcg cgtcgcggga ccctgagcaa    3180
gatatcggta ctgaaggagt atgttgacca tctgatgagc tacgtggact tctcgaactt    3240
cacccgtcca ctgaagttgg tggtgaactc cggaaacggg gctgcggggc acgtgattga    3300
tgaggtggag aaacgcttcg cggcggctgg ggtgccggta acctttatca aggtgcatca    3360
ccagccggat ggccatttcc ctaacggtat cccgaatccg ctgctgccgg agtgccgcca    3420
ggataccgcc gacgcggtgc gcgagcatca ggccgacatg gggattgcct ttgacgcgca    3480
cttcgatcgc tgcttcctgt tcgatgacga agcttcgttt atcgagggt attacattgt    3540 cggcctgctg gctgaggcgt tcctgcagaa gcagccggga gcgaaaatca ttcacgaccc    3600
gcgcttgacg tggaacacgg tagacatcgt gacccgcaac ggcggccagc cggtgatgtc    3660
gaagacgggg catgcgttca tcaaggagcg gatgcgtcag gaagacgcta tctacggcgg    3720
ggagatgagt gcgcaccatt acttccgcga tttcgcctac tgcgatagcg ggatgatccc    3780
gtggctgctg gtggcggagc tgctgtgtct gaagaacagc tcgctgaaat cgctggtggc    3840
```

```
ggaccgccag aaggcgttcc ctgcgtcggg agagatcaac cgcaagctaa gtaatgctgc    3900
tgaggcgatc gcccgcatcc gggcgcagta tgagccggcg gctgcacaca tcgacacaac    3960
ggacgggatc agtattgaat accctgaatg gcgctttaac ctgcgcacgt ctaacaccga    4020
gccggtggtg cgtctgaacg ttgagtccag agctgatgtg gcgcttatga atgaaaaaac    4080
gaccgagctg ttacacctgt taagcgggga ataaggtgag agatttacta acgacgattt    4140
atcgttatcg gggatttatc tggagcagtg ttaaacgtga ttttcaggca cgctatcaaa    4200
ctagtatgct gggcgcacta tggctcgttt tacaaccgct ctctatgatt ctggtctata    4260
ccctggtttt ttccgaggtg atgaaggcaa gaatgcccga taataccggg tcgtttgcct    4320
atagtattta tctctgttcc ggggtactga cctggggatt atttactgag atgctggata    4380
aaggtcagag cgtatttatt aacaatgcta atctgatcaa gaaactcagt tttccgaaaa    4440
tctgtctgcc gatcatcgtg acgttatcgg cggtgctaaa tttcgcgatt attttcagtc    4500
tgtttctaat ttttatcatt gtcaccggta acttccccgg ctggctcttt ctctcggtga    4560
taccggtcct gcttttgcag atcctgtttg ccggtgggct ggggatgatc cttggtgtca    4620
tgaacgtctt tttcagggat gtggggcaac tggttggcgt tgcgctgcaa ttctggtttt    4680
ggttcacacc cattgtttat gtactgaatt cattacctgc atgggcaaaa aatctgatga    4740
tgtataaccc gatgactcgg atcatgcaat cttatcagtc catcttcgcc tatcatctgg    4800
cccccaactg gtattcgcta tggccagtat tggctctcgc cattattttc tgcgtcatcg    4860
gtttcaggat gttccgcaag catgcggcgg atatggtgga tgaattataa tgagttatat    4920
cagagtaaat aatgtcggta aggcgtatcg ccagtatcac tcaaagaccg ggagactgat    4980
cgaatggtta tcccctctga ataccaaacg ccataatttg aaatggatcc tccgcgatat    5040
taatttcgaa gtcgctccgg gcgaggctgt cggtattatc ggtatcaacg gtgcaggcaa    5100
gagtaccctg cttaaactca taaccgggac gtccaggccg acgactggag aaattgaaat    5160
ctccggacgt gtcgctgcat tactcgaatt ggggatgggg tttcattctg atttcactgg    5220
tcggcagaat gtttatatgt ctgggcaact gttggggtta tcgtcagaga aaataactga    5280
actgatgccg caaattgaag agtttgctga gattggggac tatatcgatc aacctgtgcg    5340
cgtctactcc agtgggatgc aagttcgatt agcttttagt gtagcgacgg ctatccgtcc    5400
tgatgtgcta attatcgatg aggcattatc tgttggggat gcatatttcc agcataaaag    5460
ctttgagcgt attcgaaaat tcgtcagga agggaccacg ctgttgctgg tatcccatga    5520
taaacaagcg atccaaagca tttgcgaccg ggccatttta ttgaataaag gccaaattga    5580
aatggaaggt gaacctgaag cagtgatgga ttattacaat gctcttctgg ccgataaaca    5640
aaatcagtcc attaaacaag ttgagcataa tggtaaaacg caaactgttt caggcactgg    5700
tgaggtgact atctctgagg ttcatcttct cgatgaacag ggcaatgtga ctgaatttgt    5760
ttcggtaggg catcgtgtca gcttgcaggt caacgttgag gtcaaggacg atattcctga    5820
gcttgttgtc ggatatatga ttaaggatcg acttgggcag ccgattttcg ggaccaatac    5880
gtaccatctc aatcagacac tcacctccct gaaaaaagga gaaagcgtt cgttcttatt    5940
ttctttcgat gcgagattgg gggttggctc ctattctgtc gctgtcgcgt tgcatacttc    6000
cagtacgcac ctcggcaaaa actatgaatg gcgcgatctg gccgtggtat tcaacgtcgt    6060
taacacggaa caacaagagt ttgtcggcgt gtcctggttg ccgcctgaac tggagatttc    6120
ttaatgggtt cgtcgtttta tcgttcattt gaagaacgac acagaggttc ggttgaagaa    6180
atcaagcgcc gcttgagttt ttatttacct tttcttgcag gtctgaagga catttatcct    6240
```

```
gatggcgtga ttgcggatat tggttgcgga cgtggcgaat ggttggagat cctgactgaa    6300
aatggcattg cgaacatcgg cgtcgatctc gatgatggca tgctggcgcg cgccagggag    6360
gccggactga atgtgcagaa aatggattgt ctgcagtttt tgcaaagtca ggcggatcag    6420
agcctgatag cgttgaccgg ttttcatatt gctgagcatt tgccgtttga ggtcctgcag    6480
caactcgcca tgcataccct acgggtgctg aaaccaggtg gtttgctgat cctcgaaacg    6540
ccgaacccgg agaatgtaag cgtcggcacc tgttcatttt atatggatcc aacgcataat    6600
catcctctgc caccgccact gcttgagttt ttacctattc attatggttt tacccgagca    6660
attaccgttc gtctgcagga aaagaggtt cttcaatctc cggatgcagc cgttaatttg    6720
gtcgatgtac tcaaaggggt gagccccgac tacagcatca ttgctcagaa agcagcgcca    6780
acagatattc ttgaacgctt tgacaccctg tttacccagc agtacggtct gacgctggat    6840
gctctgagca accgttacga tgcgatttt cgccaacagt tttcgtccgt tgtctcacgg    6900
ctggagacgt tgaaccaaac ctatatgcaa cagataagcc aaatgtcaga gactattcag    6960
acgttgcaag gtgaggttga cgatctgagt catgtcatcg atcagaacca tcagcttcat    7020
cagcaaatgg cggatttaca taacagtcgt tcatggcgta ttactcaacc actacgctgg    7080
ttgtctttgc aacgtcaatt attacgtcag gaagggcta aagtgcgagc ccgtagggct    7140
gggaaaaaaa tattgcgcaa agggatggcg ctctcgctgg tcttttttcca tcgttaccct    7200 aagtctaagg tttatctgtt taaggttctg agaaaaactg gctgctatac attgctacaa    7260
cgtttgttcc aacgcgtaat gctggtgcaa tctgacacga tgatgatgca gtccagaaga    7320
tatgatgtgg gtactgaaga aatgacaagt cgcgcgatga gtatttataa cgaattaaaa    7380
aataaaaata cggagaaaata acgatgcgta ttgtcataga tttacaaggc gcacagacgg    7440
aaagccgctt tcgtggcatc ggtcgttata gtatcgcaat cgccagaggc ataatcagaa    7500
ataacagccg gcatgagatt ttcatcgcgc tatccgccat gctggatgag tcgattgcaa    7560
atattaaggc gcaatttgcc gatctcctgc cggcagaaaa tatagtcgta tggcatgccg    7620
taggccctgt tcgtgcgatg gaccaaggta atgaatggcg tcgggagagc gcagaactga    7680
ttcgggaagc gtttcttgaa tcattgtgtc cagatgtcgt tttcattacg agtttgtttg    7740
aaggtcatgt cgacgatgcg gctacatcgg tacacaaatt tagtcgtcag tataaagtag    7800
ccgtactgca ccacgatctt atccccctcg tgcaggcgga aacctatctg caggacgatg    7860
tatacaaacc ctactattta cagaaagttg agtggttaaa aaacgctgac cttttgttga    7920
ctaactctgc ttataccgca caggaagcga tcgagcatct gcatttacag ggcgatcatg    7980
tgcagaatat tgcagccgca gtcgattctc agttttgtat ggcggaggtg gcagcgagcg    8040
aaaaagagac cgtccttggc cattacggta ttcagcgcga gttcatgttg tatgcgcccg    8100
gaggatttga ctcaaggaaa aactttaaac ggttgattga ggcctatgcc gggctcagtg    8160
atgccttacg tcgcagtcat caactggtca tcgtcagtaa gctttccatc ggtgatcgtc    8220
agtatctgga atcccttgcg tcaggtaatg gtttacagca gggcgaactg gtactcactg    8280
gttatgtgcc ggaagatgag ctgatccagc tctatcgcct atgtaagctg ttcatctttg    8340
cttcactaca tgaaggtttt gggttgccgg ttctggaagc aatgtcgtgc ggtgcgccgg    8400
tgattggctc aaatgtcacc agtattcctg aagtcatcgg taatcctgag gcattattcg    8460
acccgtattc tgtctcttcc atgagggata agatcgcgca atgtttgact gatgatacct    8520
tcctcgcgcg tctgaaagaa atggcgcagc agcaagcgcg taatttctct tgggataaag    8580
```

```
ctgcggtgac tgctctggaa gctttcgaaa agatcgcggt agaagacacc ggtactgcgc   8640
aggttttgcc tgaagctttg attcagaaga tccttgctat ctcacaaggg cagccagatg   8700
accgcgatct gcgcttgtgc gcaacggcca ttgattacaa tctgaaaacg gcagaacttt   8760
atcaaatcga cgataaatcg ctgaactggc gtgtggaagg cccattcgat agctcatata   8820
gtctggcgtt ggtcaaccgc gaatttgccc gggcactctc agccgatggt gtagaggttt   8880
tattgcattc cactgaagga ccaggtgatt ttgccccaga tgcctcgttt atggcacagt   8940
cggaaaatag tgatcttctg gcattttata atcaatgtca gacccgcaag agtaacgaaa   9000
agatagatat tattagcaga aatatctatc caccgcgggt taccaaaatg gatgccaaag   9060
taaaattcct tcattgttat gcttgggaag aaacgggctt tccgcaaccg tggatcaatg   9120
aatttaatcg ggaacttgac ggagtgctgt gtacttcgga acatgttcgt aaaatactga   9180
ttgataacgg actgaatgtg cccgcatttg ttgttggcaa tggctgtgac cattggctca   9240
atatcccagc cgagacgaca aaagatgtgg atcacggaac attccgtttc ctgcacgtct   9300
cttcttgttt cccacgcaaa gggatacagg caatgcttca ggcttggggg aaggcgttca   9360
ctcgtcgtga caatgttatc ttaatcatta agacttttaa caatccgcac aatgaaattg   9420
acgcatggct ggctcaggcc caggctcaat tcatagacta tcccaaagtt gaagtgatca   9480
aagaggatat gtcagccacc gagcttaaag ggctttatga aagctgtgat gttttggttg   9540
ctccaggttg cgctgaaggc tttggtttac ctattgctga agcaatgctg agtgggctac   9600
cggctatcgt caccaattgg agcgggcaac ttgattttgt taattcacaa aattcatggc   9660
tggttgacta tcagttcact cgggtaaaaa cgcactttgg tctgtttttcc tcagcctggg   9720 ccagtgtgga tattgacaac ttaacagatg cattaaaagc ggcagcctca accgataaat   9780
cagtgctgcg tgacatggcc aatgctggtc gcgagcttct tctgcagcag tttacctgga   9840
aagcggtggc tgatcgttct tgccaggcgg tcaagactct gcgtgcgcat attgatattg   9900
cacagcatcg ggcgcgcatt ggctgggtga cgacctggaa cacgaaatgt gggatcgcaa   9960
cctattccca gcatctggtg gaaagcgcac ctcatggcgc ggatgttgtt tttgctcccc   10020
aggtcagcgc tggcgatctt gtgtgtgcag acgaagagtt tgtacttcgc aactggattg   10080
taggtaaaga gagcaactat ctggaaaacc tccagccaca cattgatgct ctgagactcg   10140
atgtcattgt gatccaattc aactatggat tctttaatca tcgagaactg tcggcgttta   10200
ttcgtcgcca gcatgacgcc ggtcgttcag ttgttatgac gatgcactca actgtggatc   10260
cgctggaaaa agagccgagc tggaatttcc gtcttgctga aatgaaagag gcgctggcac   10320
tttgcgaccg gttgttggtg cattcgattg ccgatatgaa ccgccttaaa gatttaggct   10380
taactgcgaa tgttgcttta ttcccgcacg gtgttatcaa ctactccgca gcgagcgtca   10440
cacgtcaaca gcagtcttta ccgctaattg cgagctatgg cttctgctta ccgcataagg   10500
gcctgatgga actagtagaa tccgtccata gactcaagca agccggtaaa ccggttcgtt   10560
tacgactggt gaacgcagag tatcctgttg gggagtcacg cgatctggtg gcagagctta   10620
aagctgctgc tcagcggtta ggtgttaccg atctgattga gatgcataat gatttcctac   10680
ctgatgcgga gagtctgcgg ttgctttcag aagccgatct tctgattttt gcttatcaga   10740
atactgggga gtctgctagc ggggcggtac gttatggtat ggcgactcaa aaacctgttg   10800
cggtaacgcc cctggcgata tttgatgatt tggacgatgc cgtctttaaa tttgatggat   10860
gcagcgtcga tgatatcagt caggggattg accggatcct gaattccatc cgtgaacaga   10920
actcttgggc aaccaggact caacaacgtg ccgatgcatg gcgggaacaa catgattatc   10980
```

-continued

```
aagctgtttc acgccgtctg gttaatatgt gtcaaggctt agctaaagct aaatatttta    11040
aataaaaata tctctcttgt attttttgcc tttgaataca agaggggtta gataatgtgt    11100
catttattat gaaaattatt tttgctactg agccaattaa atacccatta acgggcatcg    11160
gtcggtattc cctggagctg gttaagcggc tggcggtcgc ccgcgaaatt gaagaattaa    11220
agctatttca cggtgcgtcg tttatagaac agatcccttt ggtggagaat aaaagcgata    11280
ccaaagccag caatcatggt cgtctgtcgg cgtttctacg ccgacagacg ctgttgattg    11340
aggcttatcg cttgctgcat ccgcggcgcc aggcgtgggc attgcgcgac tataaggatt    11400
atatctacca tggccccaat ttttatctgc cgcataaact ggaacgcgcc gtgaccacgt    11460
ttcatgacat atccattttt acctgcccgg aatatcatcc aaaagatcgg ttcgctata    11520
tggagaagtc cctgcatgag agtctggatt cggcaaagct gatcctgacc gtttctgatt    11580
tctcgcgcag tgaaattatc cgcttgttca actatccggc ggagcggatc gtaaccacca    11640
agctagcctg cagcagtgac tatatcccac gcagcccggc agagtgtctg ccggtactgc    11700
agaaatatca gctggcgtgg caggcctacg cgctatatat cggcactatg gagccacgta    11760
aaaatatccg aggcctgctg catgcctatc agctgctacc gatggagatc cgcatgcgct    11820
atccgctaat ccttagcggc tatcgcggct gggaagacga tgtgctgtgg cagttagtcg    11880
agcgcggtac tcgggaaggc tggatccgtt acctcggata tgttccggat gaagacctgc    11940
cgtatctgta cgcagcggcc agagtctttg tttatccctc cttctacgag ggattcggtt    12000
tacctattct tgaagcgatg tcttgcggtg tgccggtagt atgctccaat gtcacctctt    12060
tgcctgaggt tgttggcgat gccggcctcg ttgccgatcc taatgatata gacgcgatta    12120
gcgcgcaaat tttgcagagc ctgcaagatg atagctggcg ggaaatcgcc accgcgcgcg    12180
gtcttgctca ggcgaaacag ttttcgtggg agaactgtgc gacacagacc attaacgcct    12240
ataaattact ctaagggtgt cagttgagag ttctacacgt ctataagact tactatcccg    12300
atacctacgg cggtattgag caggtcattt atcagctaag tcagggctgc gcccgccggg    12360
gaatcgcagc cgatgttttc acttttagcc cggacaaaga tacaggtcct gtcgcttacg    12420
aagatcatcg ggtcatttat aataaacagc ttttgaaat tgcctccacg ccgttttcgc    12480
tgaaagcgtt aaagcgtttt aagctgatta agatgactac cgatatcatc aactaccatt    12540
ttccgttttcc ctttatggat atgctgcatc tttcggcgcg gcctgacgcc aggactgtgg    12600
tgacctatca ctctgatata gtgaaacaaa acggttaat gaagctgtac cagccgctgc    12660
aggagcgatt tctcagcggc gtagattgca tcgttgcctc gtcgcccaat tacgtggctt    12720
ccagccagac cctgaaaaaa tatctggata aaacggtggt gatcccgttt ggtctggagc    12780
agcaggacgt gcagcacgat ccgcagaggg tcgcgcactg gcgggaaact gtcggcgata    12840
agttctttct cttcgtcggc actttccgct actacaaagg gctgcatatt ctgatggatg    12900
ccgctgagcg tagccgactg ccagtggtgg ttgtaggggg cgggccgctg gaatcggaag    12960
tgcggcgtga agcgcagcag cgcgggctga gcaatgtgat gtttaccggc atgctcaacg    13020
acgaagataa gtacattctc ttccagctct gccgggggcgt ggtattcccc tcgcatctgc    13080
gctctgaggc gtttggcatt acgttattgg aaggcgcacg ctttgcaagg ccgctgatct    13140
cttgcgagat cggtacaggt acctctttca ttaaccagga caaagtgagt ggttgcgtga    13200
ttccgccgaa tgatagccag gcgctggtgg aaggcgatgaa tgagctctgg aataacgagg    13260
aaacctccaa ccgctatggc gaaaactcgc gtcgtcgttt tgaagagatg tttactgccg    13320
```

```
accatatgat tgacgcctat gtcaatctct acactacatt gctggaaagc aaatcctgag   13380
cggccgcgag ctcgtcgact cgaggatccg tgtaggctgg agctgcttcg aagttcctat   13440
actttctaga gaataggaac ttcggaatag gaactaagga ggatattcat atggataaag   13500
ccgtaagcat ataagcatgg ataagctatt tatactttaa taagtacttt gtatacttat   13560
ttgcgaacat tccaggccgc gagcattcag cgcggtgatc acacctgaca ggagtatgta   13620
atgtccaagc aacagatcgg cgtagtcggt atggcagtga tgggacgcaa ccttgcgctc   13680
aacatcgaaa gccgtggtta taccgtctct attttcaacc gttcccgtga aagacggaa    13740 gaagtgattg ccgaaaatcc aggcaagaaa ctggttcctt actatacggt gaaagagttt   13800
gtcgaatctc tggaaacgcc tcgtcgcatc ctgttaatgg tgaaagcagg tgcaggcacg   13860
gatgctgcta ttgattccct caaaccatat ctcgataaag agacatcat cattgatggt     13920 ggtaacacct tcttccagga cactattcgt cgtaatcgtg agctttcagc agagggcttt   13980
aacttcatcg gtaccggtgt ttctggcggt gaagagggg cgctgaaagg tccttctatt    14040
atgcctggtg gccagaaaga agcctatgaa ttggtagcac cgatcctgac caaaatcgcc   14100
gccgtagctg aagacggtga accatgcgtt acctatattg gtgccgatgg cgcaggtcac   14160
tatgtgaaga tggttcacaa cggtattgaa tacggcgata tgcagctgat tgctgaagcc   14220
tattctctgc ttaaaggtgg cctgaacctc accaacgaag aactggcgca gacctttacc   14280
gagtggaata acggtgaact gagcagttac ctgatcgaca tcaccaaaga tatcttcacc   14340
aaaaaagatg aagacggtaa ctacctggtt gatgtgatcc tggatgaagc ggctaacaaa   14400
ggtaccggta aatggaccag ccagagcgcg ctggatctcg cgaaccgct gtcgctgatt     14460 accgagtctg tgtttgcacg ttatatctct tctctgaaag atcagcgtgt gccgcatct    14520 aaagttctct ctggtccgca agcacagcca gcaggcgaca aggctgagtt catcgaaaaa   14580
gttcgtcgtg cgctgtatct gggcaaaatc gtttcttacg cccagggctt ctctcagctg   14640
cgtgctgcgt ctgaagagta caactgggat ctgaactacg gcgaaatcgc gaagattttc   14700
cgtgctggct gcatcatccg tgcgcagttc ctgcagaaaa tcaccgatgc ttatgccgaa   14760
aatccacaga tcgctaacct gttgctggct ccgtacttca gcaaattgc cgatgactac     14820 cagcaggcgc tgcgtgatgt cgttgcttat gcagtacaga acggtattcc ggttccgacc   14880
ttctccgcag cggttgccta ttacgacagc taccgtgctg ctgttctgcc tgcgaacctg   14940
atccaggcac agcgtgacta ttttggtgcg catacttata agcgtattga taagaaggt    15000 gtgttccata ccgaatggct ggattaa                                        15027
```

<210> SEQ ID NO 15
<211> LENGTH: 11283
<212> TYPE: DNA
<213> ORGANISM: Artificial Sequence
<220> FEATURE:
<223> OTHER INFORMATION: example O15 rfb locus nucleotide sequence - O15-EPA production strain stLMTB11738

<400> SEQUENCE: 15

```
atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc   240
gtgaagcgtc aactgctggc ggaagtacag tccatctgtc cgccgggcgt gaccattatg    300
```

```
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgg caaaacgtat gccgggtgac ctctctgaat actccgtcat ccagactaaa    540
gagccgctgg accgtgaggg taaagtcagc cgcattgttg aatttatcga aaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcaatcttc ctgccgttgt tttatataaa ccatcagaat aacaacgagt    1020
tagcagtagg gttttattca aagttttcca ggattttcct tgtttccaga gcggattggt    1080
aagacaatta gcgtttgaat ttttcgggtt tagcgcgagt gggtaacgct cgtcacatca    1140
taggcatgca tgcagtgctc tggtagctgt aaagccaggg gcggtagcgt gcattaatac    1200
ctctattaat caaactgaga gccgcttatt tcacagcatg ctctgaagta atatggaata    1260
aattaagcta gcatgagcaa aactaaacta atgttctttt accttgcaat aagtcagggt    1320
gccaattacc tactgccatt attaattttt ccttatcttg ttagagtcat tggtgtatcg    1380
aattttggtg atctgagttt ttcattgata actatacaag tgttgttaat ggttgttgaa    1440
tatggttttg gatatagtgg gacaagagaa atagcactaa ataacgataa aaaataccat    1500
tctgaatttt tttgcggtgt ggtgcttgct cgttttatat taatgctaat tgcagctata    1560
atactcataa tactctgttt tttttatgtt tttaacgacg ttaagtcttt gttatgtgtt    1620
ggttttctgt ccgtaattgc aggtgttttc aatccaaatt ggttttttgca aggtaaggaa    1680
atgatgagtg tgatggctgt gctgtcacta ttttcacgag gcatagcagt cgttgcagtt    1740
tatctaatta taaaacccgc aacgccgatg tacatcagtg ccttattatt gagcatgcca    1800
tatattttgt attcattctg tggcgttgcc tacttactta ttatcaagga gattttttta    1860
tgtaggccac cgataaagaa aattcaagta attttaaaaa atggatttca ttttttttgt    1920
tcaacacttg cgactagtgc atacacaatg ttgacccctc ttgtattggg tggcgtatct    1980
ggaaagtttg atgtaggcat ctttaactca gctaacatga tcaaacaagg tttggctgga    2040
cttgcatcac cattagtcca agcttttat ccaagaatta acatttgca aagagagaat    2100
ccatatattg caaacttaaa atctagaatg attcttaaat acttgcttgt ttttacatg    2160
gctttagcaa taccattttt acttttgcc aaccaattat cattattaat attcggcatg    2220
aaaggtgaag taattgcagg tgcaatgcaa ttaatgacat tgcttcctat attcataggt    2280
tttaatacag ttgtcgggtt acttgtatta gtacctaatg ggatgcaaaa acagtatttc    2340
aaatctatttt tcctaggaac tattacttgt ttaagcatag tttatccagc atgtaaatat    2400
tatggagcaa cgggtgcgat tgtgagtctt attgtagctg aaattttcgt tggcatggga    2460
atgcttaaac aattcattaa agtaaataaa accgtatgta ggcctcataa attatgaata    2520
tctcggtaat aatatctgtt tggaaacgcc cagttcaatt agaattgatt ctctctgagc    2580
tcgattctca ggctaaagac aatagtctac acctagaagt aattgtttcc gatagtcata    2640
gtggtaaaga aattgatgat gtagttgctg ataatattca taaaagaaa aatattaata    2700
```

```
ttatccatca acatactaaa aatatactct ccgctaagcg caatttcgga gcatccctag    2760
cccatgggga ttatttaata tttcttgatg atgattgtat acccgcaagt ggatatatat    2820
catcgttgct gaactatttta aaaaaaatga atagtaaaag cgttttatgt ggggaagtta    2880
gattcgaaaa tgaactcatt gagaccagca attactatcg ctacaggaac tctttacacc    2940
ctaagtttag tgatagtcct gatatctcta tgaatgcctg gacttttgtc gcaatgaatt    3000
gtgttcttga tagaaaggca ttttcatcag gtatagtttc atataatgaa aattttattg    3060
gttatggttg tgaagatcat gagtttgggt ggcaacttga aaaaaatgac ttcaaaatta    3120
tttttgctga ttttaaaata ttacatcacg aatacagtgg cgatatagaa ggatatacaa    3180
aaaaaattcg tgctacagca cgtgatggta tgaatgtatt aagcaaagta aggcctgaaa    3240
tgttttctac taataaaaaa ttattcctag ttgagaaaat atttagtaaa cacaaaacgt    3300
ttagtaaaat atgccaatca atatttttca ataaatttat ttttaaaaaa ataatacaat    3360
ttttaaaaaa aacagatgca aataaaaaac tctatttccc aattctttac agatatgtgt    3420
tgatttcggc atatatacat ggtattggag agcgtggcac ctcaaaaaca gatgatttgc    3480
ttaagaactg gtatatatag atgatgctat cttcatttat taagacattt gtatggaagg    3540
taaaaaacaa tgaagtataa tgcattgatg gcttttttat tattttttgt tgttttttt     3600 agattgtcgc tgataatacc tttcttatat ttggcattta ttcctgcatt ttttggtatt    3660
atgtatttag tgcgtaattt tatgattact atgggcaatg gattggtatc tatagatcgt    3720
aaaaatttgt tgctgttatc tatattcata attattttt tattttgttt ggttttcgat     3780
ttgtttcaaa aaagccattc ttttcaaagt tattttaccg ttagattatt tatgttgttt    3840
ttattttcat ttgttcctgc gtattattta gtaaatagat tcataaaggg tgacttgaaa    3900
ttaatggagc gaatattagt gtattctctc tgggttcaaa tagttatttt ttttggtatg    3960
tatataagtc cagagttaaa aagattgtta tatactttct ttggtatgtc tgactctgtt    4020
aatctttggg aacaaaatgc taaagtaaga ggatttgggt tgtcgggtga aataaatttc    4080
atgacaccat ttttgatgat ctatatgtca ttttttatga tgaaaaggcg ttatgctttta   4140 attactttaa tttgtctgac tcaaatcgta aattctaaca tggctgtgat tgcagccatt    4200
attggtatcg gttgctctag acttaatatt aatataaaaa ttgcaacagt attgatttg     4260 ggagttttag tttatagctt aggagcggtg ttctttcctc gattttatga tgagttcgtt    4320
tctggagatg gcacaagaac tctggatatc ttattacagc aacatgtgtt tgttgtaggt    4380
aatttagatt tttttaatat tatatttgga ttacagcaaa acatatcttc atcaatcccc    4440
gatattaaac aaagttcgga tatgggctgg gttatactgt ttaattacgg tgggttaaca    4500
tttattacac tcttttttatt tttaatcttt actatttcta ttgcgacatt tggaatgaca    4560
tatcaagcaa ttatatggat gttaattggg ataattttca ataccaaagg tttagtttta    4620
ggatctaacg gctatttctt tctatctttt atatatgt ttttgaatag agtaacactt       4680
agtggacaga gttcaattac taataagtta ggtcaagtaa gtaaatagct tccagagtat    4740
atttgtcaat gatttgaggt tcggttatta tgttttcatc taaaacactg ttaattactg    4800
gtggtactgg ctcttttcggg aatgctgtat taaatagatt tcttgataca gatattgcag    4860
aaatccgtat atttagtcgt gatgaaaaaa aacaagatga tatgcggaaa aaatacaata    4920
atcaaaaatt aaagttctat attggtgatg tcagagatta ccgtagtatt ttgaatgcga    4980
ctcgcggtgt tgatttttata tatcatgcag cggcacttaa gcaagttcca tcatgtgaat    5040
```

```
ttcatcctat ggaagccgtt aaaactaata tccttggtac ggaaaatgtt cttgaagcag    5100
ctatagcgaa tgaagtgaag agggttgtat gcctaagtac tgataaagct gtatacccga    5160
ttaacgcaat gggtatttca aaagctatga tggaaaaggt catggtcgcg aaatcccgta    5220
atgttgatcg caataaaaca gtaatatgtg gtacccgtta tgggaatgtt atggcatctc    5280
gcggttcagt tattccatta tttgttgatc ttattagagc gggcaagcca ctcacaataa    5340
ctgatcctaa tatgacccgc tttatgatga ctcttgagga tgcggtagat ttagttcttt    5400
atgcgtttga acatggtaat aatggtgata tctttgtgca aaaagcacct gcagcaacta    5460
ttgacacatt agctattgct ttaaaggaat tactaaatgt tcctgaccat ccggtaaatg    5520
tcattggaac gcgtcatggc gagaaattat atgaagctct acttagtcgt gaggaaatga    5580
tcgctgctat agatatgggc gattattacc gtgtcccgcc agatcttcgt gaccttaatt    5640
atggcaaata tgttgagcaa ggtgatagcc gaatatctga aatagaagat tataactctc    5700
ataatactca acggttagat gttgaaggca tgaaagagct cttgctaaaa ttagcccttta    5760 ttcgagcaat tcgtgctggt gaaaaatata atctggattc atgatatgaa aatattagtt    5820
actggtgcaa atggttttat tggtcgtaat ttatgtttga ggcttgagga acttggttat    5880
aaagatctta ttagaattga tcgagaatca acgaagcaag atcttgaaca aggcttacag    5940
gatgccgatt ttatttatca cttagctggt atcaatagac ctaagactga tgatgagttt    6000
atttctggaa acagtgattt aacaaagcat atagttgagt atctcctttc tattggtaag    6060
aatacaccaa ttatgctaag ttcttcgata caagctgaac ttaataatgc ttatggggtt    6120
agcaaagctg tagctgaaag ctatgtcgaa aaatatgctg ctgctagtgg ttcttcgtat    6180
tatattttca gatatccaaa cgttttggt aaatggtgta agccaaacta taattctttt    6240
atagcaactt tttgctacaa tatttccaat gatattgaga ttactatcaa tgatgcagca    6300
gcgccagtca atctggtcta tattgatgat gtttgtactg atgctatagc tcttctctct    6360
gggacggttg aaagtggata taagttgtt gcaccaattt attcaacaac agttggtgaa    6420
gttgcagaat taatttatag cttcaaaaat agccgttcca ccctgatcac agaggctgtc    6480
ggggcgggat ttacccgtgc attgtattct acatggctga gttatttacc agcagagaag    6540
tttgcgtaca aggtaccttt ttatggggat gcccgcggag tcttttgtga gatgttgaaa    6600
acgccttcag cggggcagtt ttcatttttt actgctcacc ctggtattac gcgtggcgga    6660
cattaccatc acagtaaaaa tgagaagttt ttggtcattc gaggtcaggc atgctttaaa    6720
tttgaacatg tgattaccgg tgagcgatat gaactgaaag tttcatcggg tgagtttaag    6780
attgttgaaa cagttcctgg ttggacacat gacattacaa atattggaac tgatgaatta    6840
atagtcatgc tctgggcaaa tgaaattttc aaccgtgatg agcccgatac tattgcgaga    6900
cctctataat gaaaaaatta aagttatgt ctgttgttgg aacccgtcct gagattatcc    6960
gtttgtcgag ggttcttgct aagtttgatg aatactgcga gcatattatt gtccatactg    7020
gtcaaaatta tgattacgaa ttaaatgaag tgttcttcaa tgacttgggt gttcgaaaac    7080
ctgattattt tttaaatgca gcgggtaaaa atgcggcgga aaccattggt caggttatta    7140
ttaaggtaga tgaagtatta gaaatcgaaa aacctgaagc aatactggta ttgggcgata    7200
cgaattcatg tatttctgcc attccggcca aacgccgtaa agtgcctata tttcatatgg    7260
aagcaggtaa ccgttgtttc gatcaacgcg tgcctgaaga aaccaacaga cgtattgttg    7320
accatacggc tgatatcaat atgacctaca gtgatattgc tcgtgaatat ctcttggctg    7380
aaggtatccc agctgatcgg atcataaaaa ctggtagccc tatgtttgag gttctttcat    7440
```

| | |
|---|---|
| attatatgcc ccaaattgat ggttcagatg tgctatcgcg tttgaatcta cagtctggtg | 7500 |
| agtttttgt agtaagtgcg catcgtgaag agaatgttga ttctccaaaa cagctcgtaa | 7560 |
| agcttgcgaa cattctaaat actgttgctg aaaaatataa tcttccagtt attgtctcca | 7620 |
| cacacccaag gacacgtaac cgaatccgtg agcaaggaat tgaatttcat tcaaatataa | 7680 |
| atctactgaa accattgggt ttccatgatt ataaccactt gcagaagaac tcacgagctg | 7740 |
| tgctttcaga tagcggtact atcactgaag agtcatccat catgaatttc ccagcggtaa | 7800 |
| acatccggga agcgcatgag cgtccggaag gctttgagga agcatccgtc atgatggtgg | 7860 |
| ggttagagtg tgaacgcgta ttacaagcgc tggatattct ggcaacacaa ccgcgaggtg | 7920 |
| aagtccgtct tttacgtcag gttagtgatt acagcatgcc aaatgtgtcg gataaagttg | 7980 |
| tcagaattgt tcactcttac acagattatg ttaagagagt cgtctggaaa gaatattgat | 8040 |
| gaaacttgct ttaatcatag atgattacct gcccaacagt actcgtgttg gtgcaaaaat | 8100 |
| gtttcatgaa cttgctcaag aatttatcca gcgtgggcac gatgttacgg taattactcc | 8160 |
| tggtacgggc atgcaagaag agatttcttt tgataccttt caggggtaa aaacatggcg | 8220 |
| ttttaaaagc gggccgctca aggatgtaag taaaattcag cgagcggtca atgaaacgct | 8280 |
| tttgtcctat cgggcgtgga aagccatcaa aaaatgggta aaaaagaga cctttgaggg | 8340 |
| ggtgatttat tattcacctt ccatattctg ggggccttta gttaaaaaaa ttaaagctcg | 8400 |
| ttgccaatgt cctgcttatc ttattttaag agatatgttt ccacaatggg taattgatgc | 8460 |
| aggaatgctt aatgctggtt ccccaataga acgctacttt cgtcttttg aaaaaatatc | 8520 |
| ttatcgtcag gcaaatcgta ttggacttat gtctgataag aatcttgatg ttttcggaa | 8580 |
| agataataaa ggctatccgt gcgaagtttt gcgtaattgg gcatccctaa caccaacgat | 8640 |
| catacccaag gattatatac cactacgtaa gcgacttggc ctagaggata aaccattt | 8700 |
| cttctatggt ggaaacatag gtcatgcaca ggacatgaca aacttgatgc gacttgtgag | 8760 |
| aaacatggca gcatatcctc aagctcattt cctatttatt ggccagggg atgaagttga | 8820 |
| attaattaat tcattagcat ctgagtgggc attgacgaat ttcacctatt tgccctcggt | 8880 |
| taaccaagat gaatttaagt tcattttgtc ggaaatggat atcggcttgt tttctctttc | 8940 |
| cgctagacac tcttcccata atttttcctgg taagttatta ggctatatgg ttcagtcgct | 9000 |
| acctatttta ggtagcgtaa atgccggaaa tgatttgctc gacattgtca atcaaaataa | 9060 |
| tgcgggatta atccatgtca atggtgagga cgataaatta tgtcaatctg cgctattaat | 9120 |
| gttgcatgat attgatgtgc gccggcaact tggttcgggg gcgaatatat tgttgaaaga | 9180 |
| acaattctcc gttgagtctg cggcacagac gatagaaatg aggttggagg catgcaatgc | 9240 |
| gattaattga taatgaccaa ctcgacgaat tatatgatca agccgggcaa tcggaacgtt | 9300 |
| tacgttccca ccttatgatg cacggctcgc atcaagaaaa ggtacagcgt ttacttattg | 9360 |
| cattagtaaa gggcagctat gttgaaccgc attatcacga acttcctcat cagtgggaaa | 9420 |
| tgttcattgt tatggagggg caacttcagg tttgtttgta tggtagaaat ggtgaggtta | 9480 |
| taaagcaatt tatagcagga gataatactg gaatgagcat tgtggagttt tctccgggcg | 9540 |
| atatacacag tgtcgaatgc ctatctccgc gtgctcttat ggtggaagtt aaggaggggc | 9600 |
| catttgaccc ttcttttgca aaatcgttcg tgtgagcggc cgcgagctcg tcgactcgag | 9660 |
| gatccgtgta ggctggagct gcttcgaagt tcctatactt tctagagaat aggaacttcg | 9720 |
| gaataggaac taaggaggat attcatatgg ataaagccgt aagcatataa gcatggataa | 9780 |

```
gctatttata ctttaataag tactttgtat acttatttgc gaacattcca ggccgcgagc    9840
attcagcgcg gtgatcacac ctgacaggag tatgtaatgt ccaagcaaca gatcggcgta    9900
gtcggtatgg cagtgatggg acgcaacctt gcgctcaaca tcgaaagccg tggttatacc    9960
gtctctattt tcaaccgttc ccgtgagaag acggaagaag tgattgccga aaatccaggc   10020
aagaaactgg ttccttacta tacggtgaaa gagtttgtcg aatctctgga aacgcctcgt   10080
cgcatcctgt taatggtgaa agcaggtgca ggcacggatg ctgctattga ttccctcaaa   10140
ccatatctcg ataaaggaga catcatcatt gatggtggta acaccttctt ccaggacact   10200
attcgtcgta atcgtgagct ttcagcagag ggctttaact tcatcggtac cggtgttcct   10260
ggcggtgaag agggggcgct gaaaggtcct tctattatgc ctggtggcca gaaagaagcc   10320
tatgaattgg tagcaccgat cctgaccaaa atcgccgccg tagctgaaga cggtgaacca   10380
tgcgttacct atattggtgc cgatggcgca ggtcactatg tgaagatggt tcacaacggt   10440
attgaatacg gcgatatgca gctgattgct gaagcctatt ctctgcttaa aggtggcctg   10500
aacctcacca acgaagaact ggcgcagacc tttaccgagt ggaataacgg tgaactgagc   10560
agttacctga tcgacatcac caaagatatc ttcaccaaaa aagatgaaga cggtaactac   10620
ctggttgatg tgatcctgga tgaagcggct aacaaaggta ccggtaaatg gaccagccag   10680
agcgcgctgg atctcggcga accgctgtcg ctgattaccg agtctgtgtt tgcacgttat   10740
atctcttctc tgaaagatca gcgtgttgcc gcatctaaag ttctctctgg tccgcaagca   10800
cagccagcag gcgacaaggc tgagttcatc gaaaaagttc gtcgtgcgct gtatctgggc   10860
aaaatcgttt cttacgccca gggcttctct cagctgcgtg ctgcgtctga agagtacaac   10920
tgggatctga actacggcga aatcgcgaag attttccgtg ctggctgcat catccgtgcg   10980
cagttcctgc agaaaatcac cgatgcttat gccgaaaatc cacagatcgc taacctgttg   11040
ctggctccgt acttcaagca aattgccgat gactaccagc aggcgctgcg tgatgtcgtt   11100
gcttatgcag tacagaacgg tattccggtt ccgaccttct ccgcagcggt tgcctattac   11160
gacagctacc gtgctgctgt tctgcctgcg aacctgatcc aggcacagcg tgactatttt   11220
ggtgcgcata cttataagcg tattgataaa gaaggtgtgt tccataccga atggctggat   11280
taa                                                                 11283
```

<210> SEQ ID NO 16
<211> LENGTH: 13435
<212> TYPE: DNA
<213> ORGANISM: Artificial Sequence
<220> FEATURE:
<223> OTHER INFORMATION: example O16 rfb locus nucleotide sequence - O16-EPA production strain stLMTB11739

<400> SEQUENCE: 16

```
atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcagc    480
```

```
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagtga aaatacttgt tactggtggc gcaggattta ttggttcagc tgtagttcgt   1320
cacattataa ataatacgca ggatagtgtt gttaatgtcg ataaattaac gtacgccgga   1380
aaccgggaat cacttgctga tgtttctgat tctgaacgct atgttttga  acatgcggat   1440 atttgcgatg cacctgcaat ggcacggatt tttgctcagc atcagccgga tgcagtgatg   1500
cacctggctg ctgaaagcca tgttgaccgt tcaattacag gccctgcggc atttattgaa   1560
accaatattg ttggtactta tgtccttttg gaagccgctc gcaattactg gtctgctctt   1620
gatagcgaca agaaaaatag cttccgtttt catcatattt ctactgacga agtctatggt   1680
gatttgcctc atccagatga agtaaataat acagaagaat taccccttatt tactgagacg   1740 acagcttacg cgccaagcag ccccttattcc gcatccaaag catccagcga tcatttagtc   1800
cgcgcgtgga aacgtacata tggtttaccg acaattgtga ctaattgctc gaacaactat   1860
ggtccttatc atttcccgga aaagcttatt ccactggtta ttcttaatgc actggaaggt   1920
aaggcattac ctatttatgg caaaggagat cagatccgcg actggttgta tgttgaagat   1980
catgcgcgtg cgttatatac cgtcgtaacc gaaggtaaag cgggtgaaac ttataacatt   2040
ggtgggcaca acgaaaagaa aaacatcgat gtagtgctca ctatttgtga tttgctggat   2100
gagattgtac cgaaagagaa atcttatcgt gagcaaatca cttatgttgc tgatcgtccg   2160
ggacacgatc gccgctatgc tattgatgct gagaagattg gtcgcgcatt gggatggaaa   2220
ccacaggaaa cgtttgagag cgggattcgt aaaacggtgg aatggtacct gtccaataca   2280
aaatgggttg ataatgtgaa aagtggtgcc tatcaatcgt ggattgaaca gaactatgag   2340
ggccgccagt aatgaatatc ctccttttg  gcaaaacagg gcaggtaggt tgggaactac   2400
agcgtgctct ggcacctttg ggtaatttga ttgcttttga tgttcactct actgattatt   2460
gcggtgattt tagtaatcct gaaggtgtag ctgaaaccgt aagaagcatt cggccggata   2520
ttattgtcaa tgcagccgct cacaccgcag tagacaaagc agaatcagaa ccggagtttg   2580
cacaattaat taacgcaaca agtgtcgaag cgattgcgaa agcagcaaat gaagttggag   2640
cctgggttat ccattactcg actgattacg tcttccctgg aaatggcgat atgccatggc   2700
tggagacgga tgcaaccgca ccactaaatg tttacggtga aaccaagtta gccggagaaa   2760
aagcgttaca ggaatattgc gcgaagcatc ttattttccg gaccagctgg gtctatgcag   2820
gaaaaggaaa taacttcgcc aaaacgatgt tacgtctggc aaaagagcgt gaagaattag   2880
```

```
cggttattaa cgatcagttt ggtgcgccaa caggtgctga actgctggct gattgtacag    2940
cacatgccat tcgtgtcgca ctgaataaac cggatgtcgc aggcttgtac catttggtag    3000
ccagtggtac cacaacctgg tacgattatg ctgcgctggt ttttgaagag gcgcgcaaag    3060
caggcattcc ccttgcactc aacaagctca acgcagtacc aacaacagcc tatcctacac    3120
cagctcgtcg tccacataac tctcgcctta atacagaaaa atttcagcag aactttgcgc    3180
ttgtcttgcc tgactggcag gttggcgtga acgaatgct caatgaatta tttacgacta     3240
cagcaattta atagttttg catcttgttc gtgatggtgg agcaagatga attaaaagga     3300
atgatgaaat gaaaatgcgt aaaggtatta ttttagcggg tggttctggt acacgtcttt    3360
atcctgtgac tatggctgtc agtaaacagc tattacctat ttatgataaa ccgatgatct    3420 attaccccgct ctctacactg atgttggcgg gtattcgcga tattttgatt atcagtacac   3480
ctcaggatac tcctcgtttt caacaattgc tgggtgacgg tagccagtgg ggcctgaatc    3540
ttcagtacaa agtgcaacct agcccagatg gcctcgcgca ggcatttatc atcggtgaag    3600
agtttattgg tggtgatgat tgtgcttttgg ttcttggtga taatatcttt tacggtcacg   3660
atctgccgaa gctaatggag gccgctgtta acaaagaaag tggtgcaacg gtatttgcct    3720
atcacgttaa tgatccagaa cgctatggtg tcgttgagtt tgataaaaac ggtacggcaa    3780
tcagtctgga agaaaaaccg ttagaaccaa agagtaatta cgccgttaca ggtctgtact    3840
tttatgataa cgacgtggtt cagatggcga aaaacttgaa gccgtctgca cgtggtgagt    3900
tagaaattac agatattaac cgtatttatc ttgagcaggg acgtctgtct gtcgcgatga    3960
tggggcgtgg ctacgcgtgg ctggacacgg ggactcatca gagtctgata gaagcaagta    4020
attttattgc gacaattgaa gagcgccagg gattgaaggt ttcctgtcct gaagagattg    4080
catttcgtaa aggttttatt gatgttgagc aagtaagaaa attagctgta ccactaataa    4140
agaataatta tgggcagtat ctttataaaa tgacgaagga ttcaaattaa tgaatgtgat    4200
tagaactgaa attgaagatg tgctaattct ggagccaaga gtatttggtg atgatagagg    4260
tttcttttat gagagcttta atcaatcagc atttgaacat attctaggct atccggtcag    4320
ctttgttcaa gacaatcact cacgttcatc aaaaaatgta ctcagaggcc ttcactttca    4380
acgcggcgag tacgcacaag ataaacttgt acgctgcact catggagcag ttttttgatgt   4440 tgctgttgat attcgaccca attcggtatc ctttggtaaa tgggttggtg ttctgctttc    4500
agctgataat aagcagcagt tgtggatacc aaaagggttt gctcatggct ttttggttct    4560
gtctgatatc gctgaatttc aatataaaac tacaaactat tatcatcctg aaagcgattg    4620
tggaatatgt tggaatgatg aacgcattgc aattgattgg ccccaaacat cagggttaat    4680
cctttcgcca aaagatgaaa ggctctttac gttagatgag cttatcagat taaaattaat    4740
tgcatgaata cgaataaatt atcttttaaga agaaacgtta tatatctggc tgtcgttcaa    4800
ggtagcaatt atcttttacc attgcttaca tttccatatc ttgtaagaac acttggtcct    4860
gaaaatttcg gtatattcgg ttttttgccaa gcgactatgc tatatatgat aatgtttgtt    4920
gaatatggtt tcaatctcac agcaactcag agtattgcca aagcagcaga tagtaaagat    4980
aaagtaacgt ctatttttttg ggcggtgata ttttcaaaaa tagttcttat cgtcattaca    5040
ttgattttct taacgtcgat gaccttgctt gttcctgaat ataacaagca tgccgtaatt    5100
atatggtcgt ttgttcctgc attagtcggg aatttaatct accctatctg gctgtttcag    5160
ggaaaagaaa aaatgaaatg gctgacttta agtagtattt tatcccgctt ggctattatc    5220
```

```
cctctaacat ttatttttgt gaacacaaag tcagatatag caattgccgg ttttattcag    5280
tcaagtgcaa atctggttgc tggaattatt gcactagcta tcgttgttca tgaaggttgg    5340
attggtaaag ttacgctatc attacataat gtgcgtcgat ctttagcaga cggttttcat    5400
gtttttattt ccacatctgc tattagttta tattctacgg gaatagttat tatcctggga    5460
tttatatctg gaccaacgtc cgtagggaat tttaatgcgg ccaatactat aagaaacgcg    5520
cttcaagggc tattaaatcc tatcacccaa gcaatatacc caagaatatc aagtacgctt    5580
gttcttaatc gtgtgaaggg tgtgatttta attaaaaaat cattgacctg cttgagtttg    5640
attggtggtg ctttttcatt aattctgctc ttgggtgcat ctatactagt aaaaataagt    5700
atagggccgg atatgataa tgcagtgatt gtgctaatga ttatatcgcc tctgccttt     5760 cttatttcat taagtaatgt ctatggcatt caagttatgc tgacccataa ttataagaaa    5820
gaattcagta agattttaat cgctgcgggt ttgttgagtt tgttgttgat ttttccgcta    5880
acaactcttt ttaaagagat tggtgcagca ataacattgc ttgcaacaga gtgcttagtt    5940
acgtcactca tgctgatgtt cgtaagaaat aataaattac tggtttgctg aggattttat    6000
gtacgattat atcattgttg gttctggttt gtttggtgcc gtttgtgcga atgagttaaa    6060
aaagctaaac aaaaaagttt tagtgattga gaaaagaaat catatcggtg gaaatgcgta    6120
cacagaggac tgtgagggta tccagattca taaatatggt gcacatattt ttcataccaa    6180
tgataaatat atatgggatt acgttaatga tttagtagaa tttaatcgtt ttactaattc    6240
tccactggcg atttataaag acaaattatt caaccttcct tttaatatga atactttcca    6300
ccaaatgtgg ggagttaaag atcctcaaga agctcaaaat atcattaatg ctcagaaaaa    6360
aaagtatggt gacaaggtac ctgaaaattt ggaggagcag gcgatttcat tagttgggga    6420
ggacttatac caagcattga taaagggtta tacggagaag cagtggggaa gaagtgcaaa    6480
agaattgcct gcatttatta ttaagcgaat cccagtgaga tttacgtttg ataacaatta    6540 ttttccgat cgctatcaag gtattccggt gggaggctac actaagctta ttgaaaaaat    6600
gcttgaaggt gtggacgtaa aattaggcat tgatttttg aaagacaaag attctctagc    6660
gagtaaagcc catagaatca tctacactgg acccattgat cagtacttcg actataggtt    6720
tggagcgtta gaatatcgct ctttaaaatt tgagacggaa cgccatgaat ttccaaactt    6780
ccaagggaat gcagtaataa atttcactga tgctaatgta ccatatacca gaataattga    6840
gcataaacat tttgactatg ttgagacaaa gcatacggtt gttacaaaag aatatccatt    6900
agagtggaaa gttggcgacg aaccctacta tccagttaat gataataaaa acatggagct    6960
ttttaagaaa tatagagagt tagctagcag agaagacaag gttatatttg gcgggcgttt    7020
ggccgagtat aaatattatg atatgcatca agtgatatct gccgctcttt atcaagtgaa    7080
aaatataatg agtacggatt aatgatctat cttgtaatta gtgtctttct cattacagca    7140
tttatctgtt tatatcttaa gaaggatata ttttatccag ccgtatgcgt taatatcatc    7200
ttcgcactgg tcttattggg atatgaaata acgtcagata tatatgcttt tcagttaaat    7260
gacgctacgt tgattttttct actttgcaat gttttgacat ttaccctgtc atgtttattg    7320
acggaaagtg tattagatct aaatatcaga aaagtcaata atgctattta tagcatacca    7380
tcgaagaaag tgcataatgt aggcttgtta gttatttctt tttcgatgat atatatatgc    7440
atgaggttaa gtaactacca gttcgggact agcttactta gctatatgaa tttgataaga    7500
gatgctgatg ttgaagacac atcaagaaat ttctcagcat acatgcagcc aatcattcta    7560 actactttg ctttatttat ttggtctaaa aaatttacta atacaaaggt aagtaaaaca    7620
```

```
tttactttac ttgtttttat tgtattcatc tttgcaatta tactgaatac tggtaagcaa    7680
attgtcttta tggttatcat ctcttatgca ttcatcgtag gtgttaatag agtaaaacat    7740
tatgtttatc ttattacagc tgtaggtgtt ctattctcct tgtatatgct cttttacgt    7800 ggactgcctg gggggatggc atattatcta tccatgtatt tggtcagccc tataatcgcg    7860
tttcaggagt tttattttca gcaagtatct aactctgcca gttctcatgt cttttggttt    7920
tttgaaaggc tgatggggct attaacaggt ggagtctcta tgtcgttgca taagaatttt    7980
gtgtgggtgg gtttgccaac aaatgtttat actgcttttt cggattatgt ttatatttcc    8040
gcggagctaa gctatttgat gatggttatt catggctgta tttcaggtgt tttatggaga    8100
ttgtctcgaa attacatatc tgtgaaaata ttttattcat attttattta tacctttctct  8160 ttcattttt atcatgaaag cttcatgact aatattagca gttggataca aataactctt     8220
tgtatcatag tattctctca atttcttaag gcccagaaaa taaagtgaaa atgtattttt   8280
tgaatgattt aaatttctct agacgcgatg ctggatttaa agcaagaaaa gatgcactgg    8340
acattgcttc agattatgaa acatttctg ttgttaacat tcctctatgg ggtggagtag    8400
tccagagaat tattagttct gttaagctta gtacatttct ctgcggtctt gaaaataaag   8460
atgttttaat tttcaatttc ccgatggcca aaccattttg gcatatattg tcattctttc    8520
accgccttct aaaatttaga atagtacctc tgattcatga tattgatgaa ttaagaggag   8580
gagggggtag tgattctgtg cggcttgcta cctgtgatat ggtcataagt cacaatccac    8640
aaatgacaaa gtaccttagt aaatatatgt ctcaggataa aatcaaagac ataaaaatat   8700
ttgattacct cgtctcatct gatgtggagc atcgagatgt tacggataag caacgagggg   8760
tcatatatgc tggcaaccttt tctaggcata aatgttcttt catatatact gaaggatgcg   8820
attttactct ctttggtgtc aactatgaaa ataaagataa tcctaaatat cttggaagtt   8880
ttgatgctca atctccggaa aagattaacc tcccaggcat gcaatttgga ctcatttggg    8940
atggagattc tgtcgaaacc tgtagtggtg cctttggcga ctatttaaag tttaataacc   9000
ctcataagac atctctttat ctttcaatgg aacttccagt atttatatgg gataaagccg   9060
cccttgcgga tttcattgta gataatagaa taggatatgc agtgggatca atcaaagaaa   9120
tgcaagagat tgttgactcc atgacaatag aaacttataa gcaaattagt gagaatacaa    9180
aaattatttc tcagaaaatt cgaacaggaa gttacttcag ggatgttctt gaagaggtga    9240
tcgatgatct taaaactcgc taaacgatat ggtctctgtg gttttattcg gcttgttaga    9300
gatgtcttat tgactcgtgt attttaccgg aactgtagaa ttattcgatt tccctgctat    9360
attcgcaatg atggtagcat taattttggt gaaaatttca caagtggagt cggtctcagg    9420
ctggatgcat ttgacgtgg cgtgattttt ttttccgata atgtgcaagt taacgactat    9480
gttcatatcg cctcaattga gagcgttacg ataggtcggg atacgcttat tgcaagtaaa   9540
gtatttatta ccgatcataa tcacggttcc tttaagcact ctgatccaat gagttcgcca   9600 aatataccte cagacatgcg cacgttggaa tcttcagctg ttgtaattgg ccagagggtt    9660
tggttgggtg agaatgtgac ggttttgcct ggaacaatta ttggtaatgg agtcgtagtc    9720
ggcgccaatt ctgttgttag aggttctatt cccgaaaata ctgtcattgc gggagtacca    9780
gcaaaaatca taagaaaata caatcatgag accaaattat gggaaaaagc atagtcgttg   9840
tttctgcggt caattttacc actggcggtc catttaccat tttgaaaaaa ttttttggcag   9900 caactaataa taaagaaaat gtcagttttta tcgcattagt ccattctgct aaagagttaa   9960
```

```
aagaaagtta tccatgggtt aaattcattg agtttcctga ggttaaaggg tcgtggctaa    10020
aacgtttgca ctttgaatat gtagtttgta aaaaactttc aaaagagctg aatgctacgc    10080
attggatttg tctgcatgat attacggcca atgtcgtcac taaaaaaaga tatgtgtatt    10140
gtcataaccc tgccccttttt tataaaggaa ttttattccg tgaaattctt atggagccta    10200 gcttttttctt atttaaaatg ctatacgggc tgatatataa aataaacatt aaaaaaaata    10260
ctgcagtgtt tgttcaacaa ttctggatga aagaaaaatt tatcaagaaa tattctataa    10320
ataacatcat tgtcagtcgg ccagaaatta aattatctga taaaagccaa cttactgatg    10380
atgattctca atttaagaat aacccttctg agttgacaat attttaccct gctgttccac    10440
gagtatttaa aaattacgag cttattatta gtgcagcaag gaaattgaaa gaacaatcca    10500
atattaaatt tctgcttact atcagtggta cagaaaatgc gtatgcaaaa tatattatca    10560
gtcttgcaga aggactggat aatgttcatt tcctcgggta cttggataaa gaaaaaatcg    10620
atcattgtta taatatttca gatatagttt gttttcccctc taggttagaa acatggggat    10680
tgccgttgtc tgaggctaaa gagcgaggta agtgggtatt agcatcagat ttcccattta    10740
ctagagaaac tcttggtagt tatgaaaaga aagcttttttt tgattctaat aacgatgaca    10800
tgttagttaa acttattatt gacttcaaaa aaggtaaccct caaaaaagat atctctgatg    10860
caaatttcat ttatcgtaat gaaaatgtat tagttgggtt tgatgaacta gttaattttta    10920 ttactgaaga acattgaaat ggtatatata ataatcgttt cccacggaca tgaagactac    10980
atcaaaaaat tactcgaaaa tcttaatgct gacgatgagc actacaagat tatcgtacgc    11040
gacaacaaag actctctatt attgaaacaa atatgccagc attatgcagg cctggactat    11100
attagtggag gtgtatacgg ctttggtcat aataataata ttgcggtggc gtatgtaaag    11160
gaaaaatata gacccgcaga tgatgattac attttgtttt tgaatcccga tatcatcatg    11220
aagcatgatg atttgctgac atatattaaa tatgtcgaaa gtaagcgtta tgcttttagt    11280
acattatgcc tgttccgaga tgaagcgaaa tctttacatg attattccgt aagaaaattt    11340
cctgtgcttt ctgatttttat tgtgtcatttt atgttaggga ttaataaaac aaaaattcct    11400
aaagaaagta tctattctga tacggttgtt gattggtgcg caggatcatt tatgctggta    11460
cgtttttcag atttttgtgcg tgtaaatggc ttcgatcaag gttactttat gtactgtgaa    11520
gatattgacc tgtgcttgag gcttagcctg gctggtgtca gacttcatta tgttcccgct    11580
tttcatgcga tacattatgc tcatcatgac aatcgaagtt ttttttttcaaa agccttcaga    11640 tggcacttaa aaagtacttt tagatatttta gccagaaaac gtattttatc aaatcgcaac    11700
tttgatcgaa tttcatcagt ttttcacccg taagagctcg gtacccgggc ctagggtgta    11760
ggctggagct gcttcgaagt tcctatactt tctagagaat aggaacttcg gaataggaac    11820
taaggaggat attcatatcc gtcgacggcg gccgccctgc aggcatgcaa gcttgatcca    11880
tatggatcgc tagcttaatt aaataaagcc gtaagcatat aagcatggat aagctattta    11940
tactttaata agtactttgt atacttattt gcgaacattc caggccgcga gcattcagcg    12000
cggtgatcac acctgacagg agtatgtaat gtccaagcaa cagatcggcg tagtcggtat    12060
ggcagtgatg ggacgcaacc ttgcgctcaa catcgaaagc cgtggttata ccgtctctat    12120
tttcaaccgt tcccgtgaga agacggaaga agtgattgcc gaaaatccag gcaagaaact    12180
ggttccttac tatacggtga aagagtttgt cgaatctctg gaaacgcctc gtcgcatcct    12240
gttaatggta aaagcaggtg caggcacgga tgctgctatt gattccctca aaccatatct    12300
cgataaagga gacatcatca ttgatggtgg taacaccttc ttccaggaca ctattcgtcg    12360
```

```
taatcgtgag ctttcagcag agggctttaa cttcatcggt acgggtgttt ctggcggtga   12420
agaggggggcg ctgaaaggtc cttctattat gcctggtggc cagaaagaag cctatgaatt  12480
ggtagcaccg atcctgacca aaatcgccgc cgtagctgaa gacggtgaac catgcgttac   12540
ctatattggt gccgatggcg caggtcacta tgtgaagatg gttcacaacg gtattgaata   12600
cggcgatatg cagctgattg ctgaagccta ttctctgctt aaaggtggcc tgaacctcac   12660
caacgaagaa ctggcgcaga cctttaccga gtggaataac ggtgaactga gcagttacct   12720
gatcgacatc accaaagata tcttcaccaa aaaagatgaa gacggtaact acctggttga   12780
tgtgatcctg gatgaagcgg ctaacaaagg tacgggtaaa tggaccagcc agagcgcgct   12840
ggatctcggc gaaccgctgt cgctgattac cgagtctgtg tttgcacgtt atatctcttc   12900
tctgaaagat cagcgtgttg ccgcatctaa agttctctct ggtccgcaag cacagccagc   12960
aggcgacaag gctgagttca tcgaaaaagt tcgtcgtgcg ctgtatctgg caaaatcgt    13020
ttcttacgcc cagggcttct ctcagctgcg tgctgcgtct gaagagtaca actgggatct   13080
gaactacggc gaaatcgcga agattttccg tgctggctgc atcatccgtg cgcagttcct   13140
gcaaaaaatc accgatgctt atgccgaaaa tccacagatc gctaacctgt tgctggctcc   13200
gtacttcaag caaattgccg atgactacca gcaggcgctg cgtgatgtcg ttgcttatgc   13260
agtacagaac ggtattccgg ttccgacctt ctccgcagcg gttgcctatt acgacagcta   13320
ccgtgctgct gttctgcctg cgaacctgat ccaggcacag cgtgactatt tggtgcgca   13380
tacttataag cgtattgata agaaggtgt gttccatacc gaatggctgg attaa        13435
```

<210> SEQ ID NO 17
<211> LENGTH: 13228
<212> TYPE: DNA
<213> ORGANISM: Artificial Sequence
<220> FEATURE:
<223> OTHER INFORMATION: example O18A rfb locus nucleotide sequence - O18A-EPA production strain BVEC-L-00559

<400> SEQUENCE: 17

```
atgacgaatt taaaagcagt tattcctgta gcgggtctcg ggatgcatat gttgcctgcc   60
actaaggcga tacccaaaga gatgctacca atcgtcgaca agccaatgat tcagtacatt   120
gttgacgaga ttgtggctgc agggatcaaa gaaatcctcc tggtaactca cgcgtccaag   180
aacgcggtcg aaaaccactt cgacacctct tatgagttag aatcactcct tgagcagcgc   240
gtgaagcgtc aactgctggc ggaagtacag tccatctgtc cgccgggcgt gaccattatg   300
aacgtgcgtc agggcgaacc tttaggttta ggccactcca ttttgtgtgc gcgacctgcc   360
attggtgaca acccatttgt cgtggtactg ccagacgttg tgatcgacga tgccagcgcc   420
gacccgctac gttacaacct tgctgccatg attgcacgtt tcaacgaaac gggccgcagc   480
caggtgctgg caaaacgtat gccgggtgac ctctctgaat actccgtcat ccagactaaa   540
gagccgctgg accgtgaggg taagtcagc cgcattgttg aatttatcga aaaaccggat   600
cagccgcaga cgctggactc agacatcatg gccgtaggtc gctatgtgct ttctgccgat   660
atttggccgg aactgaacg tactcagcct ggtgcatggg gacgtattca gctgactgat   720
gctattgccg agctggcgaa aaaacaatcc gttgatgcaa tgctgatgac cggcgacagt   780
tacgactgcg gcaaaaaaat gggctatatg caggcgtttg tgaagtatgg cctacgcaac   840
ctgaaagaag gggcgaagtt ccgtaaaggt attgagaagc tgttaagcga ataatgaaaa   900
tctgaccgga tgtaacggtt gataagaaaa ttataacggc agtgaaaatt cgcagcaaaa   960
```

-continued

```
gtaatttgtt gcgaatcttc ctgccgttgt tttatataaa ccatcagaat aacaacgagt   1020
tagcagtagg gttttattca aagttttcca ggatttteet tgtttccaga gcggattggt   1080
aagacaatta gcgttgaat ttttcgggtt tagcgcgagt gggtaacgct cgtcacatca    1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagtga aaatacttgt tactggtggc gcaggattta ttggttcagc tgtagttcgt   1320
cacattataa ataatacgca ggatagtgtt gttaatgtcg ataaattaac gtacgccgga   1380
aaccgggaat cacttgctga tgtttctgat tctgaacgct atgttttga acatgcggat    1440 atttgcgatg cacctgcaat ggcacggatt tttgctcagc atcagccgga tgcagtgatg   1500
cacctggctc tgaaagcca tgttgaccgt tcaattacag gccctgcggc atttattgaa    1560
accaatattg ttggtactta tgtcctttg gaagccgctc gcaattactg gtctgctctt    1620
gatagcgaca agaaaaatag cttccgtttt catcatattt ctactgacga agtctatggt   1680
gatttgcctc atccagatga agtaaataat acagaagaat tacccttatt tactgagacg   1740
acagcttacg cgccaagcag cccttattcc gcatccaaag catccagcga tcatttagtc   1800
cgcgcgtgga aacgtacata tggtttaccg acaattgtga ctaattgctc gaacaactat   1860
ggtccttatc atttcccgga aaagcttatt ccactggtta ttcttaatgc actggaaggt   1920
aaggcattac ctatttatgg caaggagat cagatccgcg actggttgta tgttgaagat    1980
catgcgcgtg cgttatatac cgtcgtaacc gaaggtaaag cgggtgaaac ttataacatt   2040
ggtgggcaca acgaaaagaa aaacatcgat gtagtgctca ctatttgtga tttgctggat   2100
gagattgtac cgaaagagaa atcttatcgt gagcaaatca cttatgttgc tgatcgtccg   2160
ggacacgatc gccgctatgc tattgatgct gagaagattg gtcgcgcatt gggatggaaa   2220
ccacaggaaa cgtttgagag cgggattcgt aaaacggtgg aatggtacct gtccaataca   2280 aaatggggttg ataatgtgaa aagtggtgcc tatcaatcgt ggattgaaca gaactatgag   2340
ggccgccagt aatgaatatc ctcctttttg gcaaaacagg gcaggtaggt tgggaactac   2400
agcgtgctct ggcacctttg ggtaatttga ttgctttga tgttcactct actgattatt     2460
gcggtgattt tagtaatcct gaaggtgtag ctgaaaccgt aagaagcatt cggccggata   2520
ttattgtcaa tgcagccgct cacaccgcag tagacaaagc agaatcagaa ccggagtttg   2580
cacaattaat taacgcaaca agtgtcgaag cgattgcgaa agcagcaaat gaagttggag   2640
cctgggttat ccattactcg actgattacg tcttccctgg aaatggcgat atgccatggc   2700
tggagacgga tgcaaccgca ccactaaatg tttacggtga aaccaagtta gccggagaaa   2760
aagcgttaca ggaatattgc gcgaagcatc ttattttccg gaccagctgg gtctatgcag   2820
gaaaaggaaa taacttcgcc aaaacgatgt tacgtctggc aaaagagcgt gaagaattag   2880
cggttattaa cgatcagttt ggtgcgccaa caggtgctga actgctggct gattgtacag   2940
cacatgccat tcgtgtcgca ctgaataaac cggatgtcgc aggcttgtac catttggtag   3000
ccagtggtac cacaacctgg tacgattatg ctgcgctggt ttttgaagag gcgcgcaaag   3060
caggcattcc ccttgcactc aacaagctca acgcagtacc aacaacagcc tatcctacac   3120
cagctcgtcg tccacataac tctcgcctta atacagaaaa atttcagcag aactttgcgc   3180
ttgtcttgcc tgactggcag gttggcgtga acgaatgct caatgaatta tttacgacta    3240 cagcaatta atagttttg catcttgttc gtgatggtgg agcaagatga attaaaagga     3300
```

```
atgatgaaat gaaaatgcgt aaaggtatta ttttagcggg tggttctggt acacgtcttt   3360
atcctgtgac tatggctgtc agtaaacagc tattacctat ttatgataaa ccgatgatct   3420 attaccgct ctctacactg atgttggcgg gtattcgcga tattttgatt atcagtacac    3480
ctcaggatac tcctcgtttt caacaattgc tgggtgacgg tagccagtgg ggcctgaatc   3540
ttcagtacaa agtgcaacct agcccagatg gcctcgcgca ggcatttatc atcggtgaag   3600
agtttattgg tggtgatgat gtgctttgg ttcttggtga taatatcttt tacggtcacg    3660
atctgccgaa gctaatggag gccgctgtta acaagaaag tggtgcaacg gtatttgcct    3720
atcacgttaa tgatccagaa cgctatggtg tcgttgagtt tgataaaaac ggtacggcaa   3780
tcagtctgga agaaaaaccg ttagaaccaa agagtaatta cgccgttaca ggtctgtact   3840
tttatgataa cgacgtggtt cagatggcga aaaacttgaa gccgtctgca cgtggtgagt   3900
tagaaattac agatattaac cgtatttatc ttgagcaggg acgtctgtct gtcgcgatga   3960
tggggcgtgg ctacgcgtgg ctggacacgg ggactcatca gagtctgata gaagcaagta   4020
attttattgc gacaattgaa gagcgccagg gattgaaggt ttcctgtcct gaagagattg   4080
catttcgtaa aggttttatt gatgttgagc aagtaagaaa attagctgta ccactaataa   4140
agaataatta tgggcagtat ctttataaaa tgacgaagga ttcaaattaa tgaatgtgat   4200
tagaactgaa attgaagatg tgctaattct ggagccaaga gtatttggtg atgatagagg   4260 tttctttat gagagcttta atcaatcagc atttgaacat attctaggct atccggtcag    4320
ctttgttcaa gacaatcact cacgttcatc aaaaaatgta ctcagaggcc ttcactttca   4380
acgcggcgag tacgcacaag ataaacttgt acgctgcact catggagcag tttttgatgt   4440
tgctgttgat attcgaccca attcggtatc ctttggtaaa tgggttggtg ttctgctttc   4500
agctgataat aagcagcagt tgtggatacc aaaagggttt gctcatggct ttttggttct   4560
gtctgatatc gctgaatttc aatataaaac tacaaactat tatcatcctg aaagcgattg   4620
tggaatatgt tggaatgatg aacgcattgc aattgattgg ccccaaacat cagggttaat   4680
cctttcgcca aaagatgaaa ggctctttac gttagatgag cttatcagat taaaattaat   4740
tgcatgaggc cggccttaag gaggactagt cccggcgcgc catgagttta atcaaaaaca   4800 gttttttggaa ccttttgcggg tatgtacttc cagctattgt gacactacca gctttgggta   4860
ttatggggcg aaaattaggc ccagaattat ttggtgtatt cactttggca ttagctgttg   4920
tgggttatgc aagcattttt gatgcaggcc ttactcgcgc agtgatacga gaagtcgcaa   4980
ttgaaaaaga taatgaagaa ataagttga aaattatttc ttcagcgaca gttgtaatta    5040
tttatttgag tttggccgcc tcactcttat tatttttttt tagtggtcat atcgcattgc   5100
tactgaacat tagtgagact tttttttcata atgtaagtgt ctcgcttaaa attctcgcag   5160
catccatacc attatttttg attactcaaa tatggttgtc aattttagaa ggtgaagaaa   5220
gatttggttt acttaatatc tacaaatcaa ttacgggagt gatattagca atctcaccgg   5280
cattatttat acttattaaa ccctctttga tgtatgcgat aataggctta gttctagcaa   5340 ggttttatg ttttattttg gcttttataa tttgtcacga taaagtgctt aaagctaaac    5400
taacaatcga tataccaaca attaaaagat tgtttatgtt cggtggttgg attacagtaa   5460
gtaatatcat cagccctgtg ctatcatatt ttgataggtt tattgtttca aatcaacttg   5520
gggctgctaa tgttgctttt tatactgcac catcagaaat tatttctcgg cttagtataa   5580
ttccaggtgc gttttcaaga gccttatttc caagattagc taatgcaaat aattccgctg   5640
aaagatataa aacgaaaaga ttaattacaa tttcactttt aataatcatc accctatttt   5700
```

| | |
|---|---|
| tttgtattgg cgtgttattt tcagagaaga taatggtttt atggatgggg gcatcatttt | 5760 |
| ttggtgagcc tggtttggta ttatcaatat tactgattgg ctttattttt aatggattgg | 5820 |
| cacaagtacc atttgccagt attcaatccc gaggtcatgc taagataact gcatttgttc | 5880 |
| atctcttaga gttgtttcct tatttattac ttttatttta cctcataaaa gcacatgggg | 5940 |
| ttgttggcgc gggtattgcg tggtcagtga ggatgatagt agattatata gcattaagtc | 6000 |
| ttttggacgg taagtatatt aataaataaa attcaaaatg caagttaata actcatggct | 6060 |
| ttatttgggt aggtgacaat ttataatgat atatatatta actttaactc ttcttctagt | 6120 |
| tatagccata atgttttctc ttctcggcac aaaaagtagg atcacatctc cattaccttt | 6180 |
| gcattttta ccatggttac taactttaat tgtcgggata agtaattacg atcaattta | 6240 |
| cgagtttaat gaaagaagct tttactcttt gttgatttgg tttacagtta tttttatatt | 6300 |
| ttatttcata ggggaactgg ttaattataa acgtgaaaat ataaatgttt attatggtct | 6360 |
| ttcacatatt aaatatgaat gtaaaaaata ttggatcatt gtcatcccaa tttcattata | 6420 |
| taccattttc gaaatatata tggttggtat gggggagca gatggattct ttctcaattt | 6480 |
| acgtcttgca aatacattgg agggctatac gggtaaaaaa tttatcttaa tgcctgctgt | 6540 |
| atatcctcta atgatggcta tgttcgcaat tgtttgtcta acaaaaactt ccaaattaaa | 6600 |
| taaatactcc atttatttct ggatgttttt gtattgtatt ggcacaatgg gaaaattttc | 6660 |
| aatattaacg ccaatattga catatttaat tatttatgac ttcaaacata gattaaaagt | 6720 |
| aaaaaaaaca ataagtttta cattgttgat aattatatta gctttaactt tgcattttac | 6780 |
| acgtatggct gagaatgacc actcaacatt tttatctatt ttagggctct atatttattc | 6840 |
| accaataatt gctttaggcc agttgaatga agtaaatagt agtcattttg gtgagtatac | 6900 |
| gtttagattc atatatgcta taactaataa aattggcctt attaaagaat tgccagtaaa | 6960 |
| tactattctt gactattcat acgttcctgt accaacaaat gtatatactg cacttcaacc | 7020 |
| attttaccag gattttggtt atactggcat catatttgga gcagtattat acggactaat | 7080 |
| atatgtgagt ttatacacgg ccggtgttcg tggaaataat acacaggcat tactgattta | 7140 |
| cgcattgttt tcagttagca gtgcaacggc tttcttcgct gaaacgctag taacgaattt | 7200 |
| agctggaaat gtgatgttag tattatgtac catcttacta tggcgattta cagtaatatg | 7260 |
| caaaccagta cagtaaccat tctaatggcc acctacaatg gcgaggcctt catcaaaaat | 7320 |
| cagattttgt cactacaaca acaaacattt tctaactggc ggttatttat tcaggatgat | 7380 |
| gggtctacag acaatactat atctataata aaaaacttcc aaaaatctga ctccagaatt | 7440 |
| cggctagttg atgataattt gaaaggtcaa ggtgcaggaa aaaatttttt atcgctgata | 7500 |
| aagtacagcg agacagatta tacaatttat tgtgaccaag atgatatttg gttagaaaac | 7560 |
| aaaatatttg aattagtaaa gtatgcaaat gaaattaaat tgaatgtatc agatgcgcct | 7620 |
| tcgctagttt atgctgatgg ctatgcttat atggatggtg agggtacaat cgatttttct | 7680 |
| gggatatcta acaatcatgc tgatcaatta aaggattttc ttttttttaa tggtggatac | 7740 |
| caaggatgtt ctattatgtt caatcgtgca atgaccaaat tcttctgaa ttatcgagga | 7800 |
| tttgtatatc tacatgacga tatcacaaca ttagctgcat acgctcttgg taaagtttat | 7860 |
| tttctcccga aataccttat gttatataga cagcacacga atgcggtaac tggtatcaaa | 7920 |
| acattccgca atggattgac ttctaaattt aaatcaccag taaactatct tttatcacga | 7980 |
| aaacattatc aggtaaaaaa atcttttttt gaatgtaaca gctctatctt atcagagacg | 8040 |

```
aataaaaaag ttttttttgga ttttatttca ttttgtgaat caaataataa atttacagat    8100 tttttttaagt tatggcgagg tgggtttaga ttaaataaca gtagaactaa attattatta    8160
aaattcttaa tacggagaaa atttagcgaa tgatttcaat acttacacct acttttaatc    8220
ggcaacatac tttatcaagg ctattcaatt ctcttatatt acaaactgat aaagattttg    8280
agtggataat aattgatgat ggtagtatag atgcaacagc ggtacttgta gaagattttca    8340 gaaaaaaatg tgattttgac ttgatttatt gctatcagga aaataatggt aagcccatgg    8400
ctttaaacgc tggtgttaaa gcttgtagag gcgattatat ctttattgtt gacagtgatg    8460
atgcactaac tcccgatgcc ataaaattaa ttaaagaatc aatacatgat tgcttatctg    8520
agaaggaaag tttcagcgga gtcggtttta gaaaagcata tataaagggg gggattattg    8580
gtaatgattt aaataattct tcagaacata tatactattt aaatgcgact gagattagca    8640
atttaataaa tggtgatgtt gcatattgtt ttaaaaaga aagtttggta aaaaatccat    8700
tcccccgtat agaagatgaa aaatttgttc cagaattata tatttggaat aaaataactg    8760
acaaggcgaa gattcgattt aacataagca agttatata tctttgtgag tatcttgatg    8820
atggtctttc taaaaatttc cataaccagc ttaaaaaata cccaaggggg tttaagattt    8880
attacaaaga tcaagaaaaa cgagagaaaa cttatataaa aaaaacaaag atgctaatta    8940
gatatttgca atgttgttat tatgagaaaa taaaatgaaa atactatttg tcattacagg    9000
tttaggcctt ggaggtgctg agaagcaggt ttgtctttta gctgataaat taagtttaag    9060
cgggcaccat gtaaagatta tttcacttgg acatatgtct aataataaag tctttcctag    9120
cgaaaataat gttaatgtca ttaatgtaaa tatgtcaaaa aacatttctg gagttataaa    9180
aggttgtgtc agaattagag atgttatagc taatttcaaa ccagacattg tacacagtca    9240
tatgtttcat gcaaacatta tcactagatt gtctgtaatt ggaatcaaaa acagacctgg    9300
tattatatca actgcacata taaaaatga aggtgggtat ttcagaatgc tcacatatag    9360
aataaccgat tgtttaagtg attgttgtac aaatgttagc aaagaagcag tggatgagtt    9420
tttacggata aaagcccttta atcccgctaa agcaattact atgtataatg ggatagatac    9480
caataaattt aaatttgatt tattggcaag gagggaaatt cgagacggta ttaatataaa    9540
aaatgatgat atattattac ttgctgcagg tcgtttaacg ttagctaaag attatcctaa    9600
tttattgaat gcaatgactc tgcttcctga acactttaaa cttattatta ttggtgatgg    9660
tgaattgcgt gacgaaatta atatgcttat aaaaaaattg caattatcta ataggtgtc    9720 cttgttggga gttaaaaaaa atattgctcc ctattttct gcatgtgata ttttttgttct    9780 ctcttctcgt tgggaaggat ttggattagt cgtggcagaa gctatgtcat gtgagcgaat    9840
tgttgttggc acggattcag ggggagtaag agaagttatt ggtgacgatg attttcttgt    9900
acccatatct gattcaacac aacttgcaag caaaattgaa aaattgtctt tgagccagat    9960
acgtgatcac attggttttc ggaatcgtga gcgtatttta aaaaatttct caatagatac    10020
tattattatg cagtggcaag aactctatgg aactataatt tgctcaaaac atgaaaggta    10080
gatttatatt tggaacgtgt cttttgtttg aatttaattc aatctcaatt gagattttg    10140 tatttcaaaa ataccatcat agctaacgat gattggtatt tattttaaga tgcttttctat    10200 aaatatattg acgttttaa tgcgccgaaa cgattgggct gggaacagag aagtaaaact    10260
gttttgagaa tgaagagttt ttgagatgtt tatggatatt aaaaattgat ccagtgaatt    10320
aattatttat aataaatcaa gatttaatgt taataaaatga taatctttc tgacactcat    10380 attaattatg agtggtacgt ttggtaaacg gtaaactatt atatgacagc tagaacaact    10440
```

```
aaagttttgc acttacaatt actcccactc ttaagtggcg ttcaaagggt aacattaaac   10500
gaaattagtg cgttatatac tgattatgat tatacactag tttgctcaaa aaaaggtcca   10560
ctaacaaaag cattgctgga atatgatgtc gattgtcatt gtatccccga acttacgaga   10620
gaaattaccg taaagaatga ttttaaagca ttgttcaagc tttataagtt cataaaaaaa   10680
gaaaaatttg acattgtgca tacacattct tcaaaacag gtattttggg gcgagttgct    10740
gccaaattag cacgtgttgg aaaggtgatc cacactgtac atggttttc ttttccagcc    10800 gcatctagta aaaaagtta ttacctttat tttttcatgg aatggatagc aaagttcttt    10860
acggataagt taatcgtctt gaatgtagat gatgaatata tagcaataaa caattaaaa    10920 ttcaagcggg ataaagtttt tttaattcct aatggagtag acactgataa gttttctcct   10980
ttagaaaata aaatttatag tagcaccttg aatctagtaa tggttggtag attatccaag   11040
caaaaagatc ctgagacatt attgcttgct gttgaaaaac tgctgaatga aatgttaat    11100 gttaagctga cacttgtagg agatggtgaa ctaaaagaac agttagaaag caggttcaaa   11160
cggcaagatg gacgtataat ttttcatgga tggtcagata acattgttaa tattttaaaa   11220
gttaatgatc ttttttatatt accttctctt tgggagggta tgccattagc aattttagaa   11280
gcattgagct gtggacttcc atgtatagtc actaatattc caggtaataa tagcttaata   11340
gaagatggct ataatggttg tttgtttgaa attagagatt gtcagttatt atctcaaaaa   11400
atcatgtcat atgttggtaa gccagaactg attgcacagc aatctaccaa tgcacgatca   11460
tttattctga aaaattatgg attagttaaa agaaataata aggtcagaca gctatatgat   11520
aattaagagc tcggtacccg ggcctagggt gtaggctgga gctgcttcga agttcctata   11580
ctttctagag aataggaact tcggaatagg aactaaggag gatattcata tccgtcgacg   11640
gcggccgccc tgcaggcatg caagcttgat ccatatggat cgctagctta attaaataaa   11700
gccgtaagca tataagcatg gataagctat ttatactta taagtactt tgtatactta    11760 tttgcgaaca ttccaggccg cgagcattca gcgcggtgat cacacctgac aggagtatgt   11820
aatgtccaag caacagatcg gcgtagtcgg tatggcagtg atgggacgca accttgcgct   11880
caacatcgaa agccgtggtt ataccgtctc tattttcaac cgttcccgtg agaagacgga   11940
agaagtgatt gccgaaaatc caggcaagaa actggttcct tactatacgg tgaaagagtt   12000
tgtcgaatct ctggaaacgc ctcgtcgcat cctgttaatg gtgaaagcag gtgcaggcac   12060
ggatgctgct attgattccc tcaaaccata tctcgataaa ggagacatca tcattgatgg   12120
tggtaacacc ttcttccagg acactattcg tcgtaatcgt gagctttcag cagagggctt   12180
taacttcatc ggtaccggtg tttctggcgg tgaagagggg gcgctgaaag gtccttctat   12240
tatgcctggt ggccagaaag aagcctatga attggtagca ccgatcctga ccaaaatcgc   12300
cgccgtagct gaagacggtg aaccatgcgt tacctatatt ggtgccgatg gcgcaggtca   12360
ctatgtgaag atggttcaca acggtattga atacggcgat atgcagctga ttgctgaagc   12420
ctattctctg cttaaaggtg gcctgaacct caccaacgaa gaactggcgc agacctttac   12480
cgagtggaat aacggtgaac tgagcagtta cctgatcgac atcaccaaag atatcttcac   12540 caaaaagat gaagacggta actacctggt tgatgtgatc ctggatgaag cggctaacaa   12600
aggtacgggt aaatggacca gccagagcgc gctggatctc ggcgaaccgc tgtcgctgat   12660
taccgagtct gtgtttgcac gttatatctc ttctctgaaa gatcagcgtg ttgccgcatc   12720
taaagttctc tctggtccgc aagcacagcc agcaggcgac aaggctgagt tcatcgaaaa   12780
```

```
agttcgtcgt gcgctgtatc tgggcaaaat cgtttcttac gcccagggct tctctcagct    12840
gcgtgctgcg tctgaagagt acaactggga tctgaactac ggcgaaatcg cgaagatttt    12900
ccgtgctggc tgcatcatcc gtgcgcagtt cctgcaaaaa atcaccgatg cttatgccga    12960
aaatccacag atcgctaacc tgttgctggc tccgtacttc aagcaaattg ccgatgacta    13020
ccagcaggcg ctgcgtgatg tcgttgctta tgcagtacag aacggtattc cggttccgac    13080
cttctccgca gcggttgcct attacgacag ctaccgtgct gctgttctgc ctgcgaacct    13140
gatccaggca cagcgtgact attttggtgc gcatacttat aagcgtattg ataaagaagg    13200
tgtgttccat accgaatggc tggattaa                                       13228
```

<210> SEQ ID NO 18
<211> LENGTH: 13554
<212> TYPE: DNA
<213> ORGANISM: Artificial Sequence
<220> FEATURE:
<223> OTHER INFORMATION: example O25B rfb locus nucleotide sequence -
      O25B-EPA production strain stGVXN4459

<400> SEQUENCE: 18

```
atgacgaatt taaaagcagt tattcctgta gcgggtctcg ggatgcatat gttgcctgcc      60
actaaggcga tacccaaaga gatgctacca atcgtcgaca agccaatgat tcagtacatt     120
gttgacgaga ttgtggctgc agggatcaaa gaaatcctcc tggtaactca cgcgtccaag     180
aacgcggtcg aaaaccactt cgacacctct tatgagttag aatcactcct tgagcagcgc     240
gtgaagcgtc aactgctggc ggaagtacag tccatctgtc cgccgggcgt gaccattatg     300
aacgtgcgtc agggcgaacc tttaggttta ggccactcca ttttgtgtgc gcgacctgcc     360
attggtgaca acccatttgt cgtggtactg ccagacgttg tgatcgacga tgccagcgcc     420
gacccgctac gttacaacct tgctgccatg attgcacgtt tcaacgaaac gggccgcagc     480
caggtgctgg caaaacgtat gccgggtgac ctctctgaat actccgtcat ccagactaaa     540
gagccgctgg accgtgaggg taaagtcagc cgcattgttg aatttatcga aaaccggat      600 cagccgcaga cgctggactc agacatcatg gccgtaggtc gctatgtgct ttctgccgat     660
atttggccgg aactggaacg tactcagcct ggtgcatggg gacgtattca gctgactgat     720
gctattgccg agctggcgaa aaaacaatcc gttgatgcaa tgctgatgac cggcgacagt     780
tacgactgcg gcaaaaaaat gggctatatg caggcgtttg tgaagtatgg cctacgcaac     840
ctgaaagaag gggcgaagtt ccgtaaaggt attgagaagc tgttaagcga ataatgaaaa     900
tctgaccgga tgtaacggtt gataagaaaa ttataacggc agtgaaaatt cgcagcaaaa     960
gtaatttgtt gcgaatcttc ctgccgttgt tttatataaa ccatcagaat aacaacgagt    1020
tagcagtagg gttttattca aagttttcca ggattttcct tgtttccaga gcggattggt    1080
aagacaatta gcgtttgaat ttttcgggtt tagcgcgagt gggtaacgct cgtcacatca    1140
taggcatgca tgcagtgctc tggtagctgt aaagccaggg gcggtagcgt gcattaatac    1200
ctctattaat caaactgaga gccgcttatt tcacagcatg ctctgaagta atatggaata    1260
aattaagcta gcagtgaaga tacttgttac tggtggcgca ggattattg gttctgctgt     1320 tgttcgtcac ataataaata atacgcaaga tagtgttgtt aatgtcgata aattaacata    1380
cgccggaaac ctggaatcac ttgcagatgt ttctgattct gaacgctatt tctttgaaca    1440
tgcggatatt tgtgatgcag ctgcaatggc acgattttt gctcagcatc agccggatgc     1500
agtgatgcac ctggcagctg aaagccatgt tgaccgttca attacaggcc ctgcggcatt    1560
```

```
tattgaaacc aatattgtgg gtacttatgt cctttagaa gcggctcgga attattggtc  1620
tggtctggat gatgaaaaga aaaaaaactt ccgttttcat catatttcta ctgatgaggt  1680
gtatggtgac ttaccccatc cggatgaagt aaatagcaat gaaacgttgc cgctatttac  1740
ggaaacgaca gcatacgcgc caagtagtcc atattctgct tctaaagctt ccagcgatca  1800
tttggttcgc gcatggaaac gtacttatgg tttaccgacc attgtgacta attgctcgaa  1860
caactatggt cctatcatt tcccggaaaa gcttattcca ctggttattc ttaattcact  1920
ggaaggtaag gcattaccta tttatggcaa aggagatcag atccgcgact ggttgtatgt  1980
agaggatcat gctcgagcgt tatataccgt cgtaaccgaa ggtaaagcgg gcgaaactta  2040
taacattggt ggacacaacg aaagaaaaa catcgacgta gtgttcacta tttgtgattt  2100
gttggatgag atagtcccga agagaaatc ttaccgcgag caaattactt atgttaccga  2160
tcgtccggga cacgatcgcc gttatgcgat tgatgctgag aagattggtc gcgaattggg  2220
atggaaacca caggaaacgt ttgagagtgg gattcgtaaa acggtggaat ggtacctgtc  2280
caatacaaaa tgggttgata atgtgaaaag tggtgcctat caatcgtgga ttgaacagaa  2340
ctatgagggc cgccagtaat gaatatcctc cttttggca aaacagggca ggtaggttgg  2400
gaactacagc gtgctctggc acctctgggt aatttgattg ctcttgatgt tcactccact  2460
gattactgtg gtgattttag taatcctgaa ggtgtagctg aaaccgtaag aagcattcgg  2520
cctgatatta ttgtcaacgc agccgctcac accgcagtag acaaagcaga atcagaaccg  2580
aagtttgcac aattactgaa cgcgacgagt gtcgaagcga tcgcgaaagc agccaatgaa  2640
gtcggcgcct gggttattca ctactctact gactacgtat ttccggggac cggtgaaata  2700
ccatggcagg aggaggatgc aaccgcaccg ctaaatgttt acggtgaaac caagttagcg  2760
ggagaaaag cattacaaga gcattgtgcg aagcaccta ttttccggac cagctgggtc  2820
tatgcaggta aaggaaataa cttcgccaaa acaatgttgc gtctggcaaa agagcgtgaa  2880
gaattagccg ttattaatga tcagtttggt gcgccaactg gcgcagagtt actggctgat  2940
tgtacggcac atgctattcg tgtggcactg aataaaccgg aagtcgcagg cttgtaccat  3000
ctggtagcta gtggtaccac aacgtggcac gattatgctg cgctggtttt tgaagaggcg  3060
cgcaaagcag gcattcccct tgcactcaac aagctcaacg cagtaccaac aacagcctat  3120
cctacaccag ctcgtcgtcc acataactct cgccttaata cagaaaaatt tcagcagaac  3180
tttgcgcttg tcttgcctga ctggcaggtt ggcgtgaaac gaatgcttaa cgaattattt  3240
acgactacag caatttaata gtttttgcat cttgttcgta atggtggagc aagatgtatt  3300
aaaaggaatg atgaaatgaa aacgcgtaaa ggtattattt tggcgggtgg ttctggtact  3360
cgtctttatc ctgtgacgat ggccgtcagt aaacagctgt taccgattta tgataaaccg  3420
atgatctatt acccgctctc tacactgatg ttagcgggta ttcgcgatat tctgattatc  3480
agtacaccac aggatactcc tcgttttcaa caactgctgg gtgacgggag ccagtgggc  3540
ctgaatcttc agtacaaagt gcaaccgagt ccggatggtc ttgcgcaggc gtttattatc  3600
ggtgaagagt ttattggtgg tgatgattgt gctttggtac ttggtgataa tatcttctac  3660
ggccacgacc tgccgaagtt aatgacgta gctgttaaca agaaagtgg tgcaacggta  3720
tttgcctatc acgttaatga tcctgaacgt tatggtgtcg tggagtttga taataacggt  3780
actgcaatta gcctggaaga aaaccgctg gaaccaaaaa gtaactatgc ggttactggg  3840
ctttattct atgacaatga cgttgtggaa atggcgaaaa accttaagcc ttctgcccga  3900
ggtgaactgg aaattaccga tattaaccgt atttatatgg aacaaggacg tttgtctgtc  3960
```

```
gctatgatgg ggcgtggcta tgcatggctg gatacaggga cgcatcaaag tcttattgaa    4020
gcaagcaact tcattgccac cattgaagag cgccagggac taaaggtttc ctgtccggaa    4080
gaaattgctt atcgtaaagg gtttattgat gctgagcagg taaaagtatt agccgaaccg    4140
ttgaagaaaa atgcttatgg tcagtatctg ctcaaaatga ttaaaggtta ttaataagat    4200
gaacgtaatt aaaactgaaa ttcctgatgt gctgattttt gaaccaaaag ttttgggga    4260
tgaacgtggc ttctttttg agagttttaa tcagaggatt tttgaagaag cagtaggtcg    4320
taaggttgag tttgttcagg ataaccattc taagtccagt aaaggtgttt acgtggtct    4380
tcattatcag ttagaaacctt atgctcaagg aaaactggtg cgctgtgttg ttggcgaggt    4440
ttttgatgtt gcggttgata ttcgtaaatc gtcacctaca tttgggaaat gggttggggt    4500
gaatttgtct gctgagaata agcgtcagtt gtggattcct gagggatttg cacatggttt    4560
tttggtgctg agtgatttag cagaagttt atataaaacg aatcaatatt atgctccatc    4620
acatgaaaaa aatattatat ggaatgacct cttgcttaat attaaatggc cgagcacagc    4680
actgatcact ctgtctgata aggatgcaaa tggggaaaga tttgaactaa gtgagttttg    4740
aaatgtctct cttaaaacat agtatatgga atgttgcggg ctactttata ccaacattaa    4800
ttgcaattcc cgcctttgga ttaattgcga ggaaaattgg tgtagaacta tttggtttgt    4860
atacgttagc aatgattttt ataggggtatg caagtatatt tgatgctggg ttaacaagag    4920
ctgttgtgcg tgaaatagca ttactaaaaa acagagtgga cgattgtaat acgataatag    4980
taacttctat tatcgctgtg atattttag ggtttatcgg aggcggggga gtgtttctgc    5040
ttaaaggcga tattattgaa ctgttaaata tctcaccaat atattacgcc gattcgataa    5100
agtctctagt attattatca tctctgatac ctgtattctt agtcacgcaa atactattag    5160
cagagcttga gggtcgggaa tattttggga ttctaaatat acaaaaaagt gtagggaatt    5220
ctttaattgc agggttaccct gcattatttg ttttaattaa tcaaacgctt ttttctgcaa    5280
ttattggtgt agcgattgca agagttatat gcttgtggtt aagctacatt atgagcaggg    5340
aaagaataac tatcgatatc tcattttttt caataactgt tttaaagcgg ttatttagat    5400
atggcgggtg ggtaactata agtaacataa tatctcctat attagcgagt atggatagat    5460
ttattctatc ccatatccag ggagcatcaa aaatatcatt ctatacagtc cctaatgagc    5520
tggtaactag gcttggaata gttccaggct ctcttgggaa agctgttttt ccaaaattaa    5580
gtcatgcaag gaattttaca gcgtcatatg cagagcaaaa aaaagcttat atattaatga    5640
ctgtcattgt aatgcctttg gttttatttg tatattatta cgcaaagttt attttaacat    5700
tgtggatggg ggctgagtat gcaggattt cggtcgaaat attacggatt atgcttatag    5760
ggtataatttt taactgttat tcacaaatct cttttgccaa catacaggcc tttggaaaag    5820
caaaatacac tgcatacatc catatgatgg aatttattcc ttatttgata atgttatata    5880
taatttcaaa ggaatatggg gttattggtg ttgcgtggtt atggacaatt cgagtaataa    5940
ttgattttt gatgctttta tatatgagtt atcgttgtaa taatcttatg aaaaaagggt    6000
agcctgatga tatatattgt ggtattaaat tggaatgggg ctatagatac cattaattgt    6060
gttaaaagtt taatggattt aaatgttagc gattataaaa ttatcattgt tgataactgt    6120
tctatggata actccatatga tactataaaa gaaaatctta attcattata tattgctgat    6180
aaaagtatca ttgaggtgaa gtatgaggat agaaataaat ataaaacctt agaaaacgat    6240
aaaatcatat taatacaatc tccgcaaaat aatgggtacg caagtggtaa taatattggc    6300
```

```
atagagttcg ctcttaatca ggagaatatg aaatacgtct gggttctgaa taatgatact    6360
gaagtggata aagaggcttt aactcattta attagtaaat gtgattcaga taaaagtata    6420
gggatttgcg gttctcgttt agtctatttt gccgacagag agatgcagca aggactaggt    6480
ggggtgcata acaaatggtt atgcactaca aaaaattatg aaatgggaag attagtttcc    6540
aaaaaatatg atgatgaagt cattagtaat gatatagatt atataattgg cgcatcgatg    6600
tttttctcta gagaatgttt ggaaacagtt ggattgatga atgaagaata ttttttatac    6660
tatgaagagt tagatatttg cctcagagca aaagcaaaga actttaaatt aggtatttgc    6720
tcagaaagtt tggtttatca taaaataggt gcaagtactg atgggggaaa gagcatgatg    6780
gctgatcttt gctcaataaa aaataggctg gtcattacag aaaggtttta tccccaatat    6840
tattggacgg tatggttgtc acttttttgtt gtagcattta accgtgctag aagaggtgag    6900
tttaataaga tgaaaagatg tttgaatgtt atgtttaact tcaaacgaaa caaaggtagc    6960
aaatgccatt agaatatgca cttaatcatg gtgttaataa atctatagtt tgatatgtta    7020 ttaagggta tttaatgaaa gtggcttttt tatctgctta tgatccacta tctacatcca    7080
gttggtctgg cacaccttat tatatgctaa aggcattatc gaagagaaat atttccattg    7140
aaatattagg accggtaaat agctatatga tatacatgtt aaaagtatat aaattaatat    7200
taaggtgttt cggaaaagaa tatgattata gtcattcgaa gttgctttcc aggtattacg    7260
gtagaatatt cggtaggaaa ttaaaaaaaa ttgatggttt ggattttatt atcgcacctg    7320
caggttcctc acaaattgct ttttttaaaaa caaccatacc aataatatat ctatcggata    7380
caacatatga tcaattaaaa agctattatc cgaatttaaa taaaaaaaca attataaatg    7440
atgaggatgc aagtttaatc gaacgcaagg ctattgaaaa agcaacagta gtatctttcc    7500
catctaaatg ggcaatggat ttttgcagga attattacag attagatttt gataaattag    7560
ttgaaatacc atgggggggct aatttatttg atgatattca ctttgctaat aaaaaatataa    7620 ttcaaaagaa tagttatact tgtcttttct tgggagttga ttgggaaaga aaaggtggga    7680
aaacagcctt gaaagcaatt gaatatgtaa ggcagttata tgggatcgat gttagactaa    7740
aaatttgtgg atgtactccg aatcaaaaga ttttacctac ttgggttgaa ttaattgata    7800
aagtagataa aaataacgtt gacgaatatc agaaattcat cgatgtgtta tctaacgctg    7860
atatacttct tttaccaacc attgctgaat gttatggaat ggtattttgt gaagctgctg    7920
cttttggatt gcctgttgtc gctacagata caggtggagt cagttctata gttatcaacg    7980
aaaggacggg gatattaatt aaagacccgt tagactataa gcactttgga aatgcaattc    8040
ataaaataat tagttccgta gagacttatc aaaactactc ccaaaacgca agaattagat    8100
ataataatat attgcattgg gacaattggg ctaaaaagat aattgagatt atgtatgagc    8160
ataagaatag aagaatcaaa tagcacaaaa agaattatat gtttatttat acttttttctt    8220 gttttccctg attttttgtt ttatacatta ggggttgata attttagcat ttcaacgata    8280
atctcaatta cattgctttt tgttttttta agagctaaaa atatttgcaa agataatttt    8340
ctaataatag tagcgttatt catattgttg tgttttaact gttttgttaag tatgctattt    8400 aatattgaac aggctttaac atttaaagtt gtactttcaa tatatagcat cttaataatg    8460
gcatacgtct cctcttgtta tgcacagacg ttgtggttat gttctgaaga aatacttaag    8520
agatccgtct tttatttgtt cgcatttctt tgccttattg gcattataag tattctttta    8580
cagaagactg agattataca tgataaaagt atgattcttt ttcctgaacc atcagcattt    8640
gcattggttt ttatacctat cttttcattt tgtttatact atacaagagg ggggggcta    8700
```

```
ctattgctct atatattatc tttgggtatt gcgttaggta tccagaattt aacaatgttg    8760
gtaggcattg tgattagtgt ttttgtgatg aaaaaaataa ctataaggca aactattgtt    8820
atacttttgg gggcatggat tttttccatg atattaagtg atttagacat ttcttactat    8880
acatcgcggc ttgattttaa aaatactacg aacctatcag tgcttgtata tctttcagga    8940
attgaaagag ctttcttgaa ttttattaca agttatggtc ttggtattgg ttttcaacaa    9000
atgggagtga atgggagat aggaatatat caacaaattt tagctgaact tgatgcccct     9060
atgttaaata tatacgatgg ctcatttatt tcttctaagt taatatctga gtttggggtt    9120
attggtgcat taatgtgtat tttctatttt ttttatttt cccgattta tctgcgtttc      9180 aaaaaagta agagatattc accgcagtat attttagcat atagcttcta catgtgtttc     9240
ttcatccctc tttttatacg tggtgctggt tatataaacc cctatgtgtt tatgttattt    9300
tcatcaatat ttttgtgcaa atatcacgct aaaaatatct tgatgaaatc taatgtccag    9360
atagctatat aatagtagat tatattatca ttatcacgta aattacatat taatagcata    9420
tatgataact aggacataaa taatgtgcat taaaaaaaaa cttaagttaa ttaaacgata    9480 tggccttat ggtggtctta ggcttcttaa agatatattc ttaacaaaat ttttattttg     9540
ttcaaatgtt aggattatta gatttccatg ttatattaga aaagatggaa gtgttagttt    9600
tggaaaaggt tttacatcag gtgtaggatt acgagttgat gcatttatgg atgccgtagt    9660
ttccattgga gaaaatgttc aaattaatga ctatgttcac atcgcggcta ttaataatgt    9720
cattattggt agagatacat taatagcaag taaagtattt attagtgatc ataatcatgg    9780
tattttttct aaatccgata tccatagttc accaactatt attccttcgt ctaggcccct    9840
tgaatctgca cctgtgtata ttggagagcg tgtgtggatt ggcgaaaatg tgacaatatt    9900
accaggtgcg tgtataggta atggtgtagt tattggcgca aacagtgttg ttcgtggtga    9960
gattcctaat aatgtgatca ttgctggtgt tccagctaaa attgttaaaa aatataacta    10020
tgagcgtatg caatgggaaa gaatatagtt gtaatatcgg ctgttaattt tacaaccgga    10080 ggcccctttta ccgtactaaa aaatgtgctt acagcaacta agatagagc cgaatgtaaa    10140 tttattgcac tggttcatag ctctgctgaa ctaatggaat tatttccgtg ggttgaattt    10200
atagagtatc cagaagtcaa gtcttcgtgg gttaaaagat tatatttcga atatataact    10260
tgcaatagat tatctaaggt gattaaggca actcattggg tatgcttaca tgatattaca    10320
gcaaatgtta gtgtacccta tagatttgtt tattgccaca atcctgcacc gttctataaa    10380
tatttaagct atcgagatat tataggagaa cctaaatttt atcttttta tcttttttat     10440 gggcttttat acaatatcaa tataaaaaag aacacagcag ttttgttca gcagcagtgg     10500 ctaaaaaag aattcgaaaa aaatataag ttaagaatg ttgttgttag tcgccctgaa       10560
gatatttgcc cttttgaaag tgatggtttg gtaagaaata ataataaaaa ggatgtgagg    10620 atattacc cagcagtgcc ccgtatattt aaaaactttg aagttatcat acgtgctgca      10680
caaatattac aagataaaaa tattcatttt tatcttactt ttgatggtac tgaaaataag    10740
tatgcaaaaa gaatatataa attagcttcc gaactgaaaa atgtacattt cctcggttac    10800
cttaatgcaa ccgagatggt taactttat caagattcag atattatttg tttcccatcg     10860
aaactagaaa cgtggggatt accattatca gaagctaaaa catacaaaaa atggatattt    10920
gcggcagact taccttatgc tcatgaagtt ttatataact attcaaaaac tagatatttt    10980
ccatttgacg atgagaaaat acttgttcgc tacatattag agtacacaag taaaaatatg    11040
```

```
catgaagata taaaaaatag tagggtgaat tttaataatg atgcattgac tggttttgaa   11100
cagtttattg aatatatcct caagggggaac tgacgtggtt tatattataa tcgtttcaca   11160
tggccatgat gactatatag aaaatctttt attaaattta aagttgccct ctggaagatt   11220
taaaataata gttcgtgata acaaaagttc aatggtttta aaaaaaacat gcgaaaaaaa   11280
ttgcgtaacc tatttgcatg gagggcaata tggatttgga cataataata acatagcagt   11340
gtcatatata attaataact tcatgattat gaataatgat tattttctct ttcttaaccc   11400
cgatgtattc ataaccagtg aaagtttgat taattatgtt gattatataa ttagtaatga   11460
ttataagttt agcacattat gtctttatcg agattttact aaaagcaaac atgattattc   11520
aatacggagt tttccaactt tatatgattt tctttgttct tttttattgg gggtgaataa   11580
aagtaaaatt aagaaggaaa atatactttc tgatactgta gttgattggt gtgctggctc   11640
atttatgctt attcatgctt taagtttctt aaatgtgaat ggttttgatc aaaaatattt   11700
tatgtattgt gaagatattg acctttgtat gcgtttaaaa ttaagtggag tagatcttta   11760
ctatactccc cattttgatg ctattcatta tgcgcagcat gaaaatagaa gaatatttac   11820
taaagcattt cgatggcata taaggagtat tacgcgctac atattacgga aaccaattct   11880
ttcttataaa aactatagaa aaattacatc cgaactggta aagtgattaa ggatccgtgt   11940
aggctggagc tgcttcgaag ttcctatact ttctagagaa taggaacttc ggaataggaa   12000
ctaaggagga tattcatatg gataaagccg taagcatata agcatggata agctatttat   12060
actttaataa gtactttgta tacttatttg cgaacattcc aggccgcgag cattcagcgc   12120
ggtgatcaca cctgacagga gtatgtaatg tccaagcaac agatcggcgt agtcggtatg   12180
gcagtgatgg gacgcaacct tgcgctcaac atcgaaagcc gtggttatac cgtctctatt   12240
ttcaaccgtt cccgtgagaa gacggaagaa gtgattgccg aaaatccagg caagaaactg   12300
gttccttact atacggtgaa agagtttgtc gaatctctgg aaacgcctcg tcgcatcctg   12360
ttaatggtga aagcaggtgc aggcacggat gctgctattg attccctcaa accatatctc   12420
gataaaggag acatcatcat tgatggtggt aacaccttct tccaggacac tattcgtcgt   12480
aatcgtgagc tttcagcaga gggctttaac ttcatcggta ccgtgtttc tggcggtgaa   12540 gaggggcgc tgaaaggtcc ttctattatg cctggtggcc agaaagaagc ctatgaattg   12600
gtagcaccga tcctgaccaa aatcgccgcc gtagctgaag acggtgaacc atgcgttacc   12660
tatattggtg ccgatggcgc aggtcactat gtgaagatgg ttcacaacgg tattgaatac   12720
ggcgatatgc agctgattgc tgaagcctat tctctgctta aggtggcct gaacctcacc   12780 aacgaagaac tggcgcagac ctttaccgag tggaataacg gtgaactgag cagttacctg   12840
atcgacatca ccaaagatat cttcaccaaa aaagatgaag acgtaacta cctggttgat   12900 gtgatcctgg atgaagcggc taacaaaggt accggtaaat ggaccagcca gagcgcgctg   12960
gatctcggcg aaccgctgtc gctgattacc gagtctgtgt ttgcacgtta tatctcttct   13020
ctgaaagatc agcgtgttgc cgcatctaaa gttctctctg gtccgcaagc acagccagca   13080
ggcgacaagg ctgagttcat cgaaaaagtt cgtcgtgcgc tgtatctggg caaaatcgtt   13140
tcttacgccc agggcttctc tcagctgcgt gctgcgtctg aagagtacaa ctgggatctg   13200
aactacggcg aaatcgcgaa gattttccgt gctggctgca tcatccgtgc gcagttcctg   13260
cagaaaatca ccgatgctta tgccgaaaat ccacagatcg ctaacctgtt gctggctccg   13320
tacttcaagc aaattgccga tgactaccag caggcgctgc gtgatgtcgt tgcttatgca   13380
gtacagaacg gtattccggt tccgaccttc tccgcagcgg ttgcctatta cgacagctac   13440
```

```
cgtgctgctg ttctgcctgc gaacctgatc caggcacagc gtgactattt tggtgcgcat    13500
acttataagc gtattgataa agaaggtgtg ttccataccg aatggctgga ttaa          13554

<210> SEQ ID NO 19
<211> LENGTH: 15197
<212> TYPE: DNA
<213> ORGANISM: Artificial Sequence
<220> FEATURE:
<223> OTHER INFORMATION: example O75 rfb locus nucleotide sequence -
      O75-EPA production strain stLMTB11737

<400> SEQUENCE: 19
atgacgaatt taaaagcagt tattcctgta gcgggtctcg ggatgcatat gttgcctgcc      60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgc aaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagcta gcagtgaaga tacttgttac tggtggcgca ggatttattg gttctgctgt   1320
tgttcgtcac ataataaata atacgcaaga tagtgttgtt aatgtcgata aattaacata   1380
cgccggaaac ctggaatcgc tcgctgaaat ttctgattct gaacgttatt catttgagca   1440
tgcagatatc tgcgatgccg aagcgatggc tcgtattttc gcacagcacc agccagacgc   1500
ggtgatgcac ctggcagcag agagccacgt tgaccgctca ataactggcc ctgcggcatt   1560
tattgaaacc aatattgtgg gtacttatgt tcttttagaa gcggcgcgca attattggtc   1620
tggtctggat gatgaaaaga aaaaaaactt ccgctttcat catatttcta ctgatgaggt   1680
gtatggtgac ttaccccatc cggatgaagt aaatagcaat gaaacgttgc cgctatttac   1740
ggaaatgaca gcatacgcgc caagtagtcc atattctgct tctaaagctt ccagcgatca   1800
tttggttcgc gcatggaaac gtacttatgg tttaccgacc attgtgacta attgctgaa   1860 caactatggt cctatcatt tcccggaaaa gcttattcca ctggttattc ttaatgcact   1920
```

```
ggaaggtaag gcattaccta tttatggcaa aggagatcag atccgcgact ggttgtatgt    1980
agaggatcat gctcgagcgt tatataccgt cgtaaccgaa ggtaaagcgg gcgaaactta    2040
taacattggt ggacacaacg aaaagaaaaa catcgacgta gtgttcacta tttgtgattt    2100
gttggatgag atagtcccga agagaaatc ttatcgtgag caaattacct atgttgctga    2160
tcgcccaggg catgatcgcc gttatgcaat tgatgccgat aaaattagcc gcgaattggg    2220
ctggaaacca caggaaacgt tgagagcgg gattcgtaaa actgtggaat ggtatctgtc    2280
caatacaaaa tgggttgata atgtgaaaag tggtgcctat caatcgtgga ttgaacagaa    2340 ctatggggc cgccactaat gaatatcctc cttttggca aaacagggca ggttggttgg      2400
gaactacagc gtgctctggc acctctgggt aatttgattg ctcttgatgt tcactccact    2460
gattactgtg gtgattttag taaccctgaa ggtgtggctg aaaccgttag aagcattcgg    2520
cctgatatta ttgtcaacgc agccgctcac accgcagtag acaaagcaga atcagaaccg    2580
gagtttgcac aattactgaa cgcgacgagt gtcgaagcga tcgcgaaagc agccaatgaa    2640
gtcggcgctt gggttattca ctactctact gactacgtat ttccggggac cggtgaaata    2700
ccatggcagg aggaggatgc aaccgcaccg ctaaatgttt acggtgaaac caagttagca    2760
ggagaaaaag cattacaaga gcattgtgcg aagcaccttA ttttccggac cagctgggtc    2820
tatgcaggta aaggaaataa cttcgccaaa acgatgttgc gtctggcaaa agagcgtgaa    2880
gaattagccg ttattaatga tcagtttggt gcgccaactg gcgcagagtt gctggctgat    2940
tgtacggcac atgccattcg tgtggcactg aataaaccgg aagtcgcagg tttgtaccat    3000
ctggtagcca gtggtaccac aacctggcac gattatgctg cgctggtttt tgaagaggcg    3060
cgcaaagcag gcattcccct tgcactcaac aagctcaacg cagtaccaac aacagtctat    3120
cctacaccag ctcgtcgtcc acataactct cgccttaata cagaaaaatt tcagcagaac    3180
tttgcgcttg tcttgcctga ctggcaggtt ggtgtgaaac gcatgctcaa cgaattattt    3240
acgactacag caatttaata gttttttgcat cttgttcgtg atggtggaac aagatgaatt    3300
aaaaggaatg atggaatgaa tacgcgtaaa ggtattattt tagcgggtgg ttctggtaca    3360
cgtctttatc ctgtgactat ggctgtcagt aaacagctgt taccgattta tgataaaccg    3420
atgatctatt acccgctctc tacactgatg ttggcgggta ttcgcgatat tttgattatc    3480
agcacgccac aggatactcc tcgttttcaa caactgctgg gtgatgggag ccagtggggg    3540
ctaaatcttc actacaaagt gcaaccgagt ccggatggtc ttgcgcaggc atttatcatc    3600
ggtgaagagt ttatcggtgg tgatgattgt gctttggtac ttggtgataa tatcttctac    3660
ggtcacgacc tgcctaagtt aatggatgcc gctgttaaca agaaagtgg tgcaacggta    3720 tttgcctatc acgttaatga tcctgaacgc tatggtgtcg ttgagtttga taaaaacggt    3780
actgcaatca gcctggaaga aaaaccgtta caaccaaaaa gtaattatgc ggtaaccggg    3840
ctttatttct atgataacta cgttgtggaa atggcgaaaa tcttaagcc ttctgcccgc     3900 ggtgaactgg aaattaccga tattaaccgt atctatatgg aacagggca tttatctgtt     3960 gccatgatgg gacgtggata tgcctggctg gacacgggga cacatcaaag tcttattgaa    4020
gcaagcaact tcattgccac cattgaagag cgccagggct tgaaagtttc ctgcccggaa    4080
gaaattgctt accgtaaagg gtttattgat gctgagcagg tgaaagtatt agctaaaccg    4140
ctgaaaaaaa atgcttatgg tcagtatctg ctaaaaatga ttaaaggtta ttaataaaat    4200
gaatgttatt aaaacagaaa ttccagatgt actgattttt gaaccgaaag ttttggtga    4260
```

```
tgagcgtggt ttctttatgg aaagctttaa tcagaaagtt ttcgaagagg ctgtagggcg      4320
gaaggttgaa tttgttcagg ataatcattc taaatcgtgt aaaggtgtac ttagaggttt      4380
acactttcag cttcctccct tgagcaggc aaaattagta aggtgtatag ttggcgaggt       4440
atttgatgtt gcagtagaca ttagacctaa ttctgaaaca tttggttcat gggttggagt      4500
aactctttcg tcagaaaata aaaggcagct atggattcca gaaggattcg cccatggttt      4560
tttaacttta agtgatattg cagagtttgt ttataaaact aacaactatt attctttaaa      4620
tcatgaaagg ggagtcattt ggaacgatga ggaaattaac attgcctggc cctctcaatc      4680
agagaagatt ctgtcacaga aagatattaa tttaccatca tttagatttg ttcaaatgtt      4740
tagcaagtag tgttatcttt acactgcaca tagtcatcat ttttatgct ttaagtaaat       4800 tatattgcac atctataaca caaagcgcaa taatatttcg acctgatgaa ggtttgtggt      4860
tatttatctt tctaggcgtt tttatgact aaaatagttg tggtttctac agctccaata       4920
ttcccgacaa ataatgggta caaaagttct gtattaggaa gaattgatga gttattaaat      4980
gaggataatg aggtcgtttt gattgaaata aaccttgaaa atgttacgga aaagaaagat      5040
gaattaatac caacaagatt taataatatt caaagatatg aagtaaaaaa aatatctaga      5100
tcatttattg ccgagttaca aatattattt gatatcagaa ctcggtatga acaattattt      5160
tcttctgctg acattagaga taacataaaa aagataattg attagaaaa accttctatt       5220 attattgctg agtctatatg ggcgttgcaa gcattgccta ttgaaattag tgcgagaata      5280
cactgtgtta ttcatgatgt ggcaactgat ttctttaaag aaatgtttgt atctcataat      5340
gaggttgtac gaaaaatttt gttttttaat gattacctaa agttgaaaat tactgaagaa      5400
aatattatca aacgtttgag agttgagcaa tttatctttc tgacagaaga agataaatgt      5460
tggtataaaa caagatacaa tattgatgag ggttgttgtt ccttagcgag caatcatctt      5520
tatgtagaaa agattaagag aactatcaat ttccaaaccc ctttcctgct tattcccggt      5580
agcattgaat tttcacaaaa ttttttacggc ttaaattggt ttataaaaaa tatatatcct     5640
ggattaaata ggaaaataag aatagttgta acaggaaagg catcagataa aaaaataaag      5700
atgttaaact gtggagagga aattaccttt acgggagagc ttgacttttc cacatataat      5760
aaacttagct caacatgctt gtgtgttatt gcaccgatta caacgggcac tggaattaaa      5820
ataaaaatat tagaagctgt acaaaaaggt attcctgtac ttacaacaaa atttgcttca      5880
aaaggaatat gttccgattt atgttttat tgcgaggagg atactgacac aaactttgtc       5940
aatttaatta acagttttct tgaaacgaca ttaagagtcc aagaatgaat ttattgcttt      6000
tttcagtcct tgcgtttggt ttaatattgg ctttggccca taataataaa agtggagata      6060
ttaacgcata cttaatgttt tttctcgtgg tcctaatggt attaatatca gggctgcgta      6120
tgaatgatag tgattatatc gaatacagga aaatgtataa tgaagtgcct attttatgtg      6180
actttagtct cgcatctata agagatatac atggggaggt aggctatcta ttcttatcat      6240
caatctttaa aactttatgc ttgccatttc aattattcct ttttttattt gctttttat       6300 cactcctgct tacatatttt tcattcagaa aaataagttt aataccgata ctatcgttag      6360 tttttttattt aagccatgct tttatagtta gagatttgat tcaaattagg gcaggattag     6420
ctgttagcat atcattatat tcaataatta aatttaaagg aaataaaagt ataattacag      6480
gagttttatt tgcttctttg attcattctg gggcgcttat tattgctctt tgttatcctt      6540
ttttcaaaaa aaaatacata acattaaaaa tgatgttgtt tttatttta gtgtcaatta       6600 ttttttctta tttgaatggg cttaatttat cgatacaact cttatctcaa tatagtttgc      6660
```

```
ttccaactgc aatttcgaat tatgttggtt gggaagaata tgattatcgg gtgagtatat    6720
ttactaatcc ggttttatt aaggtgtttt ttttaattgt cttaatgcac aaatatgtac     6780
tttcagatat taaaaatgag aaaattatag tgctttataa cttatatgtt ttaggtgtat    6840
tagctatggt tgcattgagt gggatggcta ttctttcagg ccgtctttca tcctttctga    6900
cactaggtga aagcatttta attgtatatg ctctgttcta caaaagaaat acacctctgg    6960
cgtttctaat ttttctttt ttaacaattg tgcaattagg atatgatcta tttatttcta    7020
atgtgcatcc tgagcttact ctgattatat ttgggtgaat ctaagtgaaa aataataaaa    7080
taggcatact tatctctaaa atacaaaatc ttggacctgt gaatgtagta cgaggattga    7140
taaaagaaaa taaaaaatat gcttttactg ttttttgttt aacaaatagc gtagataaaa    7200 atatatgta tgagttatgc tgtttaggag ccaaggttat attaatacca gatggtactt     7260
ggttcagcaa aattttattt gtgagaagtt tttaaaggga acatccacat aatatcttac    7320
attcacatgg gatcacggcc gatatgtttt cttactttct gaatggcgtg aaaatatcta    7380
ctattcacaa tagactagat gaggattata tcccattatt tggcgcggtt aaagggaatg    7440
ctatatatta tcttcatcgt tttatattac gaagatttaa tcatatcgtt gcttgctcag    7500
cagcggtcca atcaaaactg aaacaatcga agtaaaaac taaaataacc accatccaga    7560
atgggattga tataactagg tttaagacac ttgagtctga taaaaaaaaa ttattgaggg    7620
aaaaacacgg atttgatagt gaaaaagaa tatttatata ttgtggctcg ttatcattaa    7680
ggaaaaatat tgcttacctc ttggaacact tagccatcga agaaaatgat atattttttaa   7740 ttctaggtga tggtgaactt tttagatatt gtaaggataa atattctaaa gatttacggt    7800 atatattat ggggaaagtt gaatgccctc ttgaatatta tcaattatca gatatttttg     7860
tttccgcttc tttatcggaa gggctcccct tggcactatt agaagctgcc tctactgggt    7920
gctatttata tgttagcgat atagagcccc atagagaaat tgcatctcta ttaggagagg    7980
aaaatatttc tatgtttaaa attaaggatg gatcatataa ttatttgcaa cctaaaataa    8040
aaaaagctga ctataacgct ctttctgacg ataaactta caatatatcc gataaaaaaa     8100
tgtcaaatct ttatgacaaa ctttttgttt ctttattaga gcagaggcac taatataatg   8160
atttatgttt cggtaatttc tcatggtcat ttcaaaactc ttaaggaatt aggagcagta    8220
tcaaaattaa ataatcacag cagaattaaa gttatcatca aagataattt aggagagagc    8280
gagcttttgg attttgtca ggaaaacaaa ataacttatt taaggtctaa agagaaaaaa     8340
ggatttggag agaataataa tgaagttttt tcctctatat cctccttaat tactaaggaa    8400
gatttttttg tggttatgaa tcctgatata tatattgagt gctctgatct attagatgtc    8460
gtagatgagt gtggttcagc gaatgttaat ctagcaacga taaatttata cagggatttt    8520
gataaaaaaa catatgataa ctcagtaagg aaatttccct cggcaattga tttttttatg    8580
tcatttttat ttaagaaaaa tgactgtgta gtaaataaga acaaaataac gaaaccaaca    8640
tatgttgatt gggctgcagg ttctttttcta atatttaatg ccttcttta ttcaaaactc    8700 aacggattca acgaaaagta tttatatgtat tgcgaagata ttgatatatg ttggcgagct   8760
aaaaaacact tcaatacttc agttttatac tatccatgct atgcagcaat tcatttggca    8820
caatttaaca atcgtaggat ttttagtaga catttcattt ggcatataaa aagtattatc    8880 cttttttat tatataaaaa tggtatgctg cgttctagta agttgcttta atgctaatat     8940
tcttttaaga ggtgagaatg atacctgtta ttttggctgg tggttcggga agtcgcttgt    9000
```

```
ggccactttc acgagaaaag ttccccaagc agttttttaaa gttgactggc agtttgacaa   9060
tgttgcagtc aacattgtca cgtcttaata atttaaatgc tgatgattca atagttatat   9120
gcaacgaaga gcatagattt attgttgcag aacaattaag agagttaggc aaactttcaa   9180
ataacattat tcttgaaccc aaaggtcgta atacagcccc tgctataaca ctcgcagcat   9240
tagcagcaaa aagaaaattc gctgatgaag atccattgat tcttatttta gctgcagatc   9300
acaacatcca agacgaacat gttttctgtg aggcaattaa taaggcgtca tctttagcta   9360
gttatggaaa actagtgact tttggtatcg ttccattcaa acctgaaact gggtatggct   9420
atattcgtcg cggtgatgaa gtgcctgtag atgagcagca tgcggtggcc tttgaagtgg   9480
cgcagtttgt cgaaaaaccg aatctggaaa ccgcgcaggc ctatgtggca agcggcgaat   9540
attactggaa cagcggtatg ttcctgttcc gtgccgacg ctatctcgaa gaactgaaaa   9600
agtatcgtcc ggatattctc gatgcctgtg aaaaagcgat gagcgccgtc gatccggatc   9660
tcgattttat tcgtgtggat gaagaggcgt ttctcgcttg tccggaagag tcggtggatt   9720
acgcggtcat ggaatgcacg gcagatgccg ttgtggtgcc gatggatgcg ggctggagcg   9780
atgtcggttc ctggtcttca ttatgggaga tcagcgccca caccgccgag ggcaacgttt   9840
gccacggcga tgtgattaat cacaaaactg aaaacagcta tgtgtacgcc gaatctggcc   9900
tggtcaccac cgtcggggtg aaagatttgg tggtagtgca gaccaaagat gcagtgctga   9960
ttgccgaccg taatgcggtg caggatgtga agaaagtggt cgagcagatc aaagctgatg  10020
gtcgccatga gcatcgggtg catcgcgaag tgtatcgtcc gtgggcaaa tatgactcta  10080
tcgacgcggg cgaccgctac caggtgaaac gcatcaccgt gaaaccgggc gaaggtttgt  10140
cggtacagat gcattatcat cgcgcggaac actgggtggt tgtcgcggga acggcaaaag  10200
tcactatcaa cggtgatatc aaactgcttg gtgaaaacga gtccatttat attccgctgg  10260
gggcgatgca ctgcctggaa aacccgggga aaatagattt agaattaatt gaagttcgct  10320
ctggtgcata tcttgaagaa gatgatgtta ttagatgtta tgatcgctat ggacgaaagt  10380
aatatataat aattatttca gaattagaaa tgataattat aagttttcgt ctggataaac  10440
aatagatagt atgggttgga aaatatgagt tcttttaactt gttttaaagc ttacgacatt  10500
cgcgggaaat taggtgaaga actgaatgaa gatatcgcct ggcgcattgg tcgcgcctat  10560
ggcgaatttc tcaaaccgaa aaccattgtg ttaggcggtg atgtccgtct caccagcgaa  10620
accttaaaac tggcgctggc aaaaggttta caggatgcgg gcgtcgatgt gctggatatt  10680
ggcatgtccg gcaccgaaga gatttatttc gccacgttcc atctcggcgt ggatggcggc  10740
attgaagtta ccgccagcca taatccgatg gattacaacg gcatgaagct ggtgcgcgaa  10800
ggggctcgcc cgatcagcgg tgataccgga ctgcgcgacg tccagcgtct ggcagaagct  10860
aacgactttc ctcccgtcga tgaaaccaaa cgcggtcgct atcagcaaat caatctgcgt  10920
gacgcttacg ttgatcacct gttcggttat atcaatgtca aaaaccttac gccgctcaag  10980
ctggtgatca actccgggaa tggcgcagcg ggtccggtgg tggacgctat cgaagcccgc  11040
tttaaagccc tcggcgcacc ggtggagtta atcaaagtgc ataacacgcc ggacggcaat  11100
ttccccaacg gtattcctaa cccgttgctg ccggaatgtc gcgacgacac ccgcaatgcg  11160
gtcatcaaac acggcgcgga tatgggcatt gcctttgatg gcgattttga ccgctgtttc  11220
ctgtttgacg aaaaagggca gtttattgag ggctactaca ttgtcggcct gctggcagaa  11280
gcgttcctcg aaaaaaatcc cggcgcgaag atcatccacg atccacgtct ctcctggaac  11340
accattgatg tggtgacggc cgcggcggc acgccggtga tgtcgaaaac aggacacgcc  11400
```

```
tttattaaag aacgtatgcg caaggaagac gccatctacg gtggcgaaat gagcgctcac    11460
cattacttcc gcgatttcgc ttactgtgac agcggcatga tcccgtggct gctggtcgcc    11520
gaactggtgt gcctgaaagg aaaaacgctg ggcgaactgg tgcgcgaccg gatggcggcg    11580
tttccggcaa gcggtgagat caacagaaaa ctggcgcacc ctgttgaggc gattaaccgc    11640
gtggaacagc attttagccg tgaggtgctg gcggtggatc gcaccgatgg catcagcatg    11700
acctttgccg actggcgctt taacctgcgc tcttccaaca ccgaaccggt ggtgcgcctg    11760
aatgtggaat ctcgcggtga tgttcaggtt atggtaatcc atactcaaga aatattatca    11820
attttgacgt cataaagaat aagccctgac aagttagggc ttaattaata tatttttt    11880 ttgaattggg gatttgtggt aagattttta atatgttatt taatgtggtt gaattaatgt    11940
tgactggaaa ataataatga gaacgaaaaa agcattacac aactttaaag ttgatttatt    12000
aattactttt ttattggttt tgctagggtt ttatattcga actgtttttg tttcaaaaat    12060
gggaagtgat attactggag tgatgttact attcacacag ttgacagcat atctcaattt    12120
ggcagaatta ggtattggaa ttgcagctgc cagcgtatta tataaaccgc tcagcgagaa    12180
tgaatacaat aaaataactt acataatatc tttgctctca gtcatataca aatatatatt    12240
tgtgtttgtt ttgattcttg gcgttgttat aggtatctgt atttattact ttattgattc    12300
tgtaaaggtt gtaaatggcg tttttttata ttgggctttg ttcgttttta atacatcgtt    12360
gacatatagt tatgctaaat actccacatt attaactgct aatcagcggt actcagcagt    12420
aagaaaaatt caaggtggcg gaaaagttat aataattgta tttcagatat taattttgtg    12480
ctttacgcaa agtttcatac tttatttgtt agttgagact ttaggtattt tttctcaata    12540
tttgattttt aaaaaaataa ttgggaacgg aaatcaatat ctcagtaatg aggttttact    12600
tattgaaagc gataaacttt tgataaaaaa agaattaaaa ataagaataa aaaatatgtt    12660
cttccataaa ataggtgctg tgcttgtcct taatacagac tacctgcttg tatcaaagtt    12720
tctgacatta agttatgtga caattttgg cagctatatg atggtatttc agatagtaac    12780
tgttttgatg tcaagttttg ttaatgctat tactgcagga atgggtaatt acttaattaa    12840
taaaagtaat ttagaaatta aggaaattac acgtcaattt tatgtgatat ttatcgcctt    12900
tgcaacattc atatcactaa atatgttttt tcttgttaat gatttatcg caaaatggat    12960 aggtgttaat tatacattaa gtaacaccct agttgcatta atgattgtta acgtattcat    13020
tagtgttgtc agggtacctt ctgatatatt aaaaaacgca agtggacatt ttggtgatat    13080
ttattatcca ttattagaag gtgtgctgaa tattacgata tccatcattt tggctatcat    13140
tattggatta cctggcatta ttatagggac aatagtatct aacttaatag taataatgct    13200
tgcgaaacca ttatatcttt actctaagtt atttaatctt agaaatccga cgagggttta    13260
ttttgaattt atttctcggc ctatgttata ttcattatgt gtgattgggg tgagctattt    13320
attgcgcgat gaaatatatt catttaaagt aagtacatgg ttggatttta ttaacaagct    13380
actcttagtc tctactccta gcatattggt aatatgtgct atttttctcta cggatagtga    13440 ctttagatta ttttcagaa aaattatata tgtgattatg aagaaataaa aatttcgaaa    13500
atgtattaat cgaaattatg caacgagctt tatttttata aatgatatgt gatcttttcg    13560
cgaataggag taaggatccg tgtaggctgg agctgcttcg aagttcctat actttctaga    13620
gaataggaac ttcggaatag gaactaagga ggatattcat atggataaag ccgtaagcat    13680
ataagcatgg ataagctatt tatactttaa taagtacttt gtatacttat ttgcgaacat    13740
```

```
tccaggccgc gagcattcag cgcggtgatc acacctgaca ggagtatgta atgtccaagc  13800
aacagatcgg cgtagtcggt atggcagtga tgggacgcaa ccttgcgctc aacatcgaaa  13860
gccgtggtta taccgtctct attttcaacc gttcccgtga gaagacggaa gaagtgattg  13920
ccgaaaatcc aggcaagaaa ctggttcctt actatacggt gaaagagttt gtcgaatctc  13980
tggaaacgcc tcgtcgcatc ctgttaatgg tgaaagcagg tgcaggcacg gatgctgcta  14040
ttgattccct caaaccatat ctcgataaag gagacatcat cattgatggt ggtaacacct  14100
tcttccagga cactattcgt cgtaatcgtg agctttcagc agagggcttt aacttcatcg  14160
gtaccggtgt ttctggcggt gaagaggggg cgctgaaagg tccttctatt atgcctggtg  14220
gccagaaaga agcctatgaa ttggtagcac cgatcctgac caaaatcgcc gccgtagctg  14280
aagacggtga accatgcgtt acctatattg gtgccgatgg cgcaggtcac tatgtgaaga  14340
tggttcacaa cggtattgaa tacggcgata tgcagctgat tgctgaagcc tattctctgc  14400
ttaaaggtgg cctgaacctc accaacgaag aactggcgca gacctttacc gagtggaata  14460
acggtgaact gagcagttac ctgatcgaca tcaccaaaga tatcttcacc aaaaaagatg  14520
aagacggtaa ctacctggtt gatgtgatcc tggatgaagc ggctaacaaa ggtaccggta  14580
aatggaccag ccagagcgcg ctggatctcg gcgaaccgct gtcgctgatt accgagtctg  14640
tgtttgcacg ttatatctct tctctgaaag atcagcgtgt tgccgcatct aaagttctct  14700
ctggtccgca agcacagcca gcaggcgaca aggctgagtt catcgaaaaa gttcgtcgtg  14760
cgctgtatct gggcaaaatc gtttcttacg cccagggctt ctctcagctg cgtgctgcgt  14820
ctgaagagta caactgggat ctgaactacg gcgaaatcgc gaagattttc cgtgctggct  14880
gcatcatccg tgcgcagttc ctgcagaaaa tcaccgatgc ttatgccgaa aatccacaga  14940
tcgctaacct gttgctggct ccgtacttca agcaaattgc cgatgactac cagcaggcgc  15000
tgcgtgatgt cgttgcttat gcagtacaga acggtattcc ggttccgacc ttctccgcag  15060
cggttgccta ttacgacagc taccgtgctg ctgttctgcc tgcgaacctg atccaggcac  15120
agcgtgacta ttttggtgcg catacttata agcgtattga taaagaaggt gtgttccata  15180
ccgaatggct ggattaa                                                  15197
```